US007927583B2

(12) United States Patent
Stahl et al.

(10) Patent No.: US 7,927,583 B2

(45) Date of Patent: Apr. 19, 2011

(54) RECEPTOR BASED ANTAGONISTS AND METHODS OF MAKING AND USING

(75) Inventors: Neil Stahl, Carmel, NY (US); George D. Yancopoulos, Yorktown Heights, NY (US)

(73) Assignee: Regeneron Pharmaceuticals, Inc., Tarrytown, NY (US)

(*) Notice: Subject to any disclaimer, the term of this patent is extended or adjusted under 35 U.S.C. 154(b) by 181 days.

(21) Appl. No.: 12/177,185

(22) Filed: Jul. 22, 2008

(65) Prior Publication Data

US 2009/0010879 A1 Jan. 8, 2009

Related U.S. Application Data

(60) Continuation of application No. 11/134,114, filed on May 20, 2005, now Pat. No. 7,417,134, which is a division of application No. 10/282,162, filed on Oct. 28, 2002, now Pat. No. 6,927,044, which is a continuation-in-part of application No. 09/787,835, filed as application No. PCT/US99/22045 on Sep. 22, 1999, now abandoned, which is a continuation of application No. 09/313,942, filed on May 19, 1999, now Pat. No. 6,472,179.

(60) Provisional application No. 60/101,858, filed on Sep. 25, 1998.

(51) Int. Cl.

| | |
|---|---|
| ***A61K 38/20*** | (2006.01) |
| ***A61K 39/00*** | (2006.01) |
| ***A61K 38/16*** | (2006.01) |

(52) U.S. Cl. .................... 424/85.2; 424/185.1; 514/21.2

(58) Field of Classification Search ........................ None
See application file for complete search history.

(56) References Cited

U.S. PATENT DOCUMENTS

| | | | | |
|---|---|---|---|---|
| 5,470,952 A | | 11/1995 | Stahl et al. | |
| 5,844,099 A | * | 12/1998 | Stahl et al. | 530/350 |
| 5,945,511 A | * | 8/1999 | Lok et al. | 530/350 |
| 6,472,179 B2 | | 10/2002 | Stahl et al. | |
| 6,610,750 B1 | | 8/2003 | Charbit et al. | |

FOREIGN PATENT DOCUMENTS

| | | |
|---|---|---|
| EP | 0835939 A2 | 6/1991 |
| EP | 0533006 A1 | 9/1992 |
| WO | WO 93/19163 | 9/1993 |
| WO | WO 93/19777 | 10/1993 |
| WO | WO 94/22914 | 10/1994 |
| WO | WO 95/06737 | 3/1995 |
| WO | WO 96/11213 | 4/1996 |
| WO | WO9611213 A1 * | 4/1996 |
| WO | WO 96/23881 | 8/1996 |
| WO | WO 96/35783 | 11/1996 |
| WO | WO 97/15669 | 5/1997 |
| WO | WO 97/31946 | 9/1997 |
| WO | WO 99/37772 | 7/1999 |

OTHER PUBLICATIONS

Greenfeeder, SA et al. 1995. Molecular Cloning and Characterization of a Second Subunit of the Interleukin-1 Receptor Complex. J Bio Chem 270(23):13757-13765.

Seipelt, I et al. 1997. Overexpression, Purification, and Use of a Soluble Human Interleukin-4 Receptor alpha chain/IgG1 Fusion Protein for Ligand Binding Studies. BioChem & BioPhys Res Comm 239:534-542.

Stahl, N et al. 1999. Cytokine Traps: Heteromeric Receptor-Based Protein Therapeutics that Function as High-Affinity Blockers of Cytokine Action. FASEB Journal Abstract 1457.

* cited by examiner

*Primary Examiner* — Christine J Saoud
*Assistant Examiner* — Jegatheesan Seharaseyon
(74) *Attorney, Agent, or Firm* — Valeta Gregg; Frank R. Cottingham

(57) ABSTRACT

The present invention provides a fusion polypeptide capable of binding a cytokine to form a nonfunctional complex. It also provides a nucleic acid sequence encoding the fusion polypeptide and methods of making and uses for the fusion polypeptide.

8 Claims, 174 Drawing Sheets

Figure 4A

Amino acid sequence of human gp130-Fc-His6

Sequence Range: 1 to 861

```
        10         20         30         40         50         60
         *          *          *          *          *          *
MVTLQTWVVQALFIFLTTES TGELLDPCGYISPESPVVQL HSNFTAVCVLKEKCMDYFHV

        70         80         90        100        110        120
         *          *          *          *          *          *
NANYIVWKTNHFTIPKEQYT IINRTASSVTFTDIASLNIQ LTCNILTFGQLEQNVYGITI

       130        140        150        160        170        180
         *          *          *          *          *          *
ISGLPPEKPKNLSCIVNEGK KMRCEWDGGRETHLETNFTL KSEWATHKFADCKAKRDTPT

       190        200        210        220        230        240
         *          *          *          *          *          *
SCTVDYSTVYFVNIEVWVEA ENALGKVTSDHINFDPVYKV KPNPPHNLSVINSEELSSIL

       250        260        270        280        290        300
         *          *          *          *          *          *
KLTWTNPSIKSVIILKYNIQ YRTKDASTWSQIPPEDTAST RSSFTVQDLKPFTEYVFRIR

       310        320        330        340        350        360
         *          *          *          *          *          *
CMKEDGKGYWSDWSEEASGI TYEDRPSKAPSFWYKIDPSH TQGYRTVQLVWKTLPPFEAN

       370        380        390        400        410        420
         *          *          *          *          *          *
GKILDYEVTLTRWKSHLQNY TVNATKLTVNLTNDRYLATL TVRNLVGKSDAAVLTIPACD

       430        440        450        460        470        480
         *          *          *          *          *          *
FQATHPVMDLKAFPKDNMLW VEWTTPRESVKKYILEWCVL SDKAPCITDWQQEDGTVHRT

       490        500        510        520        530        540
         *          *          *          *          *          *
YLRGNLAESKCYLITVTPVY ADGPGSPESIKAYLKQAPPS KGPTVRTKKVGKNEAVLEWD

       550        560        570        580        590        600
         *          *          *          *          *          *
QLPVDVQNGFIRNYTIFYRT IIGNETAVNVDSSHTEYTLS SLTSDTLYMVRMAAYTDEGG

       610        620        630        640        650        660
         *          *          * †   †    *          *          *
KDGPEFTFTTPKFAQGEIES GEPKSCDKTHTCPPCPAPEL LGGPSVFLFPPKPKDTLMIS

       670        680        690        700        710        720
         *          *          *          *          *          *
RTPEVTCVVVDVSHEDPEVK FNWYVDGVEVHNAKTKPREE QYNSTYRVVSVLTVLHQDWL

       730        740        750        760        770        780
         *          *          *          *          *          *
```

Figure 4B

```
NGKEYKCKVSNKALPAPIEK TISKAKGQPREPQVYTLPPS RDELTKNQVSLTCLVKGFYP

      790       800        810       820        830       840
        *         *          *         *          *         *
SDIAVEWESNGQPENNYKTT PPVLDSDGSFFLYSKLTVDK SRWQQGNVFSCSVMHEALHN

      850       860
        *         *
HYTQKSLSLSPGKHHHHHH•
```

Fig.5.

The amino acid sequence of human IL-6Rα-Fc

```
Sequence Range: 1 to 594

       10        20        30        40        50        60
        *         *         *         *         *         *
MVAVGCALLAALLAAPGAAL APRRCPAQEVARGVLTSLPG DSVTLTCPGVEPEDNATVHW

       70        80        90       100       110       120
        *         *         *         *         *         *
VLRKPAAGSHPSRWAGMGRR LLLRSVQLHDSGNYSCYRAG RPAGTVHLLVDVPPEEPQLS

      130       140       150       160       170       180
        *         *         *         *         *         *
CFRKSPLSNVVCEWGPRSTP SLTTKAVLLVRKFQNSPAED FQEPCQYSQESQKFSCQLAV

      190       200       210       220       230       240
        *         *         *         *         *         *
PEGDSSFYIVSMCVASSVGS KFSKTQTFQGCGILQPDPPA NITVTAVARNPRWLSVTWQD

      250       260       270       280       290       300
        *         *         *         *         *         *
PHSWNSSFYRLRFELRYRAE RSKTFTTWMVKDLQHHCVIH DAWSGLRHVVQLRAQEEFGQ

      310       320       330       340       350       360
        *         *         *         *         *         *
GEWSEWSPEAMGTPWTESRS PPAENEVSTPMQALTTNKDD DNILFRDSANATSLPVQDAG

      370       380       390       400       410       420
        *†   †    *         *         *         *         *
EPKSCDKTHTCPPCPAPELL GGPSVFLFPPKPKDTLMISR TPEVTCVVVDVSHEDPEVKF

      430       440       450       460       470       480
        *         *         *         *         *         *
NWYVDGVEVHNAKTKPREEQ YNSTYRVVSVLTVLHQDWLN GKEYKCKVSNKALPAPIEKT

      490       500       510       520       530       540
        *         *         *         *         *         *
ISKAKGQPREPQVYTLPPSR DELTKNQVSLTCLVKGFYPS DIAVEWESNGQPENNYKTTP

      550       560       570       580       590
        *         *         *         *         *
PVLDSDGSFFLYSKLTVDKS RWQQGNVFSCSVMHEALHNH YTQKSLSLSPGK•
```

Immunoglobulin Heavy/Light Chain receptor Fusions

Figure 9A

Amino acid sequence of gp130-Cγ1

```
Sequence Range: 1 to 952

         10         20         30         40         50         60
          *          *          *          *          *          *
MVTLQTWVVQALFIFLTTES TGELLDPCGYISPESPVVQL HSNFTAVCVLKEKCMDYFHV

         70         80         90        100        110        120
          *          *          *          *          *          *
NANYIVWKTNHFTIPKEQYT IINRTASSVTFTDIASLNIQ LTCNILTFGQLEQNVYGITI

        130        140        150        160        170        180
          *          *          *          *          *          *
ISGLPPEKPKNLSCIVNEGK KMRCEWDGGRETHLETNFTL KSEWATHKFADCKAKRDTPT

        190        200        210        220        230        240
          *          *          *          *          *          *
SCTVDYSTVYFVNIEVWVEA ENALGKVTSDHINFDPVYKV KPNPPHNLSVINSEELSSIL

        250        260        270        280        290        300
          *          *          *          *          *          *
KLTWTNPSIKSVIILKYNIQ YRTKDASTWSQIPPEDTAST RSSFTVQDLKPFTEYVFRIR

        310        320        330        340        350        360
          *          *          *          *          *          *
CMKEDGKGYWSDWSEEASGI TYEDRPSKAPSFWYKIDPSH TQGYRTVQLVWKTLPPFEAN

        370        380        390        400        410        420
          *          *          *          *          *          *
GKILDYEVTLTRWKSHLQNY TVNATKLTVNLTNDRYLATL TVRNLVGKSDAAVLTIPACD

        430        440        450        460        470        480
          *          *          *          *          *          *
FQATHPVMDLKAFPKDNMLW VEWTTPRESVKKYILEWCVL SDKAPCITDWQQEDGTVHRT

        490        500        510        520        530        540
          *          *          *          *          *          *
YLRGNLAESKCYLITVTPVY ADGPGSPESIKAYLKQAPPS KGPTVRTKKVGKNEAVLEWD

        550        560        570        580        590        600
          *          *          *          *          *          *
QLPVDVQNGFIRNYTIFYRT IIGNETAVNVDSSHTEYTLS SLTSDTLYMVRMAAYTDEGG

        610        620        630        640        650        660
          *          *          *          *          *          *
KDGPEFTFTTPKFAQGEIES GASTKGPSVFPLAPSSKSTS GGTAALGCLVKDYFPEPVTV

        670        680        690        700        710        720
          *          *          *          *          *          *
SWNSGALTSGVHTFPAVLQS SGLYSLSSVVTVPSSSLGTQ TYICNVNHKPSNTKVDKKVE

        730        740        750        760        770        780
          *          *          *          *          *          *
PKSCDKTHTCPPCPAPELLG GPSVFLFPPKPKDTLMISRT PEVTCVVVDVSHEDPEVKFN
```

Figure 9B

```
        790         800          810         820          830         840
          *           *            *           *            *           *
WYVDGVEVHNAKTKPREEQY NSTYRVVSVLTVLHQDWLNG KEYKCKVSNKALPAPIEKTI

        850         860          870         880          890         900
          *           *            *           *            *           *
SKAKGQPREPQVYTLPPSRD ELTKNQVSLTCLVKGFYPSD IAVEWESNGQPENNYKTTPP

        910         920          930         940          950
          *           *            *           *            *
VLDSDGSFFLYSKLTVDKSR WQQGNVFSCSVMHEALHNHY TQKSLSLSPGK*
```

Fig. 10.

Amino acid sequence of gp130Δ3fibro

```
Sequence Range: 1 to 332

         10          20           30          40           50          60
          *           *            *           *            *           *
MVTLQTWVVQALFIFLTTES TGELLDPCGYISPESPVVQL HSNFTAVCVLKEKCMDYFHV

         70          80           90         100          110         120
          *           *            *           *            *           *
NANYIVWKTNHFTIPKEQYT IINRTASSVTFTDIASLNIQ LTCNILTFGQLEQNVYGITI

        130         140          150         160          170         180
          *           *            *           *            *           *
ISGLPPEKPKNLSCIVNEGK KMRCEWDGGRETHLETNFTL KSEWATHKFADCKAKRDTPT

       190         200          210         220          230         240
          *           *            *           *            *           *
SCTVDYSTVYFVNIEVWVEA ENALGKVTSDHINFDPVYKV KPNPPHNLSVINSEELSSIL

        250         260          270         280          290         300
          *           *            *           *            *           *
KLTWTNPSIKSVIILKYNIQ YRTKDASTWSQIPPEDTAST RSSFTVQDLKPFTEYVFRIR

        310         320          330
          *           *            *
CMKEDGKGYWSDWSEEASGI TYEDRPSKAPSG
```

Fig.11.

Amino acid sequence of J-CH1

Sequence Range: 1 to 121

```
        10         20         30         40         50         60
         *          *          *          *          *          *
SGGQGTLVTVSSASTKGPSV FPLAPSSKSTSGGTAALGCL VKDYFPEPVTVSWNSGALTS

        70         80         90        100        110        120
         *          *          *          *          *          *
GVHTFPAVLQSSGLYSLSSV VTVPSSSLGTQTYICNVNHK PSNTKVDKKVEPKSCDKTHT*
```

Fig.12.

Amino acid sequence of Cγ4

Sequence Range: 1 to 330

```
        10         20         30         40         50         60
         *          *          *          *          *          *
SGASTKGPSVFPLAPCSRST SESTAALGCLVKDYFPEPVT VSWNSGALTSGVHTFPAVLQ

        70         80         90        100        110        120
         *          *          *          *          *          *
SSGLYSLSSVVTVPSSSLGT KTYTCNVDHKPSNTKVDKRV ESKYGPPCPSCPAPEFLGGP

       130        140        150        160        170        180
         *          *          *          *          *          *
SVFLFPPKPKDTLMISRTPE VTCVVVDVSQEDPEVQFNWY VDGVEVHNAKTKPREEQFNS

       190        200        210        220        230        240
         *          *          *          *          *          *
TYRVVSVLTVLHQDWLNGKE YKCKVSNKGLPSSIEKTISK AKGQPREPQVYTLPPSQEEM

       250        260        270        280        290        300
         *          *          *          *          *          *
TKNQVSLTCLVKGFYPSDIA VEWESNGQPENNYKTTPPVL DSDGSFFLYSRLTVDKSRWQ

       310        320        330
         *          *          *
EGNVFSCSVMHEALHNHYTQ KSLSLSLGK*
```

Fig.13.

Amino acid sequence of κ-domain

```
Sequence Range: 1 to 108

         10        20        30        40        50        60
          *         *         *         *         *         *
SGTVAAPSVFIFPPSDEQLK SGTASVVCLLNNFYPREAKV QWKVDNALQSGNSQESVTEQ

         70        80        90       100
          *         *         *         *
DSKDSTYSLSSTLTLSKADY EKHKVYACEVTHQGLSSPVT KSFNRGEC*
```

Fig.14.

Amino acid sequence of λ-domain:

```
Sequence Range: 1 to 107

         10        20        30        40        50        60
          *         *         *         *         *         *
SGPKAAPSVTLFPPSSEELQ ANKATLVCLISDFYPGAVTV AWKADSSPVKAGVETTTPSK

         70        80        90       100
          *         *         *         *
QSNNKYAASSYLSLTPEQWK SHRSYSCQVTHEGSTVEKTV APTECS*
```

Fig.15.

Amino acid sequence of the soluble IL-6Rα domain

```
Sequence Range: 1 to 360

        10         20         30         40         50         60
         *          *          *          *          *          *
MVAVGCALLAALLAAPGAAL APRRCPAQEVARGVLTSLPG DSVTLTCPGVEPEDNATVHW

        70         80         90        100        110        120
         *          *          *          *          *          *
VLRKPAAGSHPSRWAGMGRR LLLRSVQLHDSGNYSCYRAG RPAGTVHLLVDVPPEEPQLS

       130        140        150        160        170        180
         *          *          *          *          *          *
CFRKSPLSNVVCEWGPRSTP SLTTKAVLLVRKFQNSPAED FQEPCQYSQESQKFSCQLAV

       190        200        210        220        230        240
         *          *          *          *          *          *
PEGDSSFYIVSMCVASSVGS KFSKTQTFQGCGILQPDPPA NITVTAVARNPRWLSVTWQD

       250        260        270        280        290        300
         *          *          *          *          *          *
PHSWNSSFYRLRFELRYRAE RSKTFTTWMVKDLQHHCVIH DAWSGLRHVVQLRAQEEFGQ

       310        320        330        340        350        360
         *          *          *          *          *          *
GEWSEWSPEAMGTPWTESRS PPAENEVSTPMQALTTNKDD DNILFRDSANATSLPVQDAG
```

Fig.16.

Amino acid sequence of the soluble IL-6Rα313 domain

```
Sequence Range: 1 to 315

        10         20         30         40         50         60
         *          *          *          *          *          *
MVAVGCALLAALLAAPGAAL APRRCPAQEVARGVLTSLPG DSVTLTCPGVEPEDNATVHW

        70         80         90        100        110        120
         *          *          *          *          *          *
VLRKPAAGSHPSRWAGMGRR LLLRSVQLHDSGNYSCYRAG RPAGTVHLLVDVPPEEPQLS

       130        140        150        160        170        180
         *          *          *          *          *          *
CFRKSPLSNVVCEWGPRSTP SLTTKAVLLVRKFQNSPAED FQEPCQYSQESQKFSCQLAV

       190        200        210        220        230        240
         *          *          *          *          *          *
PEGDSSFYIVSMCVASSVGS KFSKTQTFQGCGILQPDPPA NITVTAVARNPRWLSVTWQD

       250        260        270        280        290        300
         *          *          *          *          *          *
PHSWNSSFYRLRFELRYRAE RSKTFTTWMVKDLQHHCVIH DAWSGLRHVVQLRAQEEFGQ

       310
         *
GEWSEWSPEAMGTTG
```

XG-1 cell proliferation assay

Fig.21A.

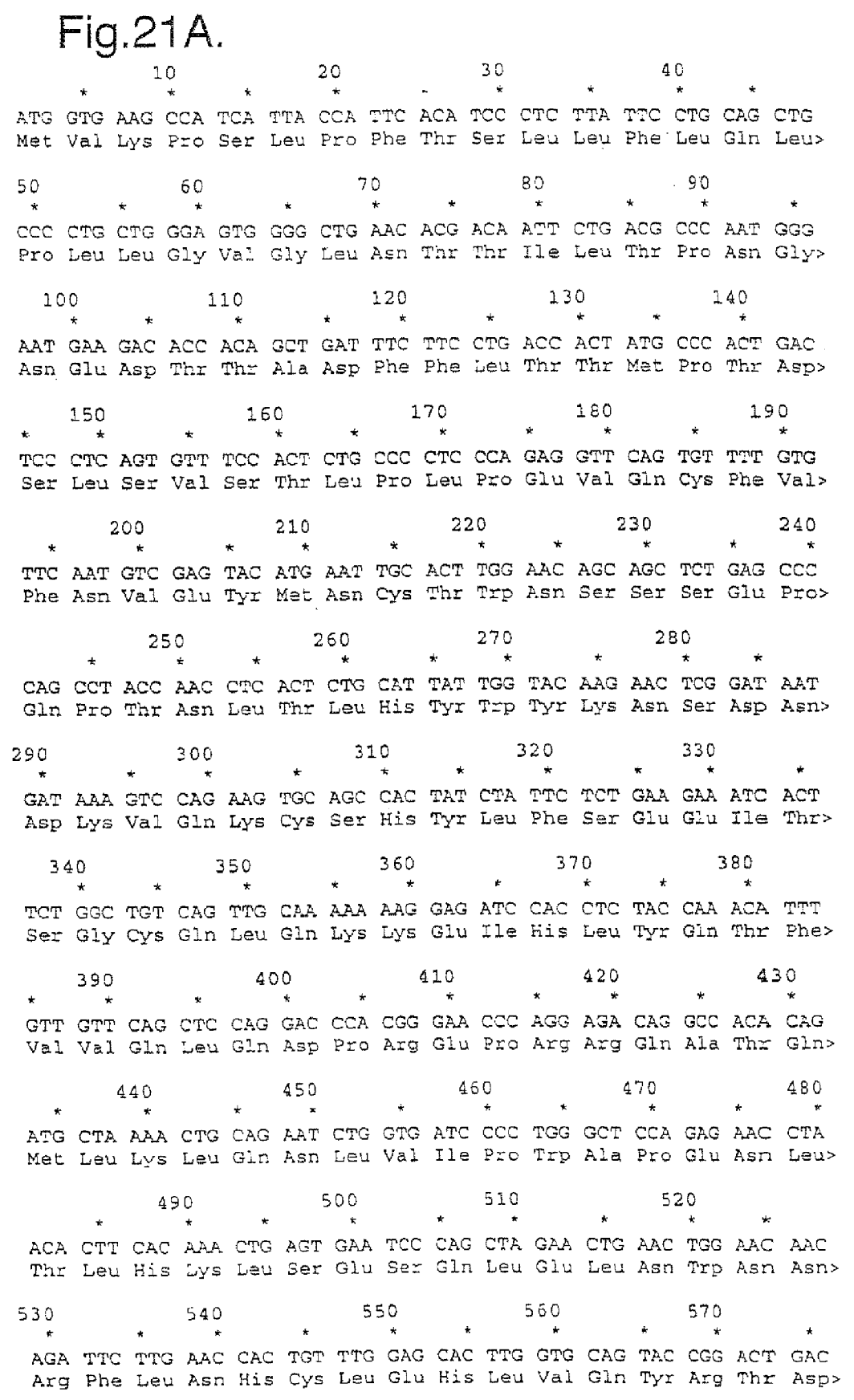

```
         10         20         30         40
ATG GTG AAG CCA TCA TTA CCA TTC ACA TCC CTC TTA TTC CTG CAG CTG
Met Val Lys Pro Ser Leu Pro Phe Thr Ser Leu Leu Phe Leu Gln Leu>

 50         60         70         80         90
CCC CTG CTG GGA GTG GGG CTG AAC ACG ACA ATT CTG ACG CCC AAT GGG
Pro Leu Leu Gly Val Gly Leu Asn Thr Thr Ile Leu Thr Pro Asn Gly>

   100        110        120        130        140
AAT GAA GAC ACC ACA GCT GAT TTC TTC CTG ACC ACT ATG CCC ACT GAC
Asn Glu Asp Thr Thr Ala Asp Phe Phe Leu Thr Thr Met Pro Thr Asp>

     150        160        170        180        190
TCC CTC AGT GTT TCC ACT CTG CCC CTC CCA GAG GTT CAG TGT TTT GTG
Ser Leu Ser Val Ser Thr Leu Pro Leu Pro Glu Val Gln Cys Phe Val>

        200        210        220        230        240
TTC AAT GTC GAG TAC ATG AAT TGC ACT TGG AAC AGC AGC TCT GAG CCC
Phe Asn Val Glu Tyr Met Asn Cys Thr Trp Asn Ser Ser Ser Glu Pro>

           250        260        270        280
CAG CCT ACC AAC CTC ACT CTG CAT TAT TGG TAC AAG AAC TCG GAT AAT
Gln Pro Thr Asn Leu Thr Leu His Tyr Trp Tyr Lys Asn Ser Asp Asn>

290         300        310        320        330
GAT AAA GTC CAG AAG TGC AGC CAC TAT CTA TTC TCT GAA GAA ATC ACT
Asp Lys Val Gln Lys Cys Ser His Tyr Leu Phe Ser Glu Glu Ile Thr>

   340        350        360        370        380
TCT GGC TGT CAG TTG CAA AAA AAG GAG ATC CAC CTC TAC CAA ACA TTT
Ser Gly Cys Gln Leu Gln Lys Lys Glu Ile His Leu Tyr Gln Thr Phe>

      390        400        410        420        430
GTT GTT CAG CTC CAG GAC CCA CGG GAA CCC AGG AGA CAG GCC ACA CAG
Val Val Gln Leu Gln Asp Pro Arg Glu Pro Arg Arg Gln Ala Thr Gln>

         440        450        460        470        480
ATG CTA AAA CTG CAG AAT CTG GTG ATC CCC TGG GCT CCA GAG AAC CTA
Met Leu Lys Leu Gln Asn Leu Val Ile Pro Trp Ala Pro Glu Asn Leu>

            490        500        510        520
ACA CTT CAC AAA CTG AGT GAA TCC CAG CTA GAA CTG AAC TGG AAC AAC
Thr Leu His Lys Leu Ser Glu Ser Gln Leu Glu Leu Asn Trp Asn Asn>

530         540        550        560        570
AGA TTC TTG AAC CAC TGT TTG GAG CAC TTG GTG CAG TAC CGG ACT GAC
Arg Phe Leu Asn His Cys Leu Glu His Leu Val Gln Tyr Arg Thr Asp>
```

Fig.21B.

```
 580        590        600         610        620
  *    *     *    *     *     *     *    *     *
TGG GAC CAC AGC TGG ACT GAA CAA TCA GTG GAT TAT AGA CAT AAG TTC
Trp Asp His Ser Trp Thr Glu Gln Ser Val Asp Tyr Arg His Lys Phe>

    630         640        650        660         670
 *    *     *     *    *     *     *     *     *     *
TCC TTG CCT AGT GTG GAT GGG CAG AAA CGC TAC ACG TTT CGT GTT CGG
Ser Leu Pro Ser Val Asp Gly Gln Lys Arg Tyr Thr Phe Arg Val Arg>

       680        690        700         710        720
  *     *     *    *     *     *     *     *     *     *
AGC CGC TTT AAC CCA CTC TGT GGA AGT GCT CAG CAT TGG AGT GAA TGG
Ser Arg Phe Asn Pro Leu Cys Gly Ser Ala Gln His Trp Ser Glu Trp>

          730        740        750         760
    *      *    *     *     *    *     *     *     *
AGC CAC CCA ATC CAC TGG GGG AGC AAT ACT TCA AAA GAG AAC GCG TCG
Ser His Pro Ile His Trp Gly Ser Asn Thr Ser Lys Glu Asn Ala Ser>

770        780        790        800        810
 *     *     *     *     *     *     *     *     *     *
TCT GGG AAC ATG AAG GTC CTG CAG GAG CCC ACC TGC GTC TCC GAC TAC
Ser Gly Asn Met Lys Val Leu Gln Glu Pro Thr Cys Val Ser Asp Tyr>

  820        830        840        850        860
   *     *     *     *     *     *     *     *     *
ATG AGC ATC TCT ACT TGC GAG TGG AAG ATG AAT GGT CCC ACC AAT TGC
Met Ser Ile Ser Thr Cys Glu Trp Lys Met Asn Gly Pro Thr Asn Cys>

    870         880        890        900         910
 *    *     *     *     *    *     *     *     *     *
AGC ACC GAG CTC CGC CTG TTG TAC CAG CTG GTT TTT CTG CTC TCC GAA
Ser Thr Glu Leu Arg Leu Leu Tyr Gln Leu Val Phe Leu Leu Ser Glu>

       920        930        940        950         960
  *     *     *    *     *     *     *     *     *     *
GCC CAC ACG TGT ATC CCT GAG AAC AAC GGA GGC GCG GGG TGC GTG TGC
Ala His Thr Cys Ile Pro Glu Asn Asn Gly Gly Ala Gly Cys Val Cys>

          970        980        990        1000
    *      *    *     *     *     *     *     *     *
CAC CTG CTC ATG GAT GAC GTG GTC AGT GCG GAT AAC TAT ACA CTG GAC
His Leu Leu Met Asp Asp Val Val Ser Ala Asp Asn Tyr Thr Leu Asp>

1010       1020       1030       1040       1050
 *     *     *     *     *     *     *     *     *     *
CTG TGG GCT GGG CAG CAG CTG CTG TGG AAG GGC TCC TTC AAG CCC AGC
Leu Trp Ala Gly Gln Gln Leu Leu Trp Lys Gly Ser Phe Lys Pro Ser>

 1060       1070       1080       1090       1100
   *     *     *     *     *     *     *     *     *
GAG CAT GTG AAA CCC AGG GCC CCA GGA AAC CTG ACA GTT CAC ACC AAT
Glu His Val Lys Pro Arg Ala Pro Gly Asn Leu Thr Val His Thr Asn>

   1110       1120       1130       1140       1150
 *    *     *     *     *     *     *     *     *     *
GTC TCC GAC ACT CTG CTG CTG ACC TGG AGC AAC CCG TAT CCC CCT GAC
Val Ser Asp Thr Leu Leu Leu Thr Trp Ser Asn Pro Tyr Pro Pro Asp>

      1160       1170       1180       1190       1200
  *     *     *     *     *     *     *     *     *     *
```

```
AAT TAC CTG TAT AAT CAT CTC ACC TAT GCA GTC AAC ATT TGG AGT GAA
Asn Tyr Leu Tyr Asn His Leu Thr Tyr Ala Val Asn Ile Trp Ser Glu>

        1210        1220        1230        1240
     *     *     *     *     *     *     *     *     *
AAC GAC CCG GCA GAT TTC AGA ATC TAT AAC GTG ACC TAC CTA GAA CCC
Asn Asp Pro Ala Asp Phe Arg Ile Tyr Asn Val Thr Tyr Leu Glu Pro>

1250        1260        1270        1280        1290
 *     *     *     *     *     *     *     *     *     *
TCC CTC CGC ATC GCA GCC AGC ACC CTG AAG TCT GGG ATT TCC TAC AGG
Ser Leu Arg Ile Ala Ala Ser Thr Leu Lys Ser Gly Ile Ser Tyr Arg>

  1300        1310        1320        1330        1340
     *     *     *     *     *     *     *     *     *
GCA CGG GTG AGG GCC TGG GCT CAG TGC TAT AAC ACC ACC TGG AGT GAG
Ala Arg Val Arg Ala Trp Ala Gln Cys Tyr Asn Thr Thr Trp Ser Glu>

    1350        1360        1370        1380        1390
 *     *     *     *     *     *     *     *     *     *
TGG AGC CCC AGC ACC AAG TGG CAC AAC TCC TAC AGG GAG CCC TTC GAG
Trp Ser Pro Ser Thr Lys Trp His Asn Ser Tyr Arg Glu Pro Phe Glu>

      1400        1410        1420        1430        1440
 *     *     *     *     *     *     *     *     *     *
CAG TCC GGA GAC AAA ACT CAC ACA TGC CCA CCG TGC CCA GCA CCT GAA
Gln Ser Gly Asp Lys Thr His Thr Cys Pro Pro Cys Pro Ala Pro Glu>

        1450        1460        1470        1480
     *     *     *     *     *     *     *     *     *
CTC CTG GGG GGA CCG TCA GTC TTC CTC TTC CCC CCA AAA CCC AAG GAC
Leu Leu Gly Gly Pro Ser Val Phe Leu Phe Pro Pro Lys Pro Lys Asp>

1490        1500        1510        1520        1530
 *     *     *     *     *     *     *     *     *     *
ACC CTC ATG ATC TCC CGG ACC CCT GAG GTC ACA TGC GTG GTG GTG GAC
Thr Leu Met Ile Ser Arg Thr Pro Glu Val Thr Cys Val Val Val Asp>

  1540        1550        1560        1570        1580
     *     *     *     *     *     *     *     *     *
GTG AGC CAC GAA GAC CCT GAG GTC AAG TTC AAC TGG TAC GTG GAC GGC
Val Ser His Glu Asp Pro Glu Val Lys Phe Asn Trp Tyr Val Asp Gly>

    1590        1600        1610        1620        1630
 *     *     *     *     *     *     *     *     *     *
GTG GAG GTG CAT AAT GCC AAG ACA AAG CCG CGG GAG GAG CAG TAC AAC
Val Glu Val His Asn Ala Lys Thr Lys Pro Arg Glu Glu Gln Tyr Asn>

      1640        1650        1660        1670        1680
 *     *     *     *     *     *     *     *     *     *
AGC ACG TAC CGT GTG GTC AGC GTC CTC ACC GTC CTG CAC CAG GAC TGG
Ser Thr Tyr Arg Val Val Ser Val Leu Thr Val Leu His Gln Asp Trp>

        1690        1700        1710        1720
     *     *     *     *     *     *     *     *     *
CTG AAT GGC AAG GAG TAC AAG TGC AAG GTC TCC AAC AAA GCC CTC CCA
Leu Asn Gly Lys Glu Tyr Lys Cys Lys Val Ser Asn Lys Ala Leu Pro>

1730        1740        1750        1760        1770
 *     *     *     *     *     *     *     *     *     *
GCC CCC ATC GAG AAA ACC ATC TCC AAA GCC AAA GGG CAG CCC CGA GAA
Ala Pro Ile Glu Lys Thr Ile Ser Lys Ala Lys Gly Gln Pro Arg Glu>
```

Fig.21D.

```
1780        1790        1800          1810        1820
  *     *     *     *     *     *     *     *     *
CCA CAG GTG TAC ACC CTG CCC CCA TCC CGG GAG GAG ATG ACC AAG AAC
Pro Gln Val Tyr Thr Leu Pro Pro Ser Arg Glu Glu Met Thr Lys Asn>

   1830        1840        1850        1860        1870
*     *     *     *     *     *     *     *     *     *
CAG GTC AGC CTG ACC TGC CTG GTC AAA GGC TTC TAT CCC AGC GAC ATC
Gln Val Ser Leu Thr Cys Leu Val Lys Gly Phe Tyr Pro Ser Asp Ile>

      1880        1890        1900        1910        1920
 *     *     *     *     *     *     *     *     *     *
GCC GTG GAG TGG GAG AGC AAT GGG CAG CCG GAG AAC AAC TAC AAG ACC
Ala Val Glu Trp Glu Ser Asn Gly Gln Pro Glu Asn Asn Tyr Lys Thr>

         1930        1940        1950        1960
    *     *     *     *     *     *     *     *     *
ACG CCT CCC GTG CTG GAC TCC GAC GGC TCC TTC TTC CTC TAT AGC AAG
Thr Pro Pro Val Leu Asp Ser Asp Gly Ser Phe Phe Leu Tyr Ser Lys>

1970        1980        1990        2000        2010
  *     *     *     *     *     *     *     *     *     *
CTC ACC GTG GAC AAG AGC AGG TGG CAG CAG GGG AAC GTC TTC TCA TGC
Leu Thr Val Asp Lys Ser Arg Trp Gln Gln Gly Asn Val Phe Ser Cys>

  2020        2030        2040        2050        2060
     *     *     *     *     *     *     *     *     *
TCC GTG ATG CAT GAG GCT CTG CAC AAC CAC TAC ACG CAG AAG AGC CTC
Ser Val Met His Glu Ala Leu His Asn His Tyr Thr Gln Lys Ser Leu>

   2070        2080
*     *     *     *     *
TCC CTG TCT CCG GGT AAA TGA
Ser Leu Ser Pro Gly Lys ***>
```

Fig.22A.

```
             10          20          30          40
      *       *       *       *       *       *       *       *
ATG GTG AAG CCA TCA TTA CCA TTC ACA TCC CTC TTA TTC CTG CAG CTG
Met Val Lys Pro Ser Leu Pro Phe Thr Ser Leu Leu Phe Leu Gln Leu>

50          60          70          80          90
 *       *       *       *       *       *       *       *       *       *
CCC CTG CTG GGA GTG GGG CTG AAC ACG ACA ATT CTG ACG CCC AAT GGG
Pro Leu Leu Gly Val Gly Leu Asn Thr Thr Ile Leu Thr Pro Asn Gly>

  100         110         120         130         140
   *       *       *       *       *       *       *       *       *
AAT GAA GAC ACC ACA GCT GAT TTC TTC CTG ACC ACT ATG CCC ACT GAC
Asn Glu Asp Thr Thr Ala Asp Phe Phe Leu Thr Thr Met Pro Thr Asp>

     150         160         170         180         190
 *       *       *       *       *       *       *       *       *       *
TCC CTC AGT GTT TCC ACT CTG CCC CTC CCA GAG GTT CAG TGT TTT GTG
Ser Leu Ser Val Ser Thr Leu Pro Leu Pro Glu Val Gln Cys Phe Val>

        200         210         220         230         240
   *       *       *       *       *       *       *       *       *       *
TTC AAT GTC GAG TAC ATG AAT TGC ACT TGG AAC AGC AGC TCT GAG CCC
Phe Asn Val Glu Tyr Met Asn Cys Thr Trp Asn Ser Ser Ser Glu Pro>

           250         260         270         280
        *       *       *       *       *       *       *       *       *
CAG CCT ACC AAC CTC ACT CTG CAT TAT TGG TAC AAG AAC TCG GAT AAT
Gln Pro Thr Asn Leu Thr Leu His Tyr Trp Tyr Lys Asn Ser Asp Asn>

290         300         310         320         330
 *       *       *       *       *       *       *       *       *       *
GAT AAA GTC CAG AAG TGC AGC CAC TAT CTA TTC TCT GAA GAA ATC ACT
Asp Lys Val Gln Lys Cys Ser His Tyr Leu Phe Ser Glu Glu Ile Thr>

  340         350         360         370         380
     *       *       *       *       *       *       *       *       *
TCT GGC TGT CAG TTG CAA AAA AAG GAG ATC CAC CTC TAC CAA ACA TTT
Ser Gly Cys Gln Leu Gln Lys Lys Glu Ile His Leu Tyr Gln Thr Phe>

     390         400         410         420         430
 *       *       *       *       *       *       *       *       *       *
GTT GTT CAG CTC CAG GAC CCA CGG GAA CCC AGG AGA CAG GCC ACA CAG
Val Val Gln Leu Gln Asp Pro Arg Glu Pro Arg Arg Gln Ala Thr Gln>

        440         450         460         470         480
   *       *       *       *       *       *       *       *       *       *
ATG CTA AAA CTG CAG AAT CTG GTG ATC CCC TGG GCT CCA GAG AAC CTA
Met Leu Lys Leu Gln Asn Leu Val Ile Pro Trp Ala Pro Glu Asn Leu>

           490         500         510         520
      *       *       *       *       *       *       *       *       *
ACA CTT CAC AAA CTG AGT GAA TCC CAG CTA GAA CTG AAC TGG AAC AAC
Thr Leu His Lys Leu Ser Glu Ser Gln Leu Glu Leu Asn Trp Asn Asn>

530         540         550         560         570
 *       *       *       *       *       *       *       *       *       *
AGA TTC TTG AAC CAC TGT TTG GAG CAC TTG GTG CAG TAC CGG ACT GAC
Arg Phe Leu Asn His Cys Leu Glu His Leu Val Gln Tyr Arg Thr Asp>
```

Fig.22B.

```
  580         590         600         610         620
   *     *     *     *     *     *     *     *     *
TGG GAC CAC AGC TGG ACT GAA CAA TCA GTG GAT TAT AGA CAT AAG TTC
Trp Asp His Ser Trp Thr Glu Gln Ser Val Asp Tyr Arg His Lys Phe>

    630         640         650         660         670
 *     *     *     *     *     *     *     *     *     *
TCC TTG CCT AGT GTG GAT GGG CAG AAA CGC TAC ACG TTT CGT GTT CGG
Ser Leu Pro Ser Val Asp Gly Gln Lys Arg Tyr Thr Phe Arg Val Arg>

      680         690         700         710         720
  *     *     *     *     *     *     *     *     *     *
AGC CGC TTT AAC CCA CTC TGT GGA AGT GCT CAG CAT TGG AGT GAA TGG
Ser Arg Phe Asn Pro Leu Cys Gly Ser Ala Gln His Trp Ser Glu Trp>

        730         740         750         760
   *     *     *     *     *     *     *     *     *
AGC CAC CCA ATC CAC TGG GGG AGC AAT ACT TCA AAA GAG AAC GGG AAC
Ser His Pro Ile His Trp Gly Ser Asn Thr Ser Lys Glu Asn Gly Asn>

770         780         790         800         810
 *     *     *     *     *     *     *     *     *     *
ATG AAG GTC CTG CAG GAG CCC ACC TGC GTC TCC GAC TAC ATG AGC ATC
Met Lys Val Leu Gln Glu Pro Thr Cys Val Ser Asp Tyr Met Ser Ile>

  820         830         840         850         860
   *     *     *     *     *     *     *     *     *
TCT ACT TGC GAG TGG AAG ATG AAT GGT CCC ACC AAT TGC AGC ACC GAG
Ser Thr Cys Glu Trp Lys Met Asn Gly Pro Thr Asn Cys Ser Thr Glu>

    870         880         890         900         910
 *     *     *     *     *     *     *     *     *     *
CTC CGC CTG TTG TAC CAG CTG GTT TTT CTG CTC TCC GAA GCC CAC ACG
Leu Arg Leu Leu Tyr Gln Leu Val Phe Leu Leu Ser Glu Ala His Thr>

      920         930         940         950         960
  *     *     *     *     *     *     *     *     *     *
TGT ATC CCT GAG AAC AAC GGA GGC GCG GGG TGC GTG TGC CAC CTG CTC
Cys Ile Pro Glu Asn Asn Gly Gly Ala Gly Cys Val Cys His Leu Leu>

        970         980         990        1000
   *     *     *     *     *     *     *     *     *
ATG GAT GAC GTG GTC AGT GCG GAT AAC TAT ACA CTG GAC CTG TGG GCT
Met Asp Asp Val Val Ser Ala Asp Asn Tyr Thr Leu Asp Leu Trp Ala>

1010        1020        1030        1040        1050
 *     *     *     *     *     *     *     *     *     *
GGG CAG CAG CTG CTG TGG AAG GGC TCC TTC AAG CCC AGC GAG CAT GTG
Gly Gln Gln Leu Leu Trp Lys Gly Ser Phe Lys Pro Ser Glu His Val>

  1060        1070        1080        1090        1100
   *     *     *     *     *     *     *     *     *
AAA CCC AGG GCC CCA GGA AAC CTG ACA GTT CAC ACC AAT GTC TCC GAC
Lys Pro Arg Ala Pro Gly Asn Leu Thr Val His Thr Asn Val Ser Asp>

    1110        1120        1130        1140        1150
 *     *     *     *     *     *     *     *     *     *
ACT CTG CTG CTG ACC TGG AGC AAC CCG TAT CCC CCT GAC AAT TAC CTG
Thr Leu Leu Leu Thr Trp Ser Asn Pro Tyr Pro Pro Asp Asn Tyr Leu>

      1160        1170        1180        1190        1200
  *     *     *     *     *     *     *     *     *     *
```

Figure 22C:
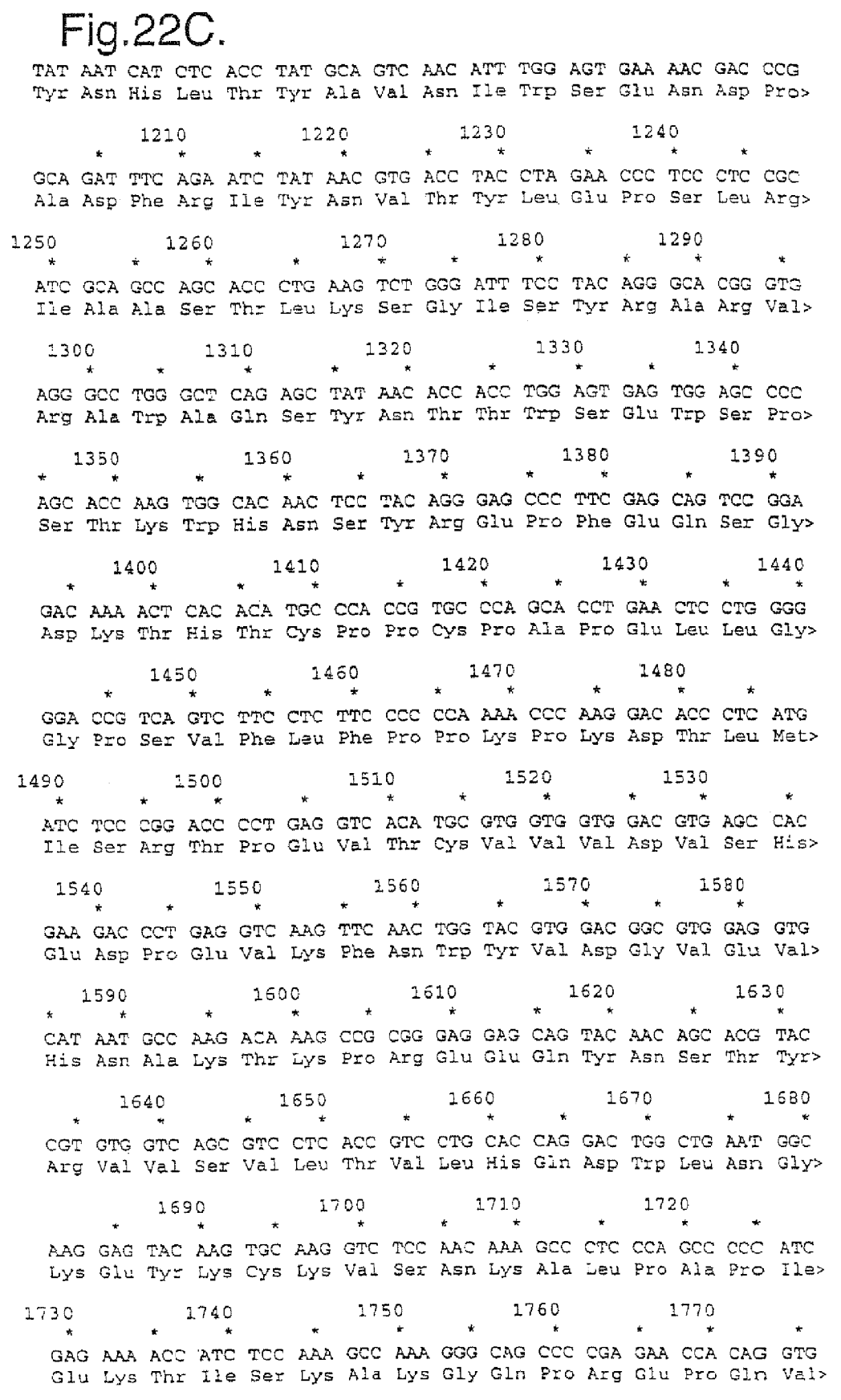

```
TAT AAT CAT CTC ACC TAT GCA GTC AAC ATT TGG AGT GAA AAC GAC CCG
Tyr Asn His Leu Thr Tyr Ala Val Asn Ile Trp Ser Glu Asn Asp Pro>

        1210      1220      1230      1240
GCA GAT TTC AGA ATC TAT AAC GTG ACC TAC CTA GAA CCC TCC CTC CGC
Ala Asp Phe Arg Ile Tyr Asn Val Thr Tyr Leu Glu Pro Ser Leu Arg>

1250      1260      1270      1280      1290
ATC GCA GCC AGC ACC CTG AAG TCT GGG ATT TCC TAC AGG GCA CGG GTG
Ile Ala Ala Ser Thr Leu Lys Ser Gly Ile Ser Tyr Arg Ala Arg Val>

1300      1310      1320      1330      1340
AGG GCC TGG GCT CAG AGC TAT AAC ACC ACC TGG AGT GAG TGG AGC CCC
Arg Ala Trp Ala Gln Ser Tyr Asn Thr Thr Trp Ser Glu Trp Ser Pro>

1350      1360      1370      1380      1390
AGC ACC AAG TGG CAC AAC TCC TAC AGG GAG CCC TTC GAG CAG TCC GGA
Ser Thr Lys Trp His Asn Ser Tyr Arg Glu Pro Phe Glu Gln Ser Gly>

1400      1410      1420      1430      1440
GAC AAA ACT CAC ACA TGC CCA CCG TGC CCA GCA CCT GAA CTC CTG GGG
Asp Lys Thr His Thr Cys Pro Pro Cys Pro Ala Pro Glu Leu Leu Gly>

1450      1460      1470      1480
GGA CCG TCA GTC TTC CTC TTC CCC CCA AAA CCC AAG GAC ACC CTC ATG
Gly Pro Ser Val Phe Leu Phe Pro Pro Lys Pro Lys Asp Thr Leu Met>

1490      1500      1510      1520      1530
ATC TCC CGG ACC CCT GAG GTC ACA TGC GTG GTG GTG GAC GTG AGC CAC
Ile Ser Arg Thr Pro Glu Val Thr Cys Val Val Val Asp Val Ser His>

1540      1550      1560      1570      1580
GAA GAC CCT GAG GTC AAG TTC AAC TGG TAC GTG GAC GGC GTG GAG GTG
Glu Asp Pro Glu Val Lys Phe Asn Trp Tyr Val Asp Gly Val Glu Val>

1590      1600      1610      1620      1630
CAT AAT GCC AAG ACA AAG CCG CGG GAG GAG CAG TAC AAC AGC ACG TAC
His Asn Ala Lys Thr Lys Pro Arg Glu Glu Gln Tyr Asn Ser Thr Tyr>

1640      1650      1660      1670      1680
CGT GTG GTC AGC GTC CTC ACC GTC CTG CAC CAG GAC TGG CTG AAT GGC
Arg Val Val Ser Val Leu Thr Val Leu His Gln Asp Trp Leu Asn Gly>

1690      1700      1710      1720
AAG GAG TAC AAG TGC AAG GTC TCC AAC AAA GCC CTC CCA GCC CCC ATC
Lys Glu Tyr Lys Cys Lys Val Ser Asn Lys Ala Leu Pro Ala Pro Ile>

1730      1740      1750      1760      1770
GAG AAA ACC ATC TCC AAA GCC AAA GGG CAG CCC CGA GAA CCA CAG GTG
Glu Lys Thr Ile Ser Lys Ala Lys Gly Gln Pro Arg Glu Pro Gln Val>
```

Fig.22D.

```
 1780         1790         1800          1810         1820
   *     *      *      *     *      *      *      *      *
TAC ACC CTG CCC CCA TCC CGG GAT GAG CTG ACC AAG AAC CAG GTC AGC
Tyr Thr Leu Pro Pro Ser Arg Asp Glu Leu Thr Lys Asn Gln Val Ser>

   1830         1840         1850         1860          1870
*      *      *      *     *      *      *      *      *      *
CTG ACC TGC CTG GTC AAA GGC TTC TAT CCC AGC GAC ATC GCC GTG GAG
Leu Thr Cys Leu Val Lys Gly Phe Tyr Pro Ser Asp Ile Ala Val Glu>

      1880         1890          1900         1910          1920
  *      *      *      *     *      *      *      *      *      *
TGG GAG AGC AAT GGG CAG CCG GAG AAC AAC TAC AAG ACC ACG CCT CCC
Trp Glu Ser Asn Gly Gln Pro Glu Asn Asn Tyr Lys Thr Thr Pro Pro>

         1930         1940         1950          1960
      *      *      *      *     *      *      *      *      *
GTG CTG GAC TCC GAC GGC TCC TTC TTC CTC TAT AGC AAG CTC ACC GTG
Val Leu Asp Ser Asp Gly Ser Phe Phe Leu Tyr Ser Lys Leu Thr Val>

1970         1980          1990         2000         2010
  *      *      *      *     *      *      *      *      *      *
GAC AAG AGC AGG TGG CAG CAG GGG AAC GTC TTC TCA TGC TCC GTG ATG
Asp Lys Ser Arg Trp Gln Gln Gly Asn Val Phe Ser Cys Ser Val Met>

 2020         2030          2040         2050          2060
   *     *      *      *     *      *      *      *      *
CAT GAG GCT CTG CAC AAC CAC TAC ACG CAG AAG AGC CTC TCC CTG TCT
His Glu Ala Leu His Asn His Tyr Thr Gln Lys Ser Leu Ser Leu Ser>

   2070
*      *      *
CCG GGT AAA TGA
Pro Gly Lys ***>
```

Fig.23A.

```
          10          20          30          40
   *      *     *      *     *     *     *     *     *
ATG GTG AAG CCA TCA TTA CCA TTC ACA TCC CTC TTA TTC CTG CAG CTG
Met Val Lys Pro Ser Leu Pro Phe Thr Ser Leu Leu Phe Leu Gln Leu>

50          60          70          80          90
*     *     *     *     *     *     *     *     *     *
CCC CTG CTG GGA GTG GGG CTG AAC ACG ACA ATT CTG ACG CCC AAT GGG
Pro Leu Leu Gly Val Gly Leu Asn Thr Thr Ile Leu Thr Pro Asn Gly>

  100         110         120         130         140
   *     *     *     *     *     *     *     *     *
AAT GAA GAC ACC ACA GCT GAT TTC TTC CTG ACC ACT ATG CCC ACT GAC
Asn Glu Asp Thr Thr Ala Asp Phe Phe Leu Thr Thr Met Pro Thr Asp>

     150         160         170         180         190
*     *     *     *     *     *     *     *     *     *
TCC CTC AGT GTT TCC ACT CTG CCC CTC CCA GAG GTT CAG TGT TTT GTG
Ser Leu Ser Val Ser Thr Leu Pro Leu Pro Glu Val Gln Cys Phe Val>

        200         210         220         230         240
   *     *     *     *     *     *     *     *     *     *
TTC AAT GTC GAG TAC ATG AAT TGC ACT TGG AAC AGC AGC TCT GAG CCC
Phe Asn Val Glu Tyr Met Asn Cys Thr Trp Asn Ser Ser Ser Glu Pro>

          250         260         270         280
      *     *     *     *     *     *     *     *     *
CAG CCT ACC AAC CTC ACT CTG CAT TAT TGG TAC AAG AAC TCG GAT AAT
Gln Pro Thr Asn Leu Thr Leu His Tyr Trp Tyr Lys Asn Ser Asp Asn>

290         300         310         320         330
 *     *     *     *     *     *     *     *     *     *
GAT AAA GTC CAG AAG TGC AGC CAC TAT CTA TTC TCT GAA GAA ATC ACT
Asp Lys Val Gln Lys Cys Ser His Tyr Leu Phe Ser Glu Glu Ile Thr>

 340         350         360         370         380
   *     *     *     *     *     *     *     *     *
TCT GGC TGT CAG TTG CAA AAA AAG GAG ATC CAC CTC TAC CAA ACA TTT
Ser Gly Cys Gln Leu Gln Lys Lys Glu Ile His Leu Tyr Gln Thr Phe>

     390         400         410         420         430
*     *     *     *     *     *     *     *     *     *
GTT GTT CAG CTC CAG GAC CCA CGG GAA CCC AGG AGA CAG GCC ACA CAG
Val Val Gln Leu Gln Asp Pro Arg Glu Pro Arg Arg Gln Ala Thr Gln>

        440         450         460         470         480
   *     *     *     *     *     *     *     *     *     *
ATG CTA AAA CTG CAG AAT CTG GTG ATC CCC TGG GCT CCA GAG AAC CTA
Met Leu Lys Leu Gln Asn Leu Val Ile Pro Trp Ala Pro Glu Asn Leu>

          490         500         510         520
      *     *     *     *     *     *     *     *     *
ACA CTT CAC AAA CTG AGT GAA TCC CAG CTA GAA CTG AAC TGG AAC AAC
Thr Leu His Lys Leu Ser Glu Ser Gln Leu Glu Leu Asn Trp Asn Asn>

530         540         550         560         570
 *     *     *     *     *     *     *     *     *     *
AGA TTC TTG AAC CAC TGT TTG GAG CAC TTG GTG CAG TAC CGG ACT GAC
Arg Phe Leu Asn His Cys Leu Glu His Leu Val Gln Tyr Arg Thr Asp>
```

Fig.23B.

```
  580         590         600          610         620
   *     *     *     *     *     *     *     *     *
TGG GAC CAC AGC TGG ACT GAA CAA TCA GTG GAT TAT AGA CAT AAG TTC
Trp Asp His Ser Trp Thr Glu Gln Ser Val Asp Tyr Arg His Lys Phe>

    630         640         650         660         670
 *     *     *     *     *     *     *     *     *     *
TCC TTG CCT AGT GTG GAT GGG CAG AAA CGC TAC ACG TTT CGT GTT CGG
Ser Leu Pro Ser Val Asp Gly Gln Lys Arg Tyr Thr Phe Arg Val Arg>

       680         690         700         710         720
   *     *     *     *     *     *     *     *     *     *
AGC CGC TTT AAC CCA CTC TGT GGA AGT GCT CAG CAT TGG AGT GAA TGG
Ser Arg Phe Asn Pro Leu Cys Gly Ser Ala Gln His Trp Ser Glu Trp>

          730         740         750         760
     *     *     *     *     *     *     *     *     *
AGC CAC CCA ATC CAC TGG GGG AGC AAT ACT TCA AAA GAG AAC GCG TCG
Ser His Pro Ile His Trp Gly Ser Asn Thr Ser Lys Glu Asn Ala Ser>

770         780         790         800         810
 *     *     *     *     *     *     *     *     *     *
TCT GGG AAC ATG AAG GTC CTG CAG GAG CCC ACC TGC GTC TCC GAC TAC
Ser Gly Asn Met Lys Val Leu Gln Glu Pro Thr Cys Val Ser Asp Tyr>

  820         830         840         850         860
   *     *     *     *     *     *     *     *     *
ATG AGC ATC TCT ACT TGC GAG TGG AAG ATG AAT GGT CCC ACC AAT TGC
Met Ser Ile Ser Thr Cys Glu Trp Lys Met Asn Gly Pro Thr Asn Cys>

    870         880         890         900         910
 *     *     *     *     *     *     *     *     *     *
AGC ACC GAG CTC CGC CTG TTG TAC CAG CTG GTT TTT CTG CTC TCC GAA
Ser Thr Glu Leu Arg Leu Leu Tyr Gln Leu Val Phe Leu Leu Ser Glu>

       920         930         940         950         960
   *     *     *     *     *     *     *     *     *     *
GCC CAC ACG TGT ATC CCT GAG AAC AAC GGA GGC GCG GGG TGC GTG TGC
Ala His Thr Cys Ile Pro Glu Asn Asn Gly Gly Ala Gly Cys Val Cys>

          970         980         990        1000
     *     *     *     *     *     *     *     *     *
CAC CTG CTC ATG GAT GAC GTG GTC AGT GCG GAT AAC TAT ACA CTG GAC
His Leu Leu Met Asp Asp Val Val Ser Ala Asp Asn Tyr Thr Leu Asp>

1010        1020        1030        1040        1050
 *     *     *     *     *     *     *     *     *     *
CTG TGG GCT GGG CAG CAG CTG CTG TGG AAG GGC TCC TTC AAG CCC AGC
Leu Trp Ala Gly Gln Gln Leu Leu Trp Lys Gly Ser Phe Lys Pro Ser>

  1060        1070        1080        1090        1100
     *     *     *     *     *     *     *     *     *
GAG CAT GTG AAA CCC AGG GCC CCA GGA AAC CTG ACA GTT CAC ACC AAT
Glu His Val Lys Pro Arg Ala Pro Gly Asn Leu Thr Val His Thr Asn>

    1110        1120        1130        1140        1150
 *     *     *     *     *     *     *     *     *     *
GTC TCC GAC ACT CTG CTG CTG ACC TGG AGC AAC CCG TAT CCC CCT GAC
Val Ser Asp Thr Leu Leu Leu Thr Trp Ser Asn Pro Tyr Pro Pro Asp>

       1160        1170        1180        1190        1200
   *     *     *     *     *     *     *     *     *     *
```

```
AAT TAC CTG TAT AAT CAT CTC ACC TAT GCA GTC AAC ATT TGG AGT GAA
Asn Tyr Leu Tyr Asn His Leu Thr Tyr Ala Val Asn Ile Trp Ser Glu>

        1210        1220        1230        1240
  *      *     *     *     *     *     *     *     *

AAC GAC CCG GCA GAT TTC AGA ATC TAT AAC GTG ACC TAC CTA GAA CCC
Asn Asp Pro Ala Asp Phe Arg Ile Tyr Asn Val Thr Tyr Leu Glu Pro>

1250        1260        1270        1280        1290
  *     *     *     *     *     *     *     *     *     *

TCC CTC CGC ATC GCA GCC AGC ACC CTG AAG TCT GGG ATT TCC TAC AGG
Ser Leu Arg Ile Ala Ala Ser Thr Leu Lys Ser Gly Ile Ser Tyr Arg>

  1300        1310        1320        1330        1340
    *     *     *     *     *     *     *     *     *

GCA CGG GTG AGG GCC TGG GCT CAG AGC TAT AAC ACC ACC TGG AGT GAG
Ala Arg Val Arg Ala Trp Ala Gln Ser Tyr Asn Thr Thr Trp Ser Glu>

    1350        1360        1370        1380        1390
 *     *     *     *     *     *     *     *     *     *

TGG AGC CCC AGC ACC AAG TGG CAC AAC TCC TAC AGG GAG CCC TTC GAG
Trp Ser Pro Ser Thr Lys Trp His Asn Ser Tyr Arg Glu Pro Phe Glu>

      1400        1410        1420        1430        1440
  *     *     *     *     *     *     *     *     *     *

CAG TCC GGA GAC AAA ACT CAC ACA TGC CCA CCG TGC CCA GCA CCT GAA
Gln Ser Gly Asp Lys Thr His Thr Cys Pro Pro Cys Pro Ala Pro Glu>

        1450        1460        1470        1480
    *     *     *     *     *     *     *     *     *

CTC CTG GGG GGA CCG TCA GTC TTC CTC TTC CCC CCA AAA CCC AAG GAC
Leu Leu Gly Gly Pro Ser Val Phe Leu Phe Pro Pro Lys Pro Lys Asp>

1490        1500        1510        1520        1530
  *     *     *     *     *     *     *     *     *     *

ACC CTC ATG ATC TCC CGG ACC CCT GAG GTC ACA TGC GTG GTG GTG GAC
Thr Leu Met Ile Ser Arg Thr Pro Glu Val Thr Cys Val Val Val Asp>

  1540        1550        1560        1570        1580
    *     *     *     *     *     *     *     *     *

GTG AGC CAC GAA GAC CCT GAG GTC AAG TTC AAC TGG TAC GTG GAC GGC
Val Ser His Glu Asp Pro Glu Val Lys Phe Asn Trp Tyr Val Asp Gly>

    1590        1600        1610        1620        1630
 *     *     *     *     *     *     *     *     *     *

GTG GAG GTG CAT AAT GCC AAG ACA AAG CCG CGG GAG GAG CAG TAC AAC
Val Glu Val His Asn Ala Lys Thr Lys Pro Arg Glu Glu Gln Tyr Asn>

      1640        1650        1660        1670        1680
  *     *     *     *     *     *     *     *     *     *

AGC ACG TAC CGT GTG GTC AGC GTC CTC ACC GTC CTG CAC CAG GAC TGG
Ser Thr Tyr Arg Val Val Ser Val Leu Thr Val Leu His Gln Asp Trp>

        1690        1700        1710        1720
    *     *     *     *     *     *     *     *     *

CTG AAT GGC AAG GAG TAC AAG TGC AAG GTC TCC AAC AAA GCC CTC CCA
Leu Asn Gly Lys Glu Tyr Lys Cys Lys Val Ser Asn Lys Ala Leu Pro>

1730        1740        1750        1760        1770
  *     *     *     *     *     *     *     *     *     *

GCC CCC ATC GAG AAA ACC ATC TCC AAA GCC AAA GGG CAG CCC CGA GAA
Ala Pro Ile Glu Lys Thr Ile Ser Lys Ala Lys Gly Gln Pro Arg Glu>
```

Fig.23D.

```
 1780        1790        1800        1810        1820
    *     *     *     *     *     *     *     *     *
CCA CAG GTG TAC ACC CTG CCC CCA TCC CGG GAT GAG CTG ACC AAG AAC
Pro Gln Val Tyr Thr Leu Pro Pro Ser Arg Asp Glu Leu Thr Lys Asn>

   1830        1840        1850        1860        1870
*     *     *     *     *     *     *     *     *     *
CAG GTC AGC CTG ACC TGC CTG GTC AAA GGC TTC TAT CCC AGC GAC ATC
Gln Val Ser Leu Thr Cys Leu Val Lys Gly Phe Tyr Pro Ser Asp Ile>

      1880        1890        1900        1910        1920
  *     *     *     *     *     *     *     *     *     *
GCC GTG GAG TGG GAG AGC AAT GGG CAG CCG GAG AAC AAC TAC AAG ACC
Ala Val Glu Trp Glu Ser Asn Gly Gln Pro Glu Asn Asn Tyr Lys Thr>

         1930        1940        1950        1960
     *     *     *     *     *     *     *     *     *
ACG CCT CCC GTG CTG GAC TCC GAC GGC TCC TTC TTC CTC TAT AGC AAG
Thr Pro Pro Val Leu Asp Ser Asp Gly Ser Phe Phe Leu Tyr Ser Lys>

1970        1980        1990        2000        2010
  *     *     *     *     *     *     *     *     *     *
CTC ACC GTG GAC AAG AGC AGG TGG CAG CAG GGG AAC GTC TTC TCA TGC
Leu Thr Val Asp Lys Ser Arg Trp Gln Gln Gly Asn Val Phe Ser Cys>

 2020        2030        2040        2050        2060
    *     *     *     *     *     *     *     *     *
TCC GTG ATG CAT GAG GCT CTG CAC AAC CAC TAC ACG CAG AAG AGC CTC
Ser Val Met His Glu Ala Leu His Asn His Tyr Thr Gln Lys Ser Leu>

   2070        2080
*     *     *     *     *
TCC CTG TCT CCG GGT AAA TGA
Ser Leu Ser Pro Gly Lys ***>
```

Fig.24A.

```
          10        20        30        40
    *     *     *     *     *     *     *     *
ATG GTG GCC GTC GGC TGC GCG CTG CTG GCT GCC CTG CTG GCC GCG CCG
Met Val Ala Val Gly Cys Ala Leu Leu Ala Ala Leu Leu Ala Ala Pro>

50        60        70        80        90
 *     *     *     *     *     *     *     *     *     *
GGA GCG GCG CTG GCC CCA AGG CGC TGC CCT GCG CAG GAG GTG GCA AGA
Gly Ala Ala Leu Ala Pro Arg Arg Cys Pro Ala Gln Glu Val Ala Arg>

  100       110       120       130       140
    *     *     *     *     *     *     *     *     *
GGC GTG CTG ACC AGT CTG CCA GGA GAC AGC GTG ACT CTG ACC TGC CCG
Gly Val Leu Thr Ser Leu Pro Gly Asp Ser Val Thr Leu Thr Cys Pro>

    150       160       170       180       190
 *     *     *     *     *     *     *     *     *     *
GGG GTA GAG CCG GAA GAC AAT GCC ACT GTT CAC TGG GTG CTC AGG AAG
Gly Val Glu Pro Glu Asp Asn Ala Thr Val His Trp Val Leu Arg Lys>

      200       210       220       230       240
 *     *     *     *     *     *     *     *     *     *
CCG GCT GCA GGC TCC CAC CCC AGC AGA TGG GCT GGC ATG GGA AGG AGG
Pro Ala Ala Gly Ser His Pro Ser Arg Trp Ala Gly Met Gly Arg Arg>

        250       260       270       280
    *     *     *     *     *     *     *     *     *
CTG CTG CTG AGG TCG GTG CAG CTC CAC GAC TCT GGA AAC TAT TCA TGC
Leu Leu Leu Arg Ser Val Gln Leu His Asp Ser Gly Asn Tyr Ser Cys>

290       300       310       320       330
 *     *     *     *     *     *     *     *     *     *
TAC CGG GCC GGC CGC CCA GCT GGG ACT GTG CAC TTG CTG GTG GAT GTT
Tyr Arg Ala Gly Arg Pro Ala Gly Thr Val His Leu Leu Val Asp Val>

  340       350       360       370       380
    *     *     *     *     *     *     *     *     *
CCC CCC GAG GAG CCC CAG CTC TCC TGC TTC CGG AAG AGC CCC CTC AGC
Pro Pro Glu Glu Pro Gln Leu Ser Cys Phe Arg Lys Ser Pro Leu Ser>

    390       400       410       420       430
 *     *     *     *     *     *     *     *     *     *
AAT GTT GTT TGT GAG TGG GGT CCT CGG AGC ACC CCA TCC CTG ACG ACA
Asn Val Val Cys Glu Trp Gly Pro Arg Ser Thr Pro Ser Leu Thr Thr>

      440       450       460       470       480
 *     *     *     *     *     *     *     *     *     *
AAG GCT GTG CTC TTG GTG AGG AAG TTT CAG AAC AGT CCG GCC GAA GAC
Lys Ala Val Leu Leu Val Arg Lys Phe Gln Asn Ser Pro Ala Glu Asp>

        490       500       510       520
    *     *     *     *     *     *     *     *     *
TTC CAG GAG CCG TGC CAG TAT TCC CAG GAG TCC CAG AAG TTC TCC TGC
Phe Gln Glu Pro Cys Gln Tyr Ser Gln Glu Ser Gln Lys Phe Ser Cys>

530       540       550       560       570
 *     *     *     *     *     *     *     *     *     *
CAG TTA GCA GTC CCG GAG GGA GAC AGC TCT TTC TAC ATA GTG TCC ATG
Gln Leu Ala Val Pro Glu Gly Asp Ser Ser Phe Tyr Ile Val Ser Met>
```

Fig.24B.

```
 580         590         600          610         620
   *     *     *     *     *     *     *     *     *
TGC GTC GCC AGT AGT GTC GGG AGC AAG TTC AGC AAA ACT CAA ACC TTT
Cys Val Ala Ser Ser Val Gly Ser Lys Phe Ser Lys Thr Gln Thr Phe>

    630         640         650          660          670
 *     *     *     *     *     *     *     *     *     *
CAG GGT TGT GGA ATC TTG CAG CCT GAT CCG CCT GCC AAC ATC ACA GTC
Gln Gly Cys Gly Ile Leu Gln Pro Asp Pro Pro Ala Asn Ile Thr Val>

      680         690          700          710         720
  *     *     *     *     *     *     *     *     *     *
ACT GCC GTG GCC AGA AAC CCC CGC TGG CTC AGT GTC ACC TGG CAA GAC
Thr Ala Val Ala Arg Asn Pro Arg Trp Leu Ser Val Thr Trp Gln Asp>

         730         740         750          760
    *     *     *     *     *     *     *     *     *
CCC CAC TCC TGG AAC TCA TCT TTC TAC AGA CTA CGG TTT GAG CTC AGA
Pro His Ser Trp Asn Ser Ser Phe Tyr Arg Leu Arg Phe Glu Leu Arg>

770         780          790         800         810
 *     *     *     *     *     *     *     *     *     *
TAT CGG GCT GAA CGG TCA AAG ACA TTC ACA ACA TGG ATG GTC AAG GAC
Tyr Arg Ala Glu Arg Ser Lys Thr Phe Thr Thr Trp Met Val Lys Asp>

  820         830         840          850         860
   *     *     *     *     *     *     *     *     *
CTC CAG CAT CAC TGT GTC ATC CAC GAC GCC TGG AGC GGC CTG AGG CAC
Leu Gln His His Cys Val Ile His Asp Ala Trp Ser Gly Leu Arg His>

    870         880         890          900          910
 *     *     *     *     *     *     *     *     *     *
GTG GTG CAG CTT CGT GCC CAG GAG GAG TTC GGG CAA GGC GAG TGG AGC
Val Val Gln Leu Arg Ala Gln Glu Glu Phe Gly Gln Gly Glu Trp Ser>

       920         930          940         950          960
  *     *     *     *     *     *     *     *     *     *
GAG TGG AGC CCG GAG GCC ATG GGC ACG CCT TGG ACA GAA TCC AGG AGT
Glu Trp Ser Pro Glu Ala Met Gly Thr Pro Trp Thr Glu Ser Arg Ser>

         970         980          990         1000
    *     *     *     *     *     *     *     *     *
CCT CCA GCT GAG AAC GAG GTG TCC ACC CCC ATG ACC GGT GGC GCG CCT
Pro Pro Ala Glu Asn Glu Val Ser Thr Pro Met Thr Gly Gly Ala Pro>

1010        1020         1030         1040        1050
 *     *     *     *     *     *     *     *     *     *
TCA GGT GCT CAG CTG GAA CTT CTA GAC CCA TGT GGT TAT ATC AGT CCT
Ser Gly Ala Gln Leu Glu Leu Leu Asp Pro Cys Gly Tyr Ile Ser Pro>

 1060        1070         1080         1090        1100
    *     *     *     *     *     *     *     *     *
GAA TCT CCA GTT GTA CAA CTT CAT TCT AAT TTC ACT GCA GTT TGT GTG
Glu Ser Pro Val Val Gln Leu His Ser Asn Phe Thr Ala Val Cys Val>

    1110         1120        1130         1140         1150
 *     *     *     *     *     *     *     *     *     *
CTA AAG GAA AAA TGT ATG GAT TAT TTT CAT GTA AAT GCT AAT TAC ATT
Leu Lys Glu Lys Cys Met Asp Tyr Phe His Val Asn Ala Asn Tyr Ile>

       1160        1170          1180        1190         1200
  *     *     *     *     *     *     *     *     *     *
```

```
GTC TGG AAA ACA AAC CAT TTT ACT ATT CCT AAG GAG CAA TAT ACT ATC
Val Trp Lys Thr Asn His Phe Thr Ile Pro Lys Glu Gln Tyr Thr Ile>

        1210        1220        1230        1240
     *     *     *     *     *     *     *     *     *
ATA AAC AGA ACA GCA TCC AGT GTC ACC TTT ACA GAT ATA GCT TCA TTA
Ile Asn Arg Thr Ala Ser Ser Val Thr Phe Thr Asp Ile Ala Ser Leu>

1250        1260        1270        1280        1290
  *     *     *     *     *     *     *     *     *     *
AAT ATT CAG CTC ACT TGC AAC ATT CTT ACA TTC GGA CAG CTT GAA CAG
Asn Ile Gln Leu Thr Cys Asn Ile Leu Thr Phe Gly Gln Leu Glu Gln>

  1300        1310        1320        1330        1340
     *     *     *     *     *     *     *     *     *
AAT GTT TAT GGA ATC ACA ATA ATT TCA GGC TTG CCT CCA GAA AAA CCT
Asn Val Tyr Gly Ile Thr Ile Ile Ser Gly Leu Pro Pro Glu Lys Pro>

    1350        1360        1370        1380        1390
  *     *     *     *     *     *     *     *     *     *
AAA AAT TTG AGT TGC ATT GTG AAC GAG GGG AAG AAA ATG AGG TGT GAG
Lys Asn Leu Ser Cys Ile Val Asn Glu Gly Lys Lys Met Arg Cys Glu>

      1400        1410        1420        1430        1440
  *     *     *     *     *     *     *     *     *     *
TGG GAT GGT GGA AGG GAA ACA CAC TTG GAG ACA AAC TTC ACT TTA AAA
Trp Asp Gly Gly Arg Glu Thr His Leu Glu Thr Asn Phe Thr Leu Lys>

        1450        1460        1470        1480
     *     *     *     *     *     *     *     *     *
TCT GAA TGG GCA ACA CAC AAG TTT GCT GAT TGC AAA GCA AAA CGT GAC
Ser Glu Trp Ala Thr His Lys Phe Ala Asp Cys Lys Ala Lys Arg Asp>

1490        1500        1510        1520        1530
  *     *     *     *     *     *     *     *     *     *
ACC CCC ACC TCA TGC ACT GTT GAT TAT TCT ACT GTG TAT TTT GTC AAC
Thr Pro Thr Ser Cys Thr Val Asp Tyr Ser Thr Val Tyr Phe Val Asn>

 1540        1550        1560        1570        1580
     *     *     *     *     *     *     *     *     *
ATT GAA GTC TGG GTA GAA GCA GAG AAT GCC CTT GGG AAG GTT ACA TCA
Ile Glu Val Trp Val Glu Ala Glu Asn Ala Leu Gly Lys Val Thr Ser>

   1590        1600        1610        1620        1630
  *     *     *     *     *     *     *     *     *     *
GAT CAT ATC AAT TTT GAT CCT GTA TAT AAA GTG AAG CCC AAT CCG CCA
Asp His Ile Asn Phe Asp Pro Val Tyr Lys Val Lys Pro Asn Pro Pro>

      1640        1650        1660        1670        1680
  *     *     *     *     *     *     *     *     *     *
CAT AAT TTA TCA GTG ATC AAC TCA GAG GAA CTG TCT AGT ATC TTA AAA
His Asn Leu Ser Val Ile Asn Ser Glu Glu Leu Ser Ser Ile Leu Lys>

        1690        1700        1710        1720
     *     *     *     *     *     *     *     *     *
TTG ACA TGG ACC AAC CCA AGT ATT AAG AGT GTT ATA ATA CTA AAA TAT
Leu Thr Trp Thr Asn Pro Ser Ile Lys Ser Val Ile Ile Leu Lys Tyr>

1730        1740        1750        1760        1770
  *     *     *     *     *     *     *     *     *     *
AAC ATT CAA TAT AGG ACC AAA GAT GCC TCA ACT TGG AGC CAG ATT CCT
Asn Ile Gln Tyr Arg Thr Lys Asp Ala Ser Thr Trp Ser Gln Ile Pro>
```

Fig.24D.

```
 1780        1790        1800        1810        1820
    *     *     *     *     *     *     *     *     *
CCT GAA GAC ACA GCA TCC ACC CGA TCT TCA TTC ACT GTC CAA GAC CTT
Pro Glu Asp Thr Ala Ser Thr Arg Ser Ser Phe Thr Val Gln Asp Leu>

   1830        1840        1850        1860        1870
 *     *     *     *     *     *     *     *     *     *
AAA CCT TTT ACA GAA TAT GTG TTT AGG ATT CGC TGT ATG AAG GAA GAT
Lys Pro Phe Thr Glu Tyr Val Phe Arg Ile Arg Cys Met Lys Glu Asp>

      1880        1890        1900        1910        1920
   *     *     *     *     *     *     *     *     *     *
GGT AAG GGA TAC TGG AGT GAC TGG AGT GAA GAA GCA AGT GGG ATC ACC
Gly Lys Gly Tyr Trp Ser Asp Trp Ser Glu Glu Ala Ser Gly Ile Thr>

         1930        1940        1950        1960
      *     *     *     *     *     *     *     *     *
TAT GAA GAT AGA CCA TCT AAA GCA CCA AGT TTC TGG TAT AAA ATA GAT
Tyr Glu Asp Arg Pro Ser Lys Ala Pro Ser Phe Trp Tyr Lys Ile Asp>

1970        1980        1990        2000        2010
  *     *     *     *     *     *     *     *     *     *
CCA TCC CAT ACT CAA GGC TAC AGA ACT GTA CAA CTC GTG TGG AAG ACA
Pro Ser His Thr Gln Gly Tyr Arg Thr Val Gln Leu Val Trp Lys Thr>

 2020        2030        2040        2050        2060
    *     *     *     *     *     *     *     *     *
TTG CCT CCT TTT GAA GCC AAT GGA AAA ATC TTG GAT TAT GAA GTG ACT
Leu Pro Pro Phe Glu Ala Asn Gly Lys Ile Leu Asp Tyr Glu Val Thr>

   2070        2080        2090        2100        2110
 *     *     *     *     *     *     *     *     *     *
CTC ACA AGA TGG AAA TCA CAT TTA CAA AAT TAC ACA GTT AAT GCC ACA
Leu Thr Arg Trp Lys Ser His Leu Gln Asn Tyr Thr Val Asn Ala Thr>

      2120        2130        2140        2150        2160
   *     *     *     *     *     *     *     *     *     *
AAA CTG ACA GTA AAT CTC ACA AAT GAT CGC TAT CTA GCA ACC CTA ACA
Lys Leu Thr Val Asn Leu Thr Asn Asp Arg Tyr Leu Ala Thr Leu Thr>

         2170        2180        2190        2200
      *     *     *     *     *     *     *     *     *
GTA AGA AAT CTT GTT GGC AAA TCA GAT GCA GCT GTT TTA ACT ATC CCT
Val Arg Asn Leu Val Gly Lys Ser Asp Ala Ala Val Leu Thr Ile Pro>

2210        2220        2230        2240        2250
  *     *     *     *     *     *     *     *     *     *
GCC TGT GAC TTT CAA GCT ACT CAC CCT GTA ATG GAT CTT AAA GCA TTC
Ala Cys Asp Phe Gln Ala Thr His Pro Val Met Asp Leu Lys Ala Phe>

 2260        2270        2280        2290        2300
    *     *     *     *     *     *     *     *     *
CCC AAA GAT AAC ATG CTT TGG GTG GAA TGG ACT ACT CCA AGG GAA TCT
Pro Lys Asp Asn Met Leu Trp Val Glu Trp Thr Thr Pro Arg Glu Ser>

   2310        2320        2330        2340        2350
 *     *     *     *     *     *     *     *     *     *
GTA AAG AAA TAT ATA CTT GAG TGG TGT GTG TTA TCA GAT AAA GCA CCC
Val Lys Lys Tyr Ile Leu Glu Trp Cys Val Leu Ser Asp Lys Ala Pro>

      2360        2370        2380        2390        2400
```

```
 *     *     *     *     *     *     *     *     *     *
TGT ATC ACA GAC TGG CAA CAA GAA GAT GGT ACC GTG CAT CGC ACC TAT
Cys Ile Thr Asp Trp Gln Gln Glu Asp Gly Thr Val His Arg Thr Tyr>

        2410        2420        2430        2440
    *     *     *     *     *     *     *     *     *
TTA AGA GGG AAC TTA GCA GAG AGC AAA TGC TAT TTG ATA ACA GTT ACT
Leu Arg Gly Asn Leu Ala Glu Ser Lys Cys Tyr Leu Ile Thr Val Thr>

2450        2460        2470        2480        2490
 *     *     *     *     *     *     *     *     *     *
CCA GTA TAT GCT GAT GGA CCA GGA AGC CCT GAA TCC ATA AAG GCA TAC
Pro Val Tyr Ala Asp Gly Pro Gly Ser Pro Glu Ser Ile Lys Ala Tyr>

 2500        2510        2520        2530        2540
    *     *     *     *     *     *     *     *     *
CTT AAA CAA GCT CCA CCT TCC AAA GGA CCT ACT GTT CGG ACA AAA AAA
Leu Lys Gln Ala Pro Pro Ser Lys Gly Pro Thr Val Arg Thr Lys Lys>

   2550        2560        2570        2580        2590
 *     *     *     *     *     *     *     *     *     *
GTA GGG AAA AAC GAA GCT GTC TTA GAG TGG GAC CAA CTT CCT GTT GAT
Val Gly Lys Asn Glu Ala Val Leu Glu Trp Asp Gln Leu Pro Val Asp>

      2600        2610        2620        2630        2640
 *     *     *     *     *     *     *     *     *     *
GTT CAG AAT GGA TTT ATC AGA AAT TAT ACT ATA TTT TAT AGA ACC ATC
Val Gln Asn Gly Phe Ile Arg Asn Tyr Thr Ile Phe Tyr Arg Thr Ile>

        2650        2660        2670        2680
    *     *     *     *     *     *     *     *     *
ATT GGA AAT GAA ACT GCT GTG AAT GTG GAT TCT TCC CAC ACA GAA TAT
Ile Gly Asn Glu Thr Ala Val Asn Val Asp Ser Ser His Thr Glu Tyr>

2690        2700        2710        2720        2730
 *     *     *     *     *     *     *     *     *     *
ACA TTG TCC TCT TTG ACT AGT GAC ACA TTG TAC ATG GTA CGA ATG GCA
Thr Leu Ser Ser Leu Thr Ser Asp Thr Leu Tyr Met Val Arg Met Ala>

 2740        2750        2760        2770        2780
    *     *     *     *     *     *     *     *     *
GCA TAC ACA GAT GAA GGT GGG AAG GAT GGT CCA GAA TTC ACT TTT ACT
Ala Tyr Thr Asp Glu Gly Gly Lys Asp Gly Pro Glu Phe Thr Phe Thr>

   2790        2800        2810        2820        2830
 *     *     *     *     *     *     *     *     *     *
ACC CCA AAG TTT GCT CAA GGA GAA ATT GAA TCC GGG GGC GAC AAA ACT
Thr Pro Lys Phe Ala Gln Gly Glu Ile Glu Ser Gly Gly Asp Lys Thr>

      2840        2850        2860        2870        2880
 *     *     *     *     *     *     *     *     *     *
CAC ACA TGC CCA CCG TGC CCA GCA CCT GAA CTC CTG GGG GGA CCG TCA
His Thr Cys Pro Pro Cys Pro Ala Pro Glu Leu Leu Gly Gly Pro Ser>

        2890        2900        2910        2920
    *     *     *     *     *     *     *     *     *
GTC TTC CTC TTC CCC CCA AAA CCC AAG GAC ACC CTC ATG ATC TCC CGG
Val Phe Leu Phe Pro Pro Lys Pro Lys Asp Thr Leu Met Ile Ser Arg>

2930        2940        2950        2960        2970
 *     *     *     *     *     *     *     *     *     *
ACC CCT GAG GTC ACA TGC GTG GTG GTG GAC GTG AGC CAC GAA GAC CCT
```

Fig.24F.

Thr Pro Glu Val Thr Cys Val Val Val Asp Val Ser His Glu Asp Pro>

2980 2990 3000 3010 3020
* * * * * * * * *
GAG GTC AAG TTC AAC TGG TAC GTG GAC GGC GTG GAG GTG CAT AAT GCC
Glu Val Lys Phe Asn Trp Tyr Val Asp Gly Val Glu Val His Asn Ala>

3030 3040 3050 3060 3070
* * * * * * * * * *
AAG ACA AAG CCG CGG GAG GAG CAG TAC AAC AGC ACG TAC CGT GTG GTC
Lys Thr Lys Pro Arg Glu Glu Gln Tyr Asn Ser Thr Tyr Arg Val Val>

3080 3090 3100 3110 3120
* * * * * * * * * *
AGC GTC CTC ACC GTC CTG CAC CAG GAC TGG CTG AAT GGC AAG GAG TAC
Ser Val Leu Thr Val Leu His Gln Asp Trp Leu Asn Gly Lys Glu Tyr>

3130 3140 3150 3160
* * * * * * * * *
AAG TGC AAG GTC TCC AAC AAA GCC CTC CCA GCC CCC ATC GAG AAA ACC
Lys Cys Lys Val Ser Asn Lys Ala Leu Pro Ala Pro Ile Glu Lys Thr>

3170 3180 3190 3200 3210
* * * * * * * * * *
ATC TCC AAA GCC AAA GGG CAG CCC CGA GAA CCA CAG GTG TAC ACC CTG
Ile Ser Lys Ala Lys Gly Gln Pro Arg Glu Pro Gln Val Tyr Thr Leu>

3220 3230 3240 3250 3260
* * * * * * * * *
CCC CCA TCC CGG GAT GAG CTG ACC AAG AAC CAG GTC AGC CTG ACC TGC
Pro Pro Ser Arg Asp Glu Leu Thr Lys Asn Gln Val Ser Leu Thr Cys>

3270 3280 3290 3300 3310
* * * * * * * * * *
CTG GTC AAA GGC TTC TAT CCC AGC GAC ATC GCC GTG GAG TGG GAG AGC
Leu Val Lys Gly Phe Tyr Pro Ser Asp Ile Ala Val Glu Trp Glu Ser>

3320 3330 3340 3350 3360
* * * * * * * * * *
AAT GGG CAG CCG GAG AAC AAC TAC AAG ACC ACG CCT CCC GTG CTG GAC
Asn Gly Gln Pro Glu Asn Asn Tyr Lys Thr Thr Pro Pro Val Leu Asp>

3370 3380 3390 3400
* * * * * * * * *
TCC GAC GGC TCC TTC TTC CTC TAC AGC AAG CTC ACC GTG GAC AAG AGC
Ser Asp Gly Ser Phe Phe Leu Tyr Ser Lys Leu Thr Val Asp Lys Ser>

3410 3420 3430 3440 3450
* * * * * * * * * *
AGG TGG CAG CAG GGG AAC GTC TTC TCA TGC TCC GTG ATG CAT GAG GCT
Arg Trp Gln Gln Gly Asn Val Phe Ser Cys Ser Val Met His Glu Ala>

3460 3470 3480 3490 3500
* * * * * * * * *
CTG CAC AAC CAC TAC ACG CAG AAG AGC CTC TCC CTG TCT CCG GGT AAA
Leu His Asn His Tyr Thr Gln Lys Ser Leu Ser Leu Ser Pro Gly Lys>

*
TGA
***>

Fig.25A.

```
          10         20         30         40
    *      *      *      *      *      *      *      *
ATG GTG GCC GTC GGC TGC GCG CTG CTG GCT GCC CTG CTG GCC GCG CCG
Met Val Ala Val Gly Cys Ala Leu Leu Ala Ala Leu Leu Ala Ala Pro>

50         60         70         80         90
 *      *      *      *      *      *      *      *      *      *
GGA GCG GCG CTG GCC CCA AGG CGC TGC CCT GCG CAG GAG GTG GCA AGA
Gly Ala Ala Leu Ala Pro Arg Arg Cys Pro Ala Gln Glu Val Ala Arg>

  100        110        120        130        140
     *      *      *      *      *      *      *      *      *
GGC GTG CTG ACC AGT CTG CCA GGA GAC AGC GTG ACT CTG ACC TGC CCG
Gly Val Leu Thr Ser Leu Pro Gly Asp Ser Val Thr Leu Thr Cys Pro>

    150        160        170        180        190
*      *      *      *      *      *      *      *      *      *
GGG GTA GAG CCG GAA GAC AAT GCC ACT GTT CAC TGG GTG CTC AGG AAG
Gly Val Glu Pro Glu Asp Asn Ala Thr Val His Trp Val Leu Arg Lys>

       200        210        220        230        240
  *      *      *      *      *      *      *      *      *      *
CCG GCT GCA GGC TCC CAC CCC AGC AGA TGG GCT GGC ATG GGA AGG AGG
Pro Ala Ala Gly Ser His Pro Ser Arg Trp Ala Gly Met Gly Arg Arg>

          250        260        270        280
     *      *      *      *      *      *      *      *      *
CTG CTG CTG AGG TCG GTG CAG CTC CAC GAC TCT GGA AAC TAT TCA TGC
Leu Leu Leu Arg Ser Val Gln Leu His Asp Ser Gly Asn Tyr Ser Cys>

290        300        310        320        330
  *      *      *      *      *      *      *      *      *      *
TAC CGG GCC GGC CGC CCA GCT GGG ACT GTG CAC TTG CTG GTG GAT GTT
Tyr Arg Ala Gly Arg Pro Ala Gly Thr Val His Leu Leu Val Asp Val>

  340        350        360        370        380
    *      *      *      *      *      *      *      *      *
CCC CCC GAG GAG CCC CAG CTC TCC TGC TTC CGG AAG AGC CCC CTC AGC
Pro Pro Glu Glu Pro Gln Leu Ser Cys Phe Arg Lys Ser Pro Leu Ser>

    390        400        410        420        430
*      *      *      *      *      *      *      *      *      *
AAT GTT GTT TGT GAG TGG GGT CCT CGG AGC ACC CCA TCC CTG ACG ACA
Asn Val Val Cys Glu Trp Gly Pro Arg Ser Thr Pro Ser Leu Thr Thr>

       440        450        460        470        480
  *      *      *      *      *      *      *      *      *      *
AAG GCT GTG CTC TTG GTG AGG AAG TTT CAG AAC AGT CCG GCC GAA GAC
Lys Ala Val Leu Leu Val Arg Lys Phe Gln Asn Ser Pro Ala Glu Asp>

          490        500        510        520
     *      *      *      *      *      *      *      *      *
TTC CAG GAG CCG TGC CAG TAT TCC CAG GAG TCC CAG AAG TTC TCC TGC
Phe Gln Glu Pro Cys Gln Tyr Ser Gln Glu Ser Gln Lys Phe Ser Cys>

530        540        550        560        570
  *      *      *      *      *      *      *      *      *      *
CAG TTA GCA GTC CCG GAG GGA GAC AGC TCT TTC TAC ATA GTG TCC ATG
Gln Leu Ala Val Pro Glu Gly Asp Ser Ser Phe Tyr Ile Val Ser Met>
```

Fig.25B.

```
 580         590         600         610         620
  *     *     *     *     *     *     *     *     *
TGC GTC GCC AGT AGT GTC GGG AGC AAG TTC AGC AAA ACT CAA ACC TTT
Cys Val Ala Ser Ser Val Gly Ser Lys Phe Ser Lys Thr Gln Thr Phe>

   630         640         650         660         670
*     *     *     *     *     *     *     *     *     *
CAG GGT TGT GGA ATC TTG CAG CCT GAT CCG CCT GCC AAC ATC ACA GTC
Gln Gly Cys Gly Ile Leu Gln Pro Asp Pro Pro Ala Asn Ile Thr Val>

      680         690         700         710         720
*     *     *     *     *     *     *     *     *     *
ACT GCC GTG GCC AGA AAC CCC CGC TGG CTC AGT GTC ACC TGG CAA GAC
Thr Ala Val Ala Arg Asn Pro Arg Trp Leu Ser Val Thr Trp Gln Asp>

         730         740         750         760
    *     *     *     *     *     *     *     *     *
CCC CAC TCC TGG AAC TCA TCT TTC TAC AGA CTA CGG TTT GAG CTC AGA
Pro His Ser Trp Asn Ser Ser Phe Tyr Arg Leu Arg Phe Glu Leu Arg>

770         780         790         800         810
*     *     *     *     *     *     *     *     *     *
TAT CGG GCT GAA CGG TCA AAG ACA TTC ACA ACA TGG ATG GTC AAG GAC
Tyr Arg Ala Glu Arg Ser Lys Thr Phe Thr Thr Trp Met Val Lys Asp>

  820         830         840         850         860
    *     *     *     *     *     *     *     *     *
CTC CAG CAT CAC TGT GTC ATC CAC GAC GCC TGG AGC GGC CTG AGG CAC
Leu Gln His His Cys Val Ile His Asp Ala Trp Ser Gly Leu Arg His>

     870         880         890         900         910
*     *     *     *     *     *     *     *     *     *
GTG GTG CAG CTT CGT GCC CAG GAG GAG TTC GGG CAA GGC GAG TGG AGC
Val Val Gln Leu Arg Ala Gln Glu Glu Phe Gly Gln Gly Glu Trp Ser>

        920         930         940         950         960
*     *     *     *     *     *     *     *     *     *
GAG TGG AGC CCG GAG GCC ATG GGC ACG CCT TGG ACA GAA TCG CGA TCG
Glu Trp Ser Pro Glu Ala Met Gly Thr Pro Trp Thr Glu Ser Arg Ser>

           970         980         990        1000
    *     *     *     *     *     *     *     *     *
CCT CCA GCT GAG AAC GAG GTG TCC ACC CCC ATG GAA CTT CTA GAC CCA
Pro Pro Ala Glu Asn Glu Val Ser Thr Pro Met Glu Leu Leu Asp Pro>

1010        1020        1030        1040        1050
*     *     *     *     *     *     *     *     *     *
TGT GGT TAT ATC AGT CCT GAA TCT CCA GTT GTA CAA CTT CAT TCT AAT
Cys Gly Tyr Ile Ser Pro Glu Ser Pro Val Val Gln Leu His Ser Asn>

 1060        1070        1080        1090        1100
    *     *     *     *     *     *     *     *     *
TTC ACT GCA GTT TGT GTG CTA AAG GAA AAA TGT ATG GAT TAT TTT CAT
Phe Thr Ala Val Cys Val Leu Lys Glu Lys Cys Met Asp Tyr Phe His>

    1110        1120        1130        1140        1150
*     *     *     *     *     *     *     *     *     *
GTA AAT GCT AAT TAC ATT GTC TGG AAA ACA AAC CAT TTT ACT ATT CCT
Val Asn Ala Asn Tyr Ile Val Trp Lys Thr Asn His Phe Thr Ile Pro>

       1160        1170        1180        1190        1200
*     *     *     *     *     *     *     *     *     *
```

```
AAG GAG CAA TAT ACT ATC ATA AAC AGA ACA GCA TCC AGT GTC ACC TTT
Lys Glu Gln Tyr Thr Ile Ile Asn Arg Thr Ala Ser Ser Val Thr Phe>

        1210        1220        1230        1240
   *     *     *     *     *     *     *     *     *
ACA GAT ATA GCT TCA TTA AAT ATT CAG CTC ACT TGC AAC ATT CTT ACA
Thr Asp Ile Ala Ser Leu Asn Ile Gln Leu Thr Cys Asn Ile Leu Thr>

1250        1260        1270        1280        1290
 *     *     *     *     *     *     *     *     *
TTC GGA CAG CTT GAA CAG AAT GTT TAT GGA ATC ACA ATA ATT TCA GGC
Phe Gly Gln Leu Glu Gln Asn Val Tyr Gly Ile Thr Ile Ile Ser Gly>

 1300        1310        1320        1330        1340
   *     *     *     *     *     *     *     *     *
TTG CCT CCA GAA AAA CCT AAA AAT TTG AGT TGC ATT GTG AAC GAG GGG
Leu Pro Pro Glu Lys Pro Lys Asn Leu Ser Cys Ile Val Asn Glu Gly>

   1350        1360        1370        1380        1390
 *     *     *     *     *     *     *     *     *     *
AAG AAA ATG AGG TGT GAG TGG GAT GGT GGA AGG GAA ACA CAC TTG GAG
Lys Lys Met Arg Cys Glu Trp Asp Gly Gly Arg Glu Thr His Leu Glu>

     1400        1410        1420        1430        1440
  *     *     *     *     *     *     *     *     *     *
ACA AAC TTC ACT TTA AAA TCT GAA TGG GCA ACA CAC AAG TTT GCT GAT
Thr Asn Phe Thr Leu Lys Ser Glu Trp Ala Thr His Lys Phe Ala Asp>

        1450        1460        1470        1480
   *     *     *     *     *     *     *     *     *
TGC AAA GCA AAA CGT GAC ACC CCC ACC TCA TGC ACT GTT GAT TAT TCT
Cys Lys Ala Lys Arg Asp Thr Pro Thr Ser Cys Thr Val Asp Tyr Ser>

1490        1500        1510        1520        1530
 *     *     *     *     *     *     *     *     *     *
ACT GTG TAT TTT GTC AAC ATT GAA GTC TGG GTA GAA GCA GAG AAT GCC
Thr Val Tyr Phe Val Asn Ile Glu Val Trp Val Glu Ala Glu Asn Ala>

 1540        1550        1560        1570        1580
   *     *     *     *     *     *     *     *     *
CTT GGG AAG GTT ACA TCA GAT CAT ATC AAT TTT GAT CCT GTA TAT AAA
Leu Gly Lys Val Thr Ser Asp His Ile Asn Phe Asp Pro Val Tyr Lys>

   1590        1600        1610        1620        1630
 *     *     *     *     *     *     *     *     *     *
GTG AAG CCC AAT CCG CCA CAT AAT TTA TCA GTG ATC AAC TCA GAG GAA
Val Lys Pro Asn Pro Pro His Asn Leu Ser Val Ile Asn Ser Glu Glu>

     1640        1650        1660        1670        1680
  *     *     *     *     *     *     *     *     *     *
CTG TCT AGT ATC TTA AAA TTG ACA TGG ACC AAC CCA AGT ATT AAG AGT
Leu Ser Ser Ile Leu Lys Leu Thr Trp Thr Asn Pro Ser Ile Lys Ser>

        1690        1700        1710        1720
   *     *     *     *     *     *     *     *     *
GTT ATA ATA CTA AAA TAT AAC ATT CAA TAT AGG ACC AAA GAT GCC TCA
Val Ile Ile Leu Lys Tyr Asn Ile Gln Tyr Arg Thr Lys Asp Ala Ser>

1730        1740        1750        1760        1770
 *     *     *     *     *     *     *     *     *     *
ACT TGG AGC CAG ATT CCT CCT GAA GAC ACA GCA TCC ACC CGA TCT TCA
Thr Trp Ser Gln Ile Pro Pro Glu Asp Thr Ala Ser Thr Arg Ser Ser>
```

Fig.25D.

```
 1780       1790       1800       1810       1820
  *    *     *    *     *    *     *    *     *
TTC ACT GTC CAA GAC CTT AAA CCT TTT ACA GAA TAT GTG TTT AGG ATT
Phe Thr Val Gln Asp Leu Lys Pro Phe Thr Glu Tyr Val Phe Arg Ile>

   1830       1840       1850       1860       1870
*    *     *    *     *    *     *    *     *    *
CGC TGT ATG AAG GAA GAT GGT AAG GGA TAC TGG AGT GAC TGG AGT GAA
Arg Cys Met Lys Glu Asp Gly Lys Gly Tyr Trp Ser Asp Trp Ser Glu>

     1880       1890       1900       1910       1920
 *    *     *    *     *    *     *    *     *    *
GAA GCA AGT GGG ATC ACC TAT GAA GAT AGA CCA TCT AAA GCA CCA AGT
Glu Ala Ser Gly Ile Thr Tyr Glu Asp Arg Pro Ser Lys Ala Pro Ser>

       1930       1940       1950       1960
   *    *     *    *     *    *     *    *     *
TTC TGG TAT AAA ATA GAT CCA TCC CAT ACT CAA GGC TAC AGA ACT GTA
Phe Trp Tyr Lys Ile Asp Pro Ser His Thr Gln Gly Tyr Arg Thr Val>

1970      1980       1990       2000       2010
 *    *     *    *     *    *     *    *     *    *
CAA CTC GTG TGG AAG ACA TTG CCT CCT TTT GAA GCC AAT GGA AAA ATC
Gln Leu Val Trp Lys Thr Leu Pro Pro Phe Glu Ala Asn Gly Lys Ile>

 2020       2030       2040       2050       2060
   *    *     *    *     *    *     *    *     *
TTG GAT TAT GAA GTG ACT CTC ACA AGA TGG AAA TCA CAT TTA CAA AAT
Leu Asp Tyr Glu Val Thr Leu Thr Arg Trp Lys Ser His Leu Gln Asn>

   2070       2080       2090       2100       2110
*    *     *    *     *    *     *    *     *    *
TAC ACA GTT AAT GCC ACA AAA CTG ACA GTA AAT CTC ACA AAT GAT CGC
Tyr Thr Val Asn Ala Thr Lys Leu Thr Val Asn Leu Thr Asn Asp Arg>

     2120       2130       2140       2150       2160
 *    *     *    *     *    *     *    *     *    *
TAT CTA GCA ACC CTA ACA GTA AGA AAT CTT GTT GGC AAA TCA GAT GCA
Tyr Leu Ala Thr Leu Thr Val Arg Asn Leu Val Gly Lys Ser Asp Ala>

       2170       2180       2190       2200
   *    *     *    *     *    *     *    *     *
GCT GTT TTA ACT ATC CCT GCC TGT GAC TTT CAA GCT ACT CAC CCT GTA
Ala Val Leu Thr Ile Pro Ala Cys Asp Phe Gln Ala Thr His Pro Val>

2210      2220       2230       2240       2250
 *    *     *    *     *    *     *    *     *    *
ATG GAT CTT AAA GCA TTC CCC AAA GAT AAC ATG CTT TGG GTG GAA TGG
Met Asp Leu Lys Ala Phe Pro Lys Asp Asn Met Leu Trp Val Glu Trp>

 2260       2270       2280       2290       2300
   *    *     *    *     *    *     *    *     *
ACT ACT CCA AGG GAA TCT GTA AAG AAA TAT ATA CTT GAG TGG TGT GTG
Thr Thr Pro Arg Glu Ser Val Lys Lys Tyr Ile Leu Glu Trp Cys Val>

   2310       2320       2330       2340       2350
*    *     *    *     *    *     *    *     *    *
TTA TCA GAT AAA GCA CCC TGT ATC ACA GAC TGG CAA CAA GAA GAT GGT
Leu Ser Asp Lys Ala Pro Cys Ile Thr Asp Trp Gln Gln Glu Asp Gly>

     2360       2370       2380       2390       2400
```

```
 *          *          *          *          *          *          *          *          *          *
ACC GTG CAT CGC ACC TAT TTA AGA GGG AAC TTA GCA GAG AGC AAA TGC
Thr Val His Arg Thr Tyr Leu Arg Gly Asn Leu Ala Glu Ser Lys Cys>

        2410        2420        2430        2440
TAT TTG ATA ACA GTT ACT CCA GTA TAT GCT GAT GGA CCA GGA AGC CCT
Tyr Leu Ile Thr Val Thr Pro Val Tyr Ala Asp Gly Pro Gly Ser Pro>

2450        2460        2470        2480        2490
GAA TCC ATA AAG GCA TAC CTT AAA CAA GCT CCA CCT TCC AAA GGA CCT
Glu Ser Ile Lys Ala Tyr Leu Lys Gln Ala Pro Pro Ser Lys Gly Pro>

 2500        2510        2520        2530        2540
ACT GTT CGG ACA AAA AAA GTA GGG AAA AAC GAA GCT GTC TTA GAG TGG
Thr Val Arg Thr Lys Lys Val Gly Lys Asn Glu Ala Val Leu Glu Trp>

  2550        2560        2570        2580        2590
GAC CAA CTT CCT GTT GAT GTT CAG AAT GGA TTT ATC AGA AAT TAT ACT
Asp Gln Leu Pro Val Asp Val Gln Asn Gly Phe Ile Arg Asn Tyr Thr>

    2600        2610        2620        2630        2640
ATA TTT TAT AGA ACC ATC ATT GGA AAT GAA ACT GCT GTG AAT GTG GAT
Ile Phe Tyr Arg Thr Ile Ile Gly Asn Glu Thr Ala Val Asn Val Asp>

      2650        2660        2670        2680
TCT TCC CAC ACA GAA TAT ACA TTG TCC TCT TTG ACT AGT GAC ACA TTG
Ser Ser His Thr Glu Tyr Thr Leu Ser Ser Leu Thr Ser Asp Thr Leu>

2690        2700        2710        2720        2730
TAC ATG GTA CGA ATG GCA GCA TAC ACA GAT GAA GGT GGG AAG GAT GGT
Tyr Met Val Arg Met Ala Ala Tyr Thr Asp Glu Gly Gly Lys Asp Gly>

 2740        2750        2760        2770        2780
CCA GAA TTC ACT TTT ACT ACC CCA AAG TTT GCT CAA GGA GAA ATT GAA
Pro Glu Phe Thr Phe Thr Thr Pro Lys Phe Ala Gln Gly Glu Ile Glu>

   2790        2800        2810        2820        2830
TCC GGG GGC GAC AAA ACT CAC ACA TGC CCA CCG TGC CCA GCA CCT GAA
Ser Gly Gly Asp Lys Thr His Thr Cys Pro Pro Cys Pro Ala Pro Glu>

     2840        2850        2860        2870        2880
CTC CTG GGG GGA CCG TCA GTC TTC CTC TTC CCC CCA AAA CCC AAG GAC
Leu Leu Gly Gly Pro Ser Val Phe Leu Phe Pro Pro Lys Pro Lys Asp>

       2890        2900        2910        2920
ACC CTC ATG ATC TCC CGG ACC CCT GAG GTC ACA TGC GTG GTG GTG GAC
Thr Leu Met Ile Ser Arg Thr Pro Glu Val Thr Cys Val Val Val Asp>

2930        2940        2950        2960        2970
GTG AGC CAC GAA GAC CCT GAG GTC AAG TTC AAC TGG TAC GTG GAC GGC
```

Fig.25F.

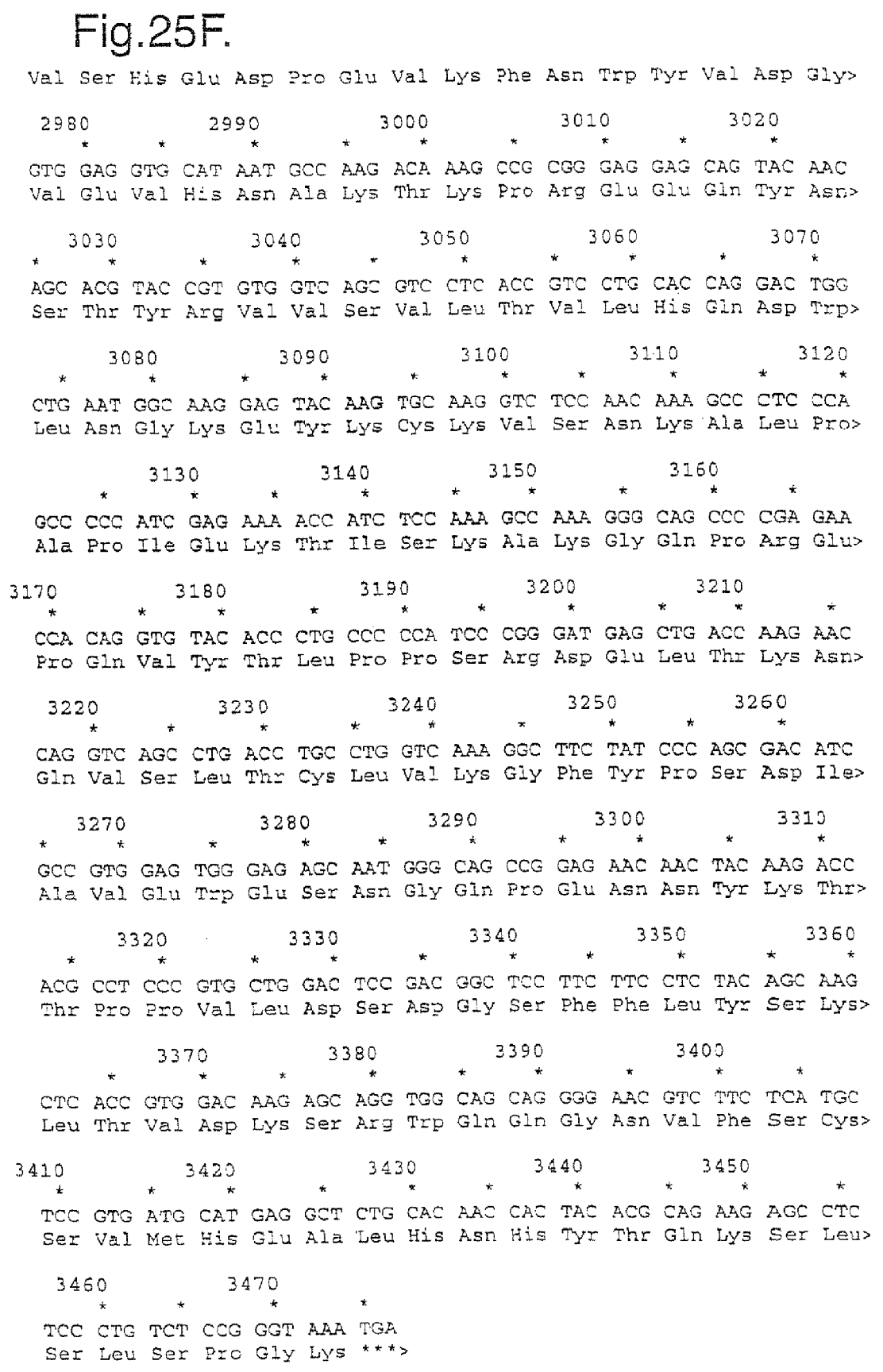

```
Val Ser His Glu Asp Pro Glu Val Lys Phe Asn Trp Tyr Val Asp Gly>

 2980      2990      3000      3010      3020
GTG GAG GTG CAT AAT GCC AAG ACA AAG CCG CGG GAG GAG CAG TAC AAC
Val Glu Val His Asn Ala Lys Thr Lys Pro Arg Glu Glu Gln Tyr Asn>

   3030      3040      3050      3060      3070
AGC ACG TAC CGT GTG GTC AGC GTC CTC ACC GTC CTG CAC CAG GAC TGG
Ser Thr Tyr Arg Val Val Ser Val Leu Thr Val Leu His Gln Asp Trp>

     3080      3090      3100      3110      3120
CTG AAT GGC AAG GAG TAC AAG TGC AAG GTC TCC AAC AAA GCC CTC CCA
Leu Asn Gly Lys Glu Tyr Lys Cys Lys Val Ser Asn Lys Ala Leu Pro>

       3130      3140      3150      3160
GCC CCC ATC GAG AAA ACC ATC TCC AAA GCC AAA GGG CAG CCC CGA GAA
Ala Pro Ile Glu Lys Thr Ile Ser Lys Ala Lys Gly Gln Pro Arg Glu>

3170      3180      3190      3200      3210
CCA CAG GTG TAC ACC CTG CCC CCA TCC CGG GAT GAG CTG ACC AAG AAC
Pro Gln Val Tyr Thr Leu Pro Pro Ser Arg Asp Glu Leu Thr Lys Asn>

 3220      3230      3240      3250      3260
CAG GTC AGC CTG ACC TGC CTG GTC AAA GGC TTC TAT CCC AGC GAC ATC
Gln Val Ser Leu Thr Cys Leu Val Lys Gly Phe Tyr Pro Ser Asp Ile>

   3270      3280      3290      3300      3310
GCC GTG GAG TGG GAG AGC AAT GGG CAG CCG GAG AAC AAC TAC AAG ACC
Ala Val Glu Trp Glu Ser Asn Gly Gln Pro Glu Asn Asn Tyr Lys Thr>

     3320      3330      3340      3350      3360
ACG CCT CCC GTG CTG GAC TCC GAC GGC TCC TTC TTC CTC TAC AGC AAG
Thr Pro Pro Val Leu Asp Ser Asp Gly Ser Phe Phe Leu Tyr Ser Lys>

       3370      3380      3390      3400
CTC ACC GTG GAC AAG AGC AGG TGG CAG CAG GGG AAC GTC TTC TCA TGC
Leu Thr Val Asp Lys Ser Arg Trp Gln Gln Gly Asn Val Phe Ser Cys>

3410      3420      3430      3440      3450
TCC GTG ATG CAT GAG GCT CTG CAC AAC CAC TAC ACG CAG AAG AGC CTC
Ser Val Met His Glu Ala Leu His Asn His Tyr Thr Gln Lys Ser Leu>

 3460      3470
TCC CTG TCT CCG GGT AAA TGA
Ser Leu Ser Pro Gly Lys ***>
```

Fig.26A.

```
                 10          20          30          40
     *     *     *     *     *     *     *     *     *
ATG GTG CTT CTG TGG TGT GTA GTG AGT CTC TAC TTT TAT GGA ATC CTG
Met Val Leu Leu Trp Cys Val Val Ser Leu Tyr Phe Tyr Gly Ile Leu>

50         60          70          80          90
 *     *     *     *     *     *     *     *     *     *
CAA AGT GAT GCC TCA GAA CGC TGC GAT GAC TGG GGA CTA GAC ACC ATG
Gln Ser Asp Ala Ser Glu Arg Cys Asp Asp Trp Gly Leu Asp Thr Met>

 100         110         120         130         140
     *     *     *     *     *     *     *     *     *
AGG CAA ATC CAA GTG TTT GAA GAT GAG CCA GCT CGC ATC AAG TGC CCA
Arg Gln Ile Gln Val Phe Glu Asp Glu Pro Ala Arg Ile Lys Cys Pro>

    150         160         170         180         190
 *     *     *     *     *     *     *     *     *     *
CTC TTT GAA CAC TTC TTG AAA TTC AAC TAC AGC ACA GCC CAT TCA GCT
Leu Phe Glu His Phe Leu Lys Phe Asn Tyr Ser Thr Ala His Ser Ala>

       200         210         220         230         240
 *     *     *     *     *     *     *     *     *     *
GGC CTT ACT CTG ATC TGG TAT TGG ACT AGG CAG GAC CGG GAC CTT GAG
Gly Leu Thr Leu Ile Trp Tyr Trp Thr Arg Gln Asp Arg Asp Leu Glu>

          250         260         270         280
     *     *     *     *     *     *     *     *     *
GAG CCA ATT AAC TTC CGC CTC CCC GAG AAC CGC ATT AGT AAG GAG AAA
Glu Pro Ile Asn Phe Arg Leu Pro Glu Asn Arg Ile Ser Lys Glu Lys>

290        300         310         320         330
 *     *     *     *     *     *     *     *     *     *
GAT GTG CTG TGG TTC CGG CCC ACT CTC CTC AAT GAC ACT GGC AAC TAT
Asp Val Leu Trp Phe Arg Pro Thr Leu Leu Asn Asp Thr Gly Asn Tyr>

  340         350         360         370         380
     *     *     *     *     *     *     *     *     *
ACC TGC ATG TTA AGG AAC ACT ACA TAT TGC AGC AAA GTT GCA TTT CCC
Thr Cys Met Leu Arg Asn Thr Thr Tyr Cys Ser Lys Val Ala Phe Pro>

     390         400         410         420         430
 *     *     *     *     *     *     *     *     *     *
TTG GAA GTT GTT CAA AAA GAC AGC TGT TTC AAT TCC CCC ATG AAA CTC
Leu Glu Val Val Gln Lys Asp Ser Cys Phe Asn Ser Pro Met Lys Leu>

        440         450         460         470         480
 *     *     *     *     *     *     *     *     *     *
CCA GTG CAT AAA CTG TAT ATA GAA TAT GGC ATT CAG AGG ATC ACT TGT
Pro Val His Lys Leu Tyr Ile Glu Tyr Gly Ile Gln Arg Ile Thr Cys>

           490         500         510         520
     *     *     *     *     *     *     *     *     *
CCA AAT GTA GAT GGA TAT TTT CCT TCC AGT GTC AAA CCG ACT ATC ACT
Pro Asn Val Asp Gly Tyr Phe Pro Ser Ser Val Lys Pro Thr Ile Thr>

530        540         550         560         570
 *     *     *     *     *     *     *     *     *     *
TGG TAT ATG GGC TGT TAT AAA ATA CAG AAT TTT AAT AAT GTA ATA CCC
Trp Tyr Met Gly Cys Tyr Lys Ile Gln Asn Phe Asn Asn Val Ile Pro>
```

Fig.26B.

```
 580         590         600         610         620
   *     *     *     *     *     *     *     *     *
GAA GGT ATG AAC TTG AGT TTC CTC ATT GCC TTA ATT TCA AAT AAT GGA
Glu Gly Met Asn Leu Ser Phe Leu Ile Ala Leu Ile Ser Asn Asn Gly>

   630         640         650         660         670
 *     *     *     *     *     *     *     *     *     *
AAT TAC ACA TGT GTT GTT ACA TAT CCA GAA AAT GGA CGT ACG TTT CAT
Asn Tyr Thr Cys Val Val Thr Tyr Pro Glu Asn Gly Arg Thr Phe His>

       680         690         700         710         720
   *     *     *     *     *     *     *     *     *     *
CTC ACC AGG ACT CTG ACT GTA AAG GTA GTA GGC TCT CCA AAA AAT GCA
Leu Thr Arg Thr Leu Thr Val Lys Val Val Gly Ser Pro Lys Asn Ala>

         730         740         750         760
     *     *     *     *     *     *     *     *     *
GTG CCC CCT GTG ATC CAT TCA CCT AAT GAT CAT GTG GTC TAT GAG AAA
Val Pro Pro Val Ile His Ser Pro Asn Asp His Val Val Tyr Glu Lys>

770         780         790         800         810
  *     *     *     *     *     *     *     *     *     *
GAA CCA GGA GAG GAG CTA CTC ATT CCC TGT ACG GTC TAT TTT AGT TTT
Glu Pro Gly Glu Glu Leu Leu Ile Pro Cys Thr Val Tyr Phe Ser Phe>

 820         830         840         850         860
   *     *     *     *     *     *     *     *     *
CTG ATG GAT TCT CGC AAT GAG GTT TGG TGG ACC ATT GAT GGA AAA AAA
Leu Met Asp Ser Arg Asn Glu Val Trp Trp Thr Ile Asp Gly Lys Lys>

    870         880         890         900         910
 *     *     *     *     *     *     *     *     *     *
CCT GAT GAC ATC ACT ATT GAT GTC ACC ATT AAC GAA AGT ATA AGT CAT
Pro Asp Asp Ile Thr Ile Asp Val Thr Ile Asn Glu Ser Ile Ser His>

       920         930         940         950         960
   *     *     *     *     *     *     *     *     *     *
AGT AGA ACA GAA GAT GAA ACA AGA ACT CAG ATT TTG AGC ATC AAG AAA
Ser Arg Thr Glu Asp Glu Thr Arg Thr Gln Ile Leu Ser Ile Lys Lys>

         970         980         990         1000
     *     *     *     *     *     *     *     *     *
GTT ACC TCT GAG GAT CTC AAG CGC AGC TAT GTC TGT CAT GCT AGA AGT
Val Thr Ser Glu Asp Leu Lys Arg Ser Tyr Val Cys His Ala Arg Ser>

1010        1020        1030        1040        1050
  *     *     *     *     *     *     *     *     *     *
GCC AAA GGC GAA GTT GCC AAA GCA GCC AAG GTG AAG CAG AAA GTG CCA
Ala Lys Gly Glu Val Ala Lys Ala Ala Lys Val Lys Gln Lys Val Pro>

 1060        1070        1080        1090        1100
    *     *     *     *     *     *     *     *     *
GCT CCA AGA TAC ACA GTG TCC GGT GGC GCG CCT ATG CTG AGC GAG GCT
Ala Pro Arg Tyr Thr Val Ser Gly Gly Ala Pro Met Leu Ser Glu Ala>

    1110        1120        1130        1140        1150
 *     *     *     *     *     *     *     *     *     *
GAT AAA TGC AAG GAA CGT GAA GAA AAA ATA ATT TTA GTG TCA TCT GCA
Asp Lys Cys Lys Glu Arg Glu Glu Lys Ile Ile Leu Val Ser Ser Ala>

      1160        1170        1180        1190        1200
   *     *     *     *     *     *     *     *     *     *
```

```
AAT GAA ATT GAT GTT CGT CCC TGT CCT CTT AAC CCA AAT GAA CAC AAA
Asn Glu Ile Asp Val Arg Pro Cys Pro Leu Asn Pro Asn Glu His Lys>

        1210        1220        1230        1240
     *     *     *     *     *     *     *     *     *
GGC ACT ATA ACT TGG TAT AAG GAT GAC AGC AAG ACA CCT GTA TCT ACA
Gly Thr Ile Thr Trp Tyr Lys Asp Asp Ser Lys Thr Pro Val Ser Thr>

1250        1260        1270        1280        1290
 *     *     *     *     *     *     *     *     *     *
GAA CAA GCC TCC AGG ATT CAT CAA CAC AAA GAG AAA CTT TGG TTT GTT
Glu Gln Ala Ser Arg Ile His Gln His Lys Glu Lys Leu Trp Phe Val>

  1300        1310        1320        1330        1340
     *     *     *     *     *     *     *     *     *
CCT GCT AAG GTG GAG GAT TCA GGA CAT TAC TAT TGC GTG GTA AGA AAT
Pro Ala Lys Val Glu Asp Ser Gly His Tyr Tyr Cys Val Val Arg Asn>

    1350        1360        1370        1380        1390
 *     *     *     *     *     *     *     *     *     *
TCA TCT TAC TGC CTC AGA ATT AAA ATA AGT GCA AAA TTT GTG GAG AAT
Ser Ser Tyr Cys Leu Arg Ile Lys Ile Ser Ala Lys Phe Val Glu Asn>

      1400        1410        1420        1430        1440
  *     *     *     *     *     *     *     *     *     *
GAG CCT AAC TTA TGT TAT AAT GCA CAA GCC ATA TTT AAG CAG AAA CTA
Glu Pro Asn Leu Cys Tyr Asn Ala Gln Ala Ile Phe Lys Gln Lys Leu>

        1450        1460        1470        1480
     *     *     *     *     *     *     *     *     *
CCC GTT GCA GGA GAC GGA GGA CTT GTG TGC CCT TAT ATG GAG TTT TTT
Pro Val Ala Gly Asp Gly Gly Leu Val Cys Pro Tyr Met Glu Phe Phe>

1490        1500        1510        1520        1530
 *     *     *     *     *     *     *     *     *     *
AAA AAT GAA AAT AAT GAG TTA CCT AAA TTA CAG TGG TAT AAG GAT TGC
Lys Asn Glu Asn Asn Glu Leu Pro Lys Leu Gln Trp Tyr Lys Asp Cys>

  1540        1550        1560        1570        1580
     *     *     *     *     *     *     *     *     *
AAA CCT CTA CTT CTT GAC AAT ATA CAC TTT AGT GGA GTC AAA GAT AGG
Lys Pro Leu Leu Leu Asp Asn Ile His Phe Ser Gly Val Lys Asp Arg>

    1590        1600        1610        1620        1630
 *     *     *     *     *     *     *     *     *     *
CTC ATC GTG ATG AAT GTG GCT GAA AAG CAT AGA GGG AAC TAT ACT TGT
Leu Ile Val Met Asn Val Ala Glu Lys His Arg Gly Asn Tyr Thr Cys>

      1640        1650        1660        1670        1680
  *     *     *     *     *     *     *     *     *     *
CAT GCA TCC TAC ACA TAC TTG GGC AAG CAA TAT CCT ATT ACC CGG GTA
His Ala Ser Tyr Thr Tyr Leu Gly Lys Gln Tyr Pro Ile Thr Arg Val>

        1690        1700        1710        1720
     *     *     *     *     *     *     *     *     *
ATA GAA TTT ATT ACT CTA GAG GAA AAC AAA CCC ACA AGG CCT GTG ATT
Ile Glu Phe Ile Thr Leu Glu Glu Asn Lys Pro Thr Arg Pro Val Ile>

1730        1740        1750        1760        1770
 *     *     *     *     *     *     *     *     *     *
GTG AGC CCA GCT AAT GAG ACA ATG GAA GTA GAC TTG GGA TCC CAG ATA
Val Ser Pro Ala Asn Glu Thr Met Glu Val Asp Leu Gly Ser Gln Ile>
```

Fig.26D.

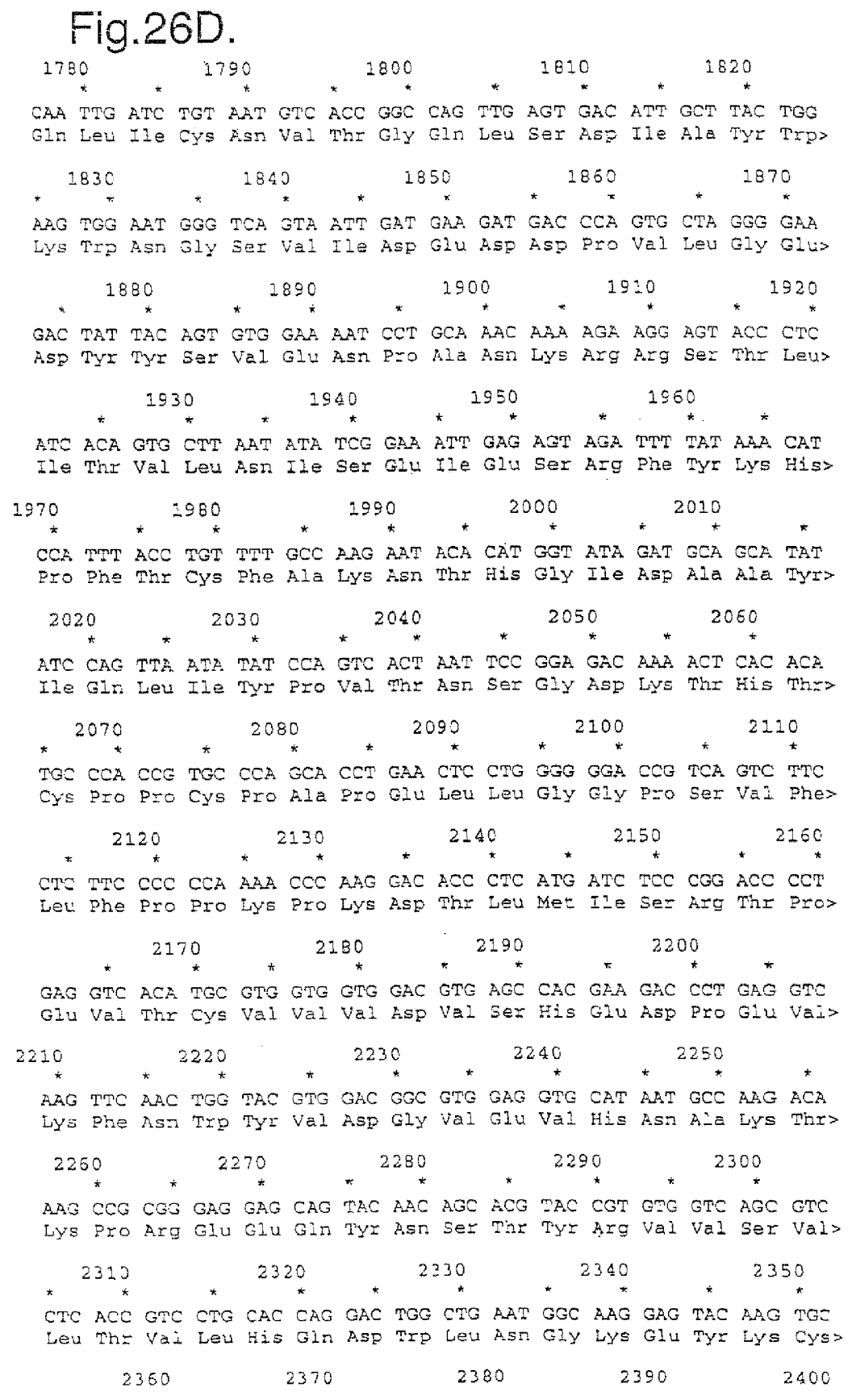

```
1780        1790        1800        1810        1820
CAA TTG ATC TGT AAT GTC ACC GGC CAG TTG AGT GAC ATT GCT TAC TGG
Gln Leu Ile Cys Asn Val Thr Gly Gln Leu Ser Asp Ile Ala Tyr Trp>

1830        1840        1850        1860        1870
AAG TGG AAT GGG TCA GTA ATT GAT GAA GAT GAC CCA GTG CTA GGG GAA
Lys Trp Asn Gly Ser Val Ile Asp Glu Asp Asp Pro Val Leu Gly Glu>

1880        1890        1900        1910        1920
GAC TAT TAC AGT GTG GAA AAT CCT GCA AAC AAA AGA AGG AGT ACC CTC
Asp Tyr Tyr Ser Val Glu Asn Pro Ala Asn Lys Arg Arg Ser Thr Leu>

1930        1940        1950        1960
ATC ACA GTG CTT AAT ATA TCG GAA ATT GAG AGT AGA TTT TAT AAA CAT
Ile Thr Val Leu Asn Ile Ser Glu Ile Glu Ser Arg Phe Tyr Lys His>

1970        1980        1990        2000        2010
CCA TTT ACC TGT TTT GCC AAG AAT ACA CAT GGT ATA GAT GCA GCA TAT
Pro Phe Thr Cys Phe Ala Lys Asn Thr His Gly Ile Asp Ala Ala Tyr>

2020        2030        2040        2050        2060
ATC CAG TTA ATA TAT CCA GTC ACT AAT TCC GGA GAC AAA ACT CAC ACA
Ile Gln Leu Ile Tyr Pro Val Thr Asn Ser Gly Asp Lys Thr His Thr>

2070        2080        2090        2100        2110
TGC CCA CCG TGC CCA GCA CCT GAA CTC CTG GGG GGA CCG TCA GTC TTC
Cys Pro Pro Cys Pro Ala Pro Glu Leu Leu Gly Gly Pro Ser Val Phe>

2120        2130        2140        2150        2160
CTC TTC CCC CCA AAA CCC AAG GAC ACC CTC ATG ATC TCC CGG ACC CCT
Leu Phe Pro Pro Lys Pro Lys Asp Thr Leu Met Ile Ser Arg Thr Pro>

2170        2180        2190        2200
GAG GTC ACA TGC GTG GTG GTG GAC GTG AGC CAC GAA GAC CCT GAG GTC
Glu Val Thr Cys Val Val Val Asp Val Ser His Glu Asp Pro Glu Val>

2210        2220        2230        2240        2250
AAG TTC AAC TGG TAC GTG GAC GGC GTG GAG GTG CAT AAT GCC AAG ACA
Lys Phe Asn Trp Tyr Val Asp Gly Val Glu Val His Asn Ala Lys Thr>

2260        2270        2280        2290        2300
AAG CCG CGG GAG GAG CAG TAC AAC AGC ACG TAC CGT GTG GTC AGC GTC
Lys Pro Arg Glu Glu Gln Tyr Asn Ser Thr Tyr Arg Val Val Ser Val>

2310        2320        2330        2340        2350
CTC ACC GTC CTG CAC CAG GAC TGG CTG AAT GGC AAG GAG TAC AAG TGC
Leu Thr Val Leu His Gln Asp Trp Leu Asn Gly Lys Glu Tyr Lys Cys>

2360        2370        2380        2390        2400
```

```
 *         *         *         *         *         *         *         *         *         *
AAG GTC TCC AAC AAA GCC CTC CCA GCC CCC ATC GAG AAA ACC ATC TCC
Lys Val Ser Asn Lys Ala Leu Pro Ala Pro Ile Glu Lys Thr Ile Ser>

          2410         2420         2430         2440
     *         *         *         *         *         *         *         *         *
AAA GCC AAA GGG CAG CCC CGA GAA CCA CAG GTG TAC ACC CTG CCC CCA
Lys Ala Lys Gly Gln Pro Arg Glu Pro Gln Val Tyr Thr Leu Pro Pro>

2450         2460         2470         2480         2490
 *         *         *         *         *         *         *         *         *         *
TCC CGG GAG GAG ATG ACC AAG AAC CAG GTC AGC CTG ACC TGC CTG GTC
Ser Arg Glu Glu Met Thr Lys Asn Gln Val Ser Leu Thr Cys Leu Val>

 2500         2510         2520         2530         2540
     *         *         *         *         *         *         *         *         *
AAA GGC TTC TAT CCC AGC GAC ATC GCC GTG GAG TGG GAG AGC AAT GGG
Lys Gly Phe Tyr Pro Ser Asp Ile Ala Val Glu Trp Glu Ser Asn Gly>

   2550         2560         2570         2580         2590
 *         *         *         *         *         *         *         *         *         *
CAG CCG GAG AAC AAC TAC AAG ACC ACG CCT CCC GTG CTG GAC TCC GAC
Gln Pro Glu Asn Asn Tyr Lys Thr Thr Pro Pro Val Leu Asp Ser Asp>

      2600         2610         2620         2630         2640
 *         *         *         *         *         *         *         *         *         *
GGC TCC TTC TTC CTC TAT AGC AAG CTC ACC GTG GAC AAG AGC AGG TGG
Gly Ser Phe Phe Leu Tyr Ser Lys Leu Thr Val Asp Lys Ser Arg Trp>

          2650         2660         2670         2680
     *         *         *         *         *         *         *         *         *
CAG CAG GGG AAC GTC TTC TCA TGC TCC GTG ATG CAT GAG GCT CTG CAC
Gln Gln Gly Asn Val Phe Ser Cys Ser Val Met His Glu Ala Leu His>

2690         2700         2710         2720         2730
 *         *         *         *         *         *         *         *
AAC CAC TAC ACG CAG AAG AGC CTC TCC CTG TCT CCG GGT AAA TGA
Asn His Tyr Thr Gln Lys Ser Leu Ser Leu Ser Pro Gly Lys ***>
```

Fig.31A.

```
               10          20          30          40
       *     *     *     *     *     *     *     *     *
ATG GTG TGG CTT TGC TCT GGG CTC CTG TTC CCT GTG AGC TGC CTG GTC
TAC CAC ACC GAA ACG AGA CCC GAG GAC AAG GGA CAC TCG ACG GAC CAG
Met Val Trp Leu Cys Ser Gly Leu Leu Phe Pro Val Ser Cys Leu Val>

50          60          70          80          90
 *     *     *     *     *     *     *     *     *     *
CTG CTG CAG GTG GCA AGC TCT GGG AAC ATG AAG GTC TTG CAG GAG CCC
GAC GAC GTC CAC CGT TCG AGA CCC TTG TAC TTC CAG AAC GTC CTC GGG
Leu Leu Gln Val Ala Ser Ser Gly Asn Met Lys Val Leu Gln Glu Pro>

  100         110         120         130         140
    *     *     *     *     *     *     *     *     *
ACC TGC GTC TCC GAC TAC ATG AGC ATC TCT ACT TGC GAG TGG AAG ATG
TGG ACG CAG AGG CTG ATG TAC TCG TAG AGA TGA ACG CTC ACC TTC TAC
Thr Cys Val Ser Asp Tyr Met Ser Ile Ser Thr Cys Glu Trp Lys Met>

    150         160         170         180         190
*     *     *     *     *     *     *     *     *     *
AAT GGT CCC ACC AAT TGC AGC ACC GAG CTC CGC CTG TTG TAC CAG CTG
TTA CCA GGG TGG TTA ACG TCG TGG CTC GAG GCG GAC AAC ATG GTC GAC
Asn Gly Pro Thr Asn Cys Ser Thr Glu Leu Arg Leu Leu Tyr Gln Leu>

       200         210         220         230         240
  *     *     *     *     *     *     *     *     *     *
GTT TTT CTG CTC TCC GAA GCC CAC ACG TGT ATC CCT GAG AAC AAC GGA
CAA AAA GAC GAG AGG CTT CGG GTG TGC ACA TAG GGA CTC TTG TTG CCT
Val Phe Leu Leu Ser Glu Ala His Thr Cys Ile Pro Glu Asn Asn Gly>

          250         260         270         280
     *     *     *     *     *     *     *     *     *
GGC GCG GGG TGC GTG TGC CAC CTG CTC ATG GAT GAC GTG GTC AGT GCG
CCG CGC CCC ACG CAC ACG GTG GAC GAG TAC CTA CTG CAC CAG TCA CGC
Gly Ala Gly Cys Val Cys His Leu Leu Met Asp Asp Val Val Ser Ala>

290         300         310         320         330
 *     *     *     *     *     *     *     *     *     *
GAT AAC TAT ACA CTG GAC CTG TGG GCT GGG CAG CAG CTG CTG TGG AAG
CTA TTG ATA TGT GAC CTG GAC ACC CGA CCC GTC GTC GAC GAC ACC TTC
Asp Asn Tyr Thr Leu Asp Leu Trp Ala Gly Gln Gln Leu Leu Trp Lys>

  340         350         360         370         380
     *     *     *     *     *     *     *     *     *
GGC TCC TTC AAG CCC AGC GAG CAT GTG AAA CCC AGG GCC CCA GGA AAC
CCG AGG AAG TTC GGG TCG CTC GTA CAC TTT GGG TCC CGG GGT CCT TTG
Gly Ser Phe Lys Pro Ser Glu His Val Lys Pro Arg Ala Pro Gly Asn>
```

Fig.31B.

```
    390         400         410         420         430
 *    *     *     *    *     *     *    *     *     *
CTG ACA GTT CAC ACC AAT GTC TCC GAC ACT CTG CTG CTG ACC TGG AGC
GAC TGT CAA GTG TGG TTA CAG AGG CTG TGA GAC GAC GAC TGG ACC TCG
Leu Thr Val His Thr Asn Val Ser Asp Thr Leu Leu Leu Thr Trp Ser>

      440         450         460         470         480
  *     *     *    *     *     *     *     *     *     *
AAC CCG TAT CCC CCT GAC AAT TAC CTG TAT AAT CAT CTC ACC TAT GCA
TTG GGC ATA GGG GGA CTG TTA ATG GAC ATA TTA GTA GAG TGG ATA CGT
Asn Pro Tyr Pro Pro Asp Asn Tyr Leu Tyr Asn His Leu Thr Tyr Ala>

         490         500         510         520
     *     *     *     *     *     *     *     *     *
GTC AAC ATT TGG AGT GAA AAC GAC CCG GCA GAT TTC AGA ATC TAT AAC
CAG TTG TAA ACC TCA CTT TTG CTG GGC CGT CTA AAG TCT TAG ATA TTG
Val Asn Ile Trp Ser Glu Asn Asp Pro Ala Asp Phe Arg Ile Tyr Asn>

530         540         550         560         570
 *     *     *     *     *     *     *     *     *     *
GTG ACC TAC CTA GAA CCC TCC CTC CGC ATC GCA GCC AGC ACC CTG AAG
CAC TGG ATG GAT CTT GGG AGG GAG GCG TAG CGT CGG TCG TGG GAC TTC
Val Thr Tyr Leu Glu Pro Ser Leu Arg Ile Ala Ala Ser Thr Leu Lys>

  580         590         600         610         620
    *     *     *     *    *     *     *     *     *
TCT GGG ATT TCC TAC AGG GCA CGG GTG AGG GCC TGG GCT CAG AGC TAT
AGA CCC TAA AGG ATG TCC CGT GCC CAC TCC CGG ACC CGA GTC TCG ATA
Ser Gly Ile Ser Tyr Arg Ala Arg Val Arg Ala Trp Ala Gln Ser Tyr>

    630         640         650         660         670
 *    *     *     *    *     *     *     *     *     *
AAC ACC ACC TGG AGT GAG TGG AGC CCC AGC ACC AAG TGG CAC AAC TCC
TTG TGG TGG ACC TCA CTC ACC TCG GGG TCG TGG TTC ACC GTG TTG AGG
Asn Thr Thr Trp Ser Glu Trp Ser Pro Ser Thr Lys Trp His Asn Ser>

       680         690         700         710         720
  *     *     *     *     *     *     *     *     *     *
TAC AGG GAG CCC TTC GAG CAG TCC GGT GGG GGC GGG GGC GCC GCG CCT
ATG TCC CTC GGG AAG CTC GTC AGG CCA CCC CCG CCC CCG CGG CGC GGA
Tyr Arg Glu Pro Phe Glu Gln Ser Gly Gly Gly Gly Gly Ala Ala Pro>

          730         740         750         760
     *     *     *     *     *     *     *     *     *
ACG GAA ACT CAG CCA CCT GTG ACA AAT TTG AGT GTC TCT GTT GAA AAC
TGC CTT TGA GTC GGT GGA CAC TGT TTA AAC TCA CAG AGA CAA CTT TTG
Thr Glu Thr Gln Pro Pro Val Thr Asn Leu Ser Val Ser Val Glu Asn>
```

Fig.31C.

```
770          780          790          800          810
 *      *     *      *      *      *      *      *      *      *
CTC TGC ACA GTA ATA TGG ACA TGG AAT CCA CCC GAG GGA GCC AGC TCA
GAG ACG TGT CAT TAT ACC TGT ACC TTA GGT GGG CTC CCT CGG TCG AGT
Leu Cys Thr Val Ile Trp Thr Trp Asn Pro Pro Glu Gly Ala Ser Ser>

  820          830          840          850          860
   *      *      *      *      *      *      *      *      *
AAT TGT AGT CTA TGG TAT TTT AGT CAT TTT GGC GAC AAA CAA GAT AAG
TTA ACA TCA GAT ACC ATA AAA TCA GTA AAA CCG CTG TTT GTT CTA TTC
Asn Cys Ser Leu Trp Tyr Phe Ser His Phe Gly Asp Lys Gln Asp Lys>

    870          880          890          900          910
 *      *      *      *      *      *      *      *      *      *
AAA ATA GCT CCG GAA ACT CGT CGT TCA ATA GAA GTA CCC CTG AAT GAG
TTT TAT CGA GGC CTT TGA GCA GCA AGT TAT CTT CAT GGG GAC TTA CTC
Lys Ile Ala Pro Glu Thr Arg Arg Ser Ile Glu Val Pro Leu Asn Glu>

      920          930          940          950          960
 *      *      *      *      *      *      *      *      *      *
AGG ATT TGT CTG CAA GTG GGG TCC CAG TGT AGC ACC AAT GAG AGT GAG
TCC TAA ACA GAC GTT CAC CCC AGG GTC ACA TCG TGG TTA CTC TCA CTC
Arg Ile Cys Leu Gln Val Gly Ser Gln Cys Ser Thr Asn Glu Ser Glu>

         970          980          990          1000
   *      *      *      *      *      *      *      *      *
AAG CCT AGC ATT TTG GTT GAA AAA TGC ATC TCA CCC CCA GAA GGT GAT
TTC GGA TCG TAA AAC CAA CTT TTT ACG TAG AGT GGG GGT CTT CCA CTA
Lys Pro Ser Ile Leu Val Glu Lys Cys Ile Ser Pro Pro Glu Gly Asp>

1010         1020         1030         1040         1050
 *      *      *      *      *      *      *      *      *      *
CCT GAG TCT GCT GTG ACT GAG CTT CAA TGC ATT TGG CAC AAC CTG AGC
GGA CTC AGA CGA CAC TGA CTC GAA GTT ACG TAA ACC GTG TTG GAC TCG
Pro Glu Ser Ala Val Thr Glu Leu Gln Cys Ile Trp His Asn Leu Ser>

  1060         1070         1080         1090         1100
   *      *      *      *      *      *      *      *      *
TAC ATG AAG TGT TCT TGG CTC CCT GGA AGG AAT ACC AGT CCC GAC ACT
ATG TAC TTC ACA AGA ACC GAG GGA CCT TCC TTA TGG TCA GGG CTG TGA
Tyr Met Lys Cys Ser Trp Leu Pro Gly Arg Asn Thr Ser Pro Asp Thr>

    1110         1120         1130         1140         1150
 *      *      *      *      *      *      *      *      *      *
AAC TAT ACT CTC TAC TAT TGG CAC AGA AGC CTG GAA AAA ATT CAT CAA
TTG ATA TGA GAG ATG ATA ACC GTG TCT TCG GAC CTT TTT TAA GTA GTT
Asn Tyr Thr Leu Tyr Tyr Trp His Arg Ser Leu Glu Lys Ile His Gln>
```

Fig.31D.

```
       1160         1170          1180         1190          1200
   *     *     *     *     *     *     *     *     *     *
 TGT GAA AAC ATC TTT AGA GAA GGC CAA TAC TTT GGT TGT TCC TTT GAT
 ACA CTT TTG TAG AAA TCT CTT CCG GTT ATG AAA CCA ACA AGG AAA CTA
 Cys Glu Asn Ile Phe Arg Glu Gly Gln Tyr Phe Gly Cys Ser Phe Asp>

         1210         1220         1230          1240
       *     *     *     *     *     *     *     *     *
 CTG ACC AAA GTG AAG GAT TCC AGT TTT GAA CAA CAC AGT GTC CAA ATA
 GAC TGG TTT CAC TTC CTA AGG TCA AAA CTT GTT GTG TCA CAG GTT TAT
 Leu Thr Lys Val Lys Asp Ser Ser Phe Glu Gln His Ser Val Gln Ile>

1250         1260         1270         1280         1290
   *     *     *     *     *     *     *     *     *     *
 ATG GTC AAG GAT AAT GCA GGA AAA ATT AAA CCA TCC TTC AAT ATA GTG
 TAC CAG TTC CTA TTA CGT CCT TTT TAA TTT GGT AGG AAG TTA TAT CAC
 Met Val Lys Asp Asn Ala Gly Lys Ile Lys Pro Ser Phe Asn Ile Val>

  1300         1310         1320          1330         1340
       *     *     *     *     *     *     *     *     *
 CCT TTA ACT TCC CGT GTG AAA CCT GAT CCT CCA CAT ATT AAA AAC CTC
 GGA AAT TGA AGG GCA CAC TTT GGA CTA GGA GGT GTA TAA TTT TTG GAG
 Pro Leu Thr Ser Arg Val Lys Pro Asp Pro Pro His Ile Lys Asn Leu>

    1350         1360         1370         1380         1390
 *     *     *     *     *     *     *     *     *     *
 TCC TTC CAC AAT GAT GAC CTA TAT GTG CAA TGG GAG AAT CCA CAG AAT
 AGG AAG GTG TTA CTA CTG GAT ATA CAC GTT ACC CTC TTA GGT GTC TTA
 Ser Phe His Asn Asp Asp Leu Tyr Val Gln Trp Glu Asn Pro Gln Asn>

       1400         1410         1420         1430         1440
   *     *     *     *     *     *     *     *     *     *
 TTT ATT AGC AGA TGC CTA TTT TAT GAA GTA GAA GTC AAT AAC AGC CAA
 AAA TAA TCG TCT ACG GAT AAA ATA CTT CAT CTT CAG TTA TTG TCG GTT
 Phe Ile Ser Arg Cys Leu Phe Tyr Glu Val Glu Val Asn Asn Ser Gln>

         1450         1460         1470          1480
       *     *     *     *     *     *     *     *     *
 ACT GAG ACA CAT AAT GTT TTC TAC GTC CAA GAG GCT AAA TGT GAG AAT
 TGA CTC TGT GTA TTA CAA AAG ATG CAG GTT CTC CGA TTT ACA CTC TTA
 Thr Glu Thr His Asn Val Phe Tyr Val Gln Glu Ala Lys Cys Glu Asn>

1490         1500         1510         1520         1530
   *     *     *     *     *     *     *     *     *     *
 CCA GAA TTT GAG AGA AAT GTG GAG AAT ACA TCT TGT TTC ATG GTC CCT
 GGT CTT AAA CTC TCT TTA CAC CTC TTA TGT AGA ACA AAG TAC CAG GGA
 Pro Glu Phe Glu Arg Asn Val Glu Asn Thr Ser Cys Phe Met Val Pro>
```

Fig.31E.

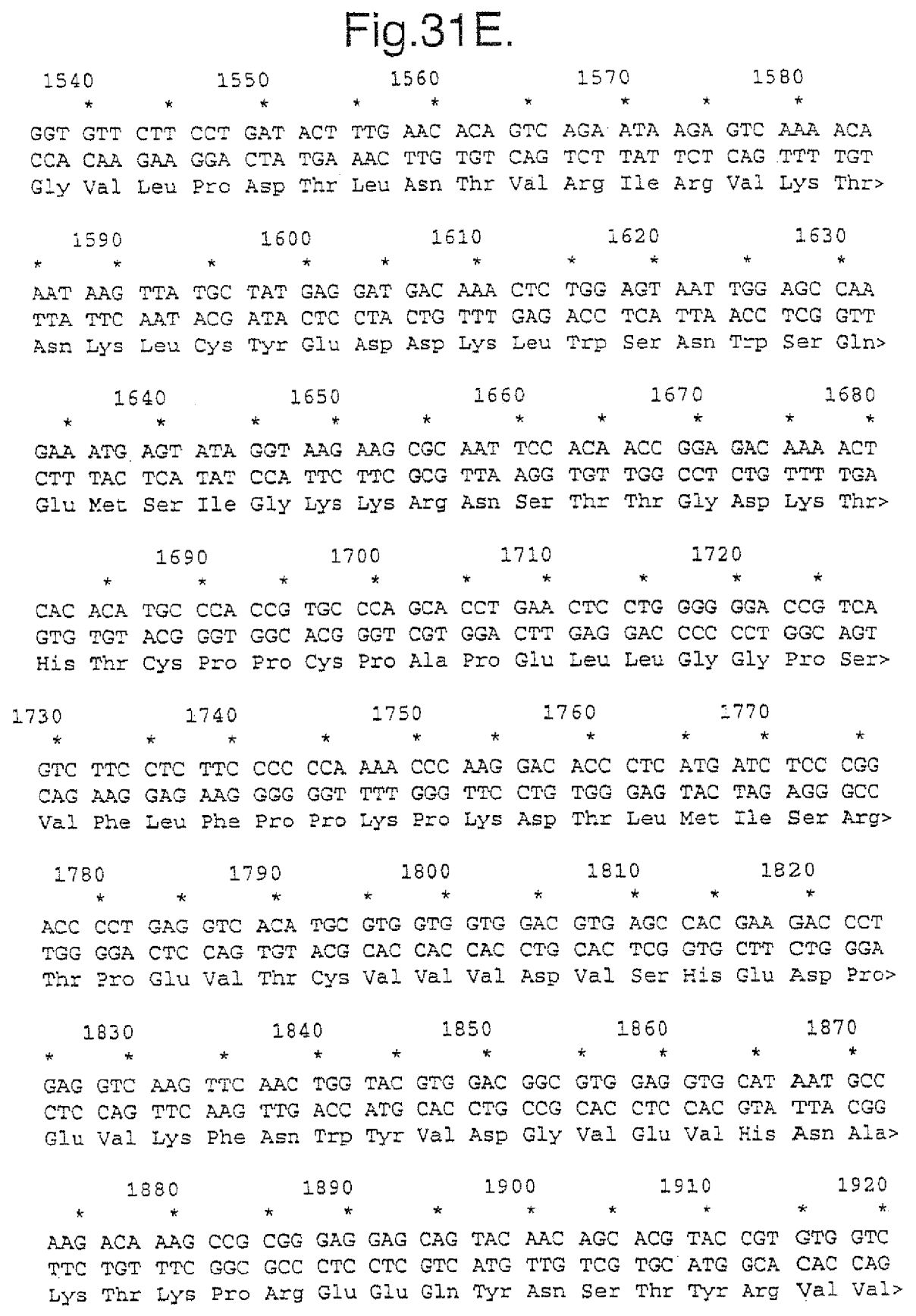

1540 1550 1560 1570 1580
GGT GTT CTT CCT GAT ACT TTG AAC ACA GTC AGA ATA AGA GTC AAA ACA
CCA CAA GAA GGA CTA TGA AAC TTG TGT CAG TCT TAT TCT CAG TTT TGT
Gly Val Leu Pro Asp Thr Leu Asn Thr Val Arg Ile Arg Val Lys Thr>

1590 1600 1610 1620 1630
AAT AAG TTA TGC TAT GAG GAT GAC AAA CTC TGG AGT AAT TGG AGC CAA
TTA TTC AAT ACG ATA CTC CTA CTG TTT GAG ACC TCA TTA ACC TCG GTT
Asn Lys Leu Cys Tyr Glu Asp Asp Lys Leu Trp Ser Asn Trp Ser Gln>

1640 1650 1660 1670 1680
GAA ATG AGT ATA GGT AAG AAG CGC AAT TCC ACA ACC GGA GAC AAA ACT
CTT TAC TCA TAT CCA TTC TTC GCG TTA AGG TGT TGG CCT CTG TTT TGA
Glu Met Ser Ile Gly Lys Lys Arg Asn Ser Thr Thr Gly Asp Lys Thr>

1690 1700 1710 1720
CAC ACA TGC CCA CCG TGC CCA GCA CCT GAA CTC CTG GGG GGA CCG TCA
GTG TGT ACG GGT GGC ACG GGT CGT GGA CTT GAG GAC CCC CCT GGC AGT
His Thr Cys Pro Pro Cys Pro Ala Pro Glu Leu Leu Gly Gly Pro Ser>

1730 1740 1750 1760 1770
GTC TTC CTC TTC CCC CCA AAA CCC AAG GAC ACC CTC ATG ATC TCC CGG
CAG AAG GAG AAG GGG GGT TTT GGG TTC CTG TGG GAG TAC TAG AGG GCC
Val Phe Leu Phe Pro Pro Lys Pro Lys Asp Thr Leu Met Ile Ser Arg>

1780 1790 1800 1810 1820
ACC CCT GAG GTC ACA TGC GTG GTG GTG GAC GTG AGC CAC GAA GAC CCT
TGG GGA CTC CAG TGT ACG CAC CAC CAC CTG CAC TCG GTG CTT CTG GGA
Thr Pro Glu Val Thr Cys Val Val Val Asp Val Ser His Glu Asp Pro>

1830 1840 1850 1860 1870
GAG GTC AAG TTC AAC TGG TAC GTG GAC GGC GTG GAG GTG CAT AAT GCC
CTC CAG TTC AAG TTG ACC ATG CAC CTG CCG CAC CTC CAC GTA TTA CGG
Glu Val Lys Phe Asn Trp Tyr Val Asp Gly Val Glu Val His Asn Ala>

1880 1890 1900 1910 1920
AAG ACA AAG CCG CGG GAG GAG CAG TAC AAC AGC ACG TAC CGT GTG GTC
TTC TGT TTC GGC GCC CTC CTC GTC ATG TTG TCG TGC ATG GCA CAC CAG
Lys Thr Lys Pro Arg Glu Glu Gln Tyr Asn Ser Thr Tyr Arg Val Val>

Fig.31F.

```
        1930        1940        1950        1960
    *      *     *      *      *     *      *      *     *
AGC GTC CTC ACC GTC CTG CAC CAG GAC TGG CTG AAT GGC AAG GAG TAC
TCG CAG GAG TGG CAG GAC GTG GTC CTG ACC GAC TTA CCG TTC CTC ATG
Ser Val Leu Thr Val Leu His Gln Asp Trp Leu Asn Gly Lys Glu Tyr>

1970       1980        1990        2000        2010
  *     *     *     *     *     *     *     *     *     *
AAG TGC AAG GTC TCC AAC AAA GCC CTC CCA GCC CCC ATC GAG AAA ACC
TTC ACG TTC CAG AGG TTG TTT CGG GAG GGT CGG GGG TAG CTC TTT TGG
Lys Cys Lys Val Ser Asn Lys Ala Leu Pro Ala Pro Ile Glu Lys Thr>

 2020       2030        2040        2050        2060
    *    *     *     *     *     *     *     *     *
ATC TCC AAA GCC AAA GGG CAG CCC CGA GAA CCA CAG GTG TAC ACC CTG
TAG AGG TTT CGG TTT CCC GTC GGG GCT CTT GGT GTC CAC ATG TGG GAC
Ile Ser Lys Ala Lys Gly Gln Pro Arg Glu Pro Gln Val Tyr Thr Leu>

   2070        2080        2090        2100        2110
 *     *     *     *     *     *     *     *     *     *
CCC CCA TCC CGG GAG GAG ATG ACC AAG AAC CAG GTC AGC CTG ACC TGC
GGG GGT AGG GCC CTC CTC TAC TGG TTC TTG GTC CAG TCG GAC TGG ACG
Pro Pro Ser Arg Glu Glu Met Thr Lys Asn Gln Val Ser Leu Thr Cys>

     2120        2130        2140        2150        2160
  *     *     *     *     *     *     *     *     *     *
CTG GTC AAA GGC TTC TAT CCC AGC GAC ATC GCC GTG GAG TGG GAG AGC
GAC CAG TTT CCG AAG ATA GGG TCG CTG TAG CGG CAC CTC ACC CTC TCG
Leu Val Lys Gly Phe Tyr Pro Ser Asp Ile Ala Val Glu Trp Glu Ser>

        2170        2180        2190        2200
    *      *     *      *     *     *      *     *     *
AAT GGG CAG CCG GAG AAC AAC TAC AAG ACC ACG CCT CCC GTG CTG GAC
TTA CCC GTC GGC CTC TTG TTG ATG TTC TGG TGC GGA GGG CAC GAC CTG
Asn Gly Gln Pro Glu Asn Asn Tyr Lys Thr Thr Pro Pro Val Leu Asp>

2210       2220        2230        2240        2250
  *     *     *     *     *     *     *     *     *     *
TCC GAC GGC TCC TTC TTC CTC TAT AGC AAG CTC ACC GTG GAC AAG AGC
AGG CTG CCG AGG AAG AAG GAG ATA TCG TTC GAG TGG CAC CTG TTC TCG
Ser Asp Gly Ser Phe Phe Leu Tyr Ser Lys Leu Thr Val Asp Lys Ser>

 2260        2270        2280        2290        2300
    *     *     *     *     *     *     *     *     *
AGG TGG CAG CAG GGG AAC GTC TTC TCA TGC TCC GTG ATG CAT GAG GCT
TCC ACC GTC GTC CCC TTG CAG AAG AGT ACG AGG CAC TAC GTA CTC CGA
Arg Trp Gln Gln Gly Asn Val Phe Ser Cys Ser Val Met His Glu Ala>
```

Fig.31G.

```
   2310            2320          2330          2340           2350
*      *      *      *      *      *      *      *      *      *
CTG CAC AAC CAC TAC ACG CAG AAG AGC CTC TCC CTG TCT CCG GGT AAA
GAC GTG TTG GTG ATG TGC GTC TTC TCG GAG AGG GAC AGA GGC CCA TTT
Leu His Asn His Tyr Thr Gln Lys Ser Leu Ser Leu Ser Pro Gly Lys>

  *
TGA
ACT
***>
```

Fig.32A.

```
              10          20          30          40
       *     *     *     *     *     *     *     *     *
ATG GTG TGG CCG GCG CGG CTC TGC GGG CTG TGG GCG CTG CTG CTC TGC
TAC CAC ACC GGC CGC GCC GAG ACG CCC GAC ACC CGC GAC GAC GAG ACG
Met Val Trp Pro Ala Arg Leu Cys Gly Leu Trp Ala Leu Leu Leu Cys>

50          60          70          80          90
 *     *     *     *     *     *     *     *     *     *
GCC GGC GGC GGG GGC GGG GGC GGG GGC GCC GCG CCT ACG GAA ACT CAG
CGG CCG CCG CCC CCG CCC CCG CCC CCG CGG CGC GGA TGC CTT TGA GTC
Ala Gly Gly Gly Gly Gly Gly Gly Gly Ala Ala Pro Thr Glu Thr Gln>

  100         110         120         130         140
    *     *     *     *     *     *     *     *     *
CCA CCT GTG ACA AAT TTG AGT GTC TCT GTT GAA AAC CTC TGC ACA GTA
GGT GGA CAC TGT TTA AAC TCA CAG AGA CAA CTT TTG GAG ACG TGT CAT
Pro Pro Val Thr Asn Leu Ser Val Ser Val Glu Asn Leu Cys Thr Val>

    150         160         170         180         190
*     *     *     *     *     *     *     *     *     *
ATA TGG ACA TGG AAT CCA CCC GAG GGA GCC AGC TCA AAT TGT AGT CTA
TAT ACC TGT ACC TTA GGT GGG CTC CCT CGG TCG AGT TTA ACA TCA GAT
Ile Trp Thr Trp Asn Pro Pro Glu Gly Ala Ser Ser Asn Cys Ser Leu>

        200         210         220         230         240
  *     *     *     *     *     *     *     *     *     *
TGG TAT TTT AGT CAT TTT GGC GAC AAA CAA GAT AAG AAA ATA GCT CCG
ACC ATA AAA TCA GTA AAA CCG CTG TTT GTT CTA TTC TTT TAT CGA GGC
Trp Tyr Phe Ser His Phe Gly Asp Lys Gln Asp Lys Lys Ile Ala Pro>

            250         260         270         280
      *     *     *     *     *     *     *     *     *
GAA ACT CGT CGT TCA ATA GAA GTA CCC CTG AAT GAG AGG ATT TGT CTG
CTT TGA GCA GCA AGT TAT CTT CAT GGG GAC TTA CTC TCC TAA ACA GAC
Glu Thr Arg Arg Ser Ile Glu Val Pro Leu Asn Glu Arg Ile Cys Leu>

290         300         310         320         330
 *     *     *     *     *     *     *     *     *     *
CAA GTG GGG TCC CAG TGT AGC ACC AAT GAG AGT GAG AAG CCT AGC ATT
GTT CAC CCC AGG GTC ACA TCG TGG TTA CTC TCA CTC TTC GGA TCG TAA
Gln Val Gly Ser Gln Cys Ser Thr Asn Glu Ser Glu Lys Pro Ser Ile>

  340         350         360         370         380
    *     *     *     *     *     *     *     *     *
TTG GTT GAA AAA TGC ATC TCA CCC CCA GAA GGT GAT CCT GAG TCT GCT
AAC CAA CTT TTT ACG TAG AGT GGG GGT CTT CCA CTA GGA CTC AGA CGA
Leu Val Glu Lys Cys Ile Ser Pro Pro Glu Gly Asp Pro Glu Ser Ala>
```

Fig.32B.

```
     390         400        410        420        430
*    *     *     *    *     *     *    *     *    *
GTG ACT GAG CTT CAA TGC ATT TGG CAC AAC CTG AGC TAC ATG AAG TGT
CAC TGA CTC GAA GTT ACG TAA ACC GTG TTG GAC TCG ATG TAC TTC ACA
Val Thr Glu Leu Gln Cys Ile Trp His Asn Leu Ser Tyr Met Lys Cys>

       440        450         460        470        480
 *     *     *    *     *     *    *     *     *    *
TCT TGG CTC CCT GGA AGG AAT ACC AGT CCC GAC ACT AAC TAT ACT CTC
AGA ACC GAG GGA CCT TCC TTA TGG TCA GGG CTG TGA TTG ATA TGA GAG
Ser Trp Leu Pro Gly Arg Asn Thr Ser Pro Asp Thr Asn Tyr Thr Leu>

          490        500        510        520
     *     *    *     *    *     *    *     *    *
TAC TAT TGG CAC AGA AGC CTG GAA AAA ATT CAT CAA TGT GAA AAC ATC
ATG ATA ACC GTG TCT TCG GAC CTT TTT TAA GTA GTT ACA CTT TTG TAG
Tyr Tyr Trp His Arg Ser Leu Glu Lys Ile His Gln Cys Glu Asn Ile>

530        540        550        560        570
 *     *    *     *     *    *     *     *    *     *
TTT AGA GAA GGC CAA TAC TTT GGT TGT TCC TTT GAT CTG ACC AAA GTG
AAA TCT CTT CCG GTT ATG AAA CCA ACA AGG AAA CTA GAC TGG TTT CAC
Phe Arg Glu Gly Gln Tyr Phe Gly Cys Ser Phe Asp Leu Thr Lys Val>

   580        590        600        610        620
    *     *     *    *     *     *    *     *    *
AAG GAT TCC AGT TTT GAA CAA CAC AGT GTC CAA ATA ATG GTC AAG GAT
TTC CTA AGG TCA AAA CTT GTT GTG TCA CAG GTT TAT TAC CAG TTC CTA
Lys Asp Ser Ser Phe Glu Gln His Ser Val Gln Ile Met Val Lys Asp>

      630        640        650        660        670
 *     *     *    *     *     *    *     *    *     *
AAT GCA GGA AAA ATT AAA CCA TCC TTC AAT ATA GTG CCT TTA ACT TCC
TTA CGT CCT TTT TAA TTT GGT AGG AAG TTA TAT CAC GGA AAT TGA AGG
Asn Ala Gly Lys Ile Lys Pro Ser Phe Asn Ile Val Pro Leu Thr Ser>

       680        690        700        710        720
  *     *     *    *     *     *    *     *    *     *
CGT GTG AAA CCT GAT CCT CCA CAT ATT AAA AAC CTC TCC TTC CAC AAT
GCA CAC TTT GGA CTA GGA GGT GTA TAA TTT TTG GAG AGG AAG GTG TTA
Arg Val Lys Pro Asp Pro Pro His Ile Lys Asn Leu Ser Phe His Asn>

          730        740        750        760
     *     *    *     *    *     *    *     *    *
GAT GAC CTA TAT GTG CAA TGG GAG AAT CCA CAG AAT TTT ATT AGC AGA
CTA CTG GAT ATA CAC GTT ACC CTC TTA GGT GTC TTA AAA TAA TCG TCT
Asp Asp Leu Tyr Val Gln Trp Glu Asn Pro Gln Asn Phe Ile Ser Arg>
```

Fig.32C.

```
770         780           790          800          810
 *      *     *      *      *     *      *      *     *      *
TGC CTA TTT TAT GAA GTA GAA GTC AAT AAC AGC CAA ACT GAG ACA CAT
ACG GAT AAA ATA CTT CAT CTT CAG TTA TTG TCG GTT TGA CTC TGT GTA
Cys Leu Phe Tyr Glu Val Glu Val Asn Asn Ser Gln Thr Glu Thr His>

   820         830          840          850          860
     *     *     *      *     *      *      *     *      *
AAT GTT TTC TAC GTC CAA GAG GCT AAA TGT GAG AAT CCA GAA TTT GAG
TTA CAA AAG ATG CAG GTT CTC CGA TTT ACA CTC TTA GGT CTT AAA CTC
Asn Val Phe Tyr Val Gln Glu Ala Lys Cys Glu Asn Pro Glu Phe Glu>

     870          880          890          900           910
*     *      *      *     *      *      *     *      *      *
AGA AAT GTG GAG AAT ACA TCT TGT TTC ATG GTC CCT GGT GTT CTT CCT
TCT TTA CAC CTC TTA TGT AGA ACA AAG TAC CAG GGA CCA CAA GAA GGA
Arg Asn Val Glu Asn Thr Ser Cys Phe Met Val Pro Gly Val Leu Pro>

        920          930           940          950          960
  *      *      *     *      *      *     *      *      *     *
GAT ACT TTG AAC ACA GTC AGA ATA AGA GTC AAA ACA AAT AAG TTA TGC
CTA TGA AAC TTG TGT CAG TCT TAT TCT CAG TTT TGT TTA TTC AAT ACG
Asp Thr Leu Asn Thr Val Arg Ile Arg Val Lys Thr Asn Lys Leu Cys>

           970          980          990         1000
      *      *     *      *      *     *      *      *     *
TAT GAG GAT GAC AAA CTC TGG AGT AAT TGG AGC CAA GAA ATG AGT ATA
ATA CTC CTA CTG TTT GAG ACC TCA TTA ACC TCG GTT CTT TAC TCA TAT
Tyr Glu Asp Asp Lys Leu Trp Ser Asn Trp Ser Gln Glu Met Ser Ile>

1010         1020          1030         1040         1050
  *      *     *      *      *     *      *      *     *      *
GGT AAG AAG CGC AAT TCC ACA GGC GCG CCT AGT GGT GGA GGT GGC CGG
CCA TTC TTC GCG TTA AGG TGT CCG CGC GGA TCA CCA CCT CCA CCG GCC
Gly Lys Lys Arg Asn Ser Thr Gly Ala Pro Ser Gly Gly Gly Gly Arg>

  1060         1070         1080          1090         1100
      *     *      *      *     *      *      *     *      *
CCC GCA AGC TCT GGG AAC ATG AAG GTC TTG CAG GAG CCC ACC TGC GTC
GGG CGT TCG AGA CCC TTG TAC TTC CAG AAC GTC CTC GGG TGG ACG CAG
Pro Ala Ser Ser Gly Asn Met Lys Val Leu Gln Glu Pro Thr Cys Val>

    1110         1120         1130         1140          1150
*      *      *      *     *      *      *     *      *      *
TCC GAC TAC ATG AGC ATC TCT ACT TGC GAG TGG AAG ATG AAT GGT CCC
AGG CTG ATG TAC TCG TAG AGA TGA ACG CTC ACC TTC TAC TTA CCA GGG
Ser Asp Tyr Met Ser Ile Ser Thr Cys Glu Trp Lys Met Asn Gly Pro>
```

Fig.32D.

```
      1160       1170       1180       1190       1200
   *     *     *     *     *     *     *     *     *     *
ACC AAT TGC AGC ACC GAG CTC CGC CTG TTG TAC CAG CTG GTT TTT CTG
TGG TTA ACG TCG TGG CTC GAG GCG GAC AAC ATG GTC GAC CAA AAA GAC
Thr Asn Cys Ser Thr Glu Leu Arg Leu Leu Tyr Gln Leu Val Phe Leu>

         1210       1220       1230       1240
      *     *     *     *     *     *     *     *     *
CTC TCC GAA GCC CAC ACG TGT ATC CCT GAG AAC AAC GGA GGC GCG GGG
GAG AGG CTT CGG GTG TGC ACA TAG GGA CTC TTG TTG CCT CCG CGC CCC
Leu Ser Glu Ala His Thr Cys Ile Pro Glu Asn Asn Gly Gly Ala Gly>

1250       1260       1270       1280       1290
   *     *     *     *     *     *     *     *     *     *
TGC GTG TGC CAC CTG CTC ATG GAT GAC GTG GTC AGT GCG GAT AAC TAT
ACG CAC ACG GTG GAC GAG TAC CTA CTG CAC CAG TCA CGC CTA TTG ATA
Cys Val Cys His Leu Leu Met Asp Asp Val Val Ser Ala Asp Asn Tyr>

  1300       1310       1320       1330       1340
      *     *     *     *     *     *     *     *     *
ACA CTG GAC CTG TGG GCT GGG CAG CAG CTG CTG TGG AAG GGC TCC TTC
TGT GAC CTG GAC ACC CGA CCC GTC GTC GAC GAC ACC TTC CCG AGG AAG
Thr Leu Asp Leu Trp Ala Gly Gln Gln Leu Leu Trp Lys Gly Ser Phe>

    1350       1360       1370       1380       1390
 *     *     *     *     *     *     *     *     *     *
AAG CCC AGC GAG CAT GTG AAA CCC AGG GCC CCA GGA AAC CTG ACA GTT
TTC GGG TCG CTC GTA CAC TTT GGG TCC CGG GGT CCT TTG GAC TGT CAA
Lys Pro Ser Glu His Val Lys Pro Arg Ala Pro Gly Asn Leu Thr Val>

       1400       1410       1420       1430       1440
  *     *     *     *     *     *     *     *     *     *
CAC ACC AAT GTC TCC GAC ACT CTG CTG CTG ACC TGG AGC AAC CCG TAT
GTG TGG TTA CAG AGG CTG TGA GAC GAC GAC TGG ACC TCG TTG GGC ATA
His Thr Asn Val Ser Asp Thr Leu Leu Leu Thr Trp Ser Asn Pro Tyr>

         1450       1460       1470       1480
      *     *     *     *     *     *     *     *     *
CCC CCT GAC AAT TAC CTG TAT AAT CAT CTC ACC TAT GCA GTC AAC ATT
GGG GGA CTG TTA ATG GAC ATA TTA GTA GAG TGG ATA CGT CAG TTG TAA
Pro Pro Asp Asn Tyr Leu Tyr Asn His Leu Thr Tyr Ala Val Asn Ile>

1490       1500       1510       1520       1530
   *     *     *     *     *     *     *     *     *     *
TGG AGT GAA AAC GAC CCG GCA GAT TTC AGA ATC TAT AAC GTG ACC TAC
ACC TCA CTT TTG CTG GGC CGT CTA AAG TCT TAG ATA TTG CAC TGG ATG
Trp Ser Glu Asn Asp Pro Ala Asp Phe Arg Ile Tyr Asn Val Thr Tyr>
```

Fig.32E.

```
 1540        1550        1560        1570        1580
   *    *     *     *     *     *     *     *     *
CTA GAA CCC TCC CTC CGC ATC GCA GCC AGC ACC CTG AAG TCT GGG ATT
GAT CTT GGG AGG GAG GCG TAG CGT CGG TCG TGG GAC TTC AGA CCC TAA
Leu Glu Pro Ser Leu Arg Ile Ala Ala Ser Thr Leu Lys Ser Gly Ile>

   1590        1600        1610        1620        1630
*     *     *     *     *     *     *     *     *     *
TCC TAC AGG GCA CGG GTG AGG GCC TGG GCT CAG TGC TAT AAC ACC ACC
AGG ATG TCC CGT GCC CAC TCC CGG ACC CGA GTC ACG ATA TTG TGG TGG
Ser Tyr Arg Ala Arg Val Arg Ala Trp Ala Gln Cys Tyr Asn Thr Thr>

      1640        1650        1660        1670        1680
  *     *     *     *     *     *     *     *     *     *
TGG AGT GAG TGG AGC CCC AGC ACC AAG TGG CAC AAC TCC TAC AGG GAG
ACC TCA CTC ACC TCG GGG TCG TGG TTC ACC GTG TTG AGG ATG TCC CTC
Trp Ser Glu Trp Ser Pro Ser Thr Lys Trp His Asn Ser Tyr Arg Glu>

         1690        1700        1710        1720
    *     *     *     *     *     *     *     *     *
CCC TTC GAG CAG TCC GGA GAC AAA ACT CAC ACA TGC CCA CCG TGC CCA
GGG AAG CTC GTC AGG CCT CTG TTT TGA GTG TGT ACG GGT GGC ACG GGT
Pro Phe Glu Gln Ser Gly Asp Lys Thr His Thr Cys Pro Pro Cys Pro>

1730        1740        1750        1760        1770
  *     *     *     *     *     *     *     *     *     *
GCA CCT GAA CTC CTG GGG GGA CCG TCA GTC TTC CTC TTC CCC CCA AAA
CGT GGA CTT GAG GAC CCC CCT GGC AGT CAG AAG GAG AAG GGG GGT TTT
Ala Pro Glu Leu Leu Gly Gly Pro Ser Val Phe Leu Phe Pro Pro Lys>

 1780        1790        1800        1810        1820
    *     *     *     *     *     *     *     *     *
CCC AAG GAC ACC CTC ATG ATC TCC CGG ACC CCT GAG GTC ACA TGC GTG
GGG TTC CTG TGG GAG TAC TAG AGG GCC TGG GGA CTC CAG TGT ACG CAC
Pro Lys Asp Thr Leu Met Ile Ser Arg Thr Pro Glu Val Thr Cys Val>

   1830        1840        1850        1860        1870
*     *     *     *     *     *     *     *     *     *
GTG GTG GAC GTG AGC CAC GAA GAC CCT GAG GTC AAG TTC AAC TGG TAC
CAC CAC CTG CAC TCG GTG CTT CTG GGA CTC CAG TTC AAG TTG ACC ATG
Val Val Asp Val Ser His Glu Asp Pro Glu Val Lys Phe Asn Trp Tyr>

      1880        1890        1900        1910        1920
  *     *     *     *     *     *     *     *     *     *
GTG GAC GGC GTG GAG GTG CAT AAT GCC AAG ACA AAG CCG CGG GAG GAG
CAC CTG CCG CAC CTC CAC GTA TTA CGG TTC TGT TTC GGC GCC CTC CTC
Val Asp Gly Val Glu Val His Asn Ala Lys Thr Lys Pro Arg Glu Glu>
```

Fig.32F.

1930 1940 1950 1960
* * * * * * * * *
CAG TAC AAC AGC ACG TAC CGT GTG GTC AGC GTC CTC ACC GTC CTG CAC
GTC ATG TTG TCG TGC ATG GCA CAC CAG TCG CAG GAG TGG CAG GAC GTG
Gln Tyr Asn Ser Thr Tyr Arg Val Val Ser Val Leu Thr Val Leu His>

1970 1980 1990 2000 2010
* * * * * * * * * *
CAG GAC TGG CTG AAT GGC AAG GAG TAC AAG TGC AAG GTC TCC AAC AAA
GTC CTG ACC GAC TTA CCG TTC CTC ATG TTC ACG TTC CAG AGG TTG TTT
Gln Asp Trp Leu Asn Gly Lys Glu Tyr Lys Cys Lys Val Ser Asn Lys>

2020 2030 2040 2050 2060
* * * * * * * * *
GCC CTC CCA GCC CCC ATC GAG AAA ACC ATC TCC AAA GCC AAA GGG CAG
CGG GAG GGT CGG GGG TAG CTC TTT TGG TAG AGG TTT CGG TTT CCC GTC
Ala Leu Pro Ala Pro Ile Glu Lys Thr Ile Ser Lys Ala Lys Gly Gln>

2070 2080 2090 2100 2110
* * * * * * * * * *
CCC CGA GAA CCA CAG GTG TAC ACC CTG CCC CCA TCC CGG GAG GAG ATG
GGG GCT CTT GGT GTC CAC ATG TGG GAC GGG GGT AGG GCC CTC CTC TAC
Pro Arg Glu Pro Gln Val Tyr Thr Leu Pro Pro Ser Arg Glu Glu Met>

2120 2130 2140 2150 2160
* * * * * * * * * *
ACC AAG AAC CAG GTC AGC CTG ACC TGC CTG GTC AAA GGC TTC TAT CCC
TGG TTC TTG GTC CAG TCG GAC TGG ACG GAC CAG TTT CCG AAG ATA GGG
Thr Lys Asn Gln Val Ser Leu Thr Cys Leu Val Lys Gly Phe Tyr Pro>

2170 2180 2190 2200
* * * * * * * * *
AGC GAC ATC GCC GTG GAG TGG GAG AGC AAT GGG CAG CCG GAG AAC AAC
TCG CTG TAG CGG CAC CTC ACC CTC TCG TTA CCC GTC GGC CTC TTG TTG
Ser Asp Ile Ala Val Glu Trp Glu Ser Asn Gly Gln Pro Glu Asn Asn>

2210 2220 2230 2240 2250
* * * * * * * * * *
TAC AAG ACC ACG CCT CCC GTG CTG GAC TCC GAC GGC TCC TTC TTC CTC
ATG TTC TGG TGC GGA GGG CAC GAC CTG AGG CTG CCG AGG AAG AAG GAG
Tyr Lys Thr Thr Pro Pro Val Leu Asp Ser Asp Gly Ser Phe Phe Leu>

2260 2270 2280 2290 2300
* * * * * * * * *
TAT AGC AAG CTC ACC GTG GAC AAG AGC AGG TGG CAG CAG GGG AAC GTC
ATA TCG TTC GAG TGG CAC CTG TTC TCG TCC ACC GTC GTC CCC TTG CAG
Tyr Ser Lys Leu Thr Val Asp Lys Ser Arg Trp Gln Gln Gly Asn Val>

```
  2310            2320            2330            2340            2350
*      *       *       *       *       *       *       *       *       *
TTC TCA TGC TCC GTG ATG CAT GAG GCT CTG CAC AAC CAC TAC ACG CAG
AAG AGT ACG AGG CAC TAC GTA CTC CGA GAC GTG TTG GTG ATG TGC GTC
Phe Ser Cys Ser Val Met His Glu Ala Leu His Asn His Tyr Thr Gln>

      2360            2370            2380
  *       *       *      *       *       *
AAG AGC CTC TCC CTG TCT CCG GGT AAA TGA
TTC TCG GAG AGG GAC AGA GGC CCA TTT ACT
Lys Ser Leu Ser Leu Ser Pro Gly Lys ***>
```

Figure 38A

```
          10         20         30         40
     *     *    *     *     *    *     *     *
ATG GTG TTA CTC AGA CTT ATT TGT TTC ATA GCT CTA CTG ATT
TAC CAC AAT GAG TCT GAA TAA ACA AAG TAT CGA GAT GAC TAA
Met Val Leu Leu Arg Leu Ile Cys Phe Ile Ala Leu Leu Ile>
_____________________SIGNAL PEPTIDE____________________>
__________________________IL-1RI_______________________>

        50         60         70         80
  *     *     *    *     *     *    *     *
TCT TCT CTG GAG GCT GAT AAA TGC AAG GAA CGT GAA GAA AAA
AGA AGA GAC CTC CGA CTA TTT ACG TTC CTT GCA CTT CTT TTT
Ser Ser Leu Glu Ala Asp>
____SIGNAL PEPTIDE_____>
                        Lys Cys Lys Glu Arg Glu Glu Lys>
__________________________IL-1RI_______________________>

     90         100        110        120
*     *     *     *    *     *     *    *     *
ATA ATT TTA GTG TCA TCT GCA AAT GAA ATT GAT GTT CGT CCC
TAT TAA AAT CAC AGT AGA CGT TTA CTT TAA CTA CAA GCA GGG
Ile Ile Leu Val Ser Ser Ala Asn Glu Ile Asp Val Arg Pro>
__________________________IL-1RI_______________________>

  130        140        150        160
    *     *     *     *     *     *     *     *
TGT CCT CTT AAC CCA AAT GAA CAC AAA GGC ACT ATA ACT TGG
ACA GGA GAA TTG GGT TTA CTT GTG TTT CCG TGA TAT TGA ACC
Cys Pro Leu Asn Pro Asn Glu His Lys Gly Thr Ile Thr Trp>
__________________________IL-1RI_______________________>

170        180        190        200        210
 *     *     *     *     *     *     *     *     *
TAT AAG GAT GAC AGC AAG ACA CCT GTA TCT ACA GAA CAA GCC
ATA TTC CTA CTG TCG TTC TGT GGA CAT AGA TGT CTT GTT CGG
Tyr Lys Asp Asp Ser Lys Thr Pro Val Ser Thr Glu Gln Ala>
__________________________IL-1RI_______________________>

          220        230        240        250
     *     *     *     *     *     *     *     *
TCC AGG ATT CAT CAA CAC AAA GAG AAA CTT TGG TTT GTT CCT
AGG TCC TAA GTA GTT GTG TTT CTC TTT GAA ACC AAA CAA GGA
Ser Arg Ile His Gln His Lys Glu Lys Leu Trp Phe Val Pro>
__________________________IL-1RI_______________________>

        260        270        280        290
  *     *     *     *     *     *     *     *
GCT AAG GTG GAG GAT TCA GGA CAT TAC TAT TGC GTG GTA AGA
CGA TTC CAC CTC CTA AGT CCT GTA ATG ATA ACG CAC CAT TCT
Ala Lys Val Glu Asp Ser Gly His Tyr Tyr Cys Val Val Arg>
__________________________IL-1RI_______________________>
```

Figure 38B

```
    300         310         320         330
 *     *     *     *     *     *     *     *     *
AAT TCA TCT TAC TGC CTC AGA ATT AAA ATA AGT GCA AAA TTT
TTA AGT AGA ATG ACG GAG TCT TAA TTT TAT TCA CGT TTT AAA
Asn Ser Ser Tyr Cys Leu Arg Ile Lys Ile Ser Ala Lys Phe>
________________________IL-1RI_______________________>

  340         350         360         370
     *     *     *     *     *     *     *     *
GTG GAG AAT GAG CCT AAC TTA TGT TAT AAT GCA CAA GCC ATA
CAC CTC TTA CTC GGA TTG AAT ACA ATA TTA CGT GTT CGG TAT
Val Glu Asn Glu Pro Asn Leu Cys Tyr Asn Ala Gln Ala Ile>
________________________IL-1RI_______________________>

380         390         400         410         420
 *      *     *     *     *     *     *     *     *
TTT AAG CAG AAA CTA CCC GTT GCA GGA GAC GGA GGA CTT GTG
AAA TTC GTC TTT GAT GGG CAA CGT CCT CTG CCT CCT GAA CAC
Phe Lys Gln Lys Leu Pro Val Ala Gly Asp Gly Gly Leu Val>
________________________IL-1RI_______________________>

        430         440         450         460
     *     *     *     *     *     *     *     *
TGC CCT TAT ATG GAG TTT TTT AAA AAT GAA AAT AAT GAG TTA
ACG GGA ATA TAC CTC AAA AAA TTT TTA CTT TTA TTA CTC AAT
Cys Pro Tyr Met Glu Phe Phe Lys Asn Glu Asn Asn Glu Leu>
________________________IL-1RI_______________________>

      470         480         490         500
 *      *     *     *     *     *     *     *
CCT AAA TTA CAG TGG TAT AAG GAT TGC AAA CCT CTA CTT CTT
GGA TTT AAT GTC ACC ATA TTC CTA ACG TTT GGA GAT GAA GAA
Pro Lys Leu Gln Trp Tyr Lys Asp Cys Lys Pro Leu Leu Leu>
________________________IL-1RI_______________________>

    510         520         530         540
 *     *     *     *     *     *     *     *     *
GAC AAT ATA CAC TTT AGT GGA GTC AAA GAT AGG CTC ATC GTG
CTG TTA TAT GTG AAA TCA CCT CAG TTT CTA TCC GAG TAG CAC
Asp Asn Ile His Phe Ser Gly Val Lys Asp Arg Leu Ile Val>
________________________IL-1RI_______________________>

  550         560         570         580
     *     *     *     *     *     *     *     *
ATG AAT GTG GCT GAA AAG CAT AGA GGG AAC TAT ACT TGT CAT
TAC TTA CAC CGA CTT TTC GTA TCT CCC TTG ATA TGA ACA GTA
Met Asn Val Ala Glu Lys His Arg Gly Asn Tyr Thr Cys His>
________________________IL-1RI_______________________>

590         600         610         620         630
 *      *     *     *     *     *     *     *     *
GCA TCC TAC ACA TAC TTG GGC AAG CAA TAT CCT ATT ACC CGG
CGT AGG ATG TGT ATG AAC CCG TTC GTT ATA GGA TAA TGG GCC
Ala Ser Tyr Thr Tyr Leu Gly Lys Gln Tyr Pro Ile Thr Arg>
________________________IL-1RI_______________________>
```

Figure 38C

```
          640          650          660           670
     *      *     *      *      *      *      *      *
GTA ATA GAA TTT ATT ACT CTA GAG GAA AAC AAA CCC ACA AGG
CAT TAT CTT AAA TAA TGA GAT CTC CTT TTG TTT GGG TGT TCC
Val Ile Glu Phe Ile Thr Leu Glu Glu Asn Lys Pro Thr Arg>
________________________IL-1RI________________________>

       680          690          700          710
  *      *      *      *      *      *      *      *
CCT GTG ATT GTG AGC CCA GCT AAT GAG ACA ATG GAA GTA GAC
GGA CAC TAA CAC TCG GGT CGA TTA CTC TGT TAC CTT CAT CTG
Pro Val Ile Val Ser Pro Ala Asn Glu Thr Met Glu Val Asp>
________________________IL-1RI________________________>

    720          730          740          750
*     *      *      *      *      *      *      *      *
TTG GGA TCC CAG ATA CAA TTG ATC TGT AAT GTC ACC GGC CAG
AAC CCT AGG GTC TAT GTT AAC TAG ACA TTA CAG TGG CCG GTC
Leu Gly Ser Gln Ile Gln Leu Ile Cys Asn Val Thr Gly Gln>
________________________IL-1RI________________________>

  760          770          780          790
     *     *      *      *      *      *      *      *
TTG AGT GAC ATT GCT TAC TGG AAG TGG AAT GGG TCA GTA ATT
AAC TCA CTG TAA CGA ATG ACC TTC ACC TTA CCC AGT CAT TAA
Leu Ser Asp Ile Ala Tyr Trp Lys Trp Asn Gly Ser Val Ile>
________________________IL-1RI________________________>

800          810          820          830          840
 *      *      *      *      *      *      *      *     *
GAT GAA GAT GAC CCA GTG CTA GGG GAA GAC TAT TAC AGT GTG
CTA CTT CTA CTG GGT CAC GAT CCC CTT CTG ATA ATG TCA CAC
Asp Glu Asp Asp Pro Val Leu Gly Glu Asp Tyr Tyr Ser Val>
________________________IL-1RI________________________>

          850          860          870           880
     *      *     *      *      *      *      *      *
GAA AAT CCT GCA AAC AAA AGA AGG AGT ACC CTC ATC ACA GTG
CTT TTA GGA CGT TTG TTT TCT TCC TCA TGG GAG TAG TGT CAC
Glu Asn Pro Ala Asn Lys Arg Arg Ser Thr Leu Ile Thr Val>
________________________IL-1RI________________________>

       890          900          910          920
  *      *      *      *      *      *      *      *
CTT AAT ATA TCG GAA ATT GAG AGT AGA TTT TAT AAA CAT CCA
GAA TTA TAT AGC CTT TAA CTC TCA TCT AAA ATA TTT GTA GGT
Leu Asn Ile Ser Glu Ile Glu Ser Arg Phe Tyr Lys His Pro>
________________________IL-1RI________________________>

    930          940          950          960
*     *      *      *      *      *      *      *      *
TTT ACC TGT TTT GCC AAG AAT ACA CAT GGT ATA GAT GCA GCA
AAA TGG ACA AAA CGG TTC TTA TGT GTA CCA TAT CTA CGT CGT
Phe Thr Cys Phe Ala Lys Asn Thr His Gly Ile Asp Ala Ala>
________________________IL-1RI________________________>
```

Figure 38D

```
   970         980         990        1000
     *     *     *     *     *     *     *     *
TAT ATC CAG TTA ATA TAT CCA GTC ACT AAT TCA GAA CGC TGC
ATA TAG GTC AAT TAT ATA GGT CAG TGA TTA AGT CTT GCG ACG
Tyr Ile Gln Leu Ile Tyr Pro Val Thr Asn>
________________IL-1RI_______________>
                                        Ser Glu Arg Cys>
                                        ___IL-1RAcP____>

1010        1020        1030        1040        1050
   *      *     *     *     *     *     *     *     *
GAT GAC TGG GGA CTA GAC ACC ATG AGG CAA ATC CAA GTG TTT
CTA CTG ACC CCT GAT CTG TGG TAC TCC GTT TAG GTT CAC AAA
Asp Asp Trp Gly Leu Asp Thr Met Arg Gln Ile Gln Val Phe>
________________________IL-1RAcP_____________________>

         1060        1070        1080        1090
     *      *     *     *     *     *     *     *
GAA GAT GAG CCA GCT CGC ATC AAG TGC CCA CTC TTT GAA CAC
CTT CTA CTC GGT CGA GCG TAG TTC ACG GGT GAG AAA CTT GTG
Glu Asp Glu Pro Ala Arg Ile Lys Cys Pro Leu Phe Glu His>
________________________IL-1RAcP_____________________>

      1100        1110        1120        1130
  *      *     *     *     *     *     *     *
TTC TTG AAA TTC AAC TAC AGC ACA GCC CAT TCA GCT GGC CTT
AAG AAC TTT AAG TTG ATG TCG TGT CGG GTA AGT CGA CCG GAA
Phe Leu Lys Phe Asn Tyr Ser Thr Ala His Ser Ala Gly Leu>
________________________IL-1RAcP_____________________>

   1140        1150        1160        1170
*     *     *     *     *     *     *     *     *
ACT CTG ATC TGG TAT TGG ACT AGG CAG GAC CGG GAC CTT GAG
TGA GAC TAG ACC ATA ACC TGA TCC GTC CTG GCC CTG GAA CTC
Thr Leu Ile Trp Tyr Trp Thr Arg Gln Asp Arg Asp Leu Glu>
________________________IL-1RAcP_____________________>

 1180        1190        1200        1210
     *     *     *     *     *     *     *     *
GAG CCA ATT AAC TTC CGC CTC CCC GAG AAC CGC ATT AGT AAG
CTC GGT TAA TTG AAG GCG GAG GGG CTC TTG GCG TAA TCA TTC
Glu Pro Ile Asn Phe Arg Leu Pro Glu Asn Arg Ile Ser Lys>
________________________IL-1RAcP_____________________>

1220        1230        1240        1250        1260
  *      *     *     *     *     *     *     *     *
GAG AAA GAT GTG CTG TGG TTC CGG CCC ACT CTC CTC AAT GAC
CTC TTT CTA CAC GAC ACC AAG GCC GGG TGA GAG GAG TTA CTG
Glu Lys Asp Val Leu Trp Phe Arg Pro Thr Leu Leu Asn Asp>
________________________IL-1RAcP_____________________>
```

Figure 38E

```
        1270        1280        1290        1300
     *     *     *     *     *     *     *     *
ACT GGC AAC TAT ACC TGC ATG TTA AGG AAC ACT ACA TAT TGC
TGA CCG TTG ATA TGG ACG TAC AAT TCC TTG TGA TGT ATA ACG
Thr Gly Asn Tyr Thr Cys Met Leu Arg Asn Thr Thr Tyr Cys>
_________________________IL-1RAcP______________________>

     1310        1320        1330        1340
  *     *     *     *     *     *     *     *
AGC AAA GTT GCA TTT CCC TTG GAA GTT GTT CAA AAA GAC AGC
TCG TTT CAA CGT AAA GGG AAC CTT CAA CAA GTT TTT CTG TCG
Ser Lys Val Ala Phe Pro Leu Glu Val Val Gln Lys Asp Ser>
_________________________IL-1RAcP______________________>

   1350        1360        1370        1380
*     *     *     *     *     *     *     *     *
TGT TTC AAT TCC CCC ATG AAA CTC CCA GTG CAT AAA CTG TAT
ACA AAG TTA AGG GGG TAC TTT GAG GGT CAC GTA TTT GAC ATA
Cys Phe Asn Ser Pro Met Lys Leu Pro Val His Lys Leu Tyr>
_________________________IL-1RAcP______________________>

 1390        1400        1410        1420
    *     *     *     *     *     *     *     *
ATA GAA TAT GGC ATT CAG AGG ATC ACT TGT CCA AAT GTA GAT
TAT CTT ATA CCG TAA GTC TCC TAG TGA ACA GGT TTA CAT CTA
Ile Glu Tyr Gly Ile Gln Arg Ile Thr Cys Pro Asn Val Asp>
_________________________IL-1RAcP______________________>

1430        1440        1450        1460        1470
  *     *     *     *     *     *     *     *     *
GGA TAT TTT CCT TCC AGT GTC AAA CCG ACT ATC ACT TGG TAT
CCT ATA AAA GGA AGG TCA CAG TTT GGC TGA TAG TGA ACC ATA
Gly Tyr Phe Pro Ser Ser Val Lys Pro Thr Ile Thr Trp Tyr>
_________________________IL-1RAcP______________________>

        1480        1490        1500        1510
     *     *     *     *     *     *     *     *
ATG GGC TGT TAT AAA ATA CAG AAT TTT AAT AAT GTA ATA CCC
TAC CCG ACA ATA TTT TAT GTC TTA AAA TTA TTA CAT TAT GGG
Met Gly Cys Tyr Lys Ile Gln Asn Phe Asn Asn Val Ile Pro>
_________________________IL-1RAcP______________________>

     1520        1530        1540        1550
  *     *     *     *     *     *     *     *
GAA GGT ATG AAC TTG AGT TTC CTC ATT GCC TTA ATT TCA AAT
CTT CCA TAC TTG AAC TCA AAG GAG TAA CGG AAT TAA AGT TTA
Glu Gly Met Asn Leu Ser Phe Leu Ile Ala Leu Ile Ser Asn>
_________________________IL-1RAcP______________________>

   1560        1570        1580        1590
*     *     *     *     *     *     *     *     *
AAT GGA AAT TAC ACA TGT GTT GTT ACA TAT CCA GAA AAT GGA
TTA CCT TTA ATG TGT ACA CAA CAA TGT ATA GGT CTT TTA CCT
Asn Gly Asn Tyr Thr Cys Val Val Thr Tyr Pro Glu Asn Gly>
_________________________IL-1RAcP______________________>
```

Figure 38F

```
 1600        1610        1620        1630
    *     *     *     *     *     *     *     *
CGT ACG TTT CAT CTC ACC AGG ACT CTG ACT GTA AAG GTA GTA
GCA TGC AAA GTA GAG TGG TCC TGA GAC TGA CAT TTC CAT CAT
Arg Thr Phe His Leu Thr Arg Thr Leu Thr Val Lys Val Val>
_________________________IL-1RAcP______________________>

1640        1650        1660        1670        1680
 *     *     *     *     *     *     *     *     *
GGC TCT CCA AAA AAT GCA GTG CCC CCT GTG ATC CAT TCA CCT
CCG AGA GGT TTT TTA CGT CAC GGG GGA CAC TAG GTA AGT GGA
Gly Ser Pro Lys Asn Ala Val Pro Pro Val Ile His Ser Pro>
_________________________IL-1RAcP______________________>

      1690        1700        1710        1720
    *     *     *     *     *     *     *     *
AAT GAT CAT GTG GTC TAT GAG AAA GAA CCA GGA GAG GAG CTA
TTA CTA GTA CAC CAG ATA CTC TTT CTT GGT CCT CTC CTC GAT
Asn Asp His Val Val Tyr Glu Lys Glu Pro Gly Glu Glu Leu>
_________________________IL-1RAcP______________________>

    1730        1740        1750        1760
 *     *     *     *     *     *     *     *
CTC ATT CCC TGT ACG GTC TAT TTT AGT TTT CTG ATG GAT TCT
GAG TAA GGG ACA TGC CAG ATA AAA TCA AAA GAC TAC CTA AGA
Leu Ile Pro Cys Thr Val Tyr Phe Ser Phe Leu Met Asp Ser>
_________________________IL-1RAcP______________________>

   1770        1780        1790        1800
*     *     *     *     *     *     *     *     *
CGC AAT GAG GTT TGG TGG ACC ATT GAT GGA AAA AAA CCT GAT
GCG TTA CTC CAA ACC ACC TGG TAA CTA CCT TTT TTT GGA CTA
Arg Asn Glu Val Trp Trp Thr Ile Asp Gly Lys Lys Pro Asp>
_________________________IL-1RAcP______________________>

 1810        1820        1830        1840
    *     *     *     *     *     *     *     *
GAC ATC ACT ATT GAT GTC ACC ATT AAC GAA AGT ATA AGT CAT
CTG TAG TGA TAA CTA CAG TGG TAA TTG CTT TCA TAT TCA GTA
Asp Ile Thr Ile Asp Val Thr Ile Asn Glu Ser Ile Ser His>
_________________________IL-1RAcP______________________>

1850        1860        1870        1880        1890
 *     *     *     *     *     *     *     *     *
AGT AGA ACA GAA GAT GAA ACA AGA ACT CAG ATT TTG AGC ATC
TCA TCT TGT CTT CTA CTT TGT TCT TGA GTC TAA AAC TCG TAG
Ser Arg Thr Glu Asp Glu Thr Arg Thr Gln Ile Leu Ser Ile>
_________________________IL-1RAcP______________________>

      1900        1910        1920        1930
    *     *     *     *     *     *     *     *
AAG AAA GTT ACC TCT GAG GAT CTC AAG CGC AGC TAT GTC TGT
TTC TTT CAA TGG AGA CTC CTA GAG TTC GCG TCG ATA CAG ACA
Lys Lys Val Thr Ser Glu Asp Leu Lys Arg Ser Tyr Val Cys>
_________________________IL-1RAcP______________________>
```

Figure 38G

```
      1940        1950         1960        1970
  *     *     *     *     *     *     *     *
CAT GCT AGA AGT GCC AAA GGC GAA GTT GCC AAA GCA GCC AAG
GTA CGA TCT TCA CGG TTT CCG CTT CAA CGG TTT CGT CGG TTC
His Ala Arg Ser Ala Lys Gly Glu Val Ala Lys Ala Ala Lys>
______________________________IL-1RAcP___________________________>

   1980        1990        2000        2010
*     *     *     *     *     *     *     *     *
GTG AAG CAG AAA GTG CCA GCT CCA AGA TAC ACA GTG GAA TCC
CAC TTC GTC TTT CAC GGT CGA GGT TCT ATG TGT CAC CTT AGG
Val Lys Gln Lys Val Pro Ala Pro Arg Tyr Thr Val Glu>
_____________________________IL-1RAcP_______________________>
                                                    Ser>
                                                    ___>

  2020        2030        2040        2050
     *     *     *     *     *     *     *     *
GGA GAC AAA ACT CAC ACA TGC CCA CCG TGC CCA GCA CCT GAA
CCT CTG TTT TGA GTG TGT ACG GGT GGC ACG GGT CGT GGA CTT
Gly Asp Lys Thr His Thr Cys Pro Pro Cys Pro Ala Pro Glu>
_____________________________FC-IgG1___________________________>

2060        2070        2080        2090        2100
  *     *     *     *     *     *     *     *     *
CTC CTG GGG GGA CCG TCA GTC TTC CTC TTC CCC CCA AAA CCC
GAG GAC CCC CCT GGC AGT CAG AAG GAG AAG GGG GGT TTT GGG
Leu Leu Gly Gly Pro Ser Val Phe Leu Phe Pro Pro Lys Pro>
_____________________________FC-IgG1___________________________>

         2110        2120        2130        2140
     *     *     *     *     *     *     *     *
AAG GAC ACC CTC ATG ATC TCC CGG ACC CCT GAG GTC ACA TGC
TTC CTG TGG GAG TAC TAG AGG GCC TGG GGA CTC CAG TGT ACG
Lys Asp Thr Leu Met Ile Ser Arg Thr Pro Glu Val Thr Cys>
_____________________________FC-IgG1___________________________>

      2150        2160        2170        2180
  *     *     *     *     *     *     *     *
GTG GTG GTG GAC GTG AGC CAC GAA GAC CCT GAG GTC AAG TTC
CAC CAC CAC CTG CAC TCG GTG CTT CTG GGA CTC CAG TTC AAG
Val Val Val Asp Val Ser His Glu Asp Pro Glu Val Lys Phe>
_____________________________FC-IgG1___________________________>

   2190        2200        2210        2220
*     *     *     *     *     *     *     *     *
AAC TGG TAC GTG GAC GGC GTG GAG GTG CAT AAT GCC AAG ACA
TTG ACC ATG CAC CTG CCG CAC CTC CAC GTA TTA CGG TTC TGT
Asn Trp Tyr Val Asp Gly Val Glu Val His Asn Ala Lys Thr>
_____________________________FC-IgG1___________________________>
```

Figure 38H

```
 2230       2240       2250        2260
    *    *     *     *    *     *     *    *
AAG CCG CGG GAG GAG CAG TAC AAC AGC ACG TAC CGT GTG GTC
TTC GGC GCC CTC CTC GTC ATG TTG TCG TGC ATG GCA CAC CAG
Lys Pro Arg Glu Glu Gln Tyr Asn Ser Thr Tyr Arg Val Val>
___________________FC-IgG1_____________________>

2270       2280        2290       2300       2310
  *     *    *     *     *    *     *     *    *
AGC GTC CTC ACC GTC CTG CAC CAG GAC TGG CTG AAT GGC AAG
TCG CAG GAG TGG CAG GAC GTG GTC CTG ACC GAC TTA CCG TTC
Ser Val Leu Thr Val Leu His Gln Asp Trp Leu Asn Gly Lys>
___________________FC-IgG1_____________________>

         2320       2330       2340        2350
     *     *    *     *     *    *     *     *
GAG TAC AAG TGC AAG GTC TCC AAC AAA GCC CTC CCA GCC CCC
CTC ATG TTC ACG TTC CAG AGG TTG TTT CGG GAG GGT CGG GGG
Glu Tyr Lys Cys Lys Val Ser Asn Lys Ala Leu Pro Ala Pro>
___________________FC-IgG1_____________________>

      2360       2370        2380       2390
 *     *     *    *     *     *    *     *
ATC GAG AAA ACC ATC TCC AAA GCC AAA GGG CAG CCC CGA GAA
TAG CTC TTT TGG TAG AGG TTT CGG TTT CCC GTC GGG GCT CTT
Ile Glu Lys Thr Ile Ser Lys Ala Lys Gly Gln Pro Arg Glu>
___________________FC-IgG1_____________________>

   2400       2410       2420       2430
*    *     *     *    *     *     *    *     *
CCA CAG GTG TAC ACC CTG CCC CCA TCC CGG GAG GAG ATG ACC
GGT GTC CAC ATG TGG GAC GGG GGT AGG GCC CTC CTC TAC TGG
Pro Gln Val Tyr Thr Leu Pro Pro Ser Arg Glu Glu Met Thr>
___________________FC-IgG1_____________________>

 2440       2450       2460        2470
    *    *     *     *    *     *     *    *
AAG AAC CAG GTC AGC CTG ACC TGC CTG GTC AAA GGC TTC TAT
TTC TTG GTC CAG TCG GAC TGG ACG GAC CAG TTT CCG AAG ATA
Lys Asn Gln Val Ser Leu Thr Cys Leu Val Lys Gly Phe Tyr>
___________________FC-IgG1_____________________>

2480       2490        2500       2510       2520
  *     *    *     *     *    *     *     *    *
CCC AGC GAC ATC GCC GTG GAG TGG GAG AGC AAT GGG CAG CCG
GGG TCG CTG TAG CGG CAC CTC ACC CTC TCG TTA CCC GTC GGC
Pro Ser Asp Ile Ala Val Glu Trp Glu Ser Asn Gly Gln Pro>
___________________FC-IgG1_____________________>

         2530       2540       2550        2560
     *     *    *     *     *    *     *     *
GAG AAC AAC TAC AAG ACC ACG CCT CCC GTG CTG GAC TCC GAC
CTC TTG TTG ATG TTC TGG TGC GGA GGG CAC GAC CTG AGG CTG
Glu Asn Asn Tyr Lys Thr Thr Pro Pro Val Leu Asp Ser Asp>
___________________FC-IgG1_____________________>
```

Figure 38I

```
      2570          2580          2590          2600
  *        *       *      *       *       *       *       *
GGC TCC TTC TTC CTC TAT AGC AAG CTC ACC GTG GAC AAG AGC
CCG AGG AAG AAG GAG ATA TCG TTC GAG TGG CAC CTG TTC TCG
Gly Ser Phe Phe Leu Tyr Ser Lys Leu Thr Val Asp Lys Ser>
_____________________________FC-IgG1____________________________>

   2610          2620          2630          2640
*       *       *       *       *       *       *       *       *
AGG TGG CAG CAG GGG AAC GTC TTC TCA TGC TCC GTG ATG CAT
TCC ACC GTC GTC CCC TTG CAG AAG AGT ACG AGG CAC TAC GTA
Arg Trp Gln Gln Gly Asn Val Phe Ser Cys Ser Val Met His>
_____________________________FC-IgG1____________________________>

  2650          2660          2670          2680
      *       *       *       *       *       *       *       *
GAG GCT CTG CAC AAC CAC TAC ACG CAG AAG AGC CTC TCC CTG
CTC CGA GAC GTG TTG GTG ATG TGC GTC TTC TCG GAG AGG GAC
Glu Ala Leu His Asn His Tyr Thr Gln Lys Ser Leu Ser Leu>
_____________________________FC-IgG1____________________________>

2690          2700
   *       *       *
TCT CCG GGT AAA TGA
AGA GGC CCA TTT ACT
Ser Pro Gly Lys ***>
_______FC-IgG1_______>
```

Figure 39A

```
            10          20          30          40
     *      *     *     *     *     *     *     *
ATG GTG TTA CTC AGA CTT ATT TGT TTC ATA GCT CTA CTG ATT
TAC CAC AAT GAG TCT GAA TAA ACA AAG TAT CGA GAT GAC TAA
Met Val Leu Leu Arg Leu Ile Cys Phe Ile Ala Leu Leu Ile>
_______________SIGNAL PEPTIDE________________>
___________________IL-1RI___________________>

         50          60          70          80
  *      *     *     *     *     *     *     *
TCT TCT CTG GAG GCT GAT AAA TGC AAG GAA CGT GAA GAA AAA
AGA AGA GAC CTC CGA CTA TTT ACG TTC CTT GCA CTT CTT TTT
Ser Ser Leu Glu Ala Asp>
___SIGNAL PEPTIDE____>
                        Lys Cys Lys Glu Arg Glu Glu Lys>
___________________IL-1RI___________________>

      90          100         110         120
*     *     *     *     *     *     *     *     *
ATA ATT TTA GTG TCA TCT GCA AAT GAA ATT GAT GTT CGT CCC
TAT TAA AAT CAC AGT AGA CGT TTA CTT TAA CTA CAA GCA GGG
Ile Ile Leu Val Ser Ser Ala Asn Glu Ile Asp Val Arg Pro>
___________________IL-1RI___________________>

  130         140         150         160
     *    *     *     *     *     *     *     *
TGT CCT CTT AAC CCA AAT GAA CAC AAA GGC ACT ATA ACT TGG
ACA GGA GAA TTG GGT TTA CTT GTG TTT CCG TGA TAT TGA ACC
Cys Pro Leu Asn Pro Asn Glu His Lys Gly Thr Ile Thr Trp>
___________________IL-1RI___________________>

170         180         190         200         210
 *     *     *     *     *     *     *     *     *
TAT AAG GAT GAC AGC AAG ACA CCT GTA TCT ACA GAA CAA GCC
ATA TTC CTA CTG TCG TTC TGT GGA CAT AGA TGT CTT GTT CGG
Tyr Lys Asp Asp Ser Lys Thr Pro Val Ser Thr Glu Gln Ala>
___________________IL-1RI___________________>

            220         230         240         250
     *      *     *     *     *     *     *     *
TCC AGG ATT CAT CAA CAC AAA GAG AAA CTT TGG TTT GTT CCT
AGG TCC TAA GTA GTT GTG TTT CTC TTT GAA ACC AAA CAA GGA
Ser Arg Ile His Gln His Lys Glu Lys Leu Trp Phe Val Pro>
___________________IL-1RI___________________>

       260         270         280         290
  *     *     *     *     *     *     *     *
GCT AAG GTG GAG GAT TCA GGA CAT TAC TAT TGC GTG GTA AGA
CGA TTC CAC CTC CTA AGT CCT GTA ATG ATA ACG CAC CAT TCT
Ala Lys Val Glu Asp Ser Gly His Tyr Tyr Cys Val Val Arg>
___________________IL-1RI___________________>
```

Figure 39B

```
    300         310         320         330
 *     *     *     *     *     *     *     *     *
AAT TCA TCT TAC TGC CTC AGA ATT AAA ATA AGT GCA AAA TTT
TTA AGT AGA ATG ACG GAG TCT TAA TTT TAT TCA CGT TTT AAA
Asn Ser Ser Tyr Cys Leu Arg Ile Lys Ile Ser Ala Lys Phe>
________________________IL-1RI_______________________>

  340         350         360         370
    *     *     *     *     *     *     *     *
GTG GAG AAT GAG CCT AAC TTA TGT TAT AAT GCA CAA GCC ATA
CAC CTC TTA CTC GGA TTG AAT ACA ATA TTA CGT GTT CGG TAT
Val Glu Asn Glu Pro Asn Leu Cys Tyr Asn Ala Gln Ala Ile>
________________________IL-1RI_______________________>

380         390         400         410         420
 *     *     *     *     *     *     *     *     *
TTT AAG CAG AAA CTA CCC GTT GCA GGA GAC GGA GGA CTT GTG
AAA TTC GTC TTT GAT GGG CAA CGT CCT CTG CCT CCT GAA CAC
Phe Lys Gln Lys Leu Pro Val Ala Gly Asp Gly Gly Leu Val>
________________________IL-1RI_______________________>

          430         440         450         460
    *     *     *     *     *     *     *     *
TGC CCT TAT ATG GAG TTT TTT AAA AAT GAA AAT AAT GAG TTA
ACG GGA ATA TAC CTC AAA AAA TTT TTA CTT TTA TTA CTC AAT
Cys Pro Tyr Met Glu Phe Phe Lys Asn Glu Asn Asn Glu Leu>
________________________IL-1RI_______________________>

       470         480         490         500
 *     *     *     *     *     *     *     *
CCT AAA TTA CAG TGG TAT AAG GAT TGC AAA CCT CTA CTT CTT
GGA TTT AAT GTC ACC ATA TTC CTA ACG TTT GGA GAT GAA GAA
Pro Lys Leu Gln Trp Tyr Lys Asp Cys Lys Pro Leu Leu Leu>
________________________IL-1RI_______________________>

    510         520         530         540
 *     *     *     *     *     *     *     *     *
GAC AAT ATA CAC TTT AGT GGA GTC AAA GAT AGG CTC ATC GTG
CTG TTA TAT GTG AAA TCA CCT CAG TTT CTA TCC GAG TAG CAC
Asp Asn Ile His Phe Ser Gly Val Lys Asp Arg Leu Ile Val>
________________________IL-1RI_______________________>

  550         560         570         580
    *     *     *     *     *     *     *     *
ATG AAT GTG GCT GAA AAG CAT AGA GGG AAC TAT ACT TGT CAT
TAC TTA CAC CGA CTT TTC GTA TCT CCC TTG ATA TGA ACA GTA
Met Asn Val Ala Glu Lys His Arg Gly Asn Tyr Thr Cys His>
________________________IL-1RI_______________________>

590         600         610         620         630
 *     *     *     *     *     *     *     *     *
GCA TCC TAC ACA TAC TTG GGC AAG CAA TAT CCT ATT ACC CGG
CGT AGG ATG TGT ATG AAC CCG TTC GTT ATA GGA TAA TGG GCC
Ala Ser Tyr Thr Tyr Leu Gly Lys Gln Tyr Pro Ile Thr Arg>
________________________IL-1RI_______________________>
```

Figure 39C

```
         640        650        660        670
      *      *     *     *     *     *     *     *
GTA ATA GAA TTT ATT ACT CTA GAG GAA AAC AAA CCC ACA AGG
CAT TAT CTT AAA TAA TGA GAT CTC CTT TTG TTT GGG TGT TCC
Val Ile Glu Phe Ile Thr Leu Glu Glu Asn Lys Pro Thr Arg>
_____________________________IL-1RI____________________________>

      680        690        700        710
   *      *     *     *     *     *     *     *
CCT GTG ATT GTG AGC CCA GCT AAT GAG ACA ATG GAA GTA GAC
GGA CAC TAA CAC TCG GGT CGA TTA CTC TGT TAC CTT CAT CTG
Pro Val Ile Val Ser Pro Ala Asn Glu Thr Met Glu Val Asp>
_____________________________IL-1RI____________________________>

    720        730        740        750
*      *     *     *     *     *     *     *     *
TTG GGA TCC CAG ATA CAA TTG ATC TGT AAT GTC ACC GGC CAG
AAC CCT AGG GTC TAT GTT AAC TAG ACA TTA CAG TGG CCG GTC
Leu Gly Ser Gln Ile Gln Leu Ile Cys Asn Val Thr Gly Gln>
_____________________________IL-1RI____________________________>

  760        770        780        790
      *     *     *     *     *     *     *     *
TTG AGT GAC ATT GCT TAC TGG AAG TGG AAT GGG TCA GTA ATT
AAC TCA CTG TAA CGA ATG ACC TTC ACC TTA CCC AGT CAT TAA
Leu Ser Asp Ile Ala Tyr Trp Lys Trp Asn Gly Ser Val Ile>
_____________________________IL-1RI____________________________>

800          810          820          830          840
  *       *     *     *     *     *     *     *     *
GAT GAA GAT GAC CCA GTG CTA GGG GAA GAC TAT TAC AGT GTG
CTA CTT CTA CTG GGT CAC GAT CCC CTT CTG ATA ATG TCA CAC
Asp Glu Asp Asp Pro Val Leu Gly Glu Asp Tyr Tyr Ser Val>
_____________________________IL-1RI____________________________>

          850        860        870        880
      *      *     *     *     *     *     *     *
GAA AAT CCT GCA AAC AAA AGA AGG AGT ACC CTC ATC ACA GTG
CTT TTA GGA CGT TTG TTT TCT TCC TCA TGG GAG TAG TGT CAC
Glu Asn Pro Ala Asn Lys Arg Arg Ser Thr Leu Ile Thr Val>
_____________________________IL-1RI____________________________>

      890        900        910        920
  *      *     *     *     *     *     *     *
CTT AAT ATA TCG GAA ATT GAG AGT AGA TTT TAT AAA CAT CCA
GAA TTA TAT AGC CTT TAA CTC TCA TCT AAA ATA TTT GTA GGT
Leu Asn Ile Ser Glu Ile Glu Ser Arg Phe Tyr Lys His Pro>
_____________________________IL-1RI____________________________>

    930        940        950        960
*      *     *     *     *     *     *     *     *
TTT ACC TGT TTT GCC AAG AAT ACA CAT GGT ATA GAT GCA GCA
AAA TGG ACA AAA CGG TTC TTA TGT GTA CCA TAT CTA CGT CGT
Phe Thr Cys Phe Ala Lys Asn Thr His Gly Ile Asp Ala Ala>
_____________________________IL-1RI____________________________>
```

Figure 39D

```
   970          980          990          1000
     *     *      *      *     *      *      *      *
TAT ATC CAG TTA ATA TAT CCA GTC ACT AAT TCA GAA CGC TGC
ATA TAG GTC AAT TAT ATA GGT CAG TGA TTA AGT CTT GCG ACG
Tyr Ile Gln Leu Ile Tyr Pro Val Thr Asn>
________________IL-1RI_______________>
                                        Ser Glu Arg Cys>
                                        ___IL-1RAcP____>

1010         1020         1030         1040         1050
  *      *      *      *      *      *      *      *      *
GAT GAC TGG GGA CTA GAC ACC ATG AGG CAA ATC CAA GTG TTT
CTA CTG ACC CCT GAT CTG TGG TAC TCC GTT TAG GTT CAC AAA
Asp Asp Trp Gly Leu Asp Thr Met Arg Gln Ile Gln Val Phe>
_______________________IL-1RAcP_____________________>

          1060         1070         1080         1090
      *      *      *      *      *      *      *      *
GAA GAT GAG CCA GCT CGC ATC AAG TGC CCA CTC TTT GAA CAC
CTT CTA CTC GGT CGA GCG TAG TTC ACG GGT GAG AAA CTT GTG
Glu Asp Glu Pro Ala Arg Ile Lys Cys Pro Leu Phe Glu His>
_______________________IL-1RAcP_____________________>

      1100         1110         1120         1130
  *      *      *      *      *      *      *      *
TTC TTG AAA TTC AAC TAC AGC ACA GCC CAT TCA GCT GGC CTT
AAG AAC TTT AAG TTG ATG TCG TGT CGG GTA AGT CGA CCG GAA
Phe Leu Lys Phe Asn Tyr Ser Thr Ala His Ser Ala Gly Leu>
_______________________IL-1RAcP_____________________>

   1140         1150         1160         1170
*      *      *      *      *      *      *      *      *
ACT CTG ATC TGG TAT TGG ACT AGG CAG GAC CGG GAC CTT GAG
TGA GAC TAG ACC ATA ACC TGA TCC GTC CTG GCC CTG GAA CTC
Thr Leu Ile Trp Tyr Trp Thr Arg Gln Asp Arg Asp Leu Glu>
_______________________IL-1RAcP_____________________>

  1180         1190         1200         1210
     *     *      *      *     *      *      *      *
GAG CCA ATT AAC TTC CGC CTC CCC GAG AAC CGC ATT AGT AAG
CTC GGT TAA TTG AAG GCG GAG GGG CTC TTG GCG TAA TCA TTC
Glu Pro Ile Asn Phe Arg Leu Pro Glu Asn Arg Ile Ser Lys>
_______________________IL-1RAcP_____________________>

1220         1230         1240         1250         1260
  *      *      *      *      *      *      *      *      *
GAG AAA GAT GTG CTG TGG TTC CGG CCC ACT CTC CTC AAT GAC
CTC TTT CTA CAC GAC ACC AAG GCC GGG TGA GAG GAG TTA CTG
Glu Lys Asp Val Leu Trp Phe Arg Pro Thr Leu Leu Asn Asp>
_______________________IL-1RAcP_____________________>
```

Figure 39E

```
        1270        1280        1290         1300
    *     *     *     *     *     *     *     *
ACT GGC AAC TAT ACC TGC ATG TTA AGG AAC ACT ACA TAT TGC
TGA CCG TTG ATA TGG ACG TAC AAT TCC TTG TGA TGT ATA ACG
Thr Gly Asn Tyr Thr Cys Met Leu Arg Asn Thr Thr Tyr Cys>
____________________________IL-1RAcP_________________________>

      1310        1320        1330        1340
  *     *     *     *     *     *     *     *
AGC AAA GTT GCA TTT CCC TTG GAA GTT GTT CAA AAA GAC AGC
TCG TTT CAA CGT AAA GGG AAC CTT CAA CAA GTT TTT CTG TCG
Ser Lys Val Ala Phe Pro Leu Glu Val Val Gln Lys Asp Ser>
____________________________IL-1RAcP_________________________>

   1350        1360        1370        1380
*     *     *     *     *     *     *     *     *
TGT TTC AAT TCC CCC ATG AAA CTC CCA GTG CAT AAA CTG TAT
ACA AAG TTA AGG GGG TAC TTT GAG GGT CAC GTA TTT GAC ATA
Cys Phe Asn Ser Pro Met Lys Leu Pro Val His Lys Leu Tyr>
____________________________IL-1RAcP_________________________>

 1390        1400        1410        1420
    *     *     *     *     *     *     *     *
ATA GAA TAT GGC ATT CAG AGG ATC ACT TGT CCA AAT GTA GAT
TAT CTT ATA CCG TAA GTC TCC TAG TGA ACA GGT TTA CAT CTA
Ile Glu Tyr Gly Ile Gln Arg Ile Thr Cys Pro Asn Val Asp>
____________________________IL-1RAcP_________________________>

1430        1440        1450        1460        1470
  *     *     *     *     *     *     *     *     *
GGA TAT TTT CCT TCC AGT GTC AAA CCG ACT ATC ACT TGG TAT
CCT ATA AAA GGA AGG TCA CAG TTT GGC TGA TAG TGA ACC ATA
Gly Tyr Phe Pro Ser Ser Val Lys Pro Thr Ile Thr Trp Tyr>
____________________________IL-1RAcP_________________________>

        1480        1490        1500        1510
    *     *     *     *     *     *     *     *
ATG GGC TGT TAT AAA ATA CAG AAT TTT AAT AAT GTA ATA CCC
TAC CCG ACA ATA TTT TAT GTC TTA AAA TTA TTA CAT TAT GGG
Met Gly Cys Tyr Lys Ile Gln Asn Phe Asn Asn Val Ile Pro>
____________________________IL-1RAcP_________________________>

      1520        1530        1540        1550
  *     *     *     *     *     *     *     *
GAA GGT ATG AAC TTG AGT TTC CTC ATT GCC TTA ATT TCA AAT
CTT CCA TAC TTG AAC TCA AAG GAG TAA CGG AAT TAA AGT TTA
Glu Gly Met Asn Leu Ser Phe Leu Ile Ala Leu Ile Ser Asn>
____________________________IL-1RAcP_________________________>

   1560        1570        1580        1590
*     *     *     *     *     *     *     *     *
AAT GGA AAT TAC ACA TGT GTT GTT ACA TAT CCA GAA AAT GGA
TTA CCT TTA ATG TGT ACA CAA CAA TGT ATA GGT CTT TTA CCT
Asn Gly Asn Tyr Thr Cys Val Val Thr Tyr Pro Glu Asn Gly>
____________________________IL-1RAcP_________________________>
```

Figure 39F

```
 1600        1610        1620        1630
    *     *     *     *     *     *     *     *
CGT ACG TTT CAT CTC ACC AGG ACT CTG ACT GTA AAG GTA GTA
GCA TGC AAA GTA GAG TGG TCC TGA GAC TGA CAT TTC CAT CAT
Arg Thr Phe His Leu Thr Arg Thr Leu Thr Val Lys Val Val>
_________________________IL-1RAcP______________________>

1640       1650        1660        1670       1680
 *     *     *     *     *     *     *     *     *
GGC TCT CCA AAA AAT GCA GTG CCC CCT GTG ATC CAT TCA CCT
CCG AGA GGT TTT TTA CGT CAC GGG GGA CAC TAG GTA AGT GGA
Gly Ser Pro Lys Asn Ala Val Pro Pro Val Ile His Ser Pro>
_________________________IL-1RAcP______________________>

        1690        1700        1710        1720
    *     *     *     *     *     *     *     *
AAT GAT CAT GTG GTC TAT GAG AAA GAA CCA GGA GAG GAG CTA
TTA CTA GTA CAC CAG ATA CTC TTT CTT GGT CCT CTC CTC GAT
Asn Asp His Val Val Tyr Glu Lys Glu Pro Gly Glu Glu Leu>
_________________________IL-1RAcP______________________>

      1730        1740        1750        1760
 *     *     *     *     *     *     *     *
CTC ATT CCC TGT ACG GTC TAT TTT AGT TTT CTG ATG GAT TCT
GAG TAA GGG ACA TGC CAG ATA AAA TCA AAA GAC TAC CTA AGA
Leu Ile Pro Cys Thr Val Tyr Phe Ser Phe Leu Met Asp Ser>
_________________________IL-1RAcP______________________>

   1770        1780        1790        1800
*     *     *     *     *     *     *     *     *
CGC AAT GAG GTT TGG TGG ACC ATT GAT GGA AAA AAA CCT GAT
GCG TTA CTC CAA ACC ACC TGG TAA CTA CCT TTT TTT GGA CTA
Arg Asn Glu Val Trp Trp Thr Ile Asp Gly Lys Lys Pro Asp>
_________________________IL-1RAcP______________________>

 1810        1820        1830        1840
    *     *     *     *     *     *     *     *
GAC ATC ACT ATT GAT GTC ACC ATT AAC GAA AGT ATA AGT CAT
CTG TAG TGA TAA CTA CAG TGG TAA TTG CTT TCA TAT TCA GTA
Asp Ile Thr Ile Asp Val Thr Ile Asn Glu Ser Ile Ser His>
_________________________IL-1RAcP______________________>

1850       1860        1870        1880       1890
 *     *     *     *     *     *     *     *     *
AGT AGA ACA GAA GAT GAA ACA AGA ACT CAG ATT TTG AGC ATC
TCA TCT TGT CTT CTA CTT TGT TCT TGA GTC TAA AAC TCG TAG
Ser Arg Thr Glu Asp Glu Thr Arg Thr Gln Ile Leu Ser Ile>
_________________________IL-1RAcP______________________>

        1900        1910        1920        1930
    *     *     *     *     *     *     *     *
AAG AAA GTT ACC TCT GAG GAT CTC AAG CGC AGC TAT GTC TGT
TTC TTT CAA TGG AGA CTC CTA GAG TTC GCG TCG ATA CAG ACA
Lys Lys Val Thr Ser Glu Asp Leu Lys Arg Ser Tyr Val Cys>
_________________________IL-1RAcP______________________>
```

Figure 39G

```
      1940          1950           1960          1970
  *       *       *      *       *       *      *       *
CAT GCT AGA AGT GCC AAA GGC GAA GTT GCC AAA GCA GCC AAG
GTA CGA TCT TCA CGG TTT CCG CTT CAA CGG TTT CGT CGG TTC
His Ala Arg Ser Ala Lys Gly Glu Val Ala Lys Ala Ala Lys>
_____________________________IL-1RAcP__________________________>

   1980          1990          2000          2010
*      *       *       *      *       *       *      *       *
GTG AAG CAG AAA GTG CCA GCT CCA AGA TAC ACA GTG GAA TCC
CAC TTC GTC TTT CAC GGT CGA GGT TCT ATG TGT CAC CTT AGG
Val Lys Gln Lys Val Pro Ala Pro Arg Tyr Thr Val Glu>
____________________________IL-1RAcP______________________>
                                                    Ser>
                                                    ____>

 2020          2030          2040           2050
    *      *       *       *      *       *       *      *
GGA GAG TCC AAA TAC GGT CCG CCA TGC CCA TCA TGC CCA GCA
CCT CTC AGG TTT ATG CCA GGC GGT ACG GGT AGT ACG GGT CGT
    Glu Ser Lys Tyr Gly Pro Pro Cys Pro Ser Cys Pro Ala>
    _________________________FC-IgG4_________________________>
Gly>
___>

2060         2070          2080          2090          2100
  *       *      *       *      *       *      *       *      *
CCT GAG TTC CTG GGG GGA CCA TCA GTC TTC CTG TTC CCC CCA
GGA CTC AAG GAC CCC CCT GGT AGT CAG AAG GAC AAG GGG GGT
Pro Glu Phe Leu Gly Gly Pro Ser Val Phe Leu Phe Pro Pro>
__________________________FC-IgG4_____________________________>

       2110          2120          2130          2140
    *       *      *       *      *       *      *       *
AAA CCC AAG GAC ACT CTC ATG ATC TCC CGG ACC CCT GAG GTC
TTT GGG TTC CTG TGA GAG TAC TAG AGG GCC TGG GGA CTC CAG
Lys Pro Lys Asp Thr Leu Met Ile Ser Arg Thr Pro Glu Val>
__________________________FC-IgG4_____________________________>

      2150          2160           2170          2180
  *       *       *      *       *       *      *       *
ACG TGC GTG GTG GTG GAC GTG AGC CAG GAA GAC CCC GAG GTC
TGC ACG CAC CAC CAC CTG CAC TCG GTC CTT CTG GGG CTC CAG
Thr Cys Val Val Val Asp Val Ser Gln Glu Asp Pro Glu Val>
__________________________FC-IgG4_____________________________>

   2190          2200          2210          2220
*      *       *       *      *       *       *      *       *
CAG TTC AAC TGG TAC GTG GAT GGC GTG GAG GTG CAT AAT GCC
GTC AAG TTG ACC ATG CAC CTA CCG CAC CTC CAC GTA TTA CGG
Gln Phe Asn Trp Tyr Val Asp Gly Val Glu Val His Asn Ala>
__________________________FC-IgG4_____________________________>
```

Figure 39H

```
       2230         2240          2250          2260
         *     *      *      *      *      *      *      *
 AAG ACA AAG CCG CGG GAG GAG CAG TTC AAC AGC ACG TAC CGT
 TTC TGT TTC GGC GCC CTC CTC GTC AAG TTG TCG TGC ATG GCA
 Lys Thr Lys Pro Arg Glu Glu Gln Phe Asn Ser Thr Tyr Arg>
 _________________________FC-IgG4____________________________>

2270        2280          2290          2300          2310
 *      *      *      *      *      *      *      *      *
 GTG GTC AGC GTC CTC ACC GTC CTG CAC CAG GAC TGG CTG AAC
 CAC CAG TCG CAG GAG TGG CAG GAC GTG GTC CTG ACC GAC TTG
 Val Val Ser Val Leu Thr Val Leu His Gln Asp Trp Leu Asn>
 _________________________FC-IgG4____________________________>

          2320          2330          2340          2350
     *      *      *      *      *      *      *      *
 GGC AAG GAG TAC AAG TGC AAG GTC TCC AAC AAA GGC CTC CCG
 CCG TTC CTC ATG TTC ACG TTC CAG AGG TTG TTT CCG GAG GGC
 Gly Lys Glu Tyr Lys Cys Lys Val Ser Asn Lys Gly Leu Pro>
 _________________________FC-IgG4____________________________>

      2360          2370          2380          2390
  *      *      *      *      *      *      *      *
 TCC TCC ATC GAG AAA ACC ATC TCC AAA GCC AAA GGG CAG CCC
 AGG AGG TAG CTC TTT TGG TAG AGG TTT CGG TTT CCC GTC GGG
 Ser Ser Ile Glu Lys Thr Ile Ser Lys Ala Lys Gly Gln Pro>
 _________________________FC-IgG4____________________________>

   2400          2410          2420          2430
 *      *      *      *      *      *      *      *      *
 CGA GAG CCA CAG GTG TAC ACC CTG CCC CCA TCC CAG GAG GAG
 GCT CTC GGT GTC CAC ATG TGG GAC GGG GGT AGG GTC CTC CTC
 Arg Glu Pro Gln Val Tyr Thr Leu Pro Pro Ser Gln Glu Glu>
 _________________________FC-IgG4____________________________>

 2440          2450          2460          2470
     *      *      *      *      *      *      *      *
 ATG ACC AAG AAC CAG GTC AGC CTG ACC TGC CTG GTC AAA GGC
 TAC TGG TTC TTG GTC CAG TCG GAC TGG ACG GAC CAG TTT CCG
 Met Thr Lys Asn Gln Val Ser Leu Thr Cys Leu Val Lys Gly>
 _________________________FC-IgG4____________________________>

2480          2490          2500          2510          2520
 *      *      *      *      *      *      *      *      *
 TTC TAC CCC AGC GAC ATC GCC GTG GAG TGG GAG AGC AAT GGG
 AAG ATG GGG TCG CTG TAG CGG CAC CTC ACC CTC TCG TTA CCC
 Phe Tyr Pro Ser Asp Ile Ala Val Glu Trp Glu Ser Asn Gly>
 _________________________FC-IgG4____________________________>

          2530          2540          2550          2560
     *      *      *      *      *      *      *      *
 CAG CCG GAG AAC AAC TAC AAG ACC ACG CCT CCC GTG CTG GAC
 GTC GGC CTC TTG TTG ATG TTC TGG TGC GGA GGG CAC GAC CTG
 Gln Pro Glu Asn Asn Tyr Lys Thr Thr Pro Pro Val Leu Asp>
 _________________________FC-IgG4____________________________>
```

Figure 39I

```
      2570        2580         2590        2600
  *      *      *    *      *     *     *     *
TCC GAC GGC TCC TTC TTC CTC TAC AGC AGG CTA ACC GTG GAC
AGG CTG CCG AGG AAG AAG GAG ATG TCG TCC GAT TGG CAC CTG
Ser Asp Gly Ser Phe Phe Leu Tyr Ser Arg Leu Thr Val Asp>
___________________________FC-IgG4_____________________________>

   2610          2620        2630        2640
*     *      *     *     *     *     *    *     *
AAG AGC AGG TGG CAG GAG GGG AAT GTC TTC TCA TGC TCC GTG
TTC TCG TCC ACC GTC CTC CCC TTA CAG AAG AGT ACG AGG CAC
Lys Ser Arg Trp Gln Glu Gly Asn Val Phe Ser Cys Ser Val>
___________________________FC-IgG4_____________________________>

  2650         2660        2670         2680
      *     *     *     *     *     *     *    *
ATG CAT GAG GCT CTG CAC AAC CAC TAC ACA CAG AAG AGC CTC
TAC GTA CTC CGA GAC GTG TTG GTG ATG TGT GTC TTC TCG GAG
Met His Glu Ala Leu His Asn His Tyr Thr Gln Lys Ser Leu>
___________________________FC-IgG4_____________________________>

2690        2700
  *      *     *     *
TCC CTG TCT CTG GGT AAA TGA
AGG GAC AGA GAC CCA TTT ACT
Ser Leu Ser Leu Gly Lys ***>
___________FC-IgG4_____________>
```

Figure 40A

```
              10          20          30          40
       *     *     *     *     *     *     *     *
ATG GTG TTA CTC AGA CTT ATT TGT TTC ATA GCT CTA CTG ATT
TAC CAC AAT GAG TCT GAA TAA ACA AAG TAT CGA GAT GAC TAA
Met Val Leu Leu Arg Leu Ile Cys Phe Ile Ala Leu Leu Ile>
_________________SIGNAL PEPTIDE______________________>
_____________________IL-1RI__________________________>

          50          60          70          80
   *     *     *     *     *     *     *     *
TCT TCT CTG GAG GCT GAT AAA TGC AAG GAA CGT GAA GAA AAA
AGA AGA GAC CTC CGA CTA TTT ACG TTC CTT GCA CTT CTT TTT
Ser Ser Leu Glu Ala Asp>
____SIGNAL PEPTIDE______>
                        Lys Cys Lys Glu Arg Glu Glu Lys>
_____________________IL-1RI__________________________>

      90          100         110         120
*     *     *     *     *     *     *     *     *
ATA ATT TTA GTG TCA TCT GCA AAT GAA ATT GAT GTT CGT CCC
TAT TAA AAT CAC AGT AGA CGT TTA CTT TAA CTA CAA GCA GGG
Ile Ile Leu Val Ser Ser Ala Asn Glu Ile Asp Val Arg Pro>
_____________________IL-1RI__________________________>

   130         140         150         160
      *     *     *     *     *     *     *     *
TGT CCT CTT AAC CCA AAT GAA CAC AAA GGC ACT ATA ACT TGG
ACA GGA GAA TTG GGT TTA CTT GTG TTT CCG TGA TAT TGA ACC
Cys Pro Leu Asn Pro Asn Glu His Lys Gly Thr Ile Thr Trp>
_____________________IL-1RI__________________________>

170          180         190         200         210
 *     *     *     *     *     *     *     *     *
TAT AAG GAT GAC AGC AAG ACA CCT GTA TCT ACA GAA CAA GCC
ATA TTC CTA CTG TCG TTC TGT GGA CAT AGA TGT CTT GTT CGG
Tyr Lys Asp Asp Ser Lys Thr Pro Val Ser Thr Glu Gln Ala>
_____________________IL-1RI__________________________>

              220         230         240         250
       *     *     *     *     *     *     *     *
TCC AGG ATT CAT CAA CAC AAA GAG AAA CTT TGG TTT GTT CCT
AGG TCC TAA GTA GTT GTG TTT CTC TTT GAA ACC AAA CAA GGA
Ser Arg Ile His Gln His Lys Glu Lys Leu Trp Phe Val Pro>
_____________________IL-1RI__________________________>

          260         270         280         290
   *     *     *     *     *     *     *     *
GCT AAG GTG GAG GAT TCA GGA CAT TAC TAT TGC GTG GTA AGA
CGA TTC CAC CTC CTA AGT CCT GTA ATG ATA ACG CAC CAT TCT
Ala Lys Val Glu Asp Ser Gly His Tyr Tyr Cys Val Val Arg>
_____________________IL-1RI__________________________>
```

Figure 40B

```
    300            310          320           330
*     *      *      *      *      *      *      *      *
AAT TCA TCT TAC TGC CTC AGA ATT AAA ATA AGT GCA AAA TTT
TTA AGT AGA ATG ACG GAG TCT TAA TTT TAT TCA CGT TTT AAA
Asn Ser Ser Tyr Cys Leu Arg Ile Lys Ile Ser Ala Lys Phe>
_________________________IL-1RI_________________________>

  340          350          360          370
     *      *      *      *      *      *      *      *
GTG GAG AAT GAG CCT AAC TTA TGT TAT AAT GCA CAA GCC ATA
CAC CTC TTA CTC GGA TTG AAT ACA ATA TTA CGT GTT CGG TAT
Val Glu Asn Glu Pro Asn Leu Cys Tyr Asn Ala Gln Ala Ile>
_________________________IL-1RI_________________________>

380          390           400           410          420
 *      *      *      *      *      *      *      *      *
TTT AAG CAG AAA CTA CCC GTT GCA GGA GAC GGA GGA CTT GTG
AAA TTC GTC TTT GAT GGG CAA CGT CCT CTG CCT CCT GAA CAC
Phe Lys Gln Lys Leu Pro Val Ala Gly Asp Gly Gly Leu Val>
_________________________IL-1RI_________________________>

           430          440           450           460
     *      *      *      *      *      *      *      *
TGC CCT TAT ATG GAG TTT TTT AAA AAT GAA AAT AAT GAG TTA
ACG GGA ATA TAC CTC AAA AAA TTT TTA CTT TTA TTA CTC AAT
Cys Pro Tyr Met Glu Phe Phe Lys Asn Glu Asn Asn Glu Leu>
_________________________IL-1RI_________________________>

        470          480           490           500
 *      *      *      *      *      *      *      *
CCT AAA TTA CAG TGG TAT AAG GAT TGC AAA CCT CTA CTT CTT
GGA TTT AAT GTC ACC ATA TTC CTA ACG TTT GGA GAT GAA GAA
Pro Lys Leu Gln Trp Tyr Lys Asp Cys Lys Pro Leu Leu Leu>
_________________________IL-1RI_________________________>

    510          520           530           540
*     *      *      *      *      *      *      *      *
GAC AAT ATA CAC TTT AGT GGA GTC AAA GAT AGG CTC ATC GTG
CTG TTA TAT GTG AAA TCA CCT CAG TTT CTA TCC GAG TAG CAC
Asp Asn Ile His Phe Ser Gly Val Lys Asp Arg Leu Ile Val>
_________________________IL-1RI_________________________>

  550          560           570           580
     *      *      *      *      *      *      *      *
ATG AAT GTG GCT GAA AAG CAT AGA GGG AAC TAT ACT TGT CAT
TAC TTA CAC CGA CTT TTC GTA TCT CCC TTG ATA TGA ACA GTA
Met Asn Val Ala Glu Lys His Arg Gly Asn Tyr Thr Cys His>
_________________________IL-1RI_________________________>

590          600           610           620          630
 *      *      *      *      *      *      *      *      *
GCA TCC TAC ACA TAC TTG GGC AAG CAA TAT CCT ATT ACC CGG
CGT AGG ATG TGT ATG AAC CCG TTC GTT ATA GGA TAA TGG GCC
Ala Ser Tyr Thr Tyr Leu Gly Lys Gln Tyr Pro Ile Thr Arg>
_________________________IL-1RI_________________________>
```

Figure 40C

```
        640        650        660        670
     *     *     *     *     *     *     *     *
GTA ATA GAA TTT ATT ACT CTA GAG GAA AAC AAA CCC ACA AGG
CAT TAT CTT AAA TAA TGA GAT CTC CTT TTG TTT GGG TGT TCC
Val Ile Glu Phe Ile Thr Leu Glu Glu Asn Lys Pro Thr Arg>
_________________________IL-1RI_________________________>

      680        690        700        710
  *     *     *     *     *     *     *     *
CCT GTG ATT GTG AGC CCA GCT AAT GAG ACA ATG GAA GTA GAC
GGA CAC TAA CAC TCG GGT CGA TTA CTC TGT TAC CTT CAT CTG
Pro Val Ile Val Ser Pro Ala Asn Glu Thr Met Glu Val Asp>
_________________________IL-1RI_________________________>

    720        730        740        750
*     *     *     *     *     *     *     *     *
TTG GGA TCC CAG ATA CAA TTG ATC TGT AAT GTC ACC GGC CAG
AAC CCT AGG GTC TAT GTT AAC TAG ACA TTA CAG TGG CCG GTC
Leu Gly Ser Gln Ile Gln Leu Ile Cys Asn Val Thr Gly Gln>
_________________________IL-1RI_________________________>

  760        770        780        790
     *     *     *                 *     *     *
TTG AGT GAC ATT GCT TAC TGG AAG TGG AAT GGG TCA GTA ATT
AAC TCA CTG TAA CGA ATG ACC TTC ACC TTA CCC AGT CAT TAA
Leu Ser Asp Ile Ala Tyr Trp Lys Trp Asn Gly Ser Val Ile>
_________________________IL-1RI_________________________>

800        810        820        830        840
  *     *     *     *     *     *     *     *     *
GAT GAA GAT GAC CCA GTG CTA GGG GAA GAC TAT TAC AGT GTG
CTA CTT CTA CTG GGT CAC GAT CCC CTT CTG ATA ATG TCA CAC
Asp Glu Asp Asp Pro Val Leu Gly Glu Asp Tyr Tyr Ser Val>
_________________________IL-1RI_________________________>

        850        860        870        880
     *     *     *     *     *     *     *     *
GAA AAT CCT GCA AAC AAA AGA AGG AGT ACC CTC ATC ACA GTG
CTT TTA GGA CGT TTG TTT TCT TCC TCA TGG GAG TAG TGT CAC
Glu Asn Pro Ala Asn Lys Arg Arg Ser Thr Leu Ile Thr Val>
_________________________IL-1RI_________________________>

      890        900        910        920
  *     *     *     *     *     *     *     *
CTT AAT ATA TCG GAA ATT GAG AGT AGA TTT TAT AAA CAT CCA
GAA TTA TAT AGC CTT TAA CTC TCA TCT AAA ATA TTT GTA GGT
Leu Asn Ile Ser Glu Ile Glu Ser Arg Phe Tyr Lys His Pro>
_________________________IL-1RI_________________________>

    930        940        950        960
*     *     *     *     *     *     *     *     *
TTT ACC TGT TTT GCC AAG AAT ACA CAT GGT ATA GAT GCA GCA
AAA TGG ACA AAA CGG TTC TTA TGT GTA CCA TAT CTA CGT CGT
Phe Thr Cys Phe Ala Lys Asn Thr His Gly Ile Asp Ala Ala>
_________________________IL-1RI_________________________>
```

Figure 40D

```
   970        980        990        1000
    *    *     *     *    *     *     *    *
TAT ATC CAG TTA ATA TAT CCA GTC ACT AAT TCA GAA CGC TGC
ATA TAG GTC AAT TAT ATA GGT CAG TGA TTA AGT CTT GCG ACG
Tyr Ile Gln Leu Ile Tyr Pro Val Thr Asn>
_______________IL-1RI______________>
                                        Ser Glu Arg Cys>
                                        ___IL-1RAcP____>

1010       1020       1030       1040       1050
  *     *    *     *     *    *     *     *    *
GAT GAC TGG GGA CTA GAC ACC ATG AGG CAA ATC CAA GTG TTT
CTA CTG ACC CCT GAT CTG TGG TAC TCC GTT TAG GTT CAC AAA
Asp Asp Trp Gly Leu Asp Thr Met Arg Gln Ile Gln Val Phe>
_____________________IL-1RAcP_____________________>

      1060       1070       1080       1090
  *     *    *     *     *    *     *     *
GAA GAT GAG CCA GCT CGC ATC AAG TGC CCA CTC TTT GAA CAC
CTT CTA CTC GGT CGA GCG TAG TTC ACG GGT GAG AAA CTT GTG
Glu Asp Glu Pro Ala Arg Ile Lys Cys Pro Leu Phe Glu His>
_____________________IL-1RAcP_____________________>

    1100       1110       1120       1130
  *     *    *     *     *    *     *     *
TTC TTG AAA TTC AAC TAC AGC ACA GCC CAT TCA GCT GGC CTT
AAG AAC TTT AAG TTG ATG TCG TGT CGG GTA AGT CGA CCG GAA
Phe Leu Lys Phe Asn Tyr Ser Thr Ala His Ser Ala Gly Leu>
_____________________IL-1RAcP_____________________>

   1140       1150       1160       1170
*     *     *    *     *    *     *     *    *
ACT CTG ATC TGG TAT TGG ACT AGG CAG GAC CGG GAC CTT GAG
TGA GAC TAG ACC ATA ACC TGA TCC GTC CTG GCC CTG GAA CTC
Thr Leu Ile Trp Tyr Trp Thr Arg Gln Asp Arg Asp Leu Glu>
_____________________IL-1RAcP_____________________>

  1180       1190       1200       1210
     *     *    *     *     *    *     *     *
GAG CCA ATT AAC TTC CGC CTC CCC GAG AAC CGC ATT AGT AAG
CTC GGT TAA TTG AAG GCG GAG GGG CTC TTG GCG TAA TCA TTC
Glu Pro Ile Asn Phe Arg Leu Pro Glu Asn Arg Ile Ser Lys>
_____________________IL-1RAcP_____________________>

1220       1230       1240       1250       1260
  *     *    *     *     *    *     *     *    *
GAG AAA GAT GTG CTG TGG TTC CGG CCC ACT CTC CTC AAT GAC
CTC TTT CTA CAC GAC ACC AAG GCC GGG TGA GAG GAG TTA CTG
Glu Lys Asp Val Leu Trp Phe Arg Pro Thr Leu Leu Asn Asp>
_____________________IL-1RAcP_____________________>
```

Figure 40E

```
        1270       1280       1290       1300
   *     *    *     *     *    *     *     *
ACT GGC AAC TAT ACC TGC ATG TTA AGG AAC ACT ACA TAT TGC
TGA CCG TTG ATA TGG ACG TAC AAT TCC TTG TGA TGT ATA ACG
Thr Gly Asn Tyr Thr Cys Met Leu Arg Asn Thr Thr Tyr Cys>
_____________________________IL-1RAcP__________________________>

      1310       1320       1330       1340
  *     *     *    *     *     *    *     *
AGC AAA GTT GCA TTT CCC TTG GAA GTT GTT CAA AAA GAC AGC
TCG TTT CAA CGT AAA GGG AAC CTT CAA CAA GTT TTT CTG TCG
Ser Lys Val Ala Phe Pro Leu Glu Val Val Gln Lys Asp Ser>
_____________________________IL-1RAcP__________________________>

   1350       1360       1370       1380
*    *     *     *    *     *     *    *     *
TGT TTC AAT TCC CCC ATG AAA CTC CCA GTG CAT AAA CTG TAT
ACA AAG TTA AGG GGG TAC TTT GAG GGT CAC GTA TTT GAC ATA
Cys Phe Asn Ser Pro Met Lys Leu Pro Val His Lys Leu Tyr>
_____________________________IL-1RAcP__________________________>

 1390       1400       1410       1420
    *    *     *     *    *     *     *    *
ATA GAA TAT GGC ATT CAG AGG ATC ACT TGT CCA AAT GTA GAT
TAT CTT ATA CCG TAA GTC TCC TAG TGA ACA GGT TTA CAT CTA
Ile Glu Tyr Gly Ile Gln Arg Ile Thr Cys Pro Asn Val Asp>
_____________________________IL-1RAcP__________________________>

1430       1440       1450       1460       1470
 *     *    *     *     *    *     *     *    *
GGA TAT TTT CCT TCC AGT GTC AAA CCG ACT ATC ACT TGG TAT
CCT ATA AAA GGA AGG TCA CAG TTT GGC TGA TAG TGA ACC ATA
Gly Tyr Phe Pro Ser Ser Val Lys Pro Thr Ile Thr Trp Tyr>
_____________________________IL-1RAcP__________________________>

        1480       1490       1500       1510
   *     *    *     *     *    *     *     *
ATG GGC TGT TAT AAA ATA CAG AAT TTT AAT AAT GTA ATA CCC
TAC CCG ACA ATA TTT TAT GTC TTA AAA TTA TTA CAT TAT GGG
Met Gly Cys Tyr Lys Ile Gln Asn Phe Asn Asn Val Ile Pro>
_____________________________IL-1RAcP__________________________>

      1520       1530       1540       1550
  *     *     *    *     *     *    *     *
GAA GGT ATG AAC TTG AGT TTC CTC ATT GCC TTA ATT TCA AAT
CTT CCA TAC TTG AAC TCA AAG GAG TAA CGG AAT TAA AGT TTA
Glu Gly Met Asn Leu Ser Phe Leu Ile Ala Leu Ile Ser Asn>
_____________________________IL-1RAcP__________________________>

   1560       1570       1580       1590
*    *     *     *    *     *     *    *     *
AAT GGA AAT TAC ACA TGT GTT GTT ACA TAT CCA GAA AAT GGA
TTA CCT TTA ATG TGT ACA CAA CAA TGT ATA GGT CTT TTA CCT
Asn Gly Asn Tyr Thr Cys Val Val Thr Tyr Pro Glu Asn Gly>
_____________________________IL-1RAcP__________________________>
```

Figure 40F

```
 1600       1610       1620        1630
    *    *     *     *    *     *    *    *
CGT ACG TTT CAT CTC ACC AGG ACT CTG ACT GTA AAG GTA GTA
GCA TGC AAA GTA GAG TGG TCC TGA GAC TGA CAT TTC CAT CAT
Arg Thr Phe His Leu Thr Arg Thr Leu Thr Val Lys Val Val>
____________________________IL-1RAcP_________________________>

1640       1650        1660       1670       1680
  *     *    *     *     *    *     *     *    *
GGC TCT CCA AAA AAT GCA GTG CCC CCT GTG ATC CAT TCA CCT
CCG AGA GGT TTT TTA CGT CAC GGG GGA CAC TAG GTA AGT GGA
Gly Ser Pro Lys Asn Ala Val Pro Pro Val Ile His Ser Pro>
____________________________IL-1RAcP_________________________>

        1690       1700       1710        1720
    *     *    *     *     *    *     *     *
AAT GAT CAT GTG GTC TAT GAG AAA GAA CCA GGA GAG GAG CTA
TTA CTA GTA CAC CAG ATA CTC TTT CTT GGT CCT CTC CTC GAT
Asn Asp His Val Val Tyr Glu Lys Glu Pro Gly Glu Glu Leu>
____________________________IL-1RAcP_________________________>

     1730       1740       1750       1760
  *     *     *    *     *     *    *     *
CTC ATT CCC TGT ACG GTC TAT TTT AGT TTT CTG ATG GAT TCT
GAG TAA GGG ACA TGC CAG ATA AAA TCA AAA GAC TAC CTA AGA
Leu Ile Pro Cys Thr Val Tyr Phe Ser Phe Leu Met Asp Ser>
____________________________IL-1RAcP_________________________>

   1770       1780       1790       1800
*     *    *     *     *    *     *    *     *
CGC AAT GAG GTT TGG TGG ACC ATT GAT GGA AAA AAA CCT GAT
GCG TTA CTC CAA ACC ACC TGG TAA CTA CCT TTT TTT GGA CTA
Arg Asn Glu Val Trp Trp Thr Ile Asp Gly Lys Lys Pro Asp>
____________________________IL-1RAcP_________________________>

 1810       1820       1830        1840
    *    *     *     *    *     *    *    *
GAC ATC ACT ATT GAT GTC ACC ATT AAC GAA AGT ATA AGT CAT
CTG TAG TGA TAA CTA CAG TGG TAA TTG CTT TCA TAT TCA GTA
Asp Ile Thr Ile Asp Val Thr Ile Asn Glu Ser Ile Ser His>
____________________________IL-1RAcP_________________________>

1850       1860        1870       1880       1890
  *     *    *     *     *    *     *     *    *
AGT AGA ACA GAA GAT GAA ACA AGA ACT CAG ATT TTG AGC ATC
TCA TCT TGT CTT CTA CTT TGT TCT TGA GTC TAA AAC TCG TAG
Ser Arg Thr Glu Asp Glu Thr Arg Thr Gln Ile Leu Ser Ile>
____________________________IL-1RAcP_________________________>

        1900       1910       1920        1930
    *     *    *     *     *    *     *     *
AAG AAA GTT ACC TCT GAG GAT CTC AAG CGC AGC TAT GTC TGT
TTC TTT CAA TGG AGA CTC CTA GAG TTC GCG TCG ATA CAG ACA
Lys Lys Val Thr Ser Glu Asp Leu Lys Arg Ser Tyr Val Cys>
____________________________IL-1RAcP_________________________>
```

Figure 40G

```
      1940          1950           1960          1970
 *       *       *      *       *       *      *       *
CAT GCT AGA AGT GCC AAA GGC GAA GTT GCC AAA GCA GCC AAG
GTA CGA TCT TCA CGG TTT CCG CTT CAA CGG TTT CGT CGG TTC
His Ala Arg Ser Ala Lys Gly Glu Val Ala Lys Ala Ala Lys>
____________________________IL-1RAcP_________________________>

   1980            1990           2000          2010
*      *       *       *      *       *       *      *       *
GTG AAG CAG AAA GTG CCA GCT CCA AGA TAC ACA GTG GAA TCC
CAC TTC GTC TTT CAC GGT CGA GGT TCT ATG TGT CAC CTT AGG
Val Lys Gln Lys Val Pro Ala Pro Arg Tyr Thr Val Glu>
___________________________IL-1RAcP_____________________>
                                                    Ser>
                                                    ___>

                                   >Mutation Serine to Proline
                                              |
 2020          2030          2040             |2050
    *      *       *       *      *       *   |   *      *
GGA GAG TCC AAA TAC GGT CCG CCA TGC CCA CCA TGC CCA GCA
CCT CTC AGG TTT ATG CCA GGC GGT ACG GGT GGT ACG GGT CGT
    Glu Ser Lys Tyr Gly Pro Pro Cys Pro Pro Cys Pro Ala>
    _________________________FC-IgG4_________________________>
Gly>
___>

2060         2070           2080          2090          2100
 *       *      *       *       *      *       *       *      *
CCT GAG TTC CTG GGG GGA CCA TCA GTC TTC CTG TTC CCC CCA
GGA CTC AAG GAC CCC CCT GGT AGT CAG AAG GAC AAG GGG GGT
Pro Glu Phe Leu Gly Gly Pro Ser Val Phe Leu Phe Pro Pro>
__________________________FC-IgG4____________________________>

           2110          2120          2130          2140
    *       *      *       *       *      *       *       *
AAA CCC AAG GAC ACT CTC ATG ATC TCC CGG ACC CCT GAG GTC
TTT GGG TTC CTG TGA GAG TAC TAG AGG GCC TGG GGA CTC CAG
Lys Pro Lys Asp Thr Leu Met Ile Ser Arg Thr Pro Glu Val>
__________________________FC-IgG4____________________________>

       2150          2160           2170          2180
  *       *       *      *       *       *      *       *
ACG TGC GTG GTG GTG GAC GTG AGC CAG GAA GAC CCC GAG GTC
TGC ACG CAC CAC CAC CTG CAC TCG GTC CTT CTG GGG CTC CAG
Thr Cys Val Val Val Asp Val Ser Gln Glu Asp Pro Glu Val>
__________________________FC-IgG4____________________________>

   2190            2200          2210          2220
*      *       *       *      *       *       *      *       *
CAG TTC AAC TGG TAC GTG GAT GGC GTG GAG GTG CAT AAT GCC
GTC AAG TTG ACC ATG CAC CTA CCG CAC CTC CAC GTA TTA CGG
Gln Phe Asn Trp Tyr Val Asp Gly Val Glu Val His Asn Ala>
__________________________FC-IgG4____________________________>
```

Figure 40H

```
  2230         2240         2250          2260
    *      *      *      *     *      *      *      *
AAG ACA AAG CCG CGG GAG GAG CAG TTC AAC AGC ACG TAC CGT
TTC TGT TTC GGC GCC CTC CTC GTC AAG TTG TCG TGC ATG GCA
Lys Thr Lys Pro Arg Glu Glu Gln Phe Asn Ser Thr Tyr Arg>
________________________FC-IgG4__________________________>

2270         2280          2290         2300          2310
  *       *      *      *      *      *      *      *     *
GTG GTC AGC GTC CTC ACC GTC CTG CAC CAG GAC TGG CTG AAC
CAC CAG TCG CAG GAG TGG CAG GAC GTG GTC CTG ACC GAC TTG
Val Val Ser Val Leu Thr Val Leu His Gln Asp Trp Leu Asn>
________________________FC-IgG4__________________________>

        2320         2330         2340          2350
    *       *      *      *      *      *      *      *
GGC AAG GAG TAC AAG TGC AAG GTC TCC AAC AAA GGC CTC CCG
CCG TTC CTC ATG TTC ACG TTC CAG AGG TTG TTT CCG GAG GGC
Gly Lys Glu Tyr Lys Cys Lys Val Ser Asn Lys Gly Leu Pro>
________________________FC-IgG4__________________________>

     2360         2370          2380          2390
  *       *      *      *      *      *      *      *
TCC TCC ATC GAG AAA ACC ATC TCC AAA GCC AAA GGG CAG CCC
AGG AGG TAG CTC TTT TGG TAG AGG TTT CGG TTT CCC GTC GGG
Ser Ser Ile Glu Lys Thr Ile Ser Lys Ala Lys Gly Gln Pro>
________________________FC-IgG4__________________________>

   2400          2410         2420          2430
*      *       *      *      *      *      *      *      *
CGA GAG CCA CAG GTG TAC ACC CTG CCC CCA TCC CAG GAG GAG
GCT CTC GGT GTC CAC ATG TGG GAC GGG GGT AGG GTC CTC CTC
Arg Glu Pro Gln Val Tyr Thr Leu Pro Pro Ser Gln Glu Glu>
________________________FC-IgG4__________________________>

  2440         2450         2460          2470
    *      *      *      *      *      *      *      *
ATG ACC AAG AAC CAG GTC AGC CTG ACC TGC CTG GTC AAA GGC
TAC TGG TTC TTG GTC CAG TCG GAC TGG ACG GAC CAG TTT CCG
Met Thr Lys Asn Gln Val Ser Leu Thr Cys Leu Val Lys Gly>
________________________FC-IgG4__________________________>

2480         2490          2500         2510          2520
  *       *      *      *      *      *      *      *     *
TTC TAC CCC AGC GAC ATC GCC GTG GAG TGG GAG AGC AAT GGG
AAG ATG GGG TCG CTG TAG CGG CAC CTC ACC CTC TCG TTA CCC
Phe Tyr Pro Ser Asp Ile Ala Val Glu Trp Glu Ser Asn Gly>
________________________FC-IgG4__________________________>

        2530         2540          2550          2560
    *       *      *      *      *      *      *      *
CAG CCG GAG AAC AAC TAC AAG ACC ACG CCT CCC GTG CTG GAC
GTC GGC CTC TTG TTG ATG TTC TGG TGC GGA GGG CAC GAC CTG
Gln Pro Glu Asn Asn Tyr Lys Thr Thr Pro Pro Val Leu Asp>
________________________FC-IgG4__________________________>
```

Figure 40I

```
      2570        2580          2590         2600
 *     *      *     *      *      *      *     *
TCC GAC GGC TCC TTC TTC CTC TAC AGC AGG CTA ACC GTG GAC
AGG CTG CCG AGG AAG AAG GAG ATG TCG TCC GAT TGG CAC CTG
Ser Asp Gly Ser Phe Phe Leu Tyr Ser Arg Leu Thr Val Asp>
___________________________FC-IgG4_____________________________>

   2610          2620         2630         2640
*      *      *      *     *      *      *     *      *
AAG AGC AGG TGG CAG GAG GGG AAT GTC TTC TCA TGC TCC GTG
TTC TCG TCC ACC GTC CTC CCC TTA CAG AAG AGT ACG AGG CAC
Lys Ser Arg Trp Gln Glu Gly Asn Val Phe Ser Cys Ser Val>
___________________________FC-IgG4_____________________________>

 2650         2660         2670          2680
     *      *      *      *     *      *       *      *
ATG CAT GAG GCT CTG CAC AAC CAC TAC ACA CAG AAG AGC CTC
TAC GTA CTC CGA GAC GTG TTG GTG ATG TGT GTC TTC TCG GAG
Met His Glu Ala Leu His Asn His Tyr Thr Gln Lys Ser Leu>
___________________________FC-IgG4_____________________________>

2690        2700
  *      *      *      *
TCC CTG TCT CTG GGT AAA TGA
AGG GAC AGA GAC CCA TTT ACT
Ser Leu Ser Leu Gly Lys ***>
__________FC-IgG4____________>
```

Figure 41A

```
              10          20          30          40
      *       *     *     *     *     *     *     *
ATG GTG CTT CTG TGG TGT GTA GTG AGT CTC TAC TTT TAT GGA
TAC CAC GAA GAC ACC ACA CAT CAC TCA GAG ATG AAA ATA CCT
Met Val Leu Leu Trp Cys Val Val Ser Leu Tyr Phe Tyr Gly>
____________________SIGNAL PEPTIDE____________________>
________________________IL-1RAcP______________________>

          50          60          70          80
  *       *     *     *     *     *     *     *
ATC CTG CAA AGT GAT GCC TCA GAA CGC TGC GAT GAC TGG GGA
TAG GAC GTT TCA CTA CGG AGT CTT GCG ACG CTA CTG ACC CCT
Ile Leu Gln Ser Asp Ala>
___SIGNAL PEPTIDE______>
                        Ser Glu Arg Cys Asp Asp Trp Gly>
_________________________IL-1RAcP______________________>

      90          100         110         120
*     *     *     *     *     *     *     *     *
CTA GAC ACC ATG AGG CAA ATC CAA GTG TTT GAA GAT GAG CCA
GAT CTG TGG TAC TCC GTT TAG GTT CAC AAA CTT CTA CTC GGT
Leu Asp Thr Met Arg Gln Ile Gln Val Phe Glu Asp Glu Pro>
_________________________IL-1RAcP______________________>

  130         140         150         160
    *     *     *     *     *     *     *     *
GCT CGC ATC AAG TGC CCA CTC TTT GAA CAC TTC TTG AAA TTC
CGA GCG TAG TTC ACG GGT GAG AAA CTT GTG AAG AAC TTT AAG
Ala Arg Ile Lys Cys Pro Leu Phe Glu His Phe Leu Lys Phe>
_________________________IL-1RAcP______________________>

170         180         190         200         210
 *     *     *     *     *     *     *     *     *
AAC TAC AGC ACA GCC CAT TCA GCT GGC CTT ACT CTG ATC TGG
TTG ATG TCG TGT CGG GTA AGT CGA CCG GAA TGA GAC TAG ACC
Asn Tyr Ser Thr Ala His Ser Ala Gly Leu Thr Leu Ile Trp>
_________________________IL-1RAcP______________________>

          220         230         240         250
      *       *     *     *     *     *     *     *
TAT TGG ACT AGG CAG GAC CGG GAC CTT GAG GAG CCA ATT AAC
ATA ACC TGA TCC GTC CTG GCC CTG GAA CTC CTC GGT TAA TTG
Tyr Trp Thr Arg Gln Asp Arg Asp Leu Glu Glu Pro Ile Asn>
_________________________IL-1RAcP______________________>

      260         270         280         290
  *       *     *     *     *     *     *     *
TTC CGC CTC CCC GAG AAC CGC ATT AGT AAG GAG AAA GAT GTG
AAG GCG GAG GGG CTC TTG GCG TAA TCA TTC CTC TTT CTA CAC
Phe Arg Leu Pro Glu Asn Arg Ile Ser Lys Glu Lys Asp Val>
_________________________IL-1RAcP______________________>

    300         310         320         330
*     *       *     *     *     *     *     *     *
CTG TGG TTC CGG CCC ACT CTC CTC AAT GAC ACT GGC AAC TAT
GAC ACC AAG GCC GGG TGA GAG GAG TTA CTG TGA CCG TTG ATA
Leu Trp Phe Arg Pro Thr Leu Leu Asn Asp Thr Gly Asn Tyr>
_________________________IL-1RAcP______________________>
```

Figure 41B

```
 340         350         360         370
  *     *     *     *     *     *     *     *
ACC TGC ATG TTA AGG AAC ACT ACA TAT TGC AGC AAA GTT GCA
TGG ACG TAC AAT TCC TTG TGA TGT ATA ACG TCG TTT CAA CGT
Thr Cys Met Leu Arg Asn Thr Thr Tyr Cys Ser Lys Val Ala>
________________________IL-1RAcP______________________>

380         390         400         410         420
 *     *     *     *     *     *     *     *     *
TTT CCC TTG GAA GTT GTT CAA AAA GAC AGC TGT TTC AAT TCC
AAA GGG AAC CTT CAA CAA GTT TTT CTG TCG ACA AAG TTA AGG
Phe Pro Leu Glu Val Val Gln Lys Asp Ser Cys Phe Asn Ser>
________________________IL-1RAcP______________________>

         430         440         450         460
    *     *     *     *     *     *     *     *
CCC ATG AAA CTC CCA GTG CAT AAA CTG TAT ATA GAA TAT GGC
GGG TAC TTT GAG GGT CAC GTA TTT GAC ATA TAT CTT ATA CCG
Pro Met Lys Leu Pro Val His Lys Leu Tyr Ile Glu Tyr Gly>
________________________IL-1RAcP______________________>

       470         480         490         500
 *     *     *     *     *     *     *     *
ATT CAG AGG ATC ACT TGT CCA AAT GTA GAT GGA TAT TTT CCT
TAA GTC TCC TAG TGA ACA GGT TTA CAT CTA CCT ATA AAA GGA
Ile Gln Arg Ile Thr Cys Pro Asn Val Asp Gly Tyr Phe Pro>
________________________IL-1RAcP______________________>

    510         520         530         540
*     *     *     *     *     *     *     *     *
TCC AGT GTC AAA CCG ACT ATC ACT TGG TAT ATG GGC TGT TAT
AGG TCA CAG TTT GGC TGA TAG TGA ACC ATA TAC CCG ACA ATA
Ser Ser Val Lys Pro Thr Ile Thr Trp Tyr Met Gly Cys Tyr>
________________________IL-1RAcP______________________>

  550         560         570         580
    *     *     *     *     *     *     *     *
AAA ATA CAG AAT TTT AAT AAT GTA ATA CCC GAA GGT ATG AAC
TTT TAT GTC TTA AAA TTA TTA CAT TAT GGG CTT CCA TAC TTG
Lys Ile Gln Asn Phe Asn Asn Val Ile Pro Glu Gly Met Asn>
________________________IL-1RAcP______________________>

590         600         610         620         630
 *     *     *     *     *     *     *     *     *
TTG AGT TTC CTC ATT GCC TTA ATT TCA AAT AAT GGA AAT TAC
AAC TCA AAG GAG TAA CGG AAT TAA AGT TTA TTA CCT TTA ATG
Leu Ser Phe Leu Ile Ala Leu Ile Ser Asn Asn Gly Asn Tyr>
________________________IL-1RAcP______________________>

         640         650         660         670
    *     *     *     *     *     *     *     *
ACA TGT GTT GTT ACA TAT CCA GAA AAT GGA CGT ACG TTT CAT
TGT ACA CAA CAA TGT ATA GGT CTT TTA CCT GCA TGC AAA GTA
Thr Cys Val Val Thr Tyr Pro Glu Asn Gly Arg Thr Phe His>
________________________IL-1RAcP______________________>
```

Figure 41C

```
       680          690           700          710
  *        *        *       *       *       *     *     *
CTC ACC AGG ACT CTG ACT GTA AAG GTA GTA GGC TCT CCA AAA
GAG TGG TCC TGA GAC TGA CAT TTC CAT CAT CCG AGA GGT TTT
Leu Thr Arg Thr Leu Thr Val Lys Val Val Gly Ser Pro Lys>
_____________________________IL-1RAcP_________________________>

    720          730          740          750
*      *       *       *      *      *      *      *      *
AAT GCA GTG CCC CCT GTG ATC CAT TCA CCT AAT GAT CAT GTG
TTA CGT CAC GGG GGA CAC TAG GTA AGT GGA TTA CTA GTA CAC
Asn Ala Val Pro Pro Val Ile His Ser Pro Asn Asp His Val>
_____________________________IL-1RAcP_________________________>

  760          770          780          790
     *      *       *       *      *      *      *      *
GTC TAT GAG AAA GAA CCA GGA GAG GAG CTA CTC ATT CCC TGT
CAG ATA CTC TTT CTT GGT CCT CTC CTC GAT GAG TAA GGG ACA
Val Tyr Glu Lys Glu Pro Gly Glu Glu Leu Leu Ile Pro Cys>
_____________________________IL-1RAcP_________________________>

800          810          820          830          840
  *       *      *       *       *      *      *       *      *
ACG GTC TAT TTT AGT TTT CTG ATG GAT TCT CGC AAT GAG GTT
TGC CAG ATA AAA TCA AAA GAC TAC CTA AGA GCG TTA CTC CAA
Thr Val Tyr Phe Ser Phe Leu Met Asp Ser Arg Asn Glu Val>
_____________________________IL-1RAcP_________________________>

          850          860          870          880
      *       *      *       *       *      *      *      *
TGG TGG ACC ATT GAT GGA AAA AAA CCT GAT GAC ATC ACT ATT
ACC ACC TGG TAA CTA CCT TTT TTT GGA CTA CTG TAG TGA TAA
Trp Trp Thr Ile Asp Gly Lys Lys Pro Asp Asp Ile Thr Ile>
_____________________________IL-1RAcP_________________________>

       890          900           910          920
  *        *        *       *       *       *     *     *
GAT GTC ACC ATT AAC GAA AGT ATA AGT CAT AGT AGA ACA GAA
CTA CAG TGG TAA TTG CTT TCA TAT TCA GTA TCA TCT TGT CTT
Asp Val Thr Ile Asn Glu Ser Ile Ser His Ser Arg Thr Glu>
_____________________________IL-1RAcP_________________________>

    930          940          950          960
*      *       *       *      *      *      *      *      *
GAT GAA ACA AGA ACT CAG ATT TTG AGC ATC AAG AAA GTT ACC
CTA CTT TGT TCT TGA GTC TAA AAC TCG TAG TTC TTT CAA TGG
Asp Glu Thr Arg Thr Gln Ile Leu Ser Ile Lys Lys Val Thr>
_____________________________IL-1RAcP_________________________>

  970          980          990          1000
     *      *       *       *      *      *      *      *
TCT GAG GAT CTC AAG CGC AGC TAT GTC TGT CAT GCT AGA AGT
AGA CTC CTA GAG TTC GCG TCG ATA CAG ACA GTA CGA TCT TCA
Ser Glu Asp Leu Lys Arg Ser Tyr Val Cys His Ala Arg Ser>
_____________________________IL-1RAcP_________________________>
```

Figure 41D

```
1010       1020        1030       1040       1050
 *     *    *     *     *    *     *     *    *
GCC AAA GGC GAA GTT GCC AAA GCA GCC AAG GTG AAG CAG AAA
CGG TTT CCG CTT CAA CGG TTT CGT CGG TTC CAC TTC GTC TTT
Ala Lys Gly Glu Val Ala Lys Ala Ala Lys Val Lys Gln Lys>
_________________________IL-1RAcP______________________>

        1060       1070       1080        1090
   *     *    *     *     *    *     *     *
GTG CCA GCT CCA AGA TAC ACA GTG GAA AAA TGC AAG GAA CGT
CAC GGT CGA GGT TCT ATG TGT CAC CTT TTT ACG TTC CTT GCA
Val Pro Ala Pro Arg Tyr Thr Val Glu>
______________IL-1RAcP_____________>
                                    Lys Cys Lys Glu Arg>
                                    _______IL-1RI______>

      1100       1110        1120       1130
  *     *     *    *     *     *    *     *
GAA GAA AAA ATA ATT TTA GTG AGC TCA GCA AAT GAA ATC GAT
CTT CTT TTT TAT TAA AAT CAC TCG AGT CGT TTA CTT TAG CTA
Glu Glu Lys Ile Ile Leu Val Ser Ser Ala Asn Glu Ile Asp>
________________________IL-1RI_________________________>

   1140       1150       1160       1170
*     *     *    *     *     *     *    *     *
GTT CGT CCC TGT CCT CTT AAC CCA AAT GAA CAC AAA GGC ACT
CAA GCA GGG ACA GGA GAA TTG GGT TTA CTT GTG TTT CCG TGA
Val Arg Pro Cys Pro Leu Asn Pro Asn Glu His Lys Gly Thr>
________________________IL-1RI_________________________>

 1180       1190       1200       1210
    *     *     *     *    *     *     *    *
ATA ACT TGG TAT AAG GAT GAC AGC AAG ACA CCT GTA TCT ACA
TAT TGA ACC ATA TTC CTA CTG TCG TTC TGT GGA CAT AGA TGT
Ile Thr Trp Tyr Lys Asp Asp Ser Lys Thr Pro Val Ser Thr>
________________________IL-1RI_________________________>

1220       1230       1240       1250       1260
 *     *    *     *     *    *     *     *    *
GAA CAA GCC TCC AGG ATT CAT CAA CAC AAA GAG AAA CTT TGG
CTT GTT CGG AGG TCC TAA GTA GTT GTG TTT CTC TTT GAA ACC
Glu Gln Ala Ser Arg Ile His Gln His Lys Glu Lys Leu Trp>
________________________IL-1RI_________________________>

        1270       1280       1290        1300
   *     *    *     *     *    *     *     *
TTT GTT CCT GCT AAG GTG GAG GAT TCA GGA CAT TAC TAT TGC
AAA CAA GGA CGA TTC CAC CTC CTA AGT CCT GTA ATG ATA ACG
Phe Val Pro Ala Lys Val Glu Asp Ser Gly His Tyr Tyr Cys>
________________________IL-1RI_________________________>

      1310       1320        1330       1340
  *     *     *    *     *     *    *     *
GTG GTA AGA AAT TCA TCT TAC TGC CTC AGA ATT AAA ATA AGT
CAC CAT TCT TTA AGT AGA ATG ACG GAG TCT TAA TTT TAT TCA
Val Val Arg Asn Ser Ser Tyr Cys Leu Arg Ile Lys Ile Ser>
________________________IL-1RI_________________________>
```

Figure 41E

```
   1350        1360        1370        1380
 *     *     *     *     *     *     *     *     *
GCA AAA TTT GTG GAG AAT GAG CCT AAC TTA TGT TAT AAT GCA
CGT TTT AAA CAC CTC TTA CTC GGA TTG AAT ACA ATA TTA CGT
Ala Lys Phe Val Glu Asn Glu Pro Asn Leu Cys Tyr Asn Ala>
________________________IL-1RI________________________>

 1390        1400        1410        1420
    *     *     *     *     *     *     *     *
CAA GCC ATA TTT AAG CAG AAA CTA CCC GTT GCA GGA GAC GGA
GTT CGG TAT AAA TTC GTC TTT GAT GGG CAA CGT CCT CTG CCT
Gln Ala Ile Phe Lys Gln Lys Leu Pro Val Ala Gly Asp Gly>
________________________IL-1RI________________________>

1430        1440        1450        1460        1470
  *     *     *     *     *     *     *     *     *
GGA CTT GTG TGC CCT TAT ATG GAG TTT TTT AAA AAT GAA AAT
CCT GAA CAC ACG GGA ATA TAC CTC AAA AAA TTT TTA CTT TTA
Gly Leu Val Cys Pro Tyr Met Glu Phe Phe Lys Asn Glu Asn>
________________________IL-1RI________________________>

        1480        1490        1500        1510
     *     *     *     *     *     *     *     *
AAT GAG TTA CCT AAA TTA CAG TGG TAT AAG GAT TGC AAA CCT
TTA CTC AAT GGA TTT AAT GTC ACC ATA TTC CTA ACG TTT GGA
Asn Glu Leu Pro Lys Leu Gln Trp Tyr Lys Asp Cys Lys Pro>
________________________IL-1RI________________________>

      1520        1530        1540        1550
 *     *     *     *     *     *     *     *
CTA CTT CTT GAC AAT ATA CAC TTT AGT GGA GTC AAA GAT AGG
GAT GAA GAA CTG TTA TAT GTG AAA TCA CCT CAG TTT CTA TCC
Leu Leu Leu Asp Asn Ile His Phe Ser Gly Val Lys Asp Arg>
________________________IL-1RI________________________>

   1560        1570        1580        1590
 *     *     *     *     *     *     *     *     *
CTC ATC GTG ATG AAT GTG GCT GAA AAG CAT AGA GGG AAC TAT
GAG TAG CAC TAC TTA CAC CGA CTT TTC GTA TCT CCC TTG ATA
Leu Ile Val Met Asn Val Ala Glu Lys His Arg Gly Asn Tyr>
________________________IL-1RI________________________>

 1600        1610        1620        1630
    *     *     *     *     *     *     *     *
ACT TGT CAT GCA TCC TAC ACA TAC TTG GGC AAG CAA TAT CCT
TGA ACA GTA CGT AGG ATG TGT ATG AAC CCG TTC GTT ATA GGA
Thr Cys His Ala Ser Tyr Thr Tyr Leu Gly Lys Gln Tyr Pro>
________________________IL-1RI________________________>

1640        1650        1660        1670        1680
  *     *     *     *     *     *     *     *     *
ATT ACC CGG GTA ATA GAA TTT ATT ACT CTA GAG GAA AAC AAA
TAA TGG GCC CAT TAT CTT AAA TAA TGA GAT CTC CTT TTG TTT
Ile Thr Arg Val Ile Glu Phe Ile Thr Leu Glu Glu Asn Lys>
________________________IL-1RI________________________>
```

Figure 41F

```
        1690        1700        1710        1720
   *     *     *     *     *     *     *     *
CCC ACA AGG CCT GTG ATT GTG AGC CCA GCT AAT GAG ACA ATG
GGG TGT TCC GGA CAC TAA CAC TCG GGT CGA TTA CTC TGT TAC
Pro Thr Arg Pro Val Ile Val Ser Pro Ala Asn Glu Thr Met>
________________________IL-1RI________________________>

      1730        1740        1750        1760
  *     *     *     *     *     *     *     *
GAA GTA GAC TTG GGA TCC CAG ATA CAA TTG ATC TGT AAT GTC
CTT CAT CTG AAC CCT AGG GTC TAT GTT AAC TAG ACA TTA CAG
Glu Val Asp Leu Gly Ser Gln Ile Gln Leu Ile Cys Asn Val>
________________________IL-1RI________________________>

   1770        1780        1790        1800
*     *     *     *     *     *     *     *     *
ACC GGC CAG TTG AGT GAC ATT GCT TAC TGG AAG TGG AAT GGG
TGG CCG GTC AAC TCA CTG TAA CGA ATG ACC TTC ACC TTA CCC
Thr Gly Gln Leu Ser Asp Ile Ala Tyr Trp Lys Trp Asn Gly>
________________________IL-1RI________________________>

 1810        1820        1830        1840
    *     *     *     *     *     *     *     *
TCA GTA ATT GAT GAA GAT GAC CCA GTG CTA GGG GAA GAC TAT
AGT CAT TAA CTA CTT CTA CTG GGT CAC GAT CCC CTT CTG ATA
Ser Val Ile Asp Glu Asp Asp Pro Val Leu Gly Glu Asp Tyr>
________________________IL-1RI________________________>

1850        1860        1870        1880        1890
  *     *     *     *     *     *     *     *     *
TAC AGT GTG GAA AAT CCT GCA AAC AAA AGA AGG AGT ACC CTC
ATG TCA CAC CTT TTA GGA CGT TTG TTT TCT TCC TCA TGG GAG
Tyr Ser Val Glu Asn Pro Ala Asn Lys Arg Arg Ser Thr Leu>
________________________IL-1RI________________________>

        1900        1910        1920        1930
     *     *     *     *     *     *     *     *
ATC ACA GTG CTT AAT ATA TCG GAA ATT GAG AGT AGA TTT TAT
TAG TGT CAC GAA TTA TAT AGC CTT TAA CTC TCA TCT AAA ATA
Ile Thr Val Leu Asn Ile Ser Glu Ile Glu Ser Arg Phe Tyr>
________________________IL-1RI________________________>

      1940        1950        1960        1970
  *     *     *     *     *     *     *     *
AAA CAT CCA TTT ACC TGT TTT GCC AAG AAT ACA CAT GGT ATA
TTT GTA GGT AAA TGG ACA AAA CGG TTC TTA TGT GTA CCA TAT
Lys His Pro Phe Thr Cys Phe Ala Lys Asn Thr His Gly Ile>
________________________IL-1RI________________________>

   1980        1990        2000        2010
*     *     *     *     *     *     *     *     *
GAT GCA GCA TAT ATC CAG TTA ATA TAT CCA GTC ACT AAT TCC
CTA CGT CGT ATA TAG GTC AAT TAT ATA GGT CAG TGA TTA AGG
                                                    Ser>
                                                    ___>
Asp Ala Ala Tyr Ile Gln Leu Ile Tyr Pro Val Thr Asn>
______________________IL-1RI______________________>
```

Figure 41G

```
 2020         2030         2040         2050
   *     *     *     *     *     *     *     *
GGA GAC AAA ACT CAC ACA TGC CCA CCG TGC CCA GCA CCT GAA
CCT CTG TTT TGA GTG TGT ACG GGT GGC ACG GGT CGT GGA CTT
Gly Asp Lys Thr His Thr Cys Pro Pro Cys Pro Ala Pro Glu>
______________________FC-IgG1________________________>

2060         2070         2080         2090         2100
  *     *     *     *     *     *     *     *     *
CTC CTG GGG GGA CCG TCA GTC TTC CTC TTC CCC CCA AAA CCC
GAG GAC CCC CCT GGC AGT CAG AAG GAG AAG GGG GGT TTT GGG
Leu Leu Gly Gly Pro Ser Val Phe Leu Phe Pro Pro Lys Pro>
______________________FC-IgG1________________________>

           2110         2120         2130         2140
     *     *     *     *     *     *     *     *
AAG GAC ACC CTC ATG ATC TCC CGG ACC CCT GAG GTC ACA TGC
TTC CTG TGG GAG TAC TAG AGG GCC TGG GGA CTC CAG TGT ACG
Lys Asp Thr Leu Met Ile Ser Arg Thr Pro Glu Val Thr Cys>
______________________FC-IgG1________________________>

        2150         2160         2170         2180
  *     *     *     *     *     *     *     *
GTG GTG GTG GAC GTG AGC CAC GAA GAC CCT GAG GTC AAG TTC
CAC CAC CAC CTG CAC TCG GTG CTT CTG GGA CTC CAG TTC AAG
Val Val Val Asp Val Ser His Glu Asp Pro Glu Val Lys Phe>
______________________FC-IgG1________________________>

    2190         2200         2210         2220
*     *     *     *     *     *     *     *     *
AAC TGG TAC GTG GAC GGC GTG GAG GTG CAT AAT GCC AAG ACA
TTG ACC ATG CAC CTG CCG CAC CTC CAC GTA TTA CGG TTC TGT
Asn Trp Tyr Val Asp Gly Val Glu Val His Asn Ala Lys Thr>
______________________FC-IgG1________________________>

 2230         2240         2250         2260
   *     *     *     *     *     *     *     *
AAG CCG CGG GAG GAG CAG TAC AAC AGC ACG TAC CGT GTG GTC
TTC GGC GCC CTC CTC GTC ATG TTG TCG TGC ATG GCA CAC CAG
Lys Pro Arg Glu Glu Gln Tyr Asn Ser Thr Tyr Arg Val Val>
______________________FC-IgG1________________________>

2270         2280         2290         2300         2310
  *     *     *     *     *     *     *     *     *
AGC GTC CTC ACC GTC CTG CAC CAG GAC TGG CTG AAT GGC AAG
TCG CAG GAG TGG CAG GAC GTG GTC CTG ACC GAC TTA CCG TTC
Ser Val Leu Thr Val Leu His Gln Asp Trp Leu Asn Gly Lys>
______________________FC-IgG1________________________>

           2320         2330         2340         2350
     *     *     *     *     *     *     *     *
GAG TAC AAG TGC AAG GTC TCC AAC AAA GCC CTC CCA GCC CCC
CTC ATG TTC ACG TTC CAG AGG TTG TTT CGG GAG GGT CGG GGG
Glu Tyr Lys Cys Lys Val Ser Asn Lys Ala Leu Pro Ala Pro>
______________________FC-IgG1________________________>
```

Figure 41H

```
      2360        2370        2380        2390
  *     *     *     *     *     *     *     *
ATC GAG AAA ACC ATC TCC AAA GCC AAA GGG CAG CCC CGA GAA
TAG CTC TTT TGG TAG AGG TTT CGG TTT CCC GTC GGG GCT CTT
Ile Glu Lys Thr Ile Ser Lys Ala Lys Gly Gln Pro Arg Glu>
_______________________FC-IgG1_________________________>

   2400        2410        2420        2430
*     *     *     *     *     *     *     *     *
CCA CAG GTG TAC ACC CTG CCC CCA TCC CGG GAT GAG CTG ACC
GGT GTC CAC ATG TGG GAC GGG GGT AGG GCC CTA CTC GAC TGG
Pro Gln Val Tyr Thr Leu Pro Pro Ser Arg Asp Glu Leu Thr>
_______________________FC-IgG1_________________________>

  2440        2450        2460        2470
     *     *     *     *     *     *     *     *
AAG AAC CAG GTC AGC CTG ACC TGC CTG GTC AAA GGC TTC TAT
TTC TTG GTC CAG TCG GAC TGG ACG GAC CAG TTT CCG AAG ATA
Lys Asn Gln Val Ser Leu Thr Cys Leu Val Lys Gly Phe Tyr>
_______________________FC-IgG1_________________________>

2480        2490        2500        2510        2520
  *     *     *     *     *     *     *     *     *
CCC AGC GAC ATC GCC GTG GAG TGG GAG AGC AAT GGG CAG CCG
GGG TCG CTG TAG CGG CAC CTC ACC CTC TCG TTA CCC GTC GGC
Pro Ser Asp Ile Ala Val Glu Trp Glu Ser Asn Gly Gln Pro>
_______________________FC-IgG1_________________________>

         2530        2540        2550        2560
      *     *     *     *     *     *     *     *
GAG AAC AAC TAC AAG ACC ACG CCT CCC GTG CTG GAC TCC GAC
CTC TTG TTG ATG TTC TGG TGC GGA GGG CAC GAC CTG AGG CTG
Glu Asn Asn Tyr Lys Thr Thr Pro Pro Val Leu Asp Ser Asp>
_______________________FC-IgG1_________________________>

      2570        2580        2590        2600
  *     *     *     *     *     *     *     *
GGC TCC TTC TTC CTC TAC AGC AAG CTC ACC GTG GAC AAG AGC
CCG AGG AAG AAG GAG ATG TCG TTC GAG TGG CAC CTG TTC TCG
Gly Ser Phe Phe Leu Tyr Ser Lys Leu Thr Val Asp Lys Ser>
_______________________FC-IgG1_________________________>

   2610        2620        2630        2640
*     *     *     *     *     *     *     *     *
AGG TGG CAG CAG GGG AAC GTC TTC TCA TGC TCC GTG ATG CAT
TCC ACC GTC GTC CCC TTG CAG AAG AGT ACG AGG CAC TAC GTA
Arg Trp Gln Gln Gly Asn Val Phe Ser Cys Ser Val Met His>
_______________________FC-IgG1_________________________>

  2650        2660        2670        2680
     *     *     *     *     *     *     *     *
GAG GCT CTG CAC AAC CAC TAC ACG CAG AAG AGC CTC TCC CTG
CTC CGA GAC GTG TTG GTG ATG TGC GTC TTC TCG GAG AGG GAC
Glu Ala Leu His Asn His Tyr Thr Gln Lys Ser Leu Ser Leu>
_______________________FC-IgG1_________________________>
```

Figure 41 I

```
2690          2700
   *       *      *
  TCT CCG GGT AAA TGA
  AGA GGC CCA TTT ACT
  Ser Pro Gly Lys ***>
  _______FC-IgG1______>
```

Figure 42A

```
          10         20         30         40
     *     *     *     *     *     *     *     *
ATG GTG CTT CTG TGG TGT GTA GTG AGT CTC TAC TTT TAT GGA
TAC CAC GAA GAC ACC ACA CAT CAC TCA GAG ATG AAA ATA CCT
Met Val Leu Leu Trp Cys Val Val Ser Leu Tyr Phe Tyr Gly>
____________________SIGNAL PEPTIDE____________________>
_________________________IL-1RAcP_____________________>

        50         60         70         80
  *     *     *     *     *     *     *     *
ATC CTG CAA AGT GAT GCC TCA GAA CGC TGC GAT GAC TGG GGA
TAG GAC GTT TCA CTA CGG AGT CTT GCG ACG CTA CTG ACC CCT
Ile Leu Gln Ser Asp Ala>
___SIGNAL PEPTIDE _____>
                        Ser Glu Arg Cys Asp Asp Trp Gly>
________________________IL-1RAcP______________________>

     90         100        110        120
*     *     *     *     *     *     *     *     *
CTA GAC ACC ATG AGG CAA ATC CAA GTG TTT GAA GAT GAG CCA
GAT CTG TGG TAC TCC GTT TAG GTT CAC AAA CTT CTA CTC GGT
Leu Asp Thr Met Arg Gln Ile Gln Val Phe Glu Asp Glu Pro>
________________________IL-1RAcP______________________>

 130        140        150        160
    *     *     *     *     *     *     *     *
GCT CGC ATC AAG TGC CCA CTC TTT GAA CAC TTC TTG AAA TTC
CGA GCG TAG TTC ACG GGT GAG AAA CTT GTG AAG AAC TTT AAG
Ala Arg Ile Lys Cys Pro Leu Phe Glu His Phe Leu Lys Phe>
________________________IL-1RAcP______________________>

170        180        190        200        210
 *     *     *     *     *     *     *     *     *
AAC TAC AGC ACA GCC CAT TCA GCT GGC CTT ACT CTG ATC TGG
TTG ATG TCG TGT CGG GTA AGT CGA CCG GAA TGA GAC TAG ACC
Asn Tyr Ser Thr Ala His Ser Ala Gly Leu Thr Leu Ile Trp>
________________________IL-1RAcP______________________>

          220        230        240        250
     *     *     *     *     *     *     *     *
TAT TGG ACT AGG CAG GAC CGG GAC CTT GAG GAG CCA ATT AAC
ATA ACC TGA TCC GTC CTG GCC CTG GAA CTC CTC GGT TAA TTG
Tyr Trp Thr Arg Gln Asp Arg Asp Leu Glu Glu Pro Ile Asn>
________________________IL-1RAcP______________________>

        260        270        280        290
  *     *     *     *     *     *     *     *
TTC CGC CTC CCC GAG AAC CGC ATT AGT AAG GAG AAA GAT GTG
AAG GCG GAG GGG CTC TTG GCG TAA TCA TTC CTC TTT CTA CAC
Phe Arg Leu Pro Glu Asn Arg Ile Ser Lys Glu Lys Asp Val>
________________________IL-1RAcP______________________>

     300        310        320        330
*     *     *     *     *     *     *     *     *
CTG TGG TTC CGG CCC ACT CTC CTC AAT GAC ACT GGC AAC TAT
GAC ACC AAG GCC GGG TGA GAG GAG TTA CTG TGA CCG TTG ATA
Leu Trp Phe Arg Pro Thr Leu Leu Asn Asp Thr Gly Asn Tyr>
________________________IL-1RAcP______________________>
```

Figure 42B

```
 340         350         360          370
   *     *     *     *     *     *     *     *
ACC TGC ATG TTA AGG AAC ACT ACA TAT TGC AGC AAA GTT GCA
TGG ACG TAC AAT TCC TTG TGA TGT ATA ACG TCG TTT CAA CGT
Thr Cys Met Leu Arg Asn Thr Thr Tyr Cys Ser Lys Val Ala>
________________________IL-1RAcP______________________>

380         390         400         410         420
 *     *     *     *     *     *     *     *     *
TTT CCC TTG GAA GTT GTT CAA AAA GAC AGC TGT TTC AAT TCC
AAA GGG AAC CTT CAA CAA GTT TTT CTG TCG ACA AAG TTA AGG
Phe Pro Leu Glu Val Val Gln Lys Asp Ser Cys Phe Asn Ser>
________________________IL-1RAcP______________________>

         430         440         450          460
     *     *     *     *     *     *     *     *
CCC ATG AAA CTC CCA GTG CAT AAA CTG TAT ATA GAA TAT GGC
GGG TAC TTT GAG GGT CAC GTA TTT GAC ATA TAT CTT ATA CCG
Pro Met Lys Leu Pro Val His Lys Leu Tyr Ile Glu Tyr Gly>
________________________IL-1RAcP______________________>

      470         480         490         500
  *     *     *     *     *     *     *     *
ATT CAG AGG ATC ACT TGT CCA AAT GTA GAT GGA TAT TTT CCT
TAA GTC TCC TAG TGA ACA GGT TTA CAT CTA CCT ATA AAA GGA
Ile Gln Arg Ile Thr Cys Pro Asn Val Asp Gly Tyr Phe Pro>
________________________IL-1RAcP______________________>

    510         520         530         540
*     *     *     *     *     *     *     *     *
TCC AGT GTC AAA CCG ACT ATC ACT TGG TAT ATG GGC TGT TAT
AGG TCA CAG TTT GGC TGA TAG TGA ACC ATA TAC CCG ACA ATA
Ser Ser Val Lys Pro Thr Ile Thr Trp Tyr Met Gly Cys Tyr>
________________________IL-1RAcP______________________>

  550         560         570          580
    *     *     *     *     *     *     *     *
AAA ATA CAG AAT TTT AAT AAT GTA ATA CCC GAA GGT ATG AAC
TTT TAT GTC TTA AAA TTA TTA CAT TAT GGG CTT CCA TAC TTG
Lys Ile Gln Asn Phe Asn Asn Val Ile Pro Glu Gly Met Asn>
________________________IL-1RAcP______________________>

590         600          610         620         630
 *     *     *     *     *     *     *     *     *
TTG AGT TTC CTC ATT GCC TTA ATT TCA AAT AAT GGA AAT TAC
AAC TCA AAG GAG TAA CGG AAT TAA AGT TTA TTA CCT TTA ATG
Leu Ser Phe Leu Ile Ala Leu Ile Ser Asn Asn Gly Asn Tyr>
________________________IL-1RAcP______________________>

         640         650         660          670
     *     *     *     *     *     *     *     *
ACA TGT GTT GTT ACA TAT CCA GAA AAT GGA CGT ACG TTT CAT
TGT ACA CAA CAA TGT ATA GGT CTT TTA CCT GCA TGC AAA GTA
Thr Cys Val Val Thr Tyr Pro Glu Asn Gly Arg Thr Phe His>
________________________IL-1RAcP______________________>
```

Figure 42C

```
        680         690         700         710
  *     *     *    *     *     *    *     *
CTC ACC AGG ACT CTG ACT GTA AAG GTA GTA GGC TCT CCA AAA
GAG TGG TCC TGA GAC TGA CAT TTC CAT CAT CCG AGA GGT TTT
Leu Thr Arg Thr Leu Thr Val Lys Val Val Gly Ser Pro Lys>
____________________IL-1RAcP__________________>

    720         730         740         750
*    *     *     *    *     *     *    *     *
AAT GCA GTG CCC CCT GTG ATC CAT TCA CCT AAT GAT CAT GTG
TTA CGT CAC GGG GGA CAC TAG GTA AGT GGA TTA CTA GTA CAC
Asn Ala Val Pro Pro Val Ile His Ser Pro Asn Asp His Val>
____________________IL-1RAcP__________________>

  760         770         780         790
    *    *     *     *    *     *     *    *
GTC TAT GAG AAA GAA CCA GGA GAG GAG CTA CTC ATT CCC TGT
CAG ATA CTC TTT CTT GGT CCT CTC CTC GAT GAG TAA GGG ACA
Val Tyr Glu Lys Glu Pro Gly Glu Glu Leu Leu Ile Pro Cys>
____________________IL-1RAcP__________________>

800         810         820         830         840
 *     *    *     *     *     *     *     *    *
ACG GTC TAT TTT AGT TTT CTG ATG GAT TCT CGC AAT GAG GTT
TGC CAG ATA AAA TCA AAA GAC TAC CTA AGA GCG TTA CTC CAA
Thr Val Tyr Phe Ser Phe Leu Met Asp Ser Arg Asn Glu Val>
____________________IL-1RAcP__________________>

          850         860         870         880
    *     *    *     *     *     *     *     *
TGG TGG ACC ATT GAT GGA AAA AAA CCT GAT GAC ATC ACT ATT
ACC ACC TGG TAA CTA CCT TTT TTT GGA CTA CTG TAG TGA TAA
Trp Trp Thr Ile Asp Gly Lys Lys Pro Asp Asp Ile Thr Ile>
____________________IL-1RAcP__________________>

        890         900         910         920
  *     *     *    *     *     *    *     *
GAT GTC ACC ATT AAC GAA AGT ATA AGT CAT AGT AGA ACA GAA
CTA CAG TGG TAA TTG CTT TCA TAT TCA GTA TCA TCT TGT CTT
Asp Val Thr Ile Asn Glu Ser Ile Ser His Ser Arg Thr Glu>
____________________IL-1RAcP__________________>

    930         940         950         960
*    *     *     *    *     *     *    *     *
GAT GAA ACA AGA ACT CAG ATT TTG AGC ATC AAG AAA GTT ACC
CTA CTT TGT TCT TGA GTC TAA AAC TCG TAG TTC TTT CAA TGG
Asp Glu Thr Arg Thr Gln Ile Leu Ser Ile Lys Lys Val Thr>
____________________IL-1RAcP__________________>

  970         980         990         1000
    *    *     *     *    *     *     *    *
TCT GAG GAT CTC AAG CGC AGC TAT GTC TGT CAT GCT AGA AGT
AGA CTC CTA GAG TTC GCG TCG ATA CAG ACA GTA CGA TCT TCA
Ser Glu Asp Leu Lys Arg Ser Tyr Val Cys His Ala Arg Ser>
____________________IL-1RAcP__________________>
```

Figure 42D

```
1010          1020          1030          1040          1050
 *       *       *       *       *       *       *       *       *
GCC AAA GGC GAA GTT GCC AAA GCA GCC AAG GTG AAG CAG AAA
CGG TTT CCG CTT CAA CGG TTT CGT CGG TTC CAC TTC GTC TTT
Ala Lys Gly Glu Val Ala Lys Ala Ala Lys Val Lys Gln Lys>
______________________________IL-1RAcP__________________________>

        1060          1070          1080          1090
   *       *       *       *       *       *       *       *
GTG CCA GCT CCA AGA TAC ACA GTG GAA AAA TGC AAG GAA CGT
CAC GGT CGA GGT TCT ATG TGT CAC CTT TTT ACG TTC CTT GCA
Val Pro Ala Pro Arg Tyr Thr Val Glu>
_________________IL-1RAcP_______________>
                                    Lys Cys Lys Glu Arg>
                                    ________IL-1RI_______>

     1100          1110          1120          1130
 *       *       *       *       *       *       *       *
GAA GAA AAA ATA ATT TTA GTG AGC TCA GCA AAT GAA ATC GAT
CTT CTT TTT TAT TAA AAT CAC TCG AGT CGT TTA CTT TAG CTA
Glu Glu Lys Ile Ile Leu Val Ser Ser Ala Asn Glu Ile Asp>
______________________________IL-1RI______________________________>

  1140          1150          1160          1170
*       *       *       *       *       *       *       *       *
GTT CGT CCC TGT CCT CTT AAC CCA AAT GAA CAC AAA GGC ACT
CAA GCA GGG ACA GGA GAA TTG GGT TTA CTT GTG TTT CCG TGA
Val Arg Pro Cys Pro Leu Asn Pro Asn Glu His Lys Gly Thr>
______________________________IL-1RI______________________________>

 1180          1190          1200          1210
     *       *       *       *       *       *       *       *
ATA ACT TGG TAT AAG GAT GAC AGC AAG ACA CCT GTA TCT ACA
TAT TGA ACC ATA TTC CTA CTG TCG TTC TGT GGA CAT AGA TGT
Ile Thr Trp Tyr Lys Asp Asp Ser Lys Thr Pro Val Ser Thr>
______________________________IL-1RI______________________________>

1220          1230          1240          1250          1260
 *       *       *       *       *       *       *       *       *
GAA CAA GCC TCC AGG ATT CAT CAA CAC AAA GAG AAA CTT TGG
CTT GTT CGG AGG TCC TAA GTA GTT GTG TTT CTC TTT GAA ACC
Glu Gln Ala Ser Arg Ile His Gln His Lys Glu Lys Leu Trp>
______________________________IL-1RI______________________________>

        1270          1280          1290          1300
   *       *       *       *       *       *       *       *
TTT GTT CCT GCT AAG GTG GAG GAT TCA GGA CAT TAC TAT TGC
AAA CAA GGA CGA TTC CAC CTC CTA AGT CCT GTA ATG ATA ACG
Phe Val Pro Ala Lys Val Glu Asp Ser Gly His Tyr Tyr Cys>
______________________________IL-1RI______________________________>

     1310          1320          1330          1340
 *       *       *       *       *       *       *       *
GTG GTA AGA AAT TCA TCT TAC TGC CTC AGA ATT AAA ATA AGT
CAC CAT TCT TTA AGT AGA ATG ACG GAG TCT TAA TTT TAT TCA
Val Val Arg Asn Ser Ser Tyr Cys Leu Arg Ile Lys Ile Ser>
______________________________IL-1RI______________________________>
```

Figure 42E

```
   1350         1360         1370         1380
*     *     *     *     *     *     *     *     *
GCA AAA TTT GTG GAG AAT GAG CCT AAC TTA TGT TAT AAT GCA
CGT TTT AAA CAC CTC TTA CTC GGA TTG AAT ACA ATA TTA CGT
Ala Lys Phe Val Glu Asn Glu Pro Asn Leu Cys Tyr Asn Ala>
________________________IL-1RI________________________>

 1390         1400         1410         1420
    *     *     *     *     *     *     *     *
CAA GCC ATA TTT AAG CAG AAA CTA CCC GTT GCA GGA GAC GGA
GTT CGG TAT AAA TTC GTC TTT GAT GGG CAA CGT CCT CTG CCT
Gln Ala Ile Phe Lys Gln Lys Leu Pro Val Ala Gly Asp Gly>
________________________IL-1RI________________________>

1430         1440         1450         1460         1470
  *     *     *     *     *     *     *     *     *
GGA CTT GTG TGC CCT TAT ATG GAG TTT TTT AAA AAT GAA AAT
CCT GAA CAC ACG GGA ATA TAC CTC AAA AAA TTT TTA CTT TTA
Gly Leu Val Cys Pro Tyr Met Glu Phe Phe Lys Asn Glu Asn>
________________________IL-1RI________________________>

         1480         1490         1500         1510
    *     *     *     *     *     *     *     *
AAT GAG TTA CCT AAA TTA CAG TGG TAT AAG GAT TGC AAA CCT
TTA CTC AAT GGA TTT AAT GTC ACC ATA TTC CTA ACG TTT GGA
Asn Glu Leu Pro Lys Leu Gln Trp Tyr Lys Asp Cys Lys Pro>
________________________IL-1RI________________________>

      1520         1530         1540         1550
  *     *     *     *     *     *     *     *
CTA CTT CTT GAC AAT ATA CAC TTT AGT GGA GTC AAA GAT AGG
GAT GAA GAA CTG TTA TAT GTG AAA TCA CCT CAG TTT CTA TCC
Leu Leu Leu Asp Asn Ile His Phe Ser Gly Val Lys Asp Arg>
________________________IL-1RI________________________>

   1560         1570         1580         1590
*     *     *     *     *     *     *     *     *
CTC ATC GTG ATG AAT GTG GCT GAA AAG CAT AGA GGG AAC TAT
GAG TAG CAC TAC TTA CAC CGA CTT TTC GTA TCT CCC TTG ATA
Leu Ile Val Met Asn Val Ala Glu Lys His Arg Gly Asn Tyr>
________________________IL-1RI________________________>

 1600         1610         1620         1630
    *     *     *     *     *     *     *     *
ACT TGT CAT GCA TCC TAC ACA TAC TTG GGC AAG CAA TAT CCT
TGA ACA GTA CGT AGG ATG TGT ATG AAC CCG TTC GTT ATA GGA
Thr Cys His Ala Ser Tyr Thr Tyr Leu Gly Lys Gln Tyr Pro>
________________________IL-1RI________________________>

1640         1650         1660         1670         1680
  *     *     *     *     *     *     *     *     *
ATT ACC CGG GTA ATA GAA TTT ATT ACT CTA GAG GAA AAC AAA
TAA TGG GCC CAT TAT CTT AAA TAA TGA GAT CTC CTT TTG TTT
Ile Thr Arg Val Ile Glu Phe Ile Thr Leu Glu Glu Asn Lys>
________________________IL-1RI________________________>
```

Figure 42F

```
        1690        1700        1710        1720
      *     *     *     *     *     *     *     *
CCC ACA AGG CCT GTG ATT GTG AGC CCA GCT AAT GAG ACA ATG
GGG TGT TCC GGA CAC TAA CAC TCG GGT CGA TTA CTC TGT TAC
Pro Thr Arg Pro Val Ile Val Ser Pro Ala Asn Glu Thr Met>
________________________IL-1RI________________________>

     1730        1740        1750        1760
  *     *     *     *     *     *     *     *
GAA GTA GAC TTG GGA TCC CAG ATA CAA TTG ATC TGT AAT GTC
CTT CAT CTG AAC CCT AGG GTC TAT GTT AAC TAG ACA TTA CAG
Glu Val Asp Leu Gly Ser Gln Ile Gln Leu Ile Cys Asn Val>
________________________IL-1RI________________________>

   1770        1780        1790        1800
*     *     *     *     *     *     *     *     *
ACC GGC CAG TTG AGT GAC ATT GCT TAC TGG AAG TGG AAT GGG
TGG CCG GTC AAC TCA CTG TAA CGA ATG ACC TTC ACC TTA CCC
Thr Gly Gln Leu Ser Asp Ile Ala Tyr Trp Lys Trp Asn Gly>
________________________IL-1RI________________________>

  1810        1820        1830        1840
     *     *     *     *     *     *     *     *
TCA GTA ATT GAT GAA GAT GAC CCA GTG CTA GGG GAA GAC TAT
AGT CAT TAA CTA CTT CTA CTG GGT CAC GAT CCC CTT CTG ATA
Ser Val Ile Asp Glu Asp Asp Pro Val Leu Gly Glu Asp Tyr>
________________________IL-1RI________________________>

1850        1860        1870        1880        1890
  *     *     *     *     *     *     *     *     *
TAC AGT GTG GAA AAT CCT GCA AAC AAA AGA AGG AGT ACC CTC
ATG TCA CAC CTT TTA GGA CGT TTG TTT TCT TCC TCA TGG GAG
Tyr Ser Val Glu Asn Pro Ala Asn Lys Arg Arg Ser Thr Leu>
________________________IL-1RI________________________>

        1900        1910        1920        1930
      *     *     *     *     *     *     *     *
ATC ACA GTG CTT AAT ATA TCG GAA ATT GAG AGT AGA TTT TAT
TAG TGT CAC GAA TTA TAT AGC CTT TAA CTC TCA TCT AAA ATA
Ile Thr Val Leu Asn Ile Ser Glu Ile Glu Ser Arg Phe Tyr>
________________________IL-1RI________________________>

     1940        1950        1960        1970
  *     *     *     *     *     *     *     *
AAA CAT CCA TTT ACC TGT TTT GCC AAG AAT ACA CAT GGT ATA
TTT GTA GGT AAA TGG ACA AAA CGG TTC TTA TGT GTA CCA TAT
Lys His Pro Phe Thr Cys Phe Ala Lys Asn Thr His Gly Ile>
________________________IL-1RI________________________>

   1980        1990        2000        2010
*     *     *     *     *     *     *     *     *
GAT GCA GCA TAT ATC CAG TTA ATA TAT CCA GTC ACT AAT TCC
CTA CGT CGT ATA TAG GTC AAT TAT ATA GGT CAG TGA TTA AGG
Asp Ala Ala Tyr Ile Gln Leu Ile Tyr Pro Val Thr Asn>
________________________IL-1RI____________________>
                                                Ser>
                                                ___>
```

Figure 42G

```
 2020        2030        2040        2050
    *     *     *     *     *     *     *     *
GGA GAG TCC AAA TAC GGT CCG CCA TGC CCA TCA TGC CCA GCA
CCT CTC AGG TTT ATG CCA GGC GGT ACG GGT AGT ACG GGT CGT
Gly>
___>
    Glu Ser Lys Tyr Gly Pro Pro Cys Pro Ser Cys Pro Ala>
    ___________________FC-IgG4__________________________>

2060        2070        2080        2090        2100
  *     *     *     *     *     *     *     *     *
CCT GAG TTC CTG GGG GGA CCA TCA GTC TTC CTG TTC CCC CCA
GGA CTC AAG GAC CCC CCT GGT AGT CAG AAG GAC AAG GGG GGT
Pro Glu Phe Leu Gly Gly Pro Ser Val Phe Leu Phe Pro Pro>
_______________________FC-IgG4__________________________>

          2110        2120        2130        2140
      *     *     *     *     *     *     *     *
AAA CCC AAG GAC ACT CTC ATG ATC TCC CGG ACC CCT GAG GTC
TTT GGG TTC CTG TGA GAG TAC TAG AGG GCC TGG GGA CTC CAG
Lys Pro Lys Asp Thr Leu Met Ile Ser Arg Thr Pro Glu Val>
_______________________FC-IgG4__________________________>

       2150        2160        2170        2180
  *     *     *     *     *     *     *     *
ACG TGC GTG GTG GTG GAC GTG AGC CAG GAA GAC CCC GAG GTC
TGC ACG CAC CAC CAC CTG CAC TCG GTC CTT CTG GGG CTC CAG
Thr Cys Val Val Val Asp Val Ser Gln Glu Asp Pro Glu Val>
_______________________FC-IgG4__________________________>

   2190        2200        2210        2220
*     *     *     *     *     *     *     *     *
CAG TTC AAC TGG TAC GTG GAT GGC GTG GAG GTG CAT AAT GCC
GTC AAG TTG ACC ATG CAC CTA CCG CAC CTC CAC GTA TTA CGG
Gln Phe Asn Trp Tyr Val Asp Gly Val Glu Val His Asn Ala>
_______________________FC-IgG4__________________________>

 2230        2240        2250        2260
    *     *     *     *     *     *     *     *
AAG ACA AAG CCG CGG GAG GAG CAG TTC AAC AGC ACG TAC CGT
TTC TGT TTC GGC GCC CTC CTC GTC AAG TTG TCG TGC ATG GCA
Lys Thr Lys Pro Arg Glu Glu Gln Phe Asn Ser Thr Tyr Arg>
_______________________FC-IgG4__________________________>

2270        2280        2290        2300        2310
  *     *     *     *     *     *     *     *     *
GTG GTC AGC GTC CTC ACC GTC CTG CAC CAG GAC TGG CTG AAC
CAC CAG TCG CAG GAG TGG CAG GAC GTG GTC CTG ACC GAC TTG
Val Val Ser Val Leu Thr Val Leu His Gln Asp Trp Leu Asn>
_______________________FC-IgG4__________________________>

          2320        2330        2340        2350
      *     *     *     *     *     *     *     *
GGC AAG GAG TAC AAG TGC AAG GTC TCC AAC AAA GGC CTC CCG
CCG TTC CTC ATG TTC ACG TTC CAG AGG TTG TTT CCG GAG GGC
Gly Lys Glu Tyr Lys Cys Lys Val Ser Asn Lys Gly Leu Pro>
_______________________FC-IgG4__________________________>
```

Figure 42H

```
     2360       2370       2380       2390
 *      *     *     *     *     *     *     *
TCC TCC ATC GAG AAA ACC ATC TCC AAA GCC AAA GGG CAG CCC
AGG AGG TAG CTC TTT TGG TAG AGG TTT CGG TTT CCC GTC GGG
Ser Ser Ile Glu Lys Thr Ile Ser Lys Ala Lys Gly Gln Pro>
_________________________FC-IgG4___________________________>

   2400       2410       2420       2430
*     *     *     *     *     *     *     *     *
CGA GAG CCA CAG GTG TAC ACC CTG CCC CCA TCC CAG GAG GAG
GCT CTC GGT GTC CAC ATG TGG GAC GGG GGT AGG GTC CTC CTC
Arg Glu Pro Gln Val Tyr Thr Leu Pro Pro Ser Gln Glu Glu>
_________________________FC-IgG4___________________________>

 2440       2450       2460       2470
    *     *     *     *     *     *     *
ATG ACC AAG AAC CAG GTC AGC CTG ACC TGC CTG GTC AAA GGC
TAC TGG TTC TTG GTC CAG TCG GAC TGG ACG GAC CAG TTT CCG
Met Thr Lys Asn Gln Val Ser Leu Thr Cys Leu Val Lys Gly>
_________________________FC-IgG4___________________________>

2480       2490       2500       2510       2520
 *     *     *     *     *     *     *     *     *
TTC TAC CCC AGC GAC ATC GCC GTG GAG TGG GAG AGC AAT GGG
AAG ATG GGG TCG CTG TAG CGG CAC CTC ACC CTC TCG TTA CCC
Phe Tyr Pro Ser Asp Ile Ala Val Glu Trp Glu Ser Asn Gly>
_________________________FC-IgG4___________________________>

       2530       2540       2550       2560
   *     *     *     *     *     *     *     *
CAG CCG GAG AAC AAC TAC AAG ACC ACG CCT CCC GTG CTG GAC
GTC GGC CTC TTG TTG ATG TTC TGG TGC GGA GGG CAC GAC CTG
Gln Pro Glu Asn Asn Tyr Lys Thr Thr Pro Pro Val Leu Asp>
_________________________FC-IgG4___________________________>

    2570       2580       2590       2600
 *     *     *     *     *     *     *     *
TCC GAC GGC TCC TTC TTC CTC TAC AGC AGG CTA ACC GTG GAC
AGG CTG CCG AGG AAG AAG GAG ATG TCG TCC GAT TGG CAC CTG
Ser Asp Gly Ser Phe Phe Leu Tyr Ser Arg Leu Thr Val Asp>
_________________________FC-IgG4___________________________>

   2610       2620       2630       2640
*     *     *     *     *     *     *     *     *
AAG AGC AGG TGG CAG GAG GGG AAT GTC TTC TCA TGC TCC GTG
TTC TCG TCC ACC GTC CTC CCC TTA CAG AAG AGT ACG AGG CAC
Lys Ser Arg Trp Gln Glu Gly Asn Val Phe Ser Cys Ser Val>
_________________________FC-IgG4___________________________>

 2650       2660       2670       2680
    *     *     *     *     *     *     *     *
ATG CAT GAG GCT CTG CAC AAC CAC TAC ACA CAG AAG AGC CTC
TAC GTA CTC CGA GAC GTG TTG GTG ATG TGT GTC TTC TCG GAG
Met His Glu Ala Leu His Asn His Tyr Thr Gln Lys Ser Leu>
_________________________FC-IgG4___________________________>
```

Figure 42 I

```
2690          2700
  *        *       *        *
TCC CTG TCT CTG GGT AAA TGA
AGG GAC AGA GAC CCA TTT ACT
Ser Leu Ser Leu Gly Lys ***>
__________FC-IgG4__________>
```

Figure 43A

```
          10          20          30          40
    *     *     *     *     *     *     *     *
ATG GTG CTT CTG TGG TGT GTA GTG AGT CTC TAC TTT TAT GGA
TAC CAC GAA GAC ACC ACA CAT CAC TCA GAG ATG AAA ATA CCT
Met Val Leu Leu Trp Cys Val Val Ser Leu Tyr Phe Tyr Gly>
____________________SIGNAL PEPTIDE____________________>
___________________________IL-1RAcP___________________>

        50          60          70          80
  *     *     *     *     *     *     *     *
ATC CTG CAA AGT GAT GCC TCA GAA CGC TGC GAT GAC TGG GGA
TAG GAC GTT TCA CTA CGG AGT CTT GCG ACG CTA CTG ACC CCT
Ile Leu Gln Ser Asp Ala>
___SIGNAL PEPTIDE  _____>
                        Ser Glu Arg Cys Asp Asp Trp Gly>
_________________________IL-1RAcP_____________________>

     90         100         110         120
*     *     *     *     *     *     *     *     *
CTA GAC ACC ATG AGG CAA ATC CAA GTG TTT GAA GAT GAG CCA
GAT CTG TGG TAC TCC GTT TAG GTT CAC AAA CTT CTA CTC GGT
Leu Asp Thr Met Arg Gln Ile Gln Val Phe Glu Asp Glu Pro>
_________________________IL-1RAcP_____________________>

 130         140         150         160
    *     *     *     *     *     *     *     *
GCT CGC ATC AAG TGC CCA CTC TTT GAA CAC TTC TTG AAA TTC
CGA GCG TAG TTC ACG GGT GAG AAA CTT GTG AAG AAC TTT AAG
Ala Arg Ile Lys Cys Pro Leu Phe Glu His Phe Leu Lys Phe>
_________________________IL-1RAcP_____________________>

170         180         190         200         210
  *     *     *     *     *     *     *     *     *
AAC TAC AGC ACA GCC CAT TCA GCT GGC CTT ACT CTG ATC TGG
TTG ATG TCG TGT CGG GTA AGT CGA CCG GAA TGA GAC TAG ACC
Asn Tyr Ser Thr Ala His Ser Ala Gly Leu Thr Leu Ile Trp>
_________________________IL-1RAcP_____________________>

          220         230         240         250
     *     *     *     *     *     *     *     *
TAT TGG ACT AGG CAG GAC CGG GAC CTT GAG GAG CCA ATT AAC
ATA ACC TGA TCC GTC CTG GCC CTG GAA CTC CTC GGT TAA TTG
Tyr Trp Thr Arg Gln Asp Arg Asp Leu Glu Glu Pro Ile Asn>
_________________________IL-1RAcP_____________________>

       260         270         280         290
  *     *     *     *     *     *     *     *
TTC CGC CTC CCC GAG AAC CGC ATT AGT AAG GAG AAA GAT GTG
AAG GCG GAG GGG CTC TTG GCG TAA TCA TTC CTC TTT CTA CAC
Phe Arg Leu Pro Glu Asn Arg Ile Ser Lys Glu Lys Asp Val>
_________________________IL-1RAcP_____________________>

     300         310         320         330
*     *     *     *     *     *     *     *     *
CTG TGG TTC CGG CCC ACT CTC CTC AAT GAC ACT GGC AAC TAT
GAC ACC AAG GCC GGG TGA GAG GAG TTA CTG TGA CCG TTG ATA
Leu Trp Phe Arg Pro Thr Leu Leu Asn Asp Thr Gly Asn Tyr>
_________________________IL-1RAcP_____________________>
```

Figure 43B

```
 340        350        360        370
  *     *     *     *     *     *     *     *
ACC TGC ATG TTA AGG AAC ACT ACA TAT TGC AGC AAA GTT GCA
TGG ACG TAC AAT TCC TTG TGA TGT ATA ACG TCG TTT CAA CGT
Thr Cys Met Leu Arg Asn Thr Thr Tyr Cys Ser Lys Val Ala>
_____________________________IL-1RAcP__________________________>

380        390        400        410        420
 *     *     *     *     *     *     *     *     *
TTT CCC TTG GAA GTT GTT CAA AAA GAC AGC TGT TTC AAT TCC
AAA GGG AAC CTT CAA CAA GTT TTT CTG TCG ACA AAG TTA AGG
Phe Pro Leu Glu Val Val Gln Lys Asp Ser Cys Phe Asn Ser>
_____________________________IL-1RAcP__________________________>

      430        440        450        460
   *     *     *     *     *     *     *     *
CCC ATG AAA CTC CCA GTG CAT AAA CTG TAT ATA GAA TAT GGC
GGG TAC TTT GAG GGT CAC GTA TTT GAC ATA TAT CTT ATA CCG
Pro Met Lys Leu Pro Val His Lys Leu Tyr Ile Glu Tyr Gly>
_____________________________IL-1RAcP__________________________>

    470        480        490        500
 *     *     *     *     *     *     *     *
ATT CAG AGG ATC ACT TGT CCA AAT GTA GAT GGA TAT TTT CCT
TAA GTC TCC TAG TGA ACA GGT TTA CAT CTA CCT ATA AAA GGA
Ile Gln Arg Ile Thr Cys Pro Asn Val Asp Gly Tyr Phe Pro>
_____________________________IL-1RAcP__________________________>

   510        520        530        540
*     *     *     *     *     *     *     *     *
TCC AGT GTC AAA CCG ACT ATC ACT TGG TAT ATG GGC TGT TAT
AGG TCA CAG TTT GGC TGA TAG TGA ACC ATA TAC CCG ACA ATA
Ser Ser Val Lys Pro Thr Ile Thr Trp Tyr Met Gly Cys Tyr>
_____________________________IL-1RAcP__________________________>

 550        560        570        580
   *     *     *     *     *     *     *     *
AAA ATA CAG AAT TTT AAT AAT GTA ATA CCC GAA GGT ATG AAC
TTT TAT GTC TTA AAA TTA TTA CAT TAT GGG CTT CCA TAC TTG
Lys Ile Gln Asn Phe Asn Asn Val Ile Pro Glu Gly Met Asn>
_____________________________IL-1RAcP__________________________>

590        600        610        620        630
 *     *     *     *     *     *     *     *     *
TTG AGT TTC CTC ATT GCC TTA ATT TCA AAT AAT GGA AAT TAC
AAC TCA AAG GAG TAA CGG AAT TAA AGT TTA TTA CCT TTA ATG
Leu Ser Phe Leu Ile Ala Leu Ile Ser Asn Asn Gly Asn Tyr>
_____________________________IL-1RAcP__________________________>

       640        650        660        670
   *     *     *     *     *     *     *     *
ACA TGT GTT GTT ACA TAT CCA GAA AAT GGA CGT ACG TTT CAT
TGT ACA CAA CAA TGT ATA GGT CTT TTA CCT GCA TGC AAA GTA
Thr Cys Val Val Thr Tyr Pro Glu Asn Gly Arg Thr Phe His>
_____________________________IL-1RAcP__________________________>
```

Figure 43C

```
      680        690         700        710
 *     *     *    *     *     *    *     *
CTC ACC AGG ACT CTG ACT GTA AAG GTA GTA GGC TCT CCA AAA
GAG TGG TCC TGA GAC TGA CAT TTC CAT CAT CCG AGA GGT TTT
Leu Thr Arg Thr Leu Thr Val Lys Val Val Gly Ser Pro Lys>
__________________________IL-1RAcP_______________________>

    720        730        740        750
*     *     *    *     *     *     *    *     *
AAT GCA GTG CCC CCT GTG ATC CAT TCA CCT AAT GAT CAT GTG
TTA CGT CAC GGG GGA CAC TAG GTA AGT GGA TTA CTA GTA CAC
Asn Ala Val Pro Pro Val Ile His Ser Pro Asn Asp His Val>
__________________________IL-1RAcP_______________________>

  760        770        780        790
    *     *     *     *     *     *     *    *
GTC TAT GAG AAA GAA CCA GGA GAG GAG CTA CTC ATT CCC TGT
CAG ATA CTC TTT CTT GGT CCT CTC CTC GAT GAG TAA GGG ACA
Val Tyr Glu Lys Glu Pro Gly Glu Glu Leu Leu Ile Pro Cys>
__________________________IL-1RAcP_______________________>

800        810        820        830        840
 *     *     *     *     *     *     *     *     *
ACG GTC TAT TTT AGT TTT CTG ATG GAT TCT CGC AAT GAG GTT
TGC CAG ATA AAA TCA AAA GAC TAC CTA AGA GCG TTA CTC CAA
Thr Val Tyr Phe Ser Phe Leu Met Asp Ser Arg Asn Glu Val>
__________________________IL-1RAcP_______________________>

        850        860        870        880
    *     *     *     *     *     *     *     *
TGG TGG ACC ATT GAT GGA AAA AAA CCT GAT GAC ATC ACT ATT
ACC ACC TGG TAA CTA CCT TTT TTT GGA CTA CTG TAG TGA TAA
Trp Trp Thr Ile Asp Gly Lys Lys Pro Asp Asp Ile Thr Ile>
__________________________IL-1RAcP_______________________>

      890        900        910        920
 *     *     *     *     *     *     *     *
GAT GTC ACC ATT AAC GAA AGT ATA AGT CAT AGT AGA ACA GAA
CTA CAG TGG TAA TTG CTT TCA TAT TCA GTA TCA TCT TGT CTT
Asp Val Thr Ile Asn Glu Ser Ile Ser His Ser Arg Thr Glu>
__________________________IL-1RAcP_______________________>

    930        940        950        960
*     *     *     *     *     *     *     *     *
GAT GAA ACA AGA ACT CAG ATT TTG AGC ATC AAG AAA GTT ACC
CTA CTT TGT TCT TGA GTC TAA AAC TCG TAG TTC TTT CAA TGG
Asp Glu Thr Arg Thr Gln Ile Leu Ser Ile Lys Lys Val Thr>
__________________________IL-1RAcP_______________________>

  970        980        990        1000
    *     *     *     *     *     *     *     *
TCT GAG GAT CTC AAG CGC AGC TAT GTC TGT CAT GCT AGA AGT
AGA CTC CTA GAG TTC GCG TCG ATA CAG ACA GTA CGA TCT TCA
Ser Glu Asp Leu Lys Arg Ser Tyr Val Cys His Ala Arg Ser>
__________________________IL-1RAcP_______________________>
```

Figure 43D

```
1010          1020          1030          1040          1050
  *       *       *       *       *       *       *       *
GCC AAA GGC GAA GTT GCC AAA GCA GCC AAG GTG AAG CAG AAA
CGG TTT CCG CTT CAA CGG TTT CGT CGG TTC CAC TTC GTC TTT
Ala Lys Gly Glu Val Ala Lys Ala Ala Lys Val Lys Gln Lys>
___________________________IL-1RAcP________________________>

          1060          1070          1080          1090
    *       *       *       *       *       *       *       *
GTG CCA GCT CCA AGA TAC ACA GTG GAA AAA TGC AAG GAA CGT
CAC GGT CGA GGT TCT ATG TGT CAC CTT TTT ACG TTC CTT GCA
Val Pro Ala Pro Arg Tyr Thr Val Glu>
________________IL-1RAcP_____________>
                                    Lys Cys Lys Glu Arg>
                                    ________IL-1RI______>

      1100          1110          1120          1130
  *       *       *       *       *       *       *       *
GAA GAA AAA ATA ATT TTA GTG AGC TCA GCA AAT GAA ATC GAT
CTT CTT TTT TAT TAA AAT CAC TCG AGT CGT TTA CTT TAG CTA
Glu Glu Lys Ile Ile Leu Val Ser Ser Ala Asn Glu Ile Asp>
__________________________IL-1RI__________________________>

   1140          1150          1160          1170
*       *       *       *       *       *       *       *
GTT CGT CCC TGT CCT CTT AAC CCA AAT GAA CAC AAA GGC ACT
CAA GCA GGG ACA GGA GAA TTG GGT TTA CTT GTG TTT CCG TGA
Val Arg Pro Cys Pro Leu Asn Pro Asn Glu His Lys Gly Thr>
__________________________IL-1RI__________________________>

1180          1190          1200          1210
    *       *       *       *       *       *       *       *
ATA ACT TGG TAT AAG GAT GAC AGC AAG ACA CCT GTA TCT ACA
TAT TGA ACC ATA TTC CTA CTG TCG TTC TGT GGA CAT AGA TGT
Ile Thr Trp Tyr Lys Asp Asp Ser Lys Thr Pro Val Ser Thr>
__________________________IL-1RI__________________________>

1220          1230          1240          1250          1260
  *       *       *       *       *       *       *       *       *
GAA CAA GCC TCC AGG ATT CAT CAA CAC AAA GAG AAA CTT TGG
CTT GTT CGG AGG TCC TAA GTA GTT GTG TTT CTC TTT GAA ACC
Glu Gln Ala Ser Arg Ile His Gln His Lys Glu Lys Leu Trp>
__________________________IL-1RI__________________________>

          1270          1280          1290          1300
    *       *       *       *       *       *       *       *
TTT GTT CCT GCT AAG GTG GAG GAT TCA GGA CAT TAC TAT TGC
AAA CAA GGA CGA TTC CAC CTC CTA AGT CCT GTA ATG ATA ACG
Phe Val Pro Ala Lys Val Glu Asp Ser Gly His Tyr Tyr Cys>
__________________________IL-1RI__________________________>

      1310          1320          1330          1340
  *       *       *       *       *       *       *       *
GTG GTA AGA AAT TCA TCT TAC TGC CTC AGA ATT AAA ATA AGT
CAC CAT TCT TTA AGT AGA ATG ACG GAG TCT TAA TTT TAT TCA
Val Val Arg Asn Ser Ser Tyr Cys Leu Arg Ile Lys Ile Ser>
__________________________IL-1RI__________________________>
```

Figure 43E

```
   1350          1360          1370          1380
 *     *      *      *      *      *      *      *      *
GCA AAA TTT GTG GAG AAT GAG CCT AAC TTA TGT TAT AAT GCA
CGT TTT AAA CAC CTC TTA CTC GGA TTG AAT ACA ATA TTA CGT
Ala Lys Phe Val Glu Asn Glu Pro Asn Leu Cys Tyr Asn Ala>
________________________IL-1RI_________________________>

 1390         1400          1410          1420
    *      *      *      *      *      *      *      *
CAA GCC ATA TTT AAG CAG AAA CTA CCC GTT GCA GGA GAC GGA
GTT CGG TAT AAA TTC GTC TTT GAT GGG CAA CGT CCT CTG CCT
Gln Ala Ile Phe Lys Gln Lys Leu Pro Val Ala Gly Asp Gly>
________________________IL-1RI_________________________>

1430        1440          1450          1460          1470
  *      *      *      *      *      *      *      *      *
GGA CTT GTG TGC CCT TAT ATG GAG TTT TTT AAA AAT GAA AAT
CCT GAA CAC ACG GGA ATA TAC CTC AAA AAA TTT TTA CTT TTA
Gly Leu Val Cys Pro Tyr Met Glu Phe Phe Lys Asn Glu Asn>
________________________IL-1RI_________________________>

        1480          1490          1500          1510
      *      *      *      *      *      *      *      *
AAT GAG TTA CCT AAA TTA CAG TGG TAT AAG GAT TGC AAA CCT
TTA CTC AAT GGA TTT AAT GTC ACC ATA TTC CTA ACG TTT GGA
Asn Glu Leu Pro Lys Leu Gln Trp Tyr Lys Asp Cys Lys Pro>
________________________IL-1RI_________________________>

     1520          1530          1540          1550
  *      *      *      *      *      *      *      *
CTA CTT CTT GAC AAT ATA CAC TTT AGT GGA GTC AAA GAT AGG
GAT GAA GAA CTG TTA TAT GTG AAA TCA CCT CAG TTT CTA TCC
Leu Leu Leu Asp Asn Ile His Phe Ser Gly Val Lys Asp Arg>
________________________IL-1RI_________________________>

   1560          1570          1580          1590
 *      *      *      *      *      *      *      *      *
CTC ATC GTG ATG AAT GTG GCT GAA AAG CAT AGA GGG AAC TAT
GAG TAG CAC TAC TTA CAC CGA CTT TTC GTA TCT CCC TTG ATA
Leu Ile Val Met Asn Val Ala Glu Lys His Arg Gly Asn Tyr>
________________________IL-1RI_________________________>

  1600          1610          1620          1630
    *      *      *      *      *      *      *      *
ACT TGT CAT GCA TCC TAC ACA TAC TTG GGC AAG CAA TAT CCT
TGA ACA GTA CGT AGG ATG TGT ATG AAC CCG TTC GTT ATA GGA
Thr Cys His Ala Ser Tyr Thr Tyr Leu Gly Lys Gln Tyr Pro>
________________________IL-1RI_________________________>

1640        1650          1660          1670          1680
  *      *      *      *      *      *      *      *      *
ATT ACC CGG GTA ATA GAA TTT ATT ACT CTA GAG GAA AAC AAA
TAA TGG GCC CAT TAT CTT AAA TAA TGA GAT CTC CTT TTG TTT
Ile Thr Arg Val Ile Glu Phe Ile Thr Leu Glu Glu Asn Lys>
________________________IL-1RI_________________________>
```

Figure 43F

```
         1690        1700        1710        1720
    *     *     *     *     *     *     *     *
CCC ACA AGG CCT GTG ATT GTG AGC CCA GCT AAT GAG ACA ATG
GGG TGT TCC GGA CAC TAA CAC TCG GGT CGA TTA CTC TGT TAC
Pro Thr Arg Pro Val Ile Val Ser Pro Ala Asn Glu Thr Met>
____________________________IL-1RI____________________________>

      1730        1740        1750        1760
  *     *     *     *     *     *     *     *
GAA GTA GAC TTG GGA TCC CAG ATA CAA TTG ATC TGT AAT GTC
CTT CAT CTG AAC CCT AGG GTC TAT GTT AAC TAG ACA TTA CAG
Glu Val Asp Leu Gly Ser Gln Ile Gln Leu Ile Cys Asn Val>
____________________________IL-1RI____________________________>

   1770        1780        1790        1800
*     *     *     *     *     *     *     *     *
ACC GGC CAG TTG AGT GAC ATT GCT TAC TGG AAG TGG AAT GGG
TGG CCG GTC AAC TCA CTG TAA CGA ATG ACC TTC ACC TTA CCC
Thr Gly Gln Leu Ser Asp Ile Ala Tyr Trp Lys Trp Asn Gly>
____________________________IL-1RI____________________________>

 1810        1820        1830        1840
    *     *     *     *     *     *     *     *
TCA GTA ATT GAT GAA GAT GAC CCA GTG CTA GGG GAA GAC TAT
AGT CAT TAA CTA CTT CTA CTG GGT CAC GAT CCC CTT CTG ATA
Ser Val Ile Asp Glu Asp Asp Pro Val Leu Gly Glu Asp Tyr>
____________________________IL-1RI____________________________>

1850        1860        1870        1880        1890
  *     *     *     *     *     *     *     *     *
TAC AGT GTG GAA AAT CCT GCA AAC AAA AGA AGG AGT ACC CTC
ATG TCA CAC CTT TTA GGA CGT TTG TTT TCT TCC TCA TGG GAG
Tyr Ser Val Glu Asn Pro Ala Asn Lys Arg Arg Ser Thr Leu>
____________________________IL-1RI____________________________>

         1900        1910        1920        1930
    *     *     *     *     *     *     *     *
ATC ACA GTG CTT AAT ATA TCG GAA ATT GAG AGT AGA TTT TAT
TAG TGT CAC GAA TTA TAT AGC CTT TAA CTC TCA TCT AAA ATA
Ile Thr Val Leu Asn Ile Ser Glu Ile Glu Ser Arg Phe Tyr>
____________________________IL-1RI____________________________>

      1940        1950        1960        1970
  *     *     *     *     *     *     *     *
AAA CAT CCA TTT ACC TGT TTT GCC AAG AAT ACA CAT GGT ATA
TTT GTA GGT AAA TGG ACA AAA CGG TTC TTA TGT GTA CCA TAT
Lys His Pro Phe Thr Cys Phe Ala Lys Asn Thr His Gly Ile>
____________________________IL-1RI____________________________>

   1980        1990        2000        2010
*     *     *     *     *     *     *     *     *
GAT GCA GCA TAT ATC CAG TTA ATA TAT CCA GTC ACT AAT TCC
CTA CGT CGT ATA TAG GTC AAT TAT ATA GGT CAG TGA TTA AGG
Asp Ala Ala Tyr Ile Gln Leu Ile Tyr Pro Val Thr Asn>
____________________________IL-1RI_________________________>
                                                     Ser>
                                                     ___>
```

Figure 43G

```
 2020        2030        2040         2050
   *     *     *     *     *     *     *     *
GGA GAG TCC AAA TAC GGT CCG CCA TGC CCA CCA TGC CCA GCA
CCT CTC AGG TTT ATG CCA GGC GGT ACG GGT GGT ACG GGT CGT
Gly>
___>
    Glu Ser Lys Tyr Gly Pro Pro Cys Pro Pro Cys Pro Ala>
    ___________________FC-IgG4__________________________>

2060        2070        2080        2090        2100
  *     *     *     *     *     *     *     *     *
CCT GAG TTC CTG GGG GGA CCA TCA GTC TTC CTG TTC CCC CCA
GGA CTC AAG GAC CCC CCT GGT AGT CAG AAG GAC AAG GGG GGT
Pro Glu Phe Leu Gly Gly Pro Ser Val Phe Leu Phe Pro Pro>
_______________________FC-IgG4__________________________>

       2110        2120        2130        2140
    *     *     *     *     *     *     *     *
AAA CCC AAG GAC ACT CTC ATG ATC TCC CGG ACC CCT GAG GTC
TTT GGG TTC CTG TGA GAG TAC TAG AGG GCC TGG GGA CTC CAG
Lys Pro Lys Asp Thr Leu Met Ile Ser Arg Thr Pro Glu Val>
_______________________FC-IgG4__________________________>

     2150        2160        2170        2180
 *     *     *     *     *     *     *     *
ACG TGC GTG GTG GTG GAC GTG AGC CAG GAA GAC CCC GAG GTC
TGC ACG CAC CAC CAC CTG CAC TCG GTC CTT CTG GGG CTC CAG
Thr Cys Val Val Val Asp Val Ser Gln Glu Asp Pro Glu Val>
_______________________FC-IgG4__________________________>

   2190        2200        2210        2220
*     *     *     *     *     *     *     *     *
CAG TTC AAC TGG TAC GTG GAT GGC GTG GAG GTG CAT AAT GCC
GTC AAG TTG ACC ATG CAC CTA CCG CAC CTC CAC GTA TTA CGG
Gln Phe Asn Trp Tyr Val Asp Gly Val Glu Val His Asn Ala>
_______________________FC-IgG4__________________________>

 2230        2240        2250        2260
     *     *     *     *     *     *     *     *
AAG ACA AAG CCG CGG GAG GAG CAG TTC AAC AGC ACG TAC CGT
TTC TGT TTC GGC GCC CTC CTC GTC AAG TTG TCG TGC ATG GCA
Lys Thr Lys Pro Arg Glu Glu Gln Phe Asn Ser Thr Tyr Arg>
_______________________FC-IgG4__________________________>

2270        2280        2290        2300        2310
  *     *     *     *     *     *     *     *     *
GTG GTC AGC GTC CTC ACC GTC CTG CAC CAG GAC TGG CTG AAC
CAC CAG TCG CAG GAG TGG CAG GAC GTG GTC CTG ACC GAC TTG
Val Val Ser Val Leu Thr Val Leu His Gln Asp Trp Leu Asn>
_______________________FC-IgG4__________________________>

       2320        2330        2340        2350
    *     *     *     *     *     *     *     *
GGC AAG GAG TAC AAG TGC AAG GTC TCC AAC AAA GGC CTC CCG
CCG TTC CTC ATG TTC ACG TTC CAG AGG TTG TTT CCG GAG GGC
Gly Lys Glu Tyr Lys Cys Lys Val Ser Asn Lys Gly Leu Pro>
_______________________FC-IgG4__________________________>
```

Figure 43H

```
     2360       2370       2380       2390
  *     *     *    *     *     *    *     *
TCC TCC ATC GAG AAA ACC ATC TCC AAA GCC AAA GGG CAG CCC
AGG AGG TAG CTC TTT TGG TAG AGG TTT CGG TTT CCC GTC GGG
Ser Ser Ile Glu Lys Thr Ile Ser Lys Ala Lys Gly Gln Pro>
_________________________FC-IgG4___________________________>

   2400       2410       2420       2430
*    *     *     *    *     *     *    *     *
CGA GAG CCA CAG GTG TAC ACC CTG CCC CCA TCC CAG GAG GAG
GCT CTC GGT GTC CAC ATG TGG GAC GGG GGT AGG GTC CTC CTC
Arg Glu Pro Gln Val Tyr Thr Leu Pro Pro Ser Gln Glu Glu>
_________________________FC-IgG4___________________________>

 2440       2450       2460       2470
    *     *     *     *    *     *     *    *
ATG ACC AAG AAC CAG GTC AGC CTG ACC TGC CTG GTC AAA GGC
TAC TGG TTC TTG GTC CAG TCG GAC TGG ACG GAC CAG TTT CCG
Met Thr Lys Asn Gln Val Ser Leu Thr Cys Leu Val Lys Gly>
_________________________FC-IgG4___________________________>

2480       2490       2500       2510       2520
  *     *    *     *     *    *     *     *    *
TTC TAC CCC AGC GAC ATC GCC GTG GAG TGG GAG AGC AAT GGG
AAG ATG GGG TCG CTG TAG CGG CAC CTC ACC CTC TCG TTA CCC
Phe Tyr Pro Ser Asp Ile Ala Val Glu Trp Glu Ser Asn Gly>
_________________________FC-IgG4___________________________>

        2530       2540       2550       2560
    *     *     *     *     *     *    *     *
CAG CCG GAG AAC AAC TAC AAG ACC ACG CCT CCC GTG CTG GAC
GTC GGC CTC TTG TTG ATG TTC TGG TGC GGA GGG CAC GAC CTG
Gln Pro Glu Asn Asn Tyr Lys Thr Thr Pro Pro Val Leu Asp>
_________________________FC-IgG4___________________________>

     2570       2580       2590       2600
  *     *     *    *     *     *    *     *
TCC GAC GGC TCC TTC TTC CTC TAC AGC AGG CTA ACC GTG GAC
AGG CTG CCG AGG AAG AAG GAG ATG TCG TCC GAT TGG CAC CTG
Ser Asp Gly Ser Phe Phe Leu Tyr Ser Arg Leu Thr Val Asp>
_________________________FC-IgG4___________________________>

   2610       2620       2630       2640
*    *     *     *    *     *     *    *     *
AAG AGC AGG TGG CAG GAG GGG AAT GTC TTC TCA TGC TCC GTG
TTC TCG TCC ACC GTC CTC CCC TTA CAG AAG AGT ACG AGG CAC
Lys Ser Arg Trp Gln Glu Gly Asn Val Phe Ser Cys Ser Val>
_________________________FC-IgG4___________________________>

 2650       2660       2670       2680
    *     *     *     *    *     *     *    *
ATG CAT GAG GCT CTG CAC AAC CAC TAC ACA CAG AAG AGC CTC
TAC GTA CTC CGA GAC GTG TTG GTG ATG TGT GTC TTC TCG GAG
Met His Glu Ala Leu His Asn His Tyr Thr Gln Lys Ser Leu>
_________________________FC-IgG4___________________________>
```

Figure 43 I

```
2690          2700
   *         *        *         *
 TCC CTG TCT CTG GGT AAA TGA
 AGG GAC AGA GAC CCA TTT ACT
 Ser Leu Ser Leu Gly Lys ***>
 ____________FC-IgG4____________>
```

Figure 44A

```
             10          20          30          40
         *     *    *     *     *    *     *     *
ATG GTG CGC TTG TAC GTG TTG GTA ATG GGA GTT TCT GCC TTC
TAC CAC GCG AAC ATG CAC AAC CAT TAC CCT CAA AGA CGG AAG
Met Val Arg Leu Tyr Val Leu Val Met Gly Val Ser Ala Phe>
_____________________SIGNAL PEPTIDE____________________>
_________________________IL-1RII_______________________>

        50          60          70          80
  *      *     *     *     *     *     *     *
ACC CTT CAG CCT GCG GCA CAC ACA GGG GCT GCC AGA AGC TGC
TGG GAA GTC GGA CGC CGT GTG TGT CCC CGA CGG TCT TCG ACG
Thr Leu Gln Pro Ala Ala>
_____SIGNAL PEPTIDE____>
                        His Thr Gly Ala Ala Arg Ser Cys>
_________________________IL-1RII_______________________>

     90          100          110         120
*     *     *     *     *     *     *     *     *
CGG TTT CGT GGG AGG CAT TAC AAG CGG GAG TTC AGG CTG GAA
GCC AAA GCA CCC TCC GTA ATG TTC GCC CTC AAG TCC GAC CTT
Arg Phe Arg Gly Arg His Tyr Lys Arg Glu Phe Arg Leu Glu>
_________________________IL-1RII_______________________>

   130          140          150         160
     *     *     *     *     *     *     *     *
GGG GAG CCT GTA GCC CTG AGG TGC CCC CAG GTG CCC TAC TGG
CCC CTC GGA CAT CGG GAC TCC ACG GGG GTC CAC GGG ATG ACC
Gly Glu Pro Val Ala Leu Arg Cys Pro Gln Val Pro Tyr Trp>
_________________________IL-1RII_______________________>

170         180          190         200          210
 *      *     *     *     *     *     *     *     *
TTG TGG GCC TCT GTC AGC CCC CGC ATC AAC CTG ACA TGG CAT
AAC ACC CGG AGA CAG TCG GGG GCG TAG TTG GAC TGT ACC GTA
Leu Trp Ala Ser Val Ser Pro Arg Ile Asn Leu Thr Trp His>
_________________________IL-1RII_______________________>

            220          230         240          250
         *     *     *     *     *     *     *     *
AAA AAT GAC TCT GCT AGG ACG GTC CCA GGA GAA GAA GAG ACA
TTT TTA CTG AGA CGA TCC TGC CAG GGT CCT CTT CTT CTC TGT
Lys Asn Asp Ser Ala Arg Thr Val Pro Gly Glu Glu Glu Thr>
_________________________IL-1RII_______________________>

        260          270          280         290
  *      *     *     *     *     *     *     *
CGG ATG TGG GCC CAG GAC GGT GCT CTG TGG CTT CTG CCA GCC
GCC TAC ACC CGG GTC CTG CCA CGA GAC ACC GAA GAC GGT CGG
Arg Met Trp Ala Gln Asp Gly Ala Leu Trp Leu Leu Pro Ala>
_________________________IL-1RII_______________________>
```

Figure 44B

```
    300         310         320         330
 *     *     *     *     *     *     *     *     *
TTG CAG GAG GAC TCT GGC ACC TAC GTC TGC ACT ACT AGA AAT
AAC GTC CTC CTG AGA CCG TGG ATG CAG ACG TGA TGA TCT TTA
Leu Gln Glu Asp Ser Gly Thr Tyr Val Cys Thr Thr Arg Asn>
______________________________IL-1RII__________________________>

  340         350         360         370
     *     *     *     *     *     *     *     *
GCT TCT TAC TGT GAC AAA ATG TCC ATT GAG CTC AGA GTT TTT
CGA AGA ATG ACA CTG TTT TAC AGG TAA CTC GAG TCT CAA AAA
Ala Ser Tyr Cys Asp Lys Met Ser Ile Glu Leu Arg Val Phe>
______________________________IL-1RII__________________________>

380         390         400         410         420
  *     *     *     *     *     *     *     *     *
GAG AAT ACA GAT GCT TTC CTG CCG TTC ATC TCA TAC CCG CAA
CTC TTA TGT CTA CGA AAG GAC GGC AAG TAG AGT ATG GGC GTT
Glu Asn Thr Asp Ala Phe Leu Pro Phe Ile Ser Tyr Pro Gln>
______________________________IL-1RII__________________________>

          430         440         450         460
     *     *     *     *     *     *     *     *
ATT TTA ACC TTG TCA ACC TCT GGG GTA TTA GTA TGC CCT GAC
TAA AAT TGG AAC AGT TGG AGA CCC CAT AAT CAT ACG GGA CTG
Ile Leu Thr Leu Ser Thr Ser Gly Val Leu Val Cys Pro Asp>
______________________________IL-1RII__________________________>

        470         480         490         500
   *     *     *     *     *     *     *     *
CTG AGT GAA TTC ACC CGT GAC AAA ACT GAC GTG AAG ATT CAA
GAC TCA CTT AAG TGG GCA CTG TTT TGA CTG CAC TTC TAA GTT
Leu Ser Glu Phe Thr Arg Asp Lys Thr Asp Val Lys Ile Gln>
______________________________IL-1RII__________________________>

    510         520         530         540
 *     *     *     *     *     *     *     *     *
TGG TAC AAG GAT TCT CTT CTT TTG GAT AAA GAC AAT GAG AAA
ACC ATG TTC CTA AGA GAA GAA AAC CTA TTT CTG TTA CTC TTT
Trp Tyr Lys Asp Ser Leu Leu Leu Asp Lys Asp Asn Glu Lys>
______________________________IL-1RII__________________________>

  550         560         570         580
     *     *     *     *     *     *     *     *
TTT CTA AGT GTG AGG GGG ACC ACT CAC TTA CTC GTA CAC GAT
AAA GAT TCA CAC TCC CCC TGG TGA GTG AAT GAG CAT GTG CTA
Phe Leu Ser Val Arg Gly Thr Thr His Leu Leu Val His Asp>
______________________________IL-1RII__________________________>
```

Figure 44C

```
590         600         610         620         630
 *     *     *     *     *     *     *     *     *
GTG GCC CTG GAA GAT GCT GGC TAT TAC CGC TGT GTC CTG ACA
CAC CGG GAC CTT CTA CGA CCG ATA ATG GCG ACA CAG GAC TGT
Val Ala Leu Glu Asp Ala Gly Tyr Tyr Arg Cys Val Leu Thr>
________________________IL-1RII________________________>

       640         650         660         670
   *     *     *     *     *     *     *     *
TTT GCC CAT GAA GGC CAG CAA TAC AAC ATC ACT AGG AGT ATT
AAA CGG GTA CTT CCG GTC GTT ATG TTG TAG TGA TCC TCA TAA
Phe Ala His Glu Gly Gln Gln Tyr Asn Ile Thr Arg Ser Ile>
________________________IL-1RII________________________>

     680         690         700         710
 *     *     *     *     *     *     *     *
GAG CTA CGC ATC AAG AAA AAA AAA GAA GAG ACC ATT CCT GTG
CTC GAT GCG TAG TTC TTT TTT TTT CTT CTC TGG TAA GGA CAC
Glu Leu Arg Ile Lys Lys Lys Lys Glu Glu Thr Ile Pro Val>
________________________IL-1RII________________________>

    720         730         740         750
*     *     *     *     *     *     *     *     *
ATC ATT TCC CCC CTC AAG ACC ATA TCA GCT TCT CTG GGG TCA
TAG TAA AGG GGG GAG TTC TGG TAT AGT CGA AGA GAC CCC AGT
Ile Ile Ser Pro Leu Lys Thr Ile Ser Ala Ser Leu Gly Ser>
________________________IL-1RII________________________>

  760         770         780         790
    *     *     *     *     *     *     *     *
AGA CTG ACA ATC CCA TGT AAG GTG TTT CTG GGA ACC GGC ACA
TCT GAC TGT TAG GGT ACA TTC CAC AAA GAC CCT TGG CCG TGT
Arg Leu Thr Ile Pro Cys Lys Val Phe Leu Gly Thr Gly Thr>
________________________IL-1RII________________________>

800         810         820         830         840
 *     *     *     *     *     *     *     *     *
CCC TTA ACC ACC ATG CTG TGG TGG ACG GCC AAT GAC ACC CAC
GGG AAT TGG TGG TAC GAC ACC ACC TGC CGG TTA CTG TGG GTG
Pro Leu Thr Thr Met Leu Trp Trp Thr Ala Asn Asp Thr His>
________________________IL-1RII________________________>

       850         860         870         880
   *     *     *     *     *     *     *     *
ATA GAG AGC GCC TAC CCG GGA GGC CGC GTG ACC GAG GGG CCA
TAT CTC TCG CGG ATG GGC CCT CCG GCG CAC TGG CTC CCC GGT
Ile Glu Ser Ala Tyr Pro Gly Gly Arg Val Thr Glu Gly Pro>
________________________IL-1RII________________________>

     890         900         910         920
 *     *     *     *     *     *     *     *
CGC CAG GAA TAT TCA GAA AAT AAT GAG AAC TAC ATT GAA GTG
GCG GTC CTT ATA AGT CTT TTA TTA CTC TTG ATG TAA CTT CAC
Arg Gln Glu Tyr Ser Glu Asn Asn Glu Asn Tyr Ile Glu Val>
________________________IL-1RII________________________>
```

Figure 44D

```
    930          940          950          960
 *     *     *     *     *     *     *     *     *
CCA TTG ATT TTT GAT CCT GTC ACA AGA GAG GAT TTG CAC ATG
GGT AAC TAA AAA CTA GGA CAG TGT TCT CTC CTA AAC GTG TAC
Pro Leu Ile Phe Asp Pro Val Thr Arg Glu Asp Leu His Met>
______________________________IL-1RII___________________________>

  970          980          990          1000
    *     *     *     *     *     *     *     *
GAT TTT AAA TGT GTT GTC CAT AAT ACC CTG AGT TTT CAG ACA
CTA AAA TTT ACA CAA CAG GTA TTA TGG GAC TCA AAA GTC TGT
Asp Phe Lys Cys Val Val His Asn Thr Leu Ser Phe Gln Thr>
______________________________IL-1RII___________________________>

1010          1020          1030          1040          1050
 *     *     *     *     *     *     *     *     *
CTA CGC ACC ACA GTC AAG GAA GCC TCC TCC ACG TTC TCA GAA
GAT GCG TGG TGT CAG TTC CTT CGG AGG AGG TGC AAG AGT CTT
                                                Ser Glu>
                                                _________>
Leu Arg Thr Thr Val Lys Glu Ala Ser Ser Thr Phe>
________________________IL-1RII________________________>

      1060          1070          1080          1090
    *     *     *     *     *     *     *     *
CGC TGC GAT GAC TGG GGA CTA GAC ACC ATG AGG CAA ATC CAA
GCG ACG CTA CTG ACC CCT GAT CTG TGG TAC TCC GTT TAG GTT
Arg Cys Asp Asp Trp Gly Leu Asp Thr Met Arg Gln Ile Gln>
______________________________IL-1RAcP__________________________>

    1100          1110          1120          1130
 *     *     *     *     *     *     *     *
GTG TTT GAA GAT GAG CCA GCT CGC ATC AAG TGC CCA CTC TTT
CAC AAA CTT CTA CTC GGT CGA GCG TAG TTC ACG GGT GAG AAA
Val Phe Glu Asp Glu Pro Ala Arg Ile Lys Cys Pro Leu Phe>
______________________________IL-1RAcP__________________________>

  1140          1150          1160          1170
 *     *     *     *     *     *     *     *     *
GAA CAC TTC TTG AAA TTC AAC TAC AGC ACA GCC CAT TCA GCT
CTT GTG AAG AAC TTT AAG TTG ATG TCG TGT CGG GTA AGT CGA
Glu His Phe Leu Lys Phe Asn Tyr Ser Thr Ala His Ser Ala>
______________________________IL-1RAcP__________________________>

 1180          1190          1200          1210
    *     *     *     *     *     *     *     *
GGC CTT ACT CTG ATC TGG TAT TGG ACT AGG CAG GAC CGG GAC
CCG GAA TGA GAC TAG ACC ATA ACC TGA TCC GTC CTG GCC CTG
Gly Leu Thr Leu Ile Trp Tyr Trp Thr Arg Gln Asp Arg Asp>
______________________________IL-1RAcP__________________________>
```

Figure 44E

```
1220       1230       1240       1250       1260
  *     *    *     *     *     *     *     *     *
CTT GAG GAG CCA ATT AAC TTC CGC CTC CCC GAG AAC CGC ATT
GAA CTC CTC GGT TAA TTG AAG GCG GAG GGG CTC TTG GCG TAA
Leu Glu Glu Pro Ile Asn Phe Arg Leu Pro Glu Asn Arg Ile>
_________________________IL-1RAcP_______________________>

       1270       1280       1290       1300
     *     *     *     *     *     *     *     *
AGT AAG GAG AAA GAT GTG CTG TGG TTC CGG CCC ACT CTC CTC
TCA TTC CTC TTT CTA CAC GAC ACC AAG GCC GGG TGA GAG GAG
Ser Lys Glu Lys Asp Val Leu Trp Phe Arg Pro Thr Leu Leu>
_________________________IL-1RAcP_______________________>

    1310       1320       1330       1340
  *     *     *     *     *     *     *     *
AAT GAC ACT GGC AAC TAT ACC TGC ATG TTA AGG AAC ACT ACA
TTA CTG TGA CCG TTG ATA TGG ACG TAC AAT TCC TTG TGA TGT
Asn Asp Thr Gly Asn Tyr Thr Cys Met Leu Arg Asn Thr Thr>
_________________________IL-1RAcP_______________________>

  1350       1360       1370       1380
*     *     *     *     *     *     *     *     *
TAT TGC AGC AAA GTT GCA TTT CCC TTG GAA GTT GTT CAA AAA
ATA ACG TCG TTT CAA CGT AAA GGG AAC CTT CAA CAA GTT TTT
Tyr Cys Ser Lys Val Ala Phe Pro Leu Glu Val Val Gln Lys>
_________________________IL-1RAcP_______________________>

 1390       1400       1410       1420
     *     *     *     *     *     *     *     *
GAC AGC TGT TTC AAT TCC CCC ATG AAA CTC CCA GTG CAT AAA
CTG TCG ACA AAG TTA AGG GGG TAC TTT GAG GGT CAC GTA TTT
Asp Ser Cys Phe Asn Ser Pro Met Lys Leu Pro Val His Lys>
_________________________IL-1RAcP_______________________>

1430       1440       1450       1460       1470
  *     *     *     *     *     *     *     *     *
CTG TAT ATA GAA TAT GGC ATT CAG AGG ATC ACT TGT CCA AAT
GAC ATA TAT CTT ATA CCG TAA GTC TCC TAG TGA ACA GGT TTA
Leu Tyr Ile Glu Tyr Gly Ile Gln Arg Ile Thr Cys Pro Asn>
_________________________IL-1RAcP_______________________>

       1480       1490       1500       1510
     *     *     *     *     *     *     *     *
GTA GAT GGA TAT TTT CCT TCC AGT GTC AAA CCG ACT ATC ACT
CAT CTA CCT ATA AAA GGA AGG TCA CAG TTT GGC TGA TAG TGA
Val Asp Gly Tyr Phe Pro Ser Ser Val Lys Pro Thr Ile Thr>
_________________________IL-1RAcP_______________________>

    1520       1530       1540       1550
  *     *     *     *     *     *     *     *
TGG TAT ATG GGC TGT TAT AAA ATA CAG AAT TTT AAT AAT GTA
ACC ATA TAC CCG ACA ATA TTT TAT GTC TTA AAA TTA TTA CAT
Trp Tyr Met Gly Cys Tyr Lys Ile Gln Asn Phe Asn Asn Val>
_________________________IL-1RAcP_______________________>
```

Figure 44F

```
   1560         1570         1580         1590
*    *     *     *     *     *     *     *     *
ATA CCC GAA GGT ATG AAC TTG AGT TTC CTC ATT GCC TTA ATT
TAT GGG CTT CCA TAC TTG AAC TCA AAG GAG TAA CGG AAT TAA
Ile Pro Glu Gly Met Asn Leu Ser Phe Leu Ile Ala Leu Ile>
_________________________IL-1RAcP______________________>

 1600         1610         1620         1630
    *     *     *     *     *     *     *     *
TCA AAT AAT GGA AAT TAC ACA TGT GTT GTT ACA TAT CCA GAA
AGT TTA TTA CCT TTA ATG TGT ACA CAA CAA TGT ATA GGT CTT
Ser Asn Asn Gly Asn Tyr Thr Cys Val Val Thr Tyr Pro Glu>
_________________________IL-1RAcP______________________>

1640         1650         1660         1670         1680
   *      *     *     *     *     *     *     *     *
AAT GGA CGT ACG TTT CAT CTC ACC AGG ACT CTG ACT GTA AAG
TTA CCT GCA TGC AAA GTA GAG TGG TCC TGA GAC TGA CAT TTC
Asn Gly Arg Thr Phe His Leu Thr Arg Thr Leu Thr Val Lys>
_________________________IL-1RAcP______________________>

         1690         1700         1710         1720
    *      *     *     *     *     *     *     *
GTA GTA GGC TCT CCA AAA AAT GCA GTG CCC CCT GTG ATC CAT
CAT CAT CCG AGA GGT TTT TTA CGT CAC GGG GGA CAC TAG GTA
Val Val Gly Ser Pro Lys Asn Ala Val Pro Pro Val Ile His>
_________________________IL-1RAcP______________________>

      1730         1740         1750         1760
  *      *     *     *     *     *     *     *
TCA CCT AAT GAT CAT GTG GTC TAT GAG AAA GAA CCA GGA GAG
AGT GGA TTA CTA GTA CAC CAG ATA CTC TTT CTT GGT CCT CTC
Ser Pro Asn Asp His Val Val Tyr Glu Lys Glu Pro Gly Glu>
_________________________IL-1RAcP______________________>

   1770         1780         1790         1800
*    *     *     *     *     *     *     *     *
GAG CTA CTC ATT CCC TGT ACG GTC TAT TTT AGT TTT CTG ATG
CTC GAT GAG TAA GGG ACA TGC CAG ATA AAA TCA AAA GAC TAC
Glu Leu Leu Ile Pro Cys Thr Val Tyr Phe Ser Phe Leu Met>
_________________________IL-1RAcP______________________>

 1810         1820         1830         1840
    *     *     *     *     *     *     *     *
GAT TCT CGC AAT GAG GTT TGG TGG ACC ATT GAT GGA AAA AAA
CTA AGA GCG TTA CTC CAA ACC ACC TGG TAA CTA CCT TTT TTT
Asp Ser Arg Asn Glu Val Trp Trp Thr Ile Asp Gly Lys Lys>
_________________________IL-1RAcP______________________>

1850         1860         1870         1880         1890
   *      *     *     *     *     *     *     *     *
CCT GAT GAC ATC ACT ATT GAT GTC ACC ATT AAC GAA AGT ATA
GGA CTA CTG TAG TGA TAA CTA CAG TGG TAA TTG CTT TCA TAT
Pro Asp Asp Ile Thr Ile Asp Val Thr Ile Asn Glu Ser Ile>
_________________________IL-1RAcP______________________>
```

Figure 44G

```
        1900       1910       1920        1930
     *     *     *     *     *     *     *     *
AGT CAT AGT AGA ACA GAA GAT GAA ACA AGA ACT CAG ATT TTG
TCA GTA TCA TCT TGT CTT CTA CTT TGT TCT TGA GTC TAA AAC
Ser His Ser Arg Thr Glu Asp Glu Thr Arg Thr Gln Ile Leu>
____________________________IL-1RAcP_________________________>

     1940       1950       1960       1970
   *     *     *     *     *     *     *     *
AGC ATC AAG AAA GTT ACC TCT GAG GAT CTC AAG CGC AGC TAT
TCG TAG TTC TTT CAA TGG AGA CTC CTA GAG TTC GCG TCG ATA
Ser Ile Lys Lys Val Thr Ser Glu Asp Leu Lys Arg Ser Tyr>
____________________________IL-1RAcP_________________________>

   1980       1990       2000       2010
*     *     *     *     *     *     *     *     *
GTC TGT CAT GCT AGA AGT GCC AAA GGC GAA GTT GCC AAA GCA
CAG ACA GTA CGA TCT TCA CGG TTT CCG CTT CAA CGG TTT CGT
Val Cys His Ala Arg Ser Ala Lys Gly Glu Val Ala Lys Ala>
____________________________IL-1RAcP_________________________>

  2020       2030       2040       2050
     *     *     *     *     *     *     *     *
GCC AAG GTG AAG CAG AAA GTG CCA GCT CCA AGA TAC ACA GTG
CGG TTC CAC TTC GTC TTT CAC GGT CGA GGT TCT ATG TGT CAC
Ala Lys Val Lys Gln Lys Val Pro Ala Pro Arg Tyr Thr Val>
____________________________IL-1RAcP_________________________>

2060       2070       2080       2090       2100
  *     *     *     *     *     *     *     *     *
TCC GGA GAC AAA ACT CAC ACA TGC CCA CCG TGC CCA GCA CCT
AGG CCT CTG TTT TGA GTG TGT ACG GGT GGC ACG GGT CGT GGA
Ser Gly Asp Lys Thr His Thr Cys Pro Pro Cys Pro Ala Pro>
__________________________FC-IgG1____________________________>

        2110       2120       2130        2140
     *     *     *     *     *     *     *     *
GAA CTC CTG GGG GGA CCG TCA GTC TTC CTC TTC CCC CCA AAA
CTT GAG GAC CCC CCT GGC AGT CAG AAG GAG AAG GGG GGT TTT
Glu Leu Leu Gly Gly Pro Ser Val Phe Leu Phe Pro Pro Lys>
__________________________FC-IgG1____________________________>

     2150       2160       2170       2180
   *     *     *     *     *     *     *     *
CCC AAG GAC ACC CTC ATG ATC TCC CGG ACC CCT GAG GTC ACA
GGG TTC CTG TGG GAG TAC TAG AGG GCC TGG GGA CTC CAG TGT
Pro Lys Asp Thr Leu Met Ile Ser Arg Thr Pro Glu Val Thr>
__________________________FC-IgG1____________________________>

   2190       2200       2210       2220
*     *     *     *     *     *     *     *     *
TGC GTG GTG GTG GAC GTG AGC CAC GAA GAC CCT GAG GTC AAG
ACG CAC CAC CAC CTG CAC TCG GTG CTT CTG GGA CTC CAG TTC
Cys Val Val Val Asp Val Ser His Glu Asp Pro Glu Val Lys>
__________________________FC-IgG1____________________________>
```

Figure 44H

```
 2230       2240       2250        2260
    *    *     *     *    *     *     *     *
TTC AAC TGG TAC GTG GAC GGC GTG GAG GTG CAT AAT GCC AAG
AAG TTG ACC ATG CAC CTG CCG CAC CTC CAC GTA TTA CGG TTC
Phe Asn Trp Tyr Val Asp Gly Val Glu Val His Asn Ala Lys>
____________________FC-IgG1______________________>

2270       2280        2290       2300       2310
 *     *    *     *     *    *     *     *     *
ACA AAG CCG CGG GAG GAG CAG TAC AAC AGC ACG TAC CGT GTG
TGT TTC GGC GCC CTC CTC GTC ATG TTG TCG TGC ATG GCA CAC
Thr Lys Pro Arg Glu Glu Gln Tyr Asn Ser Thr Tyr Arg Val>
____________________FC-IgG1______________________>

        2320       2330        2340        2350
     *     *    *     *     *    *     *     *
GTC AGC GTC CTC ACC GTC CTG CAC CAG GAC TGG CTG AAT GGC
CAG TCG CAG GAG TGG CAG GAC GTG GTC CTG ACC GAC TTA CCG
Val Ser Val Leu Thr Val Leu His Gln Asp Trp Leu Asn Gly>
____________________FC-IgG1______________________>

      2360       2370        2380       2390
  *     *     *    *     *     *    *     *
AAG GAG TAC AAG TGC AAG GTC TCC AAC AAA GCC CTC CCA GCC
TTC CTC ATG TTC ACG TTC CAG AGG TTG TTT CGG GAG GGT CGG
Lys Glu Tyr Lys Cys Lys Val Ser Asn Lys Ala Leu Pro Ala>
____________________FC-IgG1______________________>

   2400       2410       2420       2430
*     *     *     *    *     *     *     *     *
CCC ATC GAG AAA ACC ATC TCC AAA GCC AAA GGG CAG CCC CGA
GGG TAG CTC TTT TGG TAG AGG TTT CGG TTT CCC GTC GGG GCT
Pro Ile Glu Lys Thr Ile Ser Lys Ala Lys Gly Gln Pro Arg>
____________________FC-IgG1______________________>

 2440        2450       2460        2470
    *    *     *     *    *     *     *    *
GAA CCA CAG GTG TAC ACC CTG CCC CCA TCC CGG GAT GAG CTG
CTT GGT GTC CAC ATG TGG GAC GGG GGT AGG GCC CTA CTC GAC
Glu Pro Gln Val Tyr Thr Leu Pro Pro Ser Arg Asp Glu Leu>
____________________FC-IgG1______________________>

2480       2490        2500       2510       2520
 *     *    *     *     *    *     *     *     *
ACC AAG AAC CAG GTC AGC CTG ACC TGC CTG GTC AAA GGC TTC
TGG TTC TTG GTC CAG TCG GAC TGG ACG GAC CAG TTT CCG AAG
Thr Lys Asn Gln Val Ser Leu Thr Cys Leu Val Lys Gly Phe>
____________________FC-IgG1______________________>

        2530       2540        2550        2560
     *     *    *     *     *    *     *     *
TAT CCC AGC GAC ATC GCC GTG GAG TGG GAG AGC AAT GGG CAG
ATA GGG TCG CTG TAG CGG CAC CTC ACC CTC TCG TTA CCC GTC
Tyr Pro Ser Asp Ile Ala Val Glu Trp Glu Ser Asn Gly Gln>
____________________FC-IgG1______________________>
```

Figure 44I

```
      2570        2580        2590        2600
  *       *     *      *      *       *      *      *
CCG GAG AAC AAC TAC AAG ACC ACG CCT CCC GTG CTG GAC TCC
GGC CTC TTG TTG ATG TTC TGG TGC GGA GGG CAC GAC CTG AGG
Pro Glu Asn Asn Tyr Lys Thr Thr Pro Pro Val Leu Asp Ser>
____________________________FC-IgG1____________________________>

   2610        2620        2630        2640
*      *       *       *      *       *       *      *       *
GAC GGC TCC TTC TTC CTC TAT AGC AAG CTC ACC GTG GAC AAG
CTG CCG AGG AAG AAG GAG ATA TCG TTC GAG TGG CAC CTG TTC
Asp Gly Ser Phe Phe Leu Tyr Ser Lys Leu Thr Val Asp Lys>
____________________________FC-IgG1____________________________>

 2650        2660        2670        2680
     *      *       *       *      *       *       *      *
AGC AGG TGG CAG CAG GGG AAC GTC TTC TCA TGC TCC GTG ATG
TCG TCC ACC GTC GTC CCC TTG CAG AAG AGT ACG AGG CAC TAC
Ser Arg Trp Gln Gln Gly Asn Val Phe Ser Cys Ser Val Met>
____________________________FC-IgG1____________________________>

2690        2700        2710        2720        2730
  *       *      *       *       *      *       *       *      *
CAT GAG GCT CTG CAC AAC CAC TAC ACG CAG AAG AGC CTC TCC
GTA CTC CGA GAC GTG TTG GTG ATG TGC GTC TTC TCG GAG AGG
His Glu Ala Leu His Asn His Tyr Thr Gln Lys Ser Leu Ser>
____________________________FC-IgG1____________________________>

          2740
      *       *      *
CTG TCT CCG GGT AAA TGA
GAC AGA GGC CCA TTT ACT
Leu Ser Pro Gly Lys ***>
__________FC-IgG1________>
```

Figure 45A

```
          10          20          30          40
    *     *     *     *     *     *     *     *
ATG GTG CGC TTG TAC GTG TTG GTA ATG GGA GTT TCT GCC TTC
TAC CAC GCG AAC ATG CAC AAC CAT TAC CCT CAA AGA CGG AAG
Met Val Arg Leu Tyr Val Leu Val Met Gly Val Ser Ala Phe>
_____________________SIGNAL PEPTIDE____________________>
_________________________IL-1RII_______________________>

       50          60          70          80
  *     *     *     *     *     *     *     *
ACC CTT CAG CCT GCG GCA CAC ACA GGG GCT GCC AGA AGC TGC
TGG GAA GTC GGA CGC CGT GTG TGT CCC CGA CGG TCT TCG ACG
Thr Leu Gln Pro Ala Ala>
_____SIGNAL PEPTIDE____>
                        His Thr Gly Ala Ala Arg Ser Cys>
_________________________IL-1RII_______________________>

     90          100         110         120
*     *     *     *     *     *     *     *     *
CGG TTT CGT GGG AGG CAT TAC AAG CGG GAG TTC AGG CTG GAA
GCC AAA GCA CCC TCC GTA ATG TTC GCC CTC AAG TCC GAC CTT
Arg Phe Arg Gly Arg His Tyr Lys Arg Glu Phe Arg Leu Glu>
_________________________IL-1RII_______________________>

  130         140         150         160
    *     *     *     *     *     *     *     *
GGG GAG CCT GTA GCC CTG AGG TGC CCC CAG GTG CCC TAC TGG
CCC CTC GGA CAT CGG GAC TCC ACG GGG GTC CAC GGG ATG ACC
Gly Glu Pro Val Ala Leu Arg Cys Pro Gln Val Pro Tyr Trp>
_________________________IL-1RII_______________________>

170         180         190         200         210
 *     *     *     *     *     *     *     *     *
TTG TGG GCC TCT GTC AGC CCC CGC ATC AAC CTG ACA TGG CAT
AAC ACC CGG AGA CAG TCG GGG GCG TAG TTG GAC TGT ACC GTA
Leu Trp Ala Ser Val Ser Pro Arg Ile Asn Leu Thr Trp His>
_________________________IL-1RII_______________________>

          220         230         240         250
    *     *     *     *     *     *     *     *
AAA AAT GAC TCT GCT AGG ACG GTC CCA GGA GAA GAA GAG ACA
TTT TTA CTG AGA CGA TCC TGC CAG GGT CCT CTT CTT CTC TGT
Lys Asn Asp Ser Ala Arg Thr Val Pro Gly Glu Glu Glu Thr>
_________________________IL-1RII_______________________>

       260         270         280         290
  *     *     *     *     *     *     *     *
CGG ATG TGG GCC CAG GAC GGT GCT CTG TGG CTT CTG CCA GCC
GCC TAC ACC CGG GTC CTG CCA CGA GAC ACC GAA GAC GGT CGG
Arg Met Trp Ala Gln Asp Gly Ala Leu Trp Leu Leu Pro Ala>
_________________________IL-1RII_______________________>
```

Figure 45B

```
    300           310          320          330
*     *      *      *     *      *      *     *      *
TTG CAG GAG GAC TCT GGC ACC TAC GTC TGC ACT ACT AGA AAT
AAC GTC CTC CTG AGA CCG TGG ATG CAG ACG TGA TGA TCT TTA
Leu Gln Glu Asp Ser Gly Thr Tyr Val Cys Thr Thr Arg Asn>
_________________________IL-1RII_______________________>

  340          350          360           370
     *     *      *     *      *      *      *     *
GCT TCT TAC TGT GAC AAA ATG TCC ATT GAG CTC AGA GTT TTT
CGA AGA ATG ACA CTG TTT TAC AGG TAA CTC GAG TCT CAA AAA
Ala Ser Tyr Cys Asp Lys Met Ser Ile Glu Leu Arg Val Phe>
_________________________IL-1RII_______________________>

380          390           400          410          420
 *      *     *      *      *      *     *      *     *
GAG AAT ACA GAT GCT TTC CTG CCG TTC ATC TCA TAC CCG CAA
CTC TTA TGT CTA CGA AAG GAC GGC AAG TAG AGT ATG GGC GTT
Glu Asn Thr Asp Ala Phe Leu Pro Phe Ile Ser Tyr Pro Gln>
_________________________IL-1RII_______________________>

          430          440          450           460
     *      *     *      *      *     *      *     *
ATT TTA ACC TTG TCA ACC TCT GGG GTA TTA GTA TGC CCT GAC
TAA AAT TGG AAC AGT TGG AGA CCC CAT AAT CAT ACG GGA CTG
Ile Leu Thr Leu Ser Thr Ser Gly Val Leu Val Cys Pro Asp>
_________________________IL-1RII_______________________>

       470          480           490          500
  *      *      *     *      *      *     *      *
CTG AGT GAA TTC ACC CGT GAC AAA ACT GAC GTG AAG ATT CAA
GAC TCA CTT AAG TGG GCA CTG TTT TGA CTG CAC TTC TAA GTT
Leu Ser Glu Phe Thr Arg Asp Lys Thr Asp Val Lys Ile Gln>
_________________________IL-1RII_______________________>

    510           520          530          540
*     *      *      *     *      *      *     *      *
TGG TAC AAG GAT TCT CTT CTT TTG GAT AAA GAC AAT GAG AAA
ACC ATG TTC CTA AGA GAA GAA AAC CTA TTT CTG TTA CTC TTT
Trp Tyr Lys Asp Ser Leu Leu Leu Asp Lys Asp Asn Glu Lys>
_________________________IL-1RII_______________________>

  550          560          570           580
     *     *      *      *     *      *      *     *
TTT CTA AGT GTG AGG GGG ACC ACT CAC TTA CTC GTA CAC GAT
AAA GAT TCA CAC TCC CCC TGG TGA GTG AAT GAG CAT GTG CTA
Phe Leu Ser Val Arg Gly Thr Thr His Leu Leu Val His Asp>
_________________________IL-1RII_______________________>

590          600           610          620          630
 *      *     *      *      *      *     *      *     *
GTG GCC CTG GAA GAT GCT GGC TAT TAC CGC TGT GTC CTG ACA
CAC CGG GAC CTT CTA CGA CCG ATA ATG GCG ACA CAG GAC TGT
Val Ala Leu Glu Asp Ala Gly Tyr Tyr Arg Cys Val Leu Thr>
_________________________IL-1RII_______________________>
```

Figure 45C

```
           640        650        660         670
        *     *    *     *     *    *     *     *
TTT GCC CAT GAA GGC CAG CAA TAC AAC ATC ACT AGG AGT ATT
AAA CGG GTA CTT CCG GTC GTT ATG TTG TAG TGA TCC TCA TAA
Phe Ala His Glu Gly Gln Gln Tyr Asn Ile Thr Arg Ser Ile>
____________________________IL-1RII__________________________>

        680        690         700        710
  *     *     *    *     *     *     *     *
GAG CTA CGC ATC AAG AAA AAA AAA GAA GAG ACC ATT CCT GTG
CTC GAT GCG TAG TTC TTT TTT TTT CTT CTC TGG TAA GGA CAC
Glu Leu Arg Ile Lys Lys Lys Lys Glu Glu Thr Ile Pro Val>
____________________________IL-1RII__________________________>

     720        730        740        750
*    *     *     *     *     *     *     *     *
ATC ATT TCC CCC CTC AAG ACC ATA TCA GCT TCT CTG GGG TCA
TAG TAA AGG GGG GAG TTC TGG TAT AGT CGA AGA GAC CCC AGT
Ile Ile Ser Pro Leu Lys Thr Ile Ser Ala Ser Leu Gly Ser>
____________________________IL-1RII__________________________>

   760        770        780        790
     *     *     *     *     *     *     *     *
AGA CTG ACA ATC CCA TGT AAG GTG TTT CTG GGA ACC GGC ACA
TCT GAC TGT TAG GGT ACA TTC CAC AAA GAC CCT TGG CCG TGT
Arg Leu Thr Ile Pro Cys Lys Val Phe Leu Gly Thr Gly Thr>
____________________________IL-1RII__________________________>

800        810        820        830        840
 *     *     *     *     *     *     *     *     *
CCC TTA ACC ACC ATG CTG TGG TGG ACG GCC AAT GAC ACC CAC
GGG AAT TGG TGG TAC GAC ACC ACC TGC CGG TTA CTG TGG GTG
Pro Leu Thr Thr Met Leu Trp Trp Thr Ala Asn Asp Thr His>
____________________________IL-1RII__________________________>

           850        860        870         880
      *     *    *     *     *    *     *     *
ATA GAG AGC GCC TAC CCG GGA GGC CGC GTG ACC GAG GGG CCA
TAT CTC TCG CGG ATG GGC CCT CCG GCG CAC TGG CTC CCC GGT
Ile Glu Ser Ala Tyr Pro Gly Gly Arg Val Thr Glu Gly Pro>
____________________________IL-1RII__________________________>

        890        900         910        920
  *     *     *    *     *     *     *     *
CGC CAG GAA TAT TCA GAA AAT AAT GAG AAC TAC ATT GAA GTG
GCG GTC CTT ATA AGT CTT TTA TTA CTC TTG ATG TAA CTT CAC
Arg Gln Glu Tyr Ser Glu Asn Asn Glu Asn Tyr Ile Glu Val>
____________________________IL-1RII__________________________>

     930        940        950        960
*    *     *     *     *     *     *     *     *
CCA TTG ATT TTT GAT CCT GTC ACA AGA GAG GAT TTG CAC ATG
GGT AAC TAA AAA CTA GGA CAG TGT TCT CTC CTA AAC GTG TAC
Pro Leu Ile Phe Asp Pro Val Thr Arg Glu Asp Leu His Met>
____________________________IL-1RII__________________________>
```

Figure 45D

```
 970        980        990        1000
  *    *    *    *    *    *    *    *
GAT TTT AAA TGT GTT GTC CAT AAT ACC CTG AGT TTT CAG ACA
CTA AAA TTT ACA CAA CAG GTA TTA TGG GAC TCA AAA GTC TGT
Asp Phe Lys Cys Val Val His Asn Thr Leu Ser Phe Gln Thr>
________________________IL-1RII_______________________>

1010       1020       1030       1040       1050
  *    *    *    *    *    *    *    *    *
CTA CGC ACC ACA GTC AAG GAA GCC TCC TCC ACG TTC TCA GAA
GAT GCG TGG TGT CAG TTC CTT CGG AGG AGG TGC AAG AGT CTT
                                                Ser Glu>
                                                _______>
Leu Arg Thr Thr Val Lys Glu Ala Ser Ser Thr Phe>
__________________IL-1RII_____________________>

      1060       1070       1080       1090
   *    *    *    *    *    *    *    *
CGC TGC GAT GAC TGG GGA CTA GAC ACC ATG AGG CAA ATC CAA
GCG ACG CTA CTG ACC CCT GAT CTG TGG TAC TCC GTT TAG GTT
Arg Cys Asp Asp Trp Gly Leu Asp Thr Met Arg Gln Ile Gln>
________________________IL-1RAcP______________________>

    1100       1110       1120       1130
  *    *    *    *    *    *    *    *
GTG TTT GAA GAT GAG CCA GCT CGC ATC AAG TGC CCA CTC TTT
CAC AAA CTT CTA CTC GGT CGA GCG TAG TTC ACG GGT GAG AAA
Val Phe Glu Asp Glu Pro Ala Arg Ile Lys Cys Pro Leu Phe>
________________________IL-1RAcP______________________>

  1140       1150       1160       1170
 *    *    *    *    *    *    *    *    *
GAA CAC TTC TTG AAA TTC AAC TAC AGC ACA GCC CAT TCA GCT
CTT GTG AAG AAC TTT AAG TTG ATG TCG TGT CGG GTA AGT CGA
Glu His Phe Leu Lys Phe Asn Tyr Ser Thr Ala His Ser Ala>
________________________IL-1RAcP______________________>

 1180       1190       1200       1210
    *    *    *    *    *    *    *    *
GGC CTT ACT CTG ATC TGG TAT TGG ACT AGG CAG GAC CGG GAC
CCG GAA TGA GAC TAG ACC ATA ACC TGA TCC GTC CTG GCC CTG
Gly Leu Thr Leu Ile Trp Tyr Trp Thr Arg Gln Asp Arg Asp>
________________________IL-1RAcP______________________>

1220       1230       1240       1250       1260
  *    *    *    *    *    *    *    *    *
CTT GAG GAG CCA ATT AAC TTC CGC CTC CCC GAG AAC CGC ATT
GAA CTC CTC GGT TAA TTG AAG GCG GAG GGG CTC TTG GCG TAA
Leu Glu Glu Pro Ile Asn Phe Arg Leu Pro Glu Asn Arg Ile>
________________________IL-1RAcP______________________>
```

Figure 45E

```
        1270        1280        1290        1300
         *     *     *     *     *     *     *     *
AGT AAG GAG AAA GAT GTG CTG TGG TTC CGG CCC ACT CTC CTC
TCA TTC CTC TTT CTA CAC GAC ACC AAG GCC GGG TGA GAG GAG
Ser Lys Glu Lys Asp Val Leu Trp Phe Arg Pro Thr Leu Leu>
_________________________IL-1RAcP______________________>

      1310        1320        1330        1340
  *     *     *     *     *     *     *     *
AAT GAC ACT GGC AAC TAT ACC TGC ATG TTA AGG AAC ACT ACA
TTA CTG TGA CCG TTG ATA TGG ACG TAC AAT TCC TTG TGA TGT
Asn Asp Thr Gly Asn Tyr Thr Cys Met Leu Arg Asn Thr Thr>
_________________________IL-1RAcP______________________>

   1350        1360        1370        1380
*     *     *     *     *     *     *     *     *
TAT TGC AGC AAA GTT GCA TTT CCC TTG GAA GTT GTT CAA AAA
ATA ACG TCG TTT CAA CGT AAA GGG AAC CTT CAA CAA GTT TTT
Tyr Cys Ser Lys Val Ala Phe Pro Leu Glu Val Val Gln Lys>
_________________________IL-1RAcP______________________>

 1390        1400        1410        1420
     *     *     *     *     *     *     *     *
GAC AGC TGT TTC AAT TCC CCC ATG AAA CTC CCA GTG CAT AAA
CTG TCG ACA AAG TTA AGG GGG TAC TTT GAG GGT CAC GTA TTT
Asp Ser Cys Phe Asn Ser Pro Met Lys Leu Pro Val His Lys>
_________________________IL-1RAcP______________________>

1430        1440        1450        1460        1470
 *     *     *     *     *     *     *     *     *
CTG TAT ATA GAA TAT GGC ATT CAG AGG ATC ACT TGT CCA AAT
GAC ATA TAT CTT ATA CCG TAA GTC TCC TAG TGA ACA GGT TTA
Leu Tyr Ile Glu Tyr Gly Ile Gln Arg Ile Thr Cys Pro Asn>
_________________________IL-1RAcP______________________>

        1480        1490        1500        1510
     *     *     *     *     *     *     *     *
GTA GAT GGA TAT TTT CCT TCC AGT GTC AAA CCG ACT ATC ACT
CAT CTA CCT ATA AAA GGA AGG TCA CAG TTT GGC TGA TAG TGA
Val Asp Gly Tyr Phe Pro Ser Ser Val Lys Pro Thr Ile Thr>
_________________________IL-1RAcP______________________>

      1520        1530        1540        1550
  *     *     *     *     *     *     *     *
TGG TAT ATG GGC TGT TAT AAA ATA CAG AAT TTT AAT AAT GTA
ACC ATA TAC CCG ACA ATA TTT TAT GTC TTA AAA TTA TTA CAT
Trp Tyr Met Gly Cys Tyr Lys Ile Gln Asn Phe Asn Asn Val>
_________________________IL-1RAcP______________________>

   1560        1570        1580        1590
*     *     *     *     *     *     *     *     *
ATA CCC GAA GGT ATG AAC TTG AGT TTC CTC ATT GCC TTA ATT
TAT GGG CTT CCA TAC TTG AAC TCA AAG GAG TAA CGG AAT TAA
Ile Pro Glu Gly Met Asn Leu Ser Phe Leu Ile Ala Leu Ile>
_________________________IL-1RAcP______________________>
```

Figure 45F

```
 1600         1610         1620          1630
    *     *      *      *     *      *      *     *
TCA AAT AAT GGA AAT TAC ACA TGT GTT GTT ACA TAT CCA GAA
AGT TTA TTA CCT TTA ATG TGT ACA CAA CAA TGT ATA GGT CTT
Ser Asn Asn Gly Asn Tyr Thr Cys Val Val Thr Tyr Pro Glu>
_________________________IL-1RAcP______________________>

1640         1650         1660         1670         1680
  *      *      *      *      *      *      *      *    *
AAT GGA CGT ACG TTT CAT CTC ACC AGG ACT CTG ACT GTA AAG
TTA CCT GCA TGC AAA GTA GAG TGG TCC TGA GAC TGA CAT TTC
Asn Gly Arg Thr Phe His Leu Thr Arg Thr Leu Thr Val Lys>
_________________________IL-1RAcP______________________>

         1690         1700         1710          1720
     *      *      *      *      *      *      *     *
GTA GTA GGC TCT CCA AAA AAT GCA GTG CCC CCT GTG ATC CAT
CAT CAT CCG AGA GGT TTT TTA CGT CAC GGG GGA CAC TAG GTA
Val Val Gly Ser Pro Lys Asn Ala Val Pro Pro Val Ile His>
_________________________IL-1RAcP______________________>

      1730         1740          1750         1760
  *      *      *      *      *      *      *      *
TCA CCT AAT GAT CAT GTG GTC TAT GAG AAA GAA CCA GGA GAG
AGT GGA TTA CTA GTA CAC CAG ATA CTC TTT CTT GGT CCT CTC
Ser Pro Asn Asp His Val Val Tyr Glu Lys Glu Pro Gly Glu>
_________________________IL-1RAcP______________________>

   1770          1780         1790         1800
*      *      *      *     *      *      *     *      *
GAG CTA CTC ATT CCC TGT ACG GTC TAT TTT AGT TTT CTG ATG
CTC GAT GAG TAA GGG ACA TGC CAG ATA AAA TCA AAA GAC TAC
Glu Leu Leu Ile Pro Cys Thr Val Tyr Phe Ser Phe Leu Met>
_________________________IL-1RAcP______________________>

 1810         1820         1830          1840
    *     *      *      *     *      *      *     *
GAT TCT CGC AAT GAG GTT TGG TGG ACC ATT GAT GGA AAA AAA
CTA AGA GCG TTA CTC CAA ACC ACC TGG TAA CTA CCT TTT TTT
Asp Ser Arg Asn Glu Val Trp Trp Thr Ile Asp Gly Lys Lys>
_________________________IL-1RAcP______________________>

1850         1860         1870         1880         1890
  *      *      *      *      *      *      *      *    *
CCT GAT GAC ATC ACT ATT GAT GTC ACC ATT AAC GAA AGT ATA
GGA CTA CTG TAG TGA TAA CTA CAG TGG TAA TTG CTT TCA TAT
Pro Asp Asp Ile Thr Ile Asp Val Thr Ile Asn Glu Ser Ile>
_________________________IL-1RAcP______________________>

         1900         1910         1920          1930
     *      *      *      *      *      *      *     *
AGT CAT AGT AGA ACA GAA GAT GAA ACA AGA ACT CAG ATT TTG
TCA GTA TCA TCT TGT CTT CTA CTT TGT TCT TGA GTC TAA AAC
Ser His Ser Arg Thr Glu Asp Glu Thr Arg Thr Gln Ile Leu>
_________________________IL-1RAcP______________________>
```

Figure 45G

```
      1940        1950        1960        1970
  *     *     *     *     *     *     *     *
AGC ATC AAG AAA GTT ACC TCT GAG GAT CTC AAG CGC AGC TAT
TCG TAG TTC TTT CAA TGG AGA CTC CTA GAG TTC GCG TCG ATA
Ser Ile Lys Lys Val Thr Ser Glu Asp Leu Lys Arg Ser Tyr>
_____________________________IL-1RAcP__________________________>

   1980        1990        2000        2010
*     *     *     *     *     *     *     *     *
GTC TGT CAT GCT AGA AGT GCC AAA GGC GAA GTT GCC AAA GCA
CAG ACA GTA CGA TCT TCA CGG TTT CCG CTT CAA CGG TTT CGT
Val Cys His Ala Arg Ser Ala Lys Gly Glu Val Ala Lys Ala>
_____________________________IL-1RAcP__________________________>

 2020        2030        2040        2050
    *     *     *     *     *     *     *     *
GCC AAG GTG AAG CAG AAA GTG CCA GCT CCA AGA TAC ACA GTG
CGG TTC CAC TTC GTC TTT CAC GGT CGA GGT TCT ATG TGT CAC
Ala Lys Val Lys Gln Lys Val Pro Ala Pro Arg Tyr Thr Val>
_____________________________IL-1RAcP__________________________>

2060        2070        2080        2090        2100
  *     *     *     *     *     *     *     *     *
TCC GGA GAG TCC AAA TAC GGT CCG CCA TGC CCA TCA TGC CCA
AGG CCT CTC AGG TTT ATG CCA GGC GGT ACG GGT AGT ACG GGT
Ser Gly>
________>
        Glu Ser Lys Tyr Gly Pro Pro Cys Pro Ser Cys Pro>
        __________________FC-IgG4_____________________________>

      2110        2120        2130        2140
    *     *     *     *     *     *     *     *
GCA CCT GAG TTC CTG GGG GGA CCA TCA GTC TTC CTG TTC CCC
CGT GGA CTC AAG GAC CCC CCT GGT AGT CAG AAG GAC AAG GGG
Ala Pro Glu Phe Leu Gly Gly Pro Ser Val Phe Leu Phe Pro>
__________________________FC-IgG4_____________________________>

      2150        2160        2170        2180
  *     *     *     *     *     *     *     *
CCA AAA CCC AAG GAC ACT CTC ATG ATC TCC CGG ACC CCT GAG
GGT TTT GGG TTC CTG TGA GAG TAC TAG AGG GCC TGG GGA CTC
Pro Lys Pro Lys Asp Thr Leu Met Ile Ser Arg Thr Pro Glu>
__________________________FC-IgG4_____________________________>

   2190        2200        2210        2220
*     *     *     *     *     *     *     *     *
GTC ACG TGC GTG GTG GTG GAC GTG AGC CAG GAA GAC CCC GAG
CAG TGC ACG CAC CAC CAC CTG CAC TCG GTC CTT CTG GGG CTC
Val Thr Cys Val Val Val Asp Val Ser Gln Glu Asp Pro Glu>
__________________________FC-IgG4_____________________________>
```

Figure 45H

```
 2230         2240         2250          2260
    *      *      *      *     *      *      *     *
GTC CAG TTC AAC TGG TAC GTG GAT GGC GTG GAG GTG CAT AAT
CAG GTC AAG TTG ACC ATG CAC CTA CCG CAC CTC CAC GTA TTA
Val Gln Phe Asn Trp Tyr Val Asp Gly Val Glu Val His Asn>
______________________FC-IgG4________________________>

2270         2280         2290         2300         2310
 *      *      *      *      *      *      *      *     *
GCC AAG ACA AAG CCG CGG GAG GAG CAG TTC AAC AGC ACG TAC
CGG TTC TGT TTC GGC GCC CTC CTC GTC AAG TTG TCG TGC ATG
Ala Lys Thr Lys Pro Arg Glu Glu Gln Phe Asn Ser Thr Tyr>
______________________FC-IgG4________________________>

          2320         2330         2340         2350
     *      *      *      *      *      *      *      *
CGT GTG GTC AGC GTC CTC ACC GTC CTG CAC CAG GAC TGG CTG
GCA CAC CAG TCG CAG GAG TGG CAG GAC GTG GTC CTG ACC GAC
Arg Val Val Ser Val Leu Thr Val Leu His Gln Asp Trp Leu>
______________________FC-IgG4________________________>

       2360         2370          2380         2390
  *      *      *      *      *      *      *      *
AAC GGC AAG GAG TAC AAG TGC AAG GTC TCC AAC AAA GGC CTC
TTG CCG TTC CTC ATG TTC ACG TTC CAG AGG TTG TTT CCG GAG
Asn Gly Lys Glu Tyr Lys Cys Lys Val Ser Asn Lys Gly Leu>
______________________FC-IgG4________________________>

   2400          2410         2420         2430
*      *      *      *      *      *      *      *      *
CCG TCC TCC ATC GAG AAA ACC ATC TCC AAA GCC AAA GGG CAG
GGC AGG AGG TAG CTC TTT TGG TAG AGG TTT CGG TTT CCC GTC
Pro Ser Ser Ile Glu Lys Thr Ile Ser Lys Ala Lys Gly Gln>
______________________FC-IgG4________________________>

 2440         2450         2460          2470
    *      *      *      *      *      *      *     *
CCC CGA GAG CCA CAG GTG TAC ACC CTG CCC CCA TCC CAG GAG
GGG GCT CTC GGT GTC CAC ATG TGG GAC GGG GGT AGG GTC CTC
Pro Arg Glu Pro Gln Val Tyr Thr Leu Pro Pro Ser Gln Glu>
______________________FC-IgG4________________________>

2480         2490         2500         2510         2520
 *      *      *      *      *      *      *      *     *
GAG ATG ACC AAG AAC CAG GTC AGC CTG ACC TGC CTG GTC AAA
CTC TAC TGG TTC TTG GTC CAG TCG GAC TGG ACG GAC CAG TTT
Glu Met Thr Lys Asn Gln Val Ser Leu Thr Cys Leu Val Lys>
______________________FC-IgG4________________________>

          2530         2540         2550         2560
     *      *      *      *      *      *      *      *
GGC TTC TAC CCC AGC GAC ATC GCC GTG GAG TGG GAG AGC AAT
CCG AAG ATG GGG TCG CTG TAG CGG CAC CTC ACC CTC TCG TTA
Gly Phe Tyr Pro Ser Asp Ile Ala Val Glu Trp Glu Ser Asn>
______________________FC-IgG4________________________>
```

Figure 45I

```
      2570        2580         2590        2600
  *      *      *     *      *      *     *      *
GGG CAG CCG GAG AAC AAC TAC AAG ACC ACG CCT CCC GTG CTG
CCC GTC GGC CTC TTG TTG ATG TTC TGG TGC GGA GGG CAC GAC
Gly Gln Pro Glu Asn Asn Tyr Lys Thr Thr Pro Pro Val Leu>
_______________________FC-IgG4_________________________>

   2610         2620        2630        2640
*      *      *      *     *      *      *     *      *
GAC TCC GAC GGC TCC TTC TTC CTC TAC AGC AGG CTA ACC GTG
CTG AGG CTG CCG AGG AAG AAG GAG ATG TCG TCC GAT TGG CAC
Asp Ser Asp Gly Ser Phe Phe Leu Tyr Ser Arg Leu Thr Val>
_______________________FC-IgG4_________________________>

 2650         2660        2670         2680
     *      *      *      *     *      *      *     *
GAC AAG AGC AGG TGG CAG GAG GGG AAT GTC TTC TCA TGC TCC
CTG TTC TCG TCC ACC GTC CTC CCC TTA CAG AAG AGT ACG AGG
Asp Lys Ser Arg Trp Gln Glu Gly Asn Val Phe Ser Cys Ser>
_______________________FC-IgG4_________________________>

2690        2700          2710       2720          2730
  *      *      *      *      *      *      *      *     *
GTG ATG CAT GAG GCT CTG CAC AAC CAC TAC ACA CAG AAG AGC
CAC TAC GTA CTC CGA GAC GTG TTG GTG ATG TGT GTC TTC TCG
Val Met His Glu Ala Leu His Asn His Tyr Thr Gln Lys Ser>
_______________________FC-IgG4_________________________>

          2740        2750
     *       *     *      *
CTC TCC CTG TCT CTG GGT AAA TGA
GAG AGG GAC AGA GAC CCA TTT ACT
Leu Ser Leu Ser Leu Gly Lys ***>
___________FC-IgG4_____________>
```

Figure 46A

```
          10         20         30         40
    *     *     *     *     *     *     *     *
ATG GTG CGC TTG TAC GTG TTG GTA ATG GGA GTT TCT GCC TTC
TAC CAC GCG AAC ATG CAC AAC CAT TAC CCT CAA AGA CGG AAG
Met Val Arg Leu Tyr Val Leu Val Met Gly Val Ser Ala Phe>
____________________SIGNAL PEPTIDE___________________>
________________________IL-1RII______________________>

        50         60         70         80
  *     *     *     *     *     *     *     *
ACC CTT CAG CCT GCG GCA CAC ACA GGG GCT GCC AGA AGC TGC
TGG GAA GTC GGA CGC CGT GTG TGT CCC CGA CGG TCT TCG ACG
Thr Leu Gln Pro Ala Ala>
_____SIGNAL PEPTIDE____>
                        His Thr Gly Ala Ala Arg Ser Cys>
________________________IL-1RII______________________>

     90         100        110        120
*     *     *     *     *     *     *     *     *
CGG TTT CGT GGG AGG CAT TAC AAG CGG GAG TTC AGG CTG GAA
GCC AAA GCA CCC TCC GTA ATG TTC GCC CTC AAG TCC GAC CTT
Arg Phe Arg Gly Arg His Tyr Lys Arg Glu Phe Arg Leu Glu>
________________________IL-1RII______________________>

  130        140        150        160
    *     *     *     *     *     *     *     *
GGG GAG CCT GTA GCC CTG AGG TGC CCC CAG GTG CCC TAC TGG
CCC CTC GGA CAT CGG GAC TCC ACG GGG GTC CAC GGG ATG ACC
Gly Glu Pro Val Ala Leu Arg Cys Pro Gln Val Pro Tyr Trp>
________________________IL-1RII______________________>

170        180        190        200        210
 *     *     *     *     *     *     *     *     *
TTG TGG GCC TCT GTC AGC CCC CGC ATC AAC CTG ACA TGG CAT
AAC ACC CGG AGA CAG TCG GGG GCG TAG TTG GAC TGT ACC GTA
Leu Trp Ala Ser Val Ser Pro Arg Ile Asn Leu Thr Trp His>
________________________IL-1RII______________________>

          220        230        240        250
     *     *     *     *     *     *     *     *
AAA AAT GAC TCT GCT AGG ACG GTC CCA GGA GAA GAA GAG ACA
TTT TTA CTG AGA CGA TCC TGC CAG GGT CCT CTT CTT CTC TGT
Lys Asn Asp Ser Ala Arg Thr Val Pro Gly Glu Glu Glu Thr>
________________________IL-1RII______________________>

       260        270        280        290
  *     *     *     *     *     *     *     *
CGG ATG TGG GCC CAG GAC GGT GCT CTG TGG CTT CTG CCA GCC
GCC TAC ACC CGG GTC CTG CCA CGA GAC ACC GAA GAC GGT CGG
Arg Met Trp Ala Gln Asp Gly Ala Leu Trp Leu Leu Pro Ala>
________________________IL-1RII______________________>
```

Figure 46B

```
    300         310        320        330
 *    *     *     *    *     *     *    *     *
TTG CAG GAG GAC TCT GGC ACC TAC GTC TGC ACT ACT AGA AAT
AAC GTC CTC CTG AGA CCG TGG ATG CAG ACG TGA TGA TCT TTA
Leu Gln Glu Asp Ser Gly Thr Tyr Val Cys Thr Thr Arg Asn>
____________________________IL-1RII___________________________>

  340        350        360         370
    *     *     *     *    *     *     *    *
GCT TCT TAC TGT GAC AAA ATG TCC ATT GAG CTC AGA GTT TTT
CGA AGA ATG ACA CTG TTT TAC AGG TAA CTC GAG TCT CAA AAA
Ala Ser Tyr Cys Asp Lys Met Ser Ile Glu Leu Arg Val Phe>
____________________________IL-1RII___________________________>

380        390         400        410        420
 *     *    *     *     *    *     *     *    *
GAG AAT ACA GAT GCT TTC CTG CCG TTC ATC TCA TAC CCG CAA
CTC TTA TGT CTA CGA AAG GAC GGC AAG TAG AGT ATG GGC GTT
Glu Asn Thr Asp Ala Phe Leu Pro Phe Ile Ser Tyr Pro Gln>
____________________________IL-1RII___________________________>

           430        440        450         460
     *     *    *     *     *    *     *     *
ATT TTA ACC TTG TCA ACC TCT GGG GTA TTA GTA TGC CCT GAC
TAA AAT TGG AAC AGT TGG AGA CCC CAT AAT CAT ACG GGA CTG
Ile Leu Thr Leu Ser Thr Ser Gly Val Leu Val Cys Pro Asp>
____________________________IL-1RII___________________________>

        470        480         490        500
  *     *     *    *     *     *    *     *
CTG AGT GAA TTC ACC CGT GAC AAA ACT GAC GTG AAG ATT CAA
GAC TCA CTT AAG TGG GCA CTG TTT TGA CTG CAC TTC TAA GTT
Leu Ser Glu Phe Thr Arg Asp Lys Thr Asp Val Lys Ile Gln>
____________________________IL-1RII___________________________>

    510         520        530        540
 *    *     *     *    *     *     *    *     *
TGG TAC AAG GAT TCT CTT CTT TTG GAT AAA GAC AAT GAG AAA
ACC ATG TTC CTA AGA GAA GAA AAC CTA TTT CTG TTA CTC TTT
Trp Tyr Lys Asp Ser Leu Leu Leu Asp Lys Asp Asn Glu Lys>
____________________________IL-1RII___________________________>

   550        560        570         580
     *     *     *     *    *     *     *    *
TTT CTA AGT GTG AGG GGG ACC ACT CAC TTA CTC GTA CAC GAT
AAA GAT TCA CAC TCC CCC TGG TGA GTG AAT GAG CAT GTG CTA
Phe Leu Ser Val Arg Gly Thr Thr His Leu Leu Val His Asp>
____________________________IL-1RII___________________________>

590        600         610        620        630
 *     *    *     *     *    *     *     *    *
GTG GCC CTG GAA GAT GCT GGC TAT TAC CGC TGT GTC CTG ACA
CAC CGG GAC CTT CTA CGA CCG ATA ATG GCG ACA CAG GAC TGT
Val Ala Leu Glu Asp Ala Gly Tyr Tyr Arg Cys Val Leu Thr>
____________________________IL-1RII___________________________>
```

Figure 46C

```
            640          650          660          670
         *      *      *      *      *      *      *      *
TTT GCC CAT GAA GGC CAG CAA TAC AAC ATC ACT AGG AGT ATT
AAA CGG GTA CTT CCG GTC GTT ATG TTG TAG TGA TCC TCA TAA
Phe Ala His Glu Gly Gln Gln Tyr Asn Ile Thr Arg Ser Ile>
________________________IL-1RII_______________________>

         680          690          700          710
   *       *      *      *      *      *      *      *
GAG CTA CGC ATC AAG AAA AAA AAA GAA GAG ACC ATT CCT GTG
CTC GAT GCG TAG TTC TTT TTT TTT CTT CTC TGG TAA GGA CAC
Glu Leu Arg Ile Lys Lys Lys Lys Glu Glu Thr Ile Pro Val>
________________________IL-1RII_______________________>

     720          730          740          750
*      *      *      *      *      *      *      *      *
ATC ATT TCC CCC CTC AAG ACC ATA TCA GCT TCT CTG GGG TCA
TAG TAA AGG GGG GAG TTC TGG TAT AGT CGA AGA GAC CCC AGT
Ile Ile Ser Pro Leu Lys Thr Ile Ser Ala Ser Leu Gly Ser>
________________________IL-1RII_______________________>

  760          770          780          790
     *      *      *      *      *      *      *      *
AGA CTG ACA ATC CCA TGT AAG GTG TTT CTG GGA ACC GGC ACA
TCT GAC TGT TAG GGT ACA TTC CAC AAA GAC CCT TGG CCG TGT
Arg Leu Thr Ile Pro Cys Lys Val Phe Leu Gly Thr Gly Thr>
________________________IL-1RII_______________________>

800          810          820          830          840
 *      *      *      *      *      *      *      *      *
CCC TTA ACC ACC ATG CTG TGG TGG ACG GCC AAT GAC ACC CAC
GGG AAT TGG TGG TAC GAC ACC ACC TGC CGG TTA CTG TGG GTG
Pro Leu Thr Thr Met Leu Trp Trp Thr Ala Asn Asp Thr His>
________________________IL-1RII_______________________>

            850          860          870          880
         *      *      *      *      *      *      *      *
ATA GAG AGC GCC TAC CCG GGA GGC CGC GTG ACC GAG GGG CCA
TAT CTC TCG CGG ATG GGC CCT CCG GCG CAC TGG CTC CCC GGT
Ile Glu Ser Ala Tyr Pro Gly Gly Arg Val Thr Glu Gly Pro>
________________________IL-1RII_______________________>

         890          900          910          920
   *       *      *      *      *      *      *      *
CGC CAG GAA TAT TCA GAA AAT AAT GAG AAC TAC ATT GAA GTG
GCG GTC CTT ATA AGT CTT TTA TTA CTC TTG ATG TAA CTT CAC
Arg Gln Glu Tyr Ser Glu Asn Asn Glu Asn Tyr Ile Glu Val>
________________________IL-1RII_______________________>

     930          940          950          960
*      *      *      *      *      *      *      *      *
CCA TTG ATT TTT GAT CCT GTC ACA AGA GAG GAT TTG CAC ATG
GGT AAC TAA AAA CTA GGA CAG TGT TCT CTC CTA AAC GTG TAC
Pro Leu Ile Phe Asp Pro Val Thr Arg Glu Asp Leu His Met>
________________________IL-1RII_______________________>
```

Figure 46D

```
   970         980         990        1000
    *     *     *     *     *     *     *     *
GAT TTT AAA TGT GTT GTC CAT AAT ACC CTG AGT TTT CAG ACA
CTA AAA TTT ACA CAA CAG GTA TTA TGG GAC TCA AAA GTC TGT
Asp Phe Lys Cys Val Val His Asn Thr Leu Ser Phe Gln Thr>
_______________________________IL-1RII_____________________________>

1010        1020        1030        1040        1050
  *     *     *     *     *     *     *     *     *
CTA CGC ACC ACA GTC AAG GAA GCC TCC TCC ACG TTC TCA GAA
GAT GCG TGG TGT CAG TTC CTT CGG AGG AGG TGC AAG AGT CTT
                                                Ser Glu>
                                                _______>
Leu Arg Thr Thr Val Lys Glu Ala Ser Ser Thr Phe>
________________________IL-1RII___________________________>

        1060        1070        1080        1090
    *     *     *     *     *     *     *     *
CGC TGC GAT GAC TGG GGA CTA GAC ACC ATG AGG CAA ATC CAA
GCG ACG CTA CTG ACC CCT GAT CTG TGG TAC TCC GTT TAG GTT
Arg Cys Asp Asp Trp Gly Leu Asp Thr Met Arg Gln Ile Gln>
_______________________________IL-1RAcP____________________________>

      1100        1110        1120        1130
  *     *     *     *     *     *     *     *
GTG TTT GAA GAT GAG CCA GCT CGC ATC AAG TGC CCA CTC TTT
CAC AAA CTT CTA CTC GGT CGA GCG TAG TTC ACG GGT GAG AAA
Val Phe Glu Asp Glu Pro Ala Arg Ile Lys Cys Pro Leu Phe>
_______________________________IL-1RAcP____________________________>

    1140        1150        1160        1170
*     *     *     *     *     *     *     *     *
GAA CAC TTC TTG AAA TTC AAC TAC AGC ACA GCC CAT TCA GCT
CTT GTG AAG AAC TTT AAG TTG ATG TCG TGT CGG GTA AGT CGA
Glu His Phe Leu Lys Phe Asn Tyr Ser Thr Ala His Ser Ala>
_______________________________IL-1RAcP____________________________>

  1180        1190        1200        1210
    *     *     *     *     *     *     *     *
GGC CTT ACT CTG ATC TGG TAT TGG ACT AGG CAG GAC CGG GAC
CCG GAA TGA GAC TAG ACC ATA ACC TGA TCC GTC CTG GCC CTG
Gly Leu Thr Leu Ile Trp Tyr Trp Thr Arg Gln Asp Arg Asp>
_______________________________IL-1RAcP____________________________>

1220        1230        1240        1250        1260
  *     *     *     *     *     *     *     *     *
CTT GAG GAG CCA ATT AAC TTC CGC CTC CCC GAG AAC CGC ATT
GAA CTC CTC GGT TAA TTG AAG GCG GAG GGG CTC TTG GCG TAA
Leu Glu Glu Pro Ile Asn Phe Arg Leu Pro Glu Asn Arg Ile>
_______________________________IL-1RAcP____________________________>
```

Figure 46E

```
        1270        1280        1290        1300
    *      *    *      *     *     *     *     *
AGT AAG GAG AAA GAT GTG CTG TGG TTC CGG CCC ACT CTC CTC
TCA TTC CTC TTT CTA CAC GAC ACC AAG GCC GGG TGA GAG GAG
Ser Lys Glu Lys Asp Val Leu Trp Phe Arg Pro Thr Leu Leu>
_______________________________IL-1RAcP___________________________>

     1310        1320        1330        1340
  *      *     *     *     *     *     *     *
AAT GAC ACT GGC AAC TAT ACC TGC ATG TTA AGG AAC ACT ACA
TTA CTG TGA CCG TTG ATA TGG ACG TAC AAT TCC TTG TGA TGT
Asn Asp Thr Gly Asn Tyr Thr Cys Met Leu Arg Asn Thr Thr>
_______________________________IL-1RAcP___________________________>

   1350        1360        1370        1380
*    *     *     *     *     *     *     *     *
TAT TGC AGC AAA GTT GCA TTT CCC TTG GAA GTT GTT CAA AAA
ATA ACG TCG TTT CAA CGT AAA GGG AAC CTT CAA CAA GTT TTT
Tyr Cys Ser Lys Val Ala Phe Pro Leu Glu Val Val Gln Lys>
_______________________________IL-1RAcP___________________________>

 1390        1400        1410        1420
    *     *     *     *     *     *     *     *
GAC AGC TGT TTC AAT TCC CCC ATG AAA CTC CCA GTG CAT AAA
CTG TCG ACA AAG TTA AGG GGG TAC TTT GAG GGT CAC GTA TTT
Asp Ser Cys Phe Asn Ser Pro Met Lys Leu Pro Val His Lys>
_______________________________IL-1RAcP___________________________>

1430        1440        1450        1460        1470
 *     *     *     *     *     *     *     *     *
CTG TAT ATA GAA TAT GGC ATT CAG AGG ATC ACT TGT CCA AAT
GAC ATA TAT CTT ATA CCG TAA GTC TCC TAG TGA ACA GGT TTA
Leu Tyr Ile Glu Tyr Gly Ile Gln Arg Ile Thr Cys Pro Asn>
_______________________________IL-1RAcP___________________________>

        1480        1490        1500        1510
    *      *    *      *     *     *     *     *
GTA GAT GGA TAT TTT CCT TCC AGT GTC AAA CCG ACT ATC ACT
CAT CTA CCT ATA AAA GGA AGG TCA CAG TTT GGC TGA TAG TGA
Val Asp Gly Tyr Phe Pro Ser Ser Val Lys Pro Thr Ile Thr>
_______________________________IL-1RAcP___________________________>

     1520        1530        1540        1550
  *      *     *     *     *     *     *     *
TGG TAT ATG GGC TGT TAT AAA ATA CAG AAT TTT AAT AAT GTA
ACC ATA TAC CCG ACA ATA TTT TAT GTC TTA AAA TTA TTA CAT
Trp Tyr Met Gly Cys Tyr Lys Ile Gln Asn Phe Asn Asn Val>
_______________________________IL-1RAcP___________________________>

   1560        1570        1580        1590
*    *     *     *     *     *     *     *     *
ATA CCC GAA GGT ATG AAC TTG AGT TTC CTC ATT GCC TTA ATT
TAT GGG CTT CCA TAC TTG AAC TCA AAG GAG TAA CGG AAT TAA
Ile Pro Glu Gly Met Asn Leu Ser Phe Leu Ile Ala Leu Ile>
_______________________________IL-1RAcP___________________________>
```

Figure 46F

```
 1600        1610        1620         1630
    *     *     *     *     *     *     *     *
TCA AAT AAT GGA AAT TAC ACA TGT GTT GTT ACA TAT CCA GAA
AGT TTA TTA CCT TTA ATG TGT ACA CAA CAA TGT ATA GGT CTT
Ser Asn Asn Gly Asn Tyr Thr Cys Val Val Thr Tyr Pro Glu>
_____________________________IL-1RAcP__________________________>

1640        1650        1660        1670        1680
   *     *     *     *     *     *     *     *     *
AAT GGA CGT ACG TTT CAT CTC ACC AGG ACT CTG ACT GTA AAG
TTA CCT GCA TGC AAA GTA GAG TGG TCC TGA GAC TGA CAT TTC
Asn Gly Arg Thr Phe His Leu Thr Arg Thr Leu Thr Val Lys>
_____________________________IL-1RAcP__________________________>

         1690        1700        1710        1720
      *     *     *     *     *     *     *     *
GTA GTA GGC TCT CCA AAA AAT GCA GTG CCC CCT GTG ATC CAT
CAT CAT CCG AGA GGT TTT TTA CGT CAC GGG GGA CAC TAG GTA
Val Val Gly Ser Pro Lys Asn Ala Val Pro Pro Val Ile His>
_____________________________IL-1RAcP__________________________>

      1730        1740        1750        1760
   *     *     *     *     *     *     *     *
TCA CCT AAT GAT CAT GTG GTC TAT GAG AAA GAA CCA GGA GAG
AGT GGA TTA CTA GTA CAC CAG ATA CTC TTT CTT GGT CCT CTC
Ser Pro Asn Asp His Val Val Tyr Glu Lys Glu Pro Gly Glu>
_____________________________IL-1RAcP__________________________>

   1770        1780        1790        1800
*     *     *     *     *     *     *     *     *
GAG CTA CTC ATT CCC TGT ACG GTC TAT TTT AGT TTT CTG ATG
CTC GAT GAG TAA GGG ACA TGC CAG ATA AAA TCA AAA GAC TAC
Glu Leu Leu Ile Pro Cys Thr Val Tyr Phe Ser Phe Leu Met>
_____________________________IL-1RAcP__________________________>

 1810        1820        1830        1840
    *     *     *     *     *     *     *     *
GAT TCT CGC AAT GAG GTT TGG TGG ACC ATT GAT GGA AAA AAA
CTA AGA GCG TTA CTC CAA ACC ACC TGG TAA CTA CCT TTT TTT
Asp Ser Arg Asn Glu Val Trp Trp Thr Ile Asp Gly Lys Lys>
_____________________________IL-1RAcP__________________________>

1850        1860        1870        1880        1890
 *     *     *     *     *     *     *     *     *
CCT GAT GAC ATC ACT ATT GAT GTC ACC ATT AAC GAA AGT ATA
GGA CTA CTG TAG TGA TAA CTA CAG TGG TAA TTG CTT TCA TAT
Pro Asp Asp Ile Thr Ile Asp Val Thr Ile Asn Glu Ser Ile>
_____________________________IL-1RAcP__________________________>

         1900        1910        1920        1930
      *     *     *     *     *     *     *     *
AGT CAT AGT AGA ACA GAA GAT GAA ACA AGA ACT CAG ATT TTG
TCA GTA TCA TCT TGT CTT CTA CTT TGT TCT TGA GTC TAA AAC
Ser His Ser Arg Thr Glu Asp Glu Thr Arg Thr Gln Ile Leu>
_____________________________IL-1RAcP__________________________>
```

Figure 46G

```
      1940          1950          1960          1970
  *     *      *      *      *      *     *     *
AGC ATC AAG AAA GTT ACC TCT GAG GAT CTC AAG CGC AGC TAT
TCG TAG TTC TTT CAA TGG AGA CTC CTA GAG TTC GCG TCG ATA
Ser Ile Lys Lys Val Thr Ser Glu Asp Leu Lys Arg Ser Tyr>
_________________________IL-1RAcP________________________>

   1980          1990          2000          2010
*     *      *      *      *      *     *     *      *
GTC TGT CAT GCT AGA AGT GCC AAA GGC GAA GTT GCC AAA GCA
CAG ACA GTA CGA TCT TCA CGG TTT CCG CTT CAA CGG TTT CGT
Val Cys His Ala Arg Ser Ala Lys Gly Glu Val Ala Lys Ala>
_________________________IL-1RAcP________________________>

 2020          2030          2040          2050
     *     *      *      *     *      *     *     *
GCC AAG GTG AAG CAG AAA GTG CCA GCT CCA AGA TAC ACA GTG
CGG TTC CAC TTC GTC TTT CAC GGT CGA GGT TCT ATG TGT CAC
Ala Lys Val Lys Gln Lys Val Pro Ala Pro Arg Tyr Thr Val>
_________________________IL-1RAcP________________________>

                                   >Mutation Serine to Proline
                                                |
2060          2070          2080          2090  |      2100
  *      *      *      *      *      *      *   |  *     *
TCC GGA GAG TCC AAA TAC GGT CCG CCA TGC CCA CCA TGC CCA
AGG CCT CTC AGG TTT ATG CCA GGC GGT ACG GGT GGT ACG GGT
Ser Gly>
_______>
        Glu Ser Lys Tyr Gly Pro Pro Cys Pro Pro Cys Pro>
        _______________FC-IgG4_________________________>

         2110          2120          2130          2140
     *      *      *      *      *      *      *      *
GCA CCT GAG TTC CTG GGG GGA CCA TCA GTC TTC CTG TTC CCC
CGT GGA CTC AAG GAC CCC CCT GGT AGT CAG AAG GAC AAG GGG
Ala Pro Glu Phe Leu Gly Gly Pro Ser Val Phe Leu Phe Pro>
_______________________FC-IgG4_________________________>

      2150          2160          2170          2180
  *      *      *     *      *      *     *      *
CCA AAA CCC AAG GAC ACT CTC ATG ATC TCC CGG ACC CCT GAG
GGT TTT GGG TTC CTG TGA GAG TAC TAG AGG GCC TGG GGA CTC
Pro Lys Pro Lys Asp Thr Leu Met Ile Ser Arg Thr Pro Glu>
_______________________FC-IgG4_________________________>

   2190          2200          2210          2220
*     *      *      *      *      *     *     *      *
GTC ACG TGC GTG GTG GTG GAC GTG AGC CAG GAA GAC CCC GAG
CAG TGC ACG CAC CAC CAC CTG CAC TCG GTC CTT CTG GGG CTC
Val Thr Cys Val Val Val Asp Val Ser Gln Glu Asp Pro Glu>
_______________________FC-IgG4_________________________>
```

Figure 46H

```
 2230       2240       2250        2260
    *    *     *     *    *    *     *    *
GTC CAG TTC AAC TGG TAC GTG GAT GGC GTG GAG GTG CAT AAT
CAG GTC AAG TTG ACC ATG CAC CTA CCG CAC CTC CAC GTA TTA
Val Gln Phe Asn Trp Tyr Val Asp Gly Val Glu Val His Asn>
_____________________FC-IgG4_______________________>

2270        2280        2290        2300        2310
  *      *     *     *     *    *     *     *    *
GCC AAG ACA AAG CCG CGG GAG GAG CAG TTC AAC AGC ACG TAC
CGG TTC TGT TTC GGC GCC CTC CTC GTC AAG TTG TCG TGC ATG
Ala Lys Thr Lys Pro Arg Glu Glu Gln Phe Asn Ser Thr Tyr>
_____________________FC-IgG4_______________________>

        2320       2330        2340        2350
      *     *    *     *     *    *     *     *
CGT GTG GTC AGC GTC CTC ACC GTC CTG CAC CAG GAC TGG CTG
GCA CAC CAG TCG CAG GAG TGG CAG GAC GTG GTC CTG ACC GAC
Arg Val Val Ser Val Leu Thr Val Leu His Gln Asp Trp Leu>
_____________________FC-IgG4_______________________>

     2360       2370        2380        2390
 *      *     *     *     *    *     *     *
AAC GGC AAG GAG TAC AAG TGC AAG GTC TCC AAC AAA GGC CTC
TTG CCG TTC CTC ATG TTC ACG TTC CAG AGG TTG TTT CCG GAG
Asn Gly Lys Glu Tyr Lys Cys Lys Val Ser Asn Lys Gly Leu>
_____________________FC-IgG4_______________________>

   2400        2410       2420        2430
*     *     *     *     *    *     *    *     *
CCG TCC TCC ATC GAG AAA ACC ATC TCC AAA GCC AAA GGG CAG
GGC AGG AGG TAG CTC TTT TGG TAG AGG TTT CGG TTT CCC GTC
Pro Ser Ser Ile Glu Lys Thr Ile Ser Lys Ala Lys Gly Gln>
_____________________FC-IgG4_______________________>

  2440       2450        2460        2470
     *     *     *     *    *     *     *    *
CCC CGA GAG CCA CAG GTG TAC ACC CTG CCC CCA TCC CAG GAG
GGG GCT CTC GGT GTC CAC ATG TGG GAC GGG GGT AGG GTC CTC
Pro Arg Glu Pro Gln Val Tyr Thr Leu Pro Pro Ser Gln Glu>
_____________________FC-IgG4_______________________>

2480        2490        2500        2510        2520
  *     *     *     *     *    *     *     *    *
GAG ATG ACC AAG AAC CAG GTC AGC CTG ACC TGC CTG GTC AAA
CTC TAC TGG TTC TTG GTC CAG TCG GAC TGG ACG GAC CAG TTT
Glu Met Thr Lys Asn Gln Val Ser Leu Thr Cys Leu Val Lys>
_____________________FC-IgG4_______________________>

         2530       2540        2550        2560
      *     *     *     *     *    *     *     *
GGC TTC TAC CCC AGC GAC ATC GCC GTG GAG TGG GAG AGC AAT
CCG AAG ATG GGG TCG CTG TAG CGG CAC CTC ACC CTC TCG TTA
Gly Phe Tyr Pro Ser Asp Ile Ala Val Glu Trp Glu Ser Asn>
_____________________FC-IgG4_______________________>
```

Figure 46I

```
      2570        2580        2590        2600
  *     *     *     *     *     *     *     *
GGG CAG CCG GAG AAC AAC TAC AAG ACC ACG CCT CCC GTG CTG
CCC GTC GGC CTC TTG TTG ATG TTC TGG TGC GGA GGG CAC GAC
Gly Gln Pro Glu Asn Asn Tyr Lys Thr Thr Pro Pro Val Leu>
_______________________FC-IgG4________________________>

    2610        2620        2630        2640
 *     *     *     *     *     *     *     *     *
GAC TCC GAC GGC TCC TTC TTC CTC TAC AGC AGG CTA ACC GTG
CTG AGG CTG CCG AGG AAG AAG GAG ATG TCG TCC GAT TGG CAC
Asp Ser Asp Gly Ser Phe Phe Leu Tyr Ser Arg Leu Thr Val>
_______________________FC-IgG4________________________>

  2650        2660        2670        2680
     *     *     *     *     *     *     *     *
GAC AAG AGC AGG TGG CAG GAG GGG AAT GTC TTC TCA TGC TCC
CTG TTC TCG TCC ACC GTC CTC CCC TTA CAG AAG AGT ACG AGG
Asp Lys Ser Arg Trp Gln Glu Gly Asn Val Phe Ser Cys Ser>
_______________________FC-IgG4________________________>

2690        2700        2710        2720        2730
  *     *     *     *     *     *     *     *     *
GTG ATG CAT GAG GCT CTG CAC AAC CAC TAC ACA CAG AAG AGC
CAC TAC GTA CTC CGA GAC GTG TTG GTG ATG TGT GTC TTC TCG
Val Met His Glu Ala Leu His Asn His Tyr Thr Gln Lys Ser>
_______________________FC-IgG4________________________>

          2740        2750
     *     *     *     *
CTC TCC CTG TCT CTG GGT AAA TGA
GAG AGG GAC AGA GAC CCA TTT ACT
Leu Ser Leu Ser Leu Gly Lys ***>
___________FC-IgG4____________>
```

Figure 47A

```
          10          20          30          40
   *     *     *     *     *     *     *     *
ATG GTG CTT CTG TGG TGT GTA GTG AGT CTC TAC TTT TAT GGA
TAC CAC GAA GAC ACC ACA CAT CAC TCA GAG ATG AAA ATA CCT
Met Val Leu Leu Trp Cys Val Val Ser Leu Tyr Phe Tyr Gly>
______________________SIGNAL PEPTIDE____________________>
_________________________IL-1RAcP_______________________>

       50          60          70          80
 *     *     *     *     *     *     *     *
ATC CTG CAA AGT GAT GCC TCA GAA CGC TGC GAT GAC TGG GGA
TAG GAC GTT TCA CTA CGG AGT CTT GCG ACG CTA CTG ACC CCT
Ile Leu Gln Ser Asp Ala>
___ SIGNAL PEPTIDE______>
                        Ser Glu Arg Cys Asp Asp Trp Gly>
_________________________IL-1RAcP_______________________>

    90         100         110         120
*     *     *     *     *     *     *     *     *
CTA GAC ACC ATG AGG CAA ATC CAA GTG TTT GAA GAT GAG CCA
GAT CTG TGG TAC TCC GTT TAG GTT CAC AAA CTT CTA CTC GGT
Leu Asp Thr Met Arg Gln Ile Gln Val Phe Glu Asp Glu Pro>
_________________________IL-1RAcP_______________________>

  130         140         150         160
    *     *     *     *     *     *     *     *
GCT CGC ATC AAG TGC CCA CTC TTT GAA CAC TTC TTG AAA TTC
CGA GCG TAG TTC ACG GGT GAG AAA CTT GTG AAG AAC TTT AAG
Ala Arg Ile Lys Cys Pro Leu Phe Glu His Phe Leu Lys Phe>
_________________________IL-1RAcP_______________________>

170         180         190         200         210
 *     *     *     *     *     *     *     *     *
AAC TAC AGC ACA GCC CAT TCA GCT GGC CTT ACT CTG ATC TGG
TTG ATG TCG TGT CGG GTA AGT CGA CCG GAA TGA GAC TAG ACC
Asn Tyr Ser Thr Ala His Ser Ala Gly Leu Thr Leu Ile Trp>
_________________________IL-1RAcP_______________________>

          220         230         240         250
    *     *     *     *     *     *     *     *
TAT TGG ACT AGG CAG GAC CGG GAC CTT GAG GAG CCA ATT AAC
ATA ACC TGA TCC GTC CTG GCC CTG GAA CTC CTC GGT TAA TTG
Tyr Trp Thr Arg Gln Asp Arg Asp Leu Glu Glu Pro Ile Asn>
_________________________IL-1RAcP_______________________>

       260         270         280         290
 *     *     *     *     *     *     *     *
TTC CGC CTC CCC GAG AAC CGC ATT AGT AAG GAG AAA GAT GTG
AAG GCG GAG GGG CTC TTG GCG TAA TCA TTC CTC TTT CTA CAC
Phe Arg Leu Pro Glu Asn Arg Ile Ser Lys Glu Lys Asp Val>
_________________________IL-1RAcP_______________________>

    300         310         320         330
*     *     *     *     *     *     *     *     *
CTG TGG TTC CGG CCC ACT CTC CTC AAT GAC ACT GGC AAC TAT
GAC ACC AAG GCC GGG TGA GAG GAG TTA CTG TGA CCG TTG ATA
Leu Trp Phe Arg Pro Thr Leu Leu Asn Asp Thr Gly Asn Tyr>
_________________________IL-1RAcP_______________________>
```

Figure 47B

```
 340        350        360        370
  *     *     *     *     *     *     *     *
ACC TGC ATG TTA AGG AAC ACT ACA TAT TGC AGC AAA GTT GCA
TGG ACG TAC AAT TCC TTG TGA TGT ATA ACG TCG TTT CAA CGT
Thr Cys Met Leu Arg Asn Thr Thr Tyr Cys Ser Lys Val Ala>
____________________IL-1RAcP____________________>

380        390        400        410        420
 *     *     *     *     *     *     *     *     *
TTT CCC TTG GAA GTT GTT CAA AAA GAC AGC TGT TTC AAT TCC
AAA GGG AAC CTT CAA CAA GTT TTT CTG TCG ACA AAG TTA AGG
Phe Pro Leu Glu Val Val Gln Lys Asp Ser Cys Phe Asn Ser>
____________________IL-1RAcP____________________>

       430        440        450        460
    *     *     *     *     *     *     *     *
CCC ATG AAA CTC CCA GTG CAT AAA CTG TAT ATA GAA TAT GGC
GGG TAC TTT GAG GGT CAC GTA TTT GAC ATA TAT CTT ATA CCG
Pro Met Lys Leu Pro Val His Lys Leu Tyr Ile Glu Tyr Gly>
____________________IL-1RAcP____________________>

     470        480        490        500
 *     *     *     *     *     *     *     *
ATT CAG AGG ATC ACT TGT CCA AAT GTA GAT GGA TAT TTT CCT
TAA GTC TCC TAG TGA ACA GGT TTA CAT CTA CCT ATA AAA GGA
Ile Gln Arg Ile Thr Cys Pro Asn Val Asp Gly Tyr Phe Pro>
____________________IL-1RAcP____________________>

   510        520        530        540
*     *     *     *     *     *     *     *     *
TCC AGT GTC AAA CCG ACT ATC ACT TGG TAT ATG GGC TGT TAT
AGG TCA CAG TTT GGC TGA TAG TGA ACC ATA TAC CCG ACA ATA
Ser Ser Val Lys Pro Thr Ile Thr Trp Tyr Met Gly Cys Tyr>
____________________IL-1RAcP____________________>

  550        560        570        580
    *     *     *     *     *     *     *     *
AAA ATA CAG AAT TTT AAT AAT GTA ATA CCC GAA GGT ATG AAC
TTT TAT GTC TTA AAA TTA TTA CAT TAT GGG CTT CCA TAC TTG
Lys Ile Gln Asn Phe Asn Asn Val Ile Pro Glu Gly Met Asn>
____________________IL-1RAcP____________________>

590        600        610        620        630
 *     *     *     *     *     *     *     *     *
TTG AGT TTC CTC ATT GCC TTA ATT TCA AAT AAT GGA AAT TAC
AAC TCA AAG GAG TAA CGG AAT TAA AGT TTA TTA CCT TTA ATG
Leu Ser Phe Leu Ile Ala Leu Ile Ser Asn Asn Gly Asn Tyr>
____________________IL-1RAcP____________________>

       640        650        660        670
    *     *     *     *     *     *     *     *
ACA TGT GTT GTT ACA TAT CCA GAA AAT GGA CGT ACG TTT CAT
TGT ACA CAA CAA TGT ATA GGT CTT TTA CCT GCA TGC AAA GTA
Thr Cys Val Val Thr Tyr Pro Glu Asn Gly Arg Thr Phe His>
____________________IL-1RAcP____________________>
```

Figure 47C

```
       680        690         700        710
  *     *     *    *     *     *    *     *
CTC ACC AGG ACT CTG ACT GTA AAG GTA GTA GGC TCT CCA AAA
GAG TGG TCC TGA GAC TGA CAT TTC CAT CAT CCG AGA GGT TTT
Leu Thr Arg Thr Leu Thr Val Lys Val Val Gly Ser Pro Lys>
____________________________IL-1RAcP________________________>

    720        730        740        750
*    *     *     *     *     *     *    *     *
AAT GCA GTG CCC CCT GTG ATC CAT TCA CCT AAT GAT CAT GTG
TTA CGT CAC GGG GGA CAC TAG GTA AGT GGA TTA CTA GTA CAC
Asn Ala Val Pro Pro Val Ile His Ser Pro Asn Asp His Val>
____________________________IL-1RAcP________________________>

  760        770        780        790
    *     *     *     *    *     *     *    *
GTC TAT GAG AAA GAA CCA GGA GAG GAG CTA CTC ATT CCC TGT
CAG ATA CTC TTT CTT GGT CCT CTC CTC GAT GAG TAA GGG ACA
Val Tyr Glu Lys Glu Pro Gly Glu Glu Leu Leu Ile Pro Cys>
____________________________IL-1RAcP________________________>

800        810        820        830        840
 *     *     *     *     *     *     *     *    *
ACG GTC TAT TTT AGT TTT CTG ATG GAT TCT CGC AAT GAG GTT
TGC CAG ATA AAA TCA AAA GAC TAC CTA AGA GCG TTA CTC CAA
Thr Val Tyr Phe Ser Phe Leu Met Asp Ser Arg Asn Glu Val>
____________________________IL-1RAcP________________________>

          850        860        870         880
      *     *     *     *     *     *     *     *
TGG TGG ACC ATT GAT GGA AAA AAA CCT GAT GAC ATC ACT ATT
ACC ACC TGG TAA CTA CCT TTT TTT GGA CTA CTG TAG TGA TAA
Trp Trp Thr Ile Asp Gly Lys Lys Pro Asp Asp Ile Thr Ile>
____________________________IL-1RAcP________________________>

       890        900         910        920
  *     *     *     *     *     *     *     *
GAT GTC ACC ATT AAC GAA AGT ATA AGT CAT AGT AGA ACA GAA
CTA CAG TGG TAA TTG CTT TCA TAT TCA GTA TCA TCT TGT CTT
Asp Val Thr Ile Asn Glu Ser Ile Ser His Ser Arg Thr Glu>
____________________________IL-1RAcP________________________>

    930        940        950        960
*    *     *     *     *     *     *     *     *
GAT GAA ACA AGA ACT CAG ATT TTG AGC ATC AAG AAA GTT ACC
CTA CTT TGT TCT TGA GTC TAA AAC TCG TAG TTC TTT CAA TGG
Asp Glu Thr Arg Thr Gln Ile Leu Ser Ile Lys Lys Val Thr>
____________________________IL-1RAcP________________________>

  970        980        990        1000
    *     *     *     *     *     *     *     *
TCT GAG GAT CTC AAG CGC AGC TAT GTC TGT CAT GCT AGA AGT
AGA CTC CTA GAG TTC GCG TCG ATA CAG ACA GTA CGA TCT TCA
Ser Glu Asp Leu Lys Arg Ser Tyr Val Cys His Ala Arg Ser>
____________________________IL-1RAcP________________________>
```

Figure 47D

```
1010       1020       1030       1040       1050
   *     *     *     *     *     *     *     *     *
GCC AAA GGC GAA GTT GCC AAA GCA GCC AAG GTG AAG CAG AAA
CGG TTT CCG CTT CAA CGG TTT CGT CGG TTC CAC TTC GTC TTT
Ala Lys Gly Glu Val Ala Lys Ala Ala Lys Val Lys Gln Lys>
____________________________IL-1RAcP_________________________>

        1060       1070       1080       1090
   *     *     *     *     *     *     *     *
GTG CCA GCT CCA AGA TAC ACA GTG CAC ACA GGG GCT GCC AGA
CAC GGT CGA GGT TCT ATG TGT CAC GTG TGT CCC CGA CGG TCT
Val Pro Ala Pro Arg Tyr Thr Val>
____________IL-1RAcP_____________>
                                His Thr Gly Ala Ala Arg>
                                _________IL-1RII________>

    1100       1110       1120       1130
 *     *     *     *     *     *     *     *
AGC TGC CGG TTT CGT GGG AGG CAT TAC AAG CGG GAG TTC AGG
TCG ACG GCC AAA GCA CCC TCC GTA ATG TTC GCC CTC AAG TCC
Ser Cys Arg Phe Arg Gly Arg His Tyr Lys Arg Glu Phe Arg>
___________________________IL-1RII_________________________>

  1140       1150       1160       1170
*     *     *     *     *     *     *     *     *
CTG GAA GGG GAG CCT GTA GCC CTG AGG TGC CCC CAG GTG CCC
GAC CTT CCC CTC GGA CAT CGG GAC TCC ACG GGG GTC CAC GGG
Leu Glu Gly Glu Pro Val Ala Leu Arg Cys Pro Gln Val Pro>
___________________________IL-1RII_________________________>

 1180       1190       1200       1210
     *     *     *     *     *     *     *     *
TAC TGG TTG TGG GCC TCT GTC AGC CCC CGC ATC AAC CTG ACA
ATG ACC AAC ACC CGG AGA CAG TCG GGG GCG TAG TTG GAC TGT
Tyr Trp Leu Trp Ala Ser Val Ser Pro Arg Ile Asn Leu Thr>
___________________________IL-1RII_________________________>

1220       1230       1240       1250       1260
   *     *     *     *     *     *     *     *     *
TGG CAT AAA AAT GAC TCT GCT AGG ACG GTC CCA GGA GAA GAA
ACC GTA TTT TTA CTG AGA CGA TCC TGC CAG GGT CCT CTT CTT
Trp His Lys Asn Asp Ser Ala Arg Thr Val Pro Gly Glu Glu>
___________________________IL-1RII_________________________>

        1270       1280       1290       1300
      *     *     *     *     *     *     *     *
GAG ACA CGG ATG TGG GCC CAG GAC GGT GCT CTG TGG CTT CTG
CTC TGT GCC TAC ACC CGG GTC CTG CCA CGA GAC ACC GAA GAC
Glu Thr Arg Met Trp Ala Gln Asp Gly Ala Leu Trp Leu Leu>
___________________________IL-1RII_________________________>

    1310       1320       1330       1340
  *     *     *     *     *     *     *     *
CCA GCC TTG CAG GAG GAC TCT GGC ACC TAC GTC TGC ACT ACT
GGT CGG AAC GTC CTC CTG AGA CCG TGG ATG CAG ACG TGA TGA
Pro Ala Leu Gln Glu Asp Ser Gly Thr Tyr Val Cys Thr Thr>
___________________________IL-1RII_________________________>
```

Figure 47E

```
   1350         1360        1370        1380
*     *     *     *     *     *     *     *
AGA AAT GCT TCT TAC TGT GAC AAA ATG TCC ATT GAG CTC AGA
TCT TTA CGA AGA ATG ACA CTG TTT TAC AGG TAA CTC GAG TCT
Arg Asn Ala Ser Tyr Cys Asp Lys Met Ser Ile Glu Leu Arg>
_________________________IL-1RII_________________________>

 1390         1400        1410        1420
    *     *     *     *     *     *     *     *
GTT TTT GAG AAT ACA GAT GCT TTC CTG CCG TTC ATC TCA TAC
CAA AAA CTC TTA TGT CTA CGA AAG GAC GGC AAG TAG AGT ATG
Val Phe Glu Asn Thr Asp Ala Phe Leu Pro Phe Ile Ser Tyr>
_________________________IL-1RII_________________________>

1430        1440        1450        1460        1470
  *       *     *     *     *     *     *     *     *
CCG CAA ATT TTA ACC TTG TCA ACC TCT GGG GTA TTA GTA TGC
GGC GTT TAA AAT TGG AAC AGT TGG AGA CCC CAT AAT CAT ACG
Pro Gln Ile Leu Thr Leu Ser Thr Ser Gly Val Leu Val Cys>
_________________________IL-1RII_________________________>

          1480        1490        1500        1510
    *       *     *     *     *     *     *     *
CCT GAC CTG AGT GAA TTC ACC CGT GAC AAA ACT GAC GTG AAG
GGA CTG GAC TCA CTT AAG TGG GCA CTG TTT TGA CTG CAC TTC
Pro Asp Leu Ser Glu Phe Thr Arg Asp Lys Thr Asp Val Lys>
_________________________IL-1RII_________________________>

      1520        1530        1540        1550
  *       *     *     *     *     *     *     *
ATT CAA TGG TAC AAG GAT TCT CTT CTT TTG GAT AAA GAC AAT
TAA GTT ACC ATG TTC CTA AGA GAA GAA AAC CTA TTT CTG TTA
Ile Gln Trp Tyr Lys Asp Ser Leu Leu Leu Asp Lys Asp Asn>
_________________________IL-1RII_________________________>

    1560        1570        1580        1590
*     *     *     *     *     *     *     *     *
GAG AAA TTT CTA AGT GTG AGG GGG ACC ACT CAC TTA CTC GTA
CTC TTT AAA GAT TCA CAC TCC CCC TGG TGA GTG AAT GAG CAT
Glu Lys Phe Leu Ser Val Arg Gly Thr Thr His Leu Leu Val>
_________________________IL-1RII_________________________>

  1600        1610        1620        1630
    *     *     *     *     *     *     *     *
CAC GAT GTG GCC CTG GAA GAT GCT GGC TAT TAC CGC TGT GTC
GTG CTA CAC CGG GAC CTT CTA CGA CCG ATA ATG GCG ACA CAG
His Asp Val Ala Leu Glu Asp Ala Gly Tyr Tyr Arg Cys Val>
_________________________IL-1RII_________________________>

1640        1650        1660        1670        1680
  *       *     *     *     *     *     *     *     *
CTG ACA TTT GCC CAT GAA GGC CAG CAA TAC AAC ATC ACT AGG
GAC TGT AAA CGG GTA CTT CCG GTC GTT ATG TTG TAG TGA TCC
Leu Thr Phe Ala His Glu Gly Gln Gln Tyr Asn Ile Thr Arg>
_________________________IL-1RII_________________________>
```

Figure 47F

```
        1690        1700        1710        1720
     *      *     *      *      *     *      *     *
AGT ATT GAG CTA CGC ATC AAG AAA AAA AAA GAA GAG ACC ATT
TCA TAA CTC GAT GCG TAG TTC TTT TTT TTT CTT CTC TGG TAA
Ser Ile Glu Leu Arg Ile Lys Lys Lys Lys Glu Glu Thr Ile>
___________________________IL-1RII__________________________>

     1730        1740        1750        1760
  *      *     *      *      *     *      *     *
CCT GTG ATC ATT TCC CCC CTC AAG ACC ATA TCA GCT TCT CTG
GGA CAC TAG TAA AGG GGG GAG TTC TGG TAT AGT CGA AGA GAC
Pro Val Ile Ile Ser Pro Leu Lys Thr Ile Ser Ala Ser Leu>
___________________________IL-1RII__________________________>

   1770        1780        1790        1800
 *      *     *      *      *     *      *     *      *
GGG TCA AGA CTG ACA ATC CCA TGT AAG GTG TTT CTG GGA ACC
CCC AGT TCT GAC TGT TAG GGT ACA TTC CAC AAA GAC CCT TGG
Gly Ser Arg Leu Thr Ile Pro Cys Lys Val Phe Leu Gly Thr>
___________________________IL-1RII__________________________>

  1810        1820        1830        1840
     *      *     *      *      *     *      *     *
GGC ACA CCC TTA ACC ACC ATG CTG TGG TGG ACG GCC AAT GAC
CCG TGT GGG AAT TGG TGG TAC GAC ACC ACC TGC CGG TTA CTG
Gly Thr Pro Leu Thr Thr Met Leu Trp Trp Thr Ala Asn Asp>
___________________________IL-1RII__________________________>

1850        1860        1870        1880        1890
  *      *     *      *      *     *      *     *      *
ACC CAC ATA GAG AGC GCC TAC CCG GGA GGC CGC GTG ACC GAG
TGG GTG TAT CTC TCG CGG ATG GGC CCT CCG GCG CAC TGG CTC
Thr His Ile Glu Ser Ala Tyr Pro Gly Gly Arg Val Thr Glu>
___________________________IL-1RII__________________________>

        1900        1910        1920        1930
     *      *     *      *      *     *      *     *
GGG CCA CGC CAG GAA TAT TCA GAA AAT AAT GAG AAC TAC ATT
CCC GGT GCG GTC CTT ATA AGT CTT TTA TTA CTC TTG ATG TAA
Gly Pro Arg Gln Glu Tyr Ser Glu Asn Asn Glu Asn Tyr Ile>
___________________________IL-1RII__________________________>

     1940        1950        1960        1970
  *      *     *      *      *     *      *     *
GAA GTG CCA TTG ATT TTT GAT CCT GTC ACA AGA GAG GAT TTG
CTT CAC GGT AAC TAA AAA CTA GGA CAG TGT TCT CTC CTA AAC
Glu Val Pro Leu Ile Phe Asp Pro Val Thr Arg Glu Asp Leu>
___________________________IL-1RII__________________________>

   1980        1990        2000        2010
 *      *     *      *      *     *      *     *      *
CAC ATG GAT TTT AAA TGT GTT GTC CAT AAT ACC CTG AGT TTT
GTG TAC CTA AAA TTT ACA CAA CAG GTA TTA TGG GAC TCA AAA
His Met Asp Phe Lys Cys Val Val His Asn Thr Leu Ser Phe>
___________________________IL-1RII__________________________>
```

Figure 47G

```
  2020        2030        2040         2050
     *    *     *     *    *     *     *     *
CAG ACA CTA CGC ACC ACA GTC AAG GAA GCC TCC TCC ACG TTC
GTC TGT GAT GCG TGG TGT CAG TTC CTT CGG AGG AGG TGC AAG
Gln Thr Leu Arg Thr Thr Val Lys Glu Ala Ser Ser Thr Phe>
_______________________IL-1RII_______________________>

2060       2070        2080        2090       2100
  *     *    *     *     *    *     *     *    *
TCC GGA GAC AAA ACT CAC ACA TGC CCA CCG TGC CCA GCA CCT
AGG CCT CTG TTT TGA GTG TGT ACG GGT GGC ACG GGT CGT GGA
Ser Gly Asp Lys Thr His Thr Cys Pro Pro Cys Pro Ala Pro>
_______________________FC-IgG1_______________________>

        2110        2120        2130        2140
     *     *    *     *     *    *     *     *
GAA CTC CTG GGG GGA CCG TCA GTC TTC CTC TTC CCC CCA AAA
CTT GAG GAC CCC CCT GGC AGT CAG AAG GAG AAG GGG GGT TTT
Glu Leu Leu Gly Gly Pro Ser Val Phe Leu Phe Pro Pro Lys>
_______________________FC-IgG1_______________________>

      2150        2160        2170        2180
  *     *     *    *     *     *     *     *
CCC AAG GAC ACC CTC ATG ATC TCC CGG ACC CCT GAG GTC ACA
GGG TTC CTG TGG GAG TAC TAG AGG GCC TGG GGA CTC CAG TGT
Pro Lys Asp Thr Leu Met Ile Ser Arg Thr Pro Glu Val Thr>
_______________________FC-IgG1_______________________>

   2190        2200        2210        2220
*    *     *     *    *     *     *     *     *
TGC GTG GTG GTG GAC GTG AGC CAC GAA GAC CCT GAG GTC AAG
ACG CAC CAC CAC CTG CAC TCG GTG CTT CTG GGA CTC CAG TTC
Cys Val Val Val Asp Val Ser His Glu Asp Pro Glu Val Lys>
_______________________FC-IgG1_______________________>

 2230        2240        2250        2260
     *     *     *    *     *     *     *     *
TTC AAC TGG TAC GTG GAC GGC GTG GAG GTG CAT AAT GCC AAG
AAG TTG ACC ATG CAC CTG CCG CAC CTC CAC GTA TTA CGG TTC
Phe Asn Trp Tyr Val Asp Gly Val Glu Val His Asn Ala Lys>
_______________________FC-IgG1_______________________>

2270       2280        2290        2300       2310
  *     *    *     *     *    *     *     *    *
ACA AAG CCG CGG GAG GAG CAG TAC AAC AGC ACG TAC CGT GTG
TGT TTC GGC GCC CTC CTC GTC ATG TTG TCG TGC ATG GCA CAC
Thr Lys Pro Arg Glu Glu Gln Tyr Asn Ser Thr Tyr Arg Val>
_______________________FC-IgG1_______________________>

        2320        2330        2340        2350
     *     *    *     *     *    *     *     *
GTC AGC GTC CTC ACC GTC CTG CAC CAG GAC TGG CTG AAT GGC
CAG TCG CAG GAG TGG CAG GAC GTG GTC CTG ACC GAC TTA CCG
Val Ser Val Leu Thr Val Leu His Gln Asp Trp Leu Asn Gly>
_______________________FC-IgG1_______________________>
```

Figure 47H

```
     2360        2370        2380        2390
  *     *     *     *     *     *     *     *
AAG GAG TAC AAG TGC AAG GTC TCC AAC AAA GCC CTC CCA GCC
TTC CTC ATG TTC ACG TTC CAG AGG TTG TTT CGG GAG GGT CGG
Lys Glu Tyr Lys Cys Lys Val Ser Asn Lys Ala Leu Pro Ala>
______________________FC-IgG1________________________>

   2400        2410        2420        2430
*     *     *     *     *     *     *     *     *
CCC ATC GAG AAA ACC ATC TCC AAA GCC AAA GGG CAG CCC CGA
GGG TAG CTC TTT TGG TAG AGG TTT CGG TTT CCC GTC GGG GCT
Pro Ile Glu Lys Thr Ile Ser Lys Ala Lys Gly Gln Pro Arg>
______________________FC-IgG1________________________>

  2440        2450        2460        2470
    *     *     *     *     *     *     *     *
GAA CCA CAG GTG TAC ACC CTG CCC CCA TCC CGG GAT GAG CTG
CTT GGT GTC CAC ATG TGG GAC GGG GGT AGG GCC CTA CTC GAC
Glu Pro Gln Val Tyr Thr Leu Pro Pro Ser Arg Asp Glu Leu>
______________________FC-IgG1________________________>

2480        2490        2500        2510        2520
  *     *     *     *     *     *     *     *     *
ACC AAG AAC CAG GTC AGC CTG ACC TGC CTG GTC AAA GGC TTC
TGG TTC TTG GTC CAG TCG GAC TGG ACG GAC CAG TTT CCG AAG
Thr Lys Asn Gln Val Ser Leu Thr Cys Leu Val Lys Gly Phe>
______________________FC-IgG1________________________>

       2530        2540        2550        2560
    *     *     *     *     *     *     *     *
TAT CCC AGC GAC ATC GCC GTG GAG TGG GAG AGC AAT GGG CAG
ATA GGG TCG CTG TAG CGG CAC CTC ACC CTC TCG TTA CCC GTC
Tyr Pro Ser Asp Ile Ala Val Glu Trp Glu Ser Asn Gly Gln>
______________________FC-IgG1________________________>

     2570        2580        2590        2600
  *     *     *     *     *     *     *     *
CCG GAG AAC AAC TAC AAG ACC ACG CCT CCC GTG CTG GAC TCC
GGC CTC TTG TTG ATG TTC TGG TGC GGA GGG CAC GAC CTG AGG
Pro Glu Asn Asn Tyr Lys Thr Thr Pro Pro Val Leu Asp Ser>
______________________FC-IgG1________________________>

   2610        2620        2630        2640
*     *     *     *     *     *     *     *     *
GAC GGC TCC TTC TTC CTC TAT AGC AAG CTC ACC GTG GAC AAG
CTG CCG AGG AAG AAG GAG ATA TCG TTC GAG TGG CAC CTG TTC
Asp Gly Ser Phe Phe Leu Tyr Ser Lys Leu Thr Val Asp Lys>
______________________FC-IgG1________________________>

  2650        2660        2670        2680
    *     *     *     *     *     *     *     *
AGC AGG TGG CAG CAG GGG AAC GTC TTC TCA TGC TCC GTG ATG
TCG TCC ACC GTC GTC CCC TTG CAG AAG AGT ACG AGG CAC TAC
Ser Arg Trp Gln Gln Gly Asn Val Phe Ser Cys Ser Val Met>
______________________FC-IgG1________________________>
```

Figure 47 I

```
2690          2700          2710          2720          2730
  *       *      *      *       *      *       *      *      *
CAT GAG GCT CTG CAC AAC CAC TAC ACG CAG AAG AGC CTC TCC
GTA CTC CGA GAC GTG TTG GTG ATG TGC GTC TTC TCG GAG AGG
His Glu Ala Leu His Asn His Tyr Thr Gln Lys Ser Leu Ser>
_______________________FC-IgG1__________________________>

          2740
    *       *      *
CTG TCT CCG GGT AAA TGA
GAC AGA GGC CCA TTT ACT
Leu Ser Pro Gly Lys ***>
________FC-IgG1________>
```

Figure 48A

```
         10          20          30          40
     *     *     *     *     *     *     *     *
ATG GTG CTT CTG TGG TGT GTA GTG AGT CTC TAC TTT TAT GGA
TAC CAC GAA GAC ACC ACA CAT CAC TCA GAG ATG AAA ATA CCT
Met Val Leu Leu Trp Cys Val Val Ser Leu Tyr Phe Tyr Gly>
___________________SIGNAL PEPTIDE_________________>
_____________________IL-1RAcP_____________________>

       50          60          70          80
  *     *     *     *     *     *     *     *
ATC CTG CAA AGT GAT GCC TCA GAA CGC TGC GAT GAC TGG GGA
TAG GAC GTT TCA CTA CGG AGT CTT GCG ACG CTA CTG ACC CCT
Ile Leu Gln Ser Asp Ala>
____SIGNAL PEPTIDE____>
                        Ser Glu Arg Cys Asp Asp Trp Gly>
_____________________IL-1RAcP_____________________>

     90         100         110         120
*     *     *     *     *     *     *     *     *
CTA GAC ACC ATG AGG CAA ATC CAA GTG TTT GAA GAT GAG CCA
GAT CTG TGG TAC TCC GTT TAG GTT CAC AAA CTT CTA CTC GGT
Leu Asp Thr Met Arg Gln Ile Gln Val Phe Glu Asp Glu Pro>
_____________________IL-1RAcP_____________________>

  130         140         150         160
     *     *     *     *     *     *     *     *
GCT CGC ATC AAG TGC CCA CTC TTT GAA CAC TTC TTG AAA TTC
CGA GCG TAG TTC ACG GGT GAG AAA CTT GTG AAG AAC TTT AAG
Ala Arg Ile Lys Cys Pro Leu Phe Glu His Phe Leu Lys Phe>
_____________________IL-1RAcP_____________________>

170         180         190         200         210
 *     *     *     *     *     *     *     *     *
AAC TAC AGC ACA GCC CAT TCA GCT GGC CTT ACT CTG ATC TGG
TTG ATG TCG TGT CGG GTA AGT CGA CCG GAA TGA GAC TAG ACC
Asn Tyr Ser Thr Ala His Ser Ala Gly Leu Thr Leu Ile Trp>
_____________________IL-1RAcP_____________________>

         220         230         240         250
     *     *     *     *     *     *     *     *
TAT TGG ACT AGG CAG GAC CGG GAC CTT GAG GAG CCA ATT AAC
ATA ACC TGA TCC GTC CTG GCC CTG GAA CTC CTC GGT TAA TTG
Tyr Trp Thr Arg Gln Asp Arg Asp Leu Glu Glu Pro Ile Asn>
_____________________IL-1RAcP_____________________>

       260         270         280         290
  *     *     *     *     *     *     *     *
TTC CGC CTC CCC GAG AAC CGC ATT AGT AAG GAG AAA GAT GTG
AAG GCG GAG GGG CTC TTG GCG TAA TCA TTC CTC TTT CTA CAC
Phe Arg Leu Pro Glu Asn Arg Ile Ser Lys Glu Lys Asp Val>
_____________________IL-1RAcP_____________________>

    300         310         320         330
*     *     *     *     *     *     *     *     *
CTG TGG TTC CGG CCC ACT CTC CTC AAT GAC ACT GGC AAC TAT
GAC ACC AAG GCC GGG TGA GAG GAG TTA CTG TGA CCG TTG ATA
Leu Trp Phe Arg Pro Thr Leu Leu Asn Asp Thr Gly Asn Tyr>
_____________________IL-1RAcP_____________________>
```

Figure 48B

```
 340        350        360         370
  *    *     *     *    *     *     *    *
ACC TGC ATG TTA AGG AAC ACT ACA TAT TGC AGC AAA GTT GCA
TGG ACG TAC AAT TCC TTG TGA TGT ATA ACG TCG TTT CAA CGT
Thr Cys Met Leu Arg Asn Thr Thr Tyr Cys Ser Lys Val Ala>
____________________________IL-1RAcP_________________________>

380        390         400        410        420
 *     *    *     *     *     *    *     *    *
TTT CCC TTG GAA GTT GTT CAA AAA GAC AGC TGT TTC AAT TCC
AAA GGG AAC CTT CAA CAA GTT TTT CTG TCG ACA AAG TTA AGG
Phe Pro Leu Glu Val Val Gln Lys Asp Ser Cys Phe Asn Ser>
____________________________IL-1RAcP_________________________>

       430        440        450         460
    *     *    *     *     *    *     *    *
CCC ATG AAA CTC CCA GTG CAT AAA CTG TAT ATA GAA TAT GGC
GGG TAC TTT GAG GGT CAC GTA TTT GAC ATA TAT CTT ATA CCG
Pro Met Lys Leu Pro Val His Lys Leu Tyr Ile Glu Tyr Gly>
____________________________IL-1RAcP_________________________>

     470        480         490        500
 *     *     *    *     *     *    *     *
ATT CAG AGG ATC ACT TGT CCA AAT GTA GAT GGA TAT TTT CCT
TAA GTC TCC TAG TGA ACA GGT TTA CAT CTA CCT ATA AAA GGA
Ile Gln Arg Ile Thr Cys Pro Asn Val Asp Gly Tyr Phe Pro>
____________________________IL-1RAcP_________________________>

   510        520        530        540
*    *     *     *    *     *     *    *     *
TCC AGT GTC AAA CCG ACT ATC ACT TGG TAT ATG GGC TGT TAT
AGG TCA CAG TTT GGC TGA TAG TGA ACC ATA TAC CCG ACA ATA
Ser Ser Val Lys Pro Thr Ile Thr Trp Tyr Met Gly Cys Tyr>
____________________________IL-1RAcP_________________________>

 550        560        570         580
   *     *     *     *    *     *     *    *
AAA ATA CAG AAT TTT AAT AAT GTA ATA CCC GAA GGT ATG AAC
TTT TAT GTC TTA AAA TTA TTA CAT TAT GGG CTT CCA TAC TTG
Lys Ile Gln Asn Phe Asn Asn Val Ile Pro Glu Gly Met Asn>
____________________________IL-1RAcP_________________________>

590        600         610        620        630
 *     *    *     *     *     *    *     *    *
TTG AGT TTC CTC ATT GCC TTA ATT TCA AAT AAT GGA AAT TAC
AAC TCA AAG GAG TAA CGG AAT TAA AGT TTA TTA CCT TTA ATG
Leu Ser Phe Leu Ile Ala Leu Ile Ser Asn Asn Gly Asn Tyr>
____________________________IL-1RAcP_________________________>

       640        650        660         670
    *     *    *     *     *    *     *    *
ACA TGT GTT GTT ACA TAT CCA GAA AAT GGA CGT ACG TTT CAT
TGT ACA CAA CAA TGT ATA GGT CTT TTA CCT GCA TGC AAA GTA
Thr Cys Val Val Thr Tyr Pro Glu Asn Gly Arg Thr Phe His>
____________________________IL-1RAcP_________________________>
```

Figure 48C

```
      680         690          700         710
 *     *     *     *     *     *     *     *
CTC ACC AGG ACT CTG ACT GTA AAG GTA GTA GGC TCT CCA AAA
GAG TGG TCC TGA GAC TGA CAT TTC CAT CAT CCG AGA GGT TTT
Leu Thr Arg Thr Leu Thr Val Lys Val Val Gly Ser Pro Lys>
______________________IL-1RAcP___________________>

    720         730         740         750
*    *     *     *     *     *     *     *     *
AAT GCA GTG CCC CCT GTG ATC CAT TCA CCT AAT GAT CAT GTG
TTA CGT CAC GGG GGA CAC TAG GTA AGT GGA TTA CTA GTA CAC
Asn Ala Val Pro Pro Val Ile His Ser Pro Asn Asp His Val>
______________________IL-1RAcP___________________>

  760         770         780         790
    *     *     *     *     *     *     *     *
GTC TAT GAG AAA GAA CCA GGA GAG GAG CTA CTC ATT CCC TGT
CAG ATA CTC TTT CTT GGT CCT CTC CTC GAT GAG TAA GGG ACA
Val Tyr Glu Lys Glu Pro Gly Glu Glu Leu Leu Ile Pro Cys>
______________________IL-1RAcP___________________>

800         810         820         830         840
 *     *     *     *     *     *     *     *     *
ACG GTC TAT TTT AGT TTT CTG ATG GAT TCT CGC AAT GAG GTT
TGC CAG ATA AAA TCA AAA GAC TAC CTA AGA GCG TTA CTC CAA
Thr Val Tyr Phe Ser Phe Leu Met Asp Ser Arg Asn Glu Val>
______________________IL-1RAcP___________________>

          850         860         870         880
     *     *     *     *     *     *     *     *
TGG TGG ACC ATT GAT GGA AAA AAA CCT GAT GAC ATC ACT ATT
ACC ACC TGG TAA CTA CCT TTT TTT GGA CTA CTG TAG TGA TAA
Trp Trp Thr Ile Asp Gly Lys Lys Pro Asp Asp Ile Thr Ile>
______________________IL-1RAcP___________________>

      890         900         910         920
 *     *     *     *     *     *     *     *
GAT GTC ACC ATT AAC GAA AGT ATA AGT CAT AGT AGA ACA GAA
CTA CAG TGG TAA TTG CTT TCA TAT TCA GTA TCA TCT TGT CTT
Asp Val Thr Ile Asn Glu Ser Ile Ser His Ser Arg Thr Glu>
______________________IL-1RAcP___________________>

    930         940         950         960
*    *     *     *     *     *     *     *     *
GAT GAA ACA AGA ACT CAG ATT TTG AGC ATC AAG AAA GTT ACC
CTA CTT TGT TCT TGA GTC TAA AAC TCG TAG TTC TTT CAA TGG
Asp Glu Thr Arg Thr Gln Ile Leu Ser Ile Lys Lys Val Thr>
______________________IL-1RAcP___________________>

  970         980         990        1000
    *     *     *     *     *     *     *     *
TCT GAG GAT CTC AAG CGC AGC TAT GTC TGT CAT GCT AGA AGT
AGA CTC CTA GAG TTC GCG TCG ATA CAG ACA GTA CGA TCT TCA
Ser Glu Asp Leu Lys Arg Ser Tyr Val Cys His Ala Arg Ser>
______________________IL-1RAcP___________________>
```

Figure 48D

```
1010         1020          1030         1040         1050
 *        *     *        *       *     *       *       *    *
GCC AAA GGC GAA GTT GCC AAA GCA GCC AAG GTG AAG CAG AAA
CGG TTT CCG CTT CAA CGG TTT CGT CGG TTC CAC TTC GTC TTT
Ala Lys Gly Glu Val Ala Lys Ala Ala Lys Val Lys Gln Lys>
_________________________IL-1RAcP______________________>

        1060         1070         1080          1090
   *       *      *       *      *      *       *      *
GTG CCA GCT CCA AGA TAC ACA GTG CAC ACA GGG GCT GCC AGA
CAC GGT CGA GGT TCT ATG TGT CAC GTG TGT CCC CGA CGG TCT
Val Pro Ala Pro Arg Tyr Thr Val>
___________IL-1RAcP____________>
                                His Thr Gly Ala Ala Arg>
                                ________IL-1RII________>

     1100         1110          1120          1130
  *       *      *      *      *      *      *      *
AGC TGC CGG TTT CGT GGG AGG CAT TAC AAG CGG GAG TTC AGG
TCG ACG GCC AAA GCA CCC TCC GTA ATG TTC GCC CTC AAG TCC
Ser Cys Arg Phe Arg Gly Arg His Tyr Lys Arg Glu Phe Arg>
_________________________IL-1RII_______________________>

   1140          1150          1160         1170
*      *      *       *      *      *       *      *      *
CTG GAA GGG GAG CCT GTA GCC CTG AGG TGC CCC CAG GTG CCC
GAC CTT CCC CTC GGA CAT CGG GAC TCC ACG GGG GTC CAC GGG
Leu Glu Gly Glu Pro Val Ala Leu Arg Cys Pro Gln Val Pro>
_________________________IL-1RII_______________________>

 1180         1190          1200          1210
    *      *      *      *      *      *      *      *
TAC TGG TTG TGG GCC TCT GTC AGC CCC CGC ATC AAC CTG ACA
ATG ACC AAC ACC CGG AGA CAG TCG GGG GCG TAG TTG GAC TGT
Tyr Trp Leu Trp Ala Ser Val Ser Pro Arg Ile Asn Leu Thr>
_________________________IL-1RII_______________________>

1220         1230          1240          1250         1260
 *       *      *      *      *      *      *      *      *
TGG CAT AAA AAT GAC TCT GCT AGG ACG GTC CCA GGA GAA GAA
ACC GTA TTT TTA CTG AGA CGA TCC TGC CAG GGT CCT CTT CTT
Trp His Lys Asn Asp Ser Ala Arg Thr Val Pro Gly Glu Glu>
_________________________IL-1RII_______________________>

        1270          1280          1290          1300
    *       *      *      *      *      *      *      *
GAG ACA CGG ATG TGG GCC CAG GAC GGT GCT CTG TGG CTT CTG
CTC TGT GCC TAC ACC CGG GTC CTG CCA CGA GAC ACC GAA GAC
Glu Thr Arg Met Trp Ala Gln Asp Gly Ala Leu Trp Leu Leu>
_________________________IL-1RII_______________________>

     1310          1320          1330          1340
  *       *      *      *      *      *      *      *
CCA GCC TTG CAG GAG GAC TCT GGC ACC TAC GTC TGC ACT ACT
GGT CGG AAC GTC CTC CTG AGA CCG TGG ATG CAG ACG TGA TGA
Pro Ala Leu Gln Glu Asp Ser Gly Thr Tyr Val Cys Thr Thr>
_________________________IL-1RII_______________________>
```

Figure 48E

```
   1350         1360          1370          1380
 *     *      *      *     *      *      *     *      *
AGA AAT GCT TCT TAC TGT GAC AAA ATG TCC ATT GAG CTC AGA
TCT TTA CGA AGA ATG ACA CTG TTT TAC AGG TAA CTC GAG TCT
Arg Asn Ala Ser Tyr Cys Asp Lys Met Ser Ile Glu Leu Arg>
________________________IL-1RII_______________________>

 1390         1400          1410          1420
    *     *      *      *     *      *      *     *
GTT TTT GAG AAT ACA GAT GCT TTC CTG CCG TTC ATC TCA TAC
CAA AAA CTC TTA TGT CTA CGA AAG GAC GGC AAG TAG AGT ATG
Val Phe Glu Asn Thr Asp Ala Phe Leu Pro Phe Ile Ser Tyr>
________________________IL-1RII_______________________>

1430          1440          1450          1460         1470
  *      *      *      *      *     *      *      *     *
CCG CAA ATT TTA ACC TTG TCA ACC TCT GGG GTA TTA GTA TGC
GGC GTT TAA AAT TGG AAC AGT TGG AGA CCC CAT AAT CAT ACG
Pro Gln Ile Leu Thr Leu Ser Thr Ser Gly Val Leu Val Cys>
________________________IL-1RII_______________________>

          1480         1490          1500          1510
     *      *     *      *      *     *      *      *
CCT GAC CTG AGT GAA TTC ACC CGT GAC AAA ACT GAC GTG AAG
GGA CTG GAC TCA CTT AAG TGG GCA CTG TTT TGA CTG CAC TTC
Pro Asp Leu Ser Glu Phe Thr Arg Asp Lys Thr Asp Val Lys>
________________________IL-1RII_______________________>

       1520         1530          1540         1550
   *      *      *     *      *      *     *      *
ATT CAA TGG TAC AAG GAT TCT CTT CTT TTG GAT AAA GAC AAT
TAA GTT ACC ATG TTC CTA AGA GAA GAA AAC CTA TTT CTG TTA
Ile Gln Trp Tyr Lys Asp Ser Leu Leu Leu Asp Lys Asp Asn>
________________________IL-1RII_______________________>

   1560         1570          1580          1590
 *     *      *      *     *      *      *     *      *
GAG AAA TTT CTA AGT GTG AGG GGG ACC ACT CAC TTA CTC GTA
CTC TTT AAA GAT TCA CAC TCC CCC TGG TGA GTG AAT GAG CAT
Glu Lys Phe Leu Ser Val Arg Gly Thr Thr His Leu Leu Val>
________________________IL-1RII_______________________>

 1600         1610          1620          1630
    *     *      *      *     *      *      *     *
CAC GAT GTG GCC CTG GAA GAT GCT GGC TAT TAC CGC TGT GTC
GTG CTA CAC CGG GAC CTT CTA CGA CCG ATA ATG GCG ACA CAG
His Asp Val Ala Leu Glu Asp Ala Gly Tyr Tyr Arg Cys Val>
________________________IL-1RII_______________________>

1640          1650          1660          1670         1680
  *      *      *      *      *     *      *      *     *
CTG ACA TTT GCC CAT GAA GGC CAG CAA TAC AAC ATC ACT AGG
GAC TGT AAA CGG GTA CTT CCG GTC GTT ATG TTG TAG TGA TCC
Leu Thr Phe Ala His Glu Gly Gln Gln Tyr Asn Ile Thr Arg>
________________________IL-1RII_______________________>
```

Figure 48F

```
         1690        1700        1710        1720
    *     *     *     *     *     *     *     *
AGT ATT GAG CTA CGC ATC AAG AAA AAA AAA GAA GAG ACC ATT
TCA TAA CTC GAT GCG TAG TTC TTT TTT TTT CTT CTC TGG TAA
Ser Ile Glu Leu Arg Ile Lys Lys Lys Lys Glu Glu Thr Ile>
_________________________IL-1RII________________________>

      1730        1740        1750        1760
  *     *     *     *     *     *     *     *
CCT GTG ATC ATT TCC CCC CTC AAG ACC ATA TCA GCT TCT CTG
GGA CAC TAG TAA AGG GGG GAG TTC TGG TAT AGT CGA AGA GAC
Pro Val Ile Ile Ser Pro Leu Lys Thr Ile Ser Ala Ser Leu>
_________________________IL-1RII________________________>

   1770        1780        1790        1800
*     *     *     *     *     *     *     *     *
GGG TCA AGA CTG ACA ATC CCA TGT AAG GTG TTT CTG GGA ACC
CCC AGT TCT GAC TGT TAG GGT ACA TTC CAC AAA GAC CCT TGG
Gly Ser Arg Leu Thr Ile Pro Cys Lys Val Phe Leu Gly Thr>
_________________________IL-1RII________________________>

 1810        1820        1830        1840
    *     *     *     *     *     *     *     *
GGC ACA CCC TTA ACC ACC ATG CTG TGG TGG ACG GCC AAT GAC
CCG TGT GGG AAT TGG TGG TAC GAC ACC ACC TGC CGG TTA CTG
Gly Thr Pro Leu Thr Thr Met Leu Trp Trp Thr Ala Asn Asp>
_________________________IL-1RII________________________>

.850       1860        1870        1880        1890
 *     *     *     *     *     *     *     *     *
ACC CAC ATA GAG AGC GCC TAC CCG GGA GGC CGC GTG ACC GAG
TGG GTG TAT CTC TCG CGG ATG GGC CCT CCG GCG CAC TGG CTC
Thr His Ile Glu Ser Ala Tyr Pro Gly Gly Arg Val Thr Glu>
_________________________IL-1RII________________________>

         1900        1910        1920        1930
     *     *     *     *     *     *     *     *
GGG CCA CGC CAG GAA TAT TCA GAA AAT AAT GAG AAC TAC ATT
CCC GGT GCG GTC CTT ATA AGT CTT TTA TTA CTC TTG ATG TAA
Gly Pro Arg Gln Glu Tyr Ser Glu Asn Asn Glu Asn Tyr Ile>
_________________________IL-1RII________________________>

      1940        1950        1960        1970
  *     *     *     *     *     *     *     *
GAA GTG CCA TTG ATT TTT GAT CCT GTC ACA AGA GAG GAT TTG
CTT CAC GGT AAC TAA AAA CTA GGA CAG TGT TCT CTC CTA AAC
Glu Val Pro Leu Ile Phe Asp Pro Val Thr Arg Glu Asp Leu>
_________________________IL-1RII________________________>

   1980        1990        2000        2010
*     *     *     *     *     *     *     *     *
CAC ATG GAT TTT AAA TGT GTT GTC CAT AAT ACC CTG AGT TTT
GTG TAC CTA AAA TTT ACA CAA CAG GTA TTA TGG GAC TCA AAA
His Met Asp Phe Lys Cys Val Val His Asn Thr Leu Ser Phe>
_________________________IL-1RII________________________>
```

Figure 48G

```
 2020         2030         2040          2050
    *     *     *     *     *      *     *     *
CAG ACA CTA CGC ACC ACA GTC AAG GAA GCC TCC TCC ACG TTC
GTC TGT GAT GCG TGG TGT CAG TTC CTT CGG AGG AGG TGC AAG
Gln Thr Leu Arg Thr Thr Val Lys Glu Ala Ser Ser Thr Phe>
________________________IL-1RII_______________________>

2060         2070         2080         2090         2100
   *      *     *      *      *     *      *     *     *
TCC GGA GAG TCC AAA TAC GGT CCG CCA TGC CCA TCA TGC CCA
AGG CCT CTC AGG TTT ATG CCA GGC GGT ACG GGT AGT ACG GGT
Ser Gly>
_______>
        Glu Ser Lys Tyr Gly Pro Pro Cys Pro Ser Cys Pro>
        _________________FC-IgG4_______________________>

         2110         2120         2130         2140
      *      *     *      *      *     *      *     *
GCA CCT GAG TTC CTG GGG GGA CCA TCA GTC TTC CTG TTC CCC
CGT GGA CTC AAG GAC CCC CCT GGT AGT CAG AAG GAC AAG GGG
Ala Pro Glu Phe Leu Gly Gly Pro Ser Val Phe Leu Phe Pro>
_______________________FC-IgG4________________________>

      2150         2160          2170         2180
  *      *      *     *      *      *      *     *
CCA AAA CCC AAG GAC ACT CTC ATG ATC TCC CGG ACC CCT GAG
GGT TTT GGG TTC CTG TGA GAG TAC TAG AGG GCC TGG GGA CTC
Pro Lys Pro Lys Asp Thr Leu Met Ile Ser Arg Thr Pro Glu>
_______________________FC-IgG4________________________>

   2190         2200         2210         2220
*      *     *      *     *     *      *     *      *
GTC ACG TGC GTG GTG GTG GAC GTG AGC CAG GAA GAC CCC GAG
CAG TGC ACG CAC CAC CAC CTG CAC TCG GTC CTT CTG GGG CTC
Val Thr Cys Val Val Val Asp Val Ser Gln Glu Asp Pro Glu>
_______________________FC-IgG4________________________>

 2230         2240         2250          2260
    *     *      *     *     *      *     *     *
GTC CAG TTC AAC TGG TAC GTG GAT GGC GTG GAG GTG CAT AAT
CAG GTC AAG TTG ACC ATG CAC CTA CCG CAC CTC CAC GTA TTA
Val Gln Phe Asn Trp Tyr Val Asp Gly Val Glu Val His Asn>
_______________________FC-IgG4________________________>

2270         2280         2290         2300         2310
   *      *     *      *     *      *     *      *     *
GCC AAG ACA AAG CCG CGG GAG GAG CAG TTC AAC AGC ACG TAC
CGG TTC TGT TTC GGC GCC CTC CTC GTC AAG TTG TCG TGC ATG
Ala Lys Thr Lys Pro Arg Glu Glu Gln Phe Asn Ser Thr Tyr>
_______________________FC-IgG4________________________>

         2320         2330         2340         2350
      *      *     *      *     *      *     *      *
CGT GTG GTC AGC GTC CTC ACC GTC CTG CAC CAG GAC TGG CTG
GCA CAC CAG TCG CAG GAG TGG CAG GAC GTG GTC CTG ACC GAC
Arg Val Val Ser Val Leu Thr Val Leu His Gln Asp Trp Leu>
_______________________FC-IgG4________________________>
```

Figure 48H

```
      2360        2370        2380        2390
 *     *     *     *     *     *     *     *
AAC GGC AAG GAG TAC AAG TGC AAG GTC TCC AAC AAA GGC CTC
TTG CCG TTC CTC ATG TTC ACG TTC CAG AGG TTG TTT CCG GAG
Asn Gly Lys Glu Tyr Lys Cys Lys Val Ser Asn Lys Gly Leu>
_______________________FC-IgG4_________________________>

   2400        2410        2420        2430
 *     *     *     *     *     *     *     *     *
CCG TCC TCC ATC GAG AAA ACC ATC TCC AAA GCC AAA GGG CAG
GGC AGG AGG TAG CTC TTT TGG TAG AGG TTT CGG TTT CCC GTC
Pro Ser Ser Ile Glu Lys Thr Ile Ser Lys Ala Lys Gly Gln>
_______________________FC-IgG4_________________________>

  2440        2450        2460        2470
    *     *     *     *     *     *     *     *
CCC CGA GAG CCA CAG GTG TAC ACC CTG CCC CCA TCC CAG GAG
GGG GCT CTC GGT GTC CAC ATG TGG GAC GGG GGT AGG GTC CTC
Pro Arg Glu Pro Gln Val Tyr Thr Leu Pro Pro Ser Gln Glu>
_______________________FC-IgG4_________________________>

2480        2490        2500        2510        2520
 *     *     *     *     *     *     *     *     *
GAG ATG ACC AAG AAC CAG GTC AGC CTG ACC TGC CTG GTC AAA
CTC TAC TGG TTC TTG GTC CAG TCG GAC TGG ACG GAC CAG TTT
Glu Met Thr Lys Asn Gln Val Ser Leu Thr Cys Leu Val Lys>
_______________________FC-IgG4_________________________>

      2530        2540        2550        2560
    *     *     *     *     *     *     *     *
GGC TTC TAC CCC AGC GAC ATC GCC GTG GAG TGG GAG AGC AAT
CCG AAG ATG GGG TCG CTG TAG CGG CAC CTC ACC CTC TCG TTA
Gly Phe Tyr Pro Ser Asp Ile Ala Val Glu Trp Glu Ser Asn>
_______________________FC-IgG4_________________________>

      2570        2580        2590        2600
 *     *     *     *     *     *     *     *
GGG CAG CCG GAG AAC AAC TAC AAG ACC ACG CCT CCC GTG CTG
CCC GTC GGC CTC TTG TTG ATG TTC TGG TGC GGA GGG CAC GAC
Gly Gln Pro Glu Asn Asn Tyr Lys Thr Thr Pro Pro Val Leu>
_______________________FC-IgG4_________________________>

   2610        2620        2630        2640
 *     *     *     *     *     *     *     *     *
GAC TCC GAC GGC TCC TTC TTC CTC TAC AGC AGG CTA ACC GTG
CTG AGG CTG CCG AGG AAG AAG GAG ATG TCG TCC GAT TGG CAC
Asp Ser Asp Gly Ser Phe Phe Leu Tyr Ser Arg Leu Thr Val>
_______________________FC-IgG4_________________________>

  2650        2660        2670        2680
    *     *     *     *     *     *     *     *
GAC AAG AGC AGG TGG CAG GAG GGG AAT GTC TTC TCA TGC TCC
CTG TTC TCG TCC ACC GTC CTC CCC TTA CAG AAG AGT ACG AGG
Asp Lys Ser Arg Trp Gln Glu Gly Asn Val Phe Ser Cys Ser>
_______________________FC-IgG4_________________________>
```

Figure 48 I

```
2690         2700          2710          2720          2730
  *       *      *      *      *      *      *      *      *
 GTG ATG CAT GAG GCT CTG CAC AAC CAC TAC ACA CAG AAG AGC
 CAC TAC GTA CTC CGA GAC GTG TTG GTG ATG TGT GTC TTC TCG
 Val Met His Glu Ala Leu His Asn His Tyr Thr Gln Lys Ser>
 _______________________FC-IgG4__________________________>

           2740          2750
     *      *      *      *
 CTC TCC CTG TCT CTG GGT AAA TGA
 GAG AGG GAC AGA GAC CCA TTT ACT
 Leu Ser Leu Ser Leu Gly Lys ***>
 ___________FC-IgG4_____________>
```

Figure 49A

```
             10         20          30          40
      *      *     *     *     *     *     *     *
ATG GTG CTT CTG TGG TGT GTA GTG AGT CTC TAC TTT TAT GGA
TAC CAC GAA GAC ACC ACA CAT CAC TCA GAG ATG AAA ATA CCT
Met Val Leu Leu Trp Cys Val Val Ser Leu Tyr Phe Tyr Gly>
______________________SIGNAL PEPTIDE____________________>
__________________________IL-1RAcP______________________>

          50         60          70          80
  *        *      *     *     *     *     *     *
ATC CTG CAA AGT GAT GCC TCA GAA CGC TGC GAT GAC TGG GGA
TAG GAC GTT TCA CTA CGG AGT CTT GCG ACG CTA CTG ACC CCT
Ile Leu Gln Ser Asp Ala>
___ SIGNAL PEPTIDE______>
                        Ser Glu Arg Cys Asp Asp Trp Gly>
__________________________IL-1RAcP______________________>

     90         100         110         120
*     *      *     *     *     *     *     *     *
CTA GAC ACC ATG AGG CAA ATC CAA GTG TTT GAA GAT GAG CCA
GAT CTG TGG TAC TCC GTT TAG GTT CAC AAA CTT CTA CTC GGT
Leu Asp Thr Met Arg Gln Ile Gln Val Phe Glu Asp Glu Pro>
__________________________IL-1RAcP______________________>

  130         140         150         160
     *     *      *     *     *     *     *     *
GCT CGC ATC AAG TGC CCA CTC TTT GAA CAC TTC TTG AAA TTC
CGA GCG TAG TTC ACG GGT GAG AAA CTT GTG AAG AAC TTT AAG
Ala Arg Ile Lys Cys Pro Leu Phe Glu His Phe Leu Lys Phe>
__________________________IL-1RAcP______________________>

170          180         190         200         210
 *      *     *     *     *     *     *     *     *
AAC TAC AGC ACA GCC CAT TCA GCT GGC CTT ACT CTG ATC TGG
TTG ATG TCG TGT CGG GTA AGT CGA CCG GAA TGA GAC TAG ACC
Asn Tyr Ser Thr Ala His Ser Ala Gly Leu Thr Leu Ile Trp>
__________________________IL-1RAcP______________________>

            220         230         240         250
      *     *     *     *     *     *     *     *
TAT TGG ACT AGG CAG GAC CGG GAC CTT GAG GAG CCA ATT AAC
ATA ACC TGA TCC GTC CTG GCC CTG GAA CTC CTC GGT TAA TTG
Tyr Trp Thr Arg Gln Asp Arg Asp Leu Glu Glu Pro Ile Asn>
__________________________IL-1RAcP______________________>

        260         270         280         290
  *      *     *     *     *     *     *     *
TTC CGC CTC CCC GAG AAC CGC ATT AGT AAG GAG AAA GAT GTG
AAG GCG GAG GGG CTC TTG GCG TAA TCA TTC CTC TTT CTA CAC
Phe Arg Leu Pro Glu Asn Arg Ile Ser Lys Glu Lys Asp Val>
__________________________IL-1RAcP______________________>

     300         310         320         330
*     *      *     *     *     *     *     *     *
CTG TGG TTC CGG CCC ACT CTC CTC AAT GAC ACT GGC AAC TAT
GAC ACC AAG GCC GGG TGA GAG GAG TTA CTG TGA CCG TTG ATA
Leu Trp Phe Arg Pro Thr Leu Leu Asn Asp Thr Gly Asn Tyr>
__________________________IL-1RAcP______________________>
```

Figure 49B

```
  340         350         360         370
   *     *     *     *     *     *     *     *
ACC TGC ATG TTA AGG AAC ACT ACA TAT TGC AGC AAA GTT GCA
TGG ACG TAC AAT TCC TTG TGA TGT ATA ACG TCG TTT CAA CGT
Thr Cys Met Leu Arg Asn Thr Thr Tyr Cys Ser Lys Val Ala>
________________________IL-1RAcP______________________>

380         390         400         410         420
 *     *     *     *     *     *     *     *     *
TTT CCC TTG GAA GTT GTT CAA AAA GAC AGC TGT TTC AAT TCC
AAA GGG AAC CTT CAA CAA GTT TTT CTG TCG ACA AAG TTA AGG
Phe Pro Leu Glu Val Val Gln Lys Asp Ser Cys Phe Asn Ser>
________________________IL-1RAcP______________________>

         430         440         450         460
     *     *     *     *     *     *     *     *
CCC ATG AAA CTC CCA GTG CAT AAA CTG TAT ATA GAA TAT GGC
GGG TAC TTT GAG GGT CAC GTA TTT GAC ATA TAT CTT ATA CCG
Pro Met Lys Leu Pro Val His Lys Leu Tyr Ile Glu Tyr Gly>
________________________IL-1RAcP______________________>

       470         480         490         500
  *     *     *     *     *     *     *     *
ATT CAG AGG ATC ACT TGT CCA AAT GTA GAT GGA TAT TTT CCT
TAA GTC TCC TAG TGA ACA GGT TTA CAT CTA CCT ATA AAA GGA
Ile Gln Arg Ile Thr Cys Pro Asn Val Asp Gly Tyr Phe Pro>
________________________IL-1RAcP______________________>

    510         520         530         540
 *     *     *     *     *     *     *     *     *
TCC AGT GTC AAA CCG ACT ATC ACT TGG TAT ATG GGC TGT TAT
AGG TCA CAG TTT GGC TGA TAG TGA ACC ATA TAC CCG ACA ATA
Ser Ser Val Lys Pro Thr Ile Thr Trp Tyr Met Gly Cys Tyr>
________________________IL-1RAcP______________________>

  550         560         570         580
    *     *     *     *     *     *     *     *
AAA ATA CAG AAT TTT AAT AAT GTA ATA CCC GAA GGT ATG AAC
TTT TAT GTC TTA AAA TTA TTA CAT TAT GGG CTT CCA TAC TTG
Lys Ile Gln Asn Phe Asn Asn Val Ile Pro Glu Gly Met Asn>
________________________IL-1RAcP______________________>

590         600         610         620         630
 *     *     *     *     *     *     *     *     *
TTG AGT TTC CTC ATT GCC TTA ATT TCA AAT AAT GGA AAT TAC
AAC TCA AAG GAG TAA CGG AAT TAA AGT TTA TTA CCT TTA ATG
Leu Ser Phe Leu Ile Ala Leu Ile Ser Asn Asn Gly Asn Tyr>
________________________IL-1RAcP______________________>

         640         650         660         670
     *     *     *     *     *     *     *     *
ACA TGT GTT GTT ACA TAT CCA GAA AAT GGA CGT ACG TTT CAT
TGT ACA CAA CAA TGT ATA GGT CTT TTA CCT GCA TGC AAA GTA
Thr Cys Val Val Thr Tyr Pro Glu Asn Gly Arg Thr Phe His>
________________________IL-1RAcP______________________>
```

Figure 49C

```
        680          690         700        710
  *      *      *      *      *      *     *      *
CTC ACC AGG ACT CTG ACT GTA AAG GTA GTA GGC TCT CCA AAA
GAG TGG TCC TGA GAC TGA CAT TTC CAT CAT CCG AGA GGT TTT
Leu Thr Arg Thr Leu Thr Val Lys Val Val Gly Ser Pro Lys>
____________________________IL-1RAcP_________________________>

    720         730         740        750
*      *      *      *      *      *      *      *
AAT GCA GTG CCC CCT GTG ATC CAT TCA CCT AAT GAT CAT GTG
TTA CGT CAC GGG GGA CAC TAG GTA AGT GGA TTA CTA GTA CAC
Asn Ala Val Pro Pro Val Ile His Ser Pro Asn Asp His Val>
____________________________IL-1RAcP_________________________>

  760         770         780         790
    *      *      *      *      *      *      *      *
GTC TAT GAG AAA GAA CCA GGA GAG GAG CTA CTC ATT CCC TGT
CAG ATA CTC TTT CTT GGT CCT CTC CTC GAT GAG TAA GGG ACA
Val Tyr Glu Lys Glu Pro Gly Glu Glu Leu Leu Ile Pro Cys>
____________________________IL-1RAcP_________________________>

800         810         820         830         840
  *      *      *      *      *      *      *      *      *
ACG GTC TAT TTT AGT TTT CTG ATG GAT TCT CGC AAT GAG GTT
TGC CAG ATA AAA TCA AAA GAC TAC CTA AGA GCG TTA CTC CAA
Thr Val Tyr Phe Ser Phe Leu Met Asp Ser Arg Asn Glu Val>
____________________________IL-1RAcP_________________________>

        850         860         870         880
     *      *      *      *      *      *      *      *
TGG TGG ACC ATT GAT GGA AAA AAA CCT GAT GAC ATC ACT ATT
ACC ACC TGG TAA CTA CCT TTT TTT GGA CTA CTG TAG TGA TAA
Trp Trp Thr Ile Asp Gly Lys Lys Pro Asp Asp Ile Thr Ile>
____________________________IL-1RAcP_________________________>

      890         900         910         920
  *      *      *      *      *      *      *      *
GAT GTC ACC ATT AAC GAA AGT ATA AGT CAT AGT AGA ACA GAA
CTA CAG TGG TAA TTG CTT TCA TAT TCA GTA TCA TCT TGT CTT
Asp Val Thr Ile Asn Glu Ser Ile Ser His Ser Arg Thr Glu>
____________________________IL-1RAcP_________________________>

    930         940         950         960
*      *      *      *      *      *      *      *      *
GAT GAA ACA AGA ACT CAG ATT TTG AGC ATC AAG AAA GTT ACC
CTA CTT TGT TCT TGA GTC TAA AAC TCG TAG TTC TTT CAA TGG
Asp Glu Thr Arg Thr Gln Ile Leu Ser Ile Lys Lys Val Thr>
____________________________IL-1RAcP_________________________>

  970         980         990         1000
     *      *      *      *      *      *      *      *
TCT GAG GAT CTC AAG CGC AGC TAT GTC TGT CAT GCT AGA AGT
AGA CTC CTA GAG TTC GCG TCG ATA CAG ACA GTA CGA TCT TCA
Ser Glu Asp Leu Lys Arg Ser Tyr Val Cys His Ala Arg Ser>
____________________________IL-1RAcP_________________________>
```

Figure 49D

```
1010       1020       1030       1040       1050
 *          *          *          *          *
GCC AAA GGC GAA GTT GCC AAA GCA GCC AAG GTG AAG CAG AAA
CGG TTT CCG CTT CAA CGG TTT CGT CGG TTC CAC TTC GTC TTT
Ala Lys Gly Glu Val Ala Lys Ala Ala Lys Val Lys Gln Lys>
___________________________IL-1RAcP__________________________>

       1060       1070       1080       1090
 *          *          *          *          *
GTG CCA GCT CCA AGA TAC ACA GTG CAC ACA GGG GCT GCC AGA
CAC GGT CGA GGT TCT ATG TGT CAC GTG TGT CCC CGA CGG TCT
Val Pro Ala Pro Arg Tyr Thr Val>
____________IL-1RAcP____________>
                                His Thr Gly Ala Ala Arg>
                                _________IL-1RII_________>

     1100       1110       1120       1130
 *          *          *          *          *
AGC TGC CGG TTT CGT GGG AGG CAT TAC AAG CGG GAG TTC AGG
TCG ACG GCC AAA GCA CCC TCC GTA ATG TTC GCC CTC AAG TCC
Ser Cys Arg Phe Arg Gly Arg His Tyr Lys Arg Glu Phe Arg>
___________________________IL-1RII___________________________>

  1140       1150       1160       1170
 *          *          *          *          *
CTG GAA GGG GAG CCT GTA GCC CTG AGG TGC CCC CAG GTG CCC
GAC CTT CCC CTC GGA CAT CGG GAC TCC ACG GGG GTC CAC GGG
Leu Glu Gly Glu Pro Val Ala Leu Arg Cys Pro Gln Val Pro>
___________________________IL-1RII___________________________>

 1180       1190       1200       1210
 *          *          *          *          *
TAC TGG TTG TGG GCC TCT GTC AGC CCC CGC ATC AAC CTG ACA
ATG ACC AAC ACC CGG AGA CAG TCG GGG GCG TAG TTG GAC TGT
Tyr Trp Leu Trp Ala Ser Val Ser Pro Arg Ile Asn Leu Thr>
___________________________IL-1RII___________________________>

1220       1230       1240       1250       1260
 *          *          *          *          *
TGG CAT AAA AAT GAC TCT GCT AGG ACG GTC CCA GGA GAA GAA
ACC GTA TTT TTA CTG AGA CGA TCC TGC CAG GGT CCT CTT CTT
Trp His Lys Asn Asp Ser Ala Arg Thr Val Pro Gly Glu Glu>
___________________________IL-1RII___________________________>

       1270       1280       1290       1300
 *          *          *          *          *
GAG ACA CGG ATG TGG GCC CAG GAC GGT GCT CTG TGG CTT CTG
CTC TGT GCC TAC ACC CGG GTC CTG CCA CGA GAC ACC GAA GAC
Glu Thr Arg Met Trp Ala Gln Asp Gly Ala Leu Trp Leu Leu>
___________________________IL-1RII___________________________>

     1310       1320       1330       1340
 *          *          *          *          *
CCA GCC TTG CAG GAG GAC TCT GGC ACC TAC GTC TGC ACT ACT
GGT CGG AAC GTC CTC CTG AGA CCG TGG ATG CAG ACG TGA TGA
Pro Ala Leu Gln Glu Asp Ser Gly Thr Tyr Val Cys Thr Thr>
___________________________IL-1RII___________________________>
```

Figure 49E

```
   1350        1360        1370        1380
*    *    *    *    *    *    *    *    *
AGA AAT GCT TCT TAC TGT GAC AAA ATG TCC ATT GAG CTC AGA
TCT TTA CGA AGA ATG ACA CTG TTT TAC AGG TAA CTC GAG TCT
Arg Asn Ala Ser Tyr Cys Asp Lys Met Ser Ile Glu Leu Arg>
________________________IL-1RII______________________>

 1390        1400        1410        1420
    *    *    *    *    *    *    *    *
GTT TTT GAG AAT ACA GAT GCT TTC CTG CCG TTC ATC TCA TAC
CAA AAA CTC TTA TGT CTA CGA AAG GAC GGC AAG TAG AGT ATG
Val Phe Glu Asn Thr Asp Ala Phe Leu Pro Phe Ile Ser Tyr>
________________________IL-1RII______________________>

1430        1440        1450        1460        1470
  *    *    *    *    *    *    *    *    *
CCG CAA ATT TTA ACC TTG TCA ACC TCT GGG GTA TTA GTA TGC
GGC GTT TAA AAT TGG AAC AGT TGG AGA CCC CAT AAT CAT ACG
Pro Gln Ile Leu Thr Leu Ser Thr Ser Gly Val Leu Val Cys>
________________________IL-1RII______________________>

        1480        1490        1500        1510
    *    *    *    *    *    *    *    *
CCT GAC CTG AGT GAA TTC ACC CGT GAC AAA ACT GAC GTG AAG
GGA CTG GAC TCA CTT AAG TGG GCA CTG TTT TGA CTG CAC TTC
Pro Asp Leu Ser Glu Phe Thr Arg Asp Lys Thr Asp Val Lys>
________________________IL-1RII______________________>

      1520        1530        1540        1550
 *    *    *    *    *    *    *    *
ATT CAA TGG TAC AAG GAT TCT CTT CTT TTG GAT AAA GAC AAT
TAA GTT ACC ATG TTC CTA AGA GAA GAA AAC CTA TTT CTG TTA
Ile Gln Trp Tyr Lys Asp Ser Leu Leu Leu Asp Lys Asp Asn>
________________________IL-1RII______________________>

   1560        1570        1580        1590
*    *    *    *    *    *    *    *    *
GAG AAA TTT CTA AGT GTG AGG GGG ACC ACT CAC TTA CTC GTA
CTC TTT AAA GAT TCA CAC TCC CCC TGG TGA GTG AAT GAG CAT
Glu Lys Phe Leu Ser Val Arg Gly Thr Thr His Leu Leu Val>
________________________IL-1RII______________________>

 1600        1610        1620        1630
    *    *    *    *    *    *    *    *
CAC GAT GTG GCC CTG GAA GAT GCT GGC TAT TAC CGC TGT GTC
GTG CTA CAC CGG GAC CTT CTA CGA CCG ATA ATG GCG ACA CAG
His Asp Val Ala Leu Glu Asp Ala Gly Tyr Tyr Arg Cys Val>
________________________IL-1RII______________________>

1640        1650        1660        1670        1680
  *    *    *    *    *    *    *    *    *
CTG ACA TTT GCC CAT GAA GGC CAG CAA TAC AAC ATC ACT AGG
GAC TGT AAA CGG GTA CTT CCG GTC GTT ATG TTG TAG TGA TCC
Leu Thr Phe Ala His Glu Gly Gln Gln Tyr Asn Ile Thr Arg>
________________________IL-1RII______________________>
```

Figure 49F

```
        1690       1700       1710       1720
      *     *    *     *     *    *     *     *
AGT ATT GAG CTA CGC ATC AAG AAA AAA AAA GAA GAG ACC ATT
TCA TAA CTC GAT GCG TAG TTC TTT TTT TTT CTT CTC TGG TAA
Ser Ile Glu Leu Arg Ile Lys Lys Lys Lys Glu Glu Thr Ile>
____________________________IL-1RII____________________________>

     1730       1740       1750       1760
  *     *     *    *     *     *    *     *
CCT GTG ATC ATT TCC CCC CTC AAG ACC ATA TCA GCT TCT CTG
GGA CAC TAG TAA AGG GGG GAG TTC TGG TAT AGT CGA AGA GAC
Pro Val Ile Ile Ser Pro Leu Lys Thr Ile Ser Ala Ser Leu>
____________________________IL-1RII____________________________>

   1770       1780       1790       1800
*     *     *     *    *     *     *    *     *
GGG TCA AGA CTG ACA ATC CCA TGT AAG GTG TTT CTG GGA ACC
CCC AGT TCT GAC TGT TAG GGT ACA TTC CAC AAA GAC CCT TGG
Gly Ser Arg Leu Thr Ile Pro Cys Lys Val Phe Leu Gly Thr>
____________________________IL-1RII____________________________>

 1810       1820       1830       1840
     *     *     *     *    *     *     *     *
GGC ACA CCC TTA ACC ACC ATG CTG TGG TGG ACG GCC AAT GAC
CCG TGT GGG AAT TGG TGG TAC GAC ACC ACC TGC CGG TTA CTG
Gly Thr Pro Leu Thr Thr Met Leu Trp Trp Thr Ala Asn Asp>
____________________________IL-1RII____________________________>

1850       1860       1870       1880       1890
 *     *     *     *     *     *     *     *     *
ACC CAC ATA GAG AGC GCC TAC CCG GGA GGC CGC GTG ACC GAG
TGG GTG TAT CTC TCG CGG ATG GGC CCT CCG GCG CAC TGG CTC
Thr His Ile Glu Ser Ala Tyr Pro Gly Gly Arg Val Thr Glu>
____________________________IL-1RII____________________________>

        1900       1910       1920       1930
      *     *     *     *     *    *     *     *
GGG CCA CGC CAG GAA TAT TCA GAA AAT AAT GAG AAC TAC ATT
CCC GGT GCG GTC CTT ATA AGT CTT TTA TTA CTC TTG ATG TAA
Gly Pro Arg Gln Glu Tyr Ser Glu Asn Asn Glu Asn Tyr Ile>
____________________________IL-1RII____________________________>

     1940       1950       1960       1970
  *     *     *     *     *     *     *     *
GAA GTG CCA TTG ATT TTT GAT CCT GTC ACA AGA GAG GAT TTG
CTT CAC GGT AAC TAA AAA CTA GGA CAG TGT TCT CTC CTA AAC
Glu Val Pro Leu Ile Phe Asp Pro Val Thr Arg Glu Asp Leu>
____________________________IL-1RII____________________________>

   1980       1990       2000       2010
*     *     *     *     *     *     *     *     *
CAC ATG GAT TTT AAA TGT GTT GTC CAT AAT ACC CTG AGT TTT
GTG TAC CTA AAA TTT ACA CAA CAG GTA TTA TGG GAC TCA AAA
His Met Asp Phe Lys Cys Val Val His Asn Thr Leu Ser Phe>
____________________________IL-1RII____________________________>
```

Figure 49G

```
 2020        2030        2040        2050
   *     *     *     *     *     *     *     *
CAG ACA CTA CGC ACC ACA GTC AAG GAA GCC TCC TCC ACG TTC
GTC TGT GAT GCG TGG TGT CAG TTC CTT CGG AGG AGG TGC AAG
Gln Thr Leu Arg Thr Thr Val Lys Glu Ala Ser Ser Thr Phe>
________________________IL-1RII________________________>

2060        2070        2080        2090        2100
  *     *     *     *     *     *     *     *     *
TCC GGA GAG TCC AAA TAC GGT CCG CCA TGC CCA CCA TGC CCA
AGG CCT CTC AGG TTT ATG CCA GGC GGT ACG GGT GGT ACG GGT
Ser Gly>
_______>
        Glu Ser Lys Tyr Gly Pro Pro Cys Pro Pro Cys Pro>
        __________________FC-IgG4_______________________>

       2110        2120        2130        2140
   *     *     *     *     *     *     *     *
GCA CCT GAG TTC CTG GGG GGA CCA TCA GTC TTC CTG TTC CCC
CGT GGA CTC AAG GAC CCC CCT GGT AGT CAG AAG GAC AAG GGG
Ala Pro Glu Phe Leu Gly Gly Pro Ser Val Phe Leu Phe Pro>
_______________________FC-IgG4__________________________>

     2150        2160        2170        2180
  *     *     *     *     *     *     *     *
CCA AAA CCC AAG GAC ACT CTC ATG ATC TCC CGG ACC CCT GAG
GGT TTT GGG TTC CTG TGA GAG TAC TAG AGG GCC TGG GGA CTC
Pro Lys Pro Lys Asp Thr Leu Met Ile Ser Arg Thr Pro Glu>
_______________________FC-IgG4__________________________>

   2190        2200        2210        2220
*     *     *     *     *     *     *     *     *
GTC ACG TGC GTG GTG GTG GAC GTG AGC CAG GAA GAC CCC GAG
CAG TGC ACG CAC CAC CAC CTG CAC TCG GTC CTT CTG GGG CTC
Val Thr Cys Val Val Val Asp Val Ser Gln Glu Asp Pro Glu>
_______________________FC-IgG4__________________________>

 2230        2240        2250        2260
   *     *     *     *     *     *     *     *
GTC CAG TTC AAC TGG TAC GTG GAT GGC GTG GAG GTG CAT AAT
CAG GTC AAG TTG ACC ATG CAC CTA CCG CAC CTC CAC GTA TTA
Val Gln Phe Asn Trp Tyr Val Asp Gly Val Glu Val His Asn>
_______________________FC-IgG4__________________________>

270         2280        2290        2300        2310
  *     *     *     *     *     *     *     *     *
GCC AAG ACA AAG CCG CGG GAG GAG CAG TTC AAC AGC ACG TAC
CGG TTC TGT TTC GGC GCC CTC CTC GTC AAG TTG TCG TGC ATG
Ala Lys Thr Lys Pro Arg Glu Glu Gln Phe Asn Ser Thr Tyr>
_______________________FC-IgG4__________________________>

       2320        2330        2340        2350
   *     *     *     *     *     *     *     *
CGT GTG GTC AGC GTC CTC ACC GTC CTG CAC CAG GAC TGG CTG
GCA CAC CAG TCG CAG GAG TGG CAG GAC GTG GTC CTG ACC GAC
Arg Val Val Ser Val Leu Thr Val Leu His Gln Asp Trp Leu>
_______________________FC-IgG4__________________________>
```

Figure 49H

```
      2360        2370        2380        2390
 *     *     *     *     *     *     *     *
AAC GGC AAG GAG TAC AAG TGC AAG GTC TCC AAC AAA GGC CTC
TTG CCG TTC CTC ATG TTC ACG TTC CAG AGG TTG TTT CCG GAG
Asn Gly Lys Glu Tyr Lys Cys Lys Val Ser Asn Lys Gly Leu>
_________________________FC-IgG4_________________________>

   2400        2410        2420        2430
*     *     *     *     *     *     *     *     *
CCG TCC TCC ATC GAG AAA ACC ATC TCC AAA GCC AAA GGG CAG
GGC AGG AGG TAG CTC TTT TGG TAG AGG TTT CGG TTT CCC GTC
Pro Ser Ser Ile Glu Lys Thr Ile Ser Lys Ala Lys Gly Gln>
_________________________FC-IgG4_________________________>

 2440        2450        2460        2470
    *     *     *     *     *     *     *     *
CCC CGA GAG CCA CAG GTG TAC ACC CTG CCC CCA TCC CAG GAG
GGG GCT CTC GGT GTC CAC ATG TGG GAC GGG GGT AGG GTC CTC
Pro Arg Glu Pro Gln Val Tyr Thr Leu Pro Pro Ser Gln Glu>
_________________________FC-IgG4_________________________>

2480        2490        2500        2510        2520
 *     *     *     *     *     *     *     *     *
GAG ATG ACC AAG AAC CAG GTC AGC CTG ACC TGC CTG GTC AAA
CTC TAC TGG TTC TTG GTC CAG TCG GAC TGG ACG GAC CAG TTT
Glu Met Thr Lys Asn Gln Val Ser Leu Thr Cys Leu Val Lys>
_________________________FC-IgG4_________________________>

       2530        2540        2550        2560
    *     *     *     *     *     *     *     *
GGC TTC TAC CCC AGC GAC ATC GCC GTG GAG TGG GAG AGC AAT
CCG AAG ATG GGG TCG CTG TAG CGG CAC CTC ACC CTC TCG TTA
Gly Phe Tyr Pro Ser Asp Ile Ala Val Glu Trp Glu Ser Asn>
_________________________FC-IgG4_________________________>

      2570        2580        2590        2600
 *     *     *     *     *     *     *     *
GGG CAG CCG GAG AAC AAC TAC AAG ACC ACG CCT CCC GTG CTG
CCC GTC GGC CTC TTG TTG ATG TTC TGG TGC GGA GGG CAC GAC
Gly Gln Pro Glu Asn Asn Tyr Lys Thr Thr Pro Pro Val Leu>
_________________________FC-IgG4_________________________>

   2610        2620        2630        2640
*     *     *     *     *     *     *     *     *
GAC TCC GAC GGC TCC TTC TTC CTC TAC AGC AGG CTA ACC GTG
CTG AGG CTG CCG AGG AAG AAG GAG ATG TCG TCC GAT TGG CAC
Asp Ser Asp Gly Ser Phe Phe Leu Tyr Ser Arg Leu Thr Val>
_________________________FC-IgG4_________________________>

 2650        2660        2670        2680
    *     *     *     *     *     *     *     *
GAC AAG AGC AGG TGG CAG GAG GGG AAT GTC TTC TCA TGC TCC
CTG TTC TCG TCC ACC GTC CTC CCC TTA CAG AAG AGT ACG AGG
Asp Lys Ser Arg Trp Gln Glu Gly Asn Val Phe Ser Cys Ser>
_________________________FC-IgG4_________________________>
```

Figure 49 I

```
2690          2700          2710          2720          2730
   *       *      *      *      *      *      *      *      *
  GTG ATG CAT GAG GCT CTG CAC AAC CAC TAC ACA CAG AAG AGC
  CAC TAC GTA CTC CGA GAC GTG TTG GTG ATG TGT GTC TTC TCG
  Val Met His Glu Ala Leu His Asn His Tyr Thr Gln Lys Ser>
  _______________________FC-IgG4__________________________>

            2740          2750
       *       *      *      *
  CTC TCC CTG TCT CTG GGT AAA TGA
  GAG AGG GAC AGA GAC CCA TTT ACT
  Leu Ser Leu Ser Leu Gly Lys ***>
  _____________FC-IgG4____________>
```

RECEPTOR BASED ANTAGONISTS AND METHODS OF MAKING AND USING

CROSS-REFERENCE TO RELATED APPLICATIONS

This application is a continuation of U.S. application Ser. No. 11/134,114, filed 20 May 2005 now U.S. Pat. No. 7,417,134, which is a divisional of U.S. Ser. No. 10/282,162, filed 28 Oct. 2002, now U.S. Pat No. 6,927,044, which is a continuation-in-part of U.S. application Ser. No. 09/787,835, filed 22 Mar. 2001 now abandoned, which is a U.S. National Stage Application of International Application No. PCT/US99/22045, filed 22 Sep. 1999, which is a continuation of U.S. application Ser. No. 09/313,942, filed 19 May 1999, now U.S. Pat. No. 6,472,179, which claims the benefit of under 35 U.S.C. §119(e) of claims priority of U.S. Provisional Application No. 60/101,858 filed Sep. 25, 1998. The disclosures of these publications are hereby incorporated by reference into this application in their entireties.

FIELD OF THE INVENTION

The invention relates to receptor-based fusion proteins capable of binding and inhibiting the biological activity of a cytokine. More specifically, the invention relates to interleukin-1 (IL-1) fusion proteins capable of trapping and inhibiting the action of IL-1, and therapeutic uses thereof.

DESCRIPTION OF RELATED ART

Although discovered for varying biological activities, ciliary neurotrophic factor (CNTF), leukemia inhibitory factor (LIF), oncostatin M (OSM) and interleukin-6 (IL-6) comprise a defined family of cytokines (referred to herein as the "CNTF family" of cytokines). These cytokines are grouped together because of their distant structural similarities (Bazan et al. 1991 J. Neuron 7:197-208), and, perhaps more importantly, because they share "β" signal-transducing receptor components (Baumann et al. 1993 J. Biol. Chem. 265:19853-19862); Davis et al. 1993 Science 260:1805-1808; Gearing et al. 1992 Science 255:1434-1437; Ip et al. 1992 Cell 69: 1121-1132; Stahl et al. 1993 J. Biol. Chem. 268: 7628-7631; Stahl et al. 1993 Cell 74:587-590). Receptor activation by this family of cytokines results from either homo- or hetero-dimerization of these β components.

In addition to the β components, some of these cytokines also require specificity-determining "α" components that are more limited in their tissue distribution than the β components, and thus determine the cellular targets of the particular cytokines. Thus, LIF and OSM are broadly acting factors that may only require the presence of gp130 and LIFRβ on responding cells, while CNTF requires CNTFRα. Both CNTFRα and IL-6Rα (Hibi et al. Cell 63:1149-1157) can function as soluble proteins, consistent with the notion that they do not interact with intracellular signaling molecules but that they serve to help their ligands interact with the appropriate signal transducing β subunits.

Additional evidence from other cytokine systems also supports the notion that dimerization provides a common mechanism by which all cytokine receptors initiate signal transduction. Studies with the erythropoietin (EPO) receptor are also consistent with the importance of dimerization in receptor activation, as EPO receptors can be constitutively activated by a single amino acid change that introduces a cysteine residue and results in disulfide-linked homodimers (Watowich et al. 1992 Proc. Natl. Acad. Sci. USA 89:2140-2144).

In addition to homo- or hetero-dimerization of β subunits as the critical step for receptor activation, a second important feature is that formation of the final receptor complex by the CNTF family of cytokines occurs through a mechanism whereby the ligand successively binds to receptor components in an ordered manner (Davis et al. 1993 supra). Thus CNTF first binds to CNTFRα, forming a complex which then binds gp130 to form an intermediate (called here the αβ1 intermediate) that is not signaling competent because it has only a single β component, before finally recruiting LIFRβ to form a heterodimer of β components which then initiates signal transduction. Altogether, these findings led to a proposal for the structure of a generic cytokine receptor complex in which each cytokine can have up to 3 receptor binding sites: a site that binds to an optional α specificity-determining component (α site), a site that binds to the first β signal-transducing component (β1 site), and a site that binds to the second β signal-transducing component (β2 site). These 3 sites are used in sequential fashion, with the last step in complex formation—resulting in β component dimerization—critical for initiating signal transduction (Davis et al. 1993 supra). Knowledge of the details of receptor activation and the existence of the non-functional β1 intermediate for CNTF has led to the finding that CNTF is a high affinity antagonist for IL-6 under certain circumstances, and provides the strategic basis for designing ligand or receptor-based antagonists for the CNTF family of cytokines as detailed below.

BRIEF SUMMARY OF THE INVENTION

An object of the invention is the construction of several specific interleukin-1 (IL-1) cytokine antagonists, termed "IL-1 Traps", each having different sequences but all being capable of blocking the binding of IL-1 to its receptor, thus functioning as IL-1 antagonists.

BRIEF DESCRIPTION OF THE FIGURES

FIGS. 4A-4B. The amino acid sequence of human gp130-Fc-$His_6$ (SEQ ID NO: 7). Amino acids 1 to 619 are from human gp130 (Hibi et al., Cell 63:1149-1157 (1990). Note that amino acid number 2 has been changed from a Leu to a Val in order to accommodate a Kozak sequence in the coding DNA sequence. The signal peptide of gp130-Fc-$His_6$ has been italicized (amino acids 1 to 22). The Ser-Gly bridge is shown in bold type (amino acids 620, 621). Amino acids 662 to 853 are from the Fc domain of human IgG1 (Lewis, et al., J. Immunol. 151:2829-2838 (1993). (†) mark the two cysteines (amino acids number 632 and 635) of the IgG hinge preceding the Fc that form the inter-chain disulfide bridges that link two Fc domains. The hexahistine tag is shown in bold/italic type (amino acids 854 to 859). (•) shows the position of the STOP codon.

FIG. 5: The amino acid sequence of human IL-6Rα-Fc (SEQ ID NO: 8). Key: Amino acids 1 to 358 are from human IL-6Rα (Yamasaki et al. 1088 Science 241:825-828). Note that amino acid number 2 has been changed from a Leu to a Val in order to accommodate a Kozak sequence in the coding DNA sequence. The signal peptide of IL-6Rα-Fc has been italicized (amino acids 1 to 19). The Ala-Gly bridge is shown in bold type (amino acids 359, 360). Amino acids 361 to 592 are from the Fc domain of human IgG1 (Lewis et al., J. Immunol. 151:2829-2838 (1993). (\) mark the two cysteines (amino acids number 371 and 374) of the IgG hinge preceding the Fc that form the inter-chain disulfide bridges that link two Fc domains. (•) shows the position of the STOP codon.

FIGS. 9A-9B. Amino acid sequence of gp130-Cy1 (SEQ ID NO: 9). Key: Amino acids 1 to 619 are from human gp130 (Hibi, et al., Cell 63:1149-1157 (1990). Ser-Gly bridge is shown in bold type. Amino acids 662 to 651 are from the constant region of human IgG1 (Lewis et al., J. Immunol. 151:2829-2838 (1993). (*) shows the position of the STOP codon.

FIG. 10: Amino acid sequence of gp130Δ3fibro (SEQ ID NO: 10). Key: Amino acids 1 to 330 are from human gp130 (Hibi et al. Cell 63:1149-1157 (1990). Other symbols as described in FIG. 9.

FIG. 11: Amino acid sequence of J-CH1 (SEQ ID NO: 11). Key: The Ser-Gly bridge is shown in bold, the J-peptide is shown in italics, the $C_H1$ domain is underlined.

FIG. 12: Amino acid sequence of Cγ4 (SEQ ID NO: 12). Key: The Ser-Gly bridge is shown in bold type. Amino acids 2 to 239 comprise the Cγ4 sequence.

FIG. 13: Amino acid sequence of κ-domain (SEQ ID NO: 13). Key: The Ser-Gly bridge is shown in bold type. Amino acids 2 to 108 comprise the κ domain. The C-terminal cysteine (amino acid 108) is that involved in the disulfide bond of the κ domain with the $C_H1$ domain of Cγ.

FIG. 14: Amino acid sequence of λ-domain (SEQ ID NO: 14). Key: The Ser-Gly bridge is shown in bold type. Amino acids 2 to 106 comprise the λ domain (Cheung, et al., J. Virol. 66: 6714-6720 (1992). The C-terminal cysteine (amino acid 106) is that involved in the disulfide bond of the λ domain with the $C_H1$ domain of Cγ.

FIG. 15: Amino acid sequence of the soluble IL-6Rα domain (SEQ ID NO: 15). Key: Amino acids 1 to 358 comprise the soluble IL-6Rα domain (Yamasaki, et al., Science 241:825-828 (1988). The Ala-Gly bridge is shown in bold type.

FIG. 16: Amino acid sequence of the soluble IL-6Rα313 domain (SEQ ID NO: 16): Key: Amino acids 1 to 313 comprise the truncated IL-6Rα domain (IL-6Rα313). The Thr-Gly bridge is shown in bold type.

(FIG. 19A) Two different ligand Traps are depicted schematically and listed according to their ability to bind protein A. gp130-Fc•IL-6Ra-Fc (GF6F) binds protein A via its Fc-domains, whereas gp130-$C_H1$•IL-6Ra-k (G16K) does not bind to protein A. (FIG. 19B) Anti-kappa western blotting of proteins precipitated with Protein A-Sepharose from mixtures of GF6F±IL-6, G16K±IL-6, or GF6F plus G16K±IL-6, as marked.

FIGS. 21A-21D: Nucleotide sequence (SEQ ID NO: 17) encoding and deduced amino acid sequence (SEQ ID NO: 18) of fusion polypeptide designated 424 which is capable of binding the cytokine IL-4 to form a nonfunctional complex.

FIGS. 22A-22D: Nucleotide sequence (SEQ ID NO: 19) encoding and deduced amino acid sequence (SEQ ID NO: 20) of fusion polypeptide designated 603 which is capable of binding the cytokine IL-4 to form a nonfunctional complex.

FIGS. 23A-23D: Nucleotide sequence (SEQ ID NO: 21) encoding and deduced amino acid sequence (SEQ ID NO: 22) of fusion polypeptide designated 622 which is capable of binding the cytokine IL-4 to form a nonfunctional complex.

FIGS. 24A-24F: Nucleotide sequence (SEQ ID NO: 23) encoding and deduced amino acid sequence (SEQ ID NO: 24) of fusion polypeptide designated 412 which is capable of binding the cytokine IL-6 to form a nonfunctional complex.

FIGS. 25A-25F: Nucleotide sequence (SEQ ID NO: 25) encoding and deduced amino acid sequence (SEQ ID NO: 26) of fusion polypeptide designated 616 which is capable of binding the cytokine IL-6 to form a nonfunctional complex.

FIGS. 26A-26E: Nucleotide sequence (SEQ ID NO: 27) encoding and deduced amino acid sequence (SEQ ID NO: 28) of fusion polypeptide designated 569 which is capable of binding the cytokine IL-1 to form a nonfunctional complex.

FIGS. 31A-31G: The nucleotide (SEQ ID NO: 29) and encoded amino acid (SEQ ID NO: 30) sequence of the IL-4Rα.IL-13Rα1.Fc single chain Trap construct is set forth.

FIGS. 32A-32G: The nucleotide (SEQ ID NO: 31) and encoded amino acid (SEQ ID NO: 32) sequence of the IL-13Rα1.IL-4Rα.Fc single chain Trap construct is set forth.

FIG. 33: Blocking of IL-13 by IL-4Rα.IL-13Rα1.Fc and IL-13Rα1.IL-4Rα.Fc. Addition of IL-4Rα.IL-13Rα1.Fc or IL-13Rα1.IL-4Rα.Fc at a concentration of 10 nM blocks IL-13-induced growth up to ~2 nM. At an IL-13 concentration of ~4-5 nM the growth of TF1 cells is inhibited by 50%.

FIG. 36A: Cynomologus monkeys were treated in three parts as indicated. Human IL-4 (25 μg/kg) was injected subcutaneously twice daily for 4 days and human IL-4 Trap (8 mg/ml) and vehicle were given intravenously daily for 5 days, beginning 1 day prior to human IL-4 administration. Plasma was collected daily and assayed for MCP-1 levels. Results were expressed as mean +/− SEM; n=4. (ANOVA $p<0.0007$; Tukey-Kramer: Part 2 vs. Part 1, p, 0.05; Part 2 vs. Part 3, p,0.05; Part 1 vs. Part 3, not significant.) FIG. 36B: Cynomologus monkeys were treated in three parts as indicated. Human IL-4 (25 μg/kg) was injected subcutaneously twice daily for 4 days and human IL-4 Trap (8 mg/ml) and vehicle were given intravenously daily for 5 days, beginning 1 day prior to human IL-4 administration. Whole blood was collected daily for flow cytometry analysis for CD16. Results were expressed as mean +/− SEM; n=4. (ANOVA $p<0.042$; Tukey-Kramer: Part 2 vs. Part 1, $p<0.05$; Part 2 vs. Part 3 and Part 1 vs. Part 3, not significant.)

FIGS. 38A-38I: Nucleotide (SEQ ID NO: 33) and deduced amino acid (SEQ ID NO: 34) sequence of Human IL-1 Trap 570-FE.

FIG. 39A-39I: Nucleotide (SEQ ID NO: 35) and deduced amino acid (SEQ ID NO: 36) sequence of Human IL-1 Trap 570-FE.B.

FIGS. 40A-40I: Nucleotide (SEQ ID NO: 37) and deduced amino acid (SEQ ID NO: 38) sequence of Human IL-1 Trap 570-FE.C.

Figure 41I:
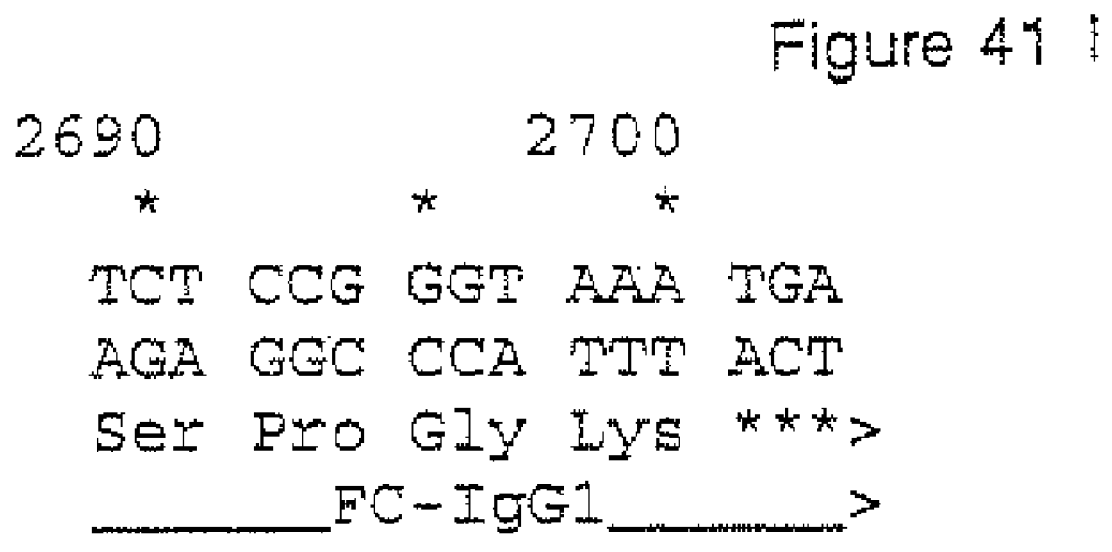

FIGS. 41A-41I: Nucleotide (SEQ ID NO: 39) and deduced amino acid (SEQ ID NO: 40) sequence of Human IL-1 Trap 823.

Figure 42I:
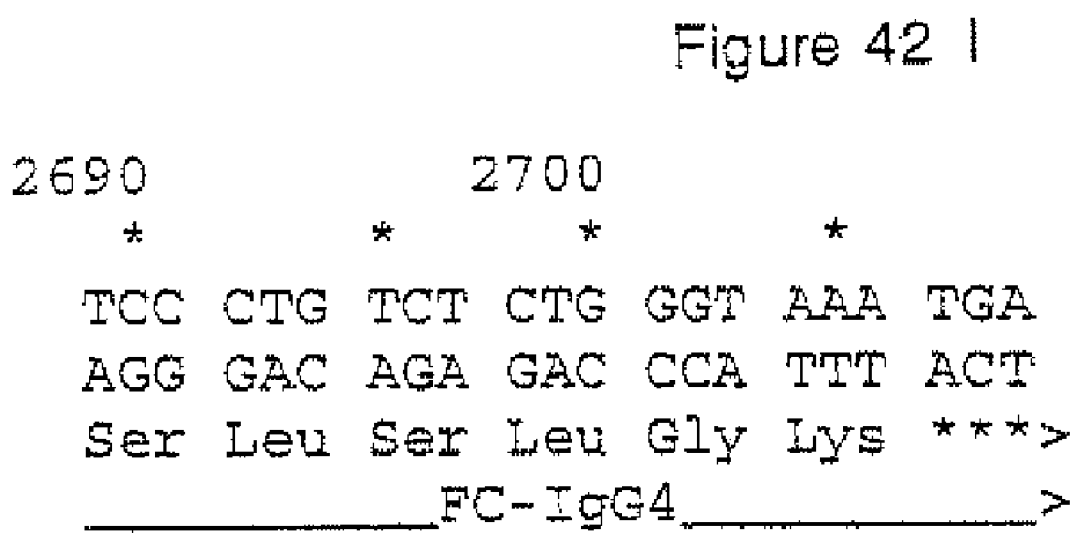

FIGS. 42A-42I: Nucleotide (SEQ ID NO: 41) and deduced amino acid (SEQ ID NO: 42) sequence of Human IL-1 Trap 823-1198.B.

Figure 43I:
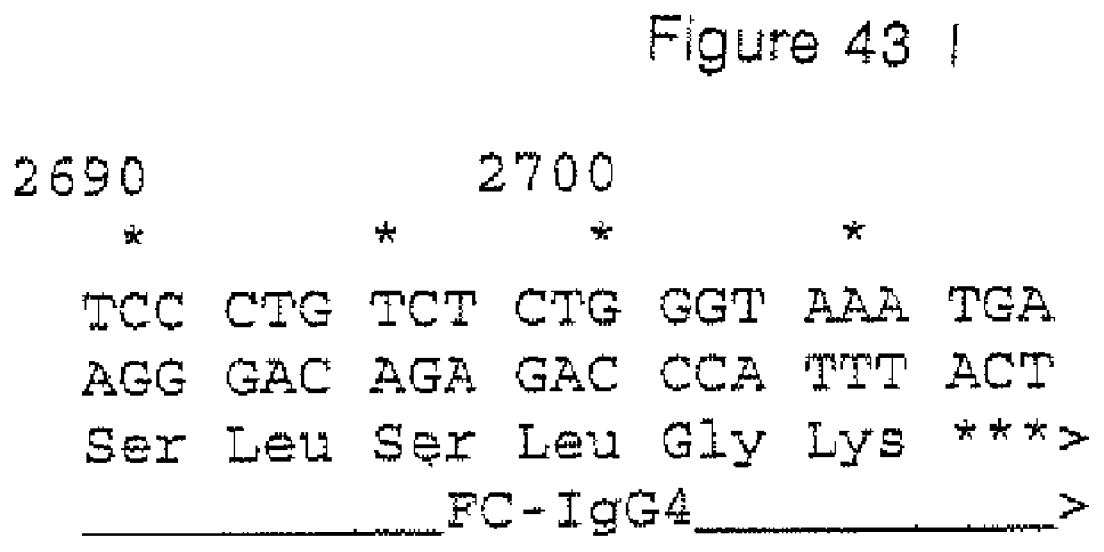

FIGS. 43A-43I: Nucleotide (SEQ ID NO: 43) and deduced amino acid (SEQ ID NO: 44) sequence of Human IL-1 Trap 823-1267.C.

FIGS. 44A-44I: Nucleotide (SEQ ID NO: 45) and deduced amino acid (SEQ ID NO: 46) sequence of Human IL-1 Trap 1647-CtF.

FIGS. 45A-45I: Nucleotide (SEQ ID NO: 47) and deduced amino acid (SEQ ID NO: 48) sequence of Human IL-1 Trap 1647-CtF.B.

FIGS. 46A-46I: Nucleotide (SEQ ID NO: 49) and deduced amino acid (SEQ ID NO: 50) sequence of Human IL-1 Trap 1647-CtF.C.

FIGS. 47A-47I: Nucleotide (SEQ ID NO: 51) and deduced amino acid (SEQ ID NO: 52) sequence of Human IL-1 Trap 1649.

FIGS. 48A-48I: Nucleotide (SEQ ID NO: 53) and deduced amino acid (SEQ ID NO: 54) sequence of Human IL-1 Trap 1649-B.

FIGS. 49A-49I: Nucleotide (SEQ ID NO: 55) and deduced amino acid (SEQ ID NO: 56) sequence of Human IL-1 Trap 1646-C.

DETAILED DESCRIPTION OF THE INVENTION

Figure 1:
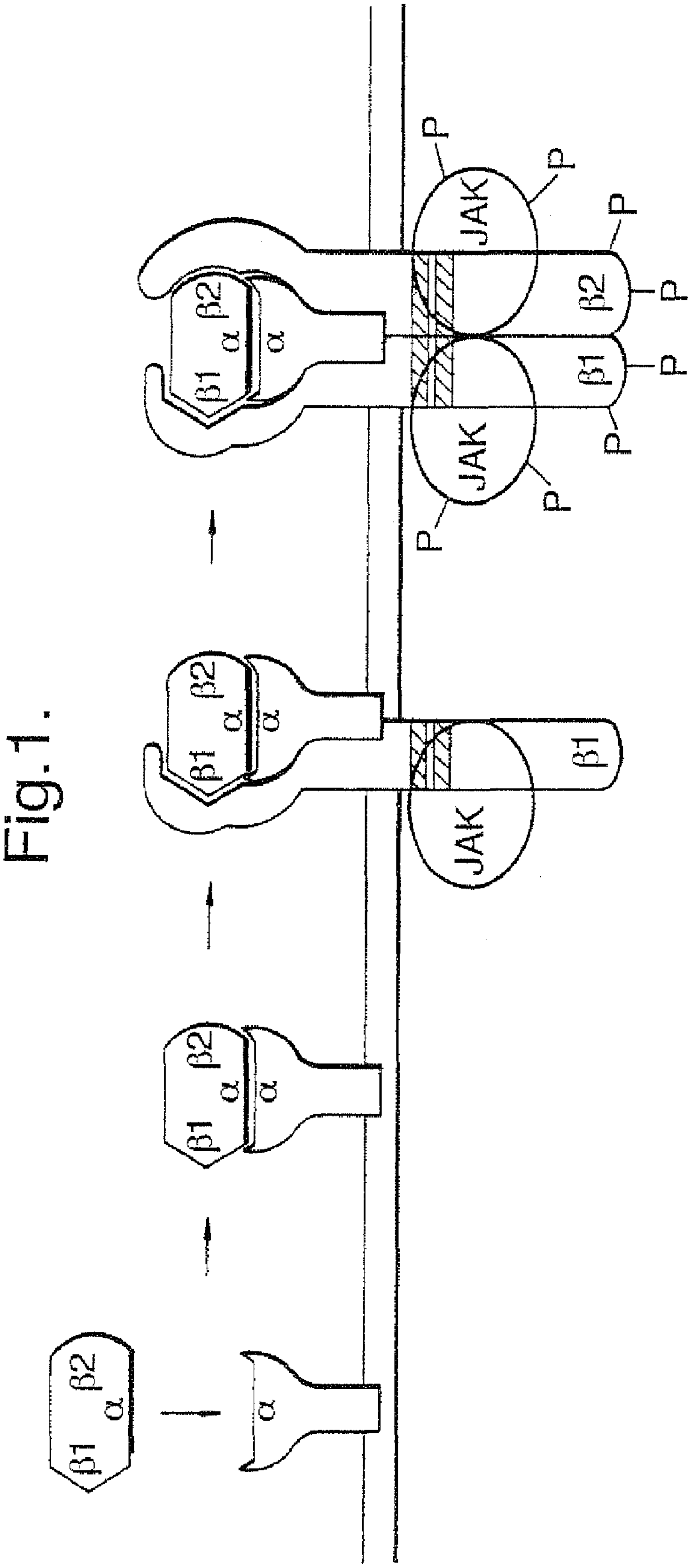
FIG. 1: Ordered binding of receptor components in a model of a generic cytokine receptor. The model indicates that cytokines contain up to 3 receptor binding sites and interact with their receptor components by binding first the optional a component, followed by binding to β1, and then β2. The β components for many cytokine receptors interact through membrane proximal regions (shaded boxes) with the Jak/Tyk family of cytoplasmic protein tyrosine kinases. Only upon dimerization of β components is signal transduction initiated, as schematized by the tyrosine phosphorylations (P) of the β components and the Jak/Tyk kinases.

The present invention provides an isolated nucleic acid molecule encoding a fusion polypeptide capable of binding a cytokine to form a nonfunctional complex comprising: (a) a nucleotide sequence encoding a first fusion polypeptide component comprising the amino acid sequence of the cytokine binding portion of the extracellular domain of the specificity determining component of a cytokine's receptor; (b) a nucleotide sequence encoding a second fusion polypeptide component comprising the amino acid sequence of the cytokine binding portion of the extracellular domain of the signal transducing component of a cytokine's receptor; and (c) a nucleotide sequence encoding a third fusion polypeptide component comprising the amino acid sequence of a multimerizing component.

By "cytokine binding portion" what is meant is the minimal portion of the extracellular domain necessary to bind the cytokine. It is accepted by those of skill in the art that a defining characteristic of a cytokine receptor is the presence of the two fibronectin-like domains that contain canonical cysteines and of the WSXWS box (Bazan 1990 supra). Sequences encoding the extracellular domains of the binding component of the cytokine's receptor and of the signal transducing component of the cytokine's receptor may also be used to create the fusion polypeptide of the invention. Similarly, longer sequences encoding larger portions of the components of the cytokine's receptor may be used. However, it is contemplated that fragments smaller than the extracellular domain will function to bind the cytokine and therefore, the invention contemplates fusion polypeptides comprising the minimal portion of the extracellular domain necessary to bind the cytokine as the cytokine binding portion.

The invention comprises a "specificity determining component" of a cytokine receptor and a "signal transducing component" of the cytokine receptor. Regardless of the nomenclature used to designate a particular component or subunit of a cytokine receptor, one skilled in the art would recognize which component or subunit of a receptor is responsible for determining the cellular target of the cytokine, and thus would know which component constitutes the "specificity determining component."

Similarly, regardless of the nomenclature used, one of skill in the art would know which component or subunit of a receptor would constitute the "signal transducing component." As used herein, the "signal transducing component" is a component of the native receptor which is not the specificity determining component and which does not bind or weakly binds the cytokine in the absence of the specificity determining component. In the native receptor, the "signal transducing component" may participate in signaling.

For example, while some cytokine receptors have components designated α and β, the IL-4 receptor has a signal transducing component referred to as IL-2Rγ. However, regardless of what name is associated with that component, one skilled in the art would know which component of the IL-4 receptor is the signal transducing component. Thus to practice the present invention and create a high affinity Trap for IL-4, one of skill in the art would create an isolated nucleic acid comprising a nucleotide sequence encoding a first fusion polypeptide component comprising the amino acid sequence of the cytokine binding portion of the extracellular domain of the specificity determining component of the IL-4 receptor (IL-4Rα); a nucleotide sequence encoding a second fusion polypeptide component comprising the amino acid sequence of the cytokine binding portion of the extracellular domain of the signal transducing component of the IL-4 receptor (IL-2Rγ); and a nucleotide sequence encoding a third fusion polypeptide component comprising the amino acid sequence of a multimerizing component (for example, an Fc domain of IgG) to create a high affinity Trap for IL-4.

In preparing the nucleic acid sequence encoding the fusion polypeptide of the invention, the first, second, and third components of the fusion polypeptide are encoded in a single strand of nucleotides which, when expressed by a host vector system, produces a monomeric species of the fusion polypeptide. The monomers thus expressed then multimerize due to the interactions between the multimerizing components (the third fusion polypeptide components). Producing the fusion polypeptides in this manner avoids the need for purification of heterodimeric mixtures that would result if the first and second components were produced as separate molecules and then multimerized. For example, U.S. Pat. No. 5,470,952 describes the production of heterodimeric proteins that function as CNTF or IL-6 antagonists. The heterodimers are purified from cell lines co-transfected with the appropriate alpha (α) and beta (β) components. Heterodimers are then separated from homodimers using methods such as passive elution from preparative, nondenaturing polyacrylamide gels or by using high pressure cation exchange chromatography. The need for this purification step is avoided by the methods of the present invention.

In addition, WO 96/11213 states that the applicant has prepared homodimers in which two IL-4 receptors are bound by a polymeric spacer and has prepared heterodimers in which an IL-4 receptor is linked by a polymeric spacer to an IL-2 receptor gamma chain. The polymeric spacer described is polyethylene glycol (PEG). The two receptor components, IL-4R and IL-2Rγ are separately expressed and purified. Pegylated homodimers and heterodimers are then produced by joining the components together using bi-functional PEG reagents. It is an advantage of the present invention that it avoids the need for such time consuming and costly purification and pegylation steps.

In one embodiment of the invention, the nucleotide sequence encoding the first component is upstream of the nucleotide sequence encoding the second component. In another embodiment of the invention, the nucleotide sequence encoding the first component is downstream of the nucleotide sequence encoding the second component. Further embodiments of the invention may be prepared in which the order of the first, second and third fusion polypeptide components are rearranged. For example, if the nucleotide sequence encoding the first component is designated 1, the nucleotide sequence encoding the second component is designated 2, and the nucleotide sequence of the third component is designated 3, then the order of the components in the isolated nucleic acid of the invention as read from 5' to 3' may be any of the following six combinations: 1,2,3; 1,3,2; 2,1,3; 2,3,1; 3,1,2; or 3,2,1.

In further embodiments of the invention, the cytokine bound by the fusion polypeptide may be a member of the hematopoietin family of cytokines selected from the group consisting of interleukin-2, interleukin-3, interleukin-4, interleukin-5, interleukin-6, interleukin-7, interleukin-9, interleukin-1 1, interleukin-1 3, interleukin-1 5, granulocyte macrophage colony stimulating factor, oncostatin M, leukemia inhibitory factor, and cardiotrophin-1.

In additional embodiments of the invention, the cytokine bound by the fusion polypeptide may be a member of the interferon family of cytokines selected from the group consisting of IFN-γ, IFN-α, and IFN-β.

In additional embodiments of the invention, the cytokine bound by the fusion polypeptide may be a member of the immunoglobulin superfamily of cytokines selected from the group consisting of B7.1 (CD80) and B7.2 (B70).

In still further embodiments of the invention, the cytokine bound by the fusion polypeptide may be a member of the TNF family of cytokines selected from the group consisting of TNF-α, TNF-β, LT-β, CD40 ligand, Fas ligand, CD 27 ligand, CD 30 ligand, and 4-1 BBL.

In additional embodiments of the invention, the cytokine bound by the fusion polypeptide may be a cytokine selected from the group consisting of interleukin-1 (IL-1), IL-10, IL-12, IL-14, IL-18, and MIF.

Because specificity determination and signal transduction occurs by a similar mechanism in the TGF-β/BMP family of cytokines (see, for example, Kingsley 1994 Genes & Development 8:133-146) the present invention may be used to produce high affinity antagonists for cytokines that are members of the TGF-β/BMP family.

Therefore, in additional embodiments of the invention, the cytokine bound by the fusion polypeptide may be a member of the TGF-β/BMP family selected from the group consisting of TGF-β1, TGF-β2, TGF-β3, BMP-2, BMP-3a, BMP-3b, BMP-4, BMP-5, BMP-6, BMP-7, BMP-8a, BMP-8b, BMP-9, BMP-10, BMP-11, BMP-15, BMP-16, endometrial bleeding associated factor (EBAF), growth differentiation factor-1 (GDF-1), GDF-2, GDF-3, GDF-5, GDF-6, GDF-7, GDF-8, GDF-9, GDF-12, GDF-14, mullerian inhibiting substance (MIS), activin-1, activin-2, activin-3, activin-4, and activin-5.

In alternative embodiments of the invention, the specificity determining component, the signal transducing component, or both, may be substituted for by a single chain Fv. A single chain Fv (scFv) is a truncated Fab having only the V region of a heavy chain linked by a stretch of synthetic peptide to a V region of a light chain. (See, for example, U.S. Pat. Nos. 5,565,332; 5,733,743; 5,837,242; 5,858,657; and 5,871,907 incorporated by reference herein). Thus the present invention contemplates, for example, an isolated nucleic acid molecule encoding a fusion polypeptide capable of binding a cytokine to form a nonfunctional complex comprising a nucleotide sequence encoding a first fusion polypeptide component comprising the amino acid sequence of the cytokine binding portion of the extracellular domain of the specificity determining component of the cytokine receptor; a nucleotide sequence encoding a second fusion polypeptide component comprising the amino acid sequence of an scFv capable of binding the cytokine at a site different from the site at which the cytokine binding portion of the extracellular domain of the specificity determining component of the cytokine receptor binds; and a nucleotide sequence encoding a third fusion polypeptide component comprising the amino acid sequence of a multimerizing component. Alternatively, the specificity-determining component may be substituted for by a scFv that binds to a site on the cytokine different from the site at which the signal transducing component binds. Thus the invention contemplates an isolated nucleic acid molecule encoding a fusion polypeptide capable of binding a cytokine to form a nonfunctional complex comprising a nucleotide sequence encoding a first fusion polypeptide component comprising the amino acid sequence of a scFv that binds to a site on the cytokine different from the site at which the cytokine binding portion of the extracellular domain of the signal transducing component of the cytokine receptor binds; a nucleotide sequence encoding a second fusion polypeptide component comprising the amino acid sequence of the cytokine binding portion of the extracellular domain of the signal transducing component of the cytokine's receptor; and a nucleotide sequence encoding a third fusion polypeptide component comprising the amino acid sequence of a multimerizing component.

In another embodiment, the invention contemplates an isolated nucleic acid molecule encoding a fusion polypeptide capable of binding a cytokine to form a nonfunctional complex comprising a nucleotide sequence encoding a first fusion polypeptide component comprising the amino acid sequence of a first scFv that binds to a site on the cytokine; a nucleotide sequence encoding a second fusion polypeptide component comprising the amino acid sequence a second scFv that binds to a site on the cytokine different from the site at which the first scFv binds; and a nucleotide sequence encoding a third fusion polypeptide component comprising the amino acid sequence of a multimerizing component.

In all of the above described embodiments comprising scFvs, the invention also contemplates embodiments in which the nucleotide sequence encoding the first component is upstream of the nucleotide sequence encoding the second component; embodiments in which the nucleotide sequence encoding the first component is downstream of the nucleotide sequence encoding the second component; and further embodiments of the invention in which the order of the first, second and third fusion polypeptide components is rearranged. For example, if the nucleotide sequence encoding the first component is designated 1, the nucleotide sequence encoding the second component is designated 2, and the nucleotide sequence of the third component is designated 3, then the order of the components in the isolated nucleic acid of the invention as read from 5' to 3' may be any of the following six combinations: 1,2,3; 1,3,2; 2,1,3; 2,3,1; 3,1,2; or 3,2,1.

In preferred embodiments of the invention, the multimerizing component comprises an immunoglobulin derived domain. More specifically, the immunoglobulin derived domain may be selected from the group consisting of the Fc domain or the heavy chain of IgG. Even more specifically, immunoglobulin domain may be selected from the group consisting of the Fc domain or the heavy chain of $IgG_1$ or $IgG_4$. In another embodiment, the multimerizing component may be an Fc domain from which the first five amino acids (including a cysteine) have been removed to produce a multimerizing component referred to as Fc(ΔC1). Alternatively, the multimerizing component may be an Fc domain in which a cysteine within the first five amino acids has been substituted for by another amino acid such as, for example, serine or alanine.

The present invention also provides for fusion polypeptides encoded by the isolated nucleic acid molecules of the invention. Preferably, the fusion polypeptides are in multimeric form, due to the function of the third component, the multimerizing component. In a preferred embodiment, the multimer is a dimer. Suitable multimerizing components are sequences encoding an immunoglobulin heavy chain hinge region (Takahashi et al. 1982 supra); immunoglobulin gene sequences, and portions thereof. In a preferred embodiment of the invention, immunoglobulin gene sequences, especially one encoding the Fc domain, are used to encode the multimerizing component.

The present invention also contemplates a vector which comprises the nucleic acid molecule of the invention as described herein.

A preferred embodiment of the invention is an isolated nucleic acid molecule having the sequence set forth in SEQ ID NO:33 encoding a fusion polypeptide having the sequence set forth in SEQ ID NO:34, wherein the fusion polypeptide forms a multimer that is capable of binding a cytokine to form a nonfunctional complex; an isolated nucleic acid molecule having the sequence set forth in SEQ ID NO:35 encoding a fusion polypeptide having the sequence set forth in SEQ ID NO:36, wherein the fusion polypeptide forms a multimer that is capable of binding a cytokine to form a nonfunctional complex; and an isolated nucleic acid molecule having the sequence set forth in SEQ ID NO:37 encoding a fusion polypeptide having the sequence set forth in SEQ ID NO:38, wherein the fusion polypeptide forms a multimer that is capable of binding a cytokine to form a nonfunctional complex; as well as fusion polypeptides encoded by the above-described nucleic acid molecules.

Other preferred embodiments of the invention are isolated nucleic acid molecules having the sequences set forth in SEQ ID NO: 39, 41, 43, 45, 47, 49, 51, 53, 55, 57, 59, 61, 63, 65, 67, 69, 71, 73, 75, 77, 79, 81, or 83 encoding fusion polypeptides having the sequences set forth in SEQ ID NO: 40, 42, 44, 46, 48, 50, 52, 54, 56, 58, 60, 62, 64, 66, 68, 70, 72, 74, 76, 78, 80, 82, or 84, respectively, wherein each fusion polypeptide forms a multimer that is capable of binding IL-1 to form a non-functional complex.

Also provided is an expression vector comprising a nucleic acid molecule of the invention as described herein, wherein the nucleic acid molecule is operatively linked to an expression control sequence. Also provided is a host-vector system for the production of a fusion polypeptide comprising the expression vector of the invention which has been introduced into a host cell suitable for expression of the fusion polypeptide. The suitable host cell may be a bacterial cell such as *E. coli*, a yeast cell, such as *Pichia pastoris*, an insect cell, such as *Spodoptera frugiperda*, or a mammalian cell, such as a COS, CHO, 293, BHK or NSO cell.

The present invention also provides for methods of producing the fusion polypeptides of the invention by growing cells of the host-vector systems described herein, under conditions permitting production of the fusion polypeptide and recovering the fusion polypeptide so produced.

The present invention provides novel antagonists which are based on receptor components that are shared by cytokines such as the CNTF family of cytokines.

The invention described herein contemplates the production of antagonists to any cytokine that utilizes an a specificity determining component which, when combined with the cytokine, binds to a first a signal transducing component to form a nonfunctional intermediate which then binds to a second β signal transducing component causing β- receptor dimerization and consequent signal transduction. According to the invention, the soluble α specificity determining component of the receptor (sRα) and the extracellular domain of the first β signal transducing component of the cytokine receptor (β1) are combined to form heterodimers (sRα:β1) that act as antagonists to the cytokine by binding the cytokine to form a nonfunctional complex.

The invention described herein also contemplates the production of antagonists to any cytokine that utilizes an α specificity determining component which, when combined with the cytokine, binds to a β signal transducing component to form a receptor complex which then initiates signal transduction. According to the invention, the soluble α specificity determining component of the receptor (sRα) and the extracellular domain of the β signal transducing component of the cytokine receptor (β) are combined to form heterodimers (sRα:β) that act as antagonists to the cytokine by binding the cytokine to form a nonfunctional complex.

As described in Example 1, CNTF and IL-6 share the β1 receptor component gp130. The fact that CNTF forms an intermediate with CNTFRα and gp130 can be demonstrated (Example 1) in cells lacking LIFRβ, where the complex of CNTF and CNTFRα binds gp130, and prevents homodimerization of gp130 by IL-6 and IL-6Rα, thereby blocking signal transduction. These studies provide the basis for the development of the IL-6 antagonists described herein, as they show that if, in the presence of a ligand, a nonfunctional intermediate complex, consisting of the ligand, its α receptor component and its β1 receptor component, can be formed, it will effectively block the action of the ligand. Other cytokines may use other β1 receptor components, such as LIFRβ, which may also be used to produce antagonists according to the present invention.

Thus for example, in one embodiment of the invention, effective antagonists of IL-6 or CNTF consist of heterodimers of the extracellular domains of the α specificity determining components of their receptors (sIL-6Rα and sCNTFRα respectively) and the extracellular domain of gp130. The resultant heterodimers, which are referred to hereinafter as sIL-6Rα:β1 and sCNTFRα:β1, respectively, function as high-affinity Traps for IL-6 or CNTF, respectively, thus rendering the cytokine inaccessible to form a signal transducing complex with the native membrane-bound forms of their receptors.

Although soluble ligand binding domains from the extracellular portion of receptors have proven to be somewhat effective as Traps for their ligands and thus act as antagonists (Bargetzi et al. 1993 Cancer Res 53:4010-4013; and 1992 Proc. Natl. Acad. Sci. USA 89:8616-8620; Mohler et al. 1993 J. Immunol. 151: 1548-1561; Narazaki et al. 1993 Blood 82:1120-1126), the IL-6 and CNTF receptors are unusual in that the a receptor components constitute ligand binding domains that, in concert with their ligands, function effectively in soluble form as receptor agonists (Davis et al. 1993 supra; Taga et al. 1989 Cell 58: 573-581). The sRα:β1 heterodimers prepared according to the present invention provide effective Traps for their ligands, binding these ligands with affinities in the picomolar range (based on binding studies for CNTF to PC12D cells) without creating functional intermediates. The technology described herein may be applied to develop a cytokine Trap for any cytokine that utilizes an α-component that confers specificity, as well as a β component which, when bound to the α-specificity component, has a higher affinity for the cytokine than either component alone. Accordingly, antagonists according to the invention include antagonists of IL-1 through IL-5 (IL-1: Greenfeder, et al. 1995 J Biol Chem 270:13757-13765; Guo et al. 1995 J Biol Chem 270:27562-27568), IL-2 (Taniguchi et al. EP 0386289-A and 0386304-A; Takeshita et al. 1992 Science 257:379-382); IL-3 (Kitamura et al. 1991 Cell 66:1165-1174), IL-4 (Idzerda et al. 1990 J Exp Med 171:861-873), IL-5 (Taverneir et al. 1991 Cell 66:1175-1184), IL-11 (Cherel et al. EMBL/GenBank/DDBJ databases Accession No. Z38102), IL-15 (Hemar et al. 1995 J Cell Biol 1295:55-64); Taniguchi et al. EP 0386289-A and 0386304-A); Takeshita et al. 1992 Science 257:379-382), granulocyte-macrophage colony stimulating factor (GM-CSF) Hayashida et al. 1990 Proc. Natl. Acad. Sci. U.S.A. 97:9655-9659), LIF, γ-interferon (Aguet 1988 et al. Cell 55:273-280; Soh et al. 1994 Cell 76:793-802), and transforming growth factor beta (TGFβ) (Inagaki et al. 1993 Proc. Natl. Acad. Sci. USA 90:5359-5363).

The α and β receptor extracellular domains may be prepared using methods known to those skilled in the art. The CNTFRα receptor has been cloned, sequenced and expressed (Davis et al. 1991 Science 253:59-63 which is incorporated by reference in its entirety herein). The cloning of LIFRβ and gp130 are described in Gearing et al. 1991 EMBO J. 10:2839-2848, Hibi et al. 1990 supra and WO 93/10151, all of which are incorporated by reference in their entirety herein.

The receptor molecules useful for practicing the present invention may be prepared by cloning and expression in a prokaryotic or eukaryotic expression system. The recombinant receptor gene may be expressed and purified utilizing any number of methods. The gene encoding the factor may be subcloned into a bacterial expression vector, such as for example, but not by way of limitation, pCP110.

The recombinant factors may be purified by any technique which allows for the subsequent formation of a stable, biologically active protein. For example, and not by way of limitation, the factors may be recovered from cells either as soluble proteins or as inclusion bodies, from which they may be extracted quantitatively by 8M guanidinium hydrochloride and dialysis. In order to further purify the factors, conventional ion exchange chromatography, hydrophobic interaction chromatography, reverse phase chromatography or gel filtration may be used.

The sRα:β heterodimeric receptors may be engineered using known fusion regions, as described in WO 93/10151 which describes production of β receptor heterodimers, or they may be prepared by crosslinking of extracellular domains by chemical means. The domains utilized may consist of the entire extracellular domain of the α and β components, or they may consist of mutants or fragments thereof that maintain the ability to form a complex with its ligand and other components in the sRα:β1 complex. For example, as described below in Example 4, IL-6 antagonists have been prepared using gp130 that is lacking its three fibronectin-like domains.

In one embodiment of the invention, the extracellular domains are engineered using leucine zippers. The leucine zipper domains of the human transcription factors c-jun and c-fos have been shown to form stable heterodimers (Busch et al. 1990 Trends Genetics 6:36-40; Gentz et al. 1989 Science 243:1695-1699) with a 1:1 stoichiometry. Although junjun homodimers have also been shown to form, they are about 1000-fold less stable than jun-fos heterodimers. Fos-fos homodimers have not been detected.

The leucine zipper domain of either c-jun or c-fos are fused in frame at the C-terminus of the soluble or extracellular domains of the above mentioned receptor components by genetically engineering chimeric genes. The fusions may be direct or they may employ a flexible linker domain, such as the hinge region of human IgG, or polypeptide linkers consisting of small amino acids such as glycine, serine, threonine or alanine, at various lengths and combinations. Additionally, the chimeric proteins may be tagged by His-His-His-His-His- His (His6) (SEQ. ID NO. 1) to allow rapid purification by metal-chelate chromatography, and/or by epitopes to which antibodies are available, to allow for detection on western blots, immunoprecipitation, or activity depletion/blocking in bioassays.

In another embodiment, as described below in Example 3, the sRα:β1 heterodimer is prepared using a similar method, but using the Fc-domain of human IgG1 (Aruffo et al. 1991 Cell 67:35-44). In contrast to the latter, formation of heterodimers must be biochemically achieved, as chimeric molecules carrying the Fc-domain will be expressed as disulfide-linked homodimers. Thus, homodimers may be reduced under conditions that favor the disruption of inter-chain disulfides but do not effect intra-chain disulfides. Then monomers with different extracellular portions are mixed in equimolar amounts and oxidized to form a mixture of homo- and heterodimers. The components of this mixture are separated by chromatographic techniques. Alternatively, the formation of this type of heterodimers may be biased by genetically engineering and expressing molecules that consist of the soluble or extracellular portion of the receptor components followed by the Fc-domain of hIgG, followed by either the c-jun or the c-fos leucine zippers described above (Kostelny et al. 1992 J Immunol 148:1547-1553). Since these leucine zippers form predominately heterodimers, they may be used to drive formation of the heterodimers where desired. As for the chimeric proteins described using leucine zippers, these may also be tagged with metal chelates or an epitope. This tagged domain can be used for rapid purification by metal-chelate chromatography, and/or by antibodies, to allow for detection on western blots, immunoprecipitation, or activity depletion/blocking in bioassays.

In additional embodiments, heterodimers may be prepared using other immunoglobulin derived domains that drive the formation of dimers. Such domains include, for example, the heavy chains of IgG (Cγ1 and Cγ4), as well as the constant regions of kappa (κ) and lambda (λ) light chains of human immunoglobulins. The heterodimerization of Cγ with the light chain occurs between the CH1 domain of Cγ and the constant region of the light chain (CL), and is stabilized by covalent linking of the two domains via a single disulfide bridge. Accordingly, as described in Example 4, constructs may be prepared using these immunoglobulin domains. Alternatively, the immunoglobulin domains include domains that may be derived from T cell receptor components which drive dimerization.

In another embodiment of the invention, the sRα:β1 heterodimers are prepared by expression as chimeric molecules utilizing flexible linker loops. A DNA construct encoding the chimeric protein is designed such that it expresses two soluble or extracellular domains fused together in tandem ("head to head") by a flexible loop. This loop may be entirely artificial (e.g. polyglycine repeats interrupted by serine or threonine at a certain interval) or "borrowed" from naturally occurring proteins (e.g. the hinge region of hIgG). Molecules may be engineered in which the order of the soluble or extracellular domains fused is switched (e.g. sIL6Rα/loop/sgp130 or sgp130/loop/sIL-6Rα) and/or in which the length and composition of the loop is varied, to allow for selection of molecules with desired characteristics.

Alternatively, the heterodimers made according to the present invention may be purified from cell lines cotransfected with the appropriate α and β components. Heterodimers may be separated from homodimers using methods available to those skilled in the art. For example, limited quantities of heterodimers may be recovered by passive elution from preparative, nondenaturing polyacrylamide gels. Alternatively, heterodimers may be purified using high pressure cation exchange chromatography. Excellent purification has been obtained using a Mono S cation exchange column.

In addition to sRα:β1 heterodimers that act as antagonists by binding free CNTF or IL-6, the present invention also contemplates the use of engineered, mutated versions of IL-6 with novel properties that allow it to bind to IL-6Rα and a single gp130 molecule, but fail to engage the second gp130 to complete β component homodimerization, and thus act as an effective IL-6 antagonist on any IL-6 responsive cell. Our model for the structure of the IL-6 and CNTF receptor complexes indicates that these cytokines have distinct sites for binding the α, β1, and β2 receptor components (Stahl et al. 1993 supra). Mutations of critical amino acid residues comprising each of these sites gives rise to novel molecules which have the desired antagonistic properties. Ablation of the β1 site would give a molecule which could still bind to the a receptor component but not the β1 component, and thereby comprise an antagonist with nanomolar affinity. Mutations of critical amino acid residues comprising the β2 site of IL-6 (IL-6β2-) would give a molecule that would bind to IL-6Rα and the first gp130 monomer, but fail to engage the second gp130 and thus be functionally inactive. Similarly, mutations of the CNTF β2 site would give a molecule (CNTFβ2-) that would bind CNTFRα and gp130, but fail to engage LIFRβ, thereby antagonizing CNTF action by forming the non-functional β1 intermediate. Based on the binding results described above where CNTF forms the β1 intermediate with high affinity, both CNTFβ2- and IL-6β2- would constitute antagonists with affinity in the range of 10 pM.

A variety of means are used to generate and identify mutations of IL-6 or CNTF that have the desired properties. Random mutagenesis by standard methods of the DNA encoding IL-6 or CNTF may be used, followed by analysis of the collection of products to identify mutated cytokines having the desired novel properties as outlined below. Mutagenesis by genetic engineering has been used extensively in order to elucidate the structural organization of functional domains of recombinant proteins. Several different approaches have been described in the literature for carrying out deletion or substitution mutagenesis. The most successful appear to be alanine scanning mutagenesis (Cunningham et al. 1989 Science 244:1081-1085) and homolog-scanning mutagenesis (Cunningham et al. 1989 Science 243:1330-1336).

Targeted mutagenesis of the IL-6 or CNTF nucleic acid sequences using such methods can be used to generate CNTFβ2- or IL-6β2- candidates. The choice of regions appropriate for targeted mutagenesis is done systematically, or determined from studies whereby panels of monoclonal antibodies against each factor are used to map regions of the cytokine that might be exposed after binding of the cytokine to the a receptor component alone, or to the αβ1 heterodimeric soluble receptors described above. Similarly, chemical modification or limited proteolysis of the cytokine alone or in a complex bound to the a receptor component or the apl heterodimeric soluble receptors described above, followed by analysis of the protected and exposed regions could reveal potential β2 binding sites.

Assays for identifying CNTF or IL-6 mutants with the desired properties involve the ability to block with high affinity the action of IL-6 or CNTF on appropriately responsive cell lines (Davis et al. 1993 supra; Murakami et al. 1991 Proc Natl Acad Sci USA 88:11349-11353). Such assays include cell proliferation, survival, or DNA synthesis driven by CNTF or IL-6, or the construction of cell lines where binding of factor induces production of reporters such as CAT or β-galactosidase (Savino et al. 1993 Proc Natl Acad Sci USA 90:4067-4071).

Alternatively, the properties of various mutants may be assessed with a receptor-based assay. One such assay consists of screening mutants for their ability to bind the sRα:β1 receptor heterodimers described above using epitope-tagged (Davis et al. 1991 supra) sRα:β1 reagents. Furthermore, one can probe for the presence or absence of the β2 site by assessing whether an epitope-tagged soluble β2 reagent will bind to the cytokine in the presence of the β1 heterodimer. For example, CNTF only binds to LIFRβ (the β2 component) in the presence of both CNTFRα and gp130 (Davis et al. 1993 supra; Stahl et al. 1993 supra). Thus a soluble LIFRβ reagent would only bind to CNTF in the presence of the soluble sRα:β1 dimer sCNTFRα:β1. For IL-6, the sRα:β1 reagent would be IL-6Rα:β1, and the probe for the β2 site would be epitope-tagged sgp130. Thus β2- mutants of CNTF would be identified as those that bound the sRα:β1 reagent, demonstrating that the α and β1 site of the cytokine were intact, yet failed to bind the β2 reagent.

In addition, the present invention provides for methods of detecting or measuring the activity of potential β2- mutants by measuring the phosphorylation of a β-receptor component or a signal transduction component selected from the group consisting of Jak1, Jak2 and Tyk2 or any other signal transduction component, such as the CLIPs, that are determined to be phosphorylated in response to a member of the CNTF family of cytokines.

A cell that expresses the signal transduction component(s) described herein may either do so naturally or be genetically engineered to do so. For example, Jak1 and Tyk-2-encoding nucleic acid sequences obtained as described in Velazquez et al. 1992 Cell 70:313-322, may be introduced into a cell by transduction, transfection, microinjection, electroporation, via a transgenic animal, etc., using any known method known in the art.

According to the invention, cells are exposed to a potential antagonist and the tyrosine phosphorylation of either the β-component(s) or the signal transduction component(s) are compared to the tyrosine phosphorylation of the same component(s) in the absence of the potential antagonist.

In another embodiment of the invention, the tyrosine phosphorylation that results from contacting the above cells with the potential antagonist is compared to the tyrosine phosphorylation of the same cells exposed to the parental CNTF family member. In such assays, the cell must either express the extracellular receptor (α-component) or the cells may be exposed to the test agent in the presence of the soluble receptor component. Thus, for example, in an assay system designed to identify agonists or antagonists of CNTF, the cell may express the α-component CNTFRα, the β-components gp130 and LIFRβ and a signal transducing component such as Jak1. The cell is exposed to test agents, and the tyrosine phosphorylation of either the β-components or the signal transducing component is compared to the phosphorylation pattern produced in the presence of CNTF. Alternatively, the tyrosine phosphorylation which results from exposure to a test agent is compared to the phosphorylation which occurs in the absence of the test agent. Alternatively, an assay system, for example, for IL-6 may involve exposing a cell that expresses the β-component gp130 and a signal transducing protein such as Jak1, Jak2 or Tyk2 to a test agent in conjunction with the soluble IL-6 receptor.

In another embodiment of the invention the above approaches are used to develop a method for screening for small molecule antagonists that act at various steps in the process of ligand binding, receptor complex formation, and subsequent signal transduction. Molecules that potentially interfere with ligand-receptor interactions are screened by assessing interference of complex formation between the soluble receptors and ligand as described above. Alternatively, cell-based assays in which IL-6 or CNTF induce response of a reporter gene are screened against libraries of small molecules or natural products to identify potential antagonists. Those molecules showing antagonist activity are rescreened on cell-based assays responding to other factors (such as GM-CSF or factors like Neurotrophin-3 that activate receptor tyrosine kinases) to evaluate their specificity against the CNTF/IL-6/OSM/LIF family of factors. Such cell-based screens are used to identify antagonists that inhibit any of numerous targets in the signal transduction process.

In one such assay system, the specific target for antagonists is the interaction of the Jak/Tyk family of kinases (Firmbach-Kraft 1990 Oncogene 5:1329-1336; Wilks et al. 1991 Mol Cell Biol 11:2057-2065) with the receptor 13 subunits. As described above, LIFRβ and gp130 preassociate with members of the Jak/Tyk family of cytoplasmic protein tyrosine kinases, which become activated in response to ligand-induced β component dimerization (Stahl et al. 1993 supra). Thus small molecules that could enter the cell cytoplasm and disrupt the interaction between the β component and the Jak/Tyk kinase could potentially block all subsequent intracellular signaling. Such activity could be screened with an in vitro scheme that assessed the ability of small molecules to block the interaction between the relevant binding domains of purified β component and Jak/Tyk kinase. Alternatively, one could easily screen for molecules that could inhibit a yeast-based assay of β component binding to Jak/Tyk kinases using the two-hybrid interaction system (Chien et al. 1991 Proc. Natl. Acad. Sci. 88: 9578-9582). In such a system, the interaction between two proteins (a component and Jak/Tyk kinase or relevant domains thereof in this example) induces production of a convenient marker such as β-galactosidase. Collections of small molecules are tested for their ability to disrupt the desired interaction without inhibiting the interaction between two control proteins. The advantage of this screen would be the requirement that the test compounds enter the cell before inhibiting the interaction between the b component and the Jak/Tyk kinase.

The CNTF family antagonists described herein either bind to, or compete with the cytokines CNTF and IL-6. Accordingly, they are useful for treating diseases or disorders mediated by CNTF or IL-6. For example, therapeutic uses of IL-6 antagonists would include the following: (1) In osteoporosis, which can be exacerbated by lowering of estrogen levels in post-menopausal women or through ovariectomy, IL-6 appears to be a critical mediator of osteoclastogenesis, leading to bone resorption (Horowitz 1993 Science 260:626-627; Jilka et al. 1992 Science 257:88-91). Importantly, IL-6 only appears to play a major role in the estrogen-depleted state, and apparently is minimally involved in normal bone maintenance. Consistent with this, experimental evidence indicates that function-blocking antibodies to IL-6 can reduce the number of osteoclasts (Jilka et al. 1992 Science 257:88-91). While estrogen replacement therapy is also used, there appear to be side effects that may include increased risk of endometrial and breast cancer. Thus, IL-6 antagonists as described herein would be more specific to reduce osteoclastogenesis to normal levels; (2) IL-6 appears to be directly involved in multiple myeloma by acting in either an autocrine or paracrine fashion to promote tumor formation (van Oers et al. 1993 Ann Hematol 66:219-223). Furthermore, the elevated IL-6 levels create undesirable secondary effects such as bone resorption, hypercalcemia, and cachexia; in limited studies function-blocking antibodies to IL-6 or IL-6Rα have some efficacy (Klein et al. 1991 Blood 78:1198-1204; Suzuki et al. 1992 Eur J Immunol 22:1989-1993). Therefore, IL-6 antagonists as described herein would be beneficial for both the secondary effects as well as for inhibiting tumor growth; (3) IL-6 may be a mediator of tumor necrosis factor (TNF) that leads to cachexia associated with AIDS and cancer (Strassmann et al. 1992 J Clin Invest 89:1681-1684), perhaps by reducing lipoprotein lipase activity in adipose tissue (Greenberg et al. 1992 Cancer Research 52:4113-4116). Accordingly, antagonists described herein would be useful in alleviating or reducing cachexia in such patients.

Effective doses useful for treating these or other CNTF family related diseases or disorders may be determined using methods known to one skilled in the art [see, for example, Fingl et al. 1975 The Pharmacological Basis of Therapeutics, Goodman and Gilman, eds. Macmillan Publishing Co., New York, pp. 1-46). Pharmaceutical compositions for use according to the invention include the antagonists described above in a pharmacologically acceptable liquid, solid or semi-solid carrier, linked to a carrier or targeting molecule (e.g., antibody, hormone, growth factor, etc.) and/or incorporated into liposomes, microcapsules, and controlled release preparation (including antagonist expressing cells) prior to administration in vivo. For example, the pharmaceutical composition may comprise one or more of the antagonists in an aqueous solution, such as sterile water, saline, phosphate buffer or dextrose solution. Alternatively, the active agents may be comprised in a solid (e.g. wax) or semi-solid (e.g. gelatinous) formulation that may be implanted into a patient in need of such treatment. The administration route may be any mode of administration known in the art, including but not limited to intravenously, intrathecally, subcutaneously, by injection into involved tissue, intraarterially, intranasally, orally, or via an implanted device.

Administration may result in the distribution of the active agent of the invention throughout the body or in a localized area. For example, in some conditions which involve distant regions of the nervous system, intravenous or intrathecal administration of agent may be desirable. In some situations, an implant containing active agent may be placed in or near the lesioned area. Suitable implants include, but are not limited to, gelfoam, wax, or microparticle-based implants.

EXAMPLES

Example 1

CNTF Competes with IL-6 for Binding to gp130

Materials and methods. A clone of PC12 cells that respond to IL-6 (PC12D) was obtained from DNAX. Rat CNTF was prepared as described (Masiakowski et al. 1991 J Neurochem 57:1003-10012). IL-6 and sIL-6Rα were purchased from R & D Systems. Antisera was raised in rabbits against a peptide derived from a region near the C-terminus of gp130 (CGTEGQVERFETVGME) (SEQ ID NO:2) by the method of Stahl et al. 1993 J Biol Chem 268:7628-7631. Anti-phosphotyrosine monoclonal 4G10 was purchased from UBI, and reagents for ECL from Amersham.

Signal Transduction Assays. Plates (10 cm) of PC12D were starved in serum-free medium (RPMI 1640+glutamine) for 1 hour, then incubated with IL-6 (50 ng/mL)+sIL-6R (1 mg/mL) in the presence or absence of added rat CNTF at the indicated concentrations for 5 minutes at 37° C. Samples were then subjected to anti-gp130 immunoprecipitation, SDS PAGE, and anti-phosphotyrosine immunoblotting.

Figure 2:
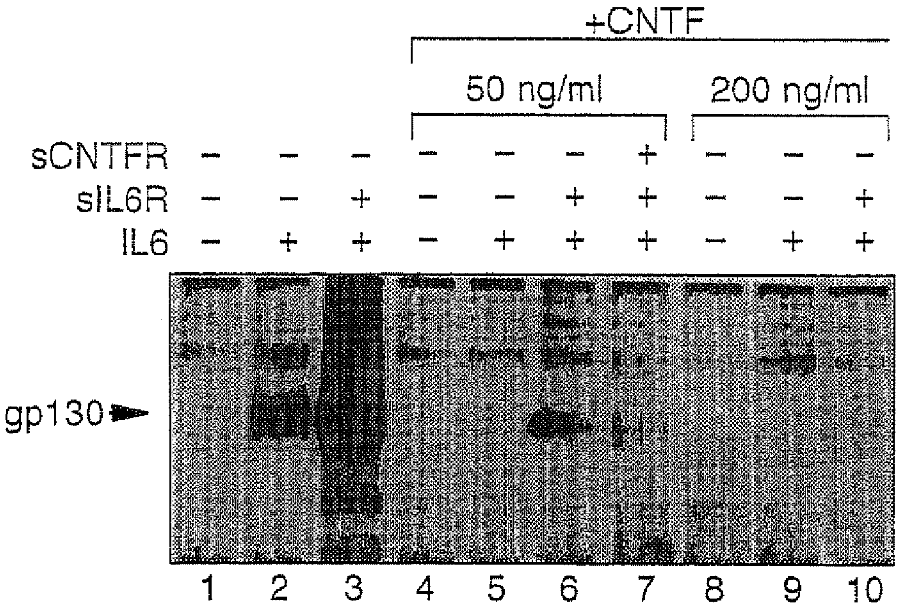
FIG. 2: CNTF inhibits IL-6 responses in a PC12 cell line (called PC12D) that expresses IL6Rα, gp130, CNTFRα, but not LIFRβ. Serum-deprived PC12D cells were incubated+ IL-6 (50 ng/mL) in the presence or absence of CNTF as indicated. Some plates also received soluble IL6Rα (1 mg/mL) or soluble CNTFRα (1 mg/mL) as indicated. Cell lysates were subjected to immunoprecipitation with anti-gp130 and immunoblotted with anti-phosphotyrosine. Tyrosine phosphorylation of gp130 is indicative of IL-6 induced activation of the IL-6 receptor system, which is blocked upon coaddition of CNTF.

Results. The ability of CNTF to block IL-6 responses was measured using a PC12 cell line (called PC12D) that expresses IL-6Rα, gp130, and CNTFRα, but not LIFRβ. As one would predict, these cells respond to IL-6, but not to CNTF (FIG. 2) since LIFRβ is a required component for CNTF signal transduction (Davis et al. 1993 supra). In accordance with results on other cell lines (Ip et al. 1992 supra), PC12D cells give tyrosine phosphorylation of gp130 (as well as a variety of other proteins called CLIPs) in response to 2 nM IL-6 (FIG. 2). Addition of recombinant soluble IL-6Rα (sIL-6Rα) enhances the level of gp130 tyrosine phosphorylation, as has been reported in some other systems (Taga et al. 1989 supra). However, addition of 2 nM CNTF simultaneously with IL-6 severely diminishes the tyrosine phosphorylation of gp130. Although a slight gp130 phosphorylation response remains in the presence of CNTF, IL-6, and sIL-6Rα, it is eliminated if the CNTF concentration is increased fourfold to 8 nM. Thus, in IL-6 responsive cells that contain CNTFRα but no LIFRβ, CNTF is a rather potent antagonist of IL-6 action.

Example 2.

Binding of CNTF to the CNTFRα:β

Scatchard Analysis of CNTF Binding. $^{125}$I-CNTF was prepared and purified as described [Stahl et al. 1993 supra). Saturation binding studies were carried out in PC12 cells, using concentrations of $^{125}$I-CNTF ranging from 20 pM to 10 nM. Binding was performed directly on a monolayer of cells. Medium was removed from wells and cells were washed once with assay buffer consisting of phosphate buffered saline (PBS; pH 7.4), 0.1 mM bacitracin, 1 mM PMSF, 1 mg/ml leupeptin, and 1 mg/ml BSA. Cells were incubated in $^{125}$I-CNTF for 2 hours at room temperature, followed by 2 quick washes with assay buffer. Cells were lysed with PBS containing 1% SDS and counted in a Packard Gamma Counter at 90-95% efficiency. Non-specific binding was defined by the presence of 100-fold excess of unlabelled CNTF. Specific binding ranged from 70% to 95%.

Figure 3:
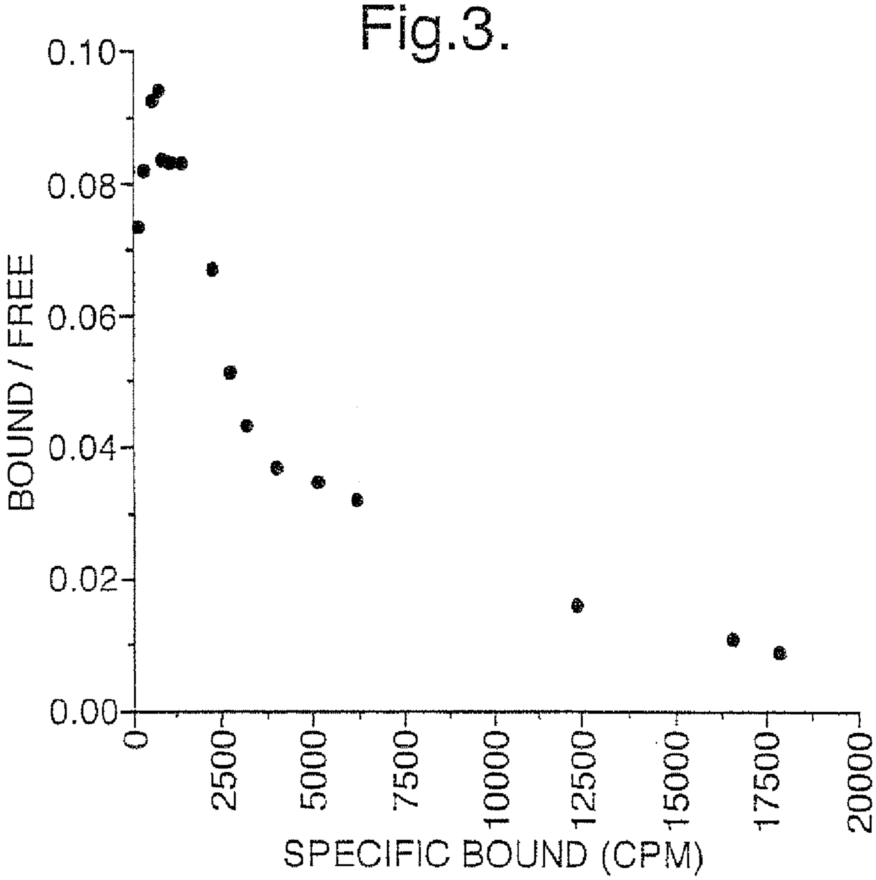
FIG. 3: Scatchard analysis of iodinated CNTF binding on PC12D cells. PC12D cells were incubated with various concentrations of iodinated CNTF in the presence or absence of excess non-radioactive competitor to determine the specific binding. The figure shows a Scatchard plot of the amount of iodinated CNTF specifically bound, and gives data consistent with two binding sites with dissociation constants of 9 pM and 3.4 nM.

Results. The equilibrium constant for binding of CNTF to CNTFRα:β1 was estimated from Scatchard analysis of iodinated CNTF binding on PC12D cells (FIG. 3). The data is consistent with a 2 site fit having dissociation constants of 9 pM and 3.4 nM. The low affinity site corresponds to interaction of CNTF with CNTFRα, which has a Kd near 3 nM (Panayotatos et al. 1993 J Biol Chem 268: 19000-19003). We interpret the high affinity complex as the intermediate containing CNTF, CNTFRα, and gp130. A Ewing sarcoma cell line (EW-1) which does contain CNTFRα, gp130, and LIFRβ, and therefore gives robust tyrosine phosphorylation in response to CNTF, displays a very similar two site fit with dissociation constants of 1 nM and 10. Thus it is apparent that CNTF binds with equally high affinity to a complex containing only CNTFR and gp130, as it does to a complex which additionally contains LIFRβ, thus demonstrating the feasibility of creating the sRα:β antagonists described herein.

Example 3

Methods of Producing Cytokine Ligand Traps

Virus Stock Production. SF21 insect cells obtained from *Spodoptera frugiperda* were grown at 27° C. in Gibco SF900 II medium to a density of 1×10$^6$ cells/mL. The individual virus stock for either GP130-Fc-$His_6$ (FIGS. 4A-4B, SEQ ID NO:7) or IL6Rα-Fc (FIG. 5, SEQ ID NO:8) was added to the bioreactorto a low multiplicity 0.01-0.1 PFU/cell to begin the infection. The infection process was allowed to continue for 5-7 days allowing maximum virus replication without incurring substantial cell lysis. The cell suspension was aseptically aliquoted into sterile centrifuge bottles and the cells removed by centrifugation. The cell-free supernatant was collected in sterile bottles and stored at 4° C. until further use.

The virus titer was determined by plaque assay and is carried out in 60 mm tissue-culture dishes which are seeded with $2\times10^6$ cells. Serial dilutions of the virus stock are added to the attached cells and the mixture incubated with rocking to allow the virus to adsorb to individual cells. An agar overlay is added and plates incubated for 5-7 days at 27° C. Staining of viable cells with neutral red revealed circular plaques resulting which were counted to give the virus titer.

Coinfection of Cells for Protein Production. Uninfected SF21 Cells were grown in a 60 Lgg ABEC bioreactor containing 40 L of SF900 II medium. Temperature was controlled at 27° C. and the dissolved oxygen level was maintained at 50% of saturation by controlling the flow rate of oxygen in the inlet gas stream. When a density of $2\times10^6$ cells/mL was reached, the cells were concentrated within the bioreactor to a volume of 20 L using a low shear steam sterilizable pump with a tangential flow filtration device with Millipore Prostak 0.65 micron membranes. After concentration fresh sterile growth medium is slowly added to the bioreactor while the filtration system continues to remove the spent growth medium by diafiltration. After two volume exchanges (40 L) have been carried out an additional 20 L of fresh medium was added to the bioreactor to resuspend the cells to the original volume of 40 L. The cell density was determined once again by counting viable cells using a hemacytometer.

The required amount of each virus stock was calculated based on the cell density, virus titer and the desired multiplicity of infection (MOI). Virus stock ratios of 5:1, 5:2, 10:2 and 10:4, IL6Rα-Fc to GP130-Fc-$His_6$ all resulted in production of significant amounts of heterodimer. The ideal virus stock ratio is highly dependent on the ease of purification of the heterodimer from each of the two homodimers. The IL6Rα-Fc homodimer is relatively easy to remove downstream by immobilized metal affinity chromatography. Virus infection ratios have been chosen to minimize the formation of the GP130-Fc-$His_6$ homodimer which is more difficult to clear downstream. The relative amount of GP130-Fc-$His_6$ virus stock chosen for infection has increased with successive batches as the purification method for clearing the resultant homodimer has improved.

The virus stocks were aseptically mixed in a single vessel then transferred to the bioreactor. This results in synchronous infection of the SF21 cells. The infection is allowed to proceed for three to four days, allowing sufficient time for maximal production of the heterodimer protein.

Recovery and Protein A Chromatographic Purification. At the conclusion of the infection phase of the bioreactor process the cells were concentrated in the bioreactor using a 10 $ft^2$ Millipore Prostak filter (0.65 micron) pore size. The cell-free permeate passing through the filter was collected in a clean process vessel. At the conclusion of the filtration operation the pH of permeate stream, containing the protein product, was adjusted to 8.0 with 10 N NaOH. The resultant precipitate was removed by forcing the extract through a 0.8 micron depth filter (Sartorious), followed by a 0.2 micron filter. Sufficient 0.5 M EDTA stock was added to give a final concentration of 5 mM. The filtered protein solution was loaded onto a 10 cm diameter column containing 100-200 mL of Pharmacia Protein A Sepharose 4 Fast Flow, equilibrated with PBS. Protein A has a very high affinity for the Fc-Fc domain of each of the 3 recombinant protein products, allowing them to bind while other proteins in the cell-free extract flow through the column. After loading the column was washed to baseline with PBS containing an additional 350 mM NaCl. The IgG-Fc tagged proteins were eluted at low pH, either with 0.5 M acetic acid or with a decreasing pH gradient of 0.1 M citric acid and 0.2 M disodium phosphate buffers. Tris base or disodium phosphate was added to the eluted protein to avoid prolonged exposure to low pH conditions.

The pooled protein was diafiltered into PBS or HEPES buffer and derivitized with 1 mM iodoacetamide to protect the exposed sulfhydryl group on the free cysteine near the hinge region of each Fc domain. This prevents disulfide mediated aggregation of proteins. A 6 $ft^2$ Millipore spiral wound ultrafiltration membrane with nominal 30 kDa cutoff was used to perform the buffer exchange. The total protein was determined by UV absorbance at 280 nm using the diafiltration buffer as a blank. The relative amounts of heterodimer and two homodimer proteins were determined by SDS PAGE gel electrophoresis using a 6% Tris-Glycine gel (Novex). Gels were Coomassie-stained then transferred into destain solution overnight. A Shimadzu scanning densitometer was used to determine the relative intensity of the individual protein bands on the SDS PAGE gel. The peak area ratios are used to compute the fraction of heterodimer and each of the homodimers in the column pool fractions.

Immobilized Metal Affinity Chromatographic Purification. The six histidine residues on the C-terminus of the GP130-Fc-$His_6$ fusion protein provides an excellent molecular handle for separation of the heterodimeric IL6 antagonist from the two homodimers. The imidazole group on each of the C-terminal histidines of the GP130-Fc-$His_6$ moiety has a strong binding constant with several divalent metals, including copper, nickel, zinc, cobalt, iron and calcium. Since the IL6Rα-Fc homodimer has no C-terminal histidine residues, it clearly has the lowest affinity. The IL6Rα-Fc-GP130-Fc-$His_6$ heterodimer has a single stand set six histidines giving it greater affinity for the metal, while the GP130-Fc-$His_6$ homodimer has two sets of six histidines each giving it the highest affinity of the three IgG tagged proteins to the metal affinity column. Selective elution of the three proteins with increasing amounts of imidazole in the elution buffer therefore elutes the proteins in the following order: 1. IL6Rα-Fc homodimers, 2. IL6Rα-Fc-GP130-Fc-His heterodimer, 3. GP130-Fc-His homodimers.

A 26 mm diameter column containing 100 mL of Pharmacia Chelating Sepharose Fast Flow was saturated with a solution of nickel sulfate until a significant green color is observed in the column eluate. The column is then washed with several column volumes of deionized water, then equilibrated with 50 mM HEPES, 40 mM imidazole, pH 8.0. The binding of imidazole to the immobilized nickel results in a green to blue color change. Imidazole was added to the protein load to a final concentration of 40 mM. Addition of imidazole to the protein load reduces the binding of IL6Rα-Fc homodimer, increasing the surface area available for the remaining two species. After loading, the column was washed with several column volumes of 50 mM HEPES, 80 mM imidazole, pH 8.0 until a steady baseline was reestablished. The heterodimer was selectively eluted with 50 mM HEPES, 150 mM imidazole, pH 8.0 over several column volumes. The protein fractions were pooled and diafiltered into PBS as described in the section above.

Example 4

Alternative Methods of Constructing Ligand Traps

Figure 6:
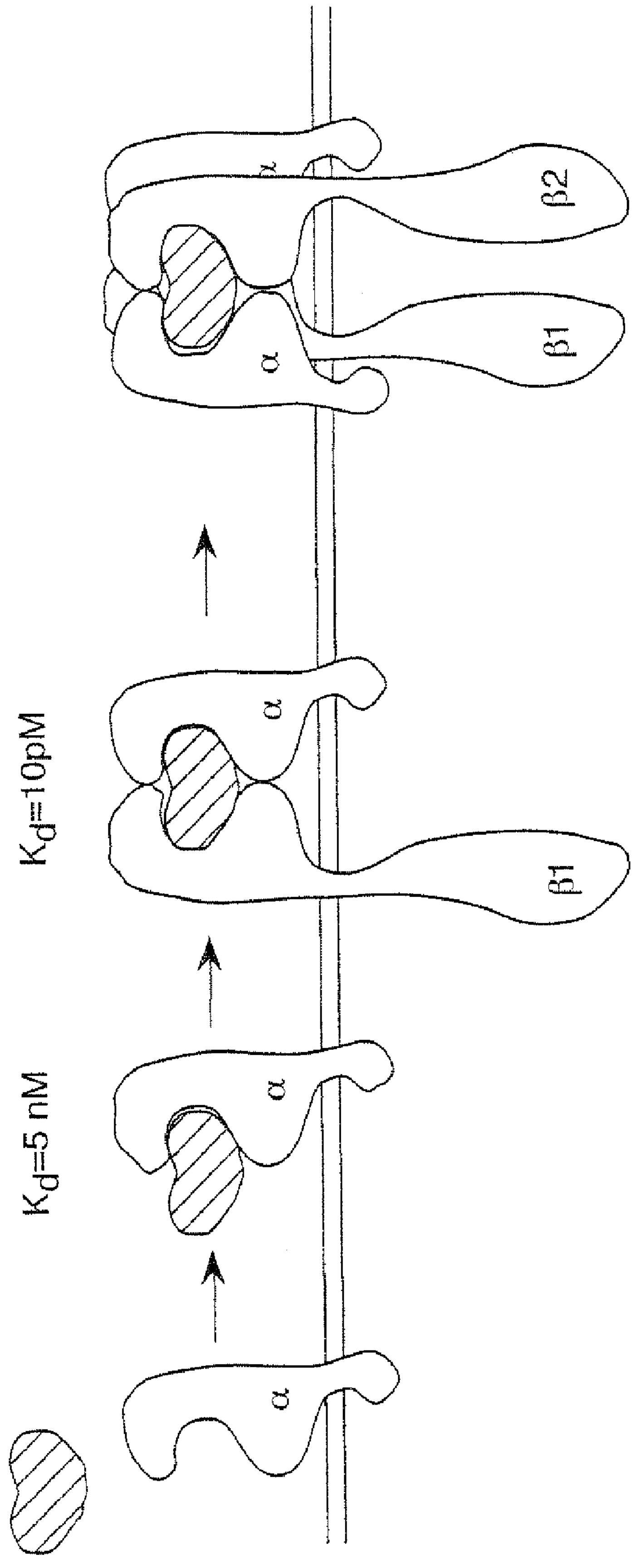
FIG. 6: The CNTF/IL-6/IL-11 receptor system. The ordered formation of the hexameric signal transducing receptor complex is depicted schematically. The cytokine associates with the Ra component to form an obligatory cytokine•Rα complex (Kd is about 5 nM). This low affinity complex next associates with the first signal transducing component, marked β1, to form a high affinity cytokine•Rα•β1 complex (Kd is about 10 pM). In the case of IL-6Rα, this component is gp130. This trimeric high affinity complex subsequently associates with another such complex. Formation of this complex results in signal transduction as it involves dimerization of two signal transducing components, marked β1 and β2 respectively (adapted from (Ward et al., J. Bio. Chem. 269:23286-23289 (1994); Stahl and Yancopoulos, J. Neurobiology 25:1454-1466 (1994); Stahl and Yancopoulos, Cell 74:587-590 (1993).

As described above, receptor activation by CNTF, and analogously by IL-6 and IL-11, follows an ordered sequence of binding events (FIG. 6). The cytokine initially binds to its cognate Rα with low affinity (Kd=3 to 10 nM); this is a required step—cells which do not express the cognate Rα do not respond to the cognate cytokine. The cytokine•Rα complex associates with the first signal transducing component, gp130, to form a high affinity complex (Kd in the order of 10 pM for the CNTF•CNTFRα•gp130 complex). This complex does not transduce signal, as it is the dimerization of the signal transducing components that brings about signaling (Stahl et al. 1994 J Neurobiology 25:1454-1466; Stahl et al. 1995 Science 267:1349-1353; Davis et al. 1993 supra; Stahl et al. 1994 Science 263:92-95; Murakami et al. 1993 Science 260:1808-1810). At least in the case of IL-6, the cytokine•Rα•signal transducer heterotrimeric complex subsequently associates with another like complex, to form a hexameric complex (FIG. 6) (Ward et al. 1994 J Biol Chem 269:23286-23289). The resulting dimerization of the signal transducers—gp130 in the case of IL-6 (Murakami et al. 1993 supra) and IL-11, gp130 and LIFR in the case of CNTF (Davis et al. 1993 supra)—brings about signal transduction.

Figure 7:
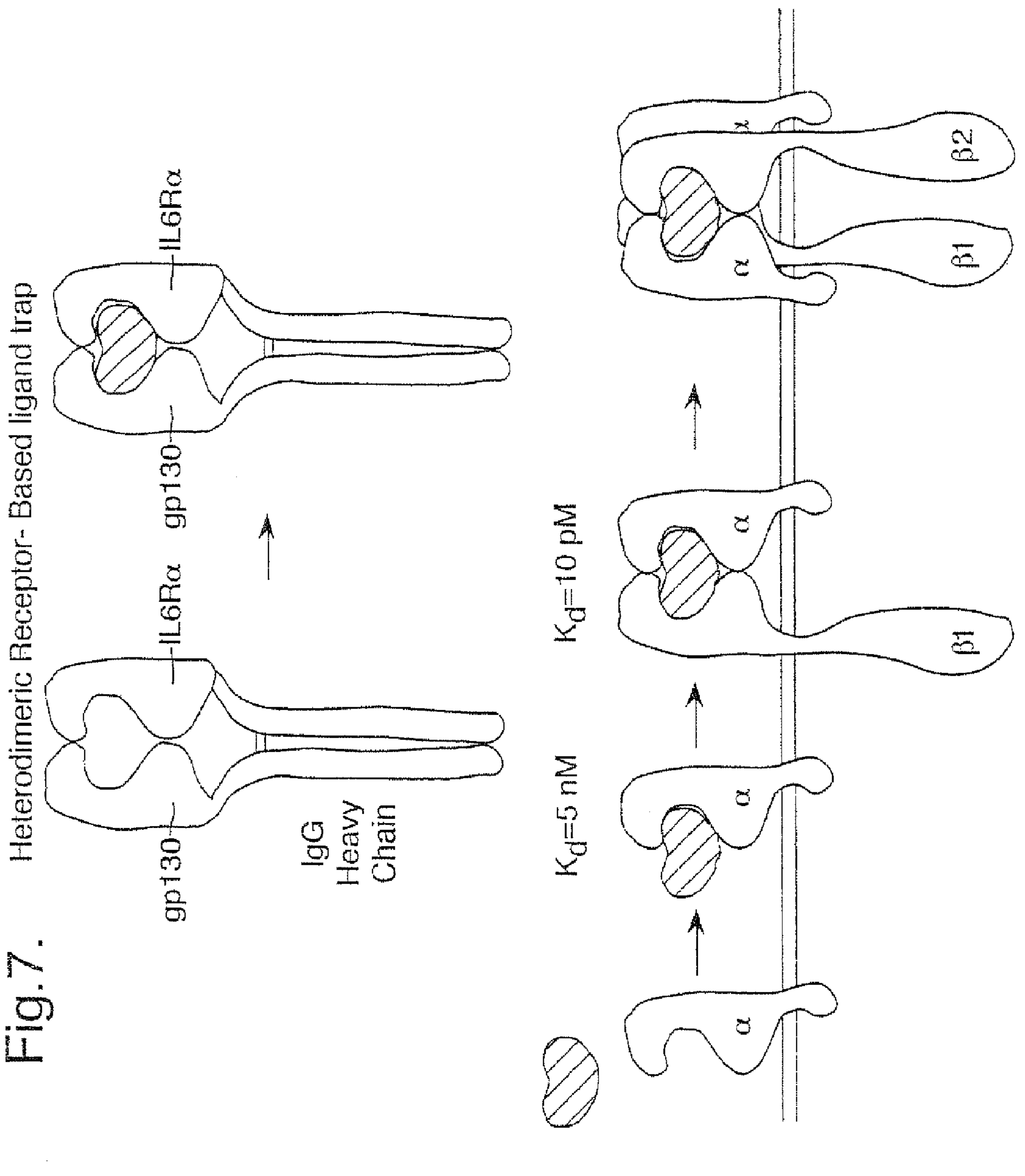
FIG. 7: Design of heterodimeric receptor-based ligand Traps for IL-6. The heterodimeric ligand Trap is comprised of two interdisulfide linked proteins, gp130-Fc and IL-6Rα-Fc. The gp130-Fc•IL-6Rα-Fc complex (upper panel) is shown to mimic the high affinity cytokine•Rα•β1 complex (lower panel). The ligand Trap functions as an antagonist by sequestering IL-6 and thus rendering unavailable to interact with the native receptors on IL-6-responsive cells.

The initial heterodimeric molecules made comprised a soluble Rα-component linked to the extracellular domain of gp130. These molecules were shown to mimic the high affinity cytokine•Rα•gp130 complex and behave as a high affinity antagonist of their cognate cytokine (FIG. 7). To make these molecules, the extracellular domain of gp130 was paired with the extracellular domain of the α-receptor components for IL-6 and CNTF, IL-6Rα and CNTFRα respectively. To link the Rα with the extracellular domain of gp130, the soluble Rα-components and gp130 were fused to the Fc portion of human IgG1 to produce Rα-Fc and gp130-Fc respectively. The Fc domain was chosen primarily but not solely because it naturally forms disulfide-linked dimers. Heterodimeric molecules comprising Rα-Fc•gp130-Fc were expressed, purified and shown to behave as highly potent antagonists of their cognate ligand. Furthermore, these molecules were found to be highly specific for their cognate cytokine since it is the choice of the a receptor component which specifies which cytokine is bound and trapped (there is no measurable binding of the cytokine to gp130 in the absence of the appropriate Rα).

Here we describe an extension of this technology which allows the engineering of different heteromeric soluble receptor ligand Traps which by virtue of their design may have additional beneficial characteristics such as stability, Fc-receptor-mediated clearance, or reduced effector functions (such as complement fixation). Furthermore, the technology described should prove suitable for the engineering of any heteromeric protein in mammalian or other suitable protein expression systems, including but not limited to heteromeric molecules which employ receptors, ligands, and catalytic components such as enzymes or catalytic antibodies.

Figure 8:
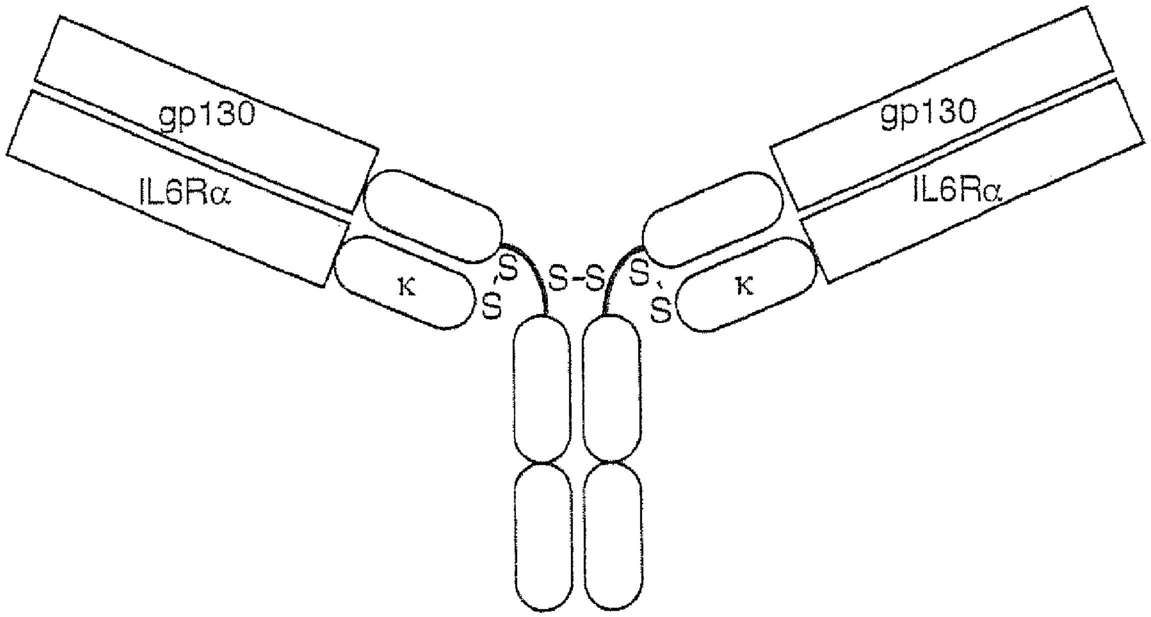
FIG. 8. Heteromeric immunoglobulin Heavy/Light Chain Receptor Fusions. An example of a heavy/light chain receptor fusion molecule is schematically depicted. The extracellular domain of gp130 is fused to Cγ, whereas the extracellular domain of IL-6Rα is fused to the constant region of the kappa chain (κ). The inter-chain disulfide bridges are also depicted (S-S).

Genetic engineering of heteromeric immunoglobulin heavy/light chain soluble receptor-based ligand Traps for IL-6. The IL-6 Traps described here were engineered using human gp130, human IL-6 α-receptor (IL-6Rα), the constant region of the heavy chains (Cγ) of human IgG1 (Cγ1) (Lewis et al. 1993 J Immunology 151:2829-2838) or IgG4 (Cγ4) with or without a join-region (J), and the constant regions of kappa (κ) and lambda (λ) (Cheung et al. 1992 J Virology 66:6714-6720) light chains of human immunoglobulin (Ig), also with or without a different j-peptide (j). This design takes advantage of the natural ability of the Cγ domain to heterodimerize with κ or λ light chains. The heterodimerization of Cγ with the light chain occurs between the CH1 domain of Cγ and the constant region of the light chain ($C_L$), and is stabilized by covalent linking of the two domains via a single disulfide bridge. We reasoned that, like the Fc domain of human IgG1, the combination of Cγ with $C_L$ could be used to produce disulfide linked heteromeric proteins comprised of the extracellular domain of gp130 on one chain and the extracellular domain of IL-6Rα on the other chain. Like their Fc-based counterparts, such proteins were postulated to be high affinity ligand Traps for IL-6 and as a result to inhibit the interaction of IL-6 with the native receptor on IL-6-responsive cells, thus functioning as IL-6 antagonists. Furthermore, constructs employing the full length Cγ region would, much like antibodies, form homodimers of the Cγ chain, giving rise to antibody-like molecules comprising of two "light chains" and two "heavy chains" (FIG. 8). The potential advantage of this design is that it may more closely mimic the IL-6•IL-6Rα•gp130 complex and may display a higher affinity for the ligand than comparable single heterodimers. An additional design is incorporated by using truncated versions of Cγ, comprised only of the $C_H1$ domain. These will form heterodimeric molecules with receptor-κ fusion proteins, and will thus resemble the Fab fragment of antibodies.

All the soluble receptor-Ig chimeric genes may be engineered in plasmid vectors including, but not limited to, vectors suitable for mammalian expression (COS monkey kidney cells, Chinese Hamster Ovary cells (CHO), and ras-transformed fibroblasts (MG-ras) and include a Kozak sequence (CGC CGC CAC CAT GGT G) (SEQ ID NO: 3) at the beginning of each chimeric gene for efficient translation. Engineering was performed using standard genetic engineering methodology. Each construct was verified by DNA sequencing, mammalian expression followed by western blotting with suitable antibodies, biophysical assays that determine ligand binding and dissociation, and by growth inhibition assays (XG-1, as described later). Since the domains utilized to engineer these chimeric proteins are flanked by appropriate restriction sites, it is possible to use these domains to engineer other chimeric proteins, including chimeras employing the extracellular domains of the receptors for factors such as IL-1, IL-2, IL-3, IL-4, IL-5, GM-CSF, LIF, IL-11, IL-15, IFNγ, TGFβ, and others. The amino acid coordinates for each component utilized in making the IL-6 Traps are listed below (Note: numbering starts with the initiating methionine as 1; long sequences are listed using the single letter code for the twenty amino acids):

(a) Constructs employing human gp130: (i) gp130-Cγ1 was engineered by fusing in frame the extracellular domain of gp130 (amino acids 1 to 619) to a Ser-Gly bridge, followed by the 330 amino acids which comprise Cγ1 and a termination codon (SEQ ID NO: 9).

(ii) gp130-J-Cγ1 was engineered in the same manner as gp130-Cγ1 except that a J-peptide (amino acid sequence: GQGTLVTVSS) (SEQ ID NO: 4) was inserted between the Ser-Gly bridge and the sequence of Cγ1 (SEQ ID NO: 9).

(iii) gp130Δ3fibro-Cγ1 was engineered by fusing in frame the extracellular domain of gp130 without its three fibronectin-like domains (SEQ ID NO: 10). The remaining part of this chimeric protein is identical to gp130-Cγ1.

(iv) gp130-J-$C_H1$ was engineered in a manner identical for that described for gp130-Cγ1, except that in place of the Cγ1 region only the $C_H1$ part of Cγ1 has been used (SEQ ID NO: 11). The C-terminal domain of this construct includes the part of the hinge that contains the cysteine residue responsible for heterodimerization of the heavy chain of IgG with a light chain. The part of the hinge that contains the two cysteines involved in Cγ1 homodimerization has been deleted along with the $C_H2$ and $C_H3$ domains.

(v) gp130-Cγ4 was engineered in a manner identical to that described for gp130-Cγ1, except that Cγ4 was used in place of Cγ1 (SEQ ID NO: 12). In addition, an RsrII DNA restriction site was engineered at the hinge region of the Cγ4 domain by introducing two silent base mutations. The RsrsII site allows for other desired genetic engineering manipulations, such as the construction of the $C_H1$ equivalent of gp130-Cγ4.

(vi) gp130-κ was engineered in a manner identical to that described for gp130-Cγ1, except that the constant region of the κ light chain of human Ig was used in place of Cγ1 (SEQ ID NO: 13).

(vi) gp130-J-κ was engineered in a manner identical to that described for gp130-J-κ, except that a j-peptide (SEQ ID NO: 5) was inserted between the Ser-Gly bridge and the κ-region.

(viii) gp130-λ was engineered in a manner identical to that described for gp130-Cγ1, except that the constant region of the λ light chain (Cheung et al. 1992 supra) of human Ig was used in place of Cγ1 (SEQ ID NO: 14).

(b) Constructs employing human IL-6Rα: (i) IL6Rα-Cγ1 was engineered by fusing in frame amino acids 1 to 358 of IL-6Rα (Yamasaki et al. 1988 Science 241:825-828), which comprise the extracellular domain of IL-6Rα (SEQ ID NO: 15), to an Ala-Gly bridge, followed by the 330 amino acids which comprise Cγ1 and a termination codon.

(ii) IL6Rα-κ was engineered as described for IL6Rα-Cγ1, except that the κ-domain (SEQ ID NO: 13) utilized for gp130-κ was used in place of Cϵ1.

(iii) IL6Rα-j-κ was engineered as described for IL6Rα-κ except that the j-peptide described for gp130-j-κ was placed between the Ala-Gly bridge and the κ-domain.

(iv) Three additional constructs, IL6Rα313-Cγ1, IL6Rα313-κ, and IL6Rα313-j-κ, were engineered as using a truncated form of IL-6Rα comprised of amino acids 1 to 313 (SEQ ID NO:16). Each of these constructs were made by fusing in frame IL6Rα313 with a Thr-Gly bridge followed by the Cγ1, κ-, and j-κ-domains described above. These constructs were engineered in order to complement the gp130Δ3fibro-derived constructs.

Expression and purification of ligand Traps. To produce covalently linked heterodimers of soluble gp130 and soluble IL-6Rα, gp130-Ig chimeric proteins were co-expressed with appropriate IL-6Rα-Ig chimeric proteins in complementing pairs. Co-expression was achieved by co-transfecting the corresponding expression vectors into suitable mammalian cell lines, either stably or transiently. The resulting disulfide-linked heterodimers were purified from conditioned media by several different methods, including but not limited to affinity chromatography on immobilized Protein A or Protein G, ligand-based affinity chromatography, ion exchange, and gel filtration.

Figure 17:
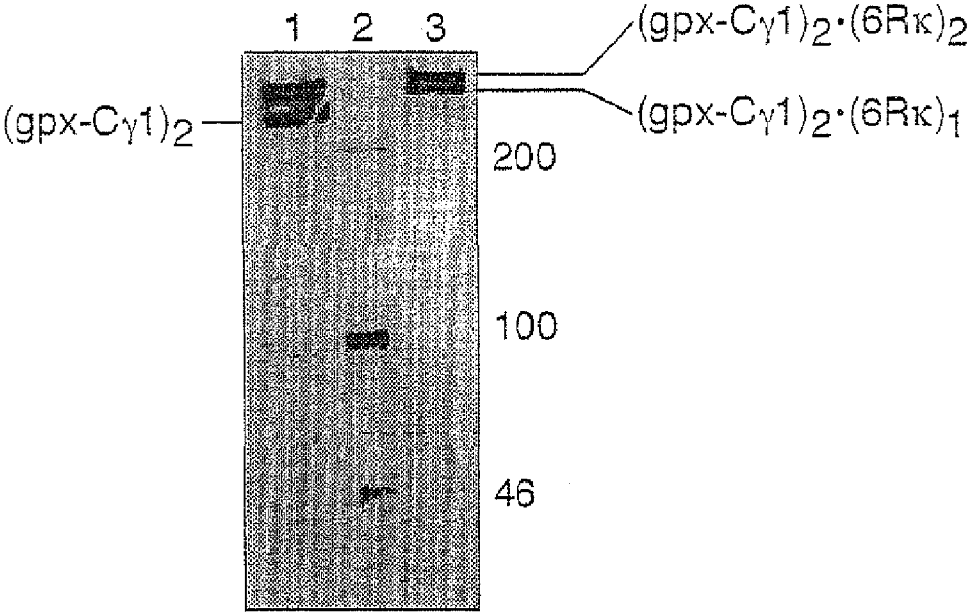
FIG. 17: Purification of gp130-Cγ1•IL-6Rα-κ4% to 12% SDS-PAGE gradient gel run under non-reducing conditions. Proteins were visualized by staining with silver. Lane 1: approximately 100 ng of material purified over Protein A Sepharose (Pharmacia). Lane 2: Molecular size standards (Amersham). Lane 3: The Protein A-purified material shown here after further purification over an IL-6 affinity chromatography step. The positions of the gp130-Cγ1 dimer [$(gp130\text{-}C\gamma1)_2$], the gp130-Cγ1 dimer associated with one IL-6Rα-κ [$(gp130\text{-}C\gamma1)_2$•$(IL\text{-}6R\alpha\text{-}\kappa)_1$], and the gp130-Cγ1 dimer associated with two IL-6Rα-κ [$(gp130\text{-}C\gamma1)_2$•$(IL\text{-}6R\alpha\text{-}\kappa)_2$] are shown, as well as the sizes for the molecular size standards in kilodaltons (200, 100, and 46).

An example of the type of methods used for purification of a heavy/light receptor fusion protein is as follows: gp130-Cγ1•IL-6Rα-κ was expressed in COS cells by co-transfecting two different vectors, encoding gp130-Cγ1 and IL-6Rα-κ respectively. Serum-free conditioned media (400 ml) were collected two days post-transfection and Cγ1-bearing proteins were purified by affinity chromatography over a 1 ml Protein A Sepharose (Pharmacia). The material generated in this step was further purified by a second affinity chromatography step over a 1 ml NHS-activated Sepharose (Pharmacia) which was derivatized with recombinant human IL-6, in order to remove gp130-Cγ1 dimer from gp130-Cγ1•IL-6Rα-κ complexes (the gp130-Cγ1 dimer does not bind IL-6). Proteins generated by this method were more than 90% pure, as evidenced by SDS-PAGE followed by silver-staining (FIG. 17). Similar protocols have been employed successfully towards the purification of other heavy/light receptor heterodimers.

Figure 18:
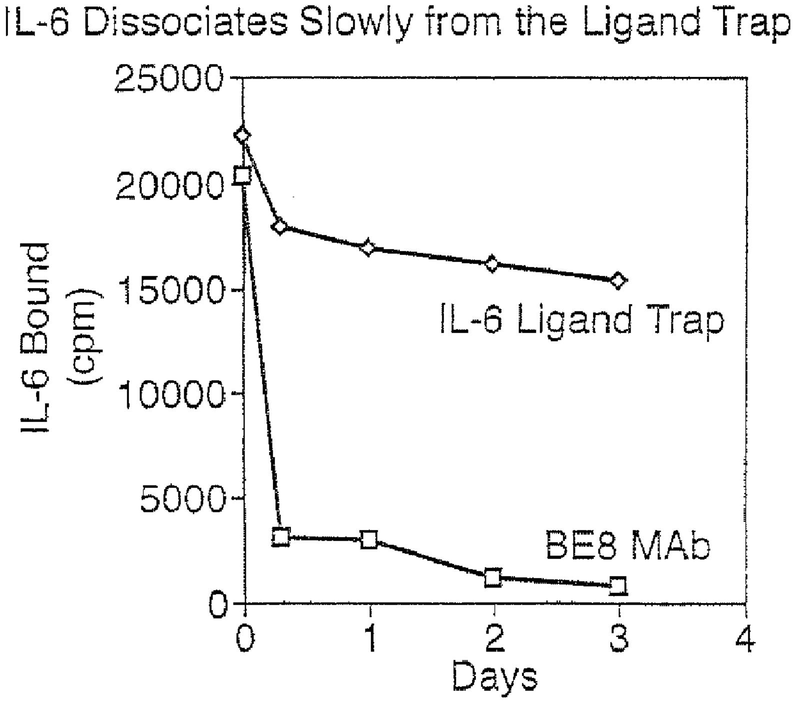
FIG. 18: IL-6 dissociates slowly from the ligand Trap. The dissociation rate of IL-6 from a heavy/light chain receptor-based ligand Trap (gp130-Cγ1•IL-6Rα-κ) was compared to that obtained with the neutralizing monoclonal antibody B-E8 (BE8 MAb).

Biological activity of immunoglobulin heavy/light chain receptor fusion antagonists. The purified ligand Traps were tested for their ability to bind IL-6 in a variety of different assays. For example, the dissociation rate of IL-6 bound to the ligand Trap was measured in parallel with the dissociation rate of IL-6 from the anti-IL-6 monoclonal neutralizing antibody B-E8 (Brochier et al. 1995 Int J Immunopharmacology 17:41-48). An example of this type of experiment is shown in FIG. 18. In this experiment 20 pM $^{125}$I-IL-6 (1000 μCi/mmol; Amersham) was preincubated with 500 pM of either gp130-Cγ1-IL-6Rα-κ or mAb B-E8 for 20 hours. At this point a 1000-fold excess (20 nM) of "cold" IL-6 was added. Periodically, aliquots of the reaction were removed, the ligand Trap or B-E8 were precipitated with Protein G-Sepharose, and the number of cpm of $^{125}$I-IL-6 that remained bound was determined. Clearly, the dissociation rate of human $^{125}$I-IL6 from the ligand Trap was very slow—after three days, approximately 75% of the initial counts were still bound to the ligand Trap. In contrast, less than 5% of the counts remained associated with the antibody after three days. This result demonstrates that the dissociation rate of the ligand from these ligand Traps is very slow.

Figure 19:
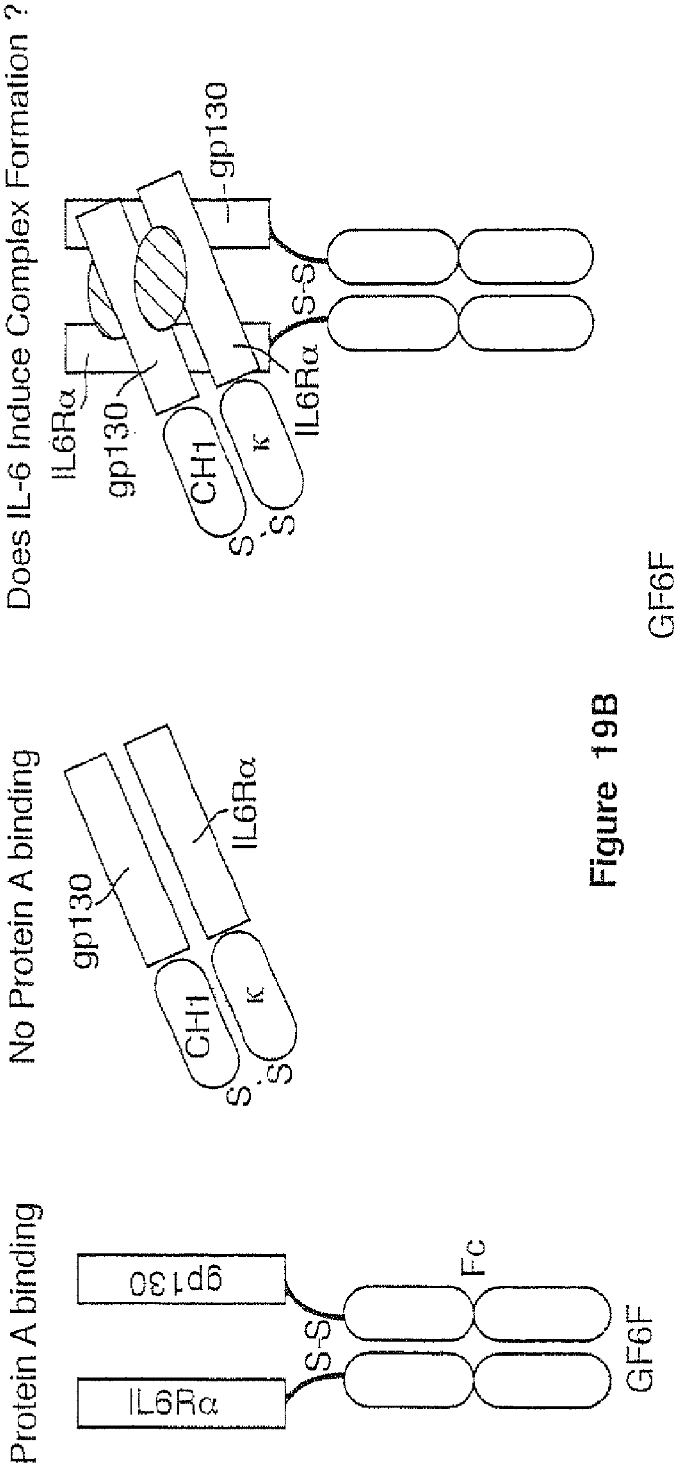
FIGS. 19A-19B: IL-6 can induce multimerization of the ligand Trap.
Figure 19B:
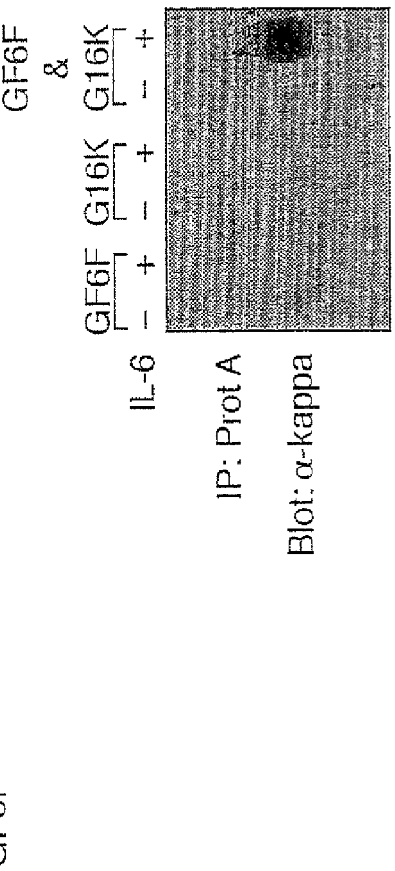

In a different set of experiments the ability of the ligand Traps to multimerize in the presence of ligand was tested. An example of this is shown in FIGS. 19A-19B. IL-6-induced association of gp130-Fc•IL-6Rα-Fc with gp130-$C_H1$-IL-6Rα-κ was determined by testing whether gp130-$C_H1$•IL-6Rα-κ, which does not by itself bind Protein A, could be precipitated by Protein A-Sepharose in the presence of gp130-Fc•IL-6Rα-Fc in an IL-6-depended manner (SEQ ID NO: 9). Precipitation of gp130-$C_H1$•IL-6Rα-κ by Protein A-Sepharose was determined by western blotting with an anti-kappa specific HRP conjugate, which does not detect gp130-Fc•IL-6Rα-Fc. gp130-$C_H1$•IL-6Rα-κ could be precipitated by Protein A-Sepharose only when both gp130-Fc•IL-6Rα-Fc and IL-6 were present. This result conclusively indicates that IL-6 can induce ligand Trap multimerization, and further indicate that the ligand Trap can mimic the hexameric cytokine-Rα•signal transducer complex (FIG. 1). Ligand-induced multimerization may play a significant role in the clearance of cytokine•ligand Trap complexes in vivo.

Figure 20:
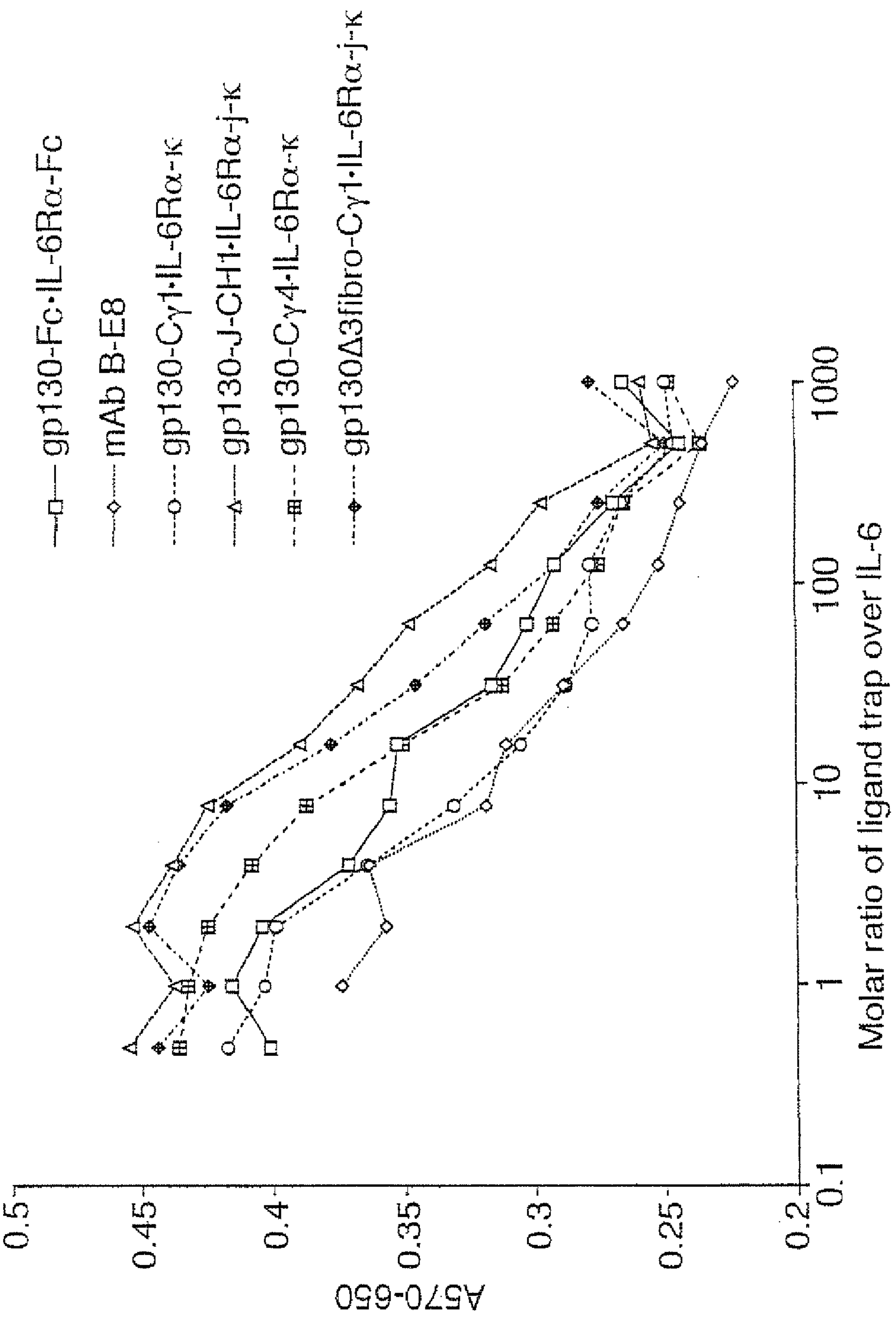
FIG. 20: Inhibition of IL-6-dependent XG-1 cell proliferation. XG-1 cells [Zhang, et al., Blood 83:3654-3663 (1994)] were prepared for a proliferation assay by starving the cells from IL-6 for 5 hours. Assays were set up in 96-well tissue culture dishes in RPMI+10% fetal calf serum+penicillin/streptomycin+0.050 nM 2-mercaptoethanol+glutamine. 0.1 ml of that media was used per well. Cells were suspended at a density of 250,000 per ml at the start of the assay. 72 hours post addition of IL-6±ligands Traps or antibodies, an MTT assay was performed as described (Panayotatos et al. Biochemistry 33:5813-5818 (1994). The different ligand Traps utilized are listed.

The biological activity of the different ligand Traps may be further tested in assays which measure ligand-depended cell proliferation. Several cell proliferation assays exist for IL-6 and they employ cell lines such as B9, CESS, or XG-1. An example of this type of assay using the XG-1 cell line is presented below: XG-1 is a cell line derived from a human multiple myeloma (Zhang et al. 1994 Blood 83:3654-3663). XG-1 depends on exogenously supplied human IL-6 for survival and proliferation. The $EC_{50}$ of IL-6 for the XG-1 line is approximately 50 pmoles/ml. The ability of several different IL-6 Traps to block IL-6-depended proliferation of XG-1 cells was tested by incubating increasing amounts of purified ligand Traps with 50 pg/ml IL-6 in XG-1 cultures. The ligand Traps which were tested had been expressed and purified by methods similar to those described above. All of the ligand Traps tested were found to inhibit IL-6-dependent proliferation of XG-1 in a dose dependent manner (FIG. 20). Of the five different Traps tested gp130-Cγ1•IL-6Rα-κ was the most active and essentially display the same neutralizing activity towards IL-6 as the antibody B-E8. As little as a 10-fold molar excess of either gp130-Cγ1•IL-6Rα-κ or B-E8 completely blocked the activity of IL-6 (a reading of A570-650=0.3 AU corresponds to no proliferation of the XG-1 cells). At a 100-fold molar excess all of the ligand Traps tested completely blocked the activity of IL-6. This observed inhibition is highly selective as neither a gp130-Fc•CNTFRα-Fc ligand Trap which blocks CNTF activity, nor gp130-Fc homodimer exhibit any blocking activity towards IL-6 even when used at a 1000-fold molar excess over IL-6 (data not shown). This data demonstrates that the heteromeric immunoglobulin heavy/light chain receptor-based ligand Traps function as selective high affinity antagonists of their cognate ligand.

Example 5

Cloning of Fusion Polypeptide Components

The extracellular domains of the human cytokine receptors were obtained by standard PCR techniques using tissue cDNAs (CLONTECH), cloned into the expression vector, pMT21 (Genetics Institute, Inc.), and the sequences were sequenced by standard techniques using an ABI 373A DNA sequencer and Taq Dideoxy Terminator Cycle Sequencing Kit (Applied Biosystems, Inc., Foster City, Calif.). For the IL-4Rα nucleotides 241 through 868 (corresponding to the amino acids 24-231) from the Genbank sequence, X52425, were cloned. For the IL-2Rγ, nucleotides 15 through 776 (corresponding to amino acids 1-233) from the Genbank sequence, D11086, were cloned. For the IL-6Rα, nucleotides 52 through 1044 (corresponding to the amino acids 1-331) from the Genbank sequence, X52425, were cloned. For gp130, nucleotides 322 through 2112 (corresponding to the amino acids 30-619) from the Genbank sequence, M57230, were cloned. For the IL-1 RAcP, nucleotides 1 through 1074 (corresponding to the amino acids 1-358) from the Genbank sequence, AB006357, were cloned. For the IL-1RI, nucleotides 55 through 999 (corresponding to the amino acids 19-333) from the Genbank sequence, X16896, were cloned.

Example 6

Production of Fusion Polypeptides (Cytokine Traps)

The nucleotide sequences encoding the cytokine Traps were constructed from the individual cloned DNAs (described supra ) by standard cloning and PCR techniques. In each case, the sequences were constructed in frame such that the sequence encoding the first fusion polypeptide component was fused to the sequence encoding the second fusion polypeptide component followed by an Fc domain (hinge, CH2 and CH3 region of human IgG1) as the multimerizing component. In some cases extra nucleotides were inserted in frame between sequences encoding the first and second fusion polypeptide components to add a linker region between the two components: Trap 424 (SEQ ID NO: 17); Trap 412 (SEQ ID NO:23); and Trap 569 (SEQ ID NO:27).

For the IL-4 Traps, 424 (SEQ ID NO: 17), 603 (SEQ ID NO: 19) and 622 (SEQ ID NO:21), the IL-2Rγ component is 5', followed by the IL4Rα component and then the Fc component. For the IL-6 Traps, 412 (SEQ ID NO: 23) and 616 (SEQ ID NO:25), the IL-6Rα component is 5' followed by the gp130 component and then the Fc domain. For the IL-1 Trap 569 (SEQ ID NO: 27), the IL-1RAcP component is 5' followed by the IL-1RI component and then the Fc domain. The final constructs were cloned into the mammalian expression vector pCDNA3.1 (STRATAGENE).

In the 569 sequence (SEQ ID NO: 27), nucleotides 1-1074 encode the IL1RAcP component, nucleotides 1075-1098 encode a linker region, nucleotides 1099-2043 encode the IL1RI component and nucleotides 2044-2730 encode the Fc domain.

In the 412 sequence (SEQ ID NO: 23), nucleotides 1-993 encode the IL6Rα component, nucleotides 994-1023 encode a linker region, nucleotides 1024-2814 encode the gp130 component and nucleotides 2815-3504 encode the Fc domain.

In the 616 sequence (SEQ ID NO: 25), nucleotides 1-993 encode the IL6Rα component, nucleotides 994-2784 encode the gp130 component and nucleotides 2785-3474 encode the Fc domain.

In the 424 (SEQ ID NO: 17) and 622 (SEQ ID NO: 21) sequences, nucleotides 1-762 encode the IL2Rγ component, nucleotides 763-771 encode a linker region, nucleotides 772-1395 encode the IL4Rα component and nucleotides 1396-2082 encode the Fc domain.

Finally, in the 603 sequence (SEQ ID NO: 19), nucleotides 1-762 encode the IL2Rγ component, nucleotides 763-1386 encode the IL4Rα component and nucleotides 1387-2073 encode the Fc domain.

DNA constructs were either transiently transfected into COS cells or stably transfected into CHO cells by standard techniques well known to one of skill in the art. Supernatants were collected and purified by Protein A affinity chromatography and size exclusion chromatography by standard techniques. (See Harlow &Lane, Antibodies—A Laboratory Manual, Cold Spring Harbor Laboratory, 1988).

Example 7

IL-4 Bioassay Protocol Using TF-1 (ATCC) Cells.

MTT Dye Solution: MTT(3-[4,5-Dimethylthiazole-2-yl]) (Sigma catalog# M2128)

Working concentration: Dissolve 5 mg of anhydrous MTT in 200 ml PBS without $Ca^{+2}$, $Mg^{+2}$. Sterile filter and store aliquoted at −20° C.

Solubilization Solution: For 1000 ml, combine 100 g SDS, 950 ml $dH_2O$, 50 ml Dimethyl Formamide, and 850 μl concentrated HCl. Filter sterilize with a 0.45 μm filter unit. Store at room temperature.

TF-1 cell Growth Medium: RPMI 1640, 10% FBS, Pen/Strep, 2 mM L-glutamine

Other: 0.4% Trypan Blue Stain, sterile tubes for dilutions, sterile 96 well cell culture plates (Falcon #3072), hemacytometer, centrifuge, ELISA plate reader, multichannel pipet for 15, 25, 50 and 100 μl volume, sterile reagent reservoirs, sterile pipet tips, gloves.

Assay Protocol: A. Preparation of Assay plates. 1. Prepare sterile 96 well tissue culture plates to contain 50 μl of growth medium per well with various concentrations of IL-4 and 10 nM IL-4 antagonist. This can be done by preparing a working dilution of IL-4 that is 4 times the highest concentration to be assayed. In separate tubes, do a twofold serial dilution of the IL-4. Add 25 μl of each dilution to one row across the plate (i.e. row A gets highest concentration, row G gets lowest concentration). Add 25 μl of growth medium without IL-4 to row H. Prepare the antagonists to be tested by making a stock that is 4 times the final concentration. Add 25 μl to a triplicate set of IL-4 containing wells (columns 1,2,3, A through H). Be sure to include antagonist in row H. 2. As a positive control, leave one set with no antagonist. These wells will contain IL-4 and media only. 3. Incubate the plate for 1-2 hours at 37° C. in a humidified 5% $CO_2$ incubator before preparing cells to be used for assay.

B. Preparation of Cells. 4. Wash cells twice by centrifugation in assay medium free of growth factor. 5. Determine cell number and trypan blue viability and suspend cells to a final concentration of $8\times10^5$ cells/ml in assay medium. 6. Dispense 50 μl of the cell suspension (40,000 cells) into all wells of the plates. Total volume should now be 100 μl/well. 7. Incubate the plate at 37° C. for 68 hours in a humidified 5% $CO_2$ incubator.

C. Color Development. 8. After incubating for 68 hours, add 15 μl of the MTT dye solution to each well. 9. Incubate the plate at 37° C. for 4 hours in a humidified 5% $CO_2$ incubator. 10. After 4 hours, add 100 μl of the solubilization solution to each well. Allow the plate to stand overnight in a sealed container to completely solubilize the formazan crystals. 11. Record the absorbance at 570/650 nm.

Figure 27:
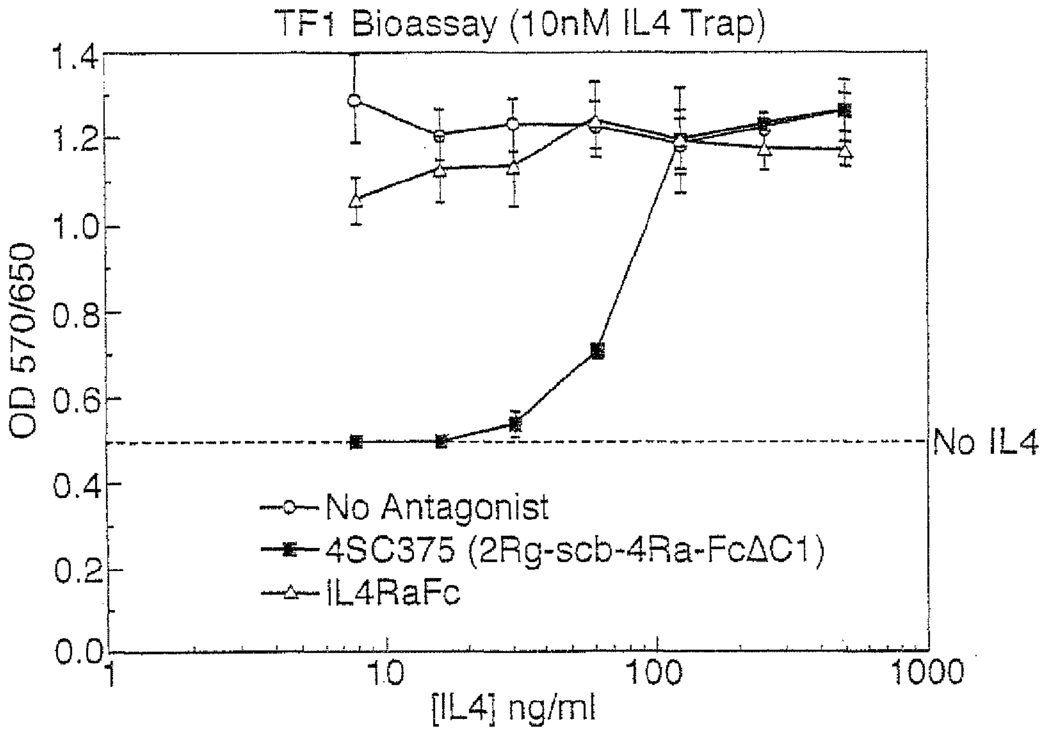
FIG. 27: Shows that an IL-4 Trap designated 4SC375, which is a fusion polypeptide of IL-2Rγ-scb-IL4Rα-FcΔC1, is several orders of magnitude better as an IL-4 antagonist than IL4RαFcΔC1 alone in the TF1 cell bioassay.
Figure 28:
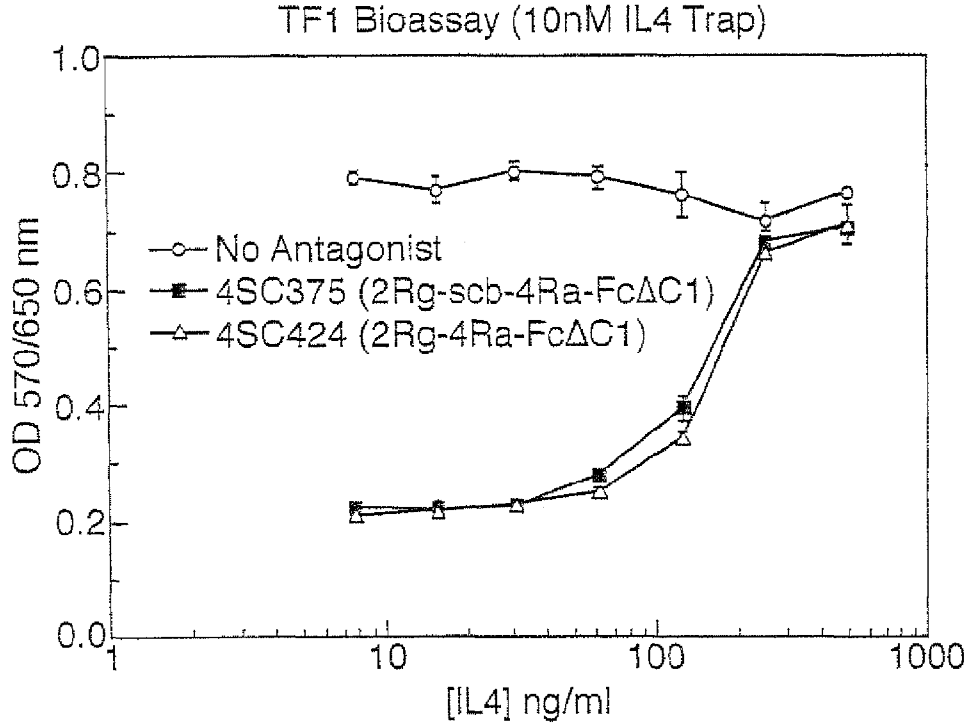
FIG. 28: Shows that an IL-4 Trap designated 4SC375 displays antagonistic activity in the TF1 cell bioassay equivalent to an IL-4 Trap designated 4SC424 (described in FIGS. 21A-21D) which is a fusion polypeptide of IL-2Rγ-IL4Rα-FcΔC1 having the IL-2Rγ component flush with the IL-4Rα component.

Results. FIG. 27 shows that an IL-4 Trap designated 4SC375, which is a fusion polypeptide of IL-2Rγ-scb-IL4Rα-FcΔC1, is several orders of magnitude better as an IL-4 antagonist than IL4RαFcΔC1 alone in the TF1 cell bioassay. FIG. 28 shows that the IL-4 Trap designated 4SC375 shows antagonistic activity in the TF1 cell bioassay equivalent to an IL-4 Trap designated 4SC424 which is a fusion polypeptide of IL-2Rγ-IL4Rα-FcΔC1 having the IL-2Rγ component flush with the IL-4Rα component.

Example 8

IL-6 Bioassay Protocol Using XG-1 Cells

MTT dye solution and solubilization solution, assay protocol, cell preparation and color development were as described above with IL-6 used instead of IL-4. Assay Medium: RPMI 1640, 10% FBS, Pen/Strep, 2 mM L-glutamine, 50 FM mercapto-ethanol.

Figure 29:
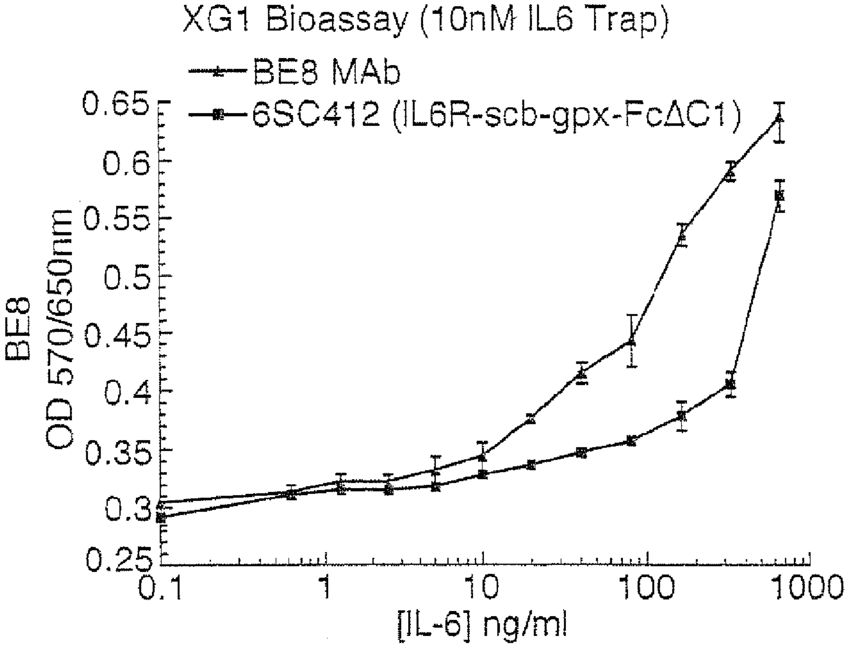
FIG. 29: Shows that the IL6 Trap (6SC412 IL6R-scb-gpx-FcΔC1) described in FIGS. 24A-24F is a better antagonist of IL-6 in the XG1 bioassay than the neutralizing monoclonal antibody to human IL-6-BE8.

Results. FIG. 29 shows that the IL6 Trap (6SC412 IL6R-scb-gpx-FcΔC1) (SEQ ID NO: 23 and 24) is a better antagonist of IL-6 in the XG1 bioassay than the neutralizing monoclonal antibody to human IL-6- BE8.

Example 9

MRC5 Bioassay for IL-1 Traps

MRC5 human lung fibroblast cells respond to IL-1 by secreting IL-6 and thus were utilized to assay the ability of IL-1 Traps to block the IL-1-dependent production of IL-6. IL1 Trap 1SC569 was tested against IL-1-RI.Fc which is the extracellular domain of the IL-1 Type I receptor fused to an Fc domain.

MRC5 cells are suspended at $1\times10^5$ cells per ml in medium and 0.1 ml of cells are plated (10,000 cells per well) into the wells of a 96 well tissue culture plate. Plates are incubated for 24 hours at 37° C. in a humidified 5% $CO_2$ incubator.

IL-1 Trap and recombinant human IL-1 at varying doses are pre-incubated in a 96 well tissue culture dish and incubated for 2 hours at 37° C. 0.1 ml of this mixture is then added to the 96 well plate containing the MRC5 cells such that the final concentration of IL-1 Trap is 10 nM and the final concentrations of the IL-1 ranges from 2.4 pM to 5 nM. Control wells contain Trap alone or nothing.

Plates are then incubated at 37° C. for 24 hours in a humidified 5% $CO_2$ incubator. Supernatant is collected and assayed for levels of IL-6 using R&D Systems Quantikine Immunoassay Kit according to the manufacturer's instructions.

Figure 30:
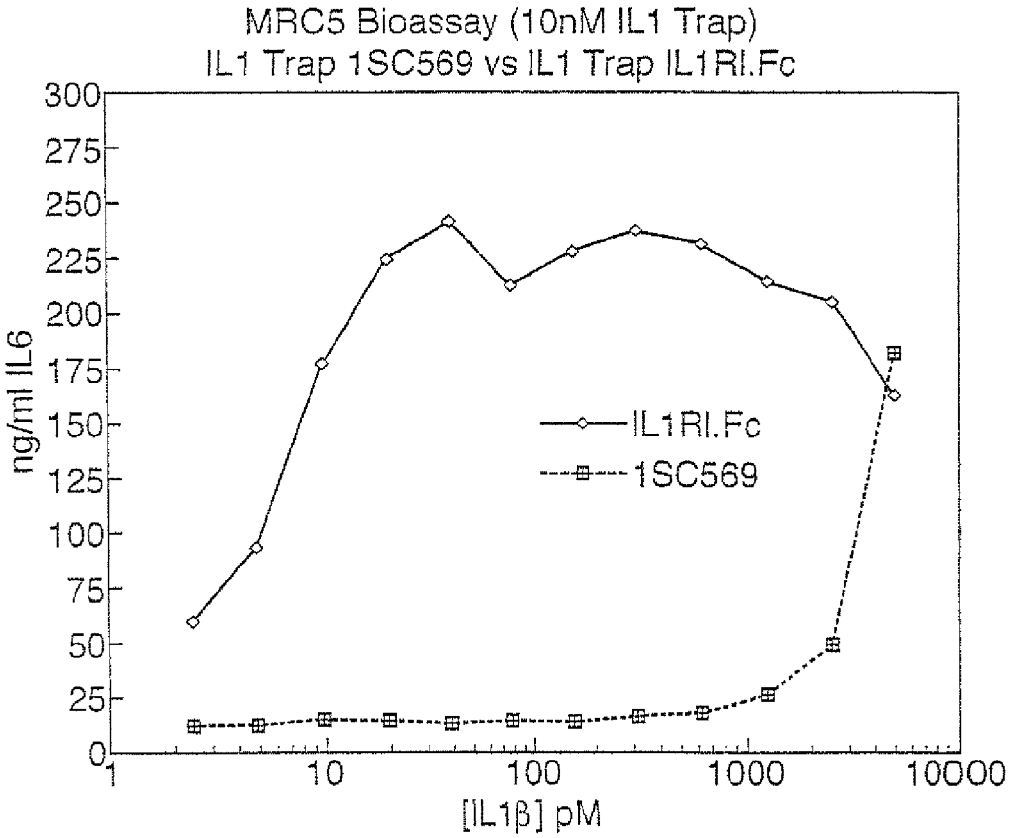
FIG. 30: Shows that the Trap 1SC569 (described in FIGS. 26A-26E) is able to antagonize the effects of IL-1 and block the IL-6 production from MRC 5 cells upon treatment with IL-1.

Results. FIG. 30 shows that the Trap 569 (SEQ ID NO:28) is able to antagonize the effects of IL-1 and block the IL-6 production from MRC 5 cells upon treatment with IL-1. At a concentration of 10 nM, the Trap 569 is able to block the production of IL-6 up to an IL-1 concentration of 3 nM. In contrast, the IL-1RI.Fc is a much poorer antagonist of IL-1. It is only able to block the effects of IL-1 up to about 10-20 pM. Thus, the Trap 569 is approximately 100× better at blocking IL-1 than

Example 10

Construction of IL-13/IL-4 Single Chain Traps

1. To create the IL-13/IL-4 dual Trap designated IL-4Rα.IL-13Rα1.Fc, the human IL-4Rα extracellular domain (corresponding to nucleotides 1-693 of SEQ ID NO: 29) and the human IL-13Rα1 extracellular domain (corresponding to nucleotides 700-1665 of SEQ ID NO: 29) were amplified by standard PCR techniques and ligated into an expression vector pMT21 which contained the human Fc sequence (corresponding to nucleotides 1671-2355 of SEQ ID NO: 29), thus creating a fusion protein consisting of the IL-4Rα, IL-13Rα1, and the hinge, CH2 and CH3 region of human IgG1 from the N to C terminus. In addition, a two amino acid linker (corresponding to nucleotides 694-699 of SEQ ID NO: 30) with the amino acid sequence SerGly was constructed in frame between the IL-4Rα and the IL-13Rα1 and a two amino acid linker (corresponding to nucleotides 1666-1671 of SEQ ID NO: 30) with the amino acid sequence ThrGly was constructed in frame between the IL-13Rα1 and the Fc portion. All sequences were sequence-verified by standard techniques. The IL-4Rα.IL-13Rα1.Fc coding sequence was then subcloned into the expression vector pCDNA3.1 (Stratagene) using standard molecular biology techniques.

2. To create the IL-13/IL-4 dual Trap designated IL-13Rα1.IL-4Rα.Fc, the IL-13Rα1 extracellular domain (corresponding to nucleotides 1-1029 of SEQ ID NO: 31) and the human IL-4Rα (corresponding to nucleotides 1060-1692 of SEQ ID NO: 31) were amplified by standard PCR techniques and ligated into the expression vector pJFE14, which contains the human Fc sequence (corresponding to nucleotides 1699-2382 of SEQ ID NO: 31) to create a fusion protein consisting of the IL-13Rα1, IL-4Rα, and the hinge, CH2 and CH3 region of human IgG1 from the N to C terminus. In addition, a ten amino acid linker with the amino acid sequence GlyAlaProSerGly-GlyGlyGlyArgPro (SEQ ID NO: 6) (corresponding to nucleotide 1030-1059 of SEQ ID NO: 31) was constructed in frame between the IL-13Rα1 and the IL-4Rα and a two amino acid linker (corresponding to nucleotides 1693-1698 of SEQ ID NO: 31) with the amino acid sequence SerGly was constructed in frame between IL-4Rα and the Fc portion. All sequences were sequence-verified using standard techniques. The coding sequence of IL-13Rα1.IL-4Rα.Fc was then subcloned into the expression vector pCDNA3.1 (Stratagene) using standard molecular biology techniques.

Example 11

Expression of IL-4Rα.IL-13Rα1.Fc and IL-13Rα1.IL-4Rα.Fc.IL-4Rα

Large scale (1 L) cultures of the pCAE801 (the DNA vector construct encoding IL-4Rα.IL-13Rα1.Fc) and pCAE802 (the DNA plasmid construct encoding IL-13Rα1.IL-4Rα.Fc) in DH10B cells were grown overnight in LB+ampicillin and the plasmid DNA was extracted using a Qiagen Endofree Mega Kit following the manufacturer's protocol. The concentration of the purified plasmid DNA was determined in a UV spectrophotometer and fluorometer. The plasmid DNA was also verified by digestion of aliquots with BbsI, XmnI and NcoI restriction enzymes. All restriction enzyme digest fragments corresponded to the predicted sizes in a 1% agarose gel.

Forty 15 cm petri plates were seeded with CHO-K1/E1A cells at a density of $4\times10^6$ cells/plate. Plating media was Gibco Ham's F-12 w/10% Hyclone Fetal Bovine Serum (FBS)+penicillin/streptomycin and supplemented with glutamine. The following day each plate was transfected with 6 μg of pCAE801, or pCAE802, using Gibco Optimem and Gibco Lipofectamine in 12 ml volume, following the manufacturer's protocol. Four hours after adding the transfection mix to the cells 12 ml/plate of Optimem with 10% FBS was added. Plates were incubated at 37° C. in a 5% $CO_2$ incubator overnight. The following day the media was removed from each plate and 25 ml expression media (Gibco CHO-S-SFM II with glutamine+1 mM sodium butyrate) was added. The plates were incubated at 37° C. for 3 days.

After 3 days of incubation the media was removed from each plate and centrifuged at 400 rpm in a swinging bucket rotor to pellet cells. The supernatant was decanted into sterile 1 L bottles and expressed protein was purified as described infra.

Example 12

Purification of IL-4Rα.IL-13Rα1.Fc and IL-13Rα1.IL-4Rα.Fc Protein

1. Purification of IL-4Rα.IL-13Rα1.Fc. Human IL-4Rα.IL- 13Rα1.Fc was transiently expressed in CHO cells and supernatants were harvested from plate transfections as described supra. Expression of the secreted protein was determined by a sandwich ELISA using goat anti-hIgG (γchain specific; Sigma 1-3382) and goat anti-hIgG (Fc specific)-FITC conjugate (Sigma F9512) capture and report antibodies, respectively. The yield ranged from 5.8 to 9.2 mg (average of 7.5 mg) per liter of conditioned media. COMPLETE$^{TM}$ protease inhibitor tablets (Roche Diagnostics Corp.) were dissolved into the media (1 tablet/L). The conditioned media was sterile filtered (0.22 μm pore size) prior to loading onto a pre-equilibrated, 5 mL HI TRAP® Protein A affinity column (Amersham Pharmacia Biotech) in Dulbecco's PBS buffer (Life Technologies), pH 7.4 at 4° C. The flow rate was ~1-2 mL/min. The column was extensively washed with PBS buffer to remove nonspecifically bound proteins from the column. IL-4Rα.IL-13Rα1.Fc was eluted using 20mM sodium citrate, 150 mM NaCl, pH 3.5. The eluate was immediately neutralized by titrating with 1 M Tris-OH. The fractions containing protein were pooled and immediately dialyzed in PBS buffer, pH 7.4 at 4° C. The recovery from Protein A purification was 6.8 mg (73%). IL-4Rα.IL-13Rα1.Fc was further purified by size exclusion chromatography using a superose 6 column (25 mL bed volume; Amersham Pharmacia Biotech) pre-equilibrated in PBS, 5% v/v glycerol, pH 7.4 at ambient temperature. The flow rate was 0.5 mL/min. Protein fractions were assessed from a Coomassie stained non-reduced and reduced SDS-PAGE (Novex NuPAGE 4-12% Bis-Tris gels). Fractions were conservatively pooled to reduce the amount of aggregated protein. The overall yield was 51% (4.4mg) with a purity of 97% as judged by SDS-PAGE. Purified IL-4Rα.IL-13Rα1. Fc was analyzed by non-reduced and reduced SDS-PAGE (4-12% Bis-Tris), analytical size exclusion chromatography (Tosohaas TSKG4000SWXL), N-terminal sequencing, and immunoblotting with goat anti-hIgG-HRP conjugate (Promega W403B), and also mouse monoclonal anti-hIL-4R (R&D MAB230) followed by anti-mIgG-HRP conjugate (Promega W402B) as the secondary antibody.

2. Purification of IL-13Rα1.IL-4Rα.Fc. Human IL-13Rα1.IL-4Rα.Fc was transiently expressed in CHO cells and supernatants were harvested from plate transfections as described supra. Expression of the secreted protein was determined by a sandwich ELISA using goat anti-hIgG (γchain specific; Sigma 1-3382) and goat anti-hIgG (Fc specific)-FITC conjugate (Sigma F9512) capture and report antibodies, respectively. The yield was 8.8 mg per liter of conditioned media. COMPLETE$^{TM}$ protease inhibitor tablets (Roche Diagnostics Corp.) were dissolved into the media (1 tablet/L). The conditioned media was sterile filtered (0.22 μm pore size) prior to loading onto a pre-equilibrated, 5 mL HI TRAP® Protein A affinity column (Amersham Pharmacia Biotech) in Dulbecco's PBS buffer (Life Technologies), pH 7.4 at 4° C. The flow rate was ~1-2 mL/min. The column was extensively washed with PBS buffer to remove nonspecifically bound proteins from the column. IL-13Rα1.IL-4Rα.Fc was eluted using 20 mM sodium citrate, 150 mM NaCl, pH 3.5. The eluate was immediately neutralized by titrating with 1 M Tris-OH. The fractions containing protein were pooled and immediately dialyzed in PBS buffer, pH 7.4 at 4° C. The recovery from Protein A purification was 3.8 mg (43%). IL-13Rα1.IL-4Rα.Fc was further purified by size exclusion chromatography using a superose 6 column (25 mL bed volume; Amersham Pharmacia Biotech) pre-equilibrated in PBS, 5% v/v glycerol, pH 7.4 at ambient temperature. The flow rate was 0.5 mL/min. Protein fractions were assessed from a Coomassie stained non-reduced and reduced SDS-PAGE (Novex NuPAGE 4-12% Bis-Tris gels). Fractions were conservatively pooled to reduce the amount of aggregated protein. The overall yield was 17% (1.5 mg) with a purity of 95% as judged by SDS-PAGE. Purified IL-13Rα1.IL-4Rα.Fc was analyzed by non-reduced and reduced SDS-PAGE (4-12% Bis-Tris), analytical size exclusion chromatography (Tosohaas TSKG4000SWXL), N-terminal sequencing, and immunoblotting with goat anti-hIgG-HRP conjugate (Promega W403B), and also mouse monoclonal anti-hIL-4Rα(R&D MAB230) followed by anti-mIgG-HRP conjugate (Promega W402B) as the secondary antibody.

Example 13

Blocking of IL-4Rα.IL-13Rα1.Fc and IL-13Rα1.IL-4Rα.Fc

TF1 Bioassay. TF1 cells were maintained in growth media (10 ng/ml GM-CSF, RPMI 1640, 10% FBS, L-glutamine, Penicillin, Streptomycin). For the bioassay, cells were washed 2 times in assay media (as above but without GM-CSF) and then plated at $2\times10^5$ cells in 50 μl of assay media. The purified IL-4Rα.IL-13Rα1.Fc and IL-13Rα1.IL-4Rα.Fc proteins were diluted into assay media at a concentration of 40 nM. 25 μl of each of the Traps was added to the cells. Either IL-13 or IL-4 were diluted to 40 nM in assay media and then 2-fold dilution series in assay media were made. 25 μl of either IL-13 or IL-4 was then added to the wells containing the cells and the Traps. Cells were then incubated at 37° C., 5% $CO_2$ for ~70 hrs. The extent of TF1 cell proliferation was measured by the MTS assay according to the manufacturer's protocol (Promega, Inc.).

Figures 32G, 33:
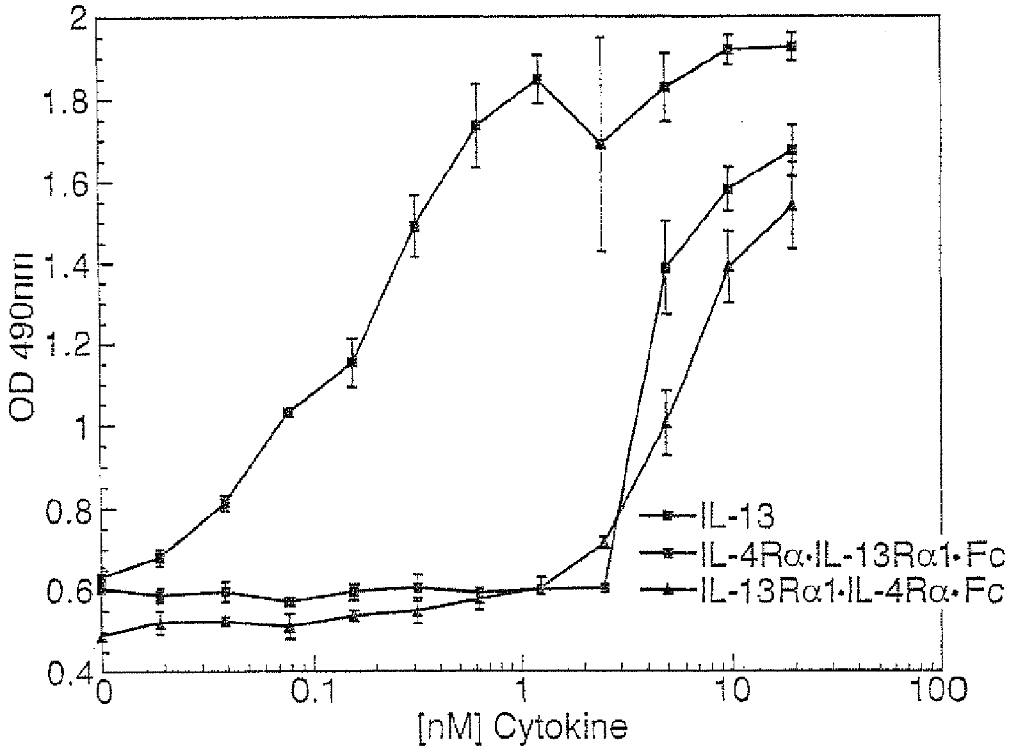
Figure 34:
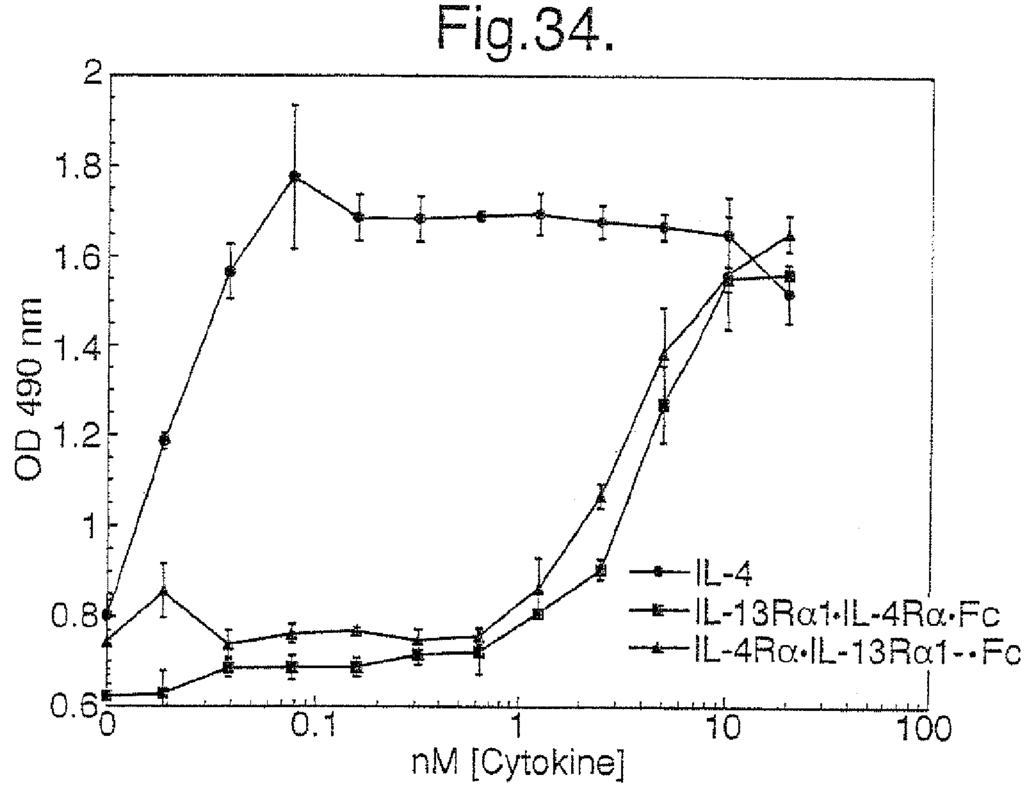
FIG. 34: Blocking of IL-4 by IL-4Rα.IL-13Rα1.Fc and IL-13Rα1.IL-4Rα.Fc. Addition of either IL-4Rα.IL-13Rα1.Fc or IL-13Rα1.IL-4Rα.Fc at a concentration of 10 nM blocks IL-4-induced growth up to ~1 nM. At an IL-4 concentration of ~3-4 nM the growth of TF1 cells is inhibited by 50%.

Results. The ability of the IL-4Rα.IL-13Rα1.Fc and IL-13Rα1.IL-4Rα.Fc Traps to block both human IL-13 and human IL-4 activity was measured in the TF1 bioassay described supra. IL-13 stimulates proliferation of TF1 cells, with half-maximal growth at a concentration of 0.2 nM. Addition of either IL-4Rα.IL-13Rα1.Fc or IL-13Rα1.1L-4Rα.Fc Trap at a concentration of 10 nM blocks IL-13-induced growth up to ~2 nM (FIG. 33). At an IL-13 concentration of ~4-5 nM the growth of TF1 cells is inhibited by 50%. TF1 cells are more sensitive to IL-4, which stimulates their proliferation with half-maximal growth at 0.02 nM. Addition of either IL-4Rα.IL-13Rα1.Fc or IL-13Rα1.IL-4Rα.Fc at a concentration of 10 nM blocks IL-4-induced growth up to ~1 nM (FIG. 34). At an IL-4 concentration of ~3-4 nM the growth of TF1 cells is inhibited by 50%. These results show that both IL-4Rα.IL-13Rα1.Fc and IL-13Ruα1.L-4Rα.Fc can block the ability of both IL-13 and IL-4 to stimulate cellular responses.

Example 14

Blocking of Injected IL-1 by IL-1 Trap In Vivo

IL-1 is a pro-inflammatory cytokine. Systemic administration of IL-1 has been shown to elicit acute responses in animals, including transient hyperglycemia, hypoinsulinemia, fever, anorexia, and increased serum levels of interleukin-6 (IL-6). Since mice are responsive to both murine and human IL-1, human IL-1 can be used and in vivo binding effects of human specific IL-1 antagonists can be evaluated. This acute mouse model was used to determine the ability of a human IL-1 Trap to antagonize the in vivo effects of exogenously administered human IL-1. This provides a rapid indication of in vivo efficacy of the human IL-1 Trap and can be used as an assay to help molecule selection.

Experimental Design: Mice were given subcutaneous injections of human IL-1 (0.3 μg/kg). Twenty-four hours prior to human IL-1 injection, the animals were pre-treated with either vehicle or 150-fold molar excess of human IL-1 Trap (0.54 mg/kg). Two hours prior to sacrifice (26 hrs), the mice were given a second injection of human IL-1 (0.3 μg/kg). Blood samples were collected at various time points and sera were assayed for IL-6 levels.

Figure 35:
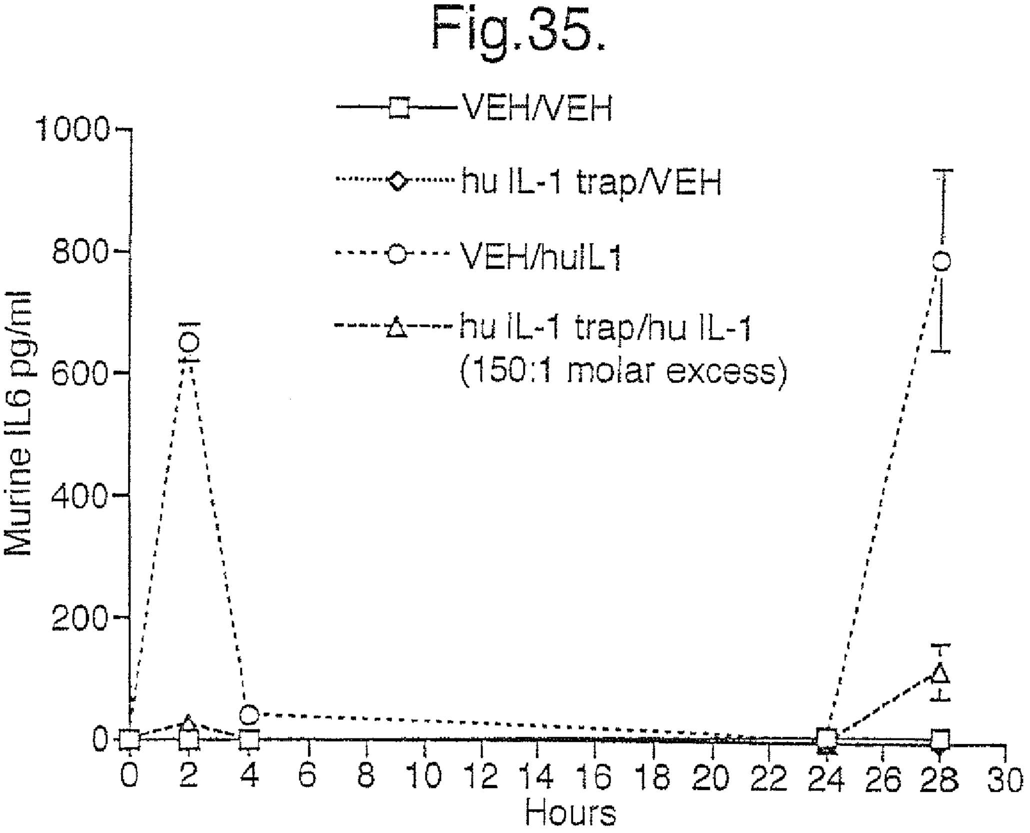
FIG. 35: Human IL-1 Trap blocks the in vivo effects of exogenously administered huIL-1. BALB/c mice were given subcutaneous injection of huIL-1 (0.3 μg/kg) at time 0. Twenty-four hours prior to huIL-1 injection, the animals were pre-treated with either vehicle or 150-fold molar excess of huIL-1 Trap. Two hours prior to sacrifice (26 hrs), the mice were re-challenged with a second injection of huIL-1 (0.3 μg/kg, s.c.). Blood samples were collected at various time points and sera were assayed for IL-1 levels (expressed as mean +/− SEM; n=5 per group).

Results. Exogenous administration of human IL-1 resulted a dramatic induction of serum IL-6 levels. At 150-fold molar excess, the human IL-1 Trap completely blocked the IL-6 increase (FIG. 35). Furthermore, the effects of the human IL-1 Trap persisted for at least another 24 hours, preventing an IL-6 increase even when IL-1 was re-administered (FIG. 35). Such long-lasting efficacy suggests that daily injection of an IL-1 Trap may not be necessary for chronic applications.

Figure 50:
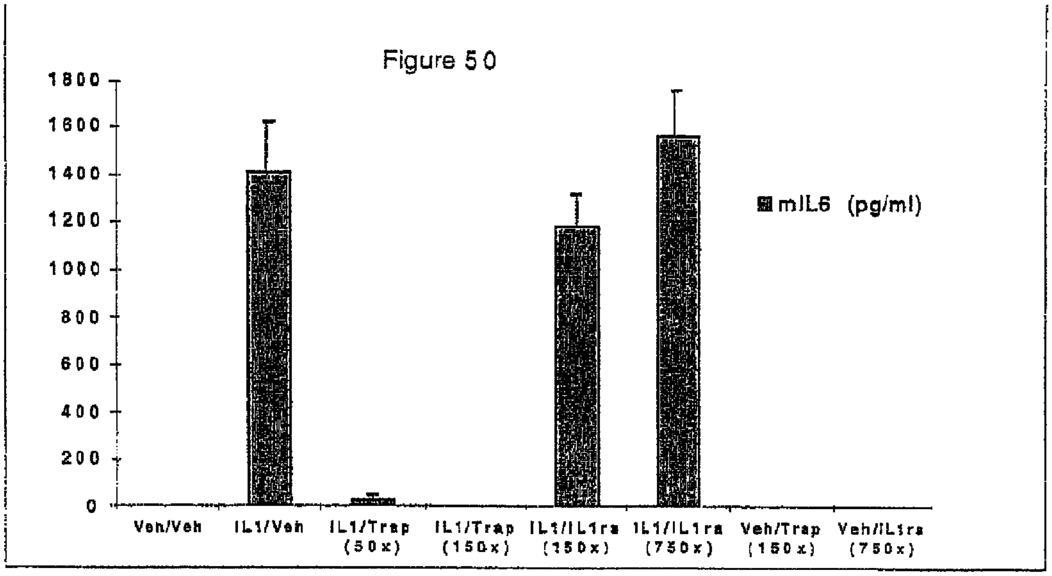
FIG. 50: Human IL-1 Trap blocks the in vivo effects of exogenously administered human IL-1. Male C57BL/6 mice were given a subcutaneous injection of recombinant human IL-1β (rhIL-1β; 0.3 mg/kg). Twenty four hours prior to rhIL-1β administration, animals were treated with either vehicle, human IL-1 Trap 569 (50 or 150-fold molar excess; 0.18 or 0.54 mg/kg, respectively), or recombinant murine IL-1 receptor antagonist (rmIL-1ra; 150 or 750-fold molar excess; 45.8 or 229 μg/kg, respectively). Blood samples were taken 2 h after administration of rhIL-1β and the sera were assayed for IL-6 levels using a mouse IL-6 ELISA. Exogenous administration of rhIL-1β significantly increased serum IL-6 levels. Pretreatment with either a 50 or 150-fold molar excess of hIL-1 Trap blocked the rhIL-1-induction of IL-6. In contrast, injection of rmIL-1ra at either a 150 or 750-fold molar excess did not block IL-6 induction.

In a separate experiment, IL-1 ra at 150-fold or 750-fold molar excess did not significantly block IL6 induction. Therefore, in this paradigm. IL-1 Trap appears to be a better blocker of IL-1 activity (see FIG. 50).

Example 15

Evaluating the Ability of an IL-4 trap to Block the Physiological Responses to Human IL-4 in Cynomologus Monkeys Systemic administration of human IL-4 elicits systemic responses in Cynomologus monkeys (Gundel et al., 1996). Thus, the effectiveness of the IL-4 Trap in blocking human IL-4 can be demonstrated by measuring these responses.

Experimental Design: The experiment consisted of 3 parts: human IL-4+vehicle (part 1), human IL-4+IL-4 Trap (part 2), and human IL-4+vehicle (part 3). Human IL-4 (25 μg/kg) was injected subcutaneously twice daily for 4 days and IL-4 Trap (8 mg/kg) and vehicle were given intravenously daily for 5 days, beginning 1 day prior to human IL-4 administration. Whole blood was collected daily for flow cytometry analysis for CD16 and plasma was obtained to assay for the cytokine monocyte chemotactic protein 1 (MCP-1). CD16 and MCP-1 are markers of IL-4-mediated inflammation in both humans and monkeys.

Figure 36A:
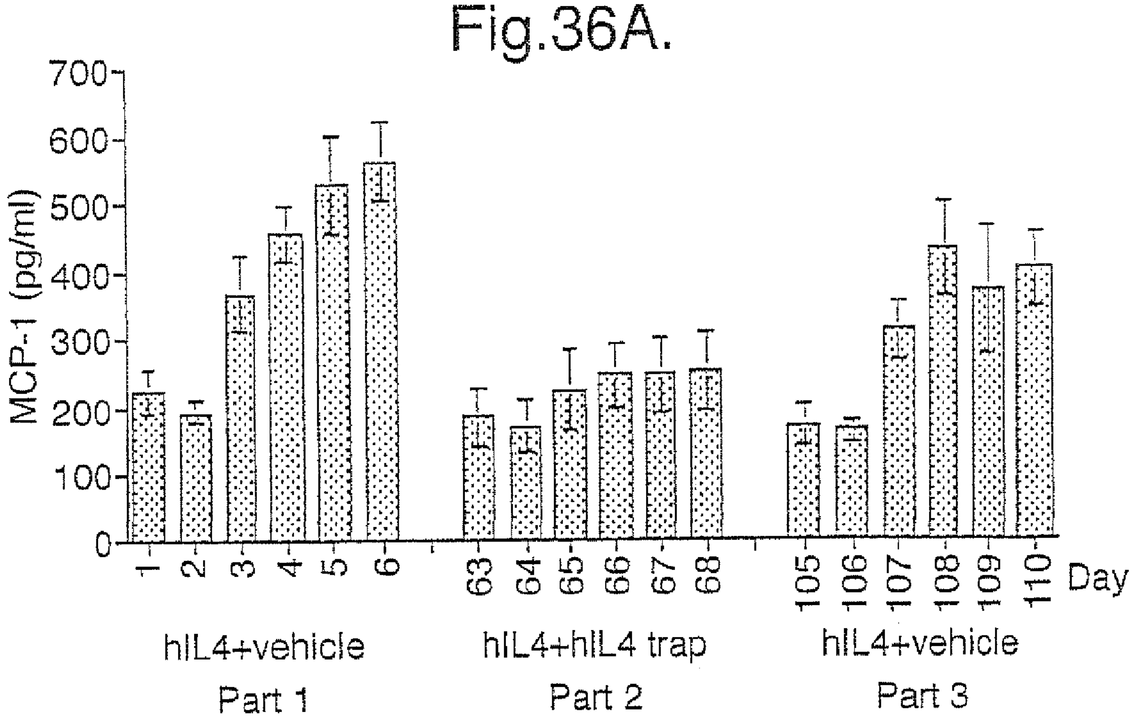
FIGS. 36A & 36B: Human IL-4 Trap antagonizes the effects of human IL-4 in monkeys.
Figure 36B:
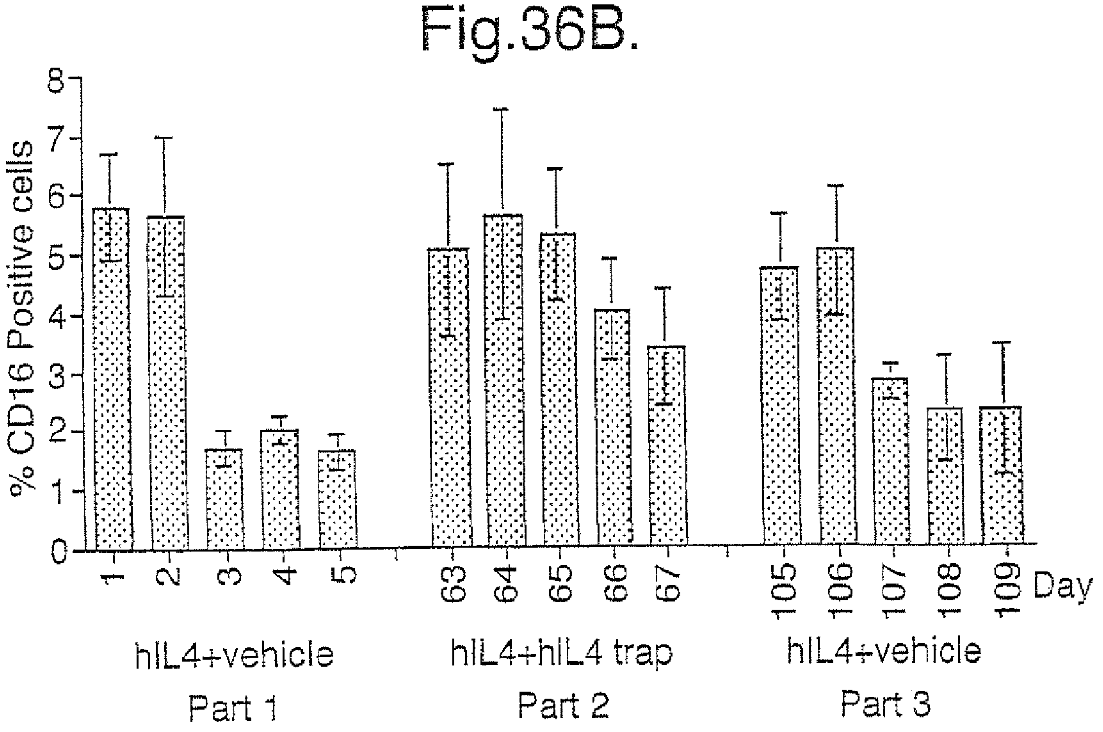

Results. In the presence of human IL-4, MCP-1 increased 2.5-fold and was significantly blocked by the IL-4 Trap (FIG. 36A). Similarly, the decrease in the percent of CD16 positive lymphocytes in peripheral blood was attenuated by the IL-4 Trap (FIG. 36B). After a rest period, the monkeys were re-injected with human IL-4 and the responsiveness of the animals to human IL-4 was re-confirmed (FIGS. 36A and 36B), suggesting that inhibition of the MCP-1 and CD 16 responses is specifically mediated by the IL-4 Trap.

Example 16

The Effects of IL-4 Trap on IL-4-Induced IgE Secretion

It has been shown that injection of anti-mouse IgD antibody stimulates an IL-4-mediated IgE increase in normal mice. This model has been widely used to evaluate IL-4 antagonists, such as soluble IL-4 receptor and anti-IL-4 monoclonal antibodies (Sato et al., 1993). We decided to use this model to evaluate the ability if the IL-4 Trap to block IL-4-mediated increases of IgE.

Experimental design: BALB/C mice injected with anti-mouse IgD (100 μl/mouse, s.c.) were randomly divided into 3 groups. Each received (on days 3-5) either vehicle, murine IL-4 Trap (1 mg/kg, s.c.), or a monoclonal antibody to mouse IL-4 (1 mg/kg, s.c.). Serum was collected at various time points and assayed for IgE levels.

Figure 37:
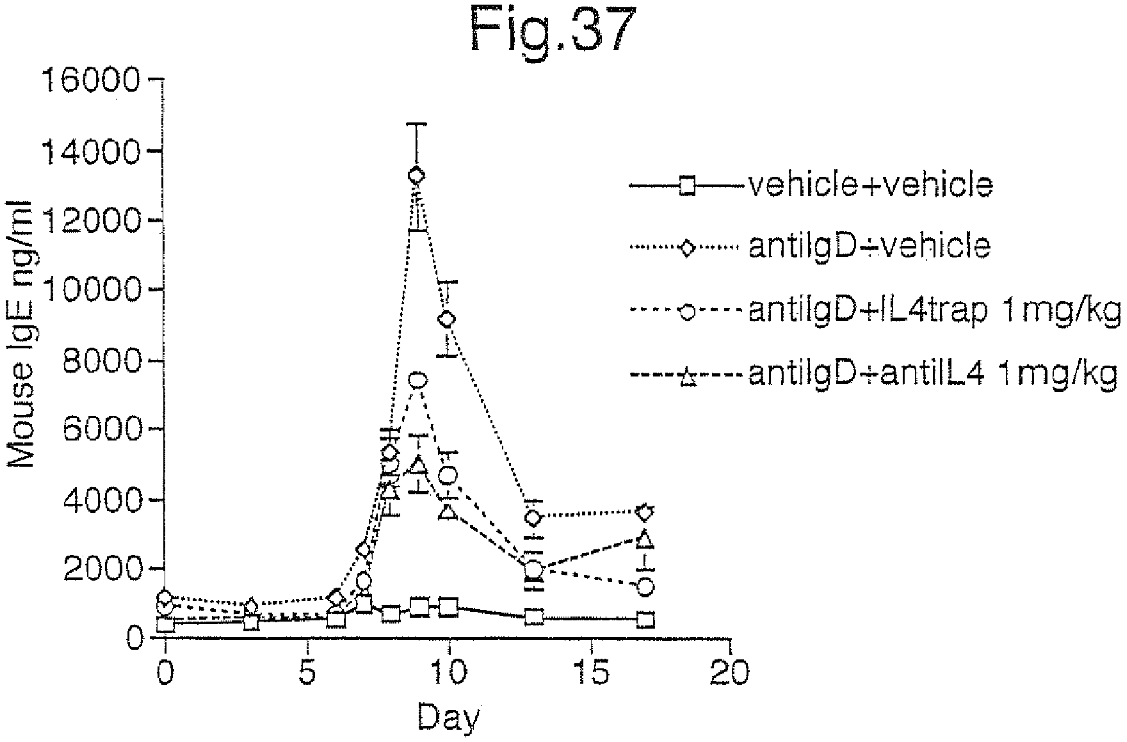
FIG. 37: Murine IL-4 Trap partially prevented IL-4-mediated IgE increase in mice. BALB/C mice injected with anti-mouse IgD (100 μl/mouse, s.c.) were randomly divided into 3 groups, each received (on days 3-5) either vehicle, murine IL-4 Trap (1 mg/kg, s.c.), or a monoclonal antibody to mouse IL-4 (1 mg/kg, s.c.). Sera were collected at various time points and assayed for IgE levels. Results were expressed as mean+/−SEM (n=5 per group). (ANOVA $p=0.0002$; Tukey-Kramer: vehicle vs. IL-4 Trap, $p<0.01$; vehicle vs. IL-4 antibody, $p<0.001$; IL-4 Trap vs. IL-4 antibody, not significant).

Results. Treatment with the murine IL-4 Trap or the mouse IL-4 antibody both significantly antagonized the IL-4-mediated IgE increase in this mouse model (FIG. 37). This suggests that the murine IL-4 Trap binds murine IL-4 and antagonizes physiological responses elicited by endogenous IL-4 in vivo.

Example 17

Construction of Additional Single Chain IL-1 Traps

The techniques used to construct the DNA vectors described herein are standard molecular biology techniques well known to the skilled artisan (see e.g., Sambrook et al. 1989 Molecular Cloning: A Laboratory Manual, Second Edition, Vols 1, 2, and 3, 1989; Current Protocols in Molecular Biology, Eds. Ausubel et al., Greene Publ. Assoc., Wiley Interscience, N.Y.). All DNA sequencing is done by standard techniques using an ABI 373A DNA sequencer and Taq Dideoxy Terminator Cycle Sequencing Kit (Applied Biosystems, Inc., Foster City, Calif.).

a) IL-1 Trap 823 Sequence—The IL-1 Trap 823 sequence consists of the extracellular domain of human IL-1 RAcP (corresponding to nucleotides 1-1077 of SEQ ID NO: 39) followed by the extracellular domain of human IL-1RI (corresponding to nucleotides 1078-2013 of SEQ ID NO: 39) followed by a part of the hinge region, the CH2 and CH3 domains of human IgG1 (corresponding to nucleotides 2014-

2703 of SEQ ID NO: 39) containing a mutation at nucleotides 2017-2019 (TGT->GGA) to change a cysteine to a glycine. The nucleic acid sequence encodes the fusion polypeptide sequence as set forth in SEQ ID NO: 40.

b) IL-1 Trap 823-1198-B Sequence—The IL-1 Trap 823-1198-B sequence consists of the extracellular domain of human IL-1 RAcP (corresponding to nucleotides 1-1077 of SEQ ID NO: 41), followed by the extracellular domain of human IL-1RI (corresponding to nucleotides 1078-2013 of SEQ ID NO: 41), followed by a stretch of amino acids (corresponding to nucleotides 2014-2019 of SEQ ID NO: 41), followed by the hinge region, the CH2 and CH3 domains of human IgG4 (corresponding to nucleotides 2020-2709 of SEQ ID NO: 41). The nucleic acid sequence encodes the fusion polypeptide sequence as set forth in SEQ ID NO: 42.

c) IL-1 Trap 823-1267-C Sequence—The IL-1 Trap 823-1267-C sequence consists of the extracellular domain of human IL-1 RAcP (corresponding to nucleotides 1-1077 of SEQ ID NO: 43), followed by the extracellular domain of human IL-1RI (corresponding to nucleotides 1078-2013 of SEQ ID NO: 43), followed by a stretch of amino acids (corresponding to nucleotides 2014-2019 of SEQ ID NO: 43), followed by the hinge region, the CH2 and CH3 domains of human IgG4 (corresponding to nucleotides 2020-2709 of SEQ ID NO: 43) containing a mutation at nucleotide 2047 (T>C) to change a serine to a proline. The nucleic acid sequence encodes the fusion polypeptide sequence as set forth in SEQ ID NO: 44.

d) IL-1 Trap 570-FE Sequence—The IL-1 Trap 570-FE sequence consists of the extracellular domain of human IL-1RI (corresponding to nucleotides 1 to 996 of SEQ ID NO: 33), followed by the extracellular domain of human IL-1 RAcP (corresponding to nucleotides 997-2013 of SEQ ID NO: 33) followed by part of the hinge region, the CH2 and CH3 domains of human IgG1 (corresponding to nucleotides 2014-2703 of SEQ ID NO: 33) containing a mutation at nucleotides 2017-2019 (TGT->GGA) to change a cysteine to a glycine. The nucleic acid sequence encodes the fusion polypeptide sequence as set forth in SEQ ID NO: 34.

e) IL-1 Trap 570-FE-B Sequence—The IL-1 Trap 570-FE-B sequence consists of the extracellular domain of human IL-1RI (corresponding to nucleotides 1 to 996 of SEQ ID NO: 35), followed by the extracellular domain of human IL-1 RAcP (corresponding to nucleotides 997-2013 of SEQ ID NO: 35) followed by a stretch of amino acids (corresponding to nucleotides 2014-2019 of SEQ ID NO: 35) followed by the hinge region, the CH2 and CH3 domains of human IgG4 (corresponding to nucleotides 2020-2709 of SEQ ID NO: 35). The nucleic acid sequence encodes the fusion polypeptide sequence as set forth in SEQ ID NO: 36.

f) IL-1 Trap 570-FE-C Sequence—The IL-1 Trap 570-FE-C sequence consists of the extracellular domain of human IL-1RI (corresponding to nucleotides 1 to 996 of SEQ ID NO: 37), followed by the extracellular domain of human IL-1 RAcP (corresponding to nucleotides 997-2013 of SEQ ID NO: 37) followed by a stretch of amino acids (corresponding to nucleotides 2014-2019 of SEQ ID NO: 37) followed by the hinge region, the CH2 and CH3 domains of human IgG4 (corresponding to nucleotides 2020-2709 of SEQ ID NO: 37) containing a mutation at nucleotide 2047 (T>C) to change a serine to a proline. The nucleic acid sequence encodes the fusion polypeptide sequence as set forth in SEQ ID NO: 38.

g) IL-1 Trap 1647-CtF Sequence—The IL-1 Trap 1647-CtF sequence consists of the extracellular domain of human IL-1 RII (corresponding to nucleotides 1-1044 of SEQ ID NO: 45) followed by the extracellular domain of human IL-1 RAcP (corresponding to nucleotides 1045-2058 of SEQ ID NO: 45) followed by a part of the hinge region, the CH2 and CH3 domains of human IgG1 (corresponding to nucleotides 2059-2748 of SEQ ID NO: 45) containing a mutation at nucleotides 2062-2064 (TGT->GGA) to change a cysteine to a glycine. The nucleic acid sequence encodes the fusion polypeptide sequence as set forth in SEQ ID NO: 46.

h) IL-1 Trap 1647-CtF-B Sequence—The IL-1 Trap 1647-CtF-B sequence consists of the extracellular domain of human IL-1 RII (corresponding to nucleotides 1-1044 of SEQ ID NO: 47) followed by the extracellular domain of human IL-1 RAcP (corresponding to nucleotides 1045-2058 of SEQ ID NO: 47) followed by a stretch of amino acids (corresponding to nucleotides 2059-2064 of SEQ ID NO: 47) followed by the hinge region, the CH2 and CH3 domains of human IgG4 (corresponding to nucleotides 2065-2754 of SEQ ID NO: 47). The nucleic acid sequence encodes the fusion polypeptide sequence as set forth in SEQ ID NO: 48.

i) IL-1 Trap 1647-CtF-C Sequence—The IL-1 Trap 1647-CtF-C sequence consists of the extracellular domain of human IL-1 RII (corresponding to nucleotides 1-1044 of SEQ ID NO: 49) followed by the extracellular domain of human IL-1 RAcP (corresponding to nucleotides 1045-2058 of SEQ ID NO: 49) followed by a stretch of amino acids (corresponding to nucleotides 2059-2064 of SEQ ID NO: 49) followed by the hinge region, the CH2 and CH3 domains of human IgG4 (corresponding to nucleotides 2065-2754 of SEQ ID NO: 49) containing a mutation at nucleotide 2092 (T>C) to change a serine to a proline. The nucleic acid sequence encodes the fusion polypeptide sequence as set forth in SEQ ID NO: 50.

j) IL-1 Trap 1649 Sequence—The IL-1 Trap 1649 sequence consists of the extracellular domain of human IL-1 RAcP (corresponding to nucleotides 1-1074 of SEQ ID NO: 51) followed by the extracellular domain of human IL-1 RII (corresponding to nucleotides 1075-2058 of SEQ ID NO: 51) followed by a part of the hinge region, the CH2 and CH3 domains of human IgG1 (corresponding to nucleotides 2059-2748 of SEQ ID NO: 51) containing a mutation at nucleotides 2062-2064 (TGT->GGA) to change a cysteine to a glycine. The nucleic acid sequence encodes the fusion polypeptide sequence as set forth in SEQ ID NO: 52.

k) IL-1 Trap 1649-B Sequence—The IL-1 Trap 1649-B sequence consists of the extracellular domain of human IL-1 RAcP (corresponding to nucleotides 1-1074 of SEQ ID NO:53) followed by the extracellular domain of human IL-1 RII (corresponding to nucleotides 1075-2058 of SEQ ID NO:53) followed by a stretch of amino acids (corresponding to nucleotides 2059-2064) followed by the hinge region, the CH2 and CH3 domains of human IgG4 (corresponding to nucleotides 2065-2754 of SEQ ID NO:53). The nucleic acid sequence encodes the fusion polypeptide sequence as set forth in SEQ ID NO:54.

I) IL-1 Trap 1649-C Sequence—The IL-1 Trap 1649-C sequence consists of the extracellular domain of human IL-1RAcP (corresponding to nucleotides 1-1074 of SEQ ID NO: 55) followed by the extracellular domain of human IL-1RII (corresponding to nucleotides 1075-2058 of SEQ ID NO: 55) followed by a stretch of amino acids (corresponding to nucleotides 2059-2064) followed by the hinge region, the CH2 and CH3 domains of human IgG4 (corresponding to nucleotides 2065-2754 of SEQ ID NO: 55) containing a mutation at nucleotide 2092(T>C) to change a serine to a proline. The nucleic acid sequence encodes the fusion polypeptide sequence as set forth in SEQ ID NO: 56.

In addition to the sequences described supra and in the associated figures, the following modifications to those sequences are also contemplated by the subject invention. For IL1 Traps 823, 823-1198.B, and 823-1267.C:AcP alternative:

A change at nucleotide 1043 from A to C to change the amino acid from Lys to Thr. SG insertion: Between nucleotides 1077 and 1078 an insertion of the nucleotides TCC GGA would add a Ser Gly stretch of amino acids between the two receptor domains of the Trap. For IL1 Traps 570-FE, 570-FE.B, and 570-FE.C: AcP alternative: A change at nucleotide 1979 from A to C to change the amino acid from Lys to Thr. SG insertion: Between nucleotides 996 and 977 an insertion of the nucleotides TCC GGA would add a Ser Gly stretch of amino acids between the two receptor domains of the Trap. For IL1 Traps1647-CtF, 1647-CtF.B, and 1647-CtF.C: AcP alternative: A change at nucleotide 2027 from A to C to change the amino acid from Lys to Thr. SG insertion: Between nucleotides 1044 and 1045 an insertion of the nucleotides TCC GGA would add a Ser Gly stretch of amino acids between the two receptor domains of the Trap. For IL1 Traps 1649, 1649-B, and 1649-C: AcP alternative: A change at nucleotide 1043 from A to C to change the amino acid from Lys to Thr. SG insertion: Between nucleotides 1074 and 1075 an insertion of the nucleotides TCC GGA would add a Ser Gly stretch of amino acids between the two receptor domains of the Trap.

In addition, one of skill in the art will recognize that it may be desirable to construct IL1 Traps in which the Fc domain is derived from immunoglobulins with different allotypes. None of the modifications described supra will alter the Trap's ability to bind IL1.

Example 18

Human IL-1 Trap Blocks the Effects of IL-1 in Inflammed Joints

Background: Zymosan is a yeast cell wall extract that when injected into the knee causes acute inflammation and upregulation of IL-1 in the joint (Joosten et al. 1994 Clin Exp Immunol 97:204-211). Chondrocytes will respond to the inflammation and local IL-1 by down regulating proteoglycan synthesis, a feature of human arthritis that contributes to the gradual destruction of cartilage in the joint (van den Berg et al. 1982 Rheum Intl 1:165-169). Antagonists to IL-1β can be used to evaluate their ability to block the effects of zymosan-induced elevations in IL-1β.

Materials and Methods: Anesthetized male C57BL/6 mice (Taconic) were given an intra-articular (i.a.) injection of Zymosan A (Sigma; 300 μg in 10 μl) into the right knee joint through the patellar ligament. Sterile PBS was injected i.a. (10 μl) into the left knee joint through the patellar ligament. Twenty four hours prior to i.a. injections, animals were treated with either vehicle or hIL-1 Trap 569 (19 mg/kg, s.c.). The patellae were removed 24 h after injection of zymosan in order to measure proteoglycan synthesis as described by van den Berg et al. 1982 supra . Briefly, each patella and associated ligament were incubated for 3 h at 37° C., 5% $CO_2$ in media (RPMI with HEPES, $HCO_3$, glutamine & penicillin/streptomycin) containing 10 μCi/ml $^{35}$S-sulfate (NEN DuPont). Following incubation, tissue was washed and fixed overnight in 10% formalin (VWR). The tissue was then placed in Decalcifing Solution (J. T. Baker) for 4 h prior to dissection of the patella from surrounding tissue. Each patella was then incubated overnight in Solvable (Packard) at 50° C. Ultima Gold liquid scintillation fluid (Packard) was added and the samples were counted in a liquid scintillation counter. Values were reported as the ratio of cpm of zymosan patella/cpm of vehicle patella for each animal.

Figure 51:
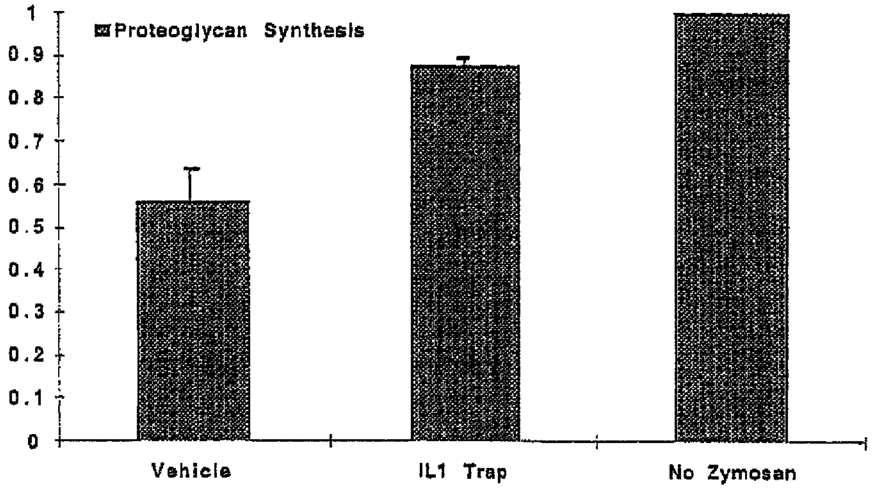
FIG. 51: Human IL-1 Trap blocks the effects of IL-1 in Inflamed Joints. Anesthetized male C57BL/6 mice were given an intra-articular (i.a.) injection of Zymosan A (300 μg in 10 μl) into the right knee joint through the patellar ligament. Sterile PBS was injected i.a. (10 μl) into the left knee joint through the patellar ligament. Twenty four hours prior to i.a. injections, animals were treated with either vehicle or hIL-1 Trap 569 (19 mg/kg, s.c.). The patellae were removed 24 h after injection of zymosan in order to measure proteoglycan synthesis, each patella and associated ligament were incubated for 3 h at 37° C., 5% $CO_2$ in media (RPMI with HEPES, $HCO_3$, glutamine & penicillin/streptomycin) containing 10 uCi/ml $^{35}$S-sulfate. Following incubation, tissue was washed and fixed ovenight in 10% formalin. The tissue was then placed in Decalcifing Solution for 4 h prior to dissection of the patella from surrounding tissue. Each patella was then incubated overnight in Solvable at 50° C. Ultima Gold liquid scintillation fluid was added and the samples were counted in a liquid scintillation counter. Values were reported as the ratio of cpm of zymosan patella/cpm of vehicle patella for each animal. Intra-articular injection of zymosan reduces proteoglycan synthesis by approximately 50% relative to vehicle injection. Administration of hIL-1 Trap prior to zymosan injection blocked the local action of IL-1β and proteoglycan synthesis returned to approximately 90% of control.

Results: Intra-articular injection of zymosan reduces proteoglycan synthesis by approximately 50% relative to vehicle injection (FIG. 51). Administration of hIL-1 Trap prior to zymosan injection blocked the local action of IL-1β and proteoglycan synthesis returned to approximately 90% of control. These data demonstrate that hIL-1 Trap 569 can penetrate the joints after subcutaneous injection to effectively neutralize the biological effect of IL-1 within these joints.

Example 19

Murine IL-1 Trap Reduces the Severity of Arthritis Symptoms in Zymosan-Accelerated Collagen-induced Arthritis (CIA) Model Background. IL-1 has been implicated in the development of inflammation and cartilage destruction in rheumatoid arthritis (Dinarello 1996 Blood 87(6):2095-2147; Wooley et al. 1993 Arthritis & Rheumatism 36(9): 1305-1314). Collagen-induced arthritis (CIA) is a widely studied animal model of inflammatory polyarthritis with similarities to rheumatoid arthritis; common histopathological features include joint inflammation and erosion, synovial hyperplasia and inflammatory cell infiltration (Joe et al. 1999 Mol Med Today 5:367-369). Since previous studies have shown that various anti-IL-1 treatments have a positive effect on reducing arthritis symptoms in CIA animals (van den Berg et al. 1994 Clin Exp Immunol 95:237-243; Joosten et al. 1999 J Immunol 163:5049-5055.; van de Loo 1992 J Rheumatol 19:348-356), Applicants examined the effect of a murine version of the IL-1 Trap (mIL-1 Trap) on the progression of arthritis symptoms in this animal model. The human version of the IL-1 Trap is poorly cross-reactive with rodent IL-1. The mIL-1 Trap consists of the extracellular domain of murine IL-1 RAcP, followed by the extracellular domain of murine IL-1 RI, followed by the hinge, CH2 and CH3 domain of murine IgG2a.

Male DBA-1 mice (Jackson Laboratories) were immunized intradermally at the base of the tail with 100 μg/50 μl bovine Type II collagen (CII; Chondrex) emulsified with complete and incomplete Freund's adjuvant (2:1:1 ratio; Chondrex) and boosted intradermally with CII (100 μg/50 μl) emulsified with incomplete Freund's adjuvant on day 21. Since CIA in DBA-1 mice occurs gradually over a long time period with a low incidence (Joosten et al. 1994 supra), Applicants synchronized the onset of arthritis symptoms by injecting the animals intraperitoneally on day 30 with 3 mg zymosan (Sigma). Two hours prior to zymosan injection, the mice were randomly distributed into treatment groups and were injected with either vehicle or mIL-1 Trap (31 or 10 mg/kg, 3×/week, 8 injections, s.c.). Arthritis symptoms (ASI scores, as described by Wooley et al. 1993 supra) in the paws were evaluated 3×/week by individuals who were blinded to the treatment groups. Animals were sacrificed 24 h after the 8th injection at which time paw width along with ASI scores were measured.

Figure 52:
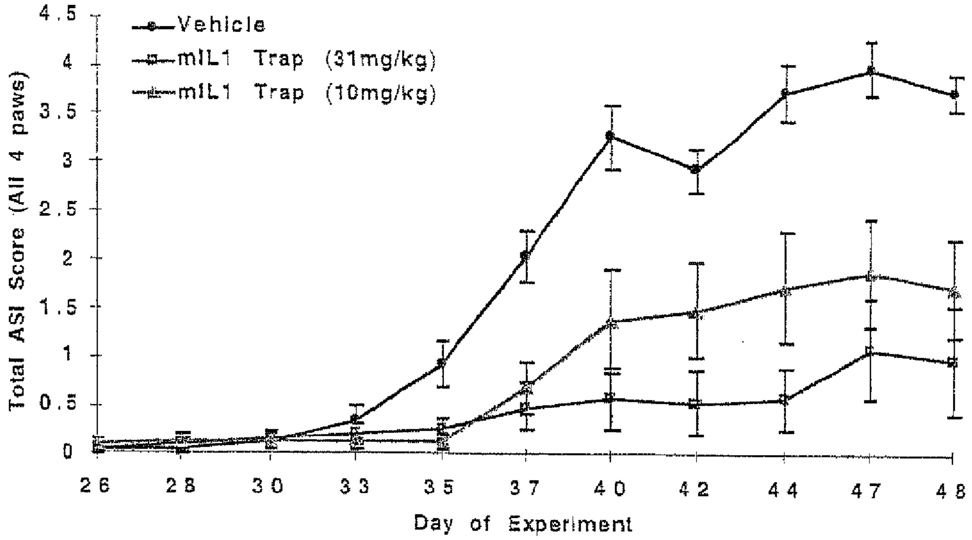
FIGS. 52-53: Murine IL-1 Trap Reduces the Severity of Arthritis Symptoms in a Zymosan-Accelerated Collagen-Induced Arthritis (CIA) model. Male DBA-1 mice were immunized intradermally at the base of the tail with 100 μg/50 μl bovine Type II collagen (CII) emulsified with complete and incomplete Freund's adjuvant (2:1:1 ratio) and boosted intradermally with CII (100 μg/50 μl) emulsified with incomplete Freund's adjuvant on day 21. Since CIA in DBA-1 mice occurs gradually over a long time period with a low incidence, we synchronized the onset of arthritis symptoms by injecting the animals intraperitoneally on day 30 with 3 mg zymosan. Two hours prior to zymosan injection, the mice were randomly distributed into treatment groups and were injected with either vehicle or mIL-1 Trap (31 or 10 mg/kg, 3×/week, 8 injections, s.c.). Arthritis symptoms (ASI scores) in the paws were evaluated 3×/week by individuals who were blinded to the treatment group. Animals were sacrificed 24 h after the 8th injection at which time paw width along with ASI scores were measured. Within 5 days after i.p injection of zymosan, vehicle treated animals had an significant increase in ASI score relative to those receiving mIL-1 Trap with symptoms reaching a maximum 10 to 14 days after zymosan injection. Murine IL-1 Trap acted in a dose-dependent fashion such that animals receiving 10 mg/kg Trap had more arthritis symptoms (greater ASI score) than those receiving 31 mg/kg. However, both mIL-1 Trap treated groups had a significantly lower degree of arthritis symptoms than vehicle. This difference in ASI score is also reflected in the paw width at the time of sacrifice. Animals receiving mIL-1 Trap had paw widths that were similar to those of naive, non-collagen immunized animals
Figure 53:
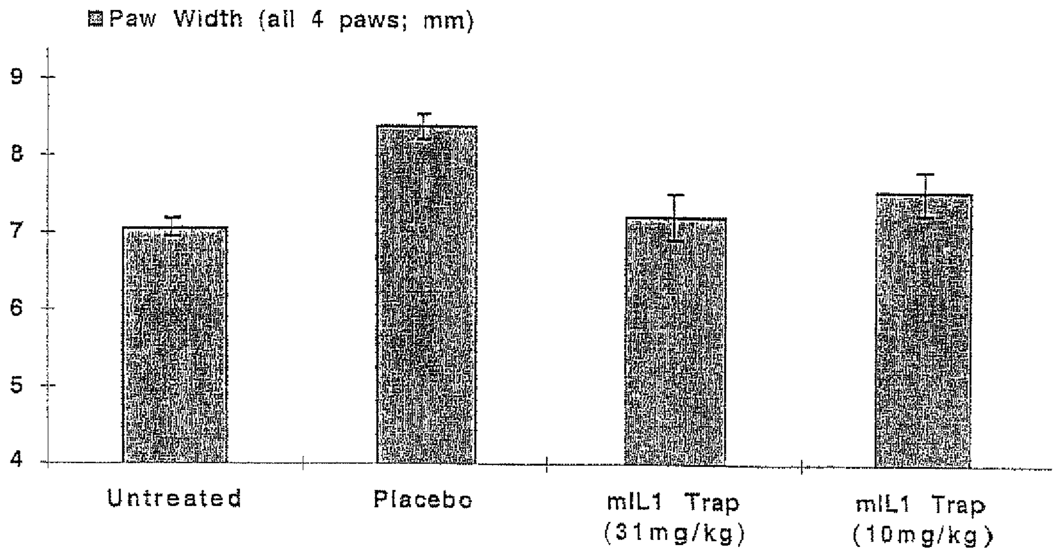

Results. Within 5 days after i.p injection of zymosan, vehicle treated animals had an significant increase in ASI score relative to those receiving mIL-1 Trap (FIG. 52) with symptoms reaching a maximum 10 to 14 days after zymosan injection. Murine IL-1 Trap acted in a dose-dependent fashion such that animals receiving 10 mg/kg Trap had more arthritis symptoms (greater ASI score) than those receiving 31 mg/kg. However, both mIL-1 Trap-treated groups had a significantly lower degree of arthritis symptoms than vehicle. This difference in ASI score is also reflected in the paw width at the time of sacrifice (FIG. 53). Animals receiving mIL-1 Trap had paw widths that were similar to those of naive, non-collagen immunized animals. These data indicate that mIL-1 Trap can effectively neutralize IL-1 and block the development of arthritic joints.

Example 20

IL-1 Trap 1649 Can Block the Activity of IL-1β

Figure 54:
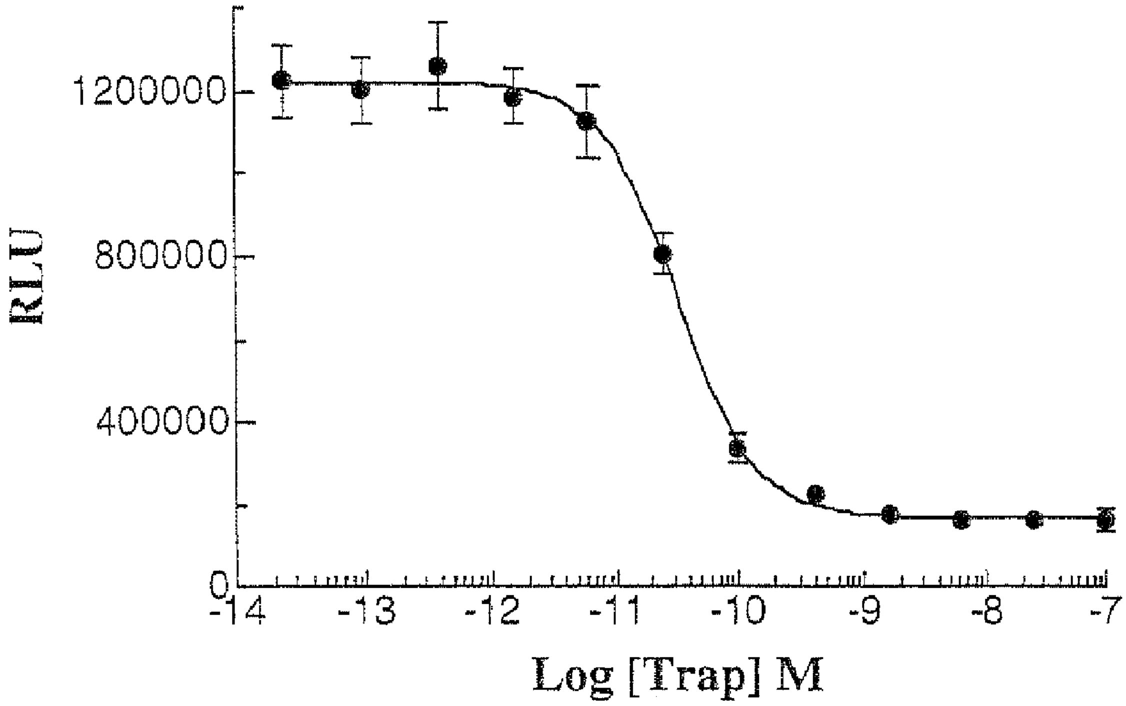
FIG. 54: Various concentrations of IL-1 Trap 1649 were incubated in the presence of 5 pM human IL-1β overnight at room temperature. The mixtures were then added to duplicate wells of 293-NFκB cells (20,000 cells/well) for 5 hrs at 37° C., 5% $CO_2$. Steady-Glo Reagent (Promega) was added to the cells for 15 min at room temperature and luciferase gene expression was quantitated as relative light units (RLU) by luminometry. IL-1 Trap 1649 displays an $IC_{50}$ of 32 pM.

Various concentrations of IL-1 Trap 1649 were incubated in the presence of 5 pM human IL-1β overnight at room temperature. The mixtures were then added to duplicate wells of 293-NFκB cells (20,000 cells/well) for 5 hrs at 37° C., 5% $CO_2$. 293-NFκB cells contain a stably integrated reporter plasmid possessing a luciferase gene driven by a promoter containing 5 NFκB sites. Addition of IL-1β results in increased luciferase gene expression. Steady-Glo Reagent (Promega) was added to the cells for 15 min at room temperature and luciferase gene expression was quantitated as relative light units (RLU) by luminometry. IL-1 Trap 1649 displays an $IC_{50}$ of 32 pM which indicates a Kd of ~30 pM (see FIG. 54). These data indicate that IL-1 Trap 1649 potently blocks IL-1.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

We claim:

1. A method of inhibiting IL-4-mediated inflammation comprising administering an IL-4 inhibitor, wherein the IL-4 inhibitor comprises a fusion polypeptide comprising an IL-2Rγ component encoded by nucleotides 1-762 of SEQ ID NO:17, an IL-4Rα component encoded by nucleotides 772-1395 of SEQ ID NO:17, and a multimerizing component.

2. The method of claim 1, wherein the multimerizing component is an immunoglobulin domain.

3. The method of claim 2, wherein the immunoglobulin domain is selected from the group consisting of an Fc domain of IgG and a heavy chain of IgG.

4. The method of claim 3, wherein the immunoglobulin domain is an Fc domain of IgG.

5. The method of claim 4, wherein the Fc domain is encoded by nucleotides 1396-2082 of SEQ ID NO:17.

6. The method of claim 5, wherein the IL-4 inhibitor further comprises a linker region between the IL-2Rγ component and the IL-4Rα component, wherein the linker region is encoded by nucleotides 763-771 of SEQ ID NO:17.

7. The method of claim 6, wherein the IL-4 inhibitor is encoded by a polynucleotide sequence having SEQ ID NO:17.

8. A method of inhibiting IL-4-mediated inflammation comprising administering an IL-4 inhibitor, wherein the IL-4 inhibitor has the amino acid sequence of SEQ ID NO:18.

* * * * *

SEQUENCE LISTING

```
<160> NUMBER OF SEQ ID NOS: 56

<210> SEQ ID NO 1
<211> LENGTH: 6
<212> TYPE: PRT
<213> ORGANISM: Artificial Sequence
<220> FEATURE:
<223> OTHER INFORMATION: Tag sequence

<400> SEQUENCE: 1

His His His His His His
 1               5


<210> SEQ ID NO 2
<211> LENGTH: 16
<212> TYPE: PRT
<213> ORGANISM: Artificial Sequence
<220> FEATURE:
<223> OTHER INFORMATION: peptide derived from region near C-terminus of
      gp130

<400> SEQUENCE: 2

Cys Gly Thr Glu Gly Gln Val Glu Arg Phe Glu Thr Val Gly Met Glu
 1               5                   10                  15


<210> SEQ ID NO 3
<211> LENGTH: 16
<212> TYPE: DNA
<213> ORGANISM: Artificial Sequence
<220> FEATURE:
<223> OTHER INFORMATION: Kozak sequence

<400> SEQUENCE: 3

cgccgccacc atggtg                                                    16


<210> SEQ ID NO 4
<211> LENGTH: 10
<212> TYPE: PRT
<213> ORGANISM: Artificial Sequence
<220> FEATURE:
<223> OTHER INFORMATION: J peptide

<400> SEQUENCE: 4

Gly Gln Gly Thr Leu Val Thr Val Ser Ser
 1               5                   10


<210> SEQ ID NO 5
<211> LENGTH: 11
<212> TYPE: PRT
<213> ORGANISM: Artificial Sequence
<220> FEATURE:
```

<223> OTHER INFORMATION: J peptide

<400> SEQUENCE: 5

Thr Phe Gly Gln Gly Thr Lys Val Glu Ile Lys
1 5 10

<210> SEQ ID NO 6
<211> LENGTH: 10
<212> TYPE: PRT
<213> ORGANISM: Artificial Sequence
<220> FEATURE:
<223> OTHER INFORMATION: linker sequence

<400> SEQUENCE: 6

Gly Ala Pro Ser Gly Gly Gly Gly Arg Pro
1 5 10

<210> SEQ ID NO 7
<211> LENGTH: 859
<212> TYPE: PRT
<213> ORGANISM: Homo sapiens

<400> SEQUENCE: 7

Met Val Thr Leu Gln Thr Trp Val Val Gln Ala Leu Phe Ile Phe Leu
1 5 10 15

Thr Thr Glu Ser Thr Gly Glu Leu Leu Asp Pro Cys Gly Tyr Ile Ser
20 25 30

Pro Glu Ser Pro Val Val Gln Leu His Ser Asn Phe Thr Ala Val Cys
35 40 45

Val Leu Lys Glu Lys Cys Met Asp Tyr Phe His Val Asn Ala Asn Tyr
50 55 60

Ile Val Trp Lys Thr Asn His Phe Thr Ile Pro Lys Glu Gln Tyr Thr
65 70 75 80

Ile Ile Asn Arg Thr Ala Ser Ser Val Thr Phe Thr Asp Ile Ala Ser
85 90 95

Leu Asn Ile Gln Leu Thr Cys Asn Ile Leu Thr Phe Gly Gln Leu Glu
100 105 110

Gln Asn Val Tyr Gly Ile Thr Ile Ile Ser Gly Leu Pro Pro Glu Lys
115 120 125

Pro Lys Asn Leu Ser Cys Ile Val Asn Glu Gly Lys Lys Met Arg Cys
130 135 140

Glu Trp Asp Gly Gly Arg Glu Thr His Leu Glu Thr Asn Phe Thr Leu
145 150 155 160

Lys Ser Glu Trp Ala Thr His Lys Phe Ala Asp Cys Lys Ala Lys Arg
165 170 175

Asp Thr Pro Thr Ser Cys Thr Val Asp Tyr Ser Thr Val Tyr Phe Val
180 185 190

Asn Ile Glu Val Trp Val Glu Ala Glu Asn Ala Leu Gly Lys Val Thr
195 200 205

Ser Asp His Ile Asn Phe Asp Pro Val Tyr Lys Val Lys Pro Asn Pro
210 215 220

Pro His Asn Leu Ser Val Ile Asn Ser Glu Glu Leu Ser Ser Ile Leu
225 230 235 240

Lys Leu Thr Trp Thr Asn Pro Ser Ile Lys Ser Val Ile Ile Leu Lys
245 250 255

Tyr Asn Ile Gln Tyr Arg Thr Lys Asp Ala Ser Thr Trp Ser Gln Ile
260 265 270

Pro Pro Glu Asp Thr Ala Ser Thr Arg Ser Ser Phe Thr Val Gln Asp

-continued

```
        275                 280                 285

Leu Lys Pro Phe Thr Glu Tyr Val Phe Arg Ile Arg Cys Met Lys Glu
    290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
            340                 345                 350

Thr Leu Pro Pro Phe Glu Ala Asn Gly Lys Ile Leu Asp Tyr Glu Val
        355                 360                 365

Thr Leu Thr Arg Trp Lys Ser His Leu Gln Asn Tyr Thr Val Asn Ala
    370                 375                 380

Thr Lys Leu Thr Val Asn Leu Thr Asn Asp Arg Tyr Leu Ala Thr Leu
385                 390                 395                 400

Thr Val Arg Asn Leu Val Gly Lys Ser Asp Ala Ala Val Leu Thr Ile
                405                 410                 415

Pro Ala Cys Asp Phe Gln Ala Thr His Pro Val Met Asp Leu Lys Ala
            420                 425                 430

Phe Pro Lys Asp Asn Met Leu Trp Val Glu Trp Thr Thr Pro Arg Glu
        435                 440                 445

Ser Val Lys Lys Tyr Ile Leu Glu Trp Cys Val Leu Ser Asp Lys Ala
    450                 455                 460

Pro Cys Ile Thr Asp Trp Gln Gln Glu Asp Gly Thr Val His Arg Thr
465                 470                 475                 480

Tyr Leu Arg Gly Asn Leu Ala Glu Ser Lys Cys Tyr Leu Ile Thr Val
                485                 490                 495

Thr Pro Val Tyr Ala Asp Gly Pro Gly Ser Pro Glu Ser Ile Lys Ala
            500                 505                 510

Tyr Leu Lys Gln Ala Pro Pro Ser Lys Gly Pro Thr Val Arg Thr Lys
        515                 520                 525

Lys Val Gly Lys Asn Glu Ala Val Leu Glu Trp Asp Gln Leu Pro Val
    530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
                565                 570                 575

Tyr Thr Leu Ser Ser Leu Thr Ser Asp Thr Leu Tyr Met Val Arg Met
            580                 585                 590

Ala Ala Tyr Thr Asp Glu Gly Gly Lys Asp Gly Pro Glu Phe Thr Phe
        595                 600                 605

Thr Thr Pro Lys Phe Ala Gln Gly Glu Ile Glu Ser Gly Glu Pro Lys
    610                 615                 620

Ser Cys Asp Lys Thr His Thr Cys Pro Pro Cys Pro Ala Pro Glu Leu
625                 630                 635                 640

Leu Gly Gly Pro Ser Val Phe Leu Phe Pro Pro Lys Pro Lys Asp Thr
                645                 650                 655

Leu Met Ile Ser Arg Thr Pro Glu Val Thr Cys Val Val Val Asp Val
            660                 665                 670

Ser His Glu Asp Pro Glu Val Lys Phe Asn Trp Tyr Val Asp Gly Val
        675                 680                 685

Glu Val His Asn Ala Lys Thr Lys Pro Arg Glu Glu Gln Tyr Asn Ser
    690                 695                 700
```

```
Thr Tyr Arg Val Val Ser Val Leu Thr Val Leu His Gln Asp Trp Leu
705                 710                 715                 720

Asn Gly Lys Glu Tyr Lys Cys Lys Val Ser Asn Lys Ala Leu Pro Ala
                725                 730                 735

Pro Ile Glu Lys Thr Ile Ser Lys Ala Lys Gly Gln Pro Arg Glu Pro
            740                 745                 750

Gln Val Tyr Thr Leu Pro Pro Ser Arg Asp Glu Leu Thr Lys Asn Gln
        755                 760                 765

Val Ser Leu Thr Cys Leu Val Lys Gly Phe Tyr Pro Ser Asp Ile Ala
    770                 775                 780

Val Glu Trp Glu Ser Asn Gly Gln Pro Glu Asn Asn Tyr Lys Thr Thr
785                 790                 795                 800

Pro Pro Val Leu Asp Ser Asp Gly Ser Phe Phe Leu Tyr Ser Lys Leu
                805                 810                 815

Thr Val Asp Lys Ser Arg Trp Gln Gln Gly Asn Val Phe Ser Cys Ser
            820                 825                 830

Val Met His Glu Ala Leu His Asn His Tyr Thr Gln Lys Ser Leu Ser
        835                 840                 845

Leu Ser Pro Gly Lys His His His His His His
    850                 855


<210> SEQ ID NO 8
<211> LENGTH: 592
<212> TYPE: PRT
<213> ORGANISM: Homo sapiens

<400> SEQUENCE: 8

Met Val Ala Val Gly Cys Ala Leu Leu Ala Ala Leu Leu Ala Ala Pro
 1               5                  10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
        35                  40                  45

Gly Val Glu Pro Glu Asp Asn Ala Thr Val His Trp Val Leu Arg Lys
    50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Leu Thr Thr
    130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
        195                 200                 205

Gln Gly Cys Gly Ile Leu Gln Pro Asp Pro Pro Ala Asn Ile Thr Val
    210                 215                 220
```

```
Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
        275                 280                 285

Val Val Gln Leu Arg Ala Gln Glu Glu Phe Gly Gln Gly Glu Trp Ser
    290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
            340                 345                 350

Ser Leu Pro Val Gln Asp Ala Gly Glu Pro Lys Ser Cys Asp Lys Thr
        355                 360                 365

His Thr Cys Pro Pro Cys Pro Ala Pro Glu Leu Leu Gly Gly Pro Ser
    370                 375                 380

Val Phe Leu Phe Pro Pro Lys Pro Lys Asp Thr Leu Met Ile Ser Arg
385                 390                 395                 400

Thr Pro Glu Val Thr Cys Val Val Val Asp Val Ser His Glu Asp Pro
                405                 410                 415

Glu Val Lys Phe Asn Trp Tyr Val Asp Gly Val Glu Val His Asn Ala
            420                 425                 430

Lys Thr Lys Pro Arg Glu Glu Gln Tyr Asn Ser Thr Tyr Arg Val Val
        435                 440                 445

Ser Val Leu Thr Val Leu His Gln Asp Trp Leu Asn Gly Lys Glu Tyr
    450                 455                 460

Lys Cys Lys Val Ser Asn Lys Ala Leu Pro Ala Pro Ile Glu Lys Thr
465                 470                 475                 480

Ile Ser Lys Ala Lys Gly Gln Pro Arg Glu Pro Gln Val Tyr Thr Leu
                485                 490                 495

Pro Pro Ser Arg Asp Glu Leu Thr Lys Asn Gln Val Ser Leu Thr Cys
            500                 505                 510

Leu Val Lys Gly Phe Tyr Pro Ser Asp Ile Ala Val Glu Trp Glu Ser
        515                 520                 525

Asn Gly Gln Pro Glu Asn Asn Tyr Lys Thr Thr Pro Pro Val Leu Asp
    530                 535                 540

Ser Asp Gly Ser Phe Phe Leu Tyr Ser Lys Leu Thr Val Asp Lys Ser
545                 550                 555                 560

Arg Trp Gln Gln Gly Asn Val Phe Ser Cys Ser Val Met His Glu Ala
                565                 570                 575

Leu His Asn His Tyr Thr Gln Lys Ser Leu Ser Leu Ser Pro Gly Lys
            580                 585                 590


<210> SEQ ID NO 9
<211> LENGTH: 951
<212> TYPE: PRT
<213> ORGANISM: Homo sapiens

<400> SEQUENCE: 9

Met Val Thr Leu Gln Thr Trp Val Val Gln Ala Leu Phe Ile Phe Leu
 1               5                  10                  15
```

-continued

```
Thr Thr Glu Ser Thr Gly Glu Leu Leu Asp Pro Cys Gly Tyr Ile Ser
            20                  25                  30

Pro Glu Ser Pro Val Val Gln Leu His Ser Asn Phe Thr Ala Val Cys
        35                  40                  45

Val Leu Lys Glu Lys Cys Met Asp Tyr Phe His Val Asn Ala Asn Tyr
    50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
        275                 280                 285

Leu Lys Pro Phe Thr Glu Tyr Val Phe Arg Ile Arg Cys Met Lys Glu
    290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
            340                 345                 350

Thr Leu Pro Pro Phe Glu Ala Asn Gly Lys Ile Leu Asp Tyr Glu Val
        355                 360                 365

Thr Leu Thr Arg Trp Lys Ser His Leu Gln Asn Tyr Thr Val Asn Ala
    370                 375                 380

Thr Lys Leu Thr Val Asn Leu Thr Asn Asp Arg Tyr Leu Ala Thr Leu
385                 390                 395                 400

Thr Val Arg Asn Leu Val Gly Lys Ser Asp Ala Ala Val Leu Thr Ile
                405                 410                 415

Pro Ala Cys Asp Phe Gln Ala Thr His Pro Val Met Asp Leu Lys Ala
            420                 425                 430

Phe Pro Lys Asp Asn Met Leu Trp Val Glu Trp Thr Thr Pro Arg Glu
        435                 440                 445
```

```
Ser Val Lys Lys Tyr Ile Leu Glu Trp Cys Val Leu Ser Asp Lys Ala
    450                 455                 460

Pro Cys Ile Thr Asp Trp Gln Gln Glu Asp Gly Thr Val His Arg Thr
465                 470                 475                 480

Tyr Leu Arg Gly Asn Leu Ala Glu Ser Lys Cys Tyr Leu Ile Thr Val
                485                 490                 495

Thr Pro Val Tyr Ala Asp Gly Pro Gly Ser Pro Glu Ser Ile Lys Ala
            500                 505                 510

Tyr Leu Lys Gln Ala Pro Pro Ser Lys Gly Pro Thr Val Arg Thr Lys
        515                 520                 525

Lys Val Gly Lys Asn Glu Ala Val Leu Glu Trp Asp Gln Leu Pro Val
    530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
                565                 570                 575

Tyr Thr Leu Ser Ser Leu Thr Ser Asp Thr Leu Tyr Met Val Arg Met
            580                 585                 590

Ala Ala Tyr Thr Asp Glu Gly Gly Lys Asp Gly Pro Glu Phe Thr Phe
        595                 600                 605

Thr Thr Pro Lys Phe Ala Gln Gly Glu Ile Glu Ser Gly Ala Ser Thr
    610                 615                 620

Lys Gly Pro Ser Val Phe Pro Leu Ala Pro Ser Ser Lys Ser Thr Ser
625                 630                 635                 640

Gly Gly Thr Ala Ala Leu Gly Cys Leu Val Lys Asp Tyr Phe Pro Glu
                645                 650                 655

Pro Val Thr Val Ser Trp Asn Ser Gly Ala Leu Thr Ser Gly Val His
            660                 665                 670

Thr Phe Pro Ala Val Leu Gln Ser Ser Gly Leu Tyr Ser Leu Ser Ser
        675                 680                 685

Val Val Thr Val Pro Ser Ser Ser Leu Gly Thr Gln Thr Tyr Ile Cys
    690                 695                 700

Asn Val Asn His Lys Pro Ser Asn Thr Lys Val Asp Lys Lys Val Glu
705                 710                 715                 720

Pro Lys Ser Cys Asp Lys Thr His Thr Cys Pro Pro Cys Pro Ala Pro
                725                 730                 735

Glu Leu Leu Gly Gly Pro Ser Val Phe Leu Phe Pro Pro Lys Pro Lys
            740                 745                 750

Asp Thr Leu Met Ile Ser Arg Thr Pro Glu Val Thr Cys Val Val Val
        755                 760                 765

Asp Val Ser His Glu Asp Pro Glu Val Lys Phe Asn Trp Tyr Val Asp
    770                 775                 780

Gly Val Glu Val His Asn Ala Lys Thr Lys Pro Arg Glu Glu Gln Tyr
785                 790                 795                 800

Asn Ser Thr Tyr Arg Val Val Ser Val Leu Thr Val Leu His Gln Asp
                805                 810                 815

Trp Leu Asn Gly Lys Glu Tyr Lys Cys Lys Val Ser Asn Lys Ala Leu
            820                 825                 830

Pro Ala Pro Ile Glu Lys Thr Ile Ser Lys Ala Lys Gly Gln Pro Arg
        835                 840                 845

Glu Pro Gln Val Tyr Thr Leu Pro Pro Ser Arg Asp Glu Leu Thr Lys
    850                 855                 860

Asn Gln Val Ser Leu Thr Cys Leu Val Lys Gly Phe Tyr Pro Ser Asp
```

-continued

```
865                 870                 875                 880

Ile Ala Val Glu Trp Glu Ser Asn Gly Gln Pro Glu Asn Asn Tyr Lys
                885                 890                 895

Thr Thr Pro Pro Val Leu Asp Ser Asp Gly Ser Phe Phe Leu Tyr Ser
            900                 905                 910

Lys Leu Thr Val Asp Lys Ser Arg Trp Gln Gln Gly Asn Val Phe Ser
        915                 920                 925

Cys Ser Val Met His Glu Ala Leu His Asn His Tyr Thr Gln Lys Ser
    930                 935                 940

Leu Ser Leu Ser Pro Gly Lys
945                 950


<210> SEQ ID NO 10
<211> LENGTH: 332
<212> TYPE: PRT
<213> ORGANISM: Homo sapiens

<400> SEQUENCE: 10

Met Val Thr Leu Gln Thr Trp Val Val Gln Ala Leu Phe Ile Phe Leu
 1               5                  10                  15

Thr Thr Glu Ser Thr Gly Glu Leu Leu Asp Pro Cys Gly Tyr Ile Ser
            20                  25                  30

Pro Glu Ser Pro Val Val Gln Leu His Ser Asn Phe Thr Ala Val Cys
        35                  40                  45

Val Leu Lys Glu Lys Cys Met Asp Tyr Phe His Val Asn Ala Asn Tyr
    50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
        275                 280                 285

Leu Lys Pro Phe Thr Glu Tyr Val Phe Arg Ile Arg Cys Met Lys Glu
```

```
    290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Gly
                325                 330


<210> SEQ ID NO 11
<211> LENGTH: 120
<212> TYPE: PRT
<213> ORGANISM: Homo sapiens

<400> SEQUENCE: 11

Ser Gly Gly Gln Gly Thr Leu Val Thr Val Ser Ser Ala Ser Thr Lys
 1               5                  10                  15

Gly Pro Ser Val Phe Pro Leu Ala Pro Ser Ser Lys Ser Thr Ser Gly
            20                  25                  30

Gly Thr Ala Ala Leu Gly Cys Leu Val Lys Asp Tyr Phe Pro Glu Pro
        35                  40                  45

Val Thr Val Ser Trp Asn Ser Gly Ala Leu Thr Ser Gly Val His Thr
    50                  55                  60

Phe Pro Ala Val Leu Gln Ser Ser Gly Leu Tyr Ser Leu Ser Ser Val
65                  70                  75                  80

Val Thr Val Pro Ser Ser Ser Leu Gly Thr Gln Thr Tyr Ile Cys Asn
                85                  90                  95

Val Asn His Lys Pro Ser Asn Thr Lys Val Asp Lys Lys Val Glu Pro
            100                 105                 110

Lys Ser Cys Asp Lys Thr His Thr
        115                 120


<210> SEQ ID NO 12
<211> LENGTH: 329
<212> TYPE: PRT
<213> ORGANISM: Homo sapiens

<400> SEQUENCE: 12

Ser Gly Ala Ser Thr Lys Gly Pro Ser Val Phe Pro Leu Ala Pro Cys
 1               5                  10                  15

Ser Arg Ser Thr Ser Glu Ser Thr Ala Ala Leu Gly Cys Leu Val Lys
            20                  25                  30

Asp Tyr Phe Pro Glu Pro Val Thr Val Ser Trp Asn Ser Gly Ala Leu
        35                  40                  45

Thr Ser Gly Val His Thr Phe Pro Ala Val Leu Gln Ser Ser Gly Leu
    50                  55                  60

Tyr Ser Leu Ser Ser Val Val Thr Val Pro Ser Ser Ser Leu Gly Thr
65                  70                  75                  80

Lys Thr Tyr Thr Cys Asn Val Asp His Lys Pro Ser Asn Thr Lys Val
                85                  90                  95

Asp Lys Arg Val Glu Ser Lys Tyr Gly Pro Pro Cys Pro Ser Cys Pro
            100                 105                 110

Ala Pro Glu Phe Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser Gln Glu Asp Pro Glu Val Gln Phe Asn Trp Tyr
145                 150                 155                 160

Val Asp Gly Val Glu Val His Asn Ala Lys Thr Lys Pro Arg Glu Glu
                165                 170                 175
```

-continued

```
Gln Phe Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Gly Leu Pro Ser Ser Ile Glu Lys Thr Ile Ser Lys Ala Lys Gly Gln
    210                 215                 220

Pro Arg Glu Pro Gln Val Tyr Thr Leu Pro Pro Ser Gln Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Arg Leu Thr Val Asp Lys Ser Arg Trp Gln Glu Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Leu Gly Lys
                325


<210> SEQ ID NO 13
<211> LENGTH: 108
<212> TYPE: PRT
<213> ORGANISM: Homo sapiens

<400> SEQUENCE: 13

Ser Gly Thr Val Ala Ala Pro Ser Val Phe Ile Phe Pro Pro Ser Asp
 1               5                  10                  15

Glu Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Asn Ala Leu
        35                  40                  45

Gln Ser Gly Asn Ser Gln Glu Ser Val Thr Glu Gln Asp Ser Lys Asp
    50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Ser
                85                  90                  95

Ser Pro Val Thr Lys Ser Phe Asn Arg Gly Glu Cys
            100                 105


<210> SEQ ID NO 14
<211> LENGTH: 106
<212> TYPE: PRT
<213> ORGANISM: Homo sapiens

<400> SEQUENCE: 14

Ser Gly Pro Lys Ala Ala Pro Ser Val Thr Leu Phe Pro Pro Ser Ser
 1               5                  10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60
```

Lys Tyr Ala Ala Ser Ser Tyr Leu Ser Leu Thr Pro Glu Gln Trp Lys
65 70 75 80

Ser His Arg Ser Tyr Ser Cys Gln Val Thr His Glu Gly Ser Thr Val
85 90 95

Glu Lys Thr Val Ala Pro Thr Glu Cys Ser
100 105

<210> SEQ ID NO 15
<211> LENGTH: 360
<212> TYPE: PRT
<213> ORGANISM: Homo sapiens

<400> SEQUENCE: 15

Met Val Ala Val Gly Cys Ala Leu Leu Ala Ala Leu Leu Ala Ala Pro
1 5 10 15

Gly Ala Ala Leu Ala Pro Arg Arg Cys Pro Ala Gln Glu Val Ala Arg
20 25 30

Gly Val Leu Thr Ser Leu Pro Gly Asp Ser Val Thr Leu Thr Cys Pro
35 40 45

Gly Val Glu Pro Glu Asp Asn Ala Thr Val His Trp Val Leu Arg Lys
50 55 60

Pro Ala Ala Gly Ser His Pro Ser Arg Trp Ala Gly Met Gly Arg Arg
65 70 75 80

Leu Leu Leu Arg Ser Val Gln Leu His Asp Ser Gly Asn Tyr Ser Cys
85 90 95

Tyr Arg Ala Gly Arg Pro Ala Gly Thr Val His Leu Leu Val Asp Val
100 105 110

Pro Pro Glu Glu Pro Gln Leu Ser Cys Phe Arg Lys Ser Pro Leu Ser
115 120 125

Asn Val Val Cys Glu Trp Gly Pro Arg Ser Thr Pro Ser Leu Thr Thr
130 135 140

Lys Ala Val Leu Leu Val Arg Lys Phe Gln Asn Ser Pro Ala Glu Asp
145 150 155 160

Phe Gln Glu Pro Cys Gln Tyr Ser Gln Glu Ser Gln Lys Phe Ser Cys
165 170 175

Gln Leu Ala Val Pro Glu Gly Asp Ser Ser Phe Tyr Ile Val Ser Met
180 185 190

Cys Val Ala Ser Ser Val Gly Ser Lys Phe Ser Lys Thr Gln Thr Phe
195 200 205

Gln Gly Cys Gly Ile Leu Gln Pro Asp Pro Pro Ala Asn Ile Thr Val
210 215 220

Thr Ala Val Ala Arg Asn Pro Arg Trp Leu Ser Val Thr Trp Gln Asp
225 230 235 240

Pro His Ser Trp Asn Ser Ser Phe Tyr Arg Leu Arg Phe Glu Leu Arg
245 250 255

Tyr Arg Ala Glu Arg Ser Lys Thr Phe Thr Thr Trp Met Val Lys Asp
260 265 270

Leu Gln His His Cys Val Ile His Asp Ala Trp Ser Gly Leu Arg His
275 280 285

Val Val Gln Leu Arg Ala Gln Glu Glu Phe Gly Gln Gly Glu Trp Ser
290 295 300

Glu Trp Ser Pro Glu Ala Met Gly Thr Pro Trp Thr Glu Ser Arg Ser
305 310 315 320

Pro Pro Ala Glu Asn Glu Val Ser Thr Pro Met Gln Ala Leu Thr Thr
325 330 335

```
Asn Lys Asp Asp Asp Asn Ile Leu Phe Arg Asp Ser Ala Asn Ala Thr
            340                 345                 350

Ser Leu Pro Val Gln Asp Ala Gly
        355                 360


<210> SEQ ID NO 16
<211> LENGTH: 315
<212> TYPE: PRT
<213> ORGANISM: Homo sapiens

<400> SEQUENCE: 16

Met Val Ala Val Gly Cys Ala Leu Leu Ala Ala Leu Leu Ala Ala Pro
 1               5                  10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
        35                  40                  45

Gly Val Glu Pro Glu Asp Asn Ala Thr Val His Trp Val Leu Arg Lys
    50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Leu Thr Thr
    130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
        195                 200                 205

Gln Gly Cys Gly Ile Leu Gln Pro Asp Pro Pro Ala Asn Ile Thr Val
    210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
        275                 280                 285

Val Val Gln Leu Arg Ala Gln Glu Glu Phe Gly Gln Gly Glu Trp Ser
    290                 295                 300

Glu Trp Ser Pro Glu Ala Met Gly Thr Thr Gly
305                 310                 315


<210> SEQ ID NO 17
<211> LENGTH: 2085
<212> TYPE: DNA
<213> ORGANISM: Homo sapiens
<220> FEATURE:
```

```
<221> NAME/KEY: CDS
<222> LOCATION: (1)...(2082)

<400> SEQUENCE: 17

atg gtg aag cca tca tta cca ttc aca tcc ctc tta ttc ctg cag ctg       48
Met Val Lys Pro Ser Leu Pro Phe Thr Ser Leu Leu Phe Leu Gln Leu
 1               5                  10                  15

ccc ctg ctg gga gtg ggg ctg aac acg aca att ctg acg ccc aat ggg       96
Pro Leu Leu Gly Val Gly Leu Asn Thr Thr Ile Leu Thr Pro Asn Gly
            20                  25                  30

aat gaa gac acc aca gct gat ttc ttc ctg acc act atg ccc act gac      144
Asn Glu Asp Thr Thr Ala Asp Phe Phe Leu Thr Thr Met Pro Thr Asp
        35                  40                  45

tcc ctc agt gtt tcc act ctg ccc ctc cca gag gtt cag tgt ttt gtg      192
Ser Leu Ser Val Ser Thr Leu Pro Leu Pro Glu Val Gln Cys Phe Val
    50                  55                  60

ttc aat gtc gag tac atg aat tgc act tgg aac agc agc tct gag ccc      240
Phe Asn Val Glu Tyr Met Asn Cys Thr Trp Asn Ser Ser Ser Glu Pro
 65                  70                  75                  80

cag cct acc aac ctc act ctg cat tat tgg tac aag aac tcg gat aat      288
Gln Pro Thr Asn Leu Thr Leu His Tyr Trp Tyr Lys Asn Ser Asp Asn
                85                  90                  95

gat aaa gtc cag aag tgc agc cac tat cta ttc tct gaa gaa atc act      336
Asp Lys Val Gln Lys Cys Ser His Tyr Leu Phe Ser Glu Glu Ile Thr
            100                 105                 110

tct ggc tgt cag ttg caa aaa aag gag atc cac ctc tac caa aca ttt      384
Ser Gly Cys Gln Leu Gln Lys Lys Glu Ile His Leu Tyr Gln Thr Phe
        115                 120                 125

gtt gtt cag ctc cag gac cca cgg gaa ccc agg aga cag gcc aca cag      432
Val Val Gln Leu Gln Asp Pro Arg Glu Pro Arg Arg Gln Ala Thr Gln
    130                 135                 140

atg cta aaa ctg cag aat ctg gtg atc ccc tgg gct cca gag aac cta      480
Met Leu Lys Leu Gln Asn Leu Val Ile Pro Trp Ala Pro Glu Asn Leu
145                 150                 155                 160

aca ctt cac aaa ctg agt gaa tcc cag cta gaa ctg aac tgg aac aac      528
Thr Leu His Lys Leu Ser Glu Ser Gln Leu Glu Leu Asn Trp Asn Asn
                165                 170                 175

aga ttc ttg aac cac tgt ttg gag cac ttg gtg cag tac cgg act gac      576
Arg Phe Leu Asn His Cys Leu Glu His Leu Val Gln Tyr Arg Thr Asp
            180                 185                 190

tgg gac cac agc tgg act gaa caa tca gtg gat tat aga cat aag ttc      624
Trp Asp His Ser Trp Thr Glu Gln Ser Val Asp Tyr Arg His Lys Phe
        195                 200                 205

tcc ttg cct agt gtg gat ggg cag aaa cgc tac acg ttt cgt gtt cgg      672
Ser Leu Pro Ser Val Asp Gly Gln Lys Arg Tyr Thr Phe Arg Val Arg
    210                 215                 220

agc cgc ttt aac cca ctc tgt gga agt gct cag cat tgg agt gaa tgg      720
Ser Arg Phe Asn Pro Leu Cys Gly Ser Ala Gln His Trp Ser Glu Trp
225                 230                 235                 240

agc cac cca atc cac tgg ggg agc aat act tca aaa gag aac gcg tcg      768
Ser His Pro Ile His Trp Gly Ser Asn Thr Ser Lys Glu Asn Ala Ser
                245                 250                 255

tct ggg aac atg aag gtc ctg cag gag ccc acc tgc gtc tcc gac tac      816
Ser Gly Asn Met Lys Val Leu Gln Glu Pro Thr Cys Val Ser Asp Tyr
            260                 265                 270

atg agc atc tct act tgc gag tgg aag atg aat ggt ccc acc aat tgc      864
Met Ser Ile Ser Thr Cys Glu Trp Lys Met Asn Gly Pro Thr Asn Cys
        275                 280                 285

agc acc gag ctc cgc ctg ttg tac cag ctg gtt ttt ctg ctc tcc gaa      912
Ser Thr Glu Leu Arg Leu Leu Tyr Gln Leu Val Phe Leu Leu Ser Glu
    290                 295                 300
```

-continued

```
gcc cac acg tgt atc cct gag aac aac gga ggc gcg ggg tgc gtg tgc      960
Ala His Thr Cys Ile Pro Glu Asn Asn Gly Gly Ala Gly Cys Val Cys
305                 310                 315                 320

cac ctg ctc atg gat gac gtg gtc agt gcg gat aac tat aca ctg gac     1008
His Leu Leu Met Asp Asp Val Val Ser Ala Asp Asn Tyr Thr Leu Asp
                325                 330                 335

ctg tgg gct ggg cag cag ctg ctg tgg aag ggc tcc ttc aag ccc agc     1056
Leu Trp Ala Gly Gln Gln Leu Leu Trp Lys Gly Ser Phe Lys Pro Ser
            340                 345                 350

gag cat gtg aaa ccc agg gcc cca gga aac ctg aca gtt cac acc aat     1104
Glu His Val Lys Pro Arg Ala Pro Gly Asn Leu Thr Val His Thr Asn
        355                 360                 365

gtc tcc gac act ctg ctg ctg acc tgg agc aac ccg tat ccc cct gac     1152
Val Ser Asp Thr Leu Leu Leu Thr Trp Ser Asn Pro Tyr Pro Pro Asp
    370                 375                 380

aat tac ctg tat aat cat ctc acc tat gca gtc aac att tgg agt gaa     1200
Asn Tyr Leu Tyr Asn His Leu Thr Tyr Ala Val Asn Ile Trp Ser Glu
385                 390                 395                 400

aac gac ccg gca gat ttc aga atc tat aac gtg acc tac cta gaa ccc     1248
Asn Asp Pro Ala Asp Phe Arg Ile Tyr Asn Val Thr Tyr Leu Glu Pro
                405                 410                 415

tcc ctc cgc atc gca gcc agc acc ctg aag tct ggg att tcc tac agg     1296
Ser Leu Arg Ile Ala Ala Ser Thr Leu Lys Ser Gly Ile Ser Tyr Arg
            420                 425                 430

gca cgg gtg agg gcc tgg gct cag tgc tat aac acc acc tgg agt gag     1344
Ala Arg Val Arg Ala Trp Ala Gln Cys Tyr Asn Thr Thr Trp Ser Glu
        435                 440                 445

tgg agc ccc agc acc aag tgg cac aac tcc tac agg gag ccc ttc gag     1392
Trp Ser Pro Ser Thr Lys Trp His Asn Ser Tyr Arg Glu Pro Phe Glu
    450                 455                 460

cag tcc gga gac aaa act cac aca tgc cca ccg tgc cca gca cct gaa     1440
Gln Ser Gly Asp Lys Thr His Thr Cys Pro Pro Cys Pro Ala Pro Glu
465                 470                 475                 480

ctc ctg ggg gga ccg tca gtc ttc ctc ttc ccc cca aaa ccc aag gac     1488
Leu Leu Gly Gly Pro Ser Val Phe Leu Phe Pro Pro Lys Pro Lys Asp
                485                 490                 495

acc ctc atg atc tcc cgg acc cct gag gtc aca tgc gtg gtg gtg gac     1536
Thr Leu Met Ile Ser Arg Thr Pro Glu Val Thr Cys Val Val Val Asp
            500                 505                 510

gtg agc cac gaa gac cct gag gtc aag ttc aac tgg tac gtg gac ggc     1584
Val Ser His Glu Asp Pro Glu Val Lys Phe Asn Trp Tyr Val Asp Gly
        515                 520                 525

gtg gag gtg cat aat gcc aag aca aag ccg cgg gag gag cag tac aac     1632
Val Glu Val His Asn Ala Lys Thr Lys Pro Arg Glu Glu Gln Tyr Asn
    530                 535                 540

agc acg tac cgt gtg gtc agc gtc ctc acc gtc ctg cac cag gac tgg     1680
Ser Thr Tyr Arg Val Val Ser Val Leu Thr Val Leu His Gln Asp Trp
545                 550                 555                 560

ctg aat ggc aag gag tac aag tgc aag gtc tcc aac aaa gcc ctc cca     1728
Leu Asn Gly Lys Glu Tyr Lys Cys Lys Val Ser Asn Lys Ala Leu Pro
                565                 570                 575

gcc ccc atc gag aaa acc atc tcc aaa gcc aaa ggg cag ccc cga gaa     1776
Ala Pro Ile Glu Lys Thr Ile Ser Lys Ala Lys Gly Gln Pro Arg Glu
            580                 585                 590

cca cag gtg tac acc ctg ccc cca tcc cgg gag gag atg acc aag aac     1824
Pro Gln Val Tyr Thr Leu Pro Pro Ser Arg Glu Glu Met Thr Lys Asn
        595                 600                 605

cag gtc agc ctg acc tgc ctg gtc aaa ggc ttc tat ccc agc gac atc     1872
Gln Val Ser Leu Thr Cys Leu Val Lys Gly Phe Tyr Pro Ser Asp Ile
    610                 615                 620
```

```
gcc gtg gag tgg gag agc aat ggg cag ccg gag aac aac tac aag acc     1920
Ala Val Glu Trp Glu Ser Asn Gly Gln Pro Glu Asn Asn Tyr Lys Thr
625                 630                 635                 640

acg cct ccc gtg ctg gac tcc gac ggc tcc ttc ttc ctc tat agc aag     1968
Thr Pro Pro Val Leu Asp Ser Asp Gly Ser Phe Phe Leu Tyr Ser Lys
                645                 650                 655

ctc acc gtg gac aag agc agg tgg cag cag ggg aac gtc ttc tca tgc     2016
Leu Thr Val Asp Lys Ser Arg Trp Gln Gln Gly Asn Val Phe Ser Cys
            660                 665                 670

tcc gtg atg cat gag gct ctg cac aac cac tac acg cag aag agc ctc     2064
Ser Val Met His Glu Ala Leu His Asn His Tyr Thr Gln Lys Ser Leu
        675                 680                 685

tcc ctg tct ccg ggt aaa tga                                         2085
Ser Leu Ser Pro Gly Lys
    690


<210> SEQ ID NO 18
<211> LENGTH: 694
<212> TYPE: PRT
<213> ORGANISM: Homo sapiens

<400> SEQUENCE: 18

Met Val Lys Pro Ser Leu Pro Phe Thr Ser Leu Leu Phe Leu Gln Leu
 1               5                  10                  15

Pro Leu Leu Gly Val Gly Leu Asn Thr Thr Ile Leu Thr Pro Asn Gly
            20                  25                  30

Asn Glu Asp Thr Thr Ala Asp Phe Phe Leu Thr Thr Met Pro Thr Asp
        35                  40                  45

Ser Leu Ser Val Ser Thr Leu Pro Leu Pro Glu Val Gln Cys Phe Val
    50                  55                  60

Phe Asn Val Glu Tyr Met Asn Cys Thr Trp Asn Ser Ser Ser Glu Pro
65                  70                  75                  80

Gln Pro Thr Asn Leu Thr Leu His Tyr Trp Tyr Lys Asn Ser Asp Asn
                85                  90                  95

Asp Lys Val Gln Lys Cys Ser His Tyr Leu Phe Ser Glu Glu Ile Thr
            100                 105                 110

Ser Gly Cys Gln Leu Gln Lys Lys Glu Ile His Leu Tyr Gln Thr Phe
        115                 120                 125

Val Val Gln Leu Gln Asp Pro Arg Glu Pro Arg Arg Gln Ala Thr Gln
    130                 135                 140

Met Leu Lys Leu Gln Asn Leu Val Ile Pro Trp Ala Pro Glu Asn Leu
145                 150                 155                 160

Thr Leu His Lys Leu Ser Glu Ser Gln Leu Glu Leu Asn Trp Asn Asn
                165                 170                 175

Arg Phe Leu Asn His Cys Leu Glu His Leu Val Gln Tyr Arg Thr Asp
            180                 185                 190

Trp Asp His Ser Trp Thr Glu Gln Ser Val Asp Tyr Arg His Lys Phe
        195                 200                 205

Ser Leu Pro Ser Val Asp Gly Gln Lys Arg Tyr Thr Phe Arg Val Arg
    210                 215                 220

Ser Arg Phe Asn Pro Leu Cys Gly Ser Ala Gln His Trp Ser Glu Trp
225                 230                 235                 240

Ser His Pro Ile His Trp Gly Ser Asn Thr Ser Lys Glu Asn Ala Ser
                245                 250                 255

Ser Gly Asn Met Lys Val Leu Gln Glu Pro Thr Cys Val Ser Asp Tyr
            260                 265                 270
```

-continued

```
Met Ser Ile Ser Thr Cys Glu Trp Lys Met Asn Gly Pro Thr Asn Cys
        275                 280                 285

Ser Thr Glu Leu Arg Leu Leu Tyr Gln Leu Val Phe Leu Leu Ser Glu
    290                 295                 300

Ala His Thr Cys Ile Pro Glu Asn Asn Gly Gly Ala Gly Cys Val Cys
305                 310                 315                 320

His Leu Leu Met Asp Asp Val Val Ser Ala Asp Asn Tyr Thr Leu Asp
                325                 330                 335

Leu Trp Ala Gly Gln Gln Leu Leu Trp Lys Gly Ser Phe Lys Pro Ser
            340                 345                 350

Glu His Val Lys Pro Arg Ala Pro Gly Asn Leu Thr Val His Thr Asn
        355                 360                 365

Val Ser Asp Thr Leu Leu Leu Thr Trp Ser Asn Pro Tyr Pro Pro Asp
    370                 375                 380

Asn Tyr Leu Tyr Asn His Leu Thr Tyr Ala Val Asn Ile Trp Ser Glu
385                 390                 395                 400

Asn Asp Pro Ala Asp Phe Arg Ile Tyr Asn Val Thr Tyr Leu Glu Pro
                405                 410                 415

Ser Leu Arg Ile Ala Ala Ser Thr Leu Lys Ser Gly Ile Ser Tyr Arg
            420                 425                 430

Ala Arg Val Arg Ala Trp Ala Gln Cys Tyr Asn Thr Thr Trp Ser Glu
        435                 440                 445

Trp Ser Pro Ser Thr Lys Trp His Asn Ser Tyr Arg Glu Pro Phe Glu
    450                 455                 460

Gln Ser Gly Asp Lys Thr His Thr Cys Pro Pro Cys Pro Ala Pro Glu
465                 470                 475                 480

Leu Leu Gly Gly Pro Ser Val Phe Leu Phe Pro Pro Lys Pro Lys Asp
                485                 490                 495

Thr Leu Met Ile Ser Arg Thr Pro Glu Val Thr Cys Val Val Val Asp
            500                 505                 510

Val Ser His Glu Asp Pro Glu Val Lys Phe Asn Trp Tyr Val Asp Gly
        515                 520                 525

Val Glu Val His Asn Ala Lys Thr Lys Pro Arg Glu Glu Gln Tyr Asn
    530                 535                 540

Ser Thr Tyr Arg Val Val Ser Val Leu Thr Val Leu His Gln Asp Trp
545                 550                 555                 560

Leu Asn Gly Lys Glu Tyr Lys Cys Lys Val Ser Asn Lys Ala Leu Pro
                565                 570                 575

Ala Pro Ile Glu Lys Thr Ile Ser Lys Ala Lys Gly Gln Pro Arg Glu
            580                 585                 590

Pro Gln Val Tyr Thr Leu Pro Pro Ser Arg Glu Glu Met Thr Lys Asn
        595                 600                 605

Gln Val Ser Leu Thr Cys Leu Val Lys Gly Phe Tyr Pro Ser Asp Ile
    610                 615                 620

Ala Val Glu Trp Glu Ser Asn Gly Gln Pro Glu Asn Asn Tyr Lys Thr
625                 630                 635                 640

Thr Pro Pro Val Leu Asp Ser Asp Gly Ser Phe Phe Leu Tyr Ser Lys
                645                 650                 655

Leu Thr Val Asp Lys Ser Arg Trp Gln Gln Gly Asn Val Phe Ser Cys
            660                 665                 670

Ser Val Met His Glu Ala Leu His Asn His Tyr Thr Gln Lys Ser Leu
        675                 680                 685

Ser Leu Ser Pro Gly Lys
    690
```

<210> SEQ ID NO 19
<211> LENGTH: 2076
<212> TYPE: DNA
<213> ORGANISM: Homo sapiens
<220> FEATURE:
<221> NAME/KEY: CDS
<222> LOCATION: (1)...(2073)

<400> SEQUENCE: 19

```
atg gtg aag cca tca tta cca ttc aca tcc ctc tta ttc ctg cag ctg       48
Met Val Lys Pro Ser Leu Pro Phe Thr Ser Leu Leu Phe Leu Gln Leu
 1               5                  10                  15

ccc ctg ctg gga gtg ggg ctg aac acg aca att ctg acg ccc aat ggg       96
Pro Leu Leu Gly Val Gly Leu Asn Thr Thr Ile Leu Thr Pro Asn Gly
            20                  25                  30

aat gaa gac acc aca gct gat ttc ttc ctg acc act atg ccc act gac      144
Asn Glu Asp Thr Thr Ala Asp Phe Phe Leu Thr Thr Met Pro Thr Asp
        35                  40                  45

tcc ctc agt gtt tcc act ctg ccc ctc cca gag gtt cag tgt ttt gtg      192
Ser Leu Ser Val Ser Thr Leu Pro Leu Pro Glu Val Gln Cys Phe Val
    50                  55                  60

ttc aat gtc gag tac atg aat tgc act tgg aac agc agc tct gag ccc      240
Phe Asn Val Glu Tyr Met Asn Cys Thr Trp Asn Ser Ser Ser Glu Pro
 65                  70                  75                  80

cag cct acc aac ctc act ctg cat tat tgg tac aag aac tcg gat aat      288
Gln Pro Thr Asn Leu Thr Leu His Tyr Trp Tyr Lys Asn Ser Asp Asn
                85                  90                  95

gat aaa gtc cag aag tgc agc cac tat cta ttc tct gaa gaa atc act      336
Asp Lys Val Gln Lys Cys Ser His Tyr Leu Phe Ser Glu Glu Ile Thr
            100                 105                 110

tct ggc tgt cag ttg caa aaa aag gag atc cac ctc tac caa aca ttt      384
Ser Gly Cys Gln Leu Gln Lys Lys Glu Ile His Leu Tyr Gln Thr Phe
        115                 120                 125

gtt gtt cag ctc cag gac cca cgg gaa ccc agg aga cag gcc aca cag      432
Val Val Gln Leu Gln Asp Pro Arg Glu Pro Arg Arg Gln Ala Thr Gln
    130                 135                 140

atg cta aaa ctg cag aat ctg gtg atc ccc tgg gct cca gag aac cta      480
Met Leu Lys Leu Gln Asn Leu Val Ile Pro Trp Ala Pro Glu Asn Leu
145                 150                 155                 160

aca ctt cac aaa ctg agt gaa tcc cag cta gaa ctg aac tgg aac aac      528
Thr Leu His Lys Leu Ser Glu Ser Gln Leu Glu Leu Asn Trp Asn Asn
                165                 170                 175

aga ttc ttg aac cac tgt ttg gag cac ttg gtg cag tac cgg act gac      576
Arg Phe Leu Asn His Cys Leu Glu His Leu Val Gln Tyr Arg Thr Asp
            180                 185                 190

tgg gac cac agc tgg act gaa caa tca gtg gat tat aga cat aag ttc      624
Trp Asp His Ser Trp Thr Glu Gln Ser Val Asp Tyr Arg His Lys Phe
        195                 200                 205

tcc ttg cct agt gtg gat ggg cag aaa cgc tac acg ttt cgt gtt cgg      672
Ser Leu Pro Ser Val Asp Gly Gln Lys Arg Tyr Thr Phe Arg Val Arg
    210                 215                 220

agc cgc ttt aac cca ctc tgt gga agt gct cag cat tgg agt gaa tgg      720
Ser Arg Phe Asn Pro Leu Cys Gly Ser Ala Gln His Trp Ser Glu Trp
225                 230                 235                 240

agc cac cca atc cac tgg ggg agc aat act tca aaa gag aac ggg aac      768
Ser His Pro Ile His Trp Gly Ser Asn Thr Ser Lys Glu Asn Gly Asn
                245                 250                 255

atg aag gtc ctg cag gag ccc acc tgc gtc tcc gac tac atg agc atc      816
Met Lys Val Leu Gln Glu Pro Thr Cys Val Ser Asp Tyr Met Ser Ile
            260                 265                 270
```

-continued

```
tct act tgc gag tgg aag atg aat ggt ccc acc aat tgc agc acc gag      864
Ser Thr Cys Glu Trp Lys Met Asn Gly Pro Thr Asn Cys Ser Thr Glu
        275                 280                 285

ctc cgc ctg ttg tac cag ctg gtt ttt ctg ctc tcc gaa gcc cac acg      912
Leu Arg Leu Leu Tyr Gln Leu Val Phe Leu Leu Ser Glu Ala His Thr
    290                 295                 300

tgt atc cct gag aac aac gga ggc gcg ggg tgc gtg tgc cac ctg ctc      960
Cys Ile Pro Glu Asn Asn Gly Gly Ala Gly Cys Val Cys His Leu Leu
305                 310                 315                 320

atg gat gac gtg gtc agt gcg gat aac tat aca ctg gac ctg tgg gct     1008
Met Asp Asp Val Val Ser Ala Asp Asn Tyr Thr Leu Asp Leu Trp Ala
                325                 330                 335

ggg cag cag ctg ctg tgg aag ggc tcc ttc aag ccc agc gag cat gtg     1056
Gly Gln Gln Leu Leu Trp Lys Gly Ser Phe Lys Pro Ser Glu His Val
            340                 345                 350

aaa ccc agg gcc cca gga aac ctg aca gtt cac acc aat gtc tcc gac     1104
Lys Pro Arg Ala Pro Gly Asn Leu Thr Val His Thr Asn Val Ser Asp
        355                 360                 365

act ctg ctg ctg acc tgg agc aac ccg tat ccc cct gac aat tac ctg     1152
Thr Leu Leu Leu Thr Trp Ser Asn Pro Tyr Pro Pro Asp Asn Tyr Leu
    370                 375                 380

tat aat cat ctc acc tat gca gtc aac att tgg agt gaa aac gac ccg     1200
Tyr Asn His Leu Thr Tyr Ala Val Asn Ile Trp Ser Glu Asn Asp Pro
385                 390                 395                 400

gca gat ttc aga atc tat aac gtg acc tac cta gaa ccc tcc ctc cgc     1248
Ala Asp Phe Arg Ile Tyr Asn Val Thr Tyr Leu Glu Pro Ser Leu Arg
                405                 410                 415

atc gca gcc agc acc ctg aag tct ggg att tcc tac agg gca cgg gtg     1296
Ile Ala Ala Ser Thr Leu Lys Ser Gly Ile Ser Tyr Arg Ala Arg Val
            420                 425                 430

agg gcc tgg gct cag agc tat aac acc acc tgg agt gag tgg agc ccc     1344
Arg Ala Trp Ala Gln Ser Tyr Asn Thr Thr Trp Ser Glu Trp Ser Pro
        435                 440                 445

agc acc aag tgg cac aac tcc tac agg gag ccc ttc gag cag tcc gga     1392
Ser Thr Lys Trp His Asn Ser Tyr Arg Glu Pro Phe Glu Gln Ser Gly
    450                 455                 460

gac aaa act cac aca tgc cca ccg tgc cca gca cct gaa ctc ctg ggg     1440
Asp Lys Thr His Thr Cys Pro Pro Cys Pro Ala Pro Glu Leu Leu Gly
465                 470                 475                 480

gga ccg tca gtc ttc ctc ttc ccc cca aaa ccc aag gac acc ctc atg     1488
Gly Pro Ser Val Phe Leu Phe Pro Pro Lys Pro Lys Asp Thr Leu Met
                485                 490                 495

atc tcc cgg acc cct gag gtc aca tgc gtg gtg gtg gac gtg agc cac     1536
Ile Ser Arg Thr Pro Glu Val Thr Cys Val Val Val Asp Val Ser His
            500                 505                 510

gaa gac cct gag gtc aag ttc aac tgg tac gtg gac ggc gtg gag gtg     1584
Glu Asp Pro Glu Val Lys Phe Asn Trp Tyr Val Asp Gly Val Glu Val
        515                 520                 525

cat aat gcc aag aca aag ccg cgg gag gag cag tac aac agc acg tac     1632
His Asn Ala Lys Thr Lys Pro Arg Glu Glu Gln Tyr Asn Ser Thr Tyr
    530                 535                 540

cgt gtg gtc agc gtc ctc acc gtc ctg cac cag gac tgg ctg aat ggc     1680
Arg Val Val Ser Val Leu Thr Val Leu His Gln Asp Trp Leu Asn Gly
545                 550                 555                 560

aag gag tac aag tgc aag gtc tcc aac aaa gcc ctc cca gcc ccc atc     1728
Lys Glu Tyr Lys Cys Lys Val Ser Asn Lys Ala Leu Pro Ala Pro Ile
                565                 570                 575

gag aaa acc atc tcc aaa gcc aaa ggg cag ccc cga gaa cca cag gtg     1776
Glu Lys Thr Ile Ser Lys Ala Lys Gly Gln Pro Arg Glu Pro Gln Val
            580                 585                 590
```

```
tac acc ctg ccc cca tcc cgg gat gag ctg acc aag aac cag gtc agc     1824
Tyr Thr Leu Pro Pro Ser Arg Asp Glu Leu Thr Lys Asn Gln Val Ser
        595                 600                 605

ctg acc tgc ctg gtc aaa ggc ttc tat ccc agc gac atc gcc gtg gag     1872
Leu Thr Cys Leu Val Lys Gly Phe Tyr Pro Ser Asp Ile Ala Val Glu
    610                 615                 620

tgg gag agc aat ggg cag ccg gag aac aac tac aag acc acg cct ccc     1920
Trp Glu Ser Asn Gly Gln Pro Glu Asn Asn Tyr Lys Thr Thr Pro Pro
625                 630                 635                 640

gtg ctg gac tcc gac ggc tcc ttc ttc ctc tat agc aag ctc acc gtg     1968
Val Leu Asp Ser Asp Gly Ser Phe Phe Leu Tyr Ser Lys Leu Thr Val
                645                 650                 655

gac aag agc agg tgg cag cag ggg aac gtc ttc tca tgc tcc gtg atg     2016
Asp Lys Ser Arg Trp Gln Gln Gly Asn Val Phe Ser Cys Ser Val Met
            660                 665                 670

cat gag gct ctg cac aac cac tac acg cag aag agc ctc tcc ctg tct     2064
His Glu Ala Leu His Asn His Tyr Thr Gln Lys Ser Leu Ser Leu Ser
        675                 680                 685

ccg ggt aaa tga                                                     2076
Pro Gly Lys
    690


<210> SEQ ID NO 20
<211> LENGTH: 691
<212> TYPE: PRT
<213> ORGANISM: Homo sapiens

<400> SEQUENCE: 20

Met Val Lys Pro Ser Leu Pro Phe Thr Ser Leu Leu Phe Leu Gln Leu
 1               5                  10                  15

Pro Leu Leu Gly Val Gly Leu Asn Thr Thr Ile Leu Thr Pro Asn Gly
            20                  25                  30

Asn Glu Asp Thr Thr Ala Asp Phe Phe Leu Thr Thr Met Pro Thr Asp
        35                  40                  45

Ser Leu Ser Val Ser Thr Leu Pro Leu Pro Glu Val Gln Cys Phe Val
    50                  55                  60

Phe Asn Val Glu Tyr Met Asn Cys Thr Trp Asn Ser Ser Ser Glu Pro
65                  70                  75                  80

Gln Pro Thr Asn Leu Thr Leu His Tyr Trp Tyr Lys Asn Ser Asp Asn
                85                  90                  95

Asp Lys Val Gln Lys Cys Ser His Tyr Leu Phe Ser Glu Glu Ile Thr
            100                 105                 110

Ser Gly Cys Gln Leu Gln Lys Lys Glu Ile His Leu Tyr Gln Thr Phe
        115                 120                 125

Val Val Gln Leu Gln Asp Pro Arg Glu Pro Arg Arg Gln Ala Thr Gln
    130                 135                 140

Met Leu Lys Leu Gln Asn Leu Val Ile Pro Trp Ala Pro Glu Asn Leu
145                 150                 155                 160

Thr Leu His Lys Leu Ser Glu Ser Gln Leu Glu Leu Asn Trp Asn Asn
                165                 170                 175

Arg Phe Leu Asn His Cys Leu Glu His Leu Val Gln Tyr Arg Thr Asp
            180                 185                 190

Trp Asp His Ser Trp Thr Glu Gln Ser Val Asp Tyr Arg His Lys Phe
        195                 200                 205

Ser Leu Pro Ser Val Asp Gly Gln Lys Arg Tyr Thr Phe Arg Val Arg
    210                 215                 220

Ser Arg Phe Asn Pro Leu Cys Gly Ser Ala Gln His Trp Ser Glu Trp
225                 230                 235                 240
```

-continued

```
Ser His Pro Ile His Trp Gly Ser Asn Thr Ser Lys Glu Asn Gly Asn
                245                 250                 255

Met Lys Val Leu Gln Glu Pro Thr Cys Val Ser Asp Tyr Met Ser Ile
            260                 265                 270

Ser Thr Cys Glu Trp Lys Met Asn Gly Pro Thr Asn Cys Ser Thr Glu
        275                 280                 285

Leu Arg Leu Leu Tyr Gln Leu Val Phe Leu Leu Ser Glu Ala His Thr
    290                 295                 300

Cys Ile Pro Glu Asn Asn Gly Gly Ala Gly Cys Val Cys His Leu Leu
305                 310                 315                 320

Met Asp Asp Val Val Ser Ala Asp Asn Tyr Thr Leu Asp Leu Trp Ala
                325                 330                 335

Gly Gln Gln Leu Leu Trp Lys Gly Ser Phe Lys Pro Ser Glu His Val
            340                 345                 350

Lys Pro Arg Ala Pro Gly Asn Leu Thr Val His Thr Asn Val Ser Asp
        355                 360                 365

Thr Leu Leu Leu Thr Trp Ser Asn Pro Tyr Pro Pro Asp Asn Tyr Leu
    370                 375                 380

Tyr Asn His Leu Thr Tyr Ala Val Asn Ile Trp Ser Glu Asn Asp Pro
385                 390                 395                 400

Ala Asp Phe Arg Ile Tyr Asn Val Thr Tyr Leu Glu Pro Ser Leu Arg
                405                 410                 415

Ile Ala Ala Ser Thr Leu Lys Ser Gly Ile Ser Tyr Arg Ala Arg Val
            420                 425                 430

Arg Ala Trp Ala Gln Ser Tyr Asn Thr Thr Trp Ser Glu Trp Ser Pro
        435                 440                 445

Ser Thr Lys Trp His Asn Ser Tyr Arg Glu Pro Phe Glu Gln Ser Gly
    450                 455                 460

Asp Lys Thr His Thr Cys Pro Pro Cys Pro Ala Pro Glu Leu Leu Gly
465                 470                 475                 480

Gly Pro Ser Val Phe Leu Phe Pro Pro Lys Pro Lys Asp Thr Leu Met
                485                 490                 495

Ile Ser Arg Thr Pro Glu Val Thr Cys Val Val Val Asp Val Ser His
            500                 505                 510

Glu Asp Pro Glu Val Lys Phe Asn Trp Tyr Val Asp Gly Val Glu Val
        515                 520                 525

His Asn Ala Lys Thr Lys Pro Arg Glu Glu Gln Tyr Asn Ser Thr Tyr
    530                 535                 540

Arg Val Val Ser Val Leu Thr Val Leu His Gln Asp Trp Leu Asn Gly
545                 550                 555                 560

Lys Glu Tyr Lys Cys Lys Val Ser Asn Lys Ala Leu Pro Ala Pro Ile
                565                 570                 575

Glu Lys Thr Ile Ser Lys Ala Lys Gly Gln Pro Arg Glu Pro Gln Val
            580                 585                 590

Tyr Thr Leu Pro Pro Ser Arg Asp Glu Leu Thr Lys Asn Gln Val Ser
        595                 600                 605

Leu Thr Cys Leu Val Lys Gly Phe Tyr Pro Ser Asp Ile Ala Val Glu
    610                 615                 620

Trp Glu Ser Asn Gly Gln Pro Glu Asn Asn Tyr Lys Thr Thr Pro Pro
625                 630                 635                 640

Val Leu Asp Ser Asp Gly Ser Phe Phe Leu Tyr Ser Lys Leu Thr Val
                645                 650                 655

Asp Lys Ser Arg Trp Gln Gln Gly Asn Val Phe Ser Cys Ser Val Met
```

```
            660                 665                 670

His Glu Ala Leu His Asn His Tyr Thr Gln Lys Ser Leu Ser Leu Ser
        675                 680                 685

Pro Gly Lys
    690


<210> SEQ ID NO 21
<211> LENGTH: 2085
<212> TYPE: DNA
<213> ORGANISM: Homo sapiens
<220> FEATURE:
<221> NAME/KEY: CDS
<222> LOCATION: (1)...(2082)

<400> SEQUENCE: 21

atg gtg aag cca tca tta cca ttc aca tcc ctc tta ttc ctg cag ctg       48
Met Val Lys Pro Ser Leu Pro Phe Thr Ser Leu Leu Phe Leu Gln Leu
 1               5                  10                  15

ccc ctg ctg gga gtg ggg ctg aac acg aca att ctg acg ccc aat ggg       96
Pro Leu Leu Gly Val Gly Leu Asn Thr Thr Ile Leu Thr Pro Asn Gly
            20                  25                  30

aat gaa gac acc aca gct gat ttc ttc ctg acc act atg ccc act gac      144
Asn Glu Asp Thr Thr Ala Asp Phe Phe Leu Thr Thr Met Pro Thr Asp
        35                  40                  45

tcc ctc agt gtt tcc act ctg ccc ctc cca gag gtt cag tgt ttt gtg      192
Ser Leu Ser Val Ser Thr Leu Pro Leu Pro Glu Val Gln Cys Phe Val
    50                  55                  60

ttc aat gtc gag tac atg aat tgc act tgg aac agc agc tct gag ccc      240
Phe Asn Val Glu Tyr Met Asn Cys Thr Trp Asn Ser Ser Ser Glu Pro
 65                  70                  75                  80

cag cct acc aac ctc act ctg cat tat tgg tac aag aac tcg gat aat      288
Gln Pro Thr Asn Leu Thr Leu His Tyr Trp Tyr Lys Asn Ser Asp Asn
                85                  90                  95

gat aaa gtc cag aag tgc agc cac tat cta ttc tct gaa gaa atc act      336
Asp Lys Val Gln Lys Cys Ser His Tyr Leu Phe Ser Glu Glu Ile Thr
            100                 105                 110

tct ggc tgt cag ttg caa aaa aag gag atc cac ctc tac caa aca ttt      384
Ser Gly Cys Gln Leu Gln Lys Lys Glu Ile His Leu Tyr Gln Thr Phe
        115                 120                 125

gtt gtt cag ctc cag gac cca cgg gaa ccc agg aga cag gcc aca cag      432
Val Val Gln Leu Gln Asp Pro Arg Glu Pro Arg Arg Gln Ala Thr Gln
    130                 135                 140

atg cta aaa ctg cag aat ctg gtg atc ccc tgg gct cca gag aac cta      480
Met Leu Lys Leu Gln Asn Leu Val Ile Pro Trp Ala Pro Glu Asn Leu
145                 150                 155                 160

aca ctt cac aaa ctg agt gaa tcc cag cta gaa ctg aac tgg aac aac      528
Thr Leu His Lys Leu Ser Glu Ser Gln Leu Glu Leu Asn Trp Asn Asn
                165                 170                 175

aga ttc ttg aac cac tgt ttg gag cac ttg gtg cag tac cgg act gac      576
Arg Phe Leu Asn His Cys Leu Glu His Leu Val Gln Tyr Arg Thr Asp
            180                 185                 190

tgg gac cac agc tgg act gaa caa tca gtg gat tat aga cat aag ttc      624
Trp Asp His Ser Trp Thr Glu Gln Ser Val Asp Tyr Arg His Lys Phe
        195                 200                 205

tcc ttg cct agt gtg gat ggg cag aaa cgc tac acg ttt cgt gtt cgg      672
Ser Leu Pro Ser Val Asp Gly Gln Lys Arg Tyr Thr Phe Arg Val Arg
    210                 215                 220

agc cgc ttt aac cca ctc tgt gga agt gct cag cat tgg agt gaa tgg      720
Ser Arg Phe Asn Pro Leu Cys Gly Ser Ala Gln His Trp Ser Glu Trp
225                 230                 235                 240

agc cac cca atc cac tgg ggg agc aat act tca aaa gag aac gcg tcg      768
```

-continued

```
Ser His Pro Ile His Trp Gly Ser Asn Thr Ser Lys Glu Asn Ala Ser
                245                 250                 255

tct ggg aac atg aag gtc ctg cag gag ccc acc tgc gtc tcc gac tac      816
Ser Gly Asn Met Lys Val Leu Gln Glu Pro Thr Cys Val Ser Asp Tyr
            260                 265                 270

atg agc atc tct act tgc gag tgg aag atg aat ggt ccc acc aat tgc      864
Met Ser Ile Ser Thr Cys Glu Trp Lys Met Asn Gly Pro Thr Asn Cys
        275                 280                 285

agc acc gag ctc cgc ctg ttg tac cag ctg gtt ttt ctg ctc tcc gaa      912
Ser Thr Glu Leu Arg Leu Leu Tyr Gln Leu Val Phe Leu Leu Ser Glu
    290                 295                 300

gcc cac acg tgt atc cct gag aac aac gga ggc gcg ggg tgc gtg tgc      960
Ala His Thr Cys Ile Pro Glu Asn Asn Gly Gly Ala Gly Cys Val Cys
305                 310                 315                 320

cac ctg ctc atg gat gac gtg gtc agt gcg gat aac tat aca ctg gac     1008
His Leu Leu Met Asp Asp Val Val Ser Ala Asp Asn Tyr Thr Leu Asp
                325                 330                 335

ctg tgg gct ggg cag cag ctg ctg tgg aag ggc tcc ttc aag ccc agc     1056
Leu Trp Ala Gly Gln Gln Leu Leu Trp Lys Gly Ser Phe Lys Pro Ser
            340                 345                 350

gag cat gtg aaa ccc agg gcc cca gga aac ctg aca gtt cac acc aat     1104
Glu His Val Lys Pro Arg Ala Pro Gly Asn Leu Thr Val His Thr Asn
        355                 360                 365

gtc tcc gac act ctg ctg ctg acc tgg agc aac ccg tat ccc cct gac     1152
Val Ser Asp Thr Leu Leu Leu Thr Trp Ser Asn Pro Tyr Pro Pro Asp
    370                 375                 380

aat tac ctg tat aat cat ctc acc tat gca gtc aac att tgg agt gaa     1200
Asn Tyr Leu Tyr Asn His Leu Thr Tyr Ala Val Asn Ile Trp Ser Glu
385                 390                 395                 400

aac gac ccg gca gat ttc aga atc tat aac gtg acc tac cta gaa ccc     1248
Asn Asp Pro Ala Asp Phe Arg Ile Tyr Asn Val Thr Tyr Leu Glu Pro
                405                 410                 415

tcc ctc cgc atc gca gcc agc acc ctg aag tct ggg att tcc tac agg     1296
Ser Leu Arg Ile Ala Ala Ser Thr Leu Lys Ser Gly Ile Ser Tyr Arg
            420                 425                 430

gca cgg gtg agg gcc tgg gct cag agc tat aac acc acc tgg agt gag     1344
Ala Arg Val Arg Ala Trp Ala Gln Ser Tyr Asn Thr Thr Trp Ser Glu
        435                 440                 445

tgg agc ccc agc acc aag tgg cac aac tcc tac agg gag ccc ttc gag     1392
Trp Ser Pro Ser Thr Lys Trp His Asn Ser Tyr Arg Glu Pro Phe Glu
    450                 455                 460

cag tcc gga gac aaa act cac aca tgc cca ccg tgc cca gca cct gaa     1440
Gln Ser Gly Asp Lys Thr His Thr Cys Pro Pro Cys Pro Ala Pro Glu
465                 470                 475                 480

ctc ctg ggg gga ccg tca gtc ttc ctc ttc ccc cca aaa ccc aag gac     1488
Leu Leu Gly Gly Pro Ser Val Phe Leu Phe Pro Pro Lys Pro Lys Asp
                485                 490                 495

acc ctc atg atc tcc cgg acc cct gag gtc aca tgc gtg gtg gtg gac     1536
Thr Leu Met Ile Ser Arg Thr Pro Glu Val Thr Cys Val Val Val Asp
            500                 505                 510

gtg agc cac gaa gac cct gag gtc aag ttc aac tgg tac gtg gac ggc     1584
Val Ser His Glu Asp Pro Glu Val Lys Phe Asn Trp Tyr Val Asp Gly
        515                 520                 525

gtg gag gtg cat aat gcc aag aca aag ccg cgg gag gag cag tac aac     1632
Val Glu Val His Asn Ala Lys Thr Lys Pro Arg Glu Glu Gln Tyr Asn
    530                 535                 540

agc acg tac cgt gtg gtc agc gtc ctc acc gtc ctg cac cag gac tgg     1680
Ser Thr Tyr Arg Val Val Ser Val Leu Thr Val Leu His Gln Asp Trp
545                 550                 555                 560

ctg aat ggc aag gag tac aag tgc aag gtc tcc aac aaa gcc ctc cca     1728
```

```
Leu Asn Gly Lys Glu Tyr Lys Cys Lys Val Ser Asn Lys Ala Leu Pro
                565                 570                 575

gcc ccc atc gag aaa acc atc tcc aaa gcc aaa ggg cag ccc cga gaa      1776
Ala Pro Ile Glu Lys Thr Ile Ser Lys Ala Lys Gly Gln Pro Arg Glu
            580                 585                 590

cca cag gtg tac acc ctg ccc cca tcc cgg gat gag ctg acc aag aac      1824
Pro Gln Val Tyr Thr Leu Pro Pro Ser Arg Asp Glu Leu Thr Lys Asn
        595                 600                 605

cag gtc agc ctg acc tgc ctg gtc aaa ggc ttc tat ccc agc gac atc      1872
Gln Val Ser Leu Thr Cys Leu Val Lys Gly Phe Tyr Pro Ser Asp Ile
    610                 615                 620

gcc gtg gag tgg gag agc aat ggg cag ccg gag aac aac tac aag acc      1920
Ala Val Glu Trp Glu Ser Asn Gly Gln Pro Glu Asn Asn Tyr Lys Thr
625                 630                 635                 640

acg cct ccc gtg ctg gac tcc gac ggc tcc ttc ttc ctc tat agc aag      1968
Thr Pro Pro Val Leu Asp Ser Asp Gly Ser Phe Phe Leu Tyr Ser Lys
                645                 650                 655

ctc acc gtg gac aag agc agg tgg cag cag ggg aac gtc ttc tca tgc      2016
Leu Thr Val Asp Lys Ser Arg Trp Gln Gln Gly Asn Val Phe Ser Cys
            660                 665                 670

tcc gtg atg cat gag gct ctg cac aac cac tac acg cag aag agc ctc      2064
Ser Val Met His Glu Ala Leu His Asn His Tyr Thr Gln Lys Ser Leu
        675                 680                 685

tcc ctg tct ccg ggt aaa tga                                          2085
Ser Leu Ser Pro Gly Lys
    690


<210> SEQ ID NO 22
<211> LENGTH: 694
<212> TYPE: PRT
<213> ORGANISM: Homo sapiens

<400> SEQUENCE: 22

Met Val Lys Pro Ser Leu Pro Phe Thr Ser Leu Leu Phe Leu Gln Leu
 1               5                  10                  15

Pro Leu Leu Gly Val Gly Leu Asn Thr Thr Ile Leu Thr Pro Asn Gly
            20                  25                  30

Asn Glu Asp Thr Thr Ala Asp Phe Phe Leu Thr Thr Met Pro Thr Asp
        35                  40                  45

Ser Leu Ser Val Ser Thr Leu Pro Leu Pro Glu Val Gln Cys Phe Val
    50                  55                  60

Phe Asn Val Glu Tyr Met Asn Cys Thr Trp Asn Ser Ser Ser Glu Pro
65                  70                  75                  80

Gln Pro Thr Asn Leu Thr Leu His Tyr Trp Tyr Lys Asn Ser Asp Asn
                85                  90                  95

Asp Lys Val Gln Lys Cys Ser His Tyr Leu Phe Ser Glu Glu Ile Thr
            100                 105                 110

Ser Gly Cys Gln Leu Gln Lys Lys Glu Ile His Leu Tyr Gln Thr Phe
        115                 120                 125

Val Val Gln Leu Gln Asp Pro Arg Glu Pro Arg Arg Gln Ala Thr Gln
    130                 135                 140

Met Leu Lys Leu Gln Asn Leu Val Ile Pro Trp Ala Pro Glu Asn Leu
145                 150                 155                 160

Thr Leu His Lys Leu Ser Glu Ser Gln Leu Glu Leu Asn Trp Asn Asn
                165                 170                 175

Arg Phe Leu Asn His Cys Leu Glu His Leu Val Gln Tyr Arg Thr Asp
            180                 185                 190

Trp Asp His Ser Trp Thr Glu Gln Ser Val Asp Tyr Arg His Lys Phe
```

-continued

```
        195                 200                 205

Ser Leu Pro Ser Val Asp Gly Gln Lys Arg Tyr Thr Phe Arg Val Arg
    210                 215                 220

Ser Arg Phe Asn Pro Leu Cys Gly Ser Ala Gln His Trp Ser Glu Trp
225                 230                 235                 240

Ser His Pro Ile His Trp Gly Ser Asn Thr Ser Lys Glu Asn Ala Ser
                245                 250                 255

Ser Gly Asn Met Lys Val Leu Gln Glu Pro Thr Cys Val Ser Asp Tyr
            260                 265                 270

Met Ser Ile Ser Thr Cys Glu Trp Lys Met Asn Gly Pro Thr Asn Cys
        275                 280                 285

Ser Thr Glu Leu Arg Leu Leu Tyr Gln Leu Val Phe Leu Leu Ser Glu
    290                 295                 300

Ala His Thr Cys Ile Pro Glu Asn Asn Gly Gly Ala Gly Cys Val Cys
305                 310                 315                 320

His Leu Leu Met Asp Asp Val Val Ser Ala Asp Asn Tyr Thr Leu Asp
                325                 330                 335

Leu Trp Ala Gly Gln Gln Leu Leu Trp Lys Gly Ser Phe Lys Pro Ser
            340                 345                 350

Glu His Val Lys Pro Arg Ala Pro Gly Asn Leu Thr Val His Thr Asn
        355                 360                 365

Val Ser Asp Thr Leu Leu Leu Thr Trp Ser Asn Pro Tyr Pro Pro Asp
    370                 375                 380

Asn Tyr Leu Tyr Asn His Leu Thr Tyr Ala Val Asn Ile Trp Ser Glu
385                 390                 395                 400

Asn Asp Pro Ala Asp Phe Arg Ile Tyr Asn Val Thr Tyr Leu Glu Pro
                405                 410                 415

Ser Leu Arg Ile Ala Ala Ser Thr Leu Lys Ser Gly Ile Ser Tyr Arg
            420                 425                 430

Ala Arg Val Arg Ala Trp Ala Gln Ser Tyr Asn Thr Thr Trp Ser Glu
        435                 440                 445

Trp Ser Pro Ser Thr Lys Trp His Asn Ser Tyr Arg Glu Pro Phe Glu
    450                 455                 460

Gln Ser Gly Asp Lys Thr His Thr Cys Pro Pro Cys Pro Ala Pro Glu
465                 470                 475                 480

Leu Leu Gly Gly Pro Ser Val Phe Leu Phe Pro Pro Lys Pro Lys Asp
                485                 490                 495

Thr Leu Met Ile Ser Arg Thr Pro Glu Val Thr Cys Val Val Val Asp
            500                 505                 510

Val Ser His Glu Asp Pro Glu Val Lys Phe Asn Trp Tyr Val Asp Gly
        515                 520                 525

Val Glu Val His Asn Ala Lys Thr Lys Pro Arg Glu Glu Gln Tyr Asn
    530                 535                 540

Ser Thr Tyr Arg Val Val Ser Val Leu Thr Val Leu His Gln Asp Trp
545                 550                 555                 560

Leu Asn Gly Lys Glu Tyr Lys Cys Lys Val Ser Asn Lys Ala Leu Pro
                565                 570                 575

Ala Pro Ile Glu Lys Thr Ile Ser Lys Ala Lys Gly Gln Pro Arg Glu
            580                 585                 590

Pro Gln Val Tyr Thr Leu Pro Pro Ser Arg Asp Glu Leu Thr Lys Asn
        595                 600                 605

Gln Val Ser Leu Thr Cys Leu Val Lys Gly Phe Tyr Pro Ser Asp Ile
    610                 615                 620
```

-continued

Ala Val Glu Trp Glu Ser Asn Gly Gln Pro Glu Asn Asn Tyr Lys Thr
625 630 635 640

Thr Pro Pro Val Leu Asp Ser Asp Gly Ser Phe Phe Leu Tyr Ser Lys
645 650 655

Leu Thr Val Asp Lys Ser Arg Trp Gln Gln Gly Asn Val Phe Ser Cys
660 665 670

Ser Val Met His Glu Ala Leu His Asn His Tyr Thr Gln Lys Ser Leu
675 680 685

Ser Leu Ser Pro Gly Lys
690

<210> SEQ ID NO 23
<211> LENGTH: 3507
<212> TYPE: DNA
<213> ORGANISM: Homo sapiens
<220> FEATURE:
<221> NAME/KEY: CDS
<222> LOCATION: (1)...(3504)

<400> SEQUENCE: 23 atg gtg gcc gtc ggc tgc gcg ctg ctg gct gcc ctg ctg gcc gcg ccg 48
Met Val Ala Val Gly Cys Ala Leu Leu Ala Ala Leu Leu Ala Ala Pro
1 5 10 15 gga gcg gcg ctg gcc cca agg cgc tgc cct gcg cag gag gtg gca aga 96
Gly Ala Ala Leu Ala Pro Arg Arg Cys Pro Ala Gln Glu Val Ala Arg
20 25 30 ggc gtg ctg acc agt ctg cca gga gac agc gtg act ctg acc tgc ccg 144
Gly Val Leu Thr Ser Leu Pro Gly Asp Ser Val Thr Leu Thr Cys Pro
35 40 45 ggg gta gag ccg gaa gac aat gcc act gtt cac tgg gtg ctc agg aag 192
Gly Val Glu Pro Glu Asp Asn Ala Thr Val His Trp Val Leu Arg Lys
50 55 60 ccg gct gca ggc tcc cac ccc agc aga tgg gct ggc atg gga agg agg 240
Pro Ala Ala Gly Ser His Pro Ser Arg Trp Ala Gly Met Gly Arg Arg
65 70 75 80 ctg ctg ctg agg tcg gtg cag ctc cac gac tct gga aac tat tca tgc 288
Leu Leu Leu Arg Ser Val Gln Leu His Asp Ser Gly Asn Tyr Ser Cys
85 90 95 tac cgg gcc ggc cgc cca gct ggg act gtg cac ttg ctg gtg gat gtt 336
Tyr Arg Ala Gly Arg Pro Ala Gly Thr Val His Leu Leu Val Asp Val
100 105 110 ccc ccc gag gag ccc cag ctc tcc tgc ttc cgg aag agc ccc ctc agc 384
Pro Pro Glu Glu Pro Gln Leu Ser Cys Phe Arg Lys Ser Pro Leu Ser
115 120 125 aat gtt gtt tgt gag tgg ggt cct cgg agc acc cca tcc ctg acg aca 432
Asn Val Val Cys Glu Trp Gly Pro Arg Ser Thr Pro Ser Leu Thr Thr
130 135 140 aag gct gtg ctc ttg gtg agg aag ttt cag aac agt ccg gcc gaa gac 480
Lys Ala Val Leu Leu Val Arg Lys Phe Gln Asn Ser Pro Ala Glu Asp
145 150 155 160 ttc cag gag ccg tgc cag tat tcc cag gag tcc cag aag ttc tcc tgc 528
Phe Gln Glu Pro Cys Gln Tyr Ser Gln Glu Ser Gln Lys Phe Ser Cys
165 170 175 cag tta gca gtc ccg gag gga gac agc tct ttc tac ata gtg tcc atg 576
Gln Leu Ala Val Pro Glu Gly Asp Ser Ser Phe Tyr Ile Val Ser Met
180 185 190 tgc gtc gcc agt agt gtc ggg agc aag ttc agc aaa act caa acc ttt 624
Cys Val Ala Ser Ser Val Gly Ser Lys Phe Ser Lys Thr Gln Thr Phe
195 200 205 cag ggt tgt gga atc ttg cag cct gat ccg cct gcc aac atc aca gtc 672
Gln Gly Cys Gly Ile Leu Gln Pro Asp Pro Pro Ala Asn Ile Thr Val -continued

```
    210                 215                 220

act gcc gtg gcc aga aac ccc cgc tgg ctc agt gtc acc tgg caa gac      720
Thr Ala Val Ala Arg Asn Pro Arg Trp Leu Ser Val Thr Trp Gln Asp
225                 230                 235                 240

ccc cac tcc tgg aac tca tct ttc tac aga cta cgg ttt gag ctc aga      768
Pro His Ser Trp Asn Ser Ser Phe Tyr Arg Leu Arg Phe Glu Leu Arg
                245                 250                 255

tat cgg gct gaa cgg tca aag aca ttc aca aca tgg atg gtc aag gac      816
Tyr Arg Ala Glu Arg Ser Lys Thr Phe Thr Thr Trp Met Val Lys Asp
            260                 265                 270

ctc cag cat cac tgt gtc atc cac gac gcc tgg agc ggc ctg agg cac      864
Leu Gln His His Cys Val Ile His Asp Ala Trp Ser Gly Leu Arg His
        275                 280                 285

gtg gtg cag ctt cgt gcc cag gag gag ttc ggg caa ggc gag tgg agc      912
Val Val Gln Leu Arg Ala Gln Glu Glu Phe Gly Gln Gly Glu Trp Ser
    290                 295                 300

gag tgg agc ccg gag gcc atg ggc acg cct tgg aca gaa tcc agg agt      960
Glu Trp Ser Pro Glu Ala Met Gly Thr Pro Trp Thr Glu Ser Arg Ser
305                 310                 315                 320

cct cca gct gag aac gag gtg tcc acc ccc atg acc ggt ggc gcg cct     1008
Pro Pro Ala Glu Asn Glu Val Ser Thr Pro Met Thr Gly Gly Ala Pro
                325                 330                 335

tca ggt gct cag ctg gaa ctt cta gac cca tgt ggt tat atc agt cct     1056
Ser Gly Ala Gln Leu Glu Leu Leu Asp Pro Cys Gly Tyr Ile Ser Pro
            340                 345                 350

gaa tct cca gtt gta caa ctt cat tct aat ttc act gca gtt tgt gtg     1104
Glu Ser Pro Val Val Gln Leu His Ser Asn Phe Thr Ala Val Cys Val
        355                 360                 365

cta aag gaa aaa tgt atg gat tat ttt cat gta aat gct aat tac att     1152
Leu Lys Glu Lys Cys Met Asp Tyr Phe His Val Asn Ala Asn Tyr Ile
    370                 375                 380

gtc tgg aaa aca aac cat ttt act att cct aag gag caa tat act atc     1200
Val Trp Lys Thr Asn His Phe Thr Ile Pro Lys Glu Gln Tyr Thr Ile
385                 390                 395                 400

ata aac aga aca gca tcc agt gtc acc ttt aca gat ata gct tca tta     1248
Ile Asn Arg Thr Ala Ser Ser Val Thr Phe Thr Asp Ile Ala Ser Leu
                405                 410                 415

aat att cag ctc act tgc aac att ctt aca ttc gga cag ctt gaa cag     1296
Asn Ile Gln Leu Thr Cys Asn Ile Leu Thr Phe Gly Gln Leu Glu Gln
            420                 425                 430

aat gtt tat gga atc aca ata att tca ggc ttg cct cca gaa aaa cct     1344
Asn Val Tyr Gly Ile Thr Ile Ile Ser Gly Leu Pro Pro Glu Lys Pro
        435                 440                 445

aaa aat ttg agt tgc att gtg aac gag ggg aag aaa atg agg tgt gag     1392
Lys Asn Leu Ser Cys Ile Val Asn Glu Gly Lys Lys Met Arg Cys Glu
    450                 455                 460

tgg gat ggt gga agg gaa aca cac ttg gag aca aac ttc act tta aaa     1440
Trp Asp Gly Gly Arg Glu Thr His Leu Glu Thr Asn Phe Thr Leu Lys
465                 470                 475                 480

tct gaa tgg gca aca cac aag ttt gct gat tgc aaa gca aaa cgt gac     1488
Ser Glu Trp Ala Thr His Lys Phe Ala Asp Cys Lys Ala Lys Arg Asp
                485                 490                 495

acc ccc acc tca tgc act gtt gat tat tct act gtg tat ttt gtc aac     1536
Thr Pro Thr Ser Cys Thr Val Asp Tyr Ser Thr Val Tyr Phe Val Asn
            500                 505                 510

att gaa gtc tgg gta gaa gca gag aat gcc ctt ggg aag gtt aca tca     1584
Ile Glu Val Trp Val Glu Ala Glu Asn Ala Leu Gly Lys Val Thr Ser
        515                 520                 525

gat cat atc aat ttt gat cct gta tat aaa gtg aag ccc aat ccg cca     1632
Asp His Ile Asn Phe Asp Pro Val Tyr Lys Val Lys Pro Asn Pro Pro
```

```
    530                 535                 540

cat aat tta tca gtg atc aac tca gag gaa ctg tct agt atc tta aaa      1680
His Asn Leu Ser Val Ile Asn Ser Glu Glu Leu Ser Ser Ile Leu Lys
545                 550                 555                 560

ttg aca tgg acc aac cca agt att aag agt gtt ata ata cta aaa tat      1728
Leu Thr Trp Thr Asn Pro Ser Ile Lys Ser Val Ile Ile Leu Lys Tyr
                565                 570                 575

aac att caa tat agg acc aaa gat gcc tca act tgg agc cag att cct      1776
Asn Ile Gln Tyr Arg Thr Lys Asp Ala Ser Thr Trp Ser Gln Ile Pro
            580                 585                 590

cct gaa gac aca gca tcc acc cga tct tca ttc act gtc caa gac ctt      1824
Pro Glu Asp Thr Ala Ser Thr Arg Ser Ser Phe Thr Val Gln Asp Leu
        595                 600                 605

aaa cct ttt aca gaa tat gtg ttt agg att cgc tgt atg aag gaa gat      1872
Lys Pro Phe Thr Glu Tyr Val Phe Arg Ile Arg Cys Met Lys Glu Asp
    610                 615                 620

ggt aag gga tac tgg agt gac tgg agt gaa gaa gca agt ggg atc acc      1920
Gly Lys Gly Tyr Trp Ser Asp Trp Ser Glu Glu Ala Ser Gly Ile Thr
625                 630                 635                 640

tat gaa gat aga cca tct aaa gca cca agt ttc tgg tat aaa ata gat      1968
Tyr Glu Asp Arg Pro Ser Lys Ala Pro Ser Phe Trp Tyr Lys Ile Asp
                645                 650                 655

cca tcc cat act caa ggc tac aga act gta caa ctc gtg tgg aag aca      2016
Pro Ser His Thr Gln Gly Tyr Arg Thr Val Gln Leu Val Trp Lys Thr
            660                 665                 670

ttg cct cct ttt gaa gcc aat gga aaa atc ttg gat tat gaa gtg act      2064
Leu Pro Pro Phe Glu Ala Asn Gly Lys Ile Leu Asp Tyr Glu Val Thr
        675                 680                 685

ctc aca aga tgg aaa tca cat tta caa aat tac aca gtt aat gcc aca      2112
Leu Thr Arg Trp Lys Ser His Leu Gln Asn Tyr Thr Val Asn Ala Thr
    690                 695                 700

aaa ctg aca gta aat ctc aca aat gat cgc tat cta gca acc cta aca      2160
Lys Leu Thr Val Asn Leu Thr Asn Asp Arg Tyr Leu Ala Thr Leu Thr
705                 710                 715                 720

gta aga aat ctt gtt ggc aaa tca gat gca gct gtt tta act atc cct      2208
Val Arg Asn Leu Val Gly Lys Ser Asp Ala Ala Val Leu Thr Ile Pro
                725                 730                 735

gcc tgt gac ttt caa gct act cac cct gta atg gat ctt aaa gca ttc      2256
Ala Cys Asp Phe Gln Ala Thr His Pro Val Met Asp Leu Lys Ala Phe
            740                 745                 750

ccc aaa gat aac atg ctt tgg gtg gaa tgg act act cca agg gaa tct      2304
Pro Lys Asp Asn Met Leu Trp Val Glu Trp Thr Thr Pro Arg Glu Ser
        755                 760                 765

gta aag aaa tat ata ctt gag tgg tgt gtg tta tca gat aaa gca ccc      2352
Val Lys Lys Tyr Ile Leu Glu Trp Cys Val Leu Ser Asp Lys Ala Pro
    770                 775                 780

tgt atc aca gac tgg caa caa gaa gat ggt acc gtg cat cgc acc tat      2400
Cys Ile Thr Asp Trp Gln Gln Glu Asp Gly Thr Val His Arg Thr Tyr
785                 790                 795                 800

tta aga ggg aac tta gca gag agc aaa tgc tat ttg ata aca gtt act      2448
Leu Arg Gly Asn Leu Ala Glu Ser Lys Cys Tyr Leu Ile Thr Val Thr
                805                 810                 815

cca gta tat gct gat gga cca gga agc cct gaa tcc ata aag gca tac      2496
Pro Val Tyr Ala Asp Gly Pro Gly Ser Pro Glu Ser Ile Lys Ala Tyr
            820                 825                 830

ctt aaa caa gct cca cct tcc aaa gga cct act gtt cgg aca aaa aaa      2544
Leu Lys Gln Ala Pro Pro Ser Lys Gly Pro Thr Val Arg Thr Lys Lys
        835                 840                 845

gta ggg aaa aac gaa gct gtc tta gag tgg gac caa ctt cct gtt gat      2592
Val Gly Lys Asn Glu Ala Val Leu Glu Trp Asp Gln Leu Pro Val Asp
```

```
    850                 855                 860

gtt cag aat gga ttt atc aga aat tat act ata ttt tat aga acc atc      2640
Val Gln Asn Gly Phe Ile Arg Asn Tyr Thr Ile Phe Tyr Arg Thr Ile
865                 870                 875                 880

att gga aat gaa act gct gtg aat gtg gat tct tcc cac aca gaa tat      2688
Ile Gly Asn Glu Thr Ala Val Asn Val Asp Ser Ser His Thr Glu Tyr
                885                 890                 895

aca ttg tcc tct ttg act agt gac aca ttg tac atg gta cga atg gca      2736
Thr Leu Ser Ser Leu Thr Ser Asp Thr Leu Tyr Met Val Arg Met Ala
            900                 905                 910

gca tac aca gat gaa ggt ggg aag gat ggt cca gaa ttc act ttt act      2784
Ala Tyr Thr Asp Glu Gly Gly Lys Asp Gly Pro Glu Phe Thr Phe Thr
        915                 920                 925

acc cca aag ttt gct caa gga gaa att gaa tcc ggg ggc gac aaa act      2832
Thr Pro Lys Phe Ala Gln Gly Glu Ile Glu Ser Gly Gly Asp Lys Thr
    930                 935                 940

cac aca tgc cca ccg tgc cca gca cct gaa ctc ctg ggg gga ccg tca      2880
His Thr Cys Pro Pro Cys Pro Ala Pro Glu Leu Leu Gly Gly Pro Ser
945                 950                 955                 960

gtc ttc ctc ttc ccc cca aaa ccc aag gac acc ctc atg atc tcc cgg      2928
Val Phe Leu Phe Pro Pro Lys Pro Lys Asp Thr Leu Met Ile Ser Arg
                965                 970                 975

acc cct gag gtc aca tgc gtg gtg gtg gac gtg agc cac gaa gac cct      2976
Thr Pro Glu Val Thr Cys Val Val Val Asp Val Ser His Glu Asp Pro
            980                 985                 990

gag gtc aag ttc aac tgg tac gtg gac ggc gtg gag gtg cat aat gcc      3024
Glu Val Lys Phe Asn Trp Tyr Val Asp Gly Val Glu Val His Asn Ala
        995                 1000                1005

aag aca aag ccg cgg gag gag cag tac aac agc acg tac cgt gtg gtc      3072
Lys Thr Lys Pro Arg Glu Glu Gln Tyr Asn Ser Thr Tyr Arg Val Val
    1010                1015                1020

agc gtc ctc acc gtc ctg cac cag gac tgg ctg aat ggc aag gag tac      3120
Ser Val Leu Thr Val Leu His Gln Asp Trp Leu Asn Gly Lys Glu Tyr
1025                1030                1035                1040

aag tgc aag gtc tcc aac aaa gcc ctc cca gcc ccc atc gag aaa acc      3168
Lys Cys Lys Val Ser Asn Lys Ala Leu Pro Ala Pro Ile Glu Lys Thr
                1045                1050                1055

atc tcc aaa gcc aaa ggg cag ccc cga gaa cca cag gtg tac acc ctg      3216
Ile Ser Lys Ala Lys Gly Gln Pro Arg Glu Pro Gln Val Tyr Thr Leu
            1060                1065                1070

ccc cca tcc cgg gat gag ctg acc aag aac cag gtc agc ctg acc tgc      3264
Pro Pro Ser Arg Asp Glu Leu Thr Lys Asn Gln Val Ser Leu Thr Cys
        1075                1080                1085

ctg gtc aaa ggc ttc tat ccc agc gac atc gcc gtg gag tgg gag agc      3312
Leu Val Lys Gly Phe Tyr Pro Ser Asp Ile Ala Val Glu Trp Glu Ser
    1090                1095                1100

aat ggg cag ccg gag aac aac tac aag acc acg cct ccc gtg ctg gac      3360
Asn Gly Gln Pro Glu Asn Asn Tyr Lys Thr Thr Pro Pro Val Leu Asp
1105                1110                1115                1120

tcc gac ggc tcc ttc ttc ctc tac agc aag ctc acc gtg gac aag agc      3408
Ser Asp Gly Ser Phe Phe Leu Tyr Ser Lys Leu Thr Val Asp Lys Ser
                1125                1130                1135

agg tgg cag cag ggg aac gtc ttc tca tgc tcc gtg atg cat gag gct      3456
Arg Trp Gln Gln Gly Asn Val Phe Ser Cys Ser Val Met His Glu Ala
            1140                1145                1150

ctg cac aac cac tac acg cag aag agc ctc tcc ctg tct ccg ggt aaa      3504
Leu His Asn His Tyr Thr Gln Lys Ser Leu Ser Leu Ser Pro Gly Lys
        1155                1160                1165

tga                                                                  3507
```

<210> SEQ ID NO 24
<211> LENGTH: 1168
<212> TYPE: PRT
<213> ORGANISM: Homo sapiens

<400> SEQUENCE: 24

```
Met Val Ala Val Gly Cys Ala Leu Leu Ala Ala Leu Leu Ala Ala Pro
 1               5                  10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
        35                  40                  45

Gly Val Glu Pro Glu Asp Asn Ala Thr Val His Trp Val Leu Arg Lys
    50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Leu Thr Thr
    130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
        195                 200                 205

Gln Gly Cys Gly Ile Leu Gln Pro Asp Pro Pro Ala Asn Ile Thr Val
    210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
        275                 280                 285

Val Val Gln Leu Arg Ala Gln Glu Glu Phe Gly Gln Gly Glu Trp Ser
    290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Thr Gly Gly Ala Pro
                325                 330                 335

Ser Gly Ala Gln Leu Glu Leu Leu Asp Pro Cys Gly Tyr Ile Ser Pro
            340                 345                 350

Glu Ser Pro Val Val Gln Leu His Ser Asn Phe Thr Ala Val Cys Val
        355                 360                 365

Leu Lys Glu Lys Cys Met Asp Tyr Phe His Val Asn Ala Asn Tyr Ile
    370                 375                 380
```

-continued

```
Val Trp Lys Thr Asn His Phe Thr Ile Pro Lys Glu Gln Tyr Thr Ile
385                 390                 395                 400

Ile Asn Arg Thr Ala Ser Ser Val Thr Phe Thr Asp Ile Ala Ser Leu
                405                 410                 415

Asn Ile Gln Leu Thr Cys Asn Ile Leu Thr Phe Gly Gln Leu Glu Gln
            420                 425                 430

Asn Val Tyr Gly Ile Thr Ile Ile Ser Gly Leu Pro Pro Glu Lys Pro
        435                 440                 445

Lys Asn Leu Ser Cys Ile Val Asn Glu Gly Lys Lys Met Arg Cys Glu
    450                 455                 460

Trp Asp Gly Gly Arg Glu Thr His Leu Glu Thr Asn Phe Thr Leu Lys
465                 470                 475                 480

Ser Glu Trp Ala Thr His Lys Phe Ala Asp Cys Lys Ala Lys Arg Asp
                485                 490                 495

Thr Pro Thr Ser Cys Thr Val Asp Tyr Ser Thr Val Tyr Phe Val Asn
            500                 505                 510

Ile Glu Val Trp Val Glu Ala Glu Asn Ala Leu Gly Lys Val Thr Ser
        515                 520                 525

Asp His Ile Asn Phe Asp Pro Val Tyr Lys Val Lys Pro Asn Pro Pro
    530                 535                 540

His Asn Leu Ser Val Ile Asn Ser Glu Glu Leu Ser Ser Ile Leu Lys
545                 550                 555                 560

Leu Thr Trp Thr Asn Pro Ser Ile Lys Ser Val Ile Ile Leu Lys Tyr
                565                 570                 575

Asn Ile Gln Tyr Arg Thr Lys Asp Ala Ser Thr Trp Ser Gln Ile Pro
            580                 585                 590

Pro Glu Asp Thr Ala Ser Thr Arg Ser Ser Phe Thr Val Gln Asp Leu
        595                 600                 605

Lys Pro Phe Thr Glu Tyr Val Phe Arg Ile Arg Cys Met Lys Glu Asp
    610                 615                 620

Gly Lys Gly Tyr Trp Ser Asp Trp Ser Glu Glu Ala Ser Gly Ile Thr
625                 630                 635                 640

Tyr Glu Asp Arg Pro Ser Lys Ala Pro Ser Phe Trp Tyr Lys Ile Asp
                645                 650                 655

Pro Ser His Thr Gln Gly Tyr Arg Thr Val Gln Leu Val Trp Lys Thr
            660                 665                 670

Leu Pro Pro Phe Glu Ala Asn Gly Lys Ile Leu Asp Tyr Glu Val Thr
        675                 680                 685

Leu Thr Arg Trp Lys Ser His Leu Gln Asn Tyr Thr Val Asn Ala Thr
    690                 695                 700

Lys Leu Thr Val Asn Leu Thr Asn Asp Arg Tyr Leu Ala Thr Leu Thr
705                 710                 715                 720

Val Arg Asn Leu Val Gly Lys Ser Asp Ala Ala Val Leu Thr Ile Pro
                725                 730                 735

Ala Cys Asp Phe Gln Ala Thr His Pro Val Met Asp Leu Lys Ala Phe
            740                 745                 750

Pro Lys Asp Asn Met Leu Trp Val Glu Trp Thr Thr Pro Arg Glu Ser
        755                 760                 765

Val Lys Lys Tyr Ile Leu Glu Trp Cys Val Leu Ser Asp Lys Ala Pro
    770                 775                 780

Cys Ile Thr Asp Trp Gln Gln Glu Asp Gly Thr Val His Arg Thr Tyr
785                 790                 795                 800

Leu Arg Gly Asn Leu Ala Glu Ser Lys Cys Tyr Leu Ile Thr Val Thr
                805                 810                 815
```

```
Pro Val Tyr Ala Asp Gly Pro Gly Ser Pro Glu Ser Ile Lys Ala Tyr
            820                 825                 830

Leu Lys Gln Ala Pro Pro Ser Lys Gly Pro Thr Val Arg Thr Lys Lys
        835                 840                 845

Val Gly Lys Asn Glu Ala Val Leu Glu Trp Asp Gln Leu Pro Val Asp
    850                 855                 860

Val Gln Asn Gly Phe Ile Arg Asn Tyr Thr Ile Phe Tyr Arg Thr Ile
865                 870                 875                 880

Ile Gly Asn Glu Thr Ala Val Asn Val Asp Ser Ser His Thr Glu Tyr
                885                 890                 895

Thr Leu Ser Ser Leu Thr Ser Asp Thr Leu Tyr Met Val Arg Met Ala
            900                 905                 910

Ala Tyr Thr Asp Glu Gly Gly Lys Asp Gly Pro Glu Phe Thr Phe Thr
        915                 920                 925

Thr Pro Lys Phe Ala Gln Gly Glu Ile Glu Ser Gly Gly Asp Lys Thr
    930                 935                 940

His Thr Cys Pro Pro Cys Pro Ala Pro Glu Leu Leu Gly Gly Pro Ser
945                 950                 955                 960

Val Phe Leu Phe Pro Pro Lys Pro Lys Asp Thr Leu Met Ile Ser Arg
                965                 970                 975

Thr Pro Glu Val Thr Cys Val Val Val Asp Val Ser His Glu Asp Pro
            980                 985                 990

Glu Val Lys Phe Asn Trp Tyr Val Asp Gly Val Glu Val His Asn Ala
        995                 1000                1005

Lys Thr Lys Pro Arg Glu Glu Gln Tyr Asn Ser Thr Tyr Arg Val Val
    1010                1015                1020

Ser Val Leu Thr Val Leu His Gln Asp Trp Leu Asn Gly Lys Glu Tyr
1025                1030                1035                1040

Lys Cys Lys Val Ser Asn Lys Ala Leu Pro Ala Pro Ile Glu Lys Thr
                1045                1050                1055

Ile Ser Lys Ala Lys Gly Gln Pro Arg Glu Pro Gln Val Tyr Thr Leu
            1060                1065                1070

Pro Pro Ser Arg Asp Glu Leu Thr Lys Asn Gln Val Ser Leu Thr Cys
        1075                1080                1085

Leu Val Lys Gly Phe Tyr Pro Ser Asp Ile Ala Val Glu Trp Glu Ser
    1090                1095                1100

Asn Gly Gln Pro Glu Asn Asn Tyr Lys Thr Thr Pro Pro Val Leu Asp
1105                1110                1115                1120

Ser Asp Gly Ser Phe Phe Leu Tyr Ser Lys Leu Thr Val Asp Lys Ser
                1125                1130                1135

Arg Trp Gln Gln Gly Asn Val Phe Ser Cys Ser Val Met His Glu Ala
            1140                1145                1150

Leu His Asn His Tyr Thr Gln Lys Ser Leu Ser Leu Ser Pro Gly Lys
        1155                1160                1165
```

<210> SEQ ID NO 25
<211> LENGTH: 3477
<212> TYPE: DNA
<213> ORGANISM: Homo sapiens
<220> FEATURE:
<221> NAME/KEY: CDS
<222> LOCATION: (1)...(3474)

<400> SEQUENCE: 25

```
atg gtg gcc gtc ggc tgc gcg ctg ctg gct gcc ctg ctg gcc gcg ccg       48
Met Val Ala Val Gly Cys Ala Leu Leu Ala Ala Leu Leu Ala Ala Pro
```

-continued

```
 1               5                  10                  15

gga gcg gcg ctg gcc cca agg cgc tgc cct gcg cag gag gtg gca aga        96
Gly Ala Ala Leu Ala Pro Arg Arg Cys Pro Ala Gln Glu Val Ala Arg
            20                  25                  30

ggc gtg ctg acc agt ctg cca gga gac agc gtg act ctg acc tgc ccg       144
Gly Val Leu Thr Ser Leu Pro Gly Asp Ser Val Thr Leu Thr Cys Pro
        35                  40                  45

ggg gta gag ccg gaa gac aat gcc act gtt cac tgg gtg ctc agg aag       192
Gly Val Glu Pro Glu Asp Asn Ala Thr Val His Trp Val Leu Arg Lys
    50                  55                  60

ccg gct gca ggc tcc cac ccc agc aga tgg gct ggc atg gga agg agg       240
Pro Ala Ala Gly Ser His Pro Ser Arg Trp Ala Gly Met Gly Arg Arg
65                  70                  75                  80

ctg ctg ctg agg tcg gtg cag ctc cac gac tct gga aac tat tca tgc       288
Leu Leu Leu Arg Ser Val Gln Leu His Asp Ser Gly Asn Tyr Ser Cys
                85                  90                  95

tac cgg gcc ggc cgc cca gct ggg act gtg cac ttg ctg gtg gat gtt       336
Tyr Arg Ala Gly Arg Pro Ala Gly Thr Val His Leu Leu Val Asp Val
            100                 105                 110

ccc ccc gag gag ccc cag ctc tcc tgc ttc cgg aag agc ccc ctc agc       384
Pro Pro Glu Glu Pro Gln Leu Ser Cys Phe Arg Lys Ser Pro Leu Ser
        115                 120                 125

aat gtt gtt tgt gag tgg ggt cct cgg agc acc cca tcc ctg acg aca       432
Asn Val Val Cys Glu Trp Gly Pro Arg Ser Thr Pro Ser Leu Thr Thr
    130                 135                 140

aag gct gtg ctc ttg gtg agg aag ttt cag aac agt ccg gcc gaa gac       480
Lys Ala Val Leu Leu Val Arg Lys Phe Gln Asn Ser Pro Ala Glu Asp
145                 150                 155                 160

ttc cag gag ccg tgc cag tat tcc cag gag tcc cag aag ttc tcc tgc       528
Phe Gln Glu Pro Cys Gln Tyr Ser Gln Glu Ser Gln Lys Phe Ser Cys
                165                 170                 175

cag tta gca gtc ccg gag gga gac agc tct ttc tac ata gtg tcc atg       576
Gln Leu Ala Val Pro Glu Gly Asp Ser Ser Phe Tyr Ile Val Ser Met
            180                 185                 190

tgc gtc gcc agt agt gtc ggg agc aag ttc agc aaa act caa acc ttt       624
Cys Val Ala Ser Ser Val Gly Ser Lys Phe Ser Lys Thr Gln Thr Phe
        195                 200                 205

cag ggt tgt gga atc ttg cag cct gat ccg cct gcc aac atc aca gtc       672
Gln Gly Cys Gly Ile Leu Gln Pro Asp Pro Pro Ala Asn Ile Thr Val
    210                 215                 220

act gcc gtg gcc aga aac ccc cgc tgg ctc agt gtc acc tgg caa gac       720
Thr Ala Val Ala Arg Asn Pro Arg Trp Leu Ser Val Thr Trp Gln Asp
225                 230                 235                 240

ccc cac tcc tgg aac tca tct ttc tac aga cta cgg ttt gag ctc aga       768
Pro His Ser Trp Asn Ser Ser Phe Tyr Arg Leu Arg Phe Glu Leu Arg
                245                 250                 255

tat cgg gct gaa cgg tca aag aca ttc aca aca tgg atg gtc aag gac       816
Tyr Arg Ala Glu Arg Ser Lys Thr Phe Thr Thr Trp Met Val Lys Asp
            260                 265                 270

ctc cag cat cac tgt gtc atc cac gac gcc tgg agc ggc ctg agg cac       864
Leu Gln His His Cys Val Ile His Asp Ala Trp Ser Gly Leu Arg His
        275                 280                 285

gtg gtg cag ctt cgt gcc cag gag gag ttc ggg caa ggc gag tgg agc       912
Val Val Gln Leu Arg Ala Gln Glu Glu Phe Gly Gln Gly Glu Trp Ser
    290                 295                 300

gag tgg agc ccg gag gcc atg ggc acg cct tgg aca gaa tcg cga tcg       960
Glu Trp Ser Pro Glu Ala Met Gly Thr Pro Trp Thr Glu Ser Arg Ser
305                 310                 315                 320

cct cca gct gag aac gag gtg tcc acc ccc atg gaa ctt cta gac cca      1008
Pro Pro Ala Glu Asn Glu Val Ser Thr Pro Met Glu Leu Leu Asp Pro
```

```
                325                 330                 335

tgt ggt tat atc agt cct gaa tct cca gtt gta caa ctt cat tct aat      1056
Cys Gly Tyr Ile Ser Pro Glu Ser Pro Val Val Gln Leu His Ser Asn
            340                 345                 350

ttc act gca gtt tgt gtg cta aag gaa aaa tgt atg gat tat ttt cat      1104
Phe Thr Ala Val Cys Val Leu Lys Glu Lys Cys Met Asp Tyr Phe His
        355                 360                 365

gta aat gct aat tac att gtc tgg aaa aca aac cat ttt act att cct      1152
Val Asn Ala Asn Tyr Ile Val Trp Lys Thr Asn His Phe Thr Ile Pro
    370                 375                 380

aag gag caa tat act atc ata aac aga aca gca tcc agt gtc acc ttt      1200
Lys Glu Gln Tyr Thr Ile Ile Asn Arg Thr Ala Ser Ser Val Thr Phe
385                 390                 395                 400

aca gat ata gct tca tta aat att cag ctc act tgc aac att ctt aca      1248
Thr Asp Ile Ala Ser Leu Asn Ile Gln Leu Thr Cys Asn Ile Leu Thr
                405                 410                 415

ttc gga cag ctt gaa cag aat gtt tat gga atc aca ata att tca ggc      1296
Phe Gly Gln Leu Glu Gln Asn Val Tyr Gly Ile Thr Ile Ile Ser Gly
            420                 425                 430

ttg cct cca gaa aaa cct aaa aat ttg agt tgc att gtg aac gag ggg      1344
Leu Pro Pro Glu Lys Pro Lys Asn Leu Ser Cys Ile Val Asn Glu Gly
        435                 440                 445

aag aaa atg agg tgt gag tgg gat ggt gga agg gaa aca cac ttg gag      1392
Lys Lys Met Arg Cys Glu Trp Asp Gly Gly Arg Glu Thr His Leu Glu
    450                 455                 460

aca aac ttc act tta aaa tct gaa tgg gca aca cac aag ttt gct gat      1440
Thr Asn Phe Thr Leu Lys Ser Glu Trp Ala Thr His Lys Phe Ala Asp
465                 470                 475                 480

tgc aaa gca aaa cgt gac acc ccc acc tca tgc act gtt gat tat tct      1488
Cys Lys Ala Lys Arg Asp Thr Pro Thr Ser Cys Thr Val Asp Tyr Ser
                485                 490                 495

act gtg tat ttt gtc aac att gaa gtc tgg gta gaa gca gag aat gcc      1536
Thr Val Tyr Phe Val Asn Ile Glu Val Trp Val Glu Ala Glu Asn Ala
            500                 505                 510

ctt ggg aag gtt aca tca gat cat atc aat ttt gat cct gta tat aaa      1584
Leu Gly Lys Val Thr Ser Asp His Ile Asn Phe Asp Pro Val Tyr Lys
        515                 520                 525

gtg aag ccc aat ccg cca cat aat tta tca gtg atc aac tca gag gaa      1632
Val Lys Pro Asn Pro Pro His Asn Leu Ser Val Ile Asn Ser Glu Glu
    530                 535                 540

ctg tct agt atc tta aaa ttg aca tgg acc aac cca agt att aag agt      1680
Leu Ser Ser Ile Leu Lys Leu Thr Trp Thr Asn Pro Ser Ile Lys Ser
545                 550                 555                 560

gtt ata ata cta aaa tat aac att caa tat agg acc aaa gat gcc tca      1728
Val Ile Ile Leu Lys Tyr Asn Ile Gln Tyr Arg Thr Lys Asp Ala Ser
                565                 570                 575

act tgg agc cag att cct cct gaa gac aca gca tcc acc cga tct tca      1776
Thr Trp Ser Gln Ile Pro Pro Glu Asp Thr Ala Ser Thr Arg Ser Ser
            580                 585                 590

ttc act gtc caa gac ctt aaa cct ttt aca gaa tat gtg ttt agg att      1824
Phe Thr Val Gln Asp Leu Lys Pro Phe Thr Glu Tyr Val Phe Arg Ile
        595                 600                 605

cgc tgt atg aag gaa gat ggt aag gga tac tgg agt gac tgg agt gaa      1872
Arg Cys Met Lys Glu Asp Gly Lys Gly Tyr Trp Ser Asp Trp Ser Glu
    610                 615                 620

gaa gca agt ggg atc acc tat gaa gat aga cca tct aaa gca cca agt      1920
Glu Ala Ser Gly Ile Thr Tyr Glu Asp Arg Pro Ser Lys Ala Pro Ser
625                 630                 635                 640

ttc tgg tat aaa ata gat cca tcc cat act caa ggc tac aga act gta      1968
Phe Trp Tyr Lys Ile Asp Pro Ser His Thr Gln Gly Tyr Arg Thr Val
```

-continued

```
                645                 650                 655

caa ctc gtg tgg aag aca ttg cct cct ttt gaa gcc aat gga aaa atc      2016
Gln Leu Val Trp Lys Thr Leu Pro Pro Phe Glu Ala Asn Gly Lys Ile
            660                 665                 670

ttg gat tat gaa gtg act ctc aca aga tgg aaa tca cat tta caa aat      2064
Leu Asp Tyr Glu Val Thr Leu Thr Arg Trp Lys Ser His Leu Gln Asn
        675                 680                 685

tac aca gtt aat gcc aca aaa ctg aca gta aat ctc aca aat gat cgc      2112
Tyr Thr Val Asn Ala Thr Lys Leu Thr Val Asn Leu Thr Asn Asp Arg
    690                 695                 700

tat cta gca acc cta aca gta aga aat ctt gtt ggc aaa tca gat gca      2160
Tyr Leu Ala Thr Leu Thr Val Arg Asn Leu Val Gly Lys Ser Asp Ala
705                 710                 715                 720

gct gtt tta act atc cct gcc tgt gac ttt caa gct act cac cct gta      2208
Ala Val Leu Thr Ile Pro Ala Cys Asp Phe Gln Ala Thr His Pro Val
                725                 730                 735

atg gat ctt aaa gca ttc ccc aaa gat aac atg ctt tgg gtg gaa tgg      2256
Met Asp Leu Lys Ala Phe Pro Lys Asp Asn Met Leu Trp Val Glu Trp
            740                 745                 750

act act cca agg gaa tct gta aag aaa tat ata ctt gag tgg tgt gtg      2304
Thr Thr Pro Arg Glu Ser Val Lys Lys Tyr Ile Leu Glu Trp Cys Val
        755                 760                 765

tta tca gat aaa gca ccc tgt atc aca gac tgg caa caa gaa gat ggt      2352
Leu Ser Asp Lys Ala Pro Cys Ile Thr Asp Trp Gln Gln Glu Asp Gly
    770                 775                 780

acc gtg cat cgc acc tat tta aga ggg aac tta gca gag agc aaa tgc      2400
Thr Val His Arg Thr Tyr Leu Arg Gly Asn Leu Ala Glu Ser Lys Cys
785                 790                 795                 800

tat ttg ata aca gtt act cca gta tat gct gat gga cca gga agc cct      2448
Tyr Leu Ile Thr Val Thr Pro Val Tyr Ala Asp Gly Pro Gly Ser Pro
                805                 810                 815

gaa tcc ata aag gca tac ctt aaa caa gct cca cct tcc aaa gga cct      2496
Glu Ser Ile Lys Ala Tyr Leu Lys Gln Ala Pro Pro Ser Lys Gly Pro
            820                 825                 830

act gtt cgg aca aaa aaa gta ggg aaa aac gaa gct gtc tta gag tgg      2544
Thr Val Arg Thr Lys Lys Val Gly Lys Asn Glu Ala Val Leu Glu Trp
        835                 840                 845

gac caa ctt cct gtt gat gtt cag aat gga ttt atc aga aat tat act      2592
Asp Gln Leu Pro Val Asp Val Gln Asn Gly Phe Ile Arg Asn Tyr Thr
    850                 855                 860

ata ttt tat aga acc atc att gga aat gaa act gct gtg aat gtg gat      2640
Ile Phe Tyr Arg Thr Ile Ile Gly Asn Glu Thr Ala Val Asn Val Asp
865                 870                 875                 880

tct tcc cac aca gaa tat aca ttg tcc tct ttg act agt gac aca ttg      2688
Ser Ser His Thr Glu Tyr Thr Leu Ser Ser Leu Thr Ser Asp Thr Leu
                885                 890                 895

tac atg gta cga atg gca gca tac aca gat gaa ggt ggg aag gat ggt      2736
Tyr Met Val Arg Met Ala Ala Tyr Thr Asp Glu Gly Gly Lys Asp Gly
            900                 905                 910

cca gaa ttc act ttt act acc cca aag ttt gct caa gga gaa att gaa      2784
Pro Glu Phe Thr Phe Thr Thr Pro Lys Phe Ala Gln Gly Glu Ile Glu
        915                 920                 925

tcc ggg ggc gac aaa act cac aca tgc cca ccg tgc cca gca cct gaa      2832
Ser Gly Gly Asp Lys Thr His Thr Cys Pro Pro Cys Pro Ala Pro Glu
    930                 935                 940

ctc ctg ggg gga ccg tca gtc ttc ctc ttc ccc cca aaa ccc aag gac      2880
Leu Leu Gly Gly Pro Ser Val Phe Leu Phe Pro Pro Lys Pro Lys Asp
945                 950                 955                 960

acc ctc atg atc tcc cgg acc cct gag gtc aca tgc gtg gtg gtg gac      2928
Thr Leu Met Ile Ser Arg Thr Pro Glu Val Thr Cys Val Val Val Asp
```

-continued

```
                965                 970                 975

gtg agc cac gaa gac cct gag gtc aag ttc aac tgg tac gtg gac ggc     2976
Val Ser His Glu Asp Pro Glu Val Lys Phe Asn Trp Tyr Val Asp Gly
            980                 985                 990

gtg gag gtg cat aat gcc aag aca aag ccg cgg gag gag cag tac aac     3024
Val Glu Val His Asn Ala Lys Thr Lys Pro Arg Glu Glu Gln Tyr Asn
        995                 1000                1005

agc acg tac cgt gtg gtc agc gtc ctc acc gtc ctg cac cag gac tgg     3072
Ser Thr Tyr Arg Val Val Ser Val Leu Thr Val Leu His Gln Asp Trp
    1010                1015                1020

ctg aat ggc aag gag tac aag tgc aag gtc tcc aac aaa gcc ctc cca     3120
Leu Asn Gly Lys Glu Tyr Lys Cys Lys Val Ser Asn Lys Ala Leu Pro
1025                1030                1035                1040

gcc ccc atc gag aaa acc atc tcc aaa gcc aaa ggg cag ccc cga gaa     3168
Ala Pro Ile Glu Lys Thr Ile Ser Lys Ala Lys Gly Gln Pro Arg Glu
                1045                1050                1055

cca cag gtg tac acc ctg ccc cca tcc cgg gat gag ctg acc aag aac     3216
Pro Gln Val Tyr Thr Leu Pro Pro Ser Arg Asp Glu Leu Thr Lys Asn
            1060                1065                1070

cag gtc agc ctg acc tgc ctg gtc aaa ggc ttc tat ccc agc gac atc     3264
Gln Val Ser Leu Thr Cys Leu Val Lys Gly Phe Tyr Pro Ser Asp Ile
        1075                1080                1085

gcc gtg gag tgg gag agc aat ggg cag ccg gag aac aac tac aag acc     3312
Ala Val Glu Trp Glu Ser Asn Gly Gln Pro Glu Asn Asn Tyr Lys Thr
    1090                1095                1100

acg cct ccc gtg ctg gac tcc gac ggc tcc ttc ttc ctc tac agc aag     3360
Thr Pro Pro Val Leu Asp Ser Asp Gly Ser Phe Phe Leu Tyr Ser Lys
1105                1110                1115                1120

ctc acc gtg gac aag agc agg tgg cag cag ggg aac gtc ttc tca tgc     3408
Leu Thr Val Asp Lys Ser Arg Trp Gln Gln Gly Asn Val Phe Ser Cys
                1125                1130                1135

tcc gtg atg cat gag gct ctg cac aac cac tac acg cag aag agc ctc     3456
Ser Val Met His Glu Ala Leu His Asn His Tyr Thr Gln Lys Ser Leu
            1140                1145                1150

tcc ctg tct ccg ggt aaa tga                                         3477
Ser Leu Ser Pro Gly Lys
        1155


<210> SEQ ID NO 26
<211> LENGTH: 1158
<212> TYPE: PRT
<213> ORGANISM: Homo sapiens

<400> SEQUENCE: 26

Met Val Ala Val Gly Cys Ala Leu Leu Ala Ala Leu Leu Ala Ala Pro
 1               5                  10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
        35                  40                  45

Gly Val Glu Pro Glu Asp Asn Ala Thr Val His Trp Val Leu Arg Lys
    50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
```

```
        115                 120                 125

Asn Val Val Cys Glu Trp Gly Pro Arg Ser Thr Pro Ser Leu Thr Thr
    130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
        195                 200                 205

Gln Gly Cys Gly Ile Leu Gln Pro Asp Pro Pro Ala Asn Ile Thr Val
    210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
        275                 280                 285

Val Val Gln Leu Arg Ala Gln Glu Glu Phe Gly Gln Gly Glu Trp Ser
    290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Glu Leu Leu Asp Pro
                325                 330                 335

Cys Gly Tyr Ile Ser Pro Glu Ser Pro Val Val Gln Leu His Ser Asn
            340                 345                 350

Phe Thr Ala Val Cys Val Leu Lys Glu Lys Cys Met Asp Tyr Phe His
        355                 360                 365

Val Asn Ala Asn Tyr Ile Val Trp Lys Thr Asn His Phe Thr Ile Pro
    370                 375                 380

Lys Glu Gln Tyr Thr Ile Ile Asn Arg Thr Ala Ser Ser Val Thr Phe
385                 390                 395                 400

Thr Asp Ile Ala Ser Leu Asn Ile Gln Leu Thr Cys Asn Ile Leu Thr
                405                 410                 415

Phe Gly Gln Leu Glu Gln Asn Val Tyr Gly Ile Thr Ile Ile Ser Gly
            420                 425                 430

Leu Pro Pro Glu Lys Pro Lys Asn Leu Ser Cys Ile Val Asn Glu Gly
        435                 440                 445

Lys Lys Met Arg Cys Glu Trp Asp Gly Gly Arg Glu Thr His Leu Glu
    450                 455                 460

Thr Asn Phe Thr Leu Lys Ser Glu Trp Ala Thr His Lys Phe Ala Asp
465                 470                 475                 480

Cys Lys Ala Lys Arg Asp Thr Pro Thr Ser Cys Thr Val Asp Tyr Ser
                485                 490                 495

Thr Val Tyr Phe Val Asn Ile Glu Val Trp Val Glu Ala Glu Asn Ala
            500                 505                 510

Leu Gly Lys Val Thr Ser Asp His Ile Asn Phe Asp Pro Val Tyr Lys
        515                 520                 525

Val Lys Pro Asn Pro Pro His Asn Leu Ser Val Ile Asn Ser Glu Glu
    530                 535                 540
```

-continued

```
Leu Ser Ser Ile Leu Lys Leu Thr Trp Thr Asn Pro Ser Ile Lys Ser
545                 550                 555                 560

Val Ile Ile Leu Lys Tyr Asn Ile Gln Tyr Arg Thr Lys Asp Ala Ser
                565                 570                 575

Thr Trp Ser Gln Ile Pro Pro Glu Asp Thr Ala Ser Thr Arg Ser Ser
            580                 585                 590

Phe Thr Val Gln Asp Leu Lys Pro Phe Thr Glu Tyr Val Phe Arg Ile
        595                 600                 605

Arg Cys Met Lys Glu Asp Gly Lys Gly Tyr Trp Ser Asp Trp Ser Glu
    610                 615                 620

Glu Ala Ser Gly Ile Thr Tyr Glu Asp Arg Pro Ser Lys Ala Pro Ser
625                 630                 635                 640

Phe Trp Tyr Lys Ile Asp Pro Ser His Thr Gln Gly Tyr Arg Thr Val
                645                 650                 655

Gln Leu Val Trp Lys Thr Leu Pro Pro Phe Glu Ala Asn Gly Lys Ile
            660                 665                 670

Leu Asp Tyr Glu Val Thr Leu Thr Arg Trp Lys Ser His Leu Gln Asn
        675                 680                 685

Tyr Thr Val Asn Ala Thr Lys Leu Thr Val Asn Leu Thr Asn Asp Arg
    690                 695                 700

Tyr Leu Ala Thr Leu Thr Val Arg Asn Leu Val Gly Lys Ser Asp Ala
705                 710                 715                 720

Ala Val Leu Thr Ile Pro Ala Cys Asp Phe Gln Ala Thr His Pro Val
                725                 730                 735

Met Asp Leu Lys Ala Phe Pro Lys Asp Asn Met Leu Trp Val Glu Trp
            740                 745                 750

Thr Thr Pro Arg Glu Ser Val Lys Lys Tyr Ile Leu Glu Trp Cys Val
        755                 760                 765

Leu Ser Asp Lys Ala Pro Cys Ile Thr Asp Trp Gln Gln Glu Asp Gly
    770                 775                 780

Thr Val His Arg Thr Tyr Leu Arg Gly Asn Leu Ala Glu Ser Lys Cys
785                 790                 795                 800

Tyr Leu Ile Thr Val Thr Pro Val Tyr Ala Asp Gly Pro Gly Ser Pro
                805                 810                 815

Glu Ser Ile Lys Ala Tyr Leu Lys Gln Ala Pro Pro Ser Lys Gly Pro
            820                 825                 830

Thr Val Arg Thr Lys Lys Val Gly Lys Asn Glu Ala Val Leu Glu Trp
        835                 840                 845

Asp Gln Leu Pro Val Asp Val Gln Asn Gly Phe Ile Arg Asn Tyr Thr
    850                 855                 860

Ile Phe Tyr Arg Thr Ile Ile Gly Asn Glu Thr Ala Val Asn Val Asp
865                 870                 875                 880

Ser Ser His Thr Glu Tyr Thr Leu Ser Ser Leu Thr Ser Asp Thr Leu
                885                 890                 895

Tyr Met Val Arg Met Ala Ala Tyr Thr Asp Glu Gly Gly Lys Asp Gly
            900                 905                 910

Pro Glu Phe Thr Phe Thr Thr Pro Lys Phe Ala Gln Gly Glu Ile Glu
        915                 920                 925

Ser Gly Gly Asp Lys Thr His Thr Cys Pro Pro Cys Pro Ala Pro Glu
    930                 935                 940

Leu Leu Gly Gly Pro Ser Val Phe Leu Phe Pro Pro Lys Pro Lys Asp
945                 950                 955                 960

Thr Leu Met Ile Ser Arg Thr Pro Glu Val Thr Cys Val Val Val Asp
                965                 970                 975
```

```
Val Ser His Glu Asp Pro Glu Val Lys Phe Asn Trp Tyr Val Asp Gly
            980                 985                 990

Val Glu Val His Asn Ala Lys Thr Lys Pro Arg Glu Glu Gln Tyr Asn
        995                 1000                1005

Ser Thr Tyr Arg Val Val Ser Val Leu Thr Val Leu His Gln Asp Trp
    1010                1015                1020

Leu Asn Gly Lys Glu Tyr Lys Cys Lys Val Ser Asn Lys Ala Leu Pro
1025                1030                1035                1040

Ala Pro Ile Glu Lys Thr Ile Ser Lys Ala Lys Gly Gln Pro Arg Glu
                1045                1050                1055

Pro Gln Val Tyr Thr Leu Pro Pro Ser Arg Asp Glu Leu Thr Lys Asn
            1060                1065                1070

Gln Val Ser Leu Thr Cys Leu Val Lys Gly Phe Tyr Pro Ser Asp Ile
        1075                1080                1085

Ala Val Glu Trp Glu Ser Asn Gly Gln Pro Glu Asn Asn Tyr Lys Thr
    1090                1095                1100

Thr Pro Pro Val Leu Asp Ser Asp Gly Ser Phe Phe Leu Tyr Ser Lys
1105                1110                1115                1120

Leu Thr Val Asp Lys Ser Arg Trp Gln Gln Gly Asn Val Phe Ser Cys
                1125                1130                1135

Ser Val Met His Glu Ala Leu His Asn His Tyr Thr Gln Lys Ser Leu
            1140                1145                1150

Ser Leu Ser Pro Gly Lys
        1155


<210> SEQ ID NO 27
<211> LENGTH: 2733
<212> TYPE: DNA
<213> ORGANISM: Homo sapiens
<220> FEATURE:
<221> NAME/KEY: CDS
<222> LOCATION: (1)...(2730)

<400> SEQUENCE: 27

atg gtg ctt ctg tgg tgt gta gtg agt ctc tac ttt tat gga atc ctg       48
Met Val Leu Leu Trp Cys Val Val Ser Leu Tyr Phe Tyr Gly Ile Leu
 1               5                  10                  15

caa agt gat gcc tca gaa cgc tgc gat gac tgg gga cta gac acc atg       96
Gln Ser Asp Ala Ser Glu Arg Cys Asp Asp Trp Gly Leu Asp Thr Met
            20                  25                  30

agg caa atc caa gtg ttt gaa gat gag cca gct cgc atc aag tgc cca      144
Arg Gln Ile Gln Val Phe Glu Asp Glu Pro Ala Arg Ile Lys Cys Pro
        35                  40                  45

ctc ttt gaa cac ttc ttg aaa ttc aac tac agc aca gcc cat tca gct      192
Leu Phe Glu His Phe Leu Lys Phe Asn Tyr Ser Thr Ala His Ser Ala
     50                  55                  60

ggc ctt act ctg atc tgg tat tgg act agg cag gac cgg gac ctt gag      240
Gly Leu Thr Leu Ile Trp Tyr Trp Thr Arg Gln Asp Arg Asp Leu Glu
 65                  70                  75                  80

gag cca att aac ttc cgc ctc ccc gag aac cgc att agt aag gag aaa      288
Glu Pro Ile Asn Phe Arg Leu Pro Glu Asn Arg Ile Ser Lys Glu Lys
                 85                  90                  95

gat gtg ctg tgg ttc cgg ccc act ctc ctc aat gac act ggc aac tat      336
Asp Val Leu Trp Phe Arg Pro Thr Leu Leu Asn Asp Thr Gly Asn Tyr
            100                 105                 110

acc tgc atg tta agg aac act aca tat tgc agc aaa gtt gca ttt ccc      384
Thr Cys Met Leu Arg Asn Thr Thr Tyr Cys Ser Lys Val Ala Phe Pro
        115                 120                 125
```

-continued

```
ttg gaa gtt gtt caa aaa gac agc tgt ttc aat tcc ccc atg aaa ctc      432
Leu Glu Val Val Gln Lys Asp Ser Cys Phe Asn Ser Pro Met Lys Leu
    130                 135                 140

cca gtg cat aaa ctg tat ata gaa tat ggc att cag agg atc act tgt      480
Pro Val His Lys Leu Tyr Ile Glu Tyr Gly Ile Gln Arg Ile Thr Cys
145                 150                 155                 160

cca aat gta gat gga tat ttt cct tcc agt gtc aaa ccg act atc act      528
Pro Asn Val Asp Gly Tyr Phe Pro Ser Ser Val Lys Pro Thr Ile Thr
                165                 170                 175

tgg tat atg ggc tgt tat aaa ata cag aat ttt aat aat gta ata ccc      576
Trp Tyr Met Gly Cys Tyr Lys Ile Gln Asn Phe Asn Asn Val Ile Pro
            180                 185                 190

gaa ggt atg aac ttg agt ttc ctc att gcc tta att tca aat aat gga      624
Glu Gly Met Asn Leu Ser Phe Leu Ile Ala Leu Ile Ser Asn Asn Gly
        195                 200                 205

aat tac aca tgt gtt gtt aca tat cca gaa aat gga cgt acg ttt cat      672
Asn Tyr Thr Cys Val Val Thr Tyr Pro Glu Asn Gly Arg Thr Phe His
    210                 215                 220

ctc acc agg act ctg act gta aag gta gta ggc tct cca aaa aat gca      720
Leu Thr Arg Thr Leu Thr Val Lys Val Val Gly Ser Pro Lys Asn Ala
225                 230                 235                 240

gtg ccc cct gtg atc cat tca cct aat gat cat gtg gtc tat gag aaa      768
Val Pro Pro Val Ile His Ser Pro Asn Asp His Val Val Tyr Glu Lys
                245                 250                 255

gaa cca gga gag gag cta ctc att ccc tgt acg gtc tat ttt agt ttt      816
Glu Pro Gly Glu Glu Leu Leu Ile Pro Cys Thr Val Tyr Phe Ser Phe
            260                 265                 270

ctg atg gat tct cgc aat gag gtt tgg tgg acc att gat gga aaa aaa      864
Leu Met Asp Ser Arg Asn Glu Val Trp Trp Thr Ile Asp Gly Lys Lys
        275                 280                 285

cct gat gac atc act att gat gtc acc att aac gaa agt ata agt cat      912
Pro Asp Asp Ile Thr Ile Asp Val Thr Ile Asn Glu Ser Ile Ser His
    290                 295                 300

agt aga aca gaa gat gaa aca aga act cag att ttg agc atc aag aaa      960
Ser Arg Thr Glu Asp Glu Thr Arg Thr Gln Ile Leu Ser Ile Lys Lys
305                 310                 315                 320

gtt acc tct gag gat ctc aag cgc agc tat gtc tgt cat gct aga agt     1008
Val Thr Ser Glu Asp Leu Lys Arg Ser Tyr Val Cys His Ala Arg Ser
                325                 330                 335

gcc aaa ggc gaa gtt gcc aaa gca gcc aag gtg aag cag aaa gtg cca     1056
Ala Lys Gly Glu Val Ala Lys Ala Ala Lys Val Lys Gln Lys Val Pro
            340                 345                 350

gct cca aga tac aca gtg tcc ggt ggc gcg cct atg ctg agc gag gct     1104
Ala Pro Arg Tyr Thr Val Ser Gly Gly Ala Pro Met Leu Ser Glu Ala
        355                 360                 365

gat aaa tgc aag gaa cgt gaa gaa aaa ata att tta gtg tca tct gca     1152
Asp Lys Cys Lys Glu Arg Glu Glu Lys Ile Ile Leu Val Ser Ser Ala
    370                 375                 380

aat gaa att gat gtt cgt ccc tgt cct ctt aac cca aat gaa cac aaa     1200
Asn Glu Ile Asp Val Arg Pro Cys Pro Leu Asn Pro Asn Glu His Lys
385                 390                 395                 400

ggc act ata act tgg tat aag gat gac agc aag aca cct gta tct aca     1248
Gly Thr Ile Thr Trp Tyr Lys Asp Asp Ser Lys Thr Pro Val Ser Thr
                405                 410                 415

gaa caa gcc tcc agg att cat caa cac aaa gag aaa ctt tgg ttt gtt     1296
Glu Gln Ala Ser Arg Ile His Gln His Lys Glu Lys Leu Trp Phe Val
            420                 425                 430

cct gct aag gtg gag gat tca gga cat tac tat tgc gtg gta aga aat     1344
Pro Ala Lys Val Glu Asp Ser Gly His Tyr Tyr Cys Val Val Arg Asn
        435                 440                 445
```

-continued

```
tca tct tac tgc ctc aga att aaa ata agt gca aaa ttt gtg gag aat      1392
Ser Ser Tyr Cys Leu Arg Ile Lys Ile Ser Ala Lys Phe Val Glu Asn
    450                 455                 460

gag cct aac tta tgt tat aat gca caa gcc ata ttt aag cag aaa cta      1440
Glu Pro Asn Leu Cys Tyr Asn Ala Gln Ala Ile Phe Lys Gln Lys Leu
465                 470                 475                 480

ccc gtt gca gga gac gga gga ctt gtg tgc cct tat atg gag ttt ttt      1488
Pro Val Ala Gly Asp Gly Gly Leu Val Cys Pro Tyr Met Glu Phe Phe
                485                 490                 495

aaa aat gaa aat aat gag tta cct aaa tta cag tgg tat aag gat tgc      1536
Lys Asn Glu Asn Asn Glu Leu Pro Lys Leu Gln Trp Tyr Lys Asp Cys
            500                 505                 510

aaa cct cta ctt ctt gac aat ata cac ttt agt gga gtc aaa gat agg      1584
Lys Pro Leu Leu Leu Asp Asn Ile His Phe Ser Gly Val Lys Asp Arg
        515                 520                 525

ctc atc gtg atg aat gtg gct gaa aag cat aga ggg aac tat act tgt      1632
Leu Ile Val Met Asn Val Ala Glu Lys His Arg Gly Asn Tyr Thr Cys
    530                 535                 540

cat gca tcc tac aca tac ttg ggc aag caa tat cct att acc cgg gta      1680
His Ala Ser Tyr Thr Tyr Leu Gly Lys Gln Tyr Pro Ile Thr Arg Val
545                 550                 555                 560

ata gaa ttt att act cta gag gaa aac aaa ccc aca agg cct gtg att      1728
Ile Glu Phe Ile Thr Leu Glu Glu Asn Lys Pro Thr Arg Pro Val Ile
                565                 570                 575

gtg agc cca gct aat gag aca atg gaa gta gac ttg gga tcc cag ata      1776
Val Ser Pro Ala Asn Glu Thr Met Glu Val Asp Leu Gly Ser Gln Ile
            580                 585                 590

caa ttg atc tgt aat gtc acc ggc cag ttg agt gac att gct tac tgg      1824
Gln Leu Ile Cys Asn Val Thr Gly Gln Leu Ser Asp Ile Ala Tyr Trp
        595                 600                 605

aag tgg aat ggg tca gta att gat gaa gat gac cca gtg cta ggg gaa      1872
Lys Trp Asn Gly Ser Val Ile Asp Glu Asp Asp Pro Val Leu Gly Glu
    610                 615                 620

gac tat tac agt gtg gaa aat cct gca aac aaa aga agg agt acc ctc      1920
Asp Tyr Tyr Ser Val Glu Asn Pro Ala Asn Lys Arg Arg Ser Thr Leu
625                 630                 635                 640

atc aca gtg ctt aat ata tcg gaa att gag agt aga ttt tat aaa cat      1968
Ile Thr Val Leu Asn Ile Ser Glu Ile Glu Ser Arg Phe Tyr Lys His
                645                 650                 655

cca ttt acc tgt ttt gcc aag aat aca cat ggt ata gat gca gca tat      2016
Pro Phe Thr Cys Phe Ala Lys Asn Thr His Gly Ile Asp Ala Ala Tyr
            660                 665                 670

atc cag tta ata tat cca gtc act aat tcc gga gac aaa act cac aca      2064
Ile Gln Leu Ile Tyr Pro Val Thr Asn Ser Gly Asp Lys Thr His Thr
        675                 680                 685

tgc cca ccg tgc cca gca cct gaa ctc ctg ggg gga ccg tca gtc ttc      2112
Cys Pro Pro Cys Pro Ala Pro Glu Leu Leu Gly Gly Pro Ser Val Phe
    690                 695                 700

ctc ttc ccc cca aaa ccc aag gac acc ctc atg atc tcc cgg acc cct      2160
Leu Phe Pro Pro Lys Pro Lys Asp Thr Leu Met Ile Ser Arg Thr Pro
705                 710                 715                 720

gag gtc aca tgc gtg gtg gtg gac gtg agc cac gaa gac cct gag gtc      2208
Glu Val Thr Cys Val Val Val Asp Val Ser His Glu Asp Pro Glu Val
                725                 730                 735

aag ttc aac tgg tac gtg gac ggc gtg gag gtg cat aat gcc aag aca      2256
Lys Phe Asn Trp Tyr Val Asp Gly Val Glu Val His Asn Ala Lys Thr
            740                 745                 750

aag ccg cgg gag gag cag tac aac agc acg tac cgt gtg gtc agc gtc      2304
Lys Pro Arg Glu Glu Gln Tyr Asn Ser Thr Tyr Arg Val Val Ser Val
        755                 760                 765
```

ctc acc gtc ctg cac cag gac tgg ctg aat ggc aag gag tac aag tgc 2352
Leu Thr Val Leu His Gln Asp Trp Leu Asn Gly Lys Glu Tyr Lys Cys
770 775 780 aag gtc tcc aac aaa gcc ctc cca gcc ccc atc gag aaa acc atc tcc 2400
Lys Val Ser Asn Lys Ala Leu Pro Ala Pro Ile Glu Lys Thr Ile Ser
785 790 795 800 aaa gcc aaa ggg cag ccc cga gaa cca cag gtg tac acc ctg ccc cca 2448
Lys Ala Lys Gly Gln Pro Arg Glu Pro Gln Val Tyr Thr Leu Pro Pro
805 810 815 tcc cgg gag gag atg acc aag aac cag gtc agc ctg acc tgc ctg gtc 2496
Ser Arg Glu Glu Met Thr Lys Asn Gln Val Ser Leu Thr Cys Leu Val
820 825 830 aaa ggc ttc tat ccc agc gac atc gcc gtg gag tgg gag agc aat ggg 2544
Lys Gly Phe Tyr Pro Ser Asp Ile Ala Val Glu Trp Glu Ser Asn Gly
835 840 845 cag ccg gag aac aac tac aag acc acg cct ccc gtg ctg gac tcc gac 2592
Gln Pro Glu Asn Asn Tyr Lys Thr Thr Pro Pro Val Leu Asp Ser Asp
850 855 860 ggc tcc ttc ttc ctc tat agc aag ctc acc gtg gac aag agc agg tgg 2640
Gly Ser Phe Phe Leu Tyr Ser Lys Leu Thr Val Asp Lys Ser Arg Trp
865 870 875 880 cag cag ggg aac gtc ttc tca tgc tcc gtg atg cat gag gct ctg cac 2688
Gln Gln Gly Asn Val Phe Ser Cys Ser Val Met His Glu Ala Leu His
885 890 895 aac cac tac acg cag aag agc ctc tcc ctg tct ccg ggt aaa 2730
Asn His Tyr Thr Gln Lys Ser Leu Ser Leu Ser Pro Gly Lys
900 905 910 tga 2733

<210> SEQ ID NO 28
<211> LENGTH: 910
<212> TYPE: PRT
<213> ORGANISM: Homo sapiens

<400> SEQUENCE: 28

Met Val Leu Leu Trp Cys Val Val Ser Leu Tyr Phe Tyr Gly Ile Leu
1 5 10 15

Gln Ser Asp Ala Ser Glu Arg Cys Asp Asp Trp Gly Leu Asp Thr Met
20 25 30

Arg Gln Ile Gln Val Phe Glu Asp Glu Pro Ala Arg Ile Lys Cys Pro
35 40 45

Leu Phe Glu His Phe Leu Lys Phe Asn Tyr Ser Thr Ala His Ser Ala
50 55 60

Gly Leu Thr Leu Ile Trp Tyr Trp Thr Arg Gln Asp Arg Asp Leu Glu
65 70 75 80

Glu Pro Ile Asn Phe Arg Leu Pro Glu Asn Arg Ile Ser Lys Glu Lys
85 90 95

Asp Val Leu Trp Phe Arg Pro Thr Leu Leu Asn Asp Thr Gly Asn Tyr
100 105 110

Thr Cys Met Leu Arg Asn Thr Thr Tyr Cys Ser Lys Val Ala Phe Pro
115 120 125

Leu Glu Val Val Gln Lys Asp Ser Cys Phe Asn Ser Pro Met Lys Leu
130 135 140

Pro Val His Lys Leu Tyr Ile Glu Tyr Gly Ile Gln Arg Ile Thr Cys
145 150 155 160

Pro Asn Val Asp Gly Tyr Phe Pro Ser Ser Val Lys Pro Thr Ile Thr
165 170 175

Trp Tyr Met Gly Cys Tyr Lys Ile Gln Asn Phe Asn Asn Val Ile Pro

```
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val Ser Gly Gly Ala Pro Met Leu Ser Glu Ala
        355                 360                 365

Asp Lys Cys Lys Glu Arg Glu Glu Lys Ile Ile Leu Val Ser Ser Ala
    370                 375                 380

Asn Glu Ile Asp Val Arg Pro Cys Pro Leu Asn Pro Asn Glu His Lys
385                 390                 395                 400

Gly Thr Ile Thr Trp Tyr Lys Asp Asp Ser Lys Thr Pro Val Ser Thr
                405                 410                 415

Glu Gln Ala Ser Arg Ile His Gln His Lys Glu Lys Leu Trp Phe Val
            420                 425                 430

Pro Ala Lys Val Glu Asp Ser Gly His Tyr Tyr Cys Val Val Arg Asn
        435                 440                 445

Ser Ser Tyr Cys Leu Arg Ile Lys Ile Ser Ala Lys Phe Val Glu Asn
    450                 455                 460

Glu Pro Asn Leu Cys Tyr Asn Ala Gln Ala Ile Phe Lys Gln Lys Leu
465                 470                 475                 480

Pro Val Ala Gly Asp Gly Gly Leu Val Cys Pro Tyr Met Glu Phe Phe
                485                 490                 495

Lys Asn Glu Asn Asn Glu Leu Pro Lys Leu Gln Trp Tyr Lys Asp Cys
            500                 505                 510

Lys Pro Leu Leu Leu Asp Asn Ile His Phe Ser Gly Val Lys Asp Arg
        515                 520                 525

Leu Ile Val Met Asn Val Ala Glu Lys His Arg Gly Asn Tyr Thr Cys
    530                 535                 540

His Ala Ser Tyr Thr Tyr Leu Gly Lys Gln Tyr Pro Ile Thr Arg Val
545                 550                 555                 560

Ile Glu Phe Ile Thr Leu Glu Glu Asn Lys Pro Thr Arg Pro Val Ile
                565                 570                 575

Val Ser Pro Ala Asn Glu Thr Met Glu Val Asp Leu Gly Ser Gln Ile
            580                 585                 590

Gln Leu Ile Cys Asn Val Thr Gly Gln Leu Ser Asp Ile Ala Tyr Trp
        595                 600                 605
```

```
Lys Trp Asn Gly Ser Val Ile Asp Glu Asp Asp Pro Val Leu Gly Glu
    610                 615                 620

Asp Tyr Tyr Ser Val Glu Asn Pro Ala Asn Lys Arg Arg Ser Thr Leu
625                 630                 635                 640

Ile Thr Val Leu Asn Ile Ser Glu Ile Glu Ser Arg Phe Tyr Lys His
                645                 650                 655

Pro Phe Thr Cys Phe Ala Lys Asn Thr His Gly Ile Asp Ala Ala Tyr
            660                 665                 670

Ile Gln Leu Ile Tyr Pro Val Thr Asn Ser Gly Asp Lys Thr His Thr
        675                 680                 685

Cys Pro Pro Cys Pro Ala Pro Glu Leu Leu Gly Gly Pro Ser Val Phe
    690                 695                 700

Leu Phe Pro Pro Lys Pro Lys Asp Thr Leu Met Ile Ser Arg Thr Pro
705                 710                 715                 720

Glu Val Thr Cys Val Val Val Asp Val Ser His Glu Asp Pro Glu Val
                725                 730                 735

Lys Phe Asn Trp Tyr Val Asp Gly Val Glu Val His Asn Ala Lys Thr
            740                 745                 750

Lys Pro Arg Glu Glu Gln Tyr Asn Ser Thr Tyr Arg Val Val Ser Val
        755                 760                 765

Leu Thr Val Leu His Gln Asp Trp Leu Asn Gly Lys Glu Tyr Lys Cys
    770                 775                 780

Lys Val Ser Asn Lys Ala Leu Pro Ala Pro Ile Glu Lys Thr Ile Ser
785                 790                 795                 800

Lys Ala Lys Gly Gln Pro Arg Glu Pro Gln Val Tyr Thr Leu Pro Pro
                805                 810                 815

Ser Arg Glu Glu Met Thr Lys Asn Gln Val Ser Leu Thr Cys Leu Val
            820                 825                 830

Lys Gly Phe Tyr Pro Ser Asp Ile Ala Val Glu Trp Glu Ser Asn Gly
        835                 840                 845

Gln Pro Glu Asn Asn Tyr Lys Thr Thr Pro Pro Val Leu Asp Ser Asp
    850                 855                 860

Gly Ser Phe Phe Leu Tyr Ser Lys Leu Thr Val Asp Lys Ser Arg Trp
865                 870                 875                 880

Gln Gln Gly Asn Val Phe Ser Cys Ser Val Met His Glu Ala Leu His
                885                 890                 895

Asn His Tyr Thr Gln Lys Ser Leu Ser Leu Ser Pro Gly Lys
            900                 905                 910


<210> SEQ ID NO 29
<211> LENGTH: 2355
<212> TYPE: DNA
<213> ORGANISM: Homo sapiens
<220> FEATURE:
<221> NAME/KEY: CDS
<222> LOCATION: (1)...(2352)

<400> SEQUENCE: 29

atg gtg tgg ctt tgc tct ggg ctc ctg ttc cct gtg agc tgc ctg gtc       48
Met Val Trp Leu Cys Ser Gly Leu Leu Phe Pro Val Ser Cys Leu Val
 1               5                  10                  15

ctg ctg cag gtg gca agc tct ggg aac atg aag gtc ttg cag gag ccc       96
Leu Leu Gln Val Ala Ser Ser Gly Asn Met Lys Val Leu Gln Glu Pro
            20                  25                  30

acc tgc gtc tcc gac tac atg agc atc tct act tgc gag tgg aag atg      144
Thr Cys Val Ser Asp Tyr Met Ser Ile Ser Thr Cys Glu Trp Lys Met
        35                  40                  45
```

-continued

```
aat ggt ccc acc aat tgc agc acc gag ctc cgc ctg ttg tac cag ctg       192
Asn Gly Pro Thr Asn Cys Ser Thr Glu Leu Arg Leu Leu Tyr Gln Leu
     50                  55                  60

gtt ttt ctg ctc tcc gaa gcc cac acg tgt atc cct gag aac aac gga       240
Val Phe Leu Leu Ser Glu Ala His Thr Cys Ile Pro Glu Asn Asn Gly
 65                  70                  75                  80

ggc gcg ggg tgc gtg tgc cac ctg ctc atg gat gac gtg gtc agt gcg       288
Gly Ala Gly Cys Val Cys His Leu Leu Met Asp Asp Val Val Ser Ala
                 85                  90                  95

gat aac tat aca ctg gac ctg tgg gct ggg cag cag ctg ctg tgg aag       336
Asp Asn Tyr Thr Leu Asp Leu Trp Ala Gly Gln Gln Leu Leu Trp Lys
            100                 105                 110

ggc tcc ttc aag ccc agc gag cat gtg aaa ccc agg gcc cca gga aac       384
Gly Ser Phe Lys Pro Ser Glu His Val Lys Pro Arg Ala Pro Gly Asn
        115                 120                 125

ctg aca gtt cac acc aat gtc tcc gac act ctg ctg ctg acc tgg agc       432
Leu Thr Val His Thr Asn Val Ser Asp Thr Leu Leu Leu Thr Trp Ser
    130                 135                 140

aac ccg tat ccc cct gac aat tac ctg tat aat cat ctc acc tat gca       480
Asn Pro Tyr Pro Pro Asp Asn Tyr Leu Tyr Asn His Leu Thr Tyr Ala
145                 150                 155                 160

gtc aac att tgg agt gaa aac gac ccg gca gat ttc aga atc tat aac       528
Val Asn Ile Trp Ser Glu Asn Asp Pro Ala Asp Phe Arg Ile Tyr Asn
                165                 170                 175

gtg acc tac cta gaa ccc tcc ctc cgc atc gca gcc agc acc ctg aag       576
Val Thr Tyr Leu Glu Pro Ser Leu Arg Ile Ala Ala Ser Thr Leu Lys
            180                 185                 190

tct ggg att tcc tac agg gca cgg gtg agg gcc tgg gct cag agc tat       624
Ser Gly Ile Ser Tyr Arg Ala Arg Val Arg Ala Trp Ala Gln Ser Tyr
        195                 200                 205

aac acc acc tgg agt gag tgg agc ccc agc acc aag tgg cac aac tcc       672
Asn Thr Thr Trp Ser Glu Trp Ser Pro Ser Thr Lys Trp His Asn Ser
    210                 215                 220

tac agg gag ccc ttc gag cag tcc ggt ggg ggc ggg ggc gcc gcg cct       720
Tyr Arg Glu Pro Phe Glu Gln Ser Gly Gly Gly Gly Gly Ala Ala Pro
225                 230                 235                 240

acg gaa act cag cca cct gtg aca aat ttg agt gtc tct gtt gaa aac       768
Thr Glu Thr Gln Pro Pro Val Thr Asn Leu Ser Val Ser Val Glu Asn
                245                 250                 255

ctc tgc aca gta ata tgg aca tgg aat cca ccc gag gga gcc agc tca       816
Leu Cys Thr Val Ile Trp Thr Trp Asn Pro Pro Glu Gly Ala Ser Ser
            260                 265                 270

aat tgt agt cta tgg tat ttt agt cat ttt ggc gac aaa caa gat aag       864
Asn Cys Ser Leu Trp Tyr Phe Ser His Phe Gly Asp Lys Gln Asp Lys
        275                 280                 285

aaa ata gct ccg gaa act cgt cgt tca ata gaa gta ccc ctg aat gag       912
Lys Ile Ala Pro Glu Thr Arg Arg Ser Ile Glu Val Pro Leu Asn Glu
    290                 295                 300

agg att tgt ctg caa gtg ggg tcc cag tgt agc acc aat gag agt gag       960
Arg Ile Cys Leu Gln Val Gly Ser Gln Cys Ser Thr Asn Glu Ser Glu
305                 310                 315                 320

aag cct agc att ttg gtt gaa aaa tgc atc tca ccc cca gaa ggt gat      1008
Lys Pro Ser Ile Leu Val Glu Lys Cys Ile Ser Pro Pro Glu Gly Asp
                325                 330                 335

cct gag tct gct gtg act gag ctt caa tgc att tgg cac aac ctg agc      1056
Pro Glu Ser Ala Val Thr Glu Leu Gln Cys Ile Trp His Asn Leu Ser
            340                 345                 350

tac atg aag tgt tct tgg ctc cct gga agg aat acc agt ccc gac act      1104
Tyr Met Lys Cys Ser Trp Leu Pro Gly Arg Asn Thr Ser Pro Asp Thr
        355                 360                 365
```

-continued

```
aac tat act ctc tac tat tgg cac aga agc ctg gaa aaa att cat caa      1152
Asn Tyr Thr Leu Tyr Tyr Trp His Arg Ser Leu Glu Lys Ile His Gln
    370                 375                 380

tgt gaa aac atc ttt aga gaa ggc caa tac ttt ggt tgt tcc ttt gat      1200
Cys Glu Asn Ile Phe Arg Glu Gly Gln Tyr Phe Gly Cys Ser Phe Asp
385                 390                 395                 400

ctg acc aaa gtg aag gat tcc agt ttt gaa caa cac agt gtc caa ata      1248
Leu Thr Lys Val Lys Asp Ser Ser Phe Glu Gln His Ser Val Gln Ile
                405                 410                 415

atg gtc aag gat aat gca gga aaa att aaa cca tcc ttc aat ata gtg      1296
Met Val Lys Asp Asn Ala Gly Lys Ile Lys Pro Ser Phe Asn Ile Val
            420                 425                 430

cct tta act tcc cgt gtg aaa cct gat cct cca cat att aaa aac ctc      1344
Pro Leu Thr Ser Arg Val Lys Pro Asp Pro Pro His Ile Lys Asn Leu
        435                 440                 445

tcc ttc cac aat gat gac cta tat gtg caa tgg gag aat cca cag aat      1392
Ser Phe His Asn Asp Asp Leu Tyr Val Gln Trp Glu Asn Pro Gln Asn
    450                 455                 460

ttt att agc aga tgc cta ttt tat gaa gta gaa gtc aat aac agc caa      1440
Phe Ile Ser Arg Cys Leu Phe Tyr Glu Val Glu Val Asn Asn Ser Gln
465                 470                 475                 480

act gag aca cat aat gtt ttc tac gtc caa gag gct aaa tgt gag aat      1488
Thr Glu Thr His Asn Val Phe Tyr Val Gln Glu Ala Lys Cys Glu Asn
                485                 490                 495

cca gaa ttt gag aga aat gtg gag aat aca tct tgt ttc atg gtc cct      1536
Pro Glu Phe Glu Arg Asn Val Glu Asn Thr Ser Cys Phe Met Val Pro
            500                 505                 510

ggt gtt ctt cct gat act ttg aac aca gtc aga ata aga gtc aaa aca      1584
Gly Val Leu Pro Asp Thr Leu Asn Thr Val Arg Ile Arg Val Lys Thr
        515                 520                 525

aat aag tta tgc tat gag gat gac aaa ctc tgg agt aat tgg agc caa      1632
Asn Lys Leu Cys Tyr Glu Asp Asp Lys Leu Trp Ser Asn Trp Ser Gln
    530                 535                 540

gaa atg agt ata ggt aag aag cgc aat tcc aca acc gga gac aaa act      1680
Glu Met Ser Ile Gly Lys Lys Arg Asn Ser Thr Thr Gly Asp Lys Thr
545                 550                 555                 560

cac aca tgc cca ccg tgc cca gca cct gaa ctc ctg ggg gga ccg tca      1728
His Thr Cys Pro Pro Cys Pro Ala Pro Glu Leu Leu Gly Gly Pro Ser
                565                 570                 575

gtc ttc ctc ttc ccc cca aaa ccc aag gac acc ctc atg atc tcc cgg      1776
Val Phe Leu Phe Pro Pro Lys Pro Lys Asp Thr Leu Met Ile Ser Arg
            580                 585                 590

acc cct gag gtc aca tgc gtg gtg gtg gac gtg agc cac gaa gac cct      1824
Thr Pro Glu Val Thr Cys Val Val Val Asp Val Ser His Glu Asp Pro
        595                 600                 605

gag gtc aag ttc aac tgg tac gtg gac ggc gtg gag gtg cat aat gcc      1872
Glu Val Lys Phe Asn Trp Tyr Val Asp Gly Val Glu Val His Asn Ala
    610                 615                 620

aag aca aag ccg cgg gag gag cag tac aac agc acg tac cgt gtg gtc      1920
Lys Thr Lys Pro Arg Glu Glu Gln Tyr Asn Ser Thr Tyr Arg Val Val
625                 630                 635                 640

agc gtc ctc acc gtc ctg cac cag gac tgg ctg aat ggc aag gag tac      1968
Ser Val Leu Thr Val Leu His Gln Asp Trp Leu Asn Gly Lys Glu Tyr
                645                 650                 655

aag tgc aag gtc tcc aac aaa gcc ctc cca gcc ccc atc gag aaa acc      2016
Lys Cys Lys Val Ser Asn Lys Ala Leu Pro Ala Pro Ile Glu Lys Thr
            660                 665                 670

atc tcc aaa gcc aaa ggg cag ccc cga gaa cca cag gtg tac acc ctg      2064
Ile Ser Lys Ala Lys Gly Gln Pro Arg Glu Pro Gln Val Tyr Thr Leu
        675                 680                 685
```

```
ccc cca tcc cgg gag gag atg acc aag aac cag gtc agc ctg acc tgc      2112
Pro Pro Ser Arg Glu Glu Met Thr Lys Asn Gln Val Ser Leu Thr Cys
    690                 695                 700

ctg gtc aaa ggc ttc tat ccc agc gac atc gcc gtg gag tgg gag agc      2160
Leu Val Lys Gly Phe Tyr Pro Ser Asp Ile Ala Val Glu Trp Glu Ser
705                 710                 715                 720

aat ggg cag ccg gag aac aac tac aag acc acg cct ccc gtg ctg gac      2208
Asn Gly Gln Pro Glu Asn Asn Tyr Lys Thr Thr Pro Pro Val Leu Asp
                725                 730                 735

tcc gac ggc tcc ttc ttc ctc tat agc aag ctc acc gtg gac aag agc      2256
Ser Asp Gly Ser Phe Phe Leu Tyr Ser Lys Leu Thr Val Asp Lys Ser
            740                 745                 750

agg tgg cag cag ggg aac gtc ttc tca tgc tcc gtg atg cat gag gct      2304
Arg Trp Gln Gln Gly Asn Val Phe Ser Cys Ser Val Met His Glu Ala
        755                 760                 765

ctg cac aac cac tac acg cag aag agc ctc tcc ctg tct ccg ggt aaa      2352
Leu His Asn His Tyr Thr Gln Lys Ser Leu Ser Leu Ser Pro Gly Lys
    770                 775                 780

tga                                                                  2355


<210> SEQ ID NO 30
<211> LENGTH: 784
<212> TYPE: PRT
<213> ORGANISM: Homo sapiens

<400> SEQUENCE: 30

Met Val Trp Leu Cys Ser Gly Leu Leu Phe Pro Val Ser Cys Leu Val
 1               5                  10                  15

Leu Leu Gln Val Ala Ser Ser Gly Asn Met Lys Val Leu Gln Glu Pro
            20                  25                  30

Thr Cys Val Ser Asp Tyr Met Ser Ile Ser Thr Cys Glu Trp Lys Met
        35                  40                  45

Asn Gly Pro Thr Asn Cys Ser Thr Glu Leu Arg Leu Leu Tyr Gln Leu
    50                  55                  60

Val Phe Leu Leu Ser Glu Ala His Thr Cys Ile Pro Glu Asn Asn Gly
65                  70                  75                  80

Gly Ala Gly Cys Val Cys His Leu Leu Met Asp Asp Val Val Ser Ala
                85                  90                  95

Asp Asn Tyr Thr Leu Asp Leu Trp Ala Gly Gln Gln Leu Leu Trp Lys
            100                 105                 110

Gly Ser Phe Lys Pro Ser Glu His Val Lys Pro Arg Ala Pro Gly Asn
        115                 120                 125

Leu Thr Val His Thr Asn Val Ser Asp Thr Leu Leu Leu Thr Trp Ser
    130                 135                 140

Asn Pro Tyr Pro Pro Asp Asn Tyr Leu Tyr Asn His Leu Thr Tyr Ala
145                 150                 155                 160

Val Asn Ile Trp Ser Glu Asn Asp Pro Ala Asp Phe Arg Ile Tyr Asn
                165                 170                 175

Val Thr Tyr Leu Glu Pro Ser Leu Arg Ile Ala Ala Ser Thr Leu Lys
            180                 185                 190

Ser Gly Ile Ser Tyr Arg Ala Arg Val Arg Ala Trp Ala Gln Ser Tyr
        195                 200                 205

Asn Thr Thr Trp Ser Glu Trp Ser Pro Ser Thr Lys Trp His Asn Ser
    210                 215                 220

Tyr Arg Glu Pro Phe Glu Gln Ser Gly Gly Gly Gly Gly Ala Ala Pro
225                 230                 235                 240

Thr Glu Thr Gln Pro Pro Val Thr Asn Leu Ser Val Ser Val Glu Asn
```

-continued

```
                245                 250                 255

Leu Cys Thr Val Ile Trp Thr Trp Asn Pro Pro Glu Gly Ala Ser Ser
            260                 265                 270

Asn Cys Ser Leu Trp Tyr Phe Ser His Phe Gly Asp Lys Gln Asp Lys
        275                 280                 285

Lys Ile Ala Pro Glu Thr Arg Arg Ser Ile Glu Val Pro Leu Asn Glu
    290                 295                 300

Arg Ile Cys Leu Gln Val Gly Ser Gln Cys Ser Thr Asn Glu Ser Glu
305                 310                 315                 320

Lys Pro Ser Ile Leu Val Glu Lys Cys Ile Ser Pro Pro Glu Gly Asp
                325                 330                 335

Pro Glu Ser Ala Val Thr Glu Leu Gln Cys Ile Trp His Asn Leu Ser
            340                 345                 350

Tyr Met Lys Cys Ser Trp Leu Pro Gly Arg Asn Thr Ser Pro Asp Thr
        355                 360                 365

Asn Tyr Thr Leu Tyr Tyr Trp His Arg Ser Leu Glu Lys Ile His Gln
    370                 375                 380

Cys Glu Asn Ile Phe Arg Glu Gly Gln Tyr Phe Gly Cys Ser Phe Asp
385                 390                 395                 400

Leu Thr Lys Val Lys Asp Ser Ser Phe Glu Gln His Ser Val Gln Ile
                405                 410                 415

Met Val Lys Asp Asn Ala Gly Lys Ile Lys Pro Ser Phe Asn Ile Val
            420                 425                 430

Pro Leu Thr Ser Arg Val Lys Pro Asp Pro Pro His Ile Lys Asn Leu
        435                 440                 445

Ser Phe His Asn Asp Asp Leu Tyr Val Gln Trp Glu Asn Pro Gln Asn
    450                 455                 460

Phe Ile Ser Arg Cys Leu Phe Tyr Glu Val Glu Val Asn Asn Ser Gln
465                 470                 475                 480

Thr Glu Thr His Asn Val Phe Tyr Val Gln Glu Ala Lys Cys Glu Asn
                485                 490                 495

Pro Glu Phe Glu Arg Asn Val Glu Asn Thr Ser Cys Phe Met Val Pro
            500                 505                 510

Gly Val Leu Pro Asp Thr Leu Asn Thr Val Arg Ile Arg Val Lys Thr
        515                 520                 525

Asn Lys Leu Cys Tyr Glu Asp Asp Lys Leu Trp Ser Asn Trp Ser Gln
    530                 535                 540

Glu Met Ser Ile Gly Lys Lys Arg Asn Ser Thr Thr Gly Asp Lys Thr
545                 550                 555                 560

His Thr Cys Pro Pro Cys Pro Ala Pro Glu Leu Leu Gly Gly Pro Ser
                565                 570                 575

Val Phe Leu Phe Pro Pro Lys Pro Lys Asp Thr Leu Met Ile Ser Arg
            580                 585                 590

Thr Pro Glu Val Thr Cys Val Val Val Asp Val Ser His Glu Asp Pro
        595                 600                 605

Glu Val Lys Phe Asn Trp Tyr Val Asp Gly Val Glu Val His Asn Ala
    610                 615                 620

Lys Thr Lys Pro Arg Glu Glu Gln Tyr Asn Ser Thr Tyr Arg Val Val
625                 630                 635                 640

Ser Val Leu Thr Val Leu His Gln Asp Trp Leu Asn Gly Lys Glu Tyr
                645                 650                 655

Lys Cys Lys Val Ser Asn Lys Ala Leu Pro Ala Pro Ile Glu Lys Thr
            660                 665                 670
```

```
Ile Ser Lys Ala Lys Gly Gln Pro Arg Glu Pro Gln Val Tyr Thr Leu
        675                 680                 685

Pro Pro Ser Arg Glu Glu Met Thr Lys Asn Gln Val Ser Leu Thr Cys
    690                 695                 700

Leu Val Lys Gly Phe Tyr Pro Ser Asp Ile Ala Val Glu Trp Glu Ser
705                 710                 715                 720

Asn Gly Gln Pro Glu Asn Asn Tyr Lys Thr Thr Pro Pro Val Leu Asp
                725                 730                 735

Ser Asp Gly Ser Phe Phe Leu Tyr Ser Lys Leu Thr Val Asp Lys Ser
            740                 745                 750

Arg Trp Gln Gln Gly Asn Val Phe Ser Cys Ser Val Met His Glu Ala
        755                 760                 765

Leu His Asn His Tyr Thr Gln Lys Ser Leu Ser Leu Ser Pro Gly Lys
    770                 775                 780


<210> SEQ ID NO 31
<211> LENGTH: 2382
<212> TYPE: DNA
<213> ORGANISM: Homo sapiens
<220> FEATURE:
<221> NAME/KEY: CDS
<222> LOCATION: (1)...(2379)

<400> SEQUENCE: 31

atg gtg tgg ccg gcg cgg ctc tgc ggg ctg tgg gcg ctg ctg ctc tgc       48
Met Val Trp Pro Ala Arg Leu Cys Gly Leu Trp Ala Leu Leu Leu Cys
 1               5                  10                  15

gcc ggc ggc ggg ggc ggg ggc ggg ggc gcc gcg cct acg gaa act cag       96
Ala Gly Gly Gly Gly Gly Gly Gly Gly Ala Ala Pro Thr Glu Thr Gln
            20                  25                  30

cca cct gtg aca aat ttg agt gtc tct gtt gaa aac ctc tgc aca gta      144
Pro Pro Val Thr Asn Leu Ser Val Ser Val Glu Asn Leu Cys Thr Val
        35                  40                  45

ata tgg aca tgg aat cca ccc gag gga gcc agc tca aat tgt agt cta      192
Ile Trp Thr Trp Asn Pro Pro Glu Gly Ala Ser Ser Asn Cys Ser Leu
    50                  55                  60

tgg tat ttt agt cat ttt ggc gac aaa caa gat aag aaa ata gct ccg      240
Trp Tyr Phe Ser His Phe Gly Asp Lys Gln Asp Lys Lys Ile Ala Pro
 65                  70                  75                  80

gaa act cgt cgt tca ata gaa gta ccc ctg aat gag agg att tgt ctg      288
Glu Thr Arg Arg Ser Ile Glu Val Pro Leu Asn Glu Arg Ile Cys Leu
                85                  90                  95

caa gtg ggg tcc cag tgt agc acc aat gag agt gag aag cct agc att      336
Gln Val Gly Ser Gln Cys Ser Thr Asn Glu Ser Glu Lys Pro Ser Ile
            100                 105                 110

ttg gtt gaa aaa tgc atc tca ccc cca gaa ggt gat cct gag tct gct      384
Leu Val Glu Lys Cys Ile Ser Pro Pro Glu Gly Asp Pro Glu Ser Ala
        115                 120                 125

gtg act gag ctt caa tgc att tgg cac aac ctg agc tac atg aag tgt      432
Val Thr Glu Leu Gln Cys Ile Trp His Asn Leu Ser Tyr Met Lys Cys
    130                 135                 140

tct tgg ctc cct gga agg aat acc agt ccc gac act aac tat act ctc      480
Ser Trp Leu Pro Gly Arg Asn Thr Ser Pro Asp Thr Asn Tyr Thr Leu
145                 150                 155                 160

tac tat tgg cac aga agc ctg gaa aaa att cat caa tgt gaa aac atc      528
Tyr Tyr Trp His Arg Ser Leu Glu Lys Ile His Gln Cys Glu Asn Ile
                165                 170                 175

ttt aga gaa ggc caa tac ttt ggt tgt tcc ttt gat ctg acc aaa gtg      576
Phe Arg Glu Gly Gln Tyr Phe Gly Cys Ser Phe Asp Leu Thr Lys Val
            180                 185                 190
```

-continued

```
aag gat tcc agt ttt gaa caa cac agt gtc caa ata atg gtc aag gat      624
Lys Asp Ser Ser Phe Glu Gln His Ser Val Gln Ile Met Val Lys Asp
        195                 200                 205

aat gca gga aaa att aaa cca tcc ttc aat ata gtg cct tta act tcc      672
Asn Ala Gly Lys Ile Lys Pro Ser Phe Asn Ile Val Pro Leu Thr Ser
    210                 215                 220

cgt gtg aaa cct gat cct cca cat att aaa aac ctc tcc ttc cac aat      720
Arg Val Lys Pro Asp Pro Pro His Ile Lys Asn Leu Ser Phe His Asn
225                 230                 235                 240

gat gac cta tat gtg caa tgg gag aat cca cag aat ttt att agc aga      768
Asp Asp Leu Tyr Val Gln Trp Glu Asn Pro Gln Asn Phe Ile Ser Arg
                245                 250                 255

tgc cta ttt tat gaa gta gaa gtc aat aac agc caa act gag aca cat      816
Cys Leu Phe Tyr Glu Val Glu Val Asn Asn Ser Gln Thr Glu Thr His
            260                 265                 270

aat gtt ttc tac gtc caa gag gct aaa tgt gag aat cca gaa ttt gag      864
Asn Val Phe Tyr Val Gln Glu Ala Lys Cys Glu Asn Pro Glu Phe Glu
        275                 280                 285

aga aat gtg gag aat aca tct tgt ttc atg gtc cct ggt gtt ctt cct      912
Arg Asn Val Glu Asn Thr Ser Cys Phe Met Val Pro Gly Val Leu Pro
    290                 295                 300

gat act ttg aac aca gtc aga ata aga gtc aaa aca aat aag tta tgc      960
Asp Thr Leu Asn Thr Val Arg Ile Arg Val Lys Thr Asn Lys Leu Cys
305                 310                 315                 320

tat gag gat gac aaa ctc tgg agt aat tgg agc caa gaa atg agt ata     1008
Tyr Glu Asp Asp Lys Leu Trp Ser Asn Trp Ser Gln Glu Met Ser Ile
                325                 330                 335

ggt aag aag cgc aat tcc aca ggc gcg cct agt ggt gga ggt ggc cgg     1056
Gly Lys Lys Arg Asn Ser Thr Gly Ala Pro Ser Gly Gly Gly Gly Arg
            340                 345                 350

ccc gca agc tct ggg aac atg aag gtc ttg cag gag ccc acc tgc gtc     1104
Pro Ala Ser Ser Gly Asn Met Lys Val Leu Gln Glu Pro Thr Cys Val
        355                 360                 365

tcc gac tac atg agc atc tct act tgc gag tgg aag atg aat ggt ccc     1152
Ser Asp Tyr Met Ser Ile Ser Thr Cys Glu Trp Lys Met Asn Gly Pro
    370                 375                 380

acc aat tgc agc acc gag ctc cgc ctg ttg tac cag ctg gtt ttt ctg     1200
Thr Asn Cys Ser Thr Glu Leu Arg Leu Leu Tyr Gln Leu Val Phe Leu
385                 390                 395                 400

ctc tcc gaa gcc cac acg tgt atc cct gag aac aac gga ggc gcg ggg     1248
Leu Ser Glu Ala His Thr Cys Ile Pro Glu Asn Asn Gly Gly Ala Gly
                405                 410                 415

tgc gtg tgc cac ctg ctc atg gat gac gtg gtc agt gcg gat aac tat     1296
Cys Val Cys His Leu Leu Met Asp Asp Val Val Ser Ala Asp Asn Tyr
            420                 425                 430

aca ctg gac ctg tgg gct ggg cag cag ctg ctg tgg aag ggc tcc ttc     1344
Thr Leu Asp Leu Trp Ala Gly Gln Gln Leu Leu Trp Lys Gly Ser Phe
        435                 440                 445

aag ccc agc gag cat gtg aaa ccc agg gcc cca gga aac ctg aca gtt     1392
Lys Pro Ser Glu His Val Lys Pro Arg Ala Pro Gly Asn Leu Thr Val
    450                 455                 460

cac acc aat gtc tcc gac act ctg ctg ctg acc tgg agc aac ccg tat     1440
His Thr Asn Val Ser Asp Thr Leu Leu Leu Thr Trp Ser Asn Pro Tyr
465                 470                 475                 480

ccc cct gac aat tac ctg tat aat cat ctc acc tat gca gtc aac att     1488
Pro Pro Asp Asn Tyr Leu Tyr Asn His Leu Thr Tyr Ala Val Asn Ile
                485                 490                 495

tgg agt gaa aac gac ccg gca gat ttc aga atc tat aac gtg acc tac     1536
Trp Ser Glu Asn Asp Pro Ala Asp Phe Arg Ile Tyr Asn Val Thr Tyr
            500                 505                 510
```

```
cta gaa ccc tcc ctc cgc atc gca gcc agc acc ctg aag tct ggg att      1584
Leu Glu Pro Ser Leu Arg Ile Ala Ala Ser Thr Leu Lys Ser Gly Ile
        515                 520                 525

tcc tac agg gca cgg gtg agg gcc tgg gct cag tgc tat aac acc acc      1632
Ser Tyr Arg Ala Arg Val Arg Ala Trp Ala Gln Cys Tyr Asn Thr Thr
    530                 535                 540

tgg agt gag tgg agc ccc agc acc aag tgg cac aac tcc tac agg gag      1680
Trp Ser Glu Trp Ser Pro Ser Thr Lys Trp His Asn Ser Tyr Arg Glu
545                 550                 555                 560

ccc ttc gag cag tcc gga gac aaa act cac aca tgc cca ccg tgc cca      1728
Pro Phe Glu Gln Ser Gly Asp Lys Thr His Thr Cys Pro Pro Cys Pro
                565                 570                 575

gca cct gaa ctc ctg ggg gga ccg tca gtc ttc ctc ttc ccc cca aaa      1776
Ala Pro Glu Leu Leu Gly Gly Pro Ser Val Phe Leu Phe Pro Pro Lys
            580                 585                 590

ccc aag gac acc ctc atg atc tcc cgg acc cct gag gtc aca tgc gtg      1824
Pro Lys Asp Thr Leu Met Ile Ser Arg Thr Pro Glu Val Thr Cys Val
        595                 600                 605

gtg gtg gac gtg agc cac gaa gac cct gag gtc aag ttc aac tgg tac      1872
Val Val Asp Val Ser His Glu Asp Pro Glu Val Lys Phe Asn Trp Tyr
    610                 615                 620

gtg gac ggc gtg gag gtg cat aat gcc aag aca aag ccg cgg gag gag      1920
Val Asp Gly Val Glu Val His Asn Ala Lys Thr Lys Pro Arg Glu Glu
625                 630                 635                 640

cag tac aac agc acg tac cgt gtg gtc agc gtc ctc acc gtc ctg cac      1968
Gln Tyr Asn Ser Thr Tyr Arg Val Val Ser Val Leu Thr Val Leu His
                645                 650                 655

cag gac tgg ctg aat ggc aag gag tac aag tgc aag gtc tcc aac aaa      2016
Gln Asp Trp Leu Asn Gly Lys Glu Tyr Lys Cys Lys Val Ser Asn Lys
            660                 665                 670

gcc ctc cca gcc ccc atc gag aaa acc atc tcc aaa gcc aaa ggg cag      2064
Ala Leu Pro Ala Pro Ile Glu Lys Thr Ile Ser Lys Ala Lys Gly Gln
        675                 680                 685

ccc cga gaa cca cag gtg tac acc ctg ccc cca tcc cgg gag gag atg      2112
Pro Arg Glu Pro Gln Val Tyr Thr Leu Pro Pro Ser Arg Glu Glu Met
    690                 695                 700

acc aag aac cag gtc agc ctg acc tgc ctg gtc aaa ggc ttc tat ccc      2160
Thr Lys Asn Gln Val Ser Leu Thr Cys Leu Val Lys Gly Phe Tyr Pro
705                 710                 715                 720

agc gac atc gcc gtg gag tgg gag agc aat ggg cag ccg gag aac aac      2208
Ser Asp Ile Ala Val Glu Trp Glu Ser Asn Gly Gln Pro Glu Asn Asn
                725                 730                 735

tac aag acc acg cct ccc gtg ctg gac tcc gac ggc tcc ttc ttc ctc      2256
Tyr Lys Thr Thr Pro Pro Val Leu Asp Ser Asp Gly Ser Phe Phe Leu
            740                 745                 750

tat agc aag ctc acc gtg gac aag agc agg tgg cag cag ggg aac gtc      2304
Tyr Ser Lys Leu Thr Val Asp Lys Ser Arg Trp Gln Gln Gly Asn Val
        755                 760                 765

ttc tca tgc tcc gtg atg cat gag gct ctg cac aac cac tac acg cag      2352
Phe Ser Cys Ser Val Met His Glu Ala Leu His Asn His Tyr Thr Gln
    770                 775                 780

aag agc ctc tcc ctg tct ccg ggt aaa tga                              2382
Lys Ser Leu Ser Leu Ser Pro Gly Lys
785                 790
```

<210> SEQ ID NO 32
<211> LENGTH: 793
<212> TYPE: PRT
<213> ORGANISM: Homo sapiens

<400> SEQUENCE: 32

-continued

```
Met Val Trp Pro Ala Arg Leu Cys Gly Leu Trp Ala Leu Leu Leu Cys
 1               5                  10                  15

Ala Gly Gly Gly Gly Gly Gly Gly Gly Ala Ala Pro Thr Glu Thr Gln
            20                  25                  30

Pro Pro Val Thr Asn Leu Ser Val Ser Val Glu Asn Leu Cys Thr Val
        35                  40                  45

Ile Trp Thr Trp Asn Pro Pro Glu Gly Ala Ser Ser Asn Cys Ser Leu
    50                  55                  60

Trp Tyr Phe Ser His Phe Gly Asp Lys Gln Asp Lys Lys Ile Ala Pro
65                  70                  75                  80

Glu Thr Arg Arg Ser Ile Glu Val Pro Leu Asn Glu Arg Ile Cys Leu
                85                  90                  95

Gln Val Gly Ser Gln Cys Ser Thr Asn Glu Ser Glu Lys Pro Ser Ile
            100                 105                 110

Leu Val Glu Lys Cys Ile Ser Pro Pro Glu Gly Asp Pro Glu Ser Ala
        115                 120                 125

Val Thr Glu Leu Gln Cys Ile Trp His Asn Leu Ser Tyr Met Lys Cys
    130                 135                 140

Ser Trp Leu Pro Gly Arg Asn Thr Ser Pro Asp Thr Asn Tyr Thr Leu
145                 150                 155                 160

Tyr Tyr Trp His Arg Ser Leu Glu Lys Ile His Gln Cys Glu Asn Ile
                165                 170                 175

Phe Arg Glu Gly Gln Tyr Phe Gly Cys Ser Phe Asp Leu Thr Lys Val
            180                 185                 190

Lys Asp Ser Ser Phe Glu Gln His Ser Val Gln Ile Met Val Lys Asp
        195                 200                 205

Asn Ala Gly Lys Ile Lys Pro Ser Phe Asn Ile Val Pro Leu Thr Ser
    210                 215                 220

Arg Val Lys Pro Asp Pro Pro His Ile Lys Asn Leu Ser Phe His Asn
225                 230                 235                 240

Asp Asp Leu Tyr Val Gln Trp Glu Asn Pro Gln Asn Phe Ile Ser Arg
                245                 250                 255

Cys Leu Phe Tyr Glu Val Glu Val Asn Asn Ser Gln Thr Glu Thr His
            260                 265                 270

Asn Val Phe Tyr Val Gln Glu Ala Lys Cys Glu Asn Pro Glu Phe Glu
        275                 280                 285

Arg Asn Val Glu Asn Thr Ser Cys Phe Met Val Pro Gly Val Leu Pro
    290                 295                 300

Asp Thr Leu Asn Thr Val Arg Ile Arg Val Lys Thr Asn Lys Leu Cys
305                 310                 315                 320

Tyr Glu Asp Asp Lys Leu Trp Ser Asn Trp Ser Gln Glu Met Ser Ile
                325                 330                 335

Gly Lys Lys Arg Asn Ser Thr Gly Ala Pro Ser Gly Gly Gly Gly Arg
            340                 345                 350

Pro Ala Ser Ser Gly Asn Met Lys Val Leu Gln Glu Pro Thr Cys Val
        355                 360                 365

Ser Asp Tyr Met Ser Ile Ser Thr Cys Glu Trp Lys Met Asn Gly Pro
    370                 375                 380

Thr Asn Cys Ser Thr Glu Leu Arg Leu Leu Tyr Gln Leu Val Phe Leu
385                 390                 395                 400

Leu Ser Glu Ala His Thr Cys Ile Pro Glu Asn Asn Gly Gly Ala Gly
                405                 410                 415

Cys Val Cys His Leu Leu Met Asp Asp Val Val Ser Ala Asp Asn Tyr
            420                 425                 430
```

```
Thr Leu Asp Leu Trp Ala Gly Gln Gln Leu Leu Trp Lys Gly Ser Phe
        435                 440                 445

Lys Pro Ser Glu His Val Lys Pro Arg Ala Pro Gly Asn Leu Thr Val
    450                 455                 460

His Thr Asn Val Ser Asp Thr Leu Leu Leu Thr Trp Ser Asn Pro Tyr
465                 470                 475                 480

Pro Pro Asp Asn Tyr Leu Tyr Asn His Leu Thr Tyr Ala Val Asn Ile
                485                 490                 495

Trp Ser Glu Asn Asp Pro Ala Asp Phe Arg Ile Tyr Asn Val Thr Tyr
            500                 505                 510

Leu Glu Pro Ser Leu Arg Ile Ala Ala Ser Thr Leu Lys Ser Gly Ile
        515                 520                 525

Ser Tyr Arg Ala Arg Val Arg Ala Trp Ala Gln Cys Tyr Asn Thr Thr
    530                 535                 540

Trp Ser Glu Trp Ser Pro Ser Thr Lys Trp His Asn Ser Tyr Arg Glu
545                 550                 555                 560

Pro Phe Glu Gln Ser Gly Asp Lys Thr His Thr Cys Pro Pro Cys Pro
                565                 570                 575

Ala Pro Glu Leu Leu Gly Gly Pro Ser Val Phe Leu Phe Pro Pro Lys
            580                 585                 590

Pro Lys Asp Thr Leu Met Ile Ser Arg Thr Pro Glu Val Thr Cys Val
        595                 600                 605

Val Val Asp Val Ser His Glu Asp Pro Glu Val Lys Phe Asn Trp Tyr
    610                 615                 620

Val Asp Gly Val Glu Val His Asn Ala Lys Thr Lys Pro Arg Glu Glu
625                 630                 635                 640

Gln Tyr Asn Ser Thr Tyr Arg Val Val Ser Val Leu Thr Val Leu His
                645                 650                 655

Gln Asp Trp Leu Asn Gly Lys Glu Tyr Lys Cys Lys Val Ser Asn Lys
            660                 665                 670

Ala Leu Pro Ala Pro Ile Glu Lys Thr Ile Ser Lys Ala Lys Gly Gln
        675                 680                 685

Pro Arg Glu Pro Gln Val Tyr Thr Leu Pro Pro Ser Arg Glu Glu Met
    690                 695                 700

Thr Lys Asn Gln Val Ser Leu Thr Cys Leu Val Lys Gly Phe Tyr Pro
705                 710                 715                 720

Ser Asp Ile Ala Val Glu Trp Glu Ser Asn Gly Gln Pro Glu Asn Asn
                725                 730                 735

Tyr Lys Thr Thr Pro Pro Val Leu Asp Ser Asp Gly Ser Phe Phe Leu
            740                 745                 750

Tyr Ser Lys Leu Thr Val Asp Lys Ser Arg Trp Gln Gln Gly Asn Val
        755                 760                 765

Phe Ser Cys Ser Val Met His Glu Ala Leu His Asn His Tyr Thr Gln
    770                 775                 780

Lys Ser Leu Ser Leu Ser Pro Gly Lys
785                 790
```

<210> SEQ ID NO 33
<211> LENGTH: 2703
<212> TYPE: DNA
<213> ORGANISM: Homo sapiens

<400> SEQUENCE: 33

```
atggtgttac tcagacttat ttgtttcata gctctactga tttcttctct ggaggctgat      60
```

-continued

```
aaatgcaagg aacgtgaaga aaaaataatt ttagtgtcat ctgcaaatga aattgatgtt    120
cgtccctgtc ctcttaaccc aaatgaacac aaaggcacta taacttggta taaggatgac    180
agcaagacac ctgtatctac agaacaagcc tccaggattc atcaacacaa agagaaactt    240
tggtttgttc ctgctaaggt ggaggattca ggacattact attgcgtggt aagaaattca    300
tcttactgcc tcagaattaa aataagtgca aaatttgtgg agaatgagcc taacttatgt    360
tataatgcac aagccatatt taagcagaaa ctacccgttg caggagacgg aggacttgtg    420
tgcccttata tggagttttt taaaaatgaa aataatgagt tacctaaatt acagtggtat    480
aaggattgca aacctctact tcttgacaat atacacttta gtggagtcaa agataggctc    540
atcgtgatga atgtggctga aaagcataga gggaactata cttgtcatgc atcctacaca    600
tacttgggca agcaatatcc tattacccgg gtaatagaat ttattactct agaggaaaac    660
aaacccacaa ggcctgtgat tgtgagccca gctaatgaga caatggaagt agacttggga    720
tcccagatac aattgatctg taatgtcacc ggccagttga gtgacattgc ttactggaag    780
tggaatgggt cagtaattga tgaagatgac ccagtgctag gggaagacta ttacagtgtg    840
gaaaatcctg caaacaaaag aaggagtacc ctcatcacag tgcttaatat atcggaaatt    900
gagagtagat tttataaaca tccatttacc tgttttgcca agaatacaca tggtatagat    960
gcagcatata tccagttaat atatccagtc actaattcag aacgctgcga tgactgggga   1020
ctagacacca tgaggcaaat ccaagtgttt gaagatgagc cagctcgcat caagtgccca   1080
ctctttgaac acttcttgaa attcaactac agcacagccc attcagctgg ccttactctg   1140
atctggtatt ggactaggca ggaccgggac cttgaggagc caattaactt ccgcctcccc   1200
gagaaccgca ttagtaagga gaaagatgtg ctgtggttcc ggcccactct cctcaatgac   1260
actggcaact atacctgcat gttaaggaac actacatatt gcagcaaagt tgcatttccc   1320
ttggaagttg ttcaaaaaga cagctgtttc aattccccca tgaaactccc agtgcataaa   1380
ctgtatatag aatatggcat tcagaggatc acttgtccaa atgtagatgg atattttcct   1440
tccagtgtca aaccgactat cacttggtat atgggctgtt ataaaataca gaattttaat   1500
aatgtaatac ccgaaggtat gaacttgagt ttcctcattg ccttaatttc aaataatgga   1560
aattacacat gtgttgttac atatccagaa aatggacgta cgtttcatct caccaggact   1620
ctgactgtaa aggtagtagg ctctccaaaa aatgcagtgc cccctgtgat ccattcacct   1680
aatgatcatg tggtctatga gaaagaacca ggagaggagc tactcattcc ctgtacggtc   1740
tattttagtt ttctgatgga ttctcgcaat gaggtttggt ggaccattga tggaaaaaaa   1800
cctgatgaca tcactattga tgtcaccatt aacgaaagta taagtcatag tagaacagaa   1860
gatgaaacaa gaactcagat tttgagcatc aagaaagtta cctctgagga tctcaagcgc   1920
agctatgtct gtcatgctag aagtgccaaa ggcgaagttg ccaaagcagc caaggtgaag   1980
cagaaagtgc cagctccaag atacacagtg gaatccggag acaaaactca cacatgccca   2040
ccgtgcccag cacctgaact cctgggggga ccgtcagtct tcctcttccc cccaaaaccc   2100
aaggacaccc tcatgatctc ccggacccct gaggtcacat gcgtggtggt ggacgtgagc   2160
cacgaagacc ctgaggtcaa gttcaactgg tacgtggacg gcgtggaggt gcataatgcc   2220
aagacaaagc cgcgggagga gcagtacaac agcacgtacc gtgtggtcag cgtcctcacc   2280
gtcctgcacc aggactggct gaatggcaag gagtacaagt gcaaggtctc caacaaagcc   2340
ctcccagccc ccatcgagaa aaccatctcc aaagccaaag ggcagccccg agaaccacag   2400
gtgtacaccc tgcccccatc ccgggaggag atgaccaaga accaggtcag cctgacctgc   2460
```

```
ctggtcaaag gcttctatcc cagcgacatc gccgtggagt gggagagcaa tgggcagccg   2520

gagaacaact acaagaccac gcctcccgtg ctggactccg acggctcctt cttcctctat   2580

agcaagctca ccgtggacaa gagcaggtgg cagcagggga acgtcttctc atgctccgtg   2640

atgcatgagg ctctgcacaa ccactacacg cagaagagcc tctccctgtc tccgggtaaa   2700

tga                                                                 2703


<210> SEQ ID NO 34
<211> LENGTH: 900
<212> TYPE: PRT
<213> ORGANISM: Homo sapiens

<400> SEQUENCE: 34

Met Val Leu Leu Arg Leu Ile Cys Phe Ile Ala Leu Leu Ile Ser Ser
1               5                   10                  15

Leu Glu Ala Asp Lys Cys Lys Glu Arg Glu Glu Lys Ile Ile Leu Val
            20                  25                  30

Ser Ser Ala Asn Glu Ile Asp Val Arg Pro Cys Pro Leu Asn Pro Asn
        35                  40                  45

Glu His Lys Gly Thr Ile Thr Trp Tyr Lys Asp Asp Ser Lys Thr Pro
    50                  55                  60

Val Ser Thr Glu Gln Ala Ser Arg Ile His Gln His Lys Glu Lys Leu
65                  70                  75                  80

Trp Phe Val Pro Ala Lys Val Glu Asp Ser Gly His Tyr Tyr Cys Val
                85                  90                  95

Val Arg Asn Ser Ser Tyr Cys Leu Arg Ile Lys Ile Ser Ala Lys Phe
            100                 105                 110

Val Glu Asn Glu Pro Asn Leu Cys Tyr Asn Ala Gln Ala Ile Phe Lys
        115                 120                 125

Gln Lys Leu Pro Val Ala Gly Asp Gly Gly Leu Val Cys Pro Tyr Met
    130                 135                 140

Glu Phe Phe Lys Asn Glu Asn Asn Glu Leu Pro Lys Leu Gln Trp Tyr
145                 150                 155                 160

Lys Asp Cys Lys Pro Leu Leu Leu Asp Asn Ile His Phe Ser Gly Val
                165                 170                 175

Lys Asp Arg Leu Ile Val Met Asn Val Ala Glu Lys His Arg Gly Asn
            180                 185                 190

Tyr Thr Cys His Ala Ser Tyr Thr Tyr Leu Gly Lys Gln Tyr Pro Ile
        195                 200                 205

Thr Arg Val Ile Glu Phe Ile Thr Leu Glu Glu Asn Lys Pro Thr Arg
    210                 215                 220

Pro Val Ile Val Ser Pro Ala Asn Glu Thr Met Glu Val Asp Leu Gly
225                 230                 235                 240

Ser Gln Ile Gln Leu Ile Cys Asn Val Thr Gly Gln Leu Ser Asp Ile
                245                 250                 255

Ala Tyr Trp Lys Trp Asn Gly Ser Val Ile Asp Glu Asp Asp Pro Val
            260                 265                 270

Leu Gly Glu Asp Tyr Tyr Ser Val Glu Asn Pro Ala Asn Lys Arg Arg
        275                 280                 285

Ser Thr Leu Ile Thr Val Leu Asn Ile Ser Glu Ile Glu Ser Arg Phe
    290                 295                 300

Tyr Lys His Pro Phe Thr Cys Phe Ala Lys Asn Thr His Gly Ile Asp
305                 310                 315                 320

Ala Ala Tyr Ile Gln Leu Ile Tyr Pro Val Thr Asn Ser Glu Arg Cys
                325                 330                 335
```

```
Asp Asp Trp Gly Leu Asp Thr Met Arg Gln Ile Gln Val Phe Glu Asp
            340                 345                 350

Glu Pro Ala Arg Ile Lys Cys Pro Leu Phe Glu His Phe Leu Lys Phe
        355                 360                 365

Asn Tyr Ser Thr Ala His Ser Ala Gly Leu Thr Leu Ile Trp Tyr Trp
    370                 375                 380

Thr Arg Gln Asp Arg Asp Leu Glu Glu Pro Ile Asn Phe Arg Leu Pro
385                 390                 395                 400

Glu Asn Arg Ile Ser Lys Glu Lys Asp Val Leu Trp Phe Arg Pro Thr
                405                 410                 415

Leu Leu Asn Asp Thr Gly Asn Tyr Thr Cys Met Leu Arg Asn Thr Thr
            420                 425                 430

Tyr Cys Ser Lys Val Ala Phe Pro Leu Glu Val Val Gln Lys Asp Ser
        435                 440                 445

Cys Phe Asn Ser Pro Met Lys Leu Pro Val His Lys Leu Tyr Ile Glu
    450                 455                 460

Tyr Gly Ile Gln Arg Ile Thr Cys Pro Asn Val Asp Gly Tyr Phe Pro
465                 470                 475                 480

Ser Ser Val Lys Pro Thr Ile Thr Trp Tyr Met Gly Cys Tyr Lys Ile
                485                 490                 495

Gln Asn Phe Asn Asn Val Ile Pro Glu Gly Met Asn Leu Ser Phe Leu
            500                 505                 510

Ile Ala Leu Ile Ser Asn Asn Gly Asn Tyr Thr Cys Val Val Thr Tyr
        515                 520                 525

Pro Glu Asn Gly Arg Thr Phe His Leu Thr Arg Thr Leu Thr Val Lys
    530                 535                 540

Val Val Gly Ser Pro Lys Asn Ala Val Pro Pro Val Ile His Ser Pro
545                 550                 555                 560

Asn Asp His Val Val Tyr Glu Lys Glu Pro Gly Glu Glu Leu Leu Ile
                565                 570                 575

Pro Cys Thr Val Tyr Phe Ser Phe Leu Met Asp Ser Arg Asn Glu Val
            580                 585                 590

Trp Trp Thr Ile Asp Gly Lys Lys Pro Asp Asp Ile Thr Ile Asp Val
        595                 600                 605

Thr Ile Asn Glu Ser Ile Ser His Ser Arg Thr Glu Asp Glu Thr Arg
    610                 615                 620

Thr Gln Ile Leu Ser Ile Lys Lys Val Thr Ser Glu Asp Leu Lys Arg
625                 630                 635                 640

Ser Tyr Val Cys His Ala Arg Ser Ala Lys Gly Glu Val Ala Lys Ala
                645                 650                 655

Ala Lys Val Lys Gln Lys Val Pro Ala Pro Arg Tyr Thr Val Glu Ser
            660                 665                 670

Gly Asp Lys Thr His Thr Cys Pro Pro Cys Pro Ala Pro Glu Leu Leu
        675                 680                 685

Gly Gly Pro Ser Val Phe Leu Phe Pro Pro Lys Pro Lys Asp Thr Leu
    690                 695                 700

Met Ile Ser Arg Thr Pro Glu Val Thr Cys Val Val Val Asp Val Ser
705                 710                 715                 720

His Glu Asp Pro Glu Val Lys Phe Asn Trp Tyr Val Asp Gly Val Glu
                725                 730                 735

Val His Asn Ala Lys Thr Lys Pro Arg Glu Glu Gln Tyr Asn Ser Thr
            740                 745                 750

Tyr Arg Val Val Ser Val Leu Thr Val Leu His Gln Asp Trp Leu Asn
```

-continued

```
        755                 760                 765

Gly Lys Glu Tyr Lys Cys Lys Val Ser Asn Lys Ala Leu Pro Ala Pro
    770                 775                 780

Ile Glu Lys Thr Ile Ser Lys Ala Lys Gly Gln Pro Arg Glu Pro Gln
785                 790                 795                 800

Val Tyr Thr Leu Pro Pro Ser Arg Glu Glu Met Thr Lys Asn Gln Val
                805                 810                 815

Ser Leu Thr Cys Leu Val Lys Gly Phe Tyr Pro Ser Asp Ile Ala Val
            820                 825                 830

Glu Trp Glu Ser Asn Gly Gln Pro Glu Asn Asn Tyr Lys Thr Thr Pro
        835                 840                 845

Pro Val Leu Asp Ser Asp Gly Ser Phe Phe Leu Tyr Ser Lys Leu Thr
    850                 855                 860

Val Asp Lys Ser Arg Trp Gln Gln Gly Asn Val Phe Ser Cys Ser Val
865                 870                 875                 880

Met His Glu Ala Leu His Asn His Tyr Thr Gln Lys Ser Leu Ser Leu
                885                 890                 895

Ser Pro Gly Lys
            900


<210> SEQ ID NO 35
<211> LENGTH: 2709
<212> TYPE: DNA
<213> ORGANISM: Homo sapiens

<400> SEQUENCE: 35

atggtgttac tcagacttat ttgtttcata gctctactga tttcttctct ggaggctgat      60

aaatgcaagg aacgtgaaga aaaaataatt ttagtgtcat ctgcaaatga aattgatgtt     120

cgtccctgtc ctcttaaccc aaatgaacac aaaggcacta taacttggta taaggatgac     180

agcaagacac ctgtatctac agaacaagcc tccaggattc atcaacacaa agagaaactt     240

tggtttgttc ctgctaaggt ggaggattca ggacattact attgcgtggt aagaaattca     300

tcttactgcc tcagaattaa aataagtgca aaatttgtgg agaatgagcc taacttatgt     360

tataatgcac aagccatatt taagcagaaa ctacccgttg caggagacgg aggacttgtg     420

tgcccttata tggagttttt taaaaatgaa aataatgagt tacctaaatt acagtggtat     480

aaggattgca aacctctact tcttgacaat atacacttta gtggagtcaa agataggctc     540

atcgtgatga atgtggctga aaagcataga gggaactata cttgtcatgc atcctacaca     600

tacttgggca agcaatatcc tattacccgg gtaatagaat ttattactct agaggaaaac     660

aaacccacaa ggcctgtgat tgtgagccca gctaatgaga caatggaagt agacttggga     720

tcccagatac aattgatctg taatgtcacc ggccagttga gtgacattgc ttactggaag     780

tggaatgggt cagtaattga tgaagatgac ccagtgctag gggaagacta ttacagtgtg     840

gaaaatcctg caaacaaaag aaggagtacc ctcatcacag tgcttaatat atcggaaatt     900

gagagtagat tttataaaca tccatttacc tgttttgcca agaatacaca tggtatagat     960

gcagcatata tccagttaat atatccagtc actaattcag aacgctgcga tgactgggga    1020

ctagacacca tgaggcaaat ccaagtgttt gaagatgagc cagctcgcat caagtgccca    1080

ctctttgaac acttcttgaa attcaactac agcacagccc attcagctgg ccttactctg    1140

atctggtatt ggactaggca ggaccgggac cttgaggagc caattaactt ccgcctcccc    1200

gagaaccgca ttagtaagga gaaagatgtg ctgtggttcc ggcccactct cctcaatgac    1260

actggcaact atacctgcat gttaaggaac actacatatt gcagcaaagt tgcatttccc    1320
```

```
ttggaagttg ttcaaaaaga cagctgtttc aattccccca tgaaactccc agtgcataaa   1380
ctgtatatag aatatggcat tcagaggatc acttgtccaa atgtagatgg atattttcct   1440
tccagtgtca aaccgactat cacttggtat atgggctgtt ataaaataca gaattttaat   1500
aatgtaatac ccgaaggtat gaacttgagt ttcctcattg ccttaatttc aaataatgga   1560
aattacacat gtgttgttac atatccagaa aatggacgta cgtttcatct caccaggact   1620
ctgactgtaa aggtagtagg ctctccaaaa aatgcagtgc cccctgtgat ccattcacct   1680
aatgatcatg tggtctatga gaaagaacca ggagaggagc tactcattcc ctgtacggtc   1740
tattttagtt ttctgatgga ttctcgcaat gaggtttggt ggaccattga tggaaaaaaa   1800
cctgatgaca tcactattga tgtcaccatt aacgaaagta taagtcatag tagaacagaa   1860
gatgaaacaa gaactcagat tttgagcatc aagaaagtta cctctgagga tctcaagcgc   1920
agctatgtct gtcatgctag aagtgccaaa ggcgaagttg ccaaagcagc caaggtgaag   1980
cagaaagtgc cagctccaag atacacagtg gaatccggag agtccaaata cggtccgcca   2040
tgcccatcat gcccagcacc tgagttcctg gggggaccat cagtcttcct gttcccccca   2100
aaacccaagg acactctcat gatctcccgg acccctgagg tcacgtgcgt ggtggtggac   2160
gtgagccagg aagaccccga ggtccagttc aactggtacg tggatggcgt ggaggtgcat   2220
aatgccaaga caaagccgcg ggaggagcag ttcaacagca cgtaccgtgt ggtcagcgtc   2280
ctcaccgtcc tgcaccagga ctggctgaac ggcaaggagt acaagtgcaa ggtctccaac   2340
aaaggcctcc cgtcctccat cgagaaaacc atctccaaag ccaaagggca gccccgagag   2400
ccacaggtgt acaccctgcc cccatcccag gaggagatga ccaagaacca ggtcagcctg   2460
acctgcctgg tcaaaggctt ctaccccagc gacatcgccg tggagtggga gagcaatggg   2520
cagccggaga acaactacaa gaccacgcct cccgtgctgg actccgacgg ctccttcttc   2580
ctctacagca ggctaaccgt ggacaagagc aggtggcagg aggggaatgt cttctcatgc   2640
tccgtgatgc atgaggctct gcacaaccac tacacacaga agagcctctc cctgtctctg   2700
ggtaaatga                                                           2709
```

```
<210> SEQ ID NO 36
<211> LENGTH: 902
<212> TYPE: PRT
<213> ORGANISM: Homo sapiens

<400> SEQUENCE: 36

Met Val Leu Leu Arg Leu Ile Cys Phe Ile Ala Leu Leu Ile Ser Ser
 1               5                  10                  15

Leu Glu Ala Asp Lys Cys Lys Glu Arg Glu Glu Lys Ile Ile Leu Val
            20                  25                  30

Ser Ser Ala Asn Glu Ile Asp Val Arg Pro Cys Pro Leu Asn Pro Asn
        35                  40                  45

Glu His Lys Gly Thr Ile Thr Trp Tyr Lys Asp Asp Ser Lys Thr Pro
    50                  55                  60

Val Ser Thr Glu Gln Ala Ser Arg Ile His Gln His Lys Glu Lys Leu
65                  70                  75                  80

Trp Phe Val Pro Ala Lys Val Glu Asp Ser Gly His Tyr Tyr Cys Val
                85                  90                  95

Val Arg Asn Ser Ser Tyr Cys Leu Arg Ile Lys Ile Ser Ala Lys Phe
            100                 105                 110

Val Glu Asn Glu Pro Asn Leu Cys Tyr Asn Ala Gln Ala Ile Phe Lys
        115                 120                 125
```

-continued

```
Gln Lys Leu Pro Val Ala Gly Asp Gly Gly Leu Val Cys Pro Tyr Met
    130                 135                 140

Glu Phe Phe Lys Asn Glu Asn Asn Glu Leu Pro Lys Leu Gln Trp Tyr
145                 150                 155                 160

Lys Asp Cys Lys Pro Leu Leu Leu Asp Asn Ile His Phe Ser Gly Val
                165                 170                 175

Lys Asp Arg Leu Ile Val Met Asn Val Ala Glu Lys His Arg Gly Asn
            180                 185                 190

Tyr Thr Cys His Ala Ser Tyr Thr Tyr Leu Gly Lys Gln Tyr Pro Ile
        195                 200                 205

Thr Arg Val Ile Glu Phe Ile Thr Leu Glu Glu Asn Lys Pro Thr Arg
    210                 215                 220

Pro Val Ile Val Ser Pro Ala Asn Glu Thr Met Glu Val Asp Leu Gly
225                 230                 235                 240

Ser Gln Ile Gln Leu Ile Cys Asn Val Thr Gly Gln Leu Ser Asp Ile
                245                 250                 255

Ala Tyr Trp Lys Trp Asn Gly Ser Val Ile Asp Glu Asp Asp Pro Val
            260                 265                 270

Leu Gly Glu Asp Tyr Tyr Ser Val Glu Asn Pro Ala Asn Lys Arg Arg
        275                 280                 285

Ser Thr Leu Ile Thr Val Leu Asn Ile Ser Glu Ile Glu Ser Arg Phe
    290                 295                 300

Tyr Lys His Pro Phe Thr Cys Phe Ala Lys Asn Thr His Gly Ile Asp
305                 310                 315                 320

Ala Ala Tyr Ile Gln Leu Ile Tyr Pro Val Thr Asn Ser Glu Arg Cys
                325                 330                 335

Asp Asp Trp Gly Leu Asp Thr Met Arg Gln Ile Gln Val Phe Glu Asp
            340                 345                 350

Glu Pro Ala Arg Ile Lys Cys Pro Leu Phe Glu His Phe Leu Lys Phe
        355                 360                 365

Asn Tyr Ser Thr Ala His Ser Ala Gly Leu Thr Leu Ile Trp Tyr Trp
    370                 375                 380

Thr Arg Gln Asp Arg Asp Leu Glu Glu Pro Ile Asn Phe Arg Leu Pro
385                 390                 395                 400

Glu Asn Arg Ile Ser Lys Glu Lys Asp Val Leu Trp Phe Arg Pro Thr
                405                 410                 415

Leu Leu Asn Asp Thr Gly Asn Tyr Thr Cys Met Leu Arg Asn Thr Thr
            420                 425                 430

Tyr Cys Ser Lys Val Ala Phe Pro Leu Glu Val Val Gln Lys Asp Ser
        435                 440                 445

Cys Phe Asn Ser Pro Met Lys Leu Pro Val His Lys Leu Tyr Ile Glu
    450                 455                 460

Tyr Gly Ile Gln Arg Ile Thr Cys Pro Asn Val Asp Gly Tyr Phe Pro
465                 470                 475                 480

Ser Ser Val Lys Pro Thr Ile Thr Trp Tyr Met Gly Cys Tyr Lys Ile
                485                 490                 495

Gln Asn Phe Asn Asn Val Ile Pro Glu Gly Met Asn Leu Ser Phe Leu
            500                 505                 510

Ile Ala Leu Ile Ser Asn Asn Gly Asn Tyr Thr Cys Val Val Thr Tyr
        515                 520                 525

Pro Glu Asn Gly Arg Thr Phe His Leu Thr Arg Thr Leu Thr Val Lys
    530                 535                 540

Val Val Gly Ser Pro Lys Asn Ala Val Pro Pro Val Ile His Ser Pro
```

```
545                 550                 555                 560

Asn Asp His Val Val Tyr Glu Lys Glu Pro Gly Glu Glu Leu Leu Ile
                565                 570                 575

Pro Cys Thr Val Tyr Phe Ser Phe Leu Met Asp Ser Arg Asn Glu Val
            580                 585                 590

Trp Trp Thr Ile Asp Gly Lys Lys Pro Asp Asp Ile Thr Ile Asp Val
        595                 600                 605

Thr Ile Asn Glu Ser Ile Ser His Ser Arg Thr Glu Asp Glu Thr Arg
    610                 615                 620

Thr Gln Ile Leu Ser Ile Lys Lys Val Thr Ser Glu Asp Leu Lys Arg
625                 630                 635                 640

Ser Tyr Val Cys His Ala Arg Ser Ala Lys Gly Glu Val Ala Lys Ala
                645                 650                 655

Ala Lys Val Lys Gln Lys Val Pro Ala Pro Arg Tyr Thr Val Glu Ser
            660                 665                 670

Gly Glu Ser Lys Tyr Gly Pro Pro Cys Pro Ser Cys Pro Ala Pro Glu
        675                 680                 685

Phe Leu Gly Gly Pro Ser Val Phe Leu Phe Pro Pro Lys Pro Lys Asp
    690                 695                 700

Thr Leu Met Ile Ser Arg Thr Pro Glu Val Thr Cys Val Val Val Asp
705                 710                 715                 720

Val Ser Gln Glu Asp Pro Glu Val Gln Phe Asn Trp Tyr Val Asp Gly
                725                 730                 735

Val Glu Val His Asn Ala Lys Thr Lys Pro Arg Glu Glu Gln Phe Asn
            740                 745                 750

Ser Thr Tyr Arg Val Val Ser Val Leu Thr Val Leu His Gln Asp Trp
        755                 760                 765

Leu Asn Gly Lys Glu Tyr Lys Cys Lys Val Ser Asn Lys Gly Leu Pro
    770                 775                 780

Ser Ser Ile Glu Lys Thr Ile Ser Lys Ala Lys Gly Gln Pro Arg Glu
785                 790                 795                 800

Pro Gln Val Tyr Thr Leu Pro Pro Ser Gln Glu Glu Met Thr Lys Asn
                805                 810                 815

Gln Val Ser Leu Thr Cys Leu Val Lys Gly Phe Tyr Pro Ser Asp Ile
            820                 825                 830

Ala Val Glu Trp Glu Ser Asn Gly Gln Pro Glu Asn Asn Tyr Lys Thr
        835                 840                 845

Thr Pro Pro Val Leu Asp Ser Asp Gly Ser Phe Phe Leu Tyr Ser Arg
    850                 855                 860

Leu Thr Val Asp Lys Ser Arg Trp Gln Glu Gly Asn Val Phe Ser Cys
865                 870                 875                 880

Ser Val Met His Glu Ala Leu His Asn His Tyr Thr Gln Lys Ser Leu
                885                 890                 895

Ser Leu Ser Leu Gly Lys
            900

<210> SEQ ID NO 37
<211> LENGTH: 2709
<212> TYPE: DNA
<213> ORGANISM: Homo sapiens

<400> SEQUENCE: 37

atggtgttac tcagacttat ttgtttcata gctctactga tttcttctct ggaggctgat      60

aaatgcaagg aacgtgaaga aaaaataatt ttagtgtcat ctgcaaatga aattgatgtt     120
```

-continued

```
cgtccctgtc ctcttaaccc aaatgaacac aaaggcacta taacttggta taaggatgac    180
agcaagacac ctgtatctac agaacaagcc tccaggattc atcaacacaa agagaaactt    240
tggtttgttc ctgctaaggt ggaggattca ggacattact attgcgtggt aagaaattca    300
tcttactgcc tcagaattaa aataagtgca aaatttgtgg agaatgagcc taacttatgt    360
tataatgcac aagccatatt taagcagaaa ctacccgttg caggagacgg aggacttgtg    420
tgcccttata tggagttttt taaaaatgaa aataatgagt tacctaaatt acagtggtat    480
aaggattgca aacctctact tcttgacaat atacacttta gtggagtcaa agataggctc    540
atcgtgatga atgtggctga aaagcataga gggaactata cttgtcatgc atcctacaca    600
tacttgggca agcaatatcc tattacccgg gtaatagaat ttattactct agaggaaaac    660
aaacccacaa ggcctgtgat tgtgagccca gctaatgaga caatggaagt agacttggga    720
tcccagatac aattgatctg taatgtcacc ggccagttga gtgacattgc ttactggaag    780
tggaatgggt cagtaattga tgaagatgac ccagtgctag gggaagacta ttacagtgtg    840
gaaaatcctg caaacaaaag aaggagtacc ctcatcacag tgcttaatat atcggaaatt    900
gagagtagat tttataaaca tccatttacc tgttttgcca agaatacaca tggtatagat    960
gcagcatata tccagttaat atatccagtc actaattcag aacgctgcga tgactgggga   1020
ctagacacca tgaggcaaat ccaagtgttt gaagatgagc cagctcgcat caagtgccca   1080
ctctttgaac acttcttgaa attcaactac agcacagccc attcagctgg ccttactctg   1140
atctggtatt ggactaggca ggaccgggac cttgaggagc caattaactt ccgcctcccc   1200
gagaaccgca ttagtaagga gaaagatgtg ctgtggttcc ggcccactct cctcaatgac   1260
actggcaact atacctgcat gttaaggaac actacatatt gcagcaaagt tgcatttccc   1320
ttggaagttg ttcaaaaaga cagctgtttc aattccccca tgaaactccc agtgcataaa   1380
ctgtatatag aatatggcat tcagaggatc acttgtccaa atgtagatgg atattttcct   1440
tccagtgtca aaccgactat cacttggtat atgggctgtt ataaaataca gaattttaat   1500
aatgtaatac ccgaaggtat gaacttgagt ttcctcattg ccttaatttc aaataatgga   1560
aattacacat gtgttgttac atatccagaa aatggacgta cgtttcatct caccaggact   1620
ctgactgtaa aggtagtagg ctctccaaaa aatgcagtgc cccctgtgat ccattcacct   1680
aatgatcatg tggtctatga gaaagaacca ggagaggagc tactcattcc ctgtacggtc   1740
tattttagtt ttctgatgga ttctcgcaat gaggtttggt ggaccattga tggaaaaaaa   1800
cctgatgaca tcactattga tgtcaccatt aacgaaagta taagtcatag tagaacagaa   1860
gatgaaacaa gaactcagat tttgagcatc aagaaagtta cctctgagga tctcaagcgc   1920
agctatgtct gtcatgctag aagtgccaaa ggcgaagttg ccaaagcagc caaggtgaag   1980
cagaaagtgc cagctccaag atacacagtg gaatccggag agtccaaata cggtccgcca   2040
tgcccaccat gcccagcacc tgagttcctg gggggaccat cagtcttcct gttcccccca   2100
aaacccaagg acactctcat gatctcccgg acccctgagg tcacgtgcgt ggtggtggac   2160
gtgagccagg aagaccccga ggtccagttc aactggtacg tggatggcgt ggaggtgcat   2220
aatgccaaga caaagccgcg ggaggagcag ttcaacagca cgtaccgtgt ggtcagcgtc   2280
ctcaccgtcc tgcaccagga ctggctgaac ggcaaggagt acaagtgcaa ggtctccaac   2340
aaaggcctcc cgtcctccat cgagaaaacc atctccaaag ccaaagggca gccccgagag   2400
ccacaggtgt acaccctgcc cccatcccag gaggagatga ccaagaacca ggtcagcctg   2460
acctgcctgg tcaaaggctt ctaccccagc gacatcgccg tggagtggga gagcaatggg   2520
```

```
cagccggaga acaactacaa gaccacgcct cccgtgctgg actccgacgg ctccttcttc   2580

ctctacagca ggctaaccgt ggacaagagc aggtggcagg aggggaatgt cttctcatgc   2640

tccgtgatgc atgaggctct gcacaaccac tacacacaga agagcctctc cctgtctctg   2700

ggtaaatga                                                           2709


<210> SEQ ID NO 38
<211> LENGTH: 902
<212> TYPE: PRT
<213> ORGANISM: Homo sapiens

<400> SEQUENCE: 38

Met Val Leu Leu Arg Leu Ile Cys Phe Ile Ala Leu Leu Ile Ser Ser
 1               5                  10                  15

Leu Glu Ala Asp Lys Cys Lys Glu Arg Glu Glu Lys Ile Ile Leu Val
            20                  25                  30

Ser Ser Ala Asn Glu Ile Asp Val Arg Pro Cys Pro Leu Asn Pro Asn
        35                  40                  45

Glu His Lys Gly Thr Ile Thr Trp Tyr Lys Asp Asp Ser Lys Thr Pro
    50                  55                  60

Val Ser Thr Glu Gln Ala Ser Arg Ile His Gln His Lys Glu Lys Leu
65                  70                  75                  80

Trp Phe Val Pro Ala Lys Val Glu Asp Ser Gly His Tyr Tyr Cys Val
                85                  90                  95

Val Arg Asn Ser Ser Tyr Cys Leu Arg Ile Lys Ile Ser Ala Lys Phe
            100                 105                 110

Val Glu Asn Glu Pro Asn Leu Cys Tyr Asn Ala Gln Ala Ile Phe Lys
        115                 120                 125

Gln Lys Leu Pro Val Ala Gly Asp Gly Gly Leu Val Cys Pro Tyr Met
    130                 135                 140

Glu Phe Phe Lys Asn Glu Asn Asn Glu Leu Pro Lys Leu Gln Trp Tyr
145                 150                 155                 160

Lys Asp Cys Lys Pro Leu Leu Leu Asp Asn Ile His Phe Ser Gly Val
                165                 170                 175

Lys Asp Arg Leu Ile Val Met Asn Val Ala Glu Lys His Arg Gly Asn
            180                 185                 190

Tyr Thr Cys His Ala Ser Tyr Thr Tyr Leu Gly Lys Gln Tyr Pro Ile
        195                 200                 205

Thr Arg Val Ile Glu Phe Ile Thr Leu Glu Glu Asn Lys Pro Thr Arg
    210                 215                 220

Pro Val Ile Val Ser Pro Ala Asn Glu Thr Met Glu Val Asp Leu Gly
225                 230                 235                 240

Ser Gln Ile Gln Leu Ile Cys Asn Val Thr Gly Gln Leu Ser Asp Ile
                245                 250                 255

Ala Tyr Trp Lys Trp Asn Gly Ser Val Ile Asp Glu Asp Asp Pro Val
            260                 265                 270

Leu Gly Glu Asp Tyr Tyr Ser Val Glu Asn Pro Ala Asn Lys Arg Arg
        275                 280                 285

Ser Thr Leu Ile Thr Val Leu Asn Ile Ser Glu Ile Glu Ser Arg Phe
    290                 295                 300

Tyr Lys His Pro Phe Thr Cys Phe Ala Lys Asn Thr His Gly Ile Asp
305                 310                 315                 320

Ala Ala Tyr Ile Gln Leu Ile Tyr Pro Val Thr Asn Ser Glu Arg Cys
                325                 330                 335

Asp Asp Trp Gly Leu Asp Thr Met Arg Gln Ile Gln Val Phe Glu Asp
```

-continued

```
            340                 345                 350

Glu Pro Ala Arg Ile Lys Cys Pro Leu Phe Glu His Phe Leu Lys Phe
        355                 360                 365

Asn Tyr Ser Thr Ala His Ser Ala Gly Leu Thr Leu Ile Trp Tyr Trp
    370                 375                 380

Thr Arg Gln Asp Arg Asp Leu Glu Glu Pro Ile Asn Phe Arg Leu Pro
385                 390                 395                 400

Glu Asn Arg Ile Ser Lys Glu Lys Asp Val Leu Trp Phe Arg Pro Thr
                405                 410                 415

Leu Leu Asn Asp Thr Gly Asn Tyr Thr Cys Met Leu Arg Asn Thr Thr
            420                 425                 430

Tyr Cys Ser Lys Val Ala Phe Pro Leu Glu Val Val Gln Lys Asp Ser
        435                 440                 445

Cys Phe Asn Ser Pro Met Lys Leu Pro Val His Lys Leu Tyr Ile Glu
    450                 455                 460

Tyr Gly Ile Gln Arg Ile Thr Cys Pro Asn Val Asp Gly Tyr Phe Pro
465                 470                 475                 480

Ser Ser Val Lys Pro Thr Ile Thr Trp Tyr Met Gly Cys Tyr Lys Ile
                485                 490                 495

Gln Asn Phe Asn Asn Val Ile Pro Glu Gly Met Asn Leu Ser Phe Leu
            500                 505                 510

Ile Ala Leu Ile Ser Asn Asn Gly Asn Tyr Thr Cys Val Val Thr Tyr
        515                 520                 525

Pro Glu Asn Gly Arg Thr Phe His Leu Thr Arg Thr Leu Thr Val Lys
    530                 535                 540

Val Val Gly Ser Pro Lys Asn Ala Val Pro Pro Val Ile His Ser Pro
545                 550                 555                 560

Asn Asp His Val Val Tyr Glu Lys Glu Pro Gly Glu Glu Leu Leu Ile
                565                 570                 575

Pro Cys Thr Val Tyr Phe Ser Phe Leu Met Asp Ser Arg Asn Glu Val
            580                 585                 590

Trp Trp Thr Ile Asp Gly Lys Lys Pro Asp Asp Ile Thr Ile Asp Val
        595                 600                 605

Thr Ile Asn Glu Ser Ile Ser His Ser Arg Thr Glu Asp Glu Thr Arg
    610                 615                 620

Thr Gln Ile Leu Ser Ile Lys Lys Val Thr Ser Glu Asp Leu Lys Arg
625                 630                 635                 640

Ser Tyr Val Cys His Ala Arg Ser Ala Lys Gly Glu Val Ala Lys Ala
                645                 650                 655

Ala Lys Val Lys Gln Lys Val Pro Ala Pro Arg Tyr Thr Val Glu Ser
            660                 665                 670

Gly Glu Ser Lys Tyr Gly Pro Pro Cys Pro Pro Cys Pro Ala Pro Glu
        675                 680                 685

Phe Leu Gly Gly Pro Ser Val Phe Leu Phe Pro Pro Lys Pro Lys Asp
    690                 695                 700

Thr Leu Met Ile Ser Arg Thr Pro Glu Val Thr Cys Val Val Val Asp
705                 710                 715                 720

Val Ser Gln Glu Asp Pro Glu Val Gln Phe Asn Trp Tyr Val Asp Gly
                725                 730                 735

Val Glu Val His Asn Ala Lys Thr Lys Pro Arg Glu Glu Gln Phe Asn
            740                 745                 750

Ser Thr Tyr Arg Val Val Ser Val Leu Thr Val Leu His Gln Asp Trp
        755                 760                 765
```

-continued

```
Leu Asn Gly Lys Glu Tyr Lys Cys Lys Val Ser Asn Lys Gly Leu Pro
    770                 775                 780

Ser Ser Ile Glu Lys Thr Ile Ser Lys Ala Lys Gly Gln Pro Arg Glu
785                 790                 795                 800

Pro Gln Val Tyr Thr Leu Pro Pro Ser Gln Glu Glu Met Thr Lys Asn
                805                 810                 815

Gln Val Ser Leu Thr Cys Leu Val Lys Gly Phe Tyr Pro Ser Asp Ile
            820                 825                 830

Ala Val Glu Trp Glu Ser Asn Gly Gln Pro Glu Asn Asn Tyr Lys Thr
        835                 840                 845

Thr Pro Pro Val Leu Asp Ser Asp Gly Ser Phe Phe Leu Tyr Ser Arg
    850                 855                 860

Leu Thr Val Asp Lys Ser Arg Trp Gln Glu Gly Asn Val Phe Ser Cys
865                 870                 875                 880

Ser Val Met His Glu Ala Leu His Asn His Tyr Thr Gln Lys Ser Leu
                885                 890                 895

Ser Leu Ser Leu Gly Lys
            900
```

<210> SEQ ID NO 39
<211> LENGTH: 2703
<212> TYPE: DNA
<213> ORGANISM: Homo sapiens

<400> SEQUENCE: 39

```
atggtgcttc tgtggtgtgt agtgagtctc tacttttatg gaatcctgca aagtgatgcc      60

tcagaacgct gcgatgactg gggactagac accatgaggc aaatccaagt gtttgaagat     120

gagccagctc gcatcaagtg cccactcttt gaacacttct tgaaattcaa ctacagcaca     180

gcccattcag ctggccttac tctgatctgg tattggacta ggcaggaccg ggaccttgag     240

gagccaatta acttccgcct ccccgagaac cgcattagta aggagaaaga tgtgctgtgg     300

ttccggccca ctctcctcaa tgacactggc aactatacct gcatgttaag gaacactaca     360

tattgcagca aagttgcatt tcccttggaa gttgttcaaa aagacagctg tttcaattcc     420

cccatgaaac tcccagtgca taaactgtat atagaatatg gcattcagag gatcacttgt     480

ccaaatgtag atggatattt tccttccagt gtcaaaccga ctatcacttg gtatatgggc     540

tgttataaaa tacagaattt taataatgta atacccgaag gtatgaactt gagtttcctc     600

attgccttaa tttcaaataa tggaaattac acatgtgttg ttacatatcc agaaaatgga     660

cgtacgtttc atctcaccag gactctgact gtaaaggtag taggctctcc aaaaaatgca     720

gtgccccctg tgatccattc acctaatgat catgtggtct atgagaaaga accaggagag     780

gagctactca ttccctgtac ggtctatttt agttttctga tggattctcg caatgaggtt     840

tggtggacca ttgatggaaa aaaacctgat gacatcacta ttgatgtcac cattaacgaa     900

agtataagtc atagtagaac agaagatgaa acaagaactc agattttgag catcaagaaa     960

gttacctctg aggatctcaa gcgcagctat gtctgtcatg ctagaagtgc caaaggcgaa    1020

gttgccaaag cagccaaggt gaagcagaaa gtgccagctc caagatacac agtggaaaaa    1080

tgcaaggaac gtgaagaaaa aataatttta gtgagctcag caaatgaaat cgatgttcgt    1140

ccctgtcctc ttaacccaaa tgaacacaaa ggcactataa cttggtataa ggatgacagc    1200

aagacacctg tatctacaga acaagcctcc aggattcatc aacacaaaga gaaactttgg    1260

tttgttcctg ctaaggtgga ggattcagga cattactatt gcgtggtaag aaattcatct    1320

tactgcctca gaattaaaat aagtgcaaaa tttgtggaga atgagcctaa cttatgttat    1380
```

```
aatgcacaag ccatatttaa gcagaaacta cccgttgcag gagacggagg acttgtgtgc   1440

ccttatatgg agttttttaa aaatgaaaat aatgagttac ctaaattaca gtggtataag   1500

gattgcaaac ctctacttct tgacaatata cactttagtg gagtcaaaga taggctcatc   1560

gtgatgaatg tggctgaaaa gcatagaggg aactatactt gtcatgcatc ctacacatac   1620

ttgggcaagc aatatcctat tacccgggta atagaattta ttactctaga ggaaaacaaa   1680

cccacaaggc ctgtgattgt gagcccagct aatgagacaa tggaagtaga cttgggatcc   1740

cagatacaat tgatctgtaa tgtcaccggc cagttgagtg acattgctta ctggaagtgg   1800

aatgggtcag taattgatga agatgaccca gtgctagggg aagactatta cagtgtggaa   1860

aatcctgcaa acaaaagaag gagtaccctc atcacagtgc ttaatatatc ggaaattgag   1920

agtagatttt ataaacatcc atttacctgt tttgccaaga atacacatgg tatagatgca   1980

gcatatatcc agttaatata tccagtcact aattccggag acaaaactca cacatgccca   2040

ccgtgcccag cacctgaact cctgggggga ccgtcagtct tcctcttccc cccaaaaccc   2100

aaggacaccc tcatgatctc ccggacccct gaggtcacat gcgtggtggt ggacgtgagc   2160

cacgaagacc ctgaggtcaa gttcaactgg tacgtggacg gcgtggaggt gcataatgcc   2220

aagacaaagc cgcgggagga gcagtacaac agcacgtacc gtgtggtcag cgtcctcacc   2280

gtcctgcacc aggactggct gaatggcaag gagtacaagt gcaaggtctc caacaaagcc   2340

ctcccagccc ccatcgagaa aaccatctcc aaagccaaag ggcagccccg agaaccacag   2400

gtgtacaccc tgcccccatc ccgggatgag ctgaccaaga accaggtcag cctgacctgc   2460

ctggtcaaag gcttctatcc cagcgacatc gccgtggagt gggagagcaa tgggcagccg   2520

gagaacaact acaagaccac gcctcccgtg ctggactccg acggctcctt cttcctctac   2580

agcaagctca ccgtggacaa gagcaggtgg cagcagggga acgtcttctc atgctccgtg   2640

atgcatgagg ctctgcacaa ccactacacg cagaagagcc tctccctgtc tccgggtaaa   2700

tga                                                                 2703
```

<210> SEQ ID NO 40
<211> LENGTH: 900
<212> TYPE: PRT
<213> ORGANISM: Homo sapiens

<400> SEQUENCE: 40

```
Met Val Leu Leu Trp Cys Val Val Ser Leu Tyr Phe Tyr Gly Ile Leu
 1               5                  10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
```

```
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val Glu Lys Cys Lys Glu Arg Glu Glu Lys Ile
        355                 360                 365

Ile Leu Val Ser Ser Ala Asn Glu Ile Asp Val Arg Pro Cys Pro Leu
    370                 375                 380

Asn Pro Asn Glu His Lys Gly Thr Ile Thr Trp Tyr Lys Asp Asp Ser
385                 390                 395                 400

Lys Thr Pro Val Ser Thr Glu Gln Ala Ser Arg Ile His Gln His Lys
                405                 410                 415

Glu Lys Leu Trp Phe Val Pro Ala Lys Val Glu Asp Ser Gly His Tyr
            420                 425                 430

Tyr Cys Val Val Arg Asn Ser Ser Tyr Cys Leu Arg Ile Lys Ile Ser
        435                 440                 445

Ala Lys Phe Val Glu Asn Glu Pro Asn Leu Cys Tyr Asn Ala Gln Ala
    450                 455                 460

Ile Phe Lys Gln Lys Leu Pro Val Ala Gly Asp Gly Gly Leu Val Cys
465                 470                 475                 480

Pro Tyr Met Glu Phe Phe Lys Asn Glu Asn Asn Glu Leu Pro Lys Leu
                485                 490                 495

Gln Trp Tyr Lys Asp Cys Lys Pro Leu Leu Leu Asp Asn Ile His Phe
            500                 505                 510

Ser Gly Val Lys Asp Arg Leu Ile Val Met Asn Val Ala Glu Lys His
        515                 520                 525

Arg Gly Asn Tyr Thr Cys His Ala Ser Tyr Thr Tyr Leu Gly Lys Gln
    530                 535                 540

Tyr Pro Ile Thr Arg Val Ile Glu Phe Ile Thr Leu Glu Glu Asn Lys
545                 550                 555                 560
```

```
Pro Thr Arg Pro Val Ile Val Ser Pro Ala Asn Glu Thr Met Glu Val
            565                 570                 575

Asp Leu Gly Ser Gln Ile Gln Leu Ile Cys Asn Val Thr Gly Gln Leu
                580                 585                 590

Ser Asp Ile Ala Tyr Trp Lys Trp Asn Gly Ser Val Ile Asp Glu Asp
            595                 600                 605

Asp Pro Val Leu Gly Glu Asp Tyr Tyr Ser Val Glu Asn Pro Ala Asn
            610                 615                 620

Lys Arg Arg Ser Thr Leu Ile Thr Val Leu Asn Ile Ser Glu Ile Glu
625                 630                 635                 640

Ser Arg Phe Tyr Lys His Pro Phe Thr Cys Phe Ala Lys Asn Thr His
                645                 650                 655

Gly Ile Asp Ala Ala Tyr Ile Gln Leu Ile Tyr Pro Val Thr Asn Ser
                660                 665                 670

Gly Asp Lys Thr His Thr Cys Pro Pro Cys Pro Ala Pro Glu Leu Leu
            675                 680                 685

Gly Gly Pro Ser Val Phe Leu Phe Pro Pro Lys Pro Lys Asp Thr Leu
            690                 695                 700

Met Ile Ser Arg Thr Pro Glu Val Thr Cys Val Val Val Asp Val Ser
705                 710                 715                 720

His Glu Asp Pro Glu Val Lys Phe Asn Trp Tyr Val Asp Gly Val Glu
                725                 730                 735

Val His Asn Ala Lys Thr Lys Pro Arg Glu Glu Gln Tyr Asn Ser Thr
                740                 745                 750

Tyr Arg Val Val Ser Val Leu Thr Val Leu His Gln Asp Trp Leu Asn
            755                 760                 765

Gly Lys Glu Tyr Lys Cys Lys Val Ser Asn Lys Ala Leu Pro Ala Pro
770                 775                 780

Ile Glu Lys Thr Ile Ser Lys Ala Lys Gly Gln Pro Arg Glu Pro Gln
785                 790                 795                 800

Val Tyr Thr Leu Pro Pro Ser Arg Asp Glu Leu Thr Lys Asn Gln Val
                805                 810                 815

Ser Leu Thr Cys Leu Val Lys Gly Phe Tyr Pro Ser Asp Ile Ala Val
            820                 825                 830

Glu Trp Glu Ser Asn Gly Gln Pro Glu Asn Asn Tyr Lys Thr Thr Pro
            835                 840                 845

Pro Val Leu Asp Ser Asp Gly Ser Phe Phe Leu Tyr Ser Lys Leu Thr
            850                 855                 860

Val Asp Lys Ser Arg Trp Gln Gln Gly Asn Val Phe Ser Cys Ser Val
865                 870                 875                 880

Met His Glu Ala Leu His Asn His Tyr Thr Gln Lys Ser Leu Ser Leu
                885                 890                 895

Ser Pro Gly Lys
            900

<210> SEQ ID NO 41
<211> LENGTH: 2709
<212> TYPE: DNA
<213> ORGANISM: Homo sapiens

<400> SEQUENCE: 41

atggtgcttc tgtggtgtgt agtgagtctc tacttttatg gaatcctgca aagtgatgcc      60

tcagaacgct gcgatgactg gggactagac accatgaggc aaatccaagt gtttgaagat     120

gagccagctc gcatcaagtg cccactcttt gaacacttct tgaaattcaa ctacagcaca     180
```

-continued

```
gcccattcag ctggccttac tctgatctgg tattggacta ggcaggaccg ggaccttgag    240
gagccaatta acttccgcct ccccgagaac cgcattagta aggagaaaga tgtgctgtgg    300
ttccggccca ctctcctcaa tgacactggc aactatacct gcatgttaag gaacactaca    360
tattgcagca aagttgcatt tcccttggaa gttgttcaaa aagacagctg tttcaattcc    420
cccatgaaac tcccagtgca taaactgtat atagaatatg gcattcagag gatcacttgt    480
ccaaatgtag atggatattt tccttccagt gtcaaaccga ctatcacttg gtatatgggc    540
tgttataaaa tacagaattt taataatgta atacccgaag gtatgaactt gagtttcctc    600
attgccttaa tttcaaataa tggaaattac acatgtgttg ttacatatcc agaaaatgga    660
cgtacgtttc atctcaccag gactctgact gtaaaggtag taggctctcc aaaaaatgca    720
gtgccccctg tgatccattc acctaatgat catgtggtct atgagaaaga accaggagag    780
gagctactca ttccctgtac ggtctatttt agttttctga tggattctcg caatgaggtt    840
tggtggacca ttgatggaaa aaaacctgat gacatcacta ttgatgtcac cattaacgaa    900
agtataagtc atagtagaac agaagatgaa acaagaactc agattttgag catcaagaaa    960
gttacctctg aggatctcaa gcgcagctat gtctgtcatg ctagaagtgc caaaggcgaa   1020
gttgccaaag cagccaaggt gaagcagaaa gtgccagctc caagatacac agtggaaaaa   1080
tgcaaggaac gtgaagaaaa aataatttta gtgagctcag caaatgaaat cgatgttcgt   1140
ccctgtcctc ttaacccaaa tgaacacaaa ggcactataa cttggtataa ggatgacagc   1200
aagacacctg tatctacaga acaagcctcc aggattcatc aacacaaaga gaaactttgg   1260
tttgttcctg ctaaggtgga ggattcagga cattactatt gcgtggtaag aaattcatct   1320
tactgcctca gaattaaaat aagtgcaaaa tttgtggaga atgagcctaa cttatgttat   1380
aatgcacaag ccatatttaa gcagaaacta cccgttgcag gagacggagg acttgtgtgc   1440
ccttatatgg agttttttaa aaatgaaaat aatgagttac ctaaattaca gtggtataag   1500
gattgcaaac ctctacttct tgacaatata cactttagtg gagtcaaaga taggctcatc   1560
gtgatgaatg tggctgaaaa gcatagaggg aactatactt gtcatgcatc ctacacatac   1620
ttgggcaagc aatatcctat tacccgggta atagaattta ttactctaga ggaaaacaaa   1680
cccacaaggc ctgtgattgt gagcccagct aatgagacaa tggaagtaga cttgggatcc   1740
cagatacaat tgatctgtaa tgtcaccggc cagttgagtg acattgctta ctggaagtgg   1800
aatgggtcag taattgatga agatgaccca gtgctagggg aagactatta cagtgtggaa   1860
aatcctgcaa acaaaagaag gagtaccctc atcacagtgc ttaatatatc ggaaattgag   1920
agtagatttt ataaacatcc atttacctgt tttgccaaga atacacatgg tatagatgca   1980
gcatatatcc agttaatata tccagtcact aattccggag agtccaaata cggtccgcca   2040
tgcccatcat gcccagcacc tgagttcctg gggggaccat cagtcttcct gttcccccca   2100
aaacccaagg acactctcat gatctcccgg acccctgagg tcacgtgcgt ggtggtggac   2160
gtgagccagg aagaccccga ggtccagttc aactggtacg tggatggcgt ggaggtgcat   2220
aatgccaaga caaagccgcg ggaggagcag ttcaacagca cgtaccgtgt ggtcagcgtc   2280
ctcaccgtcc tgcaccagga ctggctgaac ggcaaggagt acaagtgcaa ggtctccaac   2340
aaaggcctcc cgtcctccat cgagaaaacc atctccaaag ccaaagggca gccccgagag   2400
ccacaggtgt acaccctgcc cccatcccag gaggagatga ccaagaacca ggtcagcctg   2460
acctgcctgg tcaaaggctt ctaccccagc gacatcgccg tggagtggga gagcaatggg   2520
cagccggaga acaactacaa gaccacgcct cccgtgctgg actccgacgg ctccttcttc   2580
```

ctctacagca ggctaaccgt ggacaagagc aggtggcagg aggggaatgt cttctcatgc 2640
tccgtgatgc atgaggctct gcacaaccac tacacacaga agagcctctc cctgtctctg 2700
ggtaaatga 2709

<210> SEQ ID NO 42
<211> LENGTH: 902
<212> TYPE: PRT
<213> ORGANISM: Homo sapiens

<400> SEQUENCE: 42

Met Val Leu Leu Trp Cys Val Val Ser Leu Tyr Phe Tyr Gly Ile Leu
1 5 10 15

Gln Ser Asp Ala Ser Glu Arg Cys Asp Asp Trp Gly Leu Asp Thr Met
20 25 30

Arg Gln Ile Gln Val Phe Glu Asp Glu Pro Ala Arg Ile Lys Cys Pro
35 40 45

Leu Phe Glu His Phe Leu Lys Phe Asn Tyr Ser Thr Ala His Ser Ala
50 55 60

Gly Leu Thr Leu Ile Trp Tyr Trp Thr Arg Gln Asp Arg Asp Leu Glu
65 70 75 80

Glu Pro Ile Asn Phe Arg Leu Pro Glu Asn Arg Ile Ser Lys Glu Lys
85 90 95

Asp Val Leu Trp Phe Arg Pro Thr Leu Leu Asn Asp Thr Gly Asn Tyr
100 105 110

Thr Cys Met Leu Arg Asn Thr Thr Tyr Cys Ser Lys Val Ala Phe Pro
115 120 125

Leu Glu Val Val Gln Lys Asp Ser Cys Phe Asn Ser Pro Met Lys Leu
130 135 140

Pro Val His Lys Leu Tyr Ile Glu Tyr Gly Ile Gln Arg Ile Thr Cys
145 150 155 160

Pro Asn Val Asp Gly Tyr Phe Pro Ser Ser Val Lys Pro Thr Ile Thr
165 170 175

Trp Tyr Met Gly Cys Tyr Lys Ile Gln Asn Phe Asn Asn Val Ile Pro
180 185 190

Glu Gly Met Asn Leu Ser Phe Leu Ile Ala Leu Ile Ser Asn Asn Gly
195 200 205

Asn Tyr Thr Cys Val Val Thr Tyr Pro Glu Asn Gly Arg Thr Phe His
210 215 220

Leu Thr Arg Thr Leu Thr Val Lys Val Val Gly Ser Pro Lys Asn Ala
225 230 235 240

Val Pro Pro Val Ile His Ser Pro Asn Asp His Val Val Tyr Glu Lys
245 250 255

Glu Pro Gly Glu Glu Leu Leu Ile Pro Cys Thr Val Tyr Phe Ser Phe
260 265 270

Leu Met Asp Ser Arg Asn Glu Val Trp Trp Thr Ile Asp Gly Lys Lys
275 280 285

Pro Asp Asp Ile Thr Ile Asp Val Thr Ile Asn Glu Ser Ile Ser His
290 295 300

Ser Arg Thr Glu Asp Glu Thr Arg Thr Gln Ile Leu Ser Ile Lys Lys
305 310 315 320

Val Thr Ser Glu Asp Leu Lys Arg Ser Tyr Val Cys His Ala Arg Ser
325 330 335

Ala Lys Gly Glu Val Ala Lys Ala Ala Lys Val Lys Gln Lys Val Pro
340 345 350

```
Ala Pro Arg Tyr Thr Val Glu Lys Cys Lys Glu Arg Glu Glu Lys Ile
        355                 360                 365

Ile Leu Val Ser Ser Ala Asn Glu Ile Asp Val Arg Pro Cys Pro Leu
    370                 375                 380

Asn Pro Asn Glu His Lys Gly Thr Ile Thr Trp Tyr Lys Asp Asp Ser
385                 390                 395                 400

Lys Thr Pro Val Ser Thr Glu Gln Ala Ser Arg Ile His Gln His Lys
                405                 410                 415

Glu Lys Leu Trp Phe Val Pro Ala Lys Val Glu Asp Ser Gly His Tyr
            420                 425                 430

Tyr Cys Val Val Arg Asn Ser Ser Tyr Cys Leu Arg Ile Lys Ile Ser
        435                 440                 445

Ala Lys Phe Val Glu Asn Glu Pro Asn Leu Cys Tyr Asn Ala Gln Ala
    450                 455                 460

Ile Phe Lys Gln Lys Leu Pro Val Ala Gly Asp Gly Gly Leu Val Cys
465                 470                 475                 480

Pro Tyr Met Glu Phe Phe Lys Asn Glu Asn Asn Glu Leu Pro Lys Leu
                485                 490                 495

Gln Trp Tyr Lys Asp Cys Lys Pro Leu Leu Leu Asp Asn Ile His Phe
            500                 505                 510

Ser Gly Val Lys Asp Arg Leu Ile Val Met Asn Val Ala Glu Lys His
        515                 520                 525

Arg Gly Asn Tyr Thr Cys His Ala Ser Tyr Thr Tyr Leu Gly Lys Gln
    530                 535                 540

Tyr Pro Ile Thr Arg Val Ile Glu Phe Ile Thr Leu Glu Glu Asn Lys
545                 550                 555                 560

Pro Thr Arg Pro Val Ile Val Ser Pro Ala Asn Glu Thr Met Glu Val
                565                 570                 575

Asp Leu Gly Ser Gln Ile Gln Leu Ile Cys Asn Val Thr Gly Gln Leu
            580                 585                 590

Ser Asp Ile Ala Tyr Trp Lys Trp Asn Gly Ser Val Ile Asp Glu Asp
        595                 600                 605

Asp Pro Val Leu Gly Glu Asp Tyr Tyr Ser Val Glu Asn Pro Ala Asn
    610                 615                 620

Lys Arg Arg Ser Thr Leu Ile Thr Val Leu Asn Ile Ser Glu Ile Glu
625                 630                 635                 640

Ser Arg Phe Tyr Lys His Pro Phe Thr Cys Phe Ala Lys Asn Thr His
                645                 650                 655

Gly Ile Asp Ala Ala Tyr Ile Gln Leu Ile Tyr Pro Val Thr Asn Ser
            660                 665                 670

Gly Glu Ser Lys Tyr Gly Pro Pro Cys Pro Ser Cys Pro Ala Pro Glu
        675                 680                 685

Phe Leu Gly Gly Pro Ser Val Phe Leu Phe Pro Pro Lys Pro Lys Asp
    690                 695                 700

Thr Leu Met Ile Ser Arg Thr Pro Glu Val Thr Cys Val Val Val Asp
705                 710                 715                 720

Val Ser Gln Glu Asp Pro Glu Val Gln Phe Asn Trp Tyr Val Asp Gly
                725                 730                 735

Val Glu Val His Asn Ala Lys Thr Lys Pro Arg Glu Glu Gln Phe Asn
            740                 745                 750

Ser Thr Tyr Arg Val Val Ser Val Leu Thr Val Leu His Gln Asp Trp
        755                 760                 765

Leu Asn Gly Lys Glu Tyr Lys Cys Lys Val Ser Asn Lys Gly Leu Pro
    770                 775                 780
```

```
Ser Ser Ile Glu Lys Thr Ile Ser Lys Ala Lys Gly Gln Pro Arg Glu
785                 790                 795                 800

Pro Gln Val Tyr Thr Leu Pro Pro Ser Gln Glu Glu Met Thr Lys Asn
                805                 810                 815

Gln Val Ser Leu Thr Cys Leu Val Lys Gly Phe Tyr Pro Ser Asp Ile
            820                 825                 830

Ala Val Glu Trp Glu Ser Asn Gly Gln Pro Glu Asn Asn Tyr Lys Thr
        835                 840                 845

Thr Pro Pro Val Leu Asp Ser Asp Gly Ser Phe Phe Leu Tyr Ser Arg
    850                 855                 860

Leu Thr Val Asp Lys Ser Arg Trp Gln Glu Gly Asn Val Phe Ser Cys
865                 870                 875                 880

Ser Val Met His Glu Ala Leu His Asn His Tyr Thr Gln Lys Ser Leu
                885                 890                 895

Ser Leu Ser Leu Gly Lys
            900


<210> SEQ ID NO 43
<211> LENGTH: 2709
<212> TYPE: DNA
<213> ORGANISM: Homo sapiens

<400> SEQUENCE: 43

atggtgcttc tgtggtgtgt agtgagtctc tacttttatg gaatcctgca aagtgatgcc     60

tcagaacgct gcgatgactg gggactagac accatgaggc aaatccaagt gtttgaagat    120

gagccagctc gcatcaagtg cccactcttt gaacacttct tgaaattcaa ctacagcaca    180

gcccattcag ctggccttac tctgatctgg tattggacta ggcaggaccg ggaccttgag    240

gagccaatta acttccgcct ccccgagaac cgcattagta aggagaaaga tgtgctgtgg    300

ttccggccca ctctcctcaa tgacactggc aactatacct gcatgttaag gaacactaca    360

tattgcagca aagttgcatt tcccttggaa gttgttcaaa aagacagctg tttcaattcc    420

cccatgaaac tcccagtgca taaactgtat atagaatatg gcattcagag gatcacttgt    480

ccaaatgtag atggatattt tccttccagt gtcaaaccga ctatcacttg gtatatgggc    540

tgttataaaa tacagaattt taataatgta atacccgaag gtatgaactt gagtttcctc    600

attgccttaa tttcaaataa tggaaattac acatgtgttg ttacatatcc agaaaatgga    660

cgtacgtttc atctcaccag gactctgact gtaaaggtag taggctctcc aaaaaatgca    720

gtgcccccctg tgatccattc acctaatgat catgtggtct atgagaaaga accaggagag    780

gagctactca ttccctgtac ggtctatttt agttttctga tggattctcg caatgaggtt    840

tggtggacca ttgatggaaa aaaacctgat gacatcacta ttgatgtcac cattaacgaa    900

agtataagtc atagtagaac agaagatgaa acaagaactc agattttgag catcaagaaa    960

gttacctctg aggatctcaa gcgcagctat gtctgtcatg ctagaagtgc caaaggcgaa   1020

gttgccaaag cagccaaggt gaagcagaaa gtgccagctc caagatacac agtggaaaaa   1080

tgcaaggaac gtgaagaaaa aataatttta gtgagctcag caaatgaaat cgatgttcgt   1140

ccctgtcctc ttaacccaaa tgaacacaaa ggcactataa cttggtataa ggatgacagc   1200

aagacacctg tatctacaga acaagcctcc aggattcatc aacacaaaga gaaactttgg   1260

tttgttcctg ctaaggtgga ggattcagga cattactatt gcgtggtaag aaattcatct   1320

tactgcctca gaattaaaat aagtgcaaaa tttgtggaga atgagcctaa cttatgttat   1380

aatgcacaag ccatatttaa gcagaaacta cccgttgcag gagacggagg acttgtgtgc   1440
```

```
ccttatatgg agttttttaa aaatgaaaat aatgagttac ctaaattaca gtggtataag   1500

gattgcaaac ctctacttct tgacaatata cactttagtg gagtcaaaga taggctcatc   1560

gtgatgaatg tggctgaaaa gcatagaggg aactatactt gtcatgcatc ctacacatac   1620

ttgggcaagc aatatcctat tacccgggta atagaattta ttactctaga ggaaaacaaa   1680

cccacaaggc ctgtgattgt gagcccagct aatgagacaa tggaagtaga cttgggatcc   1740

cagatacaat tgatctgtaa tgtcaccggc cagttgagtg acattgctta ctggaagtgg   1800

aatgggtcag taattgatga agatgaccca gtgctagggg aagactatta cagtgtggaa   1860

aatcctgcaa acaaaagaag gagtaccctc atcacagtgc ttaatatatc ggaaattgag   1920

agtagatttt ataaacatcc atttacctgt tttgccaaga atacacatgg tatagatgca   1980

gcatatatcc agttaatata tccagtcact aattccggag agtccaaata cggtccgcca   2040

tgcccaccat gcccagcacc tgagttcctg gggggaccat cagtcttcct gttcccccca   2100

aaacccaagg acactctcat gatctcccgg acccctgagg tcacgtgcgt ggtggtggac   2160

gtgagccagg aagaccccga ggtccagttc aactggtacg tggatggcgt ggaggtgcat   2220

aatgccaaga caaagccgcg ggaggagcag ttcaacagca cgtaccgtgt ggtcagcgtc   2280

ctcaccgtcc tgcaccagga ctggctgaac ggcaaggagt acaagtgcaa ggtctccaac   2340

aaaggcctcc cgtcctccat cgagaaaacc atctccaaag ccaaagggca gccccgagag   2400

ccacaggtgt acaccctgcc cccatcccag gaggagatga ccaagaacca ggtcagcctg   2460

acctgcctgg tcaaaggctt ctaccccagc gacatcgccg tggagtggga gagcaatggg   2520

cagccggaga acaactacaa gaccacgcct cccgtgctgg actccgacgg ctccttcttc   2580

ctctacagca ggctaaccgt ggacaagagc aggtggcagg aggggaatgt cttctcatgc   2640

tccgtgatgc atgaggctct gcacaaccac tacacacaga agagcctctc cctgtctctg   2700

ggtaaatga                                                           2709
```

```
<210> SEQ ID NO 44
<211> LENGTH: 902
<212> TYPE: PRT
<213> ORGANISM: Homo sapiens

<400> SEQUENCE: 44

Met Val Leu Leu Trp Cys Val Val Ser Leu Tyr Phe Tyr Gly Ile Leu
 1               5                  10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140
```

-continued

```
Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val Glu Lys Cys Lys Glu Arg Glu Glu Lys Ile
        355                 360                 365

Ile Leu Val Ser Ser Ala Asn Glu Ile Asp Val Arg Pro Cys Pro Leu
    370                 375                 380

Asn Pro Asn Glu His Lys Gly Thr Ile Thr Trp Tyr Lys Asp Asp Ser
385                 390                 395                 400

Lys Thr Pro Val Ser Thr Glu Gln Ala Ser Arg Ile His Gln His Lys
                405                 410                 415

Glu Lys Leu Trp Phe Val Pro Ala Lys Val Glu Asp Ser Gly His Tyr
            420                 425                 430

Tyr Cys Val Val Arg Asn Ser Ser Tyr Cys Leu Arg Ile Lys Ile Ser
        435                 440                 445

Ala Lys Phe Val Glu Asn Glu Pro Asn Leu Cys Tyr Asn Ala Gln Ala
    450                 455                 460

Ile Phe Lys Gln Lys Leu Pro Val Ala Gly Asp Gly Gly Leu Val Cys
465                 470                 475                 480

Pro Tyr Met Glu Phe Phe Lys Asn Glu Asn Asn Glu Leu Pro Lys Leu
                485                 490                 495

Gln Trp Tyr Lys Asp Cys Lys Pro Leu Leu Leu Asp Asn Ile His Phe
            500                 505                 510

Ser Gly Val Lys Asp Arg Leu Ile Val Met Asn Val Ala Glu Lys His
        515                 520                 525

Arg Gly Asn Tyr Thr Cys His Ala Ser Tyr Thr Tyr Leu Gly Lys Gln
    530                 535                 540

Tyr Pro Ile Thr Arg Val Ile Glu Phe Ile Thr Leu Glu Glu Asn Lys
545                 550                 555                 560

Pro Thr Arg Pro Val Ile Val Ser Pro Ala Asn Glu Thr Met Glu Val
                565                 570                 575
```

-continued

```
Asp Leu Gly Ser Gln Ile Gln Leu Ile Cys Asn Val Thr Gly Gln Leu
            580                 585                 590

Ser Asp Ile Ala Tyr Trp Lys Trp Asn Gly Ser Val Ile Asp Glu Asp
        595                 600                 605

Asp Pro Val Leu Gly Glu Asp Tyr Tyr Ser Val Glu Asn Pro Ala Asn
    610                 615                 620

Lys Arg Arg Ser Thr Leu Ile Thr Val Leu Asn Ile Ser Glu Ile Glu
625                 630                 635                 640

Ser Arg Phe Tyr Lys His Pro Phe Thr Cys Phe Ala Lys Asn Thr His
                645                 650                 655

Gly Ile Asp Ala Ala Tyr Ile Gln Leu Ile Tyr Pro Val Thr Asn Ser
            660                 665                 670

Gly Glu Ser Lys Tyr Gly Pro Pro Cys Pro Pro Cys Pro Ala Pro Glu
        675                 680                 685

Phe Leu Gly Gly Pro Ser Val Phe Leu Phe Pro Pro Lys Pro Lys Asp
    690                 695                 700

Thr Leu Met Ile Ser Arg Thr Pro Glu Val Thr Cys Val Val Val Asp
705                 710                 715                 720

Val Ser Gln Glu Asp Pro Glu Val Gln Phe Asn Trp Tyr Val Asp Gly
                725                 730                 735

Val Glu Val His Asn Ala Lys Thr Lys Pro Arg Glu Glu Gln Phe Asn
            740                 745                 750

Ser Thr Tyr Arg Val Val Ser Val Leu Thr Val Leu His Gln Asp Trp
        755                 760                 765

Leu Asn Gly Lys Glu Tyr Lys Cys Lys Val Ser Asn Lys Gly Leu Pro
    770                 775                 780

Ser Ser Ile Glu Lys Thr Ile Ser Lys Ala Lys Gly Gln Pro Arg Glu
785                 790                 795                 800

Pro Gln Val Tyr Thr Leu Pro Pro Ser Gln Glu Glu Met Thr Lys Asn
                805                 810                 815

Gln Val Ser Leu Thr Cys Leu Val Lys Gly Phe Tyr Pro Ser Asp Ile
            820                 825                 830

Ala Val Glu Trp Glu Ser Asn Gly Gln Pro Glu Asn Asn Tyr Lys Thr
        835                 840                 845

Thr Pro Pro Val Leu Asp Ser Asp Gly Ser Phe Phe Leu Tyr Ser Arg
    850                 855                 860

Leu Thr Val Asp Lys Ser Arg Trp Gln Glu Gly Asn Val Phe Ser Cys
865                 870                 875                 880

Ser Val Met His Glu Ala Leu His Asn His Tyr Thr Gln Lys Ser Leu
                885                 890                 895

Ser Leu Ser Leu Gly Lys
            900
```

<210> SEQ ID NO 45
<211> LENGTH: 2748
<212> TYPE: DNA
<213> ORGANISM: Homo sapiens

<400> SEQUENCE: 45

```
atggtgcgct tgtacgtgtt ggtaatggga gtttctgcct tcacccttca gcctgcggca      60

cacacagggg ctgccagaag ctgccggttt cgtgggaggc attacaagcg ggagttcagg     120

ctggaagggg agcctgtagc cctgaggtgc ccccaggtgc cctactggtt gtgggcctct     180

gtcagccccc gcatcaacct gacatggcat aaaaatgact ctgctaggac ggtcccagga     240
```

-continued

```
gaagaagaga cacggatgtg ggcccaggac ggtgctctgt ggcttctgcc agccttgcag    300
gaggactctg gcacctacgt ctgcactact agaaatgctt cttactgtga caaaatgtcc    360
attgagctca gagtttttga gaatacagat gctttcctgc cgttcatctc atacccgcaa    420
attttaacct tgtcaacctc tggggtatta gtatgccctg acctgagtga attcacccgt    480
gacaaaactg acgtgaagat tcaatggtac aaggattctc ttcttttgga taaagacaat    540
gagaaatttc taagtgtgag gggaccact cacttactcg tacacgatgt ggccctggaa     600
gatgctggct attaccgctg tgtcctgaca tttgcccatg aaggccagca atacaacatc    660
actaggagta ttgagctacg catcaagaaa aaaaaagaag agaccattcc tgtgatcatt    720
tccccctca agaccatatc agcttctctg ggtcaagac tgacaatccc atgtaaggtg       780
tttctgggaa ccggcacacc cttaaccacc atgctgtggt ggacggccaa tgacacccac    840
atagagagcg cctacccggg aggccgcgtg accgaggggc cacgccagga atattcagaa    900
aataatgaga actacattga agtgccattg atttttgatc ctgtcacaag agaggatttg    960
cacatggatt ttaaatgtgt tgtccataat accctgagtt ttcagacact acgcaccaca   1020
gtcaaggaag cctcctccac gttctcagaa cgctgcgatg actggggact agacaccatg   1080
aggcaaatcc aagtgtttga agatgagcca gctcgcatca agtgcccact ctttgaacac   1140
ttcttgaaat tcaactacag cacagcccat tcagctggcc ttactctgat ctggtattgg   1200
actaggcagg accgggacct tgaggagcca attaacttcc gcctccccga gaaccgcatt   1260
agtaaggaga aagatgtgct gtggttccgg cccactctcc tcaatgacac tggcaactat   1320
acctgcatgt taaggaacac tacatattgc agcaaagttg catttccctt ggaagttgtt   1380
caaaaagaca gctgtttcaa ttcccccatg aaactcccag tgcataaact gtatatagaa   1440
tatggcattc agaggatcac ttgtccaaat gtagatggat attttccttc cagtgtcaaa   1500
ccgactatca cttggtatat gggctgttat aaaatacaga attttaataa tgtaataccc   1560
gaaggtatga acttgagttt cctcattgcc ttaatttcaa ataatggaaa ttacacatgt   1620
gttgttacat atccagaaaa tggacgtacg tttcatctca ccaggactct gactgtaaag   1680
gtagtaggct ctccaaaaaa tgcagtgccc cctgtgatcc attcacctaa tgatcatgtg   1740
gtctatgaga aagaaccagg agaggagcta ctcattccct gtacggtcta ttttagtttt   1800
ctgatggatt ctcgcaatga ggtttggtgg accattgatg gaaaaaaacc tgatgacatc   1860
actattgatg tcaccattaa cgaaagtata agtcatagta gaacagaaga tgaaacaaga   1920
actcagattt tgagcatcaa gaaagttacc tctgaggatc tcaagcgcag ctatgtctgt   1980
catgctagaa gtgccaaagg cgaagttgcc aaagcagcca aggtgaagca gaaagtgcca   2040
gctccaagat acacagtgtc cggagacaaa actcacacat gcccaccgtg cccagcacct   2100
gaactcctgg ggggaccgtc agtcttcctc ttccccccaa aacccaagga caccctcatg   2160
atctcccgga cccctgaggt cacatgcgtg gtggtggacg tgagccacga agaccctgag   2220
gtcaagttca actggtacgt ggacggcgtg gaggtgcata atgccaagac aaagccgcgg   2280
gaggagcagt acaacagcac gtaccgtgtg gtcagcgtcc tcaccgtcct gcaccaggac   2340
tggctgaatg gcaaggagta caagtgcaag gtctccaaca aagccctccc agcccccatc   2400
gagaaaacca tctccaaagc caaagggcag ccccgagaac cacaggtgta caccctgccc   2460
ccatcccggg atgagctgac caagaaccag gtcagcctga cctgcctggt caaaggcttc   2520
tatcccagcg acatcgccgt ggagtgggag agcaatgggc agccggagaa caactacaag   2580
accacgcctc ccgtgctgga ctccgacggc tccttcttcc tctatagcaa gctcaccgtg   2640
```

-continued gacaagagca ggtggcagca ggggaacgtc ttctcatgct ccgtgatgca tgaggctctg 2700
cacaaccact acacgcagaa gagcctctcc ctgtctccgg gtaaatga 2748

<210> SEQ ID NO 46
<211> LENGTH: 915
<212> TYPE: PRT
<213> ORGANISM: Homo sapiens

<400> SEQUENCE: 46

Met Val Arg Leu Tyr Val Leu Val Met Gly Val Ser Ala Phe Thr Leu
1 5 10 15

Gln Pro Ala Ala His Thr Gly Ala Ala Arg Ser Cys Arg Phe Arg Gly
20 25 30

Arg His Tyr Lys Arg Glu Phe Arg Leu Glu Gly Glu Pro Val Ala Leu
35 40 45

Arg Cys Pro Gln Val Pro Tyr Trp Leu Trp Ala Ser Val Ser Pro Arg
50 55 60

Ile Asn Leu Thr Trp His Lys Asn Asp Ser Ala Arg Thr Val Pro Gly
65 70 75 80

Glu Glu Glu Thr Arg Met Trp Ala Gln Asp Gly Ala Leu Trp Leu Leu
85 90 95

Pro Ala Leu Gln Glu Asp Ser Gly Thr Tyr Val Cys Thr Thr Arg Asn
100 105 110

Ala Ser Tyr Cys Asp Lys Met Ser Ile Glu Leu Arg Val Phe Glu Asn
115 120 125

Thr Asp Ala Phe Leu Pro Phe Ile Ser Tyr Pro Gln Ile Leu Thr Leu
130 135 140

Ser Thr Ser Gly Val Leu Val Cys Pro Asp Leu Ser Glu Phe Thr Arg
145 150 155 160

Asp Lys Thr Asp Val Lys Ile Gln Trp Tyr Lys Asp Ser Leu Leu Leu
165 170 175

Asp Lys Asp Asn Glu Lys Phe Leu Ser Val Arg Gly Thr Thr His Leu
180 185 190

Leu Val His Asp Val Ala Leu Glu Asp Ala Gly Tyr Tyr Arg Cys Val
195 200 205

Leu Thr Phe Ala His Glu Gly Gln Gln Tyr Asn Ile Thr Arg Ser Ile
210 215 220

Glu Leu Arg Ile Lys Lys Lys Lys Glu Glu Thr Ile Pro Val Ile Ile
225 230 235 240

Ser Pro Leu Lys Thr Ile Ser Ala Ser Leu Gly Ser Arg Leu Thr Ile
245 250 255

Pro Cys Lys Val Phe Leu Gly Thr Gly Thr Pro Leu Thr Thr Met Leu
260 265 270

Trp Trp Thr Ala Asn Asp Thr His Ile Glu Ser Ala Tyr Pro Gly Gly
275 280 285

Arg Val Thr Glu Gly Pro Arg Gln Glu Tyr Ser Glu Asn Asn Glu Asn
290 295 300

Tyr Ile Glu Val Pro Leu Ile Phe Asp Pro Val Thr Arg Glu Asp Leu
305 310 315 320

His Met Asp Phe Lys Cys Val Val His Asn Thr Leu Ser Phe Gln Thr
325 330 335

Leu Arg Thr Thr Val Lys Glu Ala Ser Ser Thr Phe Ser Glu Arg Cys
340 345 350

Asp Asp Trp Gly Leu Asp Thr Met Arg Gln Ile Gln Val Phe Glu Asp
355 360 365

```
Glu Pro Ala Arg Ile Lys Cys Pro Leu Phe Glu His Phe Leu Lys Phe
    370                 375                 380

Asn Tyr Ser Thr Ala His Ser Ala Gly Leu Thr Leu Ile Trp Tyr Trp
385                 390                 395                 400

Thr Arg Gln Asp Arg Asp Leu Glu Glu Pro Ile Asn Phe Arg Leu Pro
                405                 410                 415

Glu Asn Arg Ile Ser Lys Glu Lys Asp Val Leu Trp Phe Arg Pro Thr
            420                 425                 430

Leu Leu Asn Asp Thr Gly Asn Tyr Thr Cys Met Leu Arg Asn Thr Thr
        435                 440                 445

Tyr Cys Ser Lys Val Ala Phe Pro Leu Glu Val Val Gln Lys Asp Ser
    450                 455                 460

Cys Phe Asn Ser Pro Met Lys Leu Pro Val His Lys Leu Tyr Ile Glu
465                 470                 475                 480

Tyr Gly Ile Gln Arg Ile Thr Cys Pro Asn Val Asp Gly Tyr Phe Pro
                485                 490                 495

Ser Ser Val Lys Pro Thr Ile Thr Trp Tyr Met Gly Cys Tyr Lys Ile
            500                 505                 510

Gln Asn Phe Asn Asn Val Ile Pro Glu Gly Met Asn Leu Ser Phe Leu
        515                 520                 525

Ile Ala Leu Ile Ser Asn Asn Gly Asn Tyr Thr Cys Val Val Thr Tyr
    530                 535                 540

Pro Glu Asn Gly Arg Thr Phe His Leu Thr Arg Thr Leu Thr Val Lys
545                 550                 555                 560

Val Val Gly Ser Pro Lys Asn Ala Val Pro Pro Val Ile His Ser Pro
                565                 570                 575

Asn Asp His Val Val Tyr Glu Lys Glu Pro Gly Glu Glu Leu Leu Ile
            580                 585                 590

Pro Cys Thr Val Tyr Phe Ser Phe Leu Met Asp Ser Arg Asn Glu Val
        595                 600                 605

Trp Trp Thr Ile Asp Gly Lys Lys Pro Asp Asp Ile Thr Ile Asp Val
    610                 615                 620

Thr Ile Asn Glu Ser Ile Ser His Ser Arg Thr Glu Asp Glu Thr Arg
625                 630                 635                 640

Thr Gln Ile Leu Ser Ile Lys Lys Val Thr Ser Glu Asp Leu Lys Arg
                645                 650                 655

Ser Tyr Val Cys His Ala Arg Ser Ala Lys Gly Glu Val Ala Lys Ala
            660                 665                 670

Ala Lys Val Lys Gln Lys Val Pro Ala Pro Arg Tyr Thr Val Ser Gly
        675                 680                 685

Asp Lys Thr His Thr Cys Pro Pro Cys Pro Ala Pro Glu Leu Leu Gly
    690                 695                 700

Gly Pro Ser Val Phe Leu Phe Pro Pro Lys Pro Lys Asp Thr Leu Met
705                 710                 715                 720

Ile Ser Arg Thr Pro Glu Val Thr Cys Val Val Val Asp Val Ser His
                725                 730                 735

Glu Asp Pro Glu Val Lys Phe Asn Trp Tyr Val Asp Gly Val Glu Val
            740                 745                 750

His Asn Ala Lys Thr Lys Pro Arg Glu Glu Gln Tyr Asn Ser Thr Tyr
        755                 760                 765

Arg Val Val Ser Val Leu Thr Val Leu His Gln Asp Trp Leu Asn Gly
    770                 775                 780

Lys Glu Tyr Lys Cys Lys Val Ser Asn Lys Ala Leu Pro Ala Pro Ile
```

-continued 785 790 795 800

Glu Lys Thr Ile Ser Lys Ala Lys Gly Gln Pro Arg Glu Pro Gln Val
805 810 815

Tyr Thr Leu Pro Pro Ser Arg Asp Glu Leu Thr Lys Asn Gln Val Ser
820 825 830

Leu Thr Cys Leu Val Lys Gly Phe Tyr Pro Ser Asp Ile Ala Val Glu
835 840 845

Trp Glu Ser Asn Gly Gln Pro Glu Asn Asn Tyr Lys Thr Thr Pro Pro
850 855 860

Val Leu Asp Ser Asp Gly Ser Phe Phe Leu Tyr Ser Lys Leu Thr Val
865 870 875 880

Asp Lys Ser Arg Trp Gln Gln Gly Asn Val Phe Ser Cys Ser Val Met
885 890 895

His Glu Ala Leu His Asn His Tyr Thr Gln Lys Ser Leu Ser Leu Ser
900 905 910

Pro Gly Lys
915

<210> SEQ ID NO 47
<211> LENGTH: 2754
<212> TYPE: DNA
<213> ORGANISM: Homo sapiens

<400> SEQUENCE: 47
atggtgcgct tgtacgtgtt ggtaatggga gtttctgcct tcacccttca gcctgcggca 60
cacacagggg ctgccagaag ctgccggttt cgtgggaggc attacaagcg ggagttcagg 120
ctggaagggg agcctgtagc cctgaggtgc ccccaggtgc cctactggtt gtgggcctct 180
gtcagccccc gcatcaacct gacatggcat aaaaatgact ctgctaggac ggtcccagga 240
gaagaagaga cacggatgtg ggcccaggac ggtgctctgt ggcttctgcc agccttgcag 300
gaggactctg gcacctacgt ctgcactact agaaatgctt cttactgtga caaaatgtcc 360
attgagctca gagtttttga gaatacagat gctttcctgc cgttcatctc atacccgcaa 420
attttaacct tgtcaacctc tggggtatta gtatgccctg acctgagtga attcacccgt 480
gacaaaactg acgtgaagat tcaatggtac aaggattctc ttcttttgga taaagacaat 540
gagaaatttc taagtgtgag gggaccact cacttactcg tacacgatgt ggccctggaa 600
gatgctggct attaccgctg tgtcctgaca tttgcccatg aaggccagca atacaacatc 660
actaggagta ttgagctacg catcaagaaa aaaaaagaag agaccattcc tgtgatcatt 720 tccccccctca agaccatatc agcttctctg ggtcaagac tgacaatccc atgtaaggtg 780
tttctgggaa ccggcacacc cttaaccacc atgctgtggt ggacggccaa tgacacccac 840
atagagagcg cctacccggg aggccgcgtg accgaggggc cacgccagga atattcagaa 900
aataatgaga actacattga agtgccattg atttttgatc ctgtcacaag agaggatttg 960
cacatggatt ttaaatgtgt tgtccataat accctgagtt ttcagacact acgcaccaca 1020
gtcaaggaag cctcctccac gttctcagaa cgctgcgatg actggggact agacaccatg 1080
aggcaaatcc aagtgtttga agatgagcca gctcgcatca agtgcccact ctttgaacac 1140
ttcttgaaat tcaactacag cacagcccat tcagctggcc ttactctgat ctggtattgg 1200
actaggcagg accgggacct tgaggagcca attaacttcc gcctccccga gaaccgcatt 1260
agtaaggaga aagatgtgct gtggttccgg cccactctcc tcaatgacac tggcaactat 1320
acctgcatgt taaggaacac tacatattgc agcaaagttg catttccctt ggaagttgtt 1380

-continued

```
caaaaagaca gctgtttcaa ttcccccatg aaactcccag tgcataaact gtatatagaa   1440

tatggcattc agaggatcac ttgtccaaat gtagatggat attttccttc cagtgtcaaa   1500

ccgactatca cttggtatat gggctgttat aaaatacaga attttaataa tgtaataccc   1560

gaaggtatga acttgagttt cctcattgcc ttaatttcaa ataatggaaa ttacacatgt   1620

gttgttacat atccagaaaa tggacgtacg tttcatctca ccaggactct gactgtaaag   1680

gtagtaggct ctccaaaaaa tgcagtgccc cctgtgatcc attcacctaa tgatcatgtg   1740

gtctatgaga aagaaccagg agaggagcta ctcattccct gtacggtcta ttttagtttt   1800

ctgatggatt ctcgcaatga ggtttggtgg accattgatg gaaaaaaacc tgatgacatc   1860

actattgatg tcaccattaa cgaaagtata agtcatagta gaacagaaga tgaaacaaga   1920

actcagattt tgagcatcaa gaaagttacc tctgaggatc tcaagcgcag ctatgtctgt   1980

catgctagaa gtgccaaagg cgaagttgcc aaagcagcca aggtgaagca gaaagtgcca   2040

gctccaagat acacagtgtc cggagagtcc aaatacggtc cgccatgccc atcatgccca   2100

gcacctgagt tcctgggggg accatcagtc ttcctgttcc ccccaaaacc caaggacact   2160

ctcatgatct cccggacccc tgaggtcacg tgcgtggtgg tggacgtgag ccaggaagac   2220

cccgaggtcc agttcaactg gtacgtggat ggcgtggagg tgcataatgc caagacaaag   2280

ccgcgggagg agcagttcaa cagcacgtac cgtgtggtca gcgtcctcac cgtcctgcac   2340

caggactggc tgaacggcaa ggagtacaag tgcaaggtct ccaacaaagg cctcccgtcc   2400

tccatcgaga aaaccatctc caaagccaaa gggcagcccc gagagccaca ggtgtacacc   2460

ctgcccccat cccaggagga gatgaccaag aaccaggtca gcctgacctg cctggtcaaa   2520

ggcttctacc ccagcgacat cgccgtggag tgggagagca atgggcagcc ggagaacaac   2580

tacaagacca cgcctcccgt gctggactcc gacggctcct tcttcctcta cagcaggcta   2640

accgtggaca agagcaggtg gcaggagggg aatgtcttct catgctccgt gatgcatgag   2700

gctctgcaca accactacac acagaagagc ctctccctgt ctctgggtaa atga         2754
```

```
<210> SEQ ID NO 48
<211> LENGTH: 917
<212> TYPE: PRT
<213> ORGANISM: Homo sapiens

<400> SEQUENCE: 48

Met Val Arg Leu Tyr Val Leu Val Met Gly Val Ser Ala Phe Thr Leu
 1               5                  10                  15

Gln Pro Ala Ala His Thr Gly Ala Ala Arg Ser Cys Arg Phe Arg Gly
            20                  25                  30

Arg His Tyr Lys Arg Glu Phe Arg Leu Glu Gly Glu Pro Val Ala Leu
        35                  40                  45

Arg Cys Pro Gln Val Pro Tyr Trp Leu Trp Ala Ser Val Ser Pro Arg
    50                  55                  60

Ile Asn Leu Thr Trp His Lys Asn Asp Ser Ala Arg Thr Val Pro Gly
65                  70                  75                  80

Glu Glu Glu Thr Arg Met Trp Ala Gln Asp Gly Ala Leu Trp Leu Leu
                85                  90                  95

Pro Ala Leu Gln Glu Asp Ser Gly Thr Tyr Val Cys Thr Thr Arg Asn
            100                 105                 110

Ala Ser Tyr Cys Asp Lys Met Ser Ile Glu Leu Arg Val Phe Glu Asn
        115                 120                 125

Thr Asp Ala Phe Leu Pro Phe Ile Ser Tyr Pro Gln Ile Leu Thr Leu
    130                 135                 140
```

Ser Thr Ser Gly Val Leu Val Cys Pro Asp Leu Ser Glu Phe Thr Arg
145 150 155 160

Asp Lys Thr Asp Val Lys Ile Gln Trp Tyr Lys Asp Ser Leu Leu Leu
165 170 175

Asp Lys Asp Asn Glu Lys Phe Leu Ser Val Arg Gly Thr Thr His Leu
180 185 190

Leu Val His Asp Val Ala Leu Glu Asp Ala Gly Tyr Tyr Arg Cys Val
195 200 205

Leu Thr Phe Ala His Glu Gly Gln Gln Tyr Asn Ile Thr Arg Ser Ile
210 215 220

Glu Leu Arg Ile Lys Lys Lys Lys Glu Glu Thr Ile Pro Val Ile Ile
225 230 235 240

Ser Pro Leu Lys Thr Ile Ser Ala Ser Leu Gly Ser Arg Leu Thr Ile
245 250 255

Pro Cys Lys Val Phe Leu Gly Thr Gly Thr Pro Leu Thr Thr Met Leu
260 265 270

Trp Trp Thr Ala Asn Asp Thr His Ile Glu Ser Ala Tyr Pro Gly Gly
275 280 285

Arg Val Thr Glu Gly Pro Arg Gln Glu Tyr Ser Glu Asn Asn Glu Asn
290 295 300

Tyr Ile Glu Val Pro Leu Ile Phe Asp Pro Val Thr Arg Glu Asp Leu
305 310 315 320

His Met Asp Phe Lys Cys Val Val His Asn Thr Leu Ser Phe Gln Thr
325 330 335

Leu Arg Thr Thr Val Lys Glu Ala Ser Ser Thr Phe Ser Glu Arg Cys
340 345 350

Asp Asp Trp Gly Leu Asp Thr Met Arg Gln Ile Gln Val Phe Glu Asp
355 360 365

Glu Pro Ala Arg Ile Lys Cys Pro Leu Phe Glu His Phe Leu Lys Phe
370 375 380

Asn Tyr Ser Thr Ala His Ser Ala Gly Leu Thr Leu Ile Trp Tyr Trp
385 390 395 400

Thr Arg Gln Asp Arg Asp Leu Glu Glu Pro Ile Asn Phe Arg Leu Pro
405 410 415

Glu Asn Arg Ile Ser Lys Glu Lys Asp Val Leu Trp Phe Arg Pro Thr
420 425 430

Leu Leu Asn Asp Thr Gly Asn Tyr Thr Cys Met Leu Arg Asn Thr Thr
435 440 445

Tyr Cys Ser Lys Val Ala Phe Pro Leu Glu Val Val Gln Lys Asp Ser
450 455 460

Cys Phe Asn Ser Pro Met Lys Leu Pro Val His Lys Leu Tyr Ile Glu
465 470 475 480

Tyr Gly Ile Gln Arg Ile Thr Cys Pro Asn Val Asp Gly Tyr Phe Pro
485 490 495

Ser Ser Val Lys Pro Thr Ile Thr Trp Tyr Met Gly Cys Tyr Lys Ile
500 505 510

Gln Asn Phe Asn Asn Val Ile Pro Glu Gly Met Asn Leu Ser Phe Leu
515 520 525

Ile Ala Leu Ile Ser Asn Asn Gly Asn Tyr Thr Cys Val Val Thr Tyr
530 535 540

Pro Glu Asn Gly Arg Thr Phe His Leu Thr Arg Thr Leu Thr Val Lys
545 550 555 560

Val Val Gly Ser Pro Lys Asn Ala Val Pro Pro Val Ile His Ser Pro

-continued

```
                565                 570                 575

Asn Asp His Val Val Tyr Glu Lys Glu Pro Gly Glu Glu Leu Leu Ile
            580                 585                 590

Pro Cys Thr Val Tyr Phe Ser Phe Leu Met Asp Ser Arg Asn Glu Val
        595                 600                 605

Trp Trp Thr Ile Asp Gly Lys Lys Pro Asp Asp Ile Thr Ile Asp Val
    610                 615                 620

Thr Ile Asn Glu Ser Ile Ser His Ser Arg Thr Glu Asp Glu Thr Arg
625                 630                 635                 640

Thr Gln Ile Leu Ser Ile Lys Lys Val Thr Ser Glu Asp Leu Lys Arg
                645                 650                 655

Ser Tyr Val Cys His Ala Arg Ser Ala Lys Gly Glu Val Ala Lys Ala
            660                 665                 670

Ala Lys Val Lys Gln Lys Val Pro Ala Pro Arg Tyr Thr Val Ser Gly
        675                 680                 685

Glu Ser Lys Tyr Gly Pro Pro Cys Pro Ser Cys Pro Ala Pro Glu Phe
    690                 695                 700

Leu Gly Gly Pro Ser Val Phe Leu Phe Pro Pro Lys Pro Lys Asp Thr
705                 710                 715                 720

Leu Met Ile Ser Arg Thr Pro Glu Val Thr Cys Val Val Val Asp Val
                725                 730                 735

Ser Gln Glu Asp Pro Glu Val Gln Phe Asn Trp Tyr Val Asp Gly Val
            740                 745                 750

Glu Val His Asn Ala Lys Thr Lys Pro Arg Glu Glu Gln Phe Asn Ser
        755                 760                 765

Thr Tyr Arg Val Val Ser Val Leu Thr Val Leu His Gln Asp Trp Leu
    770                 775                 780

Asn Gly Lys Glu Tyr Lys Cys Lys Val Ser Asn Lys Gly Leu Pro Ser
785                 790                 795                 800

Ser Ile Glu Lys Thr Ile Ser Lys Ala Lys Gly Gln Pro Arg Glu Pro
                805                 810                 815

Gln Val Tyr Thr Leu Pro Pro Ser Gln Glu Glu Met Thr Lys Asn Gln
            820                 825                 830

Val Ser Leu Thr Cys Leu Val Lys Gly Phe Tyr Pro Ser Asp Ile Ala
        835                 840                 845

Val Glu Trp Glu Ser Asn Gly Gln Pro Glu Asn Asn Tyr Lys Thr Thr
    850                 855                 860

Pro Pro Val Leu Asp Ser Asp Gly Ser Phe Phe Leu Tyr Ser Arg Leu
865                 870                 875                 880

Thr Val Asp Lys Ser Arg Trp Gln Glu Gly Asn Val Phe Ser Cys Ser
                885                 890                 895

Val Met His Glu Ala Leu His Asn His Tyr Thr Gln Lys Ser Leu Ser
            900                 905                 910

Leu Ser Leu Gly Lys
        915


<210> SEQ ID NO 49
<211> LENGTH: 2754
<212> TYPE: DNA
<213> ORGANISM: Homo sapiens

<400> SEQUENCE: 49

atggtgcgct tgtacgtgtt ggtaatggga gtttctgcct tcacccttca gcctgcggca      60

cacacagggg ctgccagaag ctgccggttt cgtgggaggc attacaagcg ggagttcagg     120
```

-continued

```
ctggaagggg agcctgtagc cctgaggtgc ccccaggtgc cctactggtt gtgggcctct    180
gtcagccccc gcatcaacct gacatggcat aaaaatgact ctgctaggac ggtcccagga    240
gaagaagaga cacggatgtg ggcccaggac ggtgctctgt ggcttctgcc agccttgcag    300
gaggactctg gcacctacgt ctgcactact agaaatgctt cttactgtga caaaatgtcc    360
attgagctca gagtttttga gaatacagat gctttcctgc cgttcatctc atacccgcaa    420
attttaacct tgtcaacctc tggggtatta gtatgccctg acctgagtga attcacccgt    480
gacaaaactg acgtgaagat tcaatggtac aaggattctc ttcttttgga taaagacaat    540
gagaaatttc taagtgtgag ggggaccact cacttactcg tacacgatgt ggccctggaa    600
gatgctggct attaccgctg tgtcctgaca tttgcccatg aaggccagca atacaacatc    660
actaggagta ttgagctacg catcaagaaa aaaaaagaag agaccattcc tgtgatcatt    720
tccccccctca agaccatatc agcttctctg ggtcaagac tgacaatccc atgtaaggtg    780
tttctgggaa ccggcacacc cttaaccacc atgctgtggt ggacggccaa tgacacccac    840
atagagagcg cctacccggg aggccgcgtg accgaggggc cacgccagga atattcagaa    900
aataatgaga actacattga agtgccattg atttttgatc ctgtcacaag agaggatttg    960
cacatggatt ttaaatgtgt tgtccataat accctgagtt ttcagacact acgcaccaca   1020
gtcaaggaag cctcctccac gttctcagaa cgctgcgatg actggggact agacaccatg   1080
aggcaaatcc aagtgtttga agatgagcca gctcgcatca agtgcccact ctttgaacac   1140
ttcttgaaat tcaactacag cacagcccat tcagctggcc ttactctgat ctggtattgg   1200
actaggcagg accgggacct tgaggagcca attaacttcc gcctccccga gaaccgcatt   1260
agtaaggaga aagatgtgct gtggttccgg cccactctcc tcaatgacac tggcaactat   1320
acctgcatgt taaggaacac tacatattgc agcaaagttg catttccctt ggaagttgtt   1380
caaaaagaca gctgtttcaa ttcccccatg aaactcccag tgcataaact gtatatagaa   1440
tatggcattc agaggatcac ttgtccaaat gtagatggat attttccttc cagtgtcaaa   1500
ccgactatca cttggtatat gggctgttat aaaatacaga atttaataa tgtaataccc   1560
gaaggtatga acttgagttt cctcattgcc ttaatttcaa ataatggaaa ttacacatgt   1620
gttgttacat atccagaaaa tggacgtacg tttcatctca ccaggactct gactgtaaag   1680
gtagtaggct ctccaaaaaa tgcagtgccc cctgtgatcc attcacctaa tgatcatgtg   1740
gtctatgaga aagaaccagg agaggagcta ctcattccct gtacggtcta ttttagtttt   1800
ctgatggatt ctcgcaatga ggtttggtgg accattgatg gaaaaaaacc tgatgacatc   1860
actattgatg tcaccattaa cgaaagtata agtcatagta gaacagaaga tgaaacaaga   1920
actcagattt tgagcatcaa gaaagttacc tctgaggatc tcaagcgcag ctatgtctgt   1980
catgctagaa gtgccaaagg cgaagttgcc aaagcagcca aggtgaagca gaaagtgcca   2040
gctccaagat acacagtgtc cggagagtcc aaatacggtc cgccatgccc accatgccca   2100
gcacctgagt tcctgggggg accatcagtc ttcctgttcc ccccaaaacc caaggacact   2160
ctcatgatct cccggacccc tgaggtcacg tgcgtggtgg tggacgtgag ccaggaagac   2220
cccgaggtcc agttcaactg gtacgtggat ggcgtggagg tgcataatgc caagacaaag   2280
ccgcgggagg agcagttcaa cagcacgtac cgtgtggtca gcgtcctcac cgtcctgcac   2340
caggactggc tgaacggcaa ggagtacaag tgcaaggtct ccaacaaagg cctcccgtcc   2400
tccatcgaga aaaccatctc caaagccaaa gggcagcccc gagagccaca ggtgtacacc   2460
ctgcccccat cccaggagga gatgaccaag aaccaggtca gcctgacctg cctggtcaaa   2520
```

-continued

```
ggcttctacc ccagcgacat cgccgtggag tgggagagca atgggcagcc ggagaacaac   2580

tacaagacca cgcctcccgt gctggactcc gacggctcct tcttcctcta cagcaggcta   2640

accgtggaca agagcaggtg gcaggagggg aatgtcttct catgctccgt gatgcatgag   2700

gctctgcaca accactacac acagaagagc ctctccctgt ctctgggtaa atga         2754


<210> SEQ ID NO 50
<211> LENGTH: 917
<212> TYPE: PRT
<213> ORGANISM: Homo sapiens

<400> SEQUENCE: 50

Met Val Arg Leu Tyr Val Leu Val Met Gly Val Ser Ala Phe Thr Leu
 1               5                  10                  15

Gln Pro Ala Ala His Thr Gly Ala Ala Arg Ser Cys Arg Phe Arg Gly
            20                  25                  30

Arg His Tyr Lys Arg Glu Phe Arg Leu Glu Gly Glu Pro Val Ala Leu
        35                  40                  45

Arg Cys Pro Gln Val Pro Tyr Trp Leu Trp Ala Ser Val Ser Pro Arg
    50                  55                  60

Ile Asn Leu Thr Trp His Lys Asn Asp Ser Ala Arg Thr Val Pro Gly
65                  70                  75                  80

Glu Glu Glu Thr Arg Met Trp Ala Gln Asp Gly Ala Leu Trp Leu Leu
                85                  90                  95

Pro Ala Leu Gln Glu Asp Ser Gly Thr Tyr Val Cys Thr Thr Arg Asn
            100                 105                 110

Ala Ser Tyr Cys Asp Lys Met Ser Ile Glu Leu Arg Val Phe Glu Asn
        115                 120                 125

Thr Asp Ala Phe Leu Pro Phe Ile Ser Tyr Pro Gln Ile Leu Thr Leu
    130                 135                 140

Ser Thr Ser Gly Val Leu Val Cys Pro Asp Leu Ser Glu Phe Thr Arg
145                 150                 155                 160

Asp Lys Thr Asp Val Lys Ile Gln Trp Tyr Lys Asp Ser Leu Leu Leu
                165                 170                 175

Asp Lys Asp Asn Glu Lys Phe Leu Ser Val Arg Gly Thr Thr His Leu
            180                 185                 190

Leu Val His Asp Val Ala Leu Glu Asp Ala Gly Tyr Tyr Arg Cys Val
        195                 200                 205

Leu Thr Phe Ala His Glu Gly Gln Gln Tyr Asn Ile Thr Arg Ser Ile
    210                 215                 220

Glu Leu Arg Ile Lys Lys Lys Lys Glu Glu Thr Ile Pro Val Ile Ile
225                 230                 235                 240

Ser Pro Leu Lys Thr Ile Ser Ala Ser Leu Gly Ser Arg Leu Thr Ile
                245                 250                 255

Pro Cys Lys Val Phe Leu Gly Thr Gly Thr Pro Leu Thr Thr Met Leu
            260                 265                 270

Trp Trp Thr Ala Asn Asp Thr His Ile Glu Ser Ala Tyr Pro Gly Gly
        275                 280                 285

Arg Val Thr Glu Gly Pro Arg Gln Glu Tyr Ser Glu Asn Asn Glu Asn
    290                 295                 300

Tyr Ile Glu Val Pro Leu Ile Phe Asp Pro Val Thr Arg Glu Asp Leu
305                 310                 315                 320

His Met Asp Phe Lys Cys Val Val His Asn Thr Leu Ser Phe Gln Thr
                325                 330                 335

Leu Arg Thr Thr Val Lys Glu Ala Ser Ser Thr Phe Ser Glu Arg Cys
```

-continued

```
            340                 345                 350

Asp Asp Trp Gly Leu Asp Thr Met Arg Gln Ile Gln Val Phe Glu Asp
        355                 360                 365

Glu Pro Ala Arg Ile Lys Cys Pro Leu Phe Glu His Phe Leu Lys Phe
    370                 375                 380

Asn Tyr Ser Thr Ala His Ser Ala Gly Leu Thr Leu Ile Trp Tyr Trp
385                 390                 395                 400

Thr Arg Gln Asp Arg Asp Leu Glu Glu Pro Ile Asn Phe Arg Leu Pro
                405                 410                 415

Glu Asn Arg Ile Ser Lys Glu Lys Asp Val Leu Trp Phe Arg Pro Thr
            420                 425                 430

Leu Leu Asn Asp Thr Gly Asn Tyr Thr Cys Met Leu Arg Asn Thr Thr
        435                 440                 445

Tyr Cys Ser Lys Val Ala Phe Pro Leu Glu Val Val Gln Lys Asp Ser
    450                 455                 460

Cys Phe Asn Ser Pro Met Lys Leu Pro Val His Lys Leu Tyr Ile Glu
465                 470                 475                 480

Tyr Gly Ile Gln Arg Ile Thr Cys Pro Asn Val Asp Gly Tyr Phe Pro
                485                 490                 495

Ser Ser Val Lys Pro Thr Ile Thr Trp Tyr Met Gly Cys Tyr Lys Ile
            500                 505                 510

Gln Asn Phe Asn Asn Val Ile Pro Glu Gly Met Asn Leu Ser Phe Leu
        515                 520                 525

Ile Ala Leu Ile Ser Asn Asn Gly Asn Tyr Thr Cys Val Val Thr Tyr
    530                 535                 540

Pro Glu Asn Gly Arg Thr Phe His Leu Thr Arg Thr Leu Thr Val Lys
545                 550                 555                 560

Val Val Gly Ser Pro Lys Asn Ala Val Pro Pro Val Ile His Ser Pro
                565                 570                 575

Asn Asp His Val Val Tyr Glu Lys Glu Pro Gly Glu Glu Leu Leu Ile
            580                 585                 590

Pro Cys Thr Val Tyr Phe Ser Phe Leu Met Asp Ser Arg Asn Glu Val
        595                 600                 605

Trp Trp Thr Ile Asp Gly Lys Lys Pro Asp Asp Ile Thr Ile Asp Val
    610                 615                 620

Thr Ile Asn Glu Ser Ile Ser His Ser Arg Thr Glu Asp Glu Thr Arg
625                 630                 635                 640

Thr Gln Ile Leu Ser Ile Lys Lys Val Thr Ser Glu Asp Leu Lys Arg
                645                 650                 655

Ser Tyr Val Cys His Ala Arg Ser Ala Lys Gly Glu Val Ala Lys Ala
            660                 665                 670

Ala Lys Val Lys Gln Lys Val Pro Ala Pro Arg Tyr Thr Val Ser Gly
        675                 680                 685

Glu Ser Lys Tyr Gly Pro Pro Cys Pro Pro Cys Pro Ala Pro Glu Phe
    690                 695                 700

Leu Gly Gly Pro Ser Val Phe Leu Phe Pro Pro Lys Pro Lys Asp Thr
705                 710                 715                 720

Leu Met Ile Ser Arg Thr Pro Glu Val Thr Cys Val Val Val Asp Val
                725                 730                 735

Ser Gln Glu Asp Pro Glu Val Gln Phe Asn Trp Tyr Val Asp Gly Val
            740                 745                 750

Glu Val His Asn Ala Lys Thr Lys Pro Arg Glu Glu Gln Phe Asn Ser
        755                 760                 765
```

-continued

```
Thr Tyr Arg Val Val Ser Val Leu Thr Val Leu His Gln Asp Trp Leu
    770                 775                 780

Asn Gly Lys Glu Tyr Lys Cys Lys Val Ser Asn Lys Gly Leu Pro Ser
785                 790                 795                 800

Ser Ile Glu Lys Thr Ile Ser Lys Ala Lys Gly Gln Pro Arg Glu Pro
                805                 810                 815

Gln Val Tyr Thr Leu Pro Pro Ser Gln Glu Glu Met Thr Lys Asn Gln
            820                 825                 830

Val Ser Leu Thr Cys Leu Val Lys Gly Phe Tyr Pro Ser Asp Ile Ala
        835                 840                 845

Val Glu Trp Glu Ser Asn Gly Gln Pro Glu Asn Asn Tyr Lys Thr Thr
    850                 855                 860

Pro Pro Val Leu Asp Ser Asp Gly Ser Phe Phe Leu Tyr Ser Arg Leu
865                 870                 875                 880

Thr Val Asp Lys Ser Arg Trp Gln Glu Gly Asn Val Phe Ser Cys Ser
                885                 890                 895

Val Met His Glu Ala Leu His Asn His Tyr Thr Gln Lys Ser Leu Ser
            900                 905                 910

Leu Ser Leu Gly Lys
        915


<210> SEQ ID NO 51
<211> LENGTH: 2748
<212> TYPE: DNA
<213> ORGANISM: Homo sapiens

<400> SEQUENCE: 51

atggtgcttc tgtggtgtgt agtgagtctc tacttttatg gaatcctgca aagtgatgcc      60

tcagaacgct gcgatgactg gggactagac accatgaggc aaatccaagt gtttgaagat     120

gagccagctc gcatcaagtg cccactcttt gaacacttct tgaaattcaa ctacagcaca     180

gcccattcag ctggccttac tctgatctgg tattggacta ggcaggaccg ggaccttgag     240

gagccaatta acttccgcct ccccgagaac cgcattagta aggagaaaga tgtgctgtgg     300

ttccggccca ctctcctcaa tgacactggc aactatacct gcatgttaag gaacactaca     360

tattgcagca aagttgcatt tcccttggaa gttgttcaaa aagacagctg tttcaattcc     420

cccatgaaac tcccagtgca taaactgtat atagaatatg gcattcagag gatcacttgt     480

ccaaatgtag atggatattt tccttccagt gtcaaaccga ctatcacttg gtatatgggc     540

tgttataaaa tacagaattt taataatgta atacccgaag gtatgaactt gagtttcctc     600

attgccttaa tttcaaataa tggaaattac acatgtgttg ttacatatcc agaaaatgga     660

cgtacgtttc atctcaccag gactctgact gtaaaggtag taggctctcc aaaaaatgca     720

gtgccccctg tgatccattc acctaatgat catgtggtct atgagaaaga accaggagag     780

gagctactca ttccctgtac ggtctatttt agtttttctga tggattctcg caatgaggtt     840

tggtggacca ttgatggaaa aaaacctgat gacatcacta ttgatgtcac cattaacgaa     900

agtataagtc atagtagaac agaagatgaa acaagaactc agattttgag catcaagaaa     960

gttacctctg aggatctcaa gcgcagctat gtctgtcatg ctagaagtgc caaaggcgaa    1020

gttgccaaag cagccaaggt gaagcagaaa gtgccagctc caagatacac agtgcacaca    1080

ggggctgcca gaagctgccg gtttcgtggg aggcattaca agcgggagtt caggctggaa    1140

ggggagcctg tagccctgag gtgcccccag gtgccctact ggttgtgggc ctctgtcagc    1200

cccccgcatca acctgacatg gcataaaaat gactctgcta ggacggtccc aggagaagaa    1260
```

```
gagacacgga tgtgggccca ggacggtgct ctgtggcttc tgccagcctt gcaggaggac   1320

tctggcacct acgtctgcac tactagaaat gcttcttact gtgacaaaat gtccattgag   1380

ctcagagttt ttgagaatac agatgctttc ctgccgttca tctcataccc gcaaatttta   1440

accttgtcaa cctctggggt attagtatgc cctgacctga gtgaattcac ccgtgacaaa   1500

actgacgtga agattcaatg gtacaaggat tctcttcttt tggataaaga caatgagaaa   1560

tttctaagtg tgagggggac cactcactta ctcgtacacg atgtggccct ggaagatgct   1620

ggctattacc gctgtgtcct gacatttgcc catgaaggcc agcaatacaa catcactagg   1680

agtattgagc tacgcatcaa gaaaaaaaaa gaagagacca ttcctgtgat catttccccc   1740

ctcaagacca tatcagcttc tctggggtca agactgacaa tcccatgtaa ggtgtttctg   1800

ggaaccggca caccccttaac caccatgctg tggtggacgg ccaatgacac ccacatagag   1860

agcgcctacc cgggaggccg cgtgaccgag gggccacgcc aggaatattc agaaaataat   1920

gagaactaca ttgaagtgcc attgattttt gatcctgtca caagagagga tttgcacatg   1980

gattttaaat gtgttgtcca taataccctg agttttcaga cactacgcac cacagtcaag   2040

gaagcctcct ccacgttctc cggagacaaa actcacacat gcccaccgtg cccagcacct   2100

gaactcctgg ggggaccgtc agtcttcctc ttccccccaa aacccaagga caccctcatg   2160

atctcccgga cccctgaggt cacatgcgtg gtggtggacg tgagccacga agaccctgag   2220

gtcaagttca actggtacgt ggacggcgtg gaggtgcata atgccaagac aaagccgcgg   2280

gaggagcagt acaacagcac gtaccgtgtg gtcagcgtcc tcaccgtcct gcaccaggac   2340

tggctgaatg gcaaggagta caagtgcaag gtctccaaca aagccctccc agcccccatc   2400

gagaaaacca tctccaaagc caaagggcag ccccgagaac cacaggtgta caccctgccc   2460

ccatcccggg atgagctgac caagaaccag gtcagcctga cctgcctggt caaaggcttc   2520

tatcccagcg acatcgccgt ggagtgggag agcaatgggc agccggagaa caactacaag   2580

accacgcctc ccgtgctgga ctccgacggc tccttcttcc tctatagcaa gctcaccgtg   2640

gacaagagca ggtggcagca ggggaacgtc ttctcatgct ccgtgatgca tgaggctctg   2700

cacaaccact acacgcagaa gagcctctcc ctgtctccgg gtaaatga                2748
```

<210> SEQ ID NO 52
<211> LENGTH: 915
<212> TYPE: PRT
<213> ORGANISM: Homo sapiens

<400> SEQUENCE: 52

```
Met Val Leu Leu Trp Cys Val Val Ser Leu Tyr Phe Tyr Gly Ile Leu
 1               5                  10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
```

```
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val His Thr Gly Ala Ala Arg Ser Cys Arg Phe
        355                 360                 365

Arg Gly Arg His Tyr Lys Arg Glu Phe Arg Leu Glu Gly Glu Pro Val
    370                 375                 380

Ala Leu Arg Cys Pro Gln Val Pro Tyr Trp Leu Trp Ala Ser Val Ser
385                 390                 395                 400

Pro Arg Ile Asn Leu Thr Trp His Lys Asn Asp Ser Ala Arg Thr Val
                405                 410                 415

Pro Gly Glu Glu Glu Thr Arg Met Trp Ala Gln Asp Gly Ala Leu Trp
            420                 425                 430

Leu Leu Pro Ala Leu Gln Glu Asp Ser Gly Thr Tyr Val Cys Thr Thr
        435                 440                 445

Arg Asn Ala Ser Tyr Cys Asp Lys Met Ser Ile Glu Leu Arg Val Phe
    450                 455                 460

Glu Asn Thr Asp Ala Phe Leu Pro Phe Ile Ser Tyr Pro Gln Ile Leu
465                 470                 475                 480

Thr Leu Ser Thr Ser Gly Val Leu Val Cys Pro Asp Leu Ser Glu Phe
                485                 490                 495

Thr Arg Asp Lys Thr Asp Val Lys Ile Gln Trp Tyr Lys Asp Ser Leu
            500                 505                 510

Leu Leu Asp Lys Asp Asn Glu Lys Phe Leu Ser Val Arg Gly Thr Thr
        515                 520                 525

His Leu Leu Val His Asp Val Ala Leu Glu Asp Ala Gly Tyr Tyr Arg
    530                 535                 540
```

Cys Val Leu Thr Phe Ala His Glu Gly Gln Gln Tyr Asn Ile Thr Arg
545 550 555 560

Ser Ile Glu Leu Arg Ile Lys Lys Lys Lys Glu Glu Thr Ile Pro Val
565 570 575

Ile Ile Ser Pro Leu Lys Thr Ile Ser Ala Ser Leu Gly Ser Arg Leu
580 585 590

Thr Ile Pro Cys Lys Val Phe Leu Gly Thr Gly Thr Pro Leu Thr Thr
595 600 605

Met Leu Trp Trp Thr Ala Asn Asp Thr His Ile Glu Ser Ala Tyr Pro
610 615 620

Gly Gly Arg Val Thr Glu Gly Pro Arg Gln Glu Tyr Ser Glu Asn Asn
625 630 635 640

Glu Asn Tyr Ile Glu Val Pro Leu Ile Phe Asp Pro Val Thr Arg Glu
645 650 655

Asp Leu His Met Asp Phe Lys Cys Val Val His Asn Thr Leu Ser Phe
660 665 670

Gln Thr Leu Arg Thr Thr Val Lys Glu Ala Ser Ser Thr Phe Ser Gly
675 680 685

Asp Lys Thr His Thr Cys Pro Pro Cys Pro Ala Pro Glu Leu Leu Gly
690 695 700

Gly Pro Ser Val Phe Leu Phe Pro Pro Lys Pro Lys Asp Thr Leu Met
705 710 715 720

Ile Ser Arg Thr Pro Glu Val Thr Cys Val Val Val Asp Val Ser His
725 730 735

Glu Asp Pro Glu Val Lys Phe Asn Trp Tyr Val Asp Gly Val Glu Val
740 745 750

His Asn Ala Lys Thr Lys Pro Arg Glu Glu Gln Tyr Asn Ser Thr Tyr
755 760 765

Arg Val Val Ser Val Leu Thr Val Leu His Gln Asp Trp Leu Asn Gly
770 775 780

Lys Glu Tyr Lys Cys Lys Val Ser Asn Lys Ala Leu Pro Ala Pro Ile
785 790 795 800

Glu Lys Thr Ile Ser Lys Ala Lys Gly Gln Pro Arg Glu Pro Gln Val
805 810 815

Tyr Thr Leu Pro Pro Ser Arg Asp Glu Leu Thr Lys Asn Gln Val Ser
820 825 830

Leu Thr Cys Leu Val Lys Gly Phe Tyr Pro Ser Asp Ile Ala Val Glu
835 840 845

Trp Glu Ser Asn Gly Gln Pro Glu Asn Asn Tyr Lys Thr Thr Pro Pro
850 855 860

Val Leu Asp Ser Asp Gly Ser Phe Phe Leu Tyr Ser Lys Leu Thr Val
865 870 875 880

Asp Lys Ser Arg Trp Gln Gln Gly Asn Val Phe Ser Cys Ser Val Met
885 890 895

His Glu Ala Leu His Asn His Tyr Thr Gln Lys Ser Leu Ser Leu Ser
900 905 910

Pro Gly Lys
915

<210> SEQ ID NO 53
<211> LENGTH: 2754
<212> TYPE: DNA
<213> ORGANISM: Homo sapiens

<400> SEQUENCE: 53

-continued

```
atggtgcttc tgtggtgtgt agtgagtctc tacttttatg gaatcctgca aagtgatgcc     60
tcagaacgct gcgatgactg ggactagac accatgaggc aaatccaagt gtttgaagat     120
gagccagctc gcatcaagtg cccactcttt gaacacttct tgaaattcaa ctacagcaca    180
gcccattcag ctggccttac tctgatctgg tattggacta ggcaggaccg ggaccttgag    240
gagccaatta acttccgcct ccccgagaac cgcattagta aggagaaaga tgtgctgtgg    300
ttccggccca ctctcctcaa tgacactggc aactatacct gcatgttaag gaacactaca    360
tattgcagca aagttgcatt tcccttggaa gttgttcaaa aagacagctg tttcaattcc    420
cccatgaaac tcccagtgca taaactgtat atagaatatg gcattcagag gatcacttgt    480
ccaaatgtag atggatattt tccttccagt gtcaaaccga ctatcacttg gtatatgggc    540
tgttataaaa tacagaattt taataatgta atacccgaag gtatgaactt gagtttcctc    600
attgccttaa tttcaaataa tggaaattac acatgtgttg ttacatatcc agaaaatgga    660
cgtacgtttc atctcaccag gactctgact gtaaaggtag taggctctcc aaaaaatgca    720
gtgccccctg tgatccattc acctaatgat catgtggtct atgagaaaga accaggagag    780
gagctactca ttccctgtac ggtctatttt agttttctga tggattctcg caatgaggtt    840
tggtggacca ttgatggaaa aaaacctgat gacatcacta ttgatgtcac cattaacgaa    900
agtataagtc atagtagaac agaagatgaa acaagaactc agattttgag catcaagaaa    960
gttacctctg aggatctcaa gcgcagctat gtctgtcatg ctagaagtgc caaaggcgaa   1020
gttgccaaag cagccaaggt gaagcagaaa gtgccagctc caagatacac agtgcacaca   1080
ggggctgcca gaagctgccg gtttcgtggg aggcattaca agcgggagtt caggctggaa   1140
ggggagcctg tagccctgag gtgcccccag gtgccctact ggttgtgggc ctctgtcagc   1200
ccccgcatca acctgacatg gcataaaaat gactctgcta ggacggtccc aggagaagaa   1260
gagacacgga tgtgggccca ggacggtgct ctgtggcttc tgccagcctt gcaggaggac   1320
tctggcacct acgtctgcac tactagaaat gcttcttact gtgacaaaat gtccattgag   1380
ctcagagttt ttgagaatac agatgctttc ctgccgttca tctcataccc gcaaatttta   1440
accttgtcaa cctctggggt attagtatgc cctgacctga gtgaattcac ccgtgacaaa   1500
actgacgtga agattcaatg gtacaaggat tctcttcttt tggataaaga caatgagaaa   1560
tttctaagtg tgagggggac cactcactta ctcgtacacg atgtggccct ggaagatgct   1620
ggctattacc gctgtgtcct gacatttgcc catgaaggcc agcaatacaa catcactagg   1680
agtattgagc tacgcatcaa gaaaaaaaaa gaagagacca ttcctgtgat catttccccc   1740
ctcaagacca tatcagcttc tctggggtca agactgacaa tcccatgtaa ggtgtttctg   1800
ggaaccggca caccccttaac caccatgctg tggtggacgg ccaatgacac ccacatagag   1860
agcgcctacc cgggaggccg cgtgaccgag gggccacgcc aggaatattc agaaaataat   1920
gagaactaca ttgaagtgcc attgattttt gatcctgtca caagagagga tttgcacatg   1980
gattttaaat gtgttgtcca taataccctg agttttcaga cactacgcac cacagtcaag   2040
gaagcctcct ccacgttctc cggagagtcc aaatacggtc cgccatgccc atcatgccca   2100
gcacctgagt tcctgggggg accatcagtc ttcctgttcc ccccaaaacc caaggacact   2160
ctcatgatct cccggacccc tgaggtcacg tgcgtggtgg tggacgtgag ccaggaagac   2220
cccgaggtcc agttcaactg gtacgtggat ggcgtggagg tgcataatgc caagacaaag   2280
ccgcgggagg agcagttcaa cagcacgtac cgtgtggtca gcgtcctcac cgtcctgcac   2340
caggactggc tgaacggcaa ggagtacaag tgcaaggtct ccaacaaagg cctcccgtcc   2400
```

-continued

```
tccatcgaga aaaccatctc caaagccaaa gggcagcccc gagagccaca ggtgtacacc   2460

ctgcccccat cccaggagga gatgaccaag aaccaggtca gcctgacctg cctggtcaaa   2520

ggcttctacc ccagcgacat cgccgtggag tgggagagca atgggcagcc ggagaacaac   2580

tacaagacca cgcctcccgt gctggactcc gacggctcct tcttcctcta cagcaggcta   2640

accgtggaca agagcaggtg gcaggagggg aatgtcttct catgctccgt gatgcatgag   2700

gctctgcaca accactacac acagaagagc ctctccctgt ctctgggtaa atga         2754


<210> SEQ ID NO 54
<211> LENGTH: 917
<212> TYPE: PRT
<213> ORGANISM: Homo sapiens

<400> SEQUENCE: 54

Met Val Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320
```

-continued

```
Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val His Thr Gly Ala Ala Arg Ser Cys Arg Phe
        355                 360                 365

Arg Gly Arg His Tyr Lys Arg Glu Phe Arg Leu Glu Gly Glu Pro Val
    370                 375                 380

Ala Leu Arg Cys Pro Gln Val Pro Tyr Trp Leu Trp Ala Ser Val Ser
385                 390                 395                 400

Pro Arg Ile Asn Leu Thr Trp His Lys Asn Asp Ser Ala Arg Thr Val
                405                 410                 415

Pro Gly Glu Glu Glu Thr Arg Met Trp Ala Gln Asp Gly Ala Leu Trp
            420                 425                 430

Leu Leu Pro Ala Leu Gln Glu Asp Ser Gly Thr Tyr Val Cys Thr Thr
        435                 440                 445

Arg Asn Ala Ser Tyr Cys Asp Lys Met Ser Ile Glu Leu Arg Val Phe
    450                 455                 460

Glu Asn Thr Asp Ala Phe Leu Pro Phe Ile Ser Tyr Pro Gln Ile Leu
465                 470                 475                 480

Thr Leu Ser Thr Ser Gly Val Leu Val Cys Pro Asp Leu Ser Glu Phe
                485                 490                 495

Thr Arg Asp Lys Thr Asp Val Lys Ile Gln Trp Tyr Lys Asp Ser Leu
            500                 505                 510

Leu Leu Asp Lys Asp Asn Glu Lys Phe Leu Ser Val Arg Gly Thr Thr
        515                 520                 525

His Leu Leu Val His Asp Val Ala Leu Glu Asp Ala Gly Tyr Tyr Arg
    530                 535                 540

Cys Val Leu Thr Phe Ala His Glu Gly Gln Gln Tyr Asn Ile Thr Arg
545                 550                 555                 560

Ser Ile Glu Leu Arg Ile Lys Lys Lys Lys Glu Glu Thr Ile Pro Val
                565                 570                 575

Ile Ile Ser Pro Leu Lys Thr Ile Ser Ala Ser Leu Gly Ser Arg Leu
            580                 585                 590

Thr Ile Pro Cys Lys Val Phe Leu Gly Thr Gly Thr Pro Leu Thr Thr
        595                 600                 605

Met Leu Trp Trp Thr Ala Asn Asp Thr His Ile Glu Ser Ala Tyr Pro
    610                 615                 620

Gly Gly Arg Val Thr Glu Gly Pro Arg Gln Glu Tyr Ser Glu Asn Asn
625                 630                 635                 640

Glu Asn Tyr Ile Glu Val Pro Leu Ile Phe Asp Pro Val Thr Arg Glu
                645                 650                 655

Asp Leu His Met Asp Phe Lys Cys Val Val His Asn Thr Leu Ser Phe
            660                 665                 670

Gln Thr Leu Arg Thr Thr Val Lys Glu Ala Ser Ser Thr Phe Ser Gly
        675                 680                 685

Glu Ser Lys Tyr Gly Pro Pro Cys Pro Ser Cys Pro Ala Pro Glu Phe
    690                 695                 700

Leu Gly Gly Pro Ser Val Phe Leu Phe Pro Pro Lys Pro Lys Asp Thr
705                 710                 715                 720

Leu Met Ile Ser Arg Thr Pro Glu Val Thr Cys Val Val Val Asp Val
                725                 730                 735

Ser Gln Glu Asp Pro Glu Val Gln Phe Asn Trp Tyr Val Asp Gly Val
            740                 745                 750
```

-continued

```
Glu Val His Asn Ala Lys Thr Lys Pro Arg Glu Glu Gln Phe Asn Ser
        755                 760                 765

Thr Tyr Arg Val Val Ser Val Leu Thr Val Leu His Gln Asp Trp Leu
    770                 775                 780

Asn Gly Lys Glu Tyr Lys Cys Lys Val Ser Asn Lys Gly Leu Pro Ser
785                 790                 795                 800

Ser Ile Glu Lys Thr Ile Ser Lys Ala Lys Gly Gln Pro Arg Glu Pro
                805                 810                 815

Gln Val Tyr Thr Leu Pro Pro Ser Gln Glu Glu Met Thr Lys Asn Gln
            820                 825                 830

Val Ser Leu Thr Cys Leu Val Lys Gly Phe Tyr Pro Ser Asp Ile Ala
        835                 840                 845

Val Glu Trp Glu Ser Asn Gly Gln Pro Glu Asn Asn Tyr Lys Thr Thr
    850                 855                 860

Pro Pro Val Leu Asp Ser Asp Gly Ser Phe Phe Leu Tyr Ser Arg Leu
865                 870                 875                 880

Thr Val Asp Lys Ser Arg Trp Gln Glu Gly Asn Val Phe Ser Cys Ser
                885                 890                 895

Val Met His Glu Ala Leu His Asn His Tyr Thr Gln Lys Ser Leu Ser
            900                 905                 910

Leu Ser Leu Gly Lys
        915
```

<210> SEQ ID NO 55
<211> LENGTH: 2754
<212> TYPE: DNA
<213> ORGANISM: Homo sapiens

<400> SEQUENCE: 55

```
atggtgcttc tgtggtgtgt agtgagtctc tacttttatg gaatcctgca aagtgatgcc      60

tcagaacgct gcgatgactg ggactagac accatgaggc aaatccaagt gtttgaagat      120

gagccagctc gcatcaagtg cccactcttt gaacacttct tgaaattcaa ctacagcaca     180

gcccattcag ctggccttac tctgatctgg tattggacta ggcaggaccg ggaccttgag     240

gagccaatta acttccgcct ccccgagaac cgcattagta aggagaaaga tgtgctgtgg     300

ttccggccca ctctcctcaa tgacactggc aactatacct gcatgttaag gaacactaca     360

tattgcagca aagttgcatt tcccttggaa gttgttcaaa aagacagctg tttcaattcc     420

cccatgaaac tcccagtgca taaactgtat atagaatatg gcattcagag gatcacttgt     480

ccaaatgtag atggatattt tccttccagt gtcaaaccga ctatcacttg gtatatgggc     540

tgttataaaa tacagaattt taataatgta atacccgaag gtatgaactt gagtttcctc     600

attgccttaa tttcaaataa tggaaattac acatgtgttg ttacatatcc agaaaatgga     660

cgtacgtttc atctcaccag gactctgact gtaaaggtag taggctctcc aaaaaatgca     720

gtgccccctg tgatccattc acctaatgat catgtggtct atgagaaaga accaggagag     780

gagctactca ttccctgtac ggtctatttt agttttctga tggattctcg caatgaggtt     840

tggtggacca ttgatggaaa aaaacctgat gacatcacta ttgatgtcac cattaacgaa     900

agtataagtc atagtagaac agaagatgaa acaagaactc agattttgag catcaagaaa     960

gttacctctg aggatctcaa gcgcagctat gtctgtcatg ctagaagtgc caaaggcgaa    1020

gttgccaaag cagccaaggt gaagcagaaa gtgccagctc caagatacac agtgcacaca    1080

ggggctgcca gaagctgccg gtttcgtggg aggcattaca agcgggagtt caggctggaa    1140
```

```
ggggagcctg tagccctgag gtgcccccag gtgccctact ggttgtgggc ctctgtcagc   1200

ccccgcatca acctgacatg gcataaaaat gactctgcta ggacggtccc aggagaagaa   1260

gagacacgga tgtgggccca ggacggtgct ctgtggcttc tgccagcctt gcaggaggac   1320

tctggcacct acgtctgcac tactagaaat gcttcttact gtgacaaaat gtccattgag   1380

ctcagagttt ttgagaatac agatgctttc ctgccgttca tctcataccc gcaaatttta   1440

accttgtcaa cctctggggt attagtatgc cctgacctga gtgaattcac ccgtgacaaa   1500

actgacgtga agattcaatg gtacaaggat tctcttcttt tggataaaga caatgagaaa   1560

tttctaagtg tgagggggac cactcactta ctcgtacacg atgtggccct ggaagatgct   1620

ggctattacc gctgtgtcct gacatttgcc catgaaggcc agcaatacaa catcactagg   1680

agtattgagc tacgcatcaa gaaaaaaaaa gaagagacca ttcctgtgat catttccccc   1740

ctcaagacca tatcagcttc tctggggtca agactgacaa tcccatgtaa ggtgtttctg   1800

ggaaccggca caccccttaac caccatgctg tggtggacgg ccaatgacac ccacatagag   1860

agcgcctacc cgggaggccg cgtgaccgag ggccacgcc aggaatattc agaaaataat   1920

gagaactaca ttgaagtgcc attgattttt gatcctgtca caagagagga tttgcacatg   1980

gattttaaat gtgttgtcca taataccctg agttttcaga cactacgcac cacagtcaag   2040

gaagcctcct ccacgttctc cggagagtcc aaatacggtc cgccatgccc accatgccca   2100

gcacctgagt tcctgggggg accatcagtc ttcctgttcc ccccaaaacc caaggacact   2160

ctcatgatct cccggacccc tgaggtcacg tgcgtggtgg tggacgtgag ccaggaagac   2220

cccgaggtcc agttcaactg gtacgtggat ggcgtggagg tgcataatgc caagacaaag   2280

ccgcgggagg agcagttcaa cagcacgtac cgtgtggtca gcgtcctcac cgtcctgcac   2340

caggactggc tgaacggcaa ggagtacaag tgcaaggtct ccaacaaagg cctcccgtcc   2400

tccatcgaga aaaccatctc caaagccaaa gggcagcccc gagagccaca ggtgtacacc   2460

ctgcccccat cccaggagga gatgaccaag aaccaggtca gcctgacctg cctggtcaaa   2520

ggcttctacc ccagcgacat cgccgtggag tgggagagca atgggcagcc ggagaacaac   2580

tacaagacca cgcctcccgt gctggactcc gacggctcct tcttcctcta cagcaggcta   2640

accgtggaca agagcaggtg gcaggagggg aatgtcttct catgctccgt gatgcatgag   2700

gctctgcaca accactacac acagaagagc ctctccctgt ctctgggtaa atga          2754
```

<210> SEQ ID NO 56
<211> LENGTH: 917
<212> TYPE: PRT
<213> ORGANISM: Homo sapiens

<400> SEQUENCE: 56

```
Met Val Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95
```

-continued

```
Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val His Thr Gly Ala Ala Arg Ser Cys Arg Phe
        355                 360                 365

Arg Gly Arg His Tyr Lys Arg Glu Phe Arg Leu Glu Gly Glu Pro Val
    370                 375                 380

Ala Leu Arg Cys Pro Gln Val Pro Tyr Trp Leu Trp Ala Ser Val Ser
385                 390                 395                 400

Pro Arg Ile Asn Leu Thr Trp His Lys Asn Asp Ser Ala Arg Thr Val
                405                 410                 415

Pro Gly Glu Glu Glu Thr Arg Met Trp Ala Gln Asp Gly Ala Leu Trp
            420                 425                 430

Leu Leu Pro Ala Leu Gln Glu Asp Ser Gly Thr Tyr Val Cys Thr Thr
        435                 440                 445

Arg Asn Ala Ser Tyr Cys Asp Lys Met Ser Ile Glu Leu Arg Val Phe
    450                 455                 460

Glu Asn Thr Asp Ala Phe Leu Pro Phe Ile Ser Tyr Pro Gln Ile Leu
465                 470                 475                 480

Thr Leu Ser Thr Ser Gly Val Leu Val Cys Pro Asp Leu Ser Glu Phe
                485                 490                 495

Thr Arg Asp Lys Thr Asp Val Lys Ile Gln Trp Tyr Lys Asp Ser Leu
            500                 505                 510

Leu Leu Asp Lys Asp Asn Glu Lys Phe Leu Ser Val Arg Gly Thr Thr
        515                 520                 525
```

```
His Leu Leu Val His Asp Val Ala Leu Glu Asp Ala Gly Tyr Tyr Arg
    530                 535                 540

Cys Val Leu Thr Phe Ala His Glu Gly Gln Gln Tyr Asn Ile Thr Arg
545                 550                 555                 560

Ser Ile Glu Leu Arg Ile Lys Lys Lys Lys Glu Glu Thr Ile Pro Val
                565                 570                 575

Ile Ile Ser Pro Leu Lys Thr Ile Ser Ala Ser Leu Gly Ser Arg Leu
            580                 585                 590

Thr Ile Pro Cys Lys Val Phe Leu Gly Thr Gly Thr Pro Leu Thr Thr
        595                 600                 605

Met Leu Trp Trp Thr Ala Asn Asp Thr His Ile Glu Ser Ala Tyr Pro
    610                 615                 620

Gly Gly Arg Val Thr Glu Gly Pro Arg Gln Glu Tyr Ser Glu Asn Asn
625                 630                 635                 640

Glu Asn Tyr Ile Glu Val Pro Leu Ile Phe Asp Pro Val Thr Arg Glu
                645                 650                 655

Asp Leu His Met Asp Phe Lys Cys Val Val His Asn Thr Leu Ser Phe
            660                 665                 670

Gln Thr Leu Arg Thr Thr Val Lys Glu Ala Ser Ser Thr Phe Ser Gly
        675                 680                 685

Glu Ser Lys Tyr Gly Pro Pro Cys Pro Pro Cys Pro Ala Pro Glu Phe
    690                 695                 700

Leu Gly Gly Pro Ser Val Phe Leu Phe Pro Pro Lys Pro Lys Asp Thr
705                 710                 715                 720

Leu Met Ile Ser Arg Thr Pro Glu Val Thr Cys Val Val Val Asp Val
                725                 730                 735

Ser Gln Glu Asp Pro Glu Val Gln Phe Asn Trp Tyr Val Asp Gly Val
            740                 745                 750

Glu Val His Asn Ala Lys Thr Lys Pro Arg Glu Glu Gln Phe Asn Ser
        755                 760                 765

Thr Tyr Arg Val Val Ser Val Leu Thr Val Leu His Gln Asp Trp Leu
    770                 775                 780

Asn Gly Lys Glu Tyr Lys Cys Lys Val Ser Asn Lys Gly Leu Pro Ser
785                 790                 795                 800

Ser Ile Glu Lys Thr Ile Ser Lys Ala Lys Gly Gln Pro Arg Glu Pro
                805                 810                 815

Gln Val Tyr Thr Leu Pro Pro Ser Gln Glu Glu Met Thr Lys Asn Gln
            820                 825                 830

Val Ser Leu Thr Cys Leu Val Lys Gly Phe Tyr Pro Ser Asp Ile Ala
        835                 840                 845

Val Glu Trp Glu Ser Asn Gly Gln Pro Glu Asn Asn Tyr Lys Thr Thr
    850                 855                 860

Pro Pro Val Leu Asp Ser Asp Gly Ser Phe Phe Leu Tyr Ser Arg Leu
865                 870                 875                 880

Thr Val Asp Lys Ser Arg Trp Gln Glu Gly Asn Val Phe Ser Cys Ser
                885                 890                 895

Val Met His Glu Ala Leu His Asn His Tyr Thr Gln Lys Ser Leu Ser
            900                 905                 910

Leu Ser Leu Gly Lys
        915
```